US006492367B1

(12) United States Patent
DeCrescenzo et al.

(10) Patent No.: US 6,492,367 B1
(45) Date of Patent: Dec. 10, 2002

(54) SULFAMATO HYDROXAMIC ACID METALLOPROTEASE INHIBITOR

(75) Inventors: Gary A DeCrescenzo, St. Charles, MO (US); Joseph G Rico, St. Charles, MO (US); Terri Boehm, Ballwin, MO (US); Jeffery N Carroll, St. Louis, MO (US); Darren J Kassab, Chesterfield, MO (US); Deborah A Mischke, Defiance, MO (US); Shashidhar Rao, St. Louis, MO (US)

(73) Assignee: G. D. Searle & Company, St. Louis, MO (US)

( * ) Notice: Subject to any disclaimer, the term of this patent is extended or adjusted under 35 U.S.C. 154(b) by 0 days.

(21) Appl. No.: 10/084,713

(22) Filed: Feb. 26, 2002

Related U.S. Application Data

(63) Continuation of application No. 09/499,276, filed on Feb. 7, 2000.
(60) Provisional application No. 60/119,181, filed on Feb. 8, 1999.

(51) Int. Cl.[7] .................... A61K 31/496; C07D 401/12; C07D 405/12
(52) U.S. Cl. ....................... 514/252; 544/360; 544/359; 544/383; 514/255
(58) Field of Search ................................. 514/252, 255; 544/360, 359, 383

(56) References Cited

U.S. PATENT DOCUMENTS

| | | | |
|---|---|---|---|
| 1,067,965 A | 7/1913 | Hardy et al. | |
| 4,595,700 A | 6/1986 | Donald et al. | 514/616 |
| 5,932,595 A | 8/1999 | Bender et al. | 514/317 |
| 5,998,412 A | 12/1999 | Broka et al. | |

FOREIGN PATENT DOCUMENTS

| | | | |
|---|---|---|---|
| EP | 0 266 182 | 5/1988 | C07D/307/32 |
| EP | 0 336 354 B1 | 2/1994 | C07D/239/42 |
| EP | 0 606 046 | 7/1994 | C07D/213/42 |
| EP | 0 780 386 | 6/1997 | C07D/309/08 |
| EP | 0 930 067 | 7/1999 | A61K/31/40 |
| EP | 0 931 788 A2 | 7/1999 | C07C/311/03 |
| GB | 1067965 | 5/1967 | |
| JP | 4-338331 | 11/1992 | A61K/31/365 |
| WO | 90/05719 | 5/1990 | C07C/323/62 |
| WO | 93/20047 | 10/1993 | C07C/317/44 |
| WO | 94/02466 | 2/1994 | C07D/221/14 |
| WO | 94/24140 | 10/1994 | C07H/13/04 |
| WO | 95/09841 | 4/1995 | C07C/323/60 |
| WO | 95/13289 | 5/1995 | A61K/9/127 |
| WO | 96/06074 | 2/1996 | C07C/259/06 |
| WO | 96/11209 | 4/1996 | C07K/5/06 |
| WO | 97/20824 | 6/1997 | C07D/241/04 |
| WO | 97/24117 | 7/1997 | A61K/31/19 |
| WO | 97/48368 | 12/1997 | |
| WO | 98/37877 | 9/1998 | A61K/31/16 |
| WO | 98/38163 | 9/1998 | C07C/323/60 |
| WO | 99/24399 | 5/1999 | C07C/311/04 |
| WO | 99 25687 | 5/1999 | C07D/211/66 |
| WO | 99/29667 | 6/1999 | C07D/211/16 |
| WO | 99/42436 | 8/1999 | C07C/239/14 |
| WO | 00/38717 | 6/2000 | A61K/41/00 |
| WO | 00/50396 | 8/2000 | C07D/221/66 |

OTHER PUBLICATIONS

Gearing et al. *Nature*, 376, 555–557 (1994).
McGeehan et al., *Nature* 370, 558–561 (1994).
Mitchell et al., *J. Clin. Invsest.*, 97(3) 761–768 (1996).
Reboul e al., *J. Clin Invest.*, 97(9), 2011–2019 (1996).
Schwartz et al., *Progr. Med. Chem.*, 29:271–334 (1992).
Rasmussen et al., *Pharmacol. Ther.*, 75(l): 69–75 (1997).
Denis et al., *Invest. New Drugs*, 15A, 175–185 (1997).
*A Model of Angiogenesis in the Mouse Cornea*; Kenyon, BM, et al., Investigative Ophthalmology & Visual Science, vol. 37, No. 8 (Jul. 1996).
Knight et al., *FEBS Lett.* 296(3):263 (1992).
Luckow et al., *J. Virol.*, 67:4566–4579 (1993).
McClure et al. “Matrix metalloprotease . . . ” CA 131:125454 (1999).
Dack et al. “Preparation of N–hydroxytetrahydro . . . ” CA 131:44740 (1999).

*Primary Examiner*—Charanjit S. Aulakh
(74) *Attorney, Agent, or Firm*—David M. Gryte; Harness, Dickey & Pierce, P.L.C.

(57) ABSTRACT

A sulfamato hydroxamic acid compound that inter alia inhibits matrix metalloprotease activity is disclosed as are a process for preparing the same, intermediate compounds useful in those syntheses, and a treatment process that comprises administering a contemplated sulfamato hydroxamic acid compound in a MMP enzyme-inhibiting effective amount to a host having a condition associated with pathological matrix metalloprotease activity.

49 Claims, No Drawings

SULFAMATO HYDROXAMIC ACID METALLOPROTEASE INHIBITOR

CROSS-REFERENCE TO RELATED PATENT APPLICATIONS

This patent is a continuation of U.S. patent application Ser. No. 09/499,276 (filed Feb. 7, 2000), which, in turn, claims priority to U.S. Provisional Patent Application No. 60/119,181 (filed Feb. 8, 1999). The entire texts of the above-referenced patent applications are hereby incorporated by reference into this patent.

TECHNICAL FIELD

This invention is directed to proteinase (protease) inhibitors, and more particularly to the use of sulfamato hydroxamic acid compounds that, inter alia, are selective inhibitors of matrix metalloproteinases in a process for treating conditions associated with pathological matrix metalloproteinase activity, the selective inhibitors themselves, compositions of proteinase inhibitors, intermediates for the syntheses of proteinase inhibitors, and processes for the preparation of proteinase inhibitors.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimers Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Metalloproteases are also involved in the biosynthesis of tumor necrosis factor (TNF), and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal, and TNF can help control the growth of tumor cells.

TNF-$\alpha$ convertase is a metalloprotease involved in the formation of soluble TNF-$\alpha$. Inhibition of TNF-$\alpha$ convertase (TACE) inhibits production of active TNF-$\alpha$. Compounds that inhibit both MMPs activity and TNF-$\alpha$ production have been disclosed in WIPO International Publication Nos. WO 94/24140, WO 94/02466 and WO 97/20824. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)). There remains a need for effective MMP inhibitors. There also remains a need for effective TNF-$\alpha$ convertase inhibiting agents.

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin, gelatinase A or B, or collagenase III appear to be the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation of inflamed joints is at least partially caused by MMP-13 released from cells such as stimulated chrondrocytes, may be best treated by administration of drugs one of whose modes of action is inhibition of MMP- 13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitors of metalloproteinases (TIMPs), $\alpha_2$-macroglobulin and their analogs or derivatives. These endogenous inhibitors are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997). In addition, application EP 0757 984 A1 discloses aromatic sulfonamide hydroxamates in which the sulfonamido sulfonyl group is bonded on one side to a phenyl ring and the sulfonamido nitrogen is bonded to the hydroxamate group via a chain of one to four carbon atoms.

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, is toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

International application WO 98/38163, published on Sep. 3, 1998 disclose a large group of hydroxamate inhibitors of MMPs and TACE. The compounds of WO 98/38163 contain one or two substituents adjacent to the hydroxamate functionality and a substituent that can be an aromatic sulfonyl group adjacent to those one or two substituents.

International application WO 98/37877, published on Sep. 3, 1998 discloses compounds that contain a 5- to 7-membered heterocyclic ring adjacent to the hydroxamate functionality and can contain an aromatic sulfonyl group adjacent to the heterocyclic ring.

More recently, WO 99/24399, published on May, 20, 1999, teaches hydroxamate compounds said to have activity in inhibiting MMP and TNF. Those inhibitors are exemplified by compounds having a three carbon atom chain linked to a sulfonamido group. The hydroxamate carbon is linked to a carbon that can be substituted and that carbon is linked to a methylene. The methylene is linked to a sulfonyl that is bonded to a nitrogen that is further substituted. This disclosure also lacks disclosure as to possible specificity of activity among the substrate enzymes.

Another recent disclosure is that of WO 99/29667, published on Jun. 17, 1999, that discloses two carbon hydroxamate containing a sulfonamido group whose nitrogen atom is in a ring that is typically bonded directly to another one or two ring group without the intermediacy of another atom. This publication suggests that some of its compounds are selective inhibitors, but provides scant data for only seven compounds.

Although many of the known MMP inhibitors such as batimastat, marimastat and the hydroxamates of WO 98/37877 and WO 98/38163 exhibit a broad spectrum of activity against MMPs, those compounds are not particularly selective in their inhibitory activity. This lack of selectivity may be the cause of the musculoskeletal pain and stiffness observed with their use. In addition, it can be therapeutically advantageous to utilize a medicament that is selective in its activity as compared to a generally active material so that treatment can be more closely tailored to the pathological condition presented by the host mammal. The disclosure that follows describes a process for treating a host mammal having a condition associated with pathological matrix metalloprotease activity that utilizes a compound that selectively inhibits one or more MMPs, while exhibiting less activity against at least MMP-1.

SUMMARY OF THE INVENTION

The present invention is directed to a treatment process that comprises administering a contemplated sulfamato hydroxamic acid metalloprotease inhibitor in an effective-amount to a host mammal having a condition associated with pathological metalloprotease activity. A contemplated molecule, inter alia, exhibits excellent inhibitory activity of one or more matrix metalloprotease (MMP) enzymes, such as MMP-2 and MMP-13, while exhibiting substantially less inhibition at least of MMP-1. By "substantially less" it is meant that a contemplated compound exhibits an $IC_{50}$ value ratio against one or both of MMP-2 or MMP-13 as compared to its $IC_{50}$ value against MMP-1, e.g., $IC_{50}$ MMP-2:$IC_{50}$ MMP-1, that is less than about 1:10, preferably less than about 1:100, and most preferably less than about 1:1000 in the in vitro inhibition assay utilized hereinafter. The invention also contemplates particular compounds that selectively inhibit the activity of MMP-2 to a greater extent than MMP-13, as well as a composition containing such a MMP inhibitor as active ingredient and a process for using the same. A contemplated compound also exhibits inhibition of the activity of the adamalysin family of enzymes, exemplified by the enzyme ADAM 10. The invention further contemplates intermediates in the preparation of a contemplated sulfamato hydroxamic acid molecule and a process for preparing a sulfamato hydroxamic acid molecule.

Briefly, one embodiment of the present invention is directed to a treatment process that comprises administering a contemplated sulfamato hydroxamic acid metalloprotease inhibitor that selectively inhibits matrix metalloprotease and adamalysin activity as above in an effective amount to a host mammal having a condition associated with pathological metalloprotease activity. The administered enzyme inhibitor sulfamato hydroxamic acid (hydroxamate) corresponds in structure to formula I, below, or a pharmaceutically acceptable salt thereof:

I

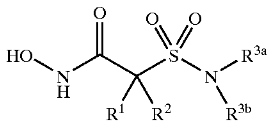

wherein $R^1$ and $R^2$ are preferably taken together with the carbon to which they are bonded form a cycloalkyl or more preferably a heterocyclo group either of which is optionally substituted by one, two or three $R^x$ substituents, or $R^1$ and $R^2$ are independently selected from the group consisting of:

hydrido, an alkyl group, optionally substituted with one, two or three groups independently selected from $R^x$ substituents, an alkyloxyalkyl group, optionally substituted with one, two or three groups independently selected from $R^x$ substituents, an alkylthioalkyl group, optionally substituted with one, two or three groups independently selected from $R^x$ substituents, an alkenyl group, optionally substituted with one, two or three groups independently selected from $R^x$ substituents, an alkynyl group, optionally substituted with one, two or three groups independently selected from $R^x$ substituents, an aryl group, optionally substituted with one, two or three groups independently selected from $R^x$ substituents, an arylalkyl group, optionally substituted with one, two or three groups independently selected from $R^x$ substituents, an arylalkyloxyalkyl group, optionally substituted with one, two or three groups independently selected from $R^x$ substituents, an aryloxyalkyl group, optionally substituted with one, two or three groups independently selected from $R^x$ substituents, an arylthioalkyl group, optionally substituted with one, two or three groups independently selected from $R^x$ substituents, an arylalkylthioalkyl group, optionally substituted with one, two or three groups independently selected from $R^x$ substituents, a cycloalkyl or bicycloalkyl group, optionally substituted with one, two or three groups independently selected from $R^x$ substituents, a cycloalkenyl group, optionally substituted with one, two or three groups independently selected from $R^x$ substituents, a cycloalkylalkyl or bicycloalkylalkyl group, optionally substituted with one, two or three groups independently selected from $R^x$ substituents, a cycloalkyloxyalkyl or bicycloalkyloxyalkyl group, optionally substituted with one, two or three groups independently selected from $R^x$ substituents, a cycloalkylalkyloxyalkyl or bicycloalkyloxyalkyl group, optionally substituted with one, two or three groups independently selected from $R^x$ substituents, a cycloalkylthioalkyl or bicycloalkylthioalkyl group, optionally substituted with one, two or three groups independently selected from $R^x$;

cycloalkylalkylthioalkyl or bicycloalkylalkylthioalkyl, optionally substituted with one, two or three groups independently selected from $R^x$ substituents, a heterocyclo group, optionally substituted with one, two or three groups independently selected from $R^x$ substituents, a heterocycloalkyl group, optionally substituted with one, two or three groups independently selected from $R^x$ substituents a heteroaryl group, optionally substituted with one, two or three groups independently selected from $R^x$ substituents, a biarylalkyl group, optionally substituted with one, two or three groups independently selected from $R^x$ substituents, an arylalkenyl group, optionally substituted with one, two or three groups independently selected from $R^x$ substituents, an arylalkynyl group, optionally substituted with one, two or three groups independently-selected from $R^x$ substituents, a heterocycloalkylthio group, optionally substituted with one, two or three groups selected independently from $R^x$ substituents, a heterocycloalkyloxyalkyl group, optionally substituted with one, two or three groups selected independently from $R^x$ substituents, a heteroarylalkenyl group, optionally substituted with one, two or three groups independently selected from $R^x$ substituents, and a heteroarylalkyloxyalkyl group, optionally substituted with one, two or three groups independently selected from $R^x$ substituents;

wherein an $R^x$ substituent is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, $R^cR^d$-amino (—$NR^cR^d$), $R^cR^d$-aminoalkyl, nitro, nitroso, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, alkoxyalkyl, $R^c$-oxyalkyl, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, alkyloxycarbonyl-$R^c$-amino, arylalkyloxycarbonyl-$R^c$-amino, aryloxycarbonyloxy, carboxy, $R^cR^d$-aminocarbonyloxy, $R^cR^d$-aminocarbonyl, $R^cR^d$-aminoalkanoyl, hydroxy-$R^c$-aminocarbonyl, $R^cR^d$-aminosulfonyl, arylsulfonyl($R^c$)amino, $R^cR^d$-aminoalkoxy, $R^cR^d$-aminocarbonyl($R^c$)amino, trifluoromethylsulfonyl($R^c$)amino, heteroarylsulfonyl($R^c$)amino, alkylsulfonyl, arylsulfonyl($R^c$)amino, arylsulfonyl($R^c$)aminocarbonyl, alkylsulfonyl($R^c$)amino, arylcarbonyl($R^c$)-aminosulfonyl, and an alkylsulfonyl($R^c$)aminocarbonyl substituent;

wherein $R^c$ and $R^d$ are independently selected from the group consisting of a hydrido, alkanoyl, arylalkyl, aroyl, bisalkoxyalkyl, alkyl, haloalkyl, perfluoroalkyl, trifluoromethylalkyl, perfluoroalkoxyalkyl, alkoxyalkyl, cycloalkyl, heterocycloalkyl, heterocycloalkylcarbonyl, aryl, heterocyclo, heteroaryl, cycloalkylalkyl, aryloxyalkyl, heteroaryloxyalkyl, heteroarylalkoxyalkyl, heteroarylthioalkyl, arylsulfonyl, alkylsulfonyl, heteroarylsulfonyl, carboxyalkyl, alkoxycarbonylalkyl, aminocarbonyl, alkyliminocarbonyl, aryliminocarbonyl, heterocycloiminocarbonyl, arylthioalkyl, alkylthioalkyl, arylthioalkenyl, alkylthioalkenyl, heteroarylalkyl, haloalkanoyl, hydroxyalkanoyl, thiolalkanoyl, alkenyl, alkynyl, alkoxyalkyl, alkoxycarbonyl, aryloxycarbonyl, aminoalkylcarbonyl, hydroxyalkyl, aminoalkyl, aminoalkylsulfonyl, aminosulfonyl wherein the amino nitrogen is (i) unsubstituted or (ii) independently substituted with one or two $R^y$ radicals, or the substituents on the amino group taken together with the amino nitrogen form a saturated or partially unsaturated heterocyclo group optionally substituted with one, two or three groups independently selected from $R^w$ substituents or a heteroaryl group optionally substituted with one, two or three groups independently selected from $R^v$ substituents;

wherein $R^y$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups is optionally substituted by one or two groups independently selected from Ru substituents as are the substituents of the substituted aminoalkyl and substituted aminoalkanoyl groups;

wherein $R^v$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, $R^yR^z$-aminocarbonyloxy, $R^yR^z$-aminocarbonyl, $R^yR^z$-aminoalkanoyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl($R^y$)amino, arylsulfonyl($R^y$)amino, arylsulfonyl($R^y$)aminocarbonyl, alkylsulfonyl($R^y$)amino, arylcarbonyl($R^y$)aminosulfonyl, and an alkylsulfonyl($R^y$)aminocarbonyl substituent;

wherein $R^w$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, $R^yR^z$-aminocarbonyloxy, $R^yR^z$-aminocarbonyl, $R^yR^z$-aminoalkanoyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl($R^y$)amino, arylsulfonyl($R^y$)amino, arylsulfonyl($R^y$)aminocarbonyl, alkylsulfonyl($R^y$)amino, arylcarbonyl($R^y$)aminosulfonyl, and an alkylsulfonyl($R^y$)aminocarbonyl substituent;

$R^z$ is selected from the group consisting of an arylalkyl, aryl, heteroaryl, heterocyclo, alkyl, alkynyl, alkenyl, alkoxyalkyl, alkoxyalkylalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups are optionally substituted by one or two $R^u$ substituents;

wherein $R^u$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, wherein the substituents of the substituted aminoalkyl and substituted aminoalkanoyl groups are selected from the group consisting of an alkyl, alkenyl, alkenyl, aryl, arylalkyl, heteroaryl, heteroarylalkyl, aryloxycarbonyl and an alkyloxycarbonyl group;

$R^{3a}$ and $R^{3b}$ are independently selected from the group consisting of a hydrido, alkyl, alkenyl, alkynyl, aryl, heterocyclo, heteroaryl, cycloalkyl, and an alkoxyalkyl group, each of which groups is optionally substituted by an —AREY substituent;

in that AREY substituent, A is selected from the group consisting of (1) —O—;
(2) —S—;
(3) —N($R^e$)—;
(4) —CO—N($R^e$) or —N($R^e$)—CO—;
(5) —CO—O— or —O—CO—;
(6) —Q—CO—O—;
(7) —HC═CH—;
(8) —NH—CO—NH—;
(9) —C═C—;
(10) —NH—CO—O— or —O—CO—NH—;
(11) —N═N—;
(12) —NH—NH—;
(13) —CS—N($R^e$)— or —N($R^e$)—CS—;
(14) —$CH_2$—;
(15) —O—[$(CH_2)_{1-8}$]— or —[$(CH_2)_{1-8}$]O—; and
(16) —S—$CH_2$— or —$CH_2$—S—; or
(17) A is absent and R is directly connected to $R^{3a}$ or $R^{3b}$, or both $R^{3a}$ and $R^{3b}$;

the moiety R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl, heteroaryl, cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group;

the group E is selected from the group consisting of
(1) —CO($R^w$)— or —($R^w$)CO—;
(2) —CON($R^e$)— or —($R^e$)NCO—;
(3) —CO—;
(4) —$SO_2$—$R^w$ or —$R^w SO_2$—;
(5) —$SO_2$—;
(6) —N($R^e$)—$SO_2$— or —$SO_2$—N($R^e$)—; or
(7) E is absent and R is bonded directly to Y; and Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, $R^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group;

is wherein $R^e$ is selected from hydrido, alkyl, alkenyl, alkenyl, aryl, arylalkyl, heteroaryl, heteroarylalkyl, aryloxycarbonyl, alkyloxycarbonyl, $R^cR^d$amino carbonyl, $R^cR^d$aminosulfonyl, $R^cR^d$aminoalkanoyl and $R^cR^d$aminoalkysulfonyl, and $R^c$, $R^d$ and $R^w$ are as defined before; or $R^{3a}$ and $R^{3b}$ taken together with the nitrogen atom to which they are bonded form a group —GAREY wherein
G is a N-heterocyclo group;
the substituent A is selected from the group consisting of
(1) —O—;
(2) —S—;
(3) —$NR^e$—;
(4) —CO—N($R^e$) or —N($R^e$)—CO—;
(5) —CO—O— or —O—CO—;
(6) —O—CO—O—;
(7) —HC=CH—;
(8) —NH—CO—NH—;
(9) —C≡C—;
(10) —NH—CO—O— or —O—CO—NH—;
(11) —N=N—;
(12) —NH—NH—;
(13) —CS—N($R^e$)— or —N($R^e$)—CS—;
(14) —$CH_2$—;
(15) —O—[$(CH_2)_{1-8}$]— or —[$(CH_2)_{1-8}$]O—; and
(16) —S—$CH_2$— or —$CH_2$—S—; or
(17) A is absent and R is directly connected to G;

The moiety R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group;

The moiety E is selected from the group consisting of
(1) —CO($R^w$)— or —($R^w$)CO—;
(2) —CONH— or —HNCO—;
(3) —CO—;
(4) —$SO_2$—$R^w$— or —$R^w$—$SO_2$—;
(5) —$SO_2$—;
(6) —NH—$SO_2$— or —$SO_2$—NH—; or
(7) E is absent and Y is bonded directly to R; and The moiety Y is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl or heteroaryl or heterocycloalkyl group is (i) unsubstituted or (ii) substituted with one or two radicals independently selected from the group consisting of an alkanoyl, halo, nitro, aralkyl, aryl, alkoxy, and an amino group wherein the amino nitrogen is (i) unsubstituted or (ii) substituted with one or two groups independently selected from hydrido, alkyl, and an aralkyl group.

More generally, a contemplated compound includes an inhibitor utilized as discussed above, as well as a pro-drug form of such a compound and also an intermediate used in the synthesis of a hydroxamate or hydroxamate pro-drug. Such a more general compound corresponds in structure to formula II, below,

II

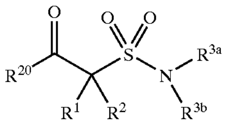

wherein $R^1$, $R^2$, $R^{3a}$ and $R^{3b}$ are as before described, and $R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$, wherein $R^{22}$ is a selectively removable protecting group such as a 2-tetrahydropyranyl, benzyl, p-methoxybenzyl (MOZ) carbonyl-$C_1$–$C_6$-alkoxy, trisubstituted silyl group or o-nitrophenyl group, peptide systhesis resin and the like, wherein trisubstituted silyl group is substituted with $C_1$–$C_6$-alkyl, aryl, or ar-$C_1$–$C_6$-alkyl, or (c)

—NH—O—$R^{14}$, where $R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring.

Among the several benefits and advantages of the present invention are the provision of compounds and compositions effective as inhibitors of matrix metalloproteinase activity, the provision of such compounds and compositions that are effective for the inhibition of metalloproteinases implicated in diseases and disorders involving uncontrolled breakdown of connective tissue.

More particularly, a benefit of this invention is the provision of a compound and composition effective for selectively inhibiting certain metalloproteinases, such as one or both of MMP-2 and MMP-13, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of compounds, compositions and methods effective for treating such pathological conditions by selective inhibition of a metalloproteinase such as MMP-2 or MMP-13 associated with such conditions with minimal side effects resulting from inhibition of other metalloproteinases, such as MMP-1, whose activity is necessary or desirable for normal body function.

A still further benefit of the invention is that a contemplated compound exhibits greater inhibition of MMP-2 than MMP-13.

A still further advantage of the invention is that a contemplated compound exhibits inhibitory activity against the adamalysin family of enzymes.

Yet another advantage of the invention is the provision of a process for preparing such compounds.

Another benefit is the provision of a method for treating a pathological condition associated with abnormal matrix metalloproteinase activity.

A further advantage of the invention is the provision of a process for preparing such compositions.

Still further benefits and advantages of the invention will be apparent to the skilled worker from the disclosure that follows.

DETAILED DESCRIPTION OF THE INVENTION

In accordance with the present invention, it has been discovered that certain sulfamato hydroxamic acids (hydroxamates) are effective for inhibition of matrix metalloproteinases ("MMPs") believed to be associated with uncontrolled or otherwise pathological breakdown of connective tissue. In particular, it has been found that these certain sulfamato hydroxamates are effective for inhibition of one or both of MMP-2 and MMP-13, which can be particularly destructive to tissue if present or generated in abnormal quantities or concentrations, and thus exhibit a pathological activity. Included in that pathological activity is the assistance of tumors and tumor cells in the process of penetrating basement membrane, and developing a new or improved blood supply; i.e., angiogenesis.

Moreover, it has been discovered that these sulfamato hydroxamates are selective in the inhibition of one or both of MMP-2 and MMP-13 without excessive inhibition of other collagenases essential to normal bodily function such as tissue turnover and repair. More particularly, it has been found that a contemplated sulfamato hydroxamate of the invention, or a pharmaceutically acceptable salt thereof, is particularly active in inhibiting of one or both of MMP-2 and MMP-13 in an in vitro assay that is predictive of in vivo activity. In addition, while being selective for one or both of MMP-2 and MMP-13, a contemplated sulfamato hydroxamate, or its salt, has a limited or minimal in vitro inhibitory effect on MMP-1. This point is illustrated in the Inhibition Table hereinafter. Put differently, a contemplated compound can inhibit the activity of MMP-2 or MMP-13 compared to MMP-1.

The advantages of the selectivity of a contemplated compound can be appreciated, without wishing to be bound by theory, by considering the therapeutic uses the compounds. For example, inhibition of MMP-1 is suggested to be undesirable due to its role as a housekeeping enzyme, helping to maintain normal connective tissue turnover and repair. Inhibition of MMP-1 can lead to toxicities or side effects such as such as joint or connective tissue deterioration and pain. On the other hand, MMP-13 has been suggested to be intimately involved in the destruction of joint components in diseases such as osteoarthritis. Thus, potent and selective inhibition of MMP-13 compared with inhibition MMP-1 is highly desirable because a MMP-13 inhibitor can have a positive effect on disease progression in a patient in addition to having an anti-inflammatory effect.

Inhibition of MMP-2 can be desirable for inhibition of tumor growth, metastasis, invasion and/or angiogenesis. A profile of selective inhibition of MMP-2 relative to MMP-1 can provide a therapeutic advantage. A contemplated compound not only is substantially more active in inhibiting MMP-2 than MMP-1, a contemplated compound also exhibits greater inhibition of MMP-2 than MMP-13.

A further advantage to MMP inhibitors with selective inhibition profiles is their suitability for use in combination with other types of medicaments. For example, a patient can be treated with an MMP inhibitor compound for the inhibition of angiogenesis in combination with a second, third or fourth drug of the traditional anti-tumor type, such as taxol, cis-platinum or doxorubicin. A further advantage is that the administration of a MMP inhibitor with a selective inhibition profile can permit the reduction in dosage of the drugs being administered to the patient This is an especially important advantage given both the toxicities and dosing limits of traditional anti-tumor drugs.

A contemplated selective MMP inhibitor compound useful in a contemplated process can be administered to by various routes and provide adequate therapeutic blood levels of enzymatically active inhibitor. A compound can be administered, for example, by the oral (IG, PO) or intravenous (IV) routes. Oral administration is advantageous if the patient is ambulatory, not hospitalized, physically able and sufficiently responsible to take drug at the required intervals. This is true even if the person is being treated with more than one drug for one or more diseases. On the other hand, IV drug administration is an advantage in a hospital setting wherein the dose and thus the blood levels can well controlled. A contemplated inhibitor can also be formulated for IM administration if desired. This route of administration can be desirable for the administration of prodrugs or regular drug delivery to patients that are either physically weak or have a poor compliance record or require constant drug blood levels.

Thus, in one embodiment, the present invention is directed to a treatment process that comprises administering a contemplated sulfamato hydroxamic acid metalloprotease inhibitor, or a pharmaceutically acceptable salt thereof, in an effective amount to a host mammal having a condition associated with pathological matrix metalloprotease activity A contemplated sulfamato hydroxamate inhibitor compound useful in such a process inhibits the activity of one or both of MMP-2 and MMP-13, and exhibits substantially less inhibitory activity against at least MMP-1 in the in vitro assay noted above and discussed in detail hereinafter. A sulfamato hydroxamate inhibitor compound for use in a contemplated process corresponds in structure to formula I, below, or a pharmaceutically acceptable salt thereof:

I

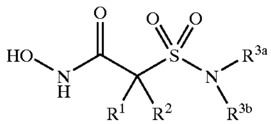

wherein $R^1$ and $R^2$ are preferably taken together with the carbon to which they are bonded form a cycloalkyl or more preferably a heterocyclo group either of which is optionally substituted by one, two or three $R^x$ substituents, or $R^1$ and $R^2$ are independently selected from the group consisting of:

hydrido, an alkyl group, optionally substituted with one, two or three groups independently selected from $R^x$ substituents, an alkyloxyalkyl group, optionally substituted with one, two or three groups independently selected from $R^x$ substituents, an alkylthioalkyl group, optionally substituted with one, two or three groups independently selected from $R^x$ substituents, an alkenyl group, optionally substituted with one, two or three groups independently selected from $R^x$ substituents, an alkynyl group, optionally substituted with one, two or three groups independently selected from $R^x$ substituents, an aryl group, optionally substituted with one, two or three groups independently selected from $R^x$ substituents, an arylalkyl group, optionally substituted with one, two or three groups independently selected from $R^x$ substituents, an arylalkyloxyalkyl group, optionally substituted with one, two or three groups independently selected from $R^x$ substituents, an aryloxyalkyl group, optionally substituted with one, two or three groups independently selected from $R^x$ substituents, an arylthioalkyl group, optionally substituted with one, two or three groups independently selected from $R^x$ substituents, an arylalkylthioalkyl group, optionally substituted with one, two or three groups independently selected from $R^x$ substituents, a cycloalkyl or bicycloalkyl group, optionally substituted with one, two or three groups independently selected from $R^x$ substituents, a cycloalkenyl group, optionally substituted with one, two or three groups independently selected from $R^x$ substituents, a cycloalkylalkyl or bicycloalkylalkyl group, optionally substituted with one, two or three groups independently selected from $R^x$ substituents, a cycloalkyloxyalkyl or bicycloalkyloxyalkyl group, optionally substituted with one, two or three groups independently selected from $R^x$ substituents, a cycloalkylalkyloxyalkyl or bicycloalkyloxyalkyl group, optionally substituted with one, two or three groups independently selected from $R^x$ substituents, a cycloalkylthioalkyl or bicycloalkylthioalkyl group, optionally substituted with one, two or three groups independently selected from $R^x$;

cycloalkylalkylthioalkyl or bicycloalkylalkylthioalkyl, optionally substituted with one, two or three groups independently selected from $R^x$ substituents, a heterocyclo group, optionally substituted with one, two or three groups independently selected from $R^x$ substituents, a heterocycloalkyl group, optionally substituted with one, two or three groups independently selected from $R^x$ substituents a heteroaryl group, optionally substituted with one, two or three groups independently selected from $R^x$ substituents, a biarylalkyl group, optionally substituted with one, two or three groups independently selected from $R^x$ substituents, an arylalkenyl group, optionally substituted with one, two or three groups independently selected from $R^x$ substituents, an arylalkynyl group, optionally substituted with one, two or three groups independently selected from $R^x$ substituents, a heterocycloalkylthio group, optionally substituted with one, two or three groups selected independently from $R^x$ substituents, a heterocycloalkyloxyalkyl group, optionally substituted with one, two or three groups selected independently from $R^x$ substituents, a heteroarylalkenyl group, optionally substituted with one, two or three groups independently selected from $R^x$ substituents, and a heteroarylalkyloxyalkyl group, optionally substituted with one, two or three groups independently selected from $R^x$ substituents;

wherein an $R^x$ substituent is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, $R^cR^d$-amino (—$NR^cR^d$), $R^cR^d$-aminoalkyl, nitro, nitroso, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, alkoxyalkyl, $R^c$-oxyalkyl, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, alkyloxycarbonyl-$R^c$-amino, arylalkyloxycarbonyl-$R^c$-amino, aryloxycarbonyloxy, carboxy, $R^cR^d$-aminocarbonyloxy, $R^cR^d$-aminocarbonyl, $R^cR^d$-aminoalkanoyl, hydroxy-$R^c$-aminocarbonyl, $R^cR^d$-aminosulfonyl, arylsulfonyl ($R^c$)amino, $R^cR^d$-aminoalkoxy, $R^cR^d$-aminocarbonyl ($R^c$)amino, trifluoromethylsulfonyl ($R^c$)amino, heteroarylsulfonyl($R^c$)amino, alkylsulfonyl, arylsulfonyl($R^c$)amino, arylsulfonyl ($R^c$)aminocarbonyl, alkylsulfonyl($R^c$)amino, arylcarbonyl($R^c$)-aminosulfonyl, and an alkylsulfonyl($R^c$)aminocarbonyl substituent;

wherein $R^c$ and $R^d$ are independently selected from the group consisting of a hydrido, alkanoyl, arylalkyl, aroyl, bisalkoxyalkyl, alkyl, haloalkyl, perfluoroalkyl, trifluoromethylalkyl, perfluoroalkoxyalkyl, alkoxyalkyl, cycloalkyl, heterocycloalkyl, heterocycloalkylcarbonyl, aryl, heterocyclo, heteroaryl, cycloalkylalkyl, aryloxyalkyl, heteroaryloxyalkyl, heteroarylalkoxyalkyl, heteroarylthioalkyl, arylsulfonyl, alkylsulfonyl, heteroarylsulfonyl, carboxyalkyl, alkoxycarbonylalkyl, aminocarbonyl, alkyliminocarbonyl, aryliminocarbonyl, heterocycloiminocarbonyl, arylthioalkyl, alkylthioalkyl, arylthioalkenyl, alkylthioalkenyl, heteroarylalkyl, haloalkanoyl, hydroxyalkanoyl, thiolalkanoyl, alkenyl, alkynyl, alkoxyalkyl, alkoxycarbonyl, aryloxycarbonyl, aminoalkylcarbonyl, hydroxyalkyl, aminoalkyl, aminoalkylsulfonyl, aminosulfonyl wherein the amino nitrogen is (i) unsubstituted or (ii) independently substituted with one or two $R^y$ radicals, or the substituents on the amino group taken together with the amino nitrogen form a saturated or partially unsaturated heterocyclo group optionally substituted with one, two or three groups independently selected from $R^w$ substituents or a heteroaryl group optionally substituted with one, two or three groups independently selected from $R^v$ substituents;

wherein $R^y$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups is optionally substituted by one or two groups independently selected from $R^u$ substituents as are the substituents of the substituted aminoalkyl and substituted aminoalkanoyl groups;

wherein $R^v$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, $R^yR^z$-aminocarbonyloxy, $R^yR^z$-aminocarbonyl, $R^yR^z$-aminoalkanoyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl($R^y$) amino, arylsulfonyl ($R^y$)amino, arylsulfonyl($R^y$)-aminocarbonyl, alkylsulfonyl($R^y$)amino, arylcarbonyl($R^y$) aminosulfonyl, and an alkylsulfonyl($R^y$)aminocarbonyl substituent;

wherein $R^w$ is selected from the group consisting of a hydrido, aryl, heteroaryl, heterocyclo, aroyl, alkanoyl, heteroaroyl, halogen (F, Cl, Br, I), cyano, aldehydo (CHO, formyl), hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkyloxycarbonyl, alkyloxycarbonyloxy, aryloxycarbonyl, arylalkyloxycarbonyl, arylalkyloxycarbonylamino, aryloxycarbonyloxy, carboxy, $R^yR^z$-aminocarbonyloxy, $R^yR^z$-aminocarbonyl, $R^yR^z$-aminoalkanoyl, hydroxyaminocarbonyl, $R^yR^z$-aminosulfonyl, $R^yR^z$-aminocarbonyl($R^y$)amino, trifluoromethylsulfonyl ($R^y$)amino, heteroarylsulfonyl($R^y$)amino, arylsulfonyl($R^y$)amino, arylsulfonyl($R^y$) aminocarbonyl, alkylsulfonyl($R^y$)amino, arylcarbonyl($R^y$)aminosulfonyl, and an alkylsulfonyl($R^y$)aminocarbonyl substituent;

$R^z$ is selected from the group consisting of an arylalkyl, aryl, heteroaryl, heterocyclo, alkyl, alkynyl, alkenyl, alkoxyalkyl, alkoxyalkylalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, each of which groups are optionally substituted by one or two $R^u$ substituents;

wherein $R^u$ is selected from the group consisting of an arylalkyl, aryl, heteroaryl, heterocyclo, alkyl, alkynyl, alkenyl, alkoxyalkyl, alkoxyalkyl, substituted or unsubstituted aminoalkyl, alkyloxycarbonyl, arylalkyloxycarbonyl, carboxyalkyl, haloalkyl, alkanoyl, aroyl, substituted or unsubstituted aminoalkanoyl, halo alkanoyl and a hydroxyalkyl group, wherein the substituents of the substituted aminoalkyl and substituted aminoalkanoyl groups are selected from the group consisting of an alkyl, alkenyl, alkenyl, aryl, arylalkyl, heteroaryl, heteroarylalkyl, aryloxycarbonyl and an alkyloxycarbonyl group;

$R^{3a}$ and $R^{3b}$ are independently selected from the group consisting of a hydrido, alkyl, alkenyl, alkynyl, aryl, heterocyclo, heteroaryl, cycloalkyl, and an alkoxyalkyl group, each of which groups is optionally substituted by an —AREY substituent;

in that AREY substituent, A is selected from the group consisting of (1) —O—;
(2) —S—;
(3) —N($R^e$)—;
(4) —CO—N($R^e$) or —N($R^e$)—CO—;
(5) —CO—O— or —O—CO—;
(6) —O—CO—O—;
(7) —HC=CH—;
(8) —NH—CO—NH—;
(9) —C≡C—;
(10) —NH—CO—O— or —O—CO—NH—;
(11) —N=N—;
(12) —NH—NH—;
(13) —CS—N($R^e$)— or —N($R^e$)—CS—;
(14) —$CH_2$—;
(15) —O—[$(CH_2)_{1-8}$]— or —[$(CH_2)_{1-8}$]O—; and

(16) —S—$CH_2$— or —$CH_2$—S—; or

(17) A is absent and R is directly connected to $R^{3a}$ or $R^{3b}$, or both $R^{3a}$ and $R^{3b}$;

the moiety R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl, heteroaryl, cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group;

the group E is selected from the group consisting of (1) —CO($R^w$)— or —($R^w$)CO—;

(2) —CON($R^e$)— or —($R^e$)NCO—;

(3) —CO—;

(4) —$SO_2$—$R^w$ or —$R^wSO_2$—;

(5) —$SO_2$—;

(6) —N($R^e$)—$SO_2$— or —$SO_2$—N($R^e$)—; or (7) E is absent and R is bonded directly to Y; and Y is absent or is selected from the group consisting of a hydrido, alkyl, alkoxy, haloalkyl, aryl, aralkyl, cycloalkyl, heteroaryl, hydroxy, nitrile, nitro, aryloxy, aralkoxy, heteroaryloxy, heteroaralkyl, $R^c$oxyalkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl, heteroaryl or heterocycloalkyl group is (i) unsubstituted or (ii) substituted with one or two radicals independently selected from the group consisting of an alkanoyl, halo, nitro, nitrile, haloalkyl, alkyl, aralkyl, aryl, alkoxy, and an amino group wherein the amino nitrogen is (i) unsubstituted or (ii) substituted with one or two groups independently selected from hydrido, alkyl, and an aralkyl group;

wherein $R^e$ is selected from hydrido, alkyl, alkenyl, alkenyl, aryl, arylalkyl, heteroaryl, heteroarylalkyl, aryloxycarbonyl, alkyloxycarbonyl, $R^cR^d$amino carbonyl, $R^cR^d$aminosulfonyl, $R^cR^d$aminoalkanoyl and $R^cR^d$aminoalkysulfonyl, and $R^c$, $R^d$ and $R^w$ are as defined before; or $R^{3a}$ and $R^{3b}$ taken together with the nitrogen atom to which they are bonded form a group —GAREY ($R^3$) wherein G is a N-heterocyclo group;

the substituent A is selected from the group consisting of (1) —O—;

(2) —S—;

(3) —$NR^e$—;

(4) —CO—N($R^e$) or —N($R^e$)—CO—;

(5) —CO—O— or —O—CO—;

(6) —O—CO—O—;

(7) —HC=CH—;

(8) —NH—CO—NH—;

(9) —C≡C—;

(10) —NH—CO—O— or —O—CO—NH—;

(11) —N=N—;

(12) —NH—NH—;

(13) —CS—N($R^e$)— or —N($R^e$)—CS—;

(14) —$CH_2$—;

(15) —O—[$(CH_2)_{1-8}$]— or —[$(CH_2)_{1-8}$]O—; and

(16) —S—$CH_2$— or —$CH_2$—S—; or

(17) A is absent and R is directly connected to G;

the moiety R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylenedioxy, hydroxycarbonylalkyl, hydroxycarbonylalkylamino, nitro, hydroxy, hydroxyalkyl, alkanoylamino, and a alkoxycarbonyl group;

The moiety E is selected from the group consisting of (1) —CO($R^w$)— or —($R^w$)CO—;

(2) —CONH— or —HNCO—;

(3) —CO—;

(4) —$SO_2$—$R^w$— or —$R^w$—$SO_2$—;

(5) —$SO_2$—;

(6) —NH—$SO_2$— or —$SO_2$—NH—; or (7) E is absent and R is bonded directly to Y; and The moiety Y is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl or heteroaryl or heterocycloalkyl group is (i) unsubstituted or (ii) substituted with one or two radicals independently selected from the group consisting of an alkanoyl, halo, nitro, aralkyl, aryl, alkoxy, and an amino group wherein the amino nitrogen is (i) unsubstituted or (ii) substituted with one or two groups independently selected from hydrido, alkyl, and an aralkyl group.

More generally, a contemplated compound includes an inhibitor utilized as discussed above, as well as a pro-drug form of such a compound and also an intermediate used in the synthesis of a hydroxamate or hydroxamate pro-drug. Such a more general compound corresponds in structure to formula II, below,

II

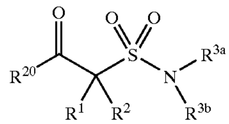

wherein $R^1$, $R^2$, $R^{3a}$ and $R^{3b}$ are as before described with the above preferences, and $R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, (b) —NH—O—$R^{22}$, wherein $R^{22}$ is a selectively removable protecting group such as a 2-tetrahydropyranyl, benzyl, p-methoxybenzyl (MOZ) carbonyl-$C_1$–$C_6$-alkoxy, trisubstituted silyl group or o-nitrophenyl group, peptide systhesis resin and the like, wherein trisubstituted silyl group is substituted with $C_1$–$C_6$-alkyl, aryl, or ar-$C_1$–$C_6$-alkyl, or (c) —NH—O—$R^{14}$, where $R^{14}$ is hydrido, a pharmaceutically acceptable cation or C(W)$R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring.

The substituent —N$R^{3a}R^{3b}$ can also be referred to as a $R^3$ group. One exemplary $R^3$ group is —N$(CH_3)_2$, whereas another is the before-discussed substituent group —GAREY that is present in more preferred compounds as is discussed hereinbelow.

One group of more preferred compounds correspond ion structure to formula III, formula IIIA or a pharmaceutically acceptable salt thereof:

III

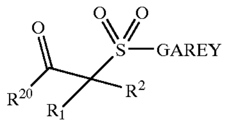

IIIA

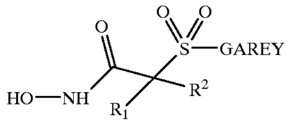

wherein substituents $R^1$, $R^2$, $R^{20}$ and —GAREY are as discussed before, with the before-described preferences.

Yet another more preferred group of contemplated compounds correspond ion structure to formula IV, formula IVA or a pharmaceutically acceptable salt thereof:

IV

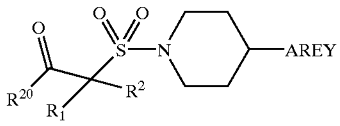

-continued

IVA

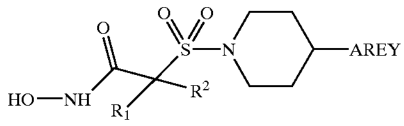

wherein substituents $R^1$, $R^2$, $R^{20}$ and —AREY are as discussed before,with the before-described preferences.

A still more preferred group of contemplated compounds correspond ion structure to formula V, formula VA or a pharmaceutically acceptable salt thereof:

V

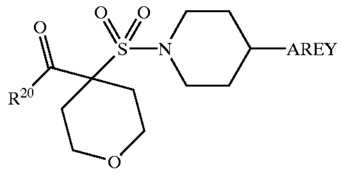

VA

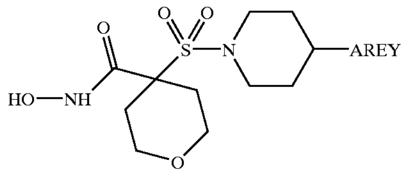

wherein substituents $R^{20}$ and —AREY are as discussed before, with the before-described preferences.

Another more preferred group of contemplated compounds correspond ion structure to formula VI, formula VIA or a pharmaceutically acceptable salt thereof:

VI

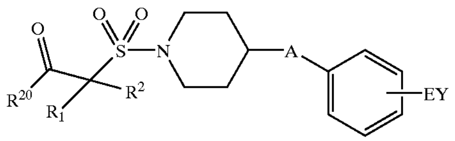

VIA

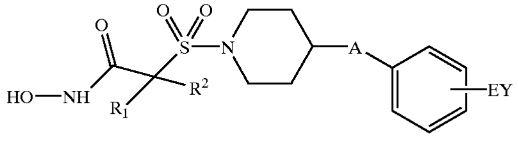

wherein substituents $R^1$, $R^2$, $R^{20}$ and —EY are as discussed before,with the before-described preferences, and A is —$CH_2$—, —O—$CH_2$—, —$CH_2$—C—O—, —S—$CH_2$— or —$CH_2$—S—.

A still more preferred group of contemplated compounds correspond ion structure to formula VII, formula VIIA or a pharmaceutically acceptable salt thereof:

VII

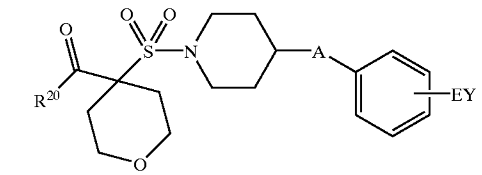

VIIA

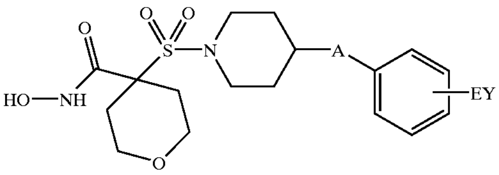

wherein substituents $R^{20}$ and —EY are as discussed before as part of an —AREY or —GAREY group, with the before-described preferences, and A is —$CH_2$—, —O—$CH_2$—, —$CH_2$—O—, —S—$CH_2$— or —$CH_2$—S—.

Another group of preferred compounds for use in a contemplated process has a structure that corresponds to formulas VIII and VIIIA, below, or a pharmaceutically acceptable salt thereof:

VIII

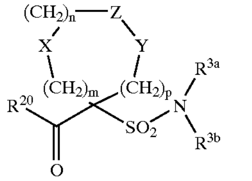

VIIIA

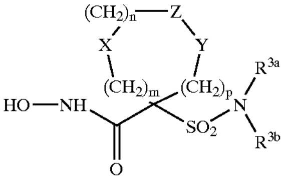

wherein $R^{3a}$, $R^{3b}$ and $R^{20}$ are as defined before, with the before-described preferences; and m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

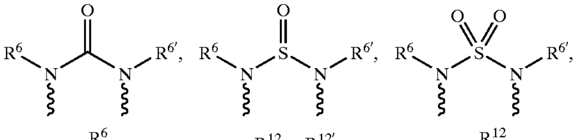
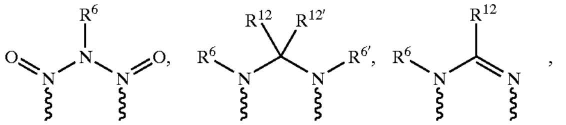
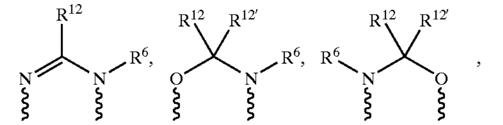
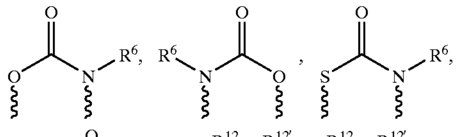
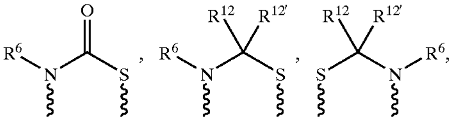
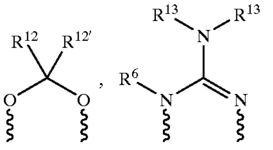

and

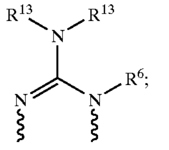

wherein wavy lines are bonds to the atoms of the depicted ring;

$R^6$ and $R^{6'}$ are independently selected from the group consisting of hydrido, $C_1$–$C_6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, an aminocarbonyl wherein the aminocarbonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, hydroxyaminocarbonyl, an aminosulfonyl group wherein the aminosulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, an amino-$C_1$–$C_6$-alkylsulfonyl group wherein the amino-$C_1$–$C_6$-alkylsulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group;

$R^7$ is selected from the group consisting of a arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group.

A compound of formulas VIII and VIIIA thus includes a compound illustrated by formulas V, VA, VII and VIIA discussed above, as well as other compounds of formulas I and II.

A group of particularly preferred compounds of formula VIII and VIIIA correspond in structure to formula IX or IX, below, or a pharmaceutically acceptable salt thereof:

IX

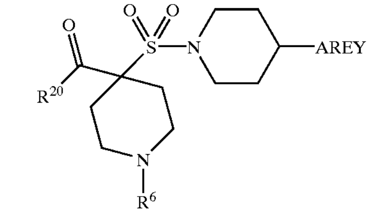

IXA

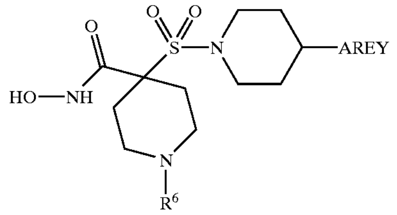

wherein $R^6$, $R^{20}$ and —AREY are as described before, with the before-described preferences.

A still more preferred group of contemplated compounds correspond in structure to formula X, formula XA or a pharmaceutically acceptable salt thereof:

X

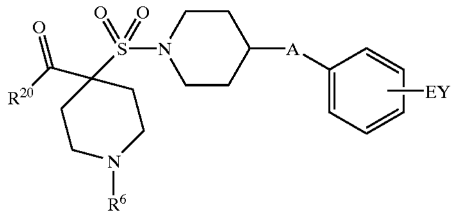

XA

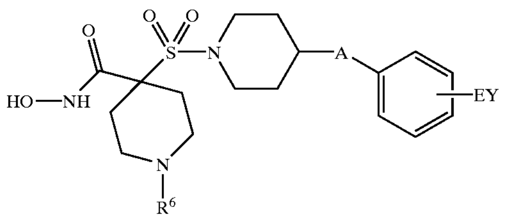

wherein substituents $R^6$, $R^{20}$ and —EY are as discussed before as part of an —AREY or —GAREY group, with the before-described preferences, and wherein A is —$CH_2$—, —O—$CH_2$—, —$CH_2$—O—, —S—$CH_2$— or —$CH_2$—S—.

A group of contemplated compounds that is even still more preferred contain a —$NR^{3a}R^{3b}$ group in which $R^{3a}$ and $R^{3b}$ taken together with the nitrogen atom to which they are bonded form a group —GAREY where G is a disubstituted piperazinyl group correspond in structure to formula XI, formula XIA or a pharmaceutically acceptable salt thereof:

XI

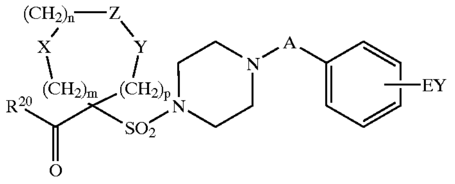

XIA

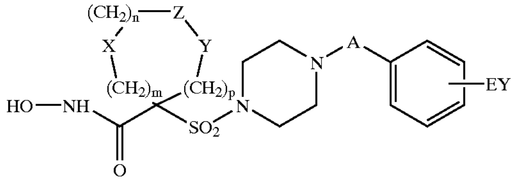

wherein the definitions for X, Y, Z, m, n, p A, E, Y and $R^{20}$ are as before discussed, with the before-described preferences and A being absent.

Without wishing to be bound by theory, it is believed that when substituent A is absent so that R is bonded directly to G, the bond flexibility provided by the non-sulfamido nitrogen of the piperazinyl group, —G—, to the remainder of the —AREY substituent present provides enhanced fit of an inhibitor into the binding pocket of gelatinase and MMP-13 enzymes, while not appreciably altering the binding to MMP-1. It is also believed that similar flexibility and enhanced binding to these enzymes is achieved where —$SO_2G$— is a substituted N-sulfonamidopiperadinyl group and substituent A is a single atom such as —O—, —S—, or —$CH_2$— or —NH—.

Of the compounds of formulas XI and XIA, a compound corresponding in formula to formulas XII or XII, formulas XIIA or XIIIA or a pharmaceutically acceptable salt thereof is yet more preferred,

XII

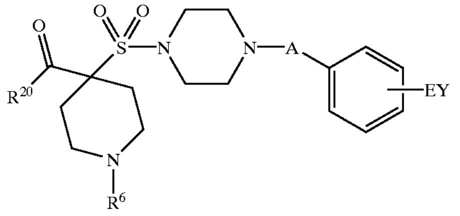

XIIA

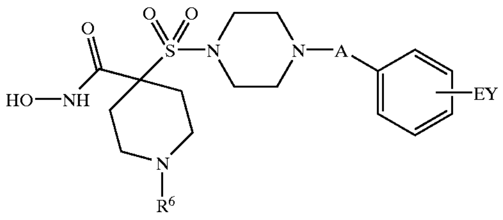

-continued

XIII

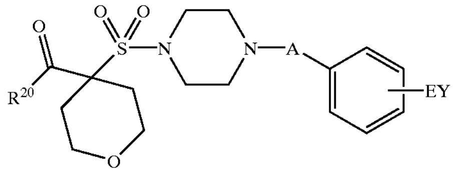

XIIIA

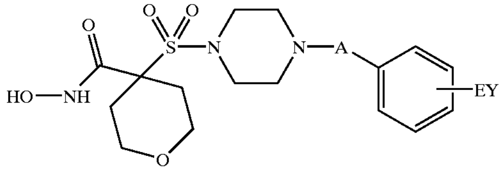

wherein $R^6$, $R^{20}$ and —EY are as described before, with the before-described preferences.

It is particularly preferred that both substituents A and E be absent in a compound of formulas XII, XIII, XIIA and XIIIA so that the substituted phenyl ring, substituent or moiety R, is bonded on one side directly to one nitrogen atom of the piperazinyl ring, and on the other side, that phenyl ring is bonded directly to the Y group.

The structures of several particularly preferred compounds of the above formulas are shown below along with the Example in which the particular compound is synthesized.

EXAMPLE 1

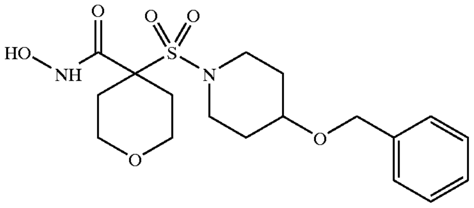

EXAMPLE 3

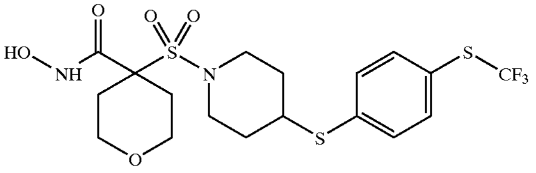

EXAMPLE 2

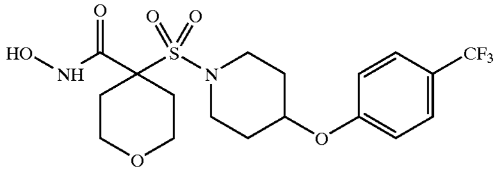

EXAMPLE 2H

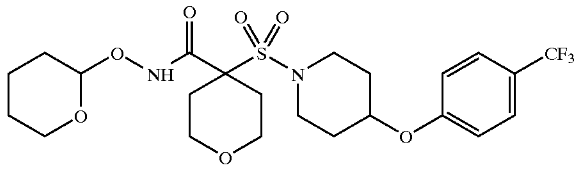

-continued

EXAMPLE 4

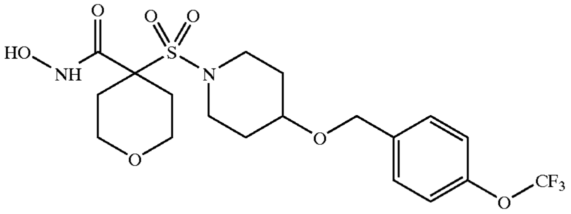

EXAMPLE 5

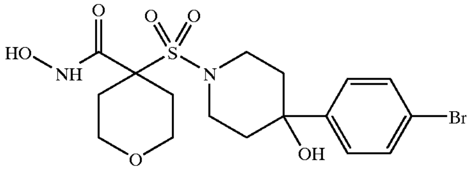

EXAMPLE 6

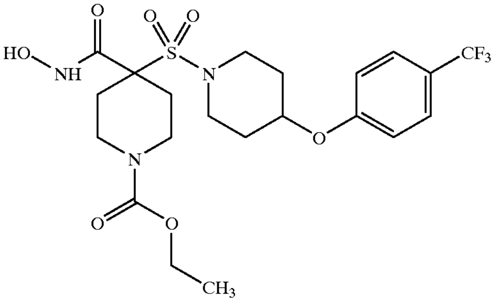

EXAMPLE 6H

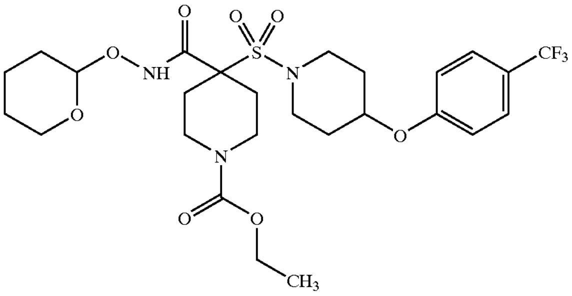

EXAMPLE 7

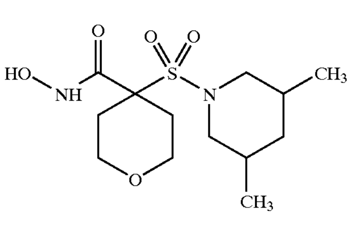

EXAMPLE 8

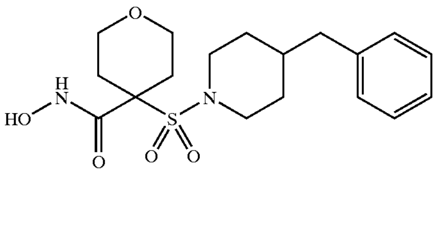

-continued

EXAMPLE 9

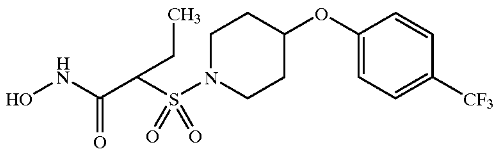

Further particularly preferred compounds include:

4-[(hydroxyamino)-carbonyl)]-4-[[4-[4-(trifluoromethyl)-phenoxy]-1-piperidinyl]sulfonyl]-1-piperidinecarboxylate;

N-hydroxy-2-[[4-[4-(trifluoromethyl)phenoxy]-1-piperidinyl]-sulfonyl]acetamide;

N-[(tetrahydro-2H-pyran-2-yl)oxy]-2-[[4-[4-(trifluoromethyl)phenoxy]-1-piperidinyl]sulfonyl] acetamide;

N-hydroxy-1-(2-methoxyethyl)-4-[[4-[4-(trifluoromethyl)-phenoxy]-1-piperidinyl)sulfonyl]-4-piperidinecarboxamide, monohydrochloride;

1-(2-Methoxyethyl)-N-[(tetrahydro-2H-pyran-2-yl)oxy]-4-[[4-[4-(trifluoromethyl)phenoxy]-1-piperidinyl] sulfonyl]-4-piperidinecarboxamide;

tetrahydro-N-hydroxy-4-[[4-(4-nitrophenoxy)-1-piperidinyl]sulfonyl]-2H-pyran-4-carboxamide;

tetrahydro-N-hydroxy-4-[[4-(4-nitrophenoxy)-1-piperidinyl]sulfonyl]-2H-pyran-4-carboxamide;

N-hydroxy-1-(phenylmethyl)-4-[[4-[4-(trifluoromethoxy)phenoxy]-1-piperidinyl]sulfonyl]-4-piperidinecarboxamide, monohydrochloride;

1-(phenylmethyl)-N-[(tetrahydro-2H-pyran-2-yl)oxy-4-[[4-[4-(trifluoromethoxy)phenoxy]-1-piperidinyl]-sulfonyl]-4-piperidinecarboxylate;

N-hydroxy-1-(2-methoxyethyl)-4-[[4-[4-(trifluoromethoxy)phenoxy]-1-piperidinyl]sulfonyl]-4-piperidinecarboxamide, monohydrochloride;

1-(2-methoxyethyl)-N-[(tetrahydro-2H-pyran-2-yl)oxy]-4-[[4-[4-(trifluoromethoxy)phenoxy]-1-piperidinyl] sulfonyl]-4-piperidinecarboxylate;

N-hydroxy-2-[[4-[4-(trifluoromethoxy)phenoxy]-1-piperidinyl]sulfonyl]acetamide;

N-[(tetrahydro-2H-pyran-2-yl)oxy]-2-[[4-[4-(trifluoromethoxy)phenoxy]-1-piperidinyl]sulfonyl]-acetamide;

tetrahydro-N-hydroxy-4-[[4-[4-(trifluoromethoxy)-phenoxy]-1-piperidinyl]sulfonyl]-2H-pyran-4-carboxamide;

tetrahydro-N-[(tetrahydro-2H-pyran-2-yl)oxy]-4-[[4-[4-(trifluoromethoxy)phenoxy]-1-piperidinyl]sulfonyl]-2H-pyran-4-carboxamide;

N-hydroxy-1-(phenylmethyl)-4-[[4-[4-(trifluoromethyl) phenoxy]-1-piperidinyl]-sulfonyl]-4-piperidinecarboxamide, monohydrochloride;

1-(phenylmethyl)-N-[(tetrahydro-2H-pyran-2-yl)oxy]-4-[[4-[4-(trifluoromethyl)phenoxy]-1-piperidinyl] sulfonyl]-4-piperidinecarboxamide;

N-hydroxy-1-(2-pyridinylmethyl)-4-[[4-[4-(trifluoromethoxy)phenoxy]-1-piperidinyl]sulfonyl]-4-piperidinecarboxamide, monohydrochloride;

1-(2-pyridinylmethyl)-N-[(tetrahydro-2H-pyran-2-yl) oxy]-4-[[4-[4-(trifluoromethoxy)phenoxy]-1-piperidinyl]-sulfonyl]-4-piperidinecarboxamide;

N-hydroxy-1-(2-pyrimidinyl)-4-[[4-[4-(trifluoromethyl)phenoxy]-1-piperidinyl]sulfonyl]-4-piperidinecarboxamide, monohydrochloride;

1-(2-pyrimidinyl)-N-[(tetrahydro-2H-pyran-2-yl)oxy]-4-[[4-[4-(trifluoromethyl)phenoxy]-1-piperidinyl]-sulfonyl]-4-piperidinecarboxamide;

N-hydroxy-4-[[4-[4-(trifluoromethyl)phenoxy]-1-piperidinyl]sulfonyl]-1-[4-(trifluoromethyl)-2-pyrimidinyl]-4-piperidinecarboxamide, monohydrochloride;

N-[(tetrahydro-2H-pyran-2-yl)oxy]-4-[[4-[4-(trifluoromethyl)phenoxy]-1-piperidinyl]sulfonyl]-1-[4-(trifluoromethyl)-2-pyrimidinyl]-4-piperidinecarboxamide;

1-(5-ethyl-2-pyrimidinyl)-N-hydroxy-4-[[4-[4-(trifluoromethyl)phenoxy]-1-piperidinyl]sulfonyl]-4-piperidinecarboxamide, monohydrochloride;

1-(5-ethyl-2-pyrimidinyl)-N-[(tetrahydro-2H-pyran-2-yl)oxy]-4-[[4-[4-(trifluoromethyl)phenoxy]-1-piperidinyl]sulfonyl]-4-piperidinecarboxamide;

tetrahydro-N-hydroxy-4-[[4-[4-(trifluoromethoxy)-phenoxy]-1-piperidinyl]sulfonyl]-2H-thiopyran-4-carboxamide;

tetrahydro-N-hydroxy-4-[[4-[4-(trifluoromethoxy)-phenoxy]-1-piperidinyl]sulfonyl]-2H-thiopyran-4-carboxamide;

tetrahydro-N-hydroxy-4-[[4-[4-(trifluoromethoxy)-phenoxy]-1-piperidinyl]sulfonyl]-2H-thiopyran-4-carboxamide, 1,1-dioxide;

tetrahydro-N-hydroxy-4-[[4-[4-(trifluoromethoxy)-phenoxy]-1-piperidinyl]sulfonyl]-2H-thiopyran-4-carboxamide, 1,1-dioxide;

tetrahydro-N-hydroxy-4-[[4-[4-(trifluoromethyl)-phenoxy]-1-piperidinyl]sulfonyl]-2H-thiopyran-4-carboxamide;

tetrahydro-N-hydroxy-4-[[4-[4-(trifluoromethyl)phenoxy]-1-piperidinyl]sulfonyl]-2H-thiopyran-4-carboxamide;

N-hydroxy-4[[1'-(n-pentyl)[4,4'-bipiperidin]-1-yl]sulfonyl]-tetrahydro-2H-pyran-4-carboxamide;

N-hydroxy-4[[1'-(4-methoxybenzoyl)[4,4'-bipiperidin]-1-yl]sulfonyl]-tetrahydro-2H-pyran-4-carboxamide;

N-hydroxy-4-[[4-(4-(trifluoromethyl)phenoxy]-1-piperidinyl]sulfonyl]-4-piperidinecarboxamide, monohydrochloride;

1-(2-furanylmethyl)-N-hydroxy-4-[[4-[4-(trifluoromethyl)phenoxy]-1-piperidinyl]sulfonyl)-4-piperidinecarboxamide;

4-[[4-[4-[4-(trifluoromethyl)phenoxy]phenoxy]-1-piperidinyl]sulfonyl]tetrahydro-N-hydroxy-2H-pyran-4-carboxamide;

tetrahydro-N-hydroxy-4-[[4-(4-pentylphenyl)-1-piperazinyl]sulfonyl]-2H-pyran-4-carboxamide, monohydrochloride;

tetrahydro-N-hydroxy-4-[(4-phenyl-1-piperazinyl)-sulfonyl]-2H-pyran-4-carboxamide;

N-hydroxy-1-(2-methoxyethyl)-4-[[4-[[4-(trifluoromethyl)benzoyl]amino]-1-piperidinyl]-sulfonyl]-4-piperidinecarboxamide, monohydrochloride;

N-hydroxy-1-phenyl-4-[[4-[4-(trifluoromethoxy)phenoxy]-1-piperidinyl]sulfonyl]-4-piperidinecarboxamide, monohydrochloride;

N-hydroxy-1-phenyl-4-[[4-[4-(trifluoromethyl)phenoxy]-1-piperidinyl]sulfonyl]-4-piperidinecarboxamide, monohydrochloride;

4-[[4-[4-(1,1-dimethylethyl)phenyl]-1-piperazinyl]-sulfonyl]-N-hydroxy-1-(2-methoxyethyl)-4-piperidinecarboxamide, monohydrochloride;

4-[[4-(4-butoxyphenyl)-1-piperazinyl]sulfonyl]-N-hydroxy-1-(2-methoxyethyl)-4-piperidinecarboxamide, dihydrochloride;

tetrahydro-N-hydroxy-4-[[4-[[4-[(trifluoromethyl)-thio]phenyl]-thio]-1-piperidinyl]sulfonyl]-2H-pyran-4-carboxamide;

4-[[4-(4-bromophenyl)-4-fluoro-1-piperidinyl]-sulfonyl]tetrahydro-N-hydroxy-2H-pyran-4-carboxamide;

4-[[4-[4-(3,5-dimethylphenoxy)phenoxy]-1-piperidinyl]sulfonyl]tetrahydro-N-hydroxy-2H-pyran-4-carboxamide;

1-cyclopropyl-N-hydroxy-4-[[4-[4-(trifluoromethyl)phenoxy]-1-piperidinyl]sulfonyl]-4-piperidinecarboxamide, monohydrochloride;

N-hydroxy-1-(iminophenylmethyl)-4-[[4-[4-(trifluoromethyl)phenoxy]-1-piperidinyl]sulfonyl]-4-piperidinecarboxamide, monohydrochloride;

N-hydroxy-1-[(4-hydroxyphenyl)iminomethyl]-4-[[4-[4-(trifluoromethyl)phenoxy]-1-piperidinyl]sulfonyl]-4-piperidinecarboxamide, monohydrochloride;

1-(2-furanylcarbonyl)-N-hydroxy-4-[[4-[4-(trifluoromethyl)phenoxy]-1-piperidinyl]sulfonyl]-4-piperidinecarboxamide;

N-hydroxy-1-[2-(methylthio)-4-pyrimidinyl]-4-[[4-[4-(trifluoromethyl)phenoxy]-1-piperidinyl]sulfonyl]-4-piperidinecarboxamide, monohydrochloride;

1-cyclopropyl-N-hydroxy-4-[[4-[4-(trifluoromethoxy)phenoxy]-1-piperidinyl]sulfonyl]-4-piperidinecarboxamide, monohydrochloride;

N-hydroxy-4-[[1'-(2-methoxyphenyl)[4,4'-bipiperidin]-1-yl]sulfonyl]-1-(phenylmethyl)-4-piperidinecarboxamide, dihydrochloride;

4-(1,4-dioxa-8-azaspiro-[4.5]dec-8-ylsulfonyl)tetrahydro-N-hydroxy-2H-pyran-4-carboxamide;

4-[[4-[[(3R,5R)-rel-3,5-dimethyl-1-piperidinyl]carbonyl]-1-piperidinyl]sulfonyl]tetrahydro-N-hydroxy-2H-pyran-4-carboxamide;

4-[[4-[[(3R,5S)-rel-3,5-dimethyl-1-piperidinyl]-carbonyl]-1-piperidinyl]sulfonyl]tetrahydro-N-hydroxy-2H-pyran-4-carboxamide;

N-hydroxy-1-(4-methylphenyl)-4-[[4-[4-(trifluoromethyl)phenoxy]-1-piperidinyl]sulfonyl]-4-piperidinecarboxamide, monohydrochloride;

N-hydroxy-1-(4-methylphenyl)-4-[[4-[4-(trifluoromethoxy)phenoxy]-1-piperidinyl]-sulfonyl]-4-piperidinecarboxamide, monohydrochloride;

tetrahydro-N-hydroxy-4-[[4-(phenylmethyl)-1-piperazinyl]-sulfonyl]-2H-pyran-4-carboxatide, monohydrochloride;

N-hydroxy-1-(phenylmethyl)-4-[(4-phenyl-1-piperazinyl)sulfonyl]-4-piperidinecarboxamide, bis(trifluoroacetate);

N-hydroxy-1-(phenylmethyl)-4-[(4-phenyl-1-piperazinyl)sulfonyl]-4-piperidinecarboxamide, dihydrochloride; and 4-[[4-(4-butoxy-3-methylphenyl)-1-piperazinyl]sulfonyl]-tetrahydro-N-hydroxy-2H-pyran-4-carboxamide.

Most preferred are compounds or their salts are those of Examples 19, 51, 47, 17, 42, 15, 12, 14, 35, 32, 23, 3, 2, 36, 43, 44, 13, 6, 46,28, 30, 10, 50, 9, 18, 31, 16, 8, 55, 11, 38, 53, 33, 41, 40, 4, 54, 34 and 5.

Table 1 through Table 221, below, illustrate several compounds useful in a process of this invention. Each group of compounds is illustrated by a generic formula, or formulae, followed by a series of preferred moieties or groups that constitute various substituents that can be attached at the position clearly shown in the generic structure. The generic symbols, e.g., $R^1$, $R^2$ and the like, are as shown in the tables and are not necessarily as defined before. This system is well known in the chemical communication arts and is widely used in scientific papers and presentations. For example in Table 1, $R^1$ and $R^2$ groups of the generic structure shown and of formula I are illustrated as being taken together with the carbon to which they are bonded illustrate structural variables that can substitute for the $R^1$ and $R^2$ groups shown in the balance of the table. There are 12 $R^1$ and $R^2$ groups shown that are used to represent, in a non-limiting manner, 12 distinct compounds that can be prepared for use in the invention.

TABLE 1

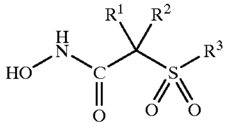

| | |
|---|---|
| 1 | 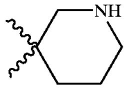 |
| 2 | 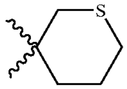 |
| 3 | 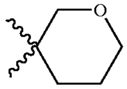 |
| 4 | 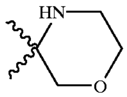 |
| 5 | 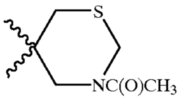 |
| 6 | 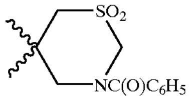 |
| 7 | 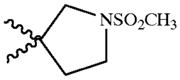 |

TABLE 1-continued

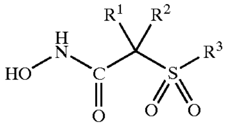

| | |
|---|---|
| 8 | 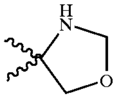 |
| 9 | 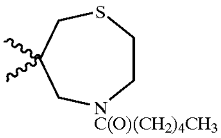 |
| 10 | 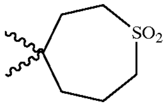 |
| 11 | 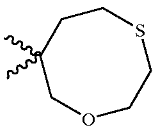 |
| 12 | 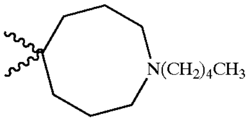 |

TABLE 2

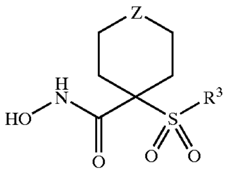

II

| | |
|---|---|
| 1 | 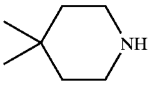 |
| 2 | 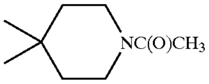 |
| 3 | 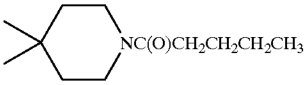 |
| 4 | 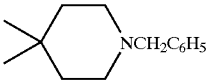 |

TABLE 2-continued
| 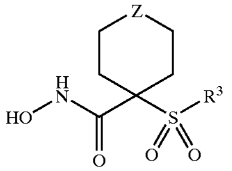<br>II | |
|---|---|
| 5 | 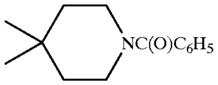 |
| 6 | 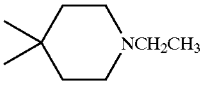 |
| 7 | 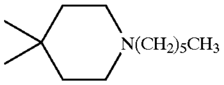 |
| 8 | 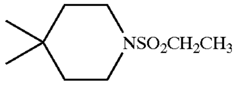 |
| 9 | 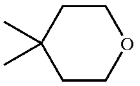 |
| 10 | 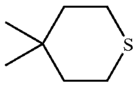 |
| 11 | 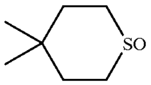 |
| 12 | 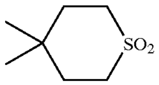 |
TABLE 3
| 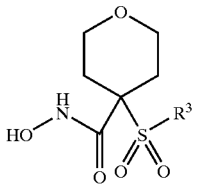<br>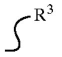 | |
|---|---|
| 1 | 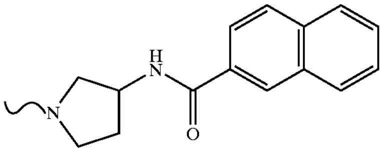 |
TABLE 3-continued
| 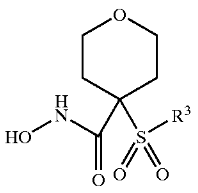<br>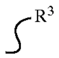 | |
|---|---|
| 2 | 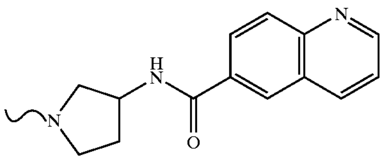 |
| 3 | 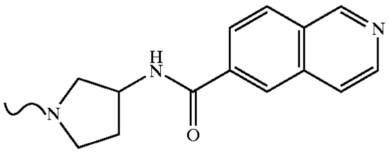 |
| 4 | 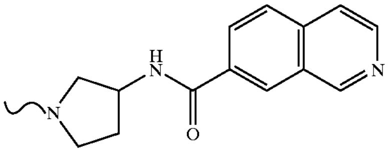 |
| 5 | 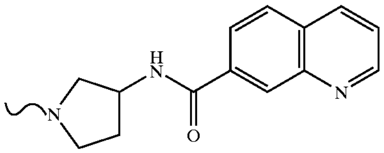 |
| 6 | 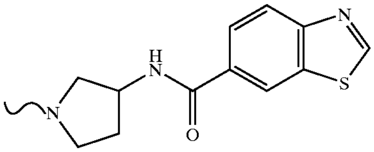 |
| 7 | 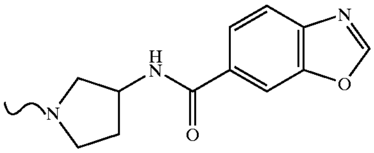 |
| 8 | 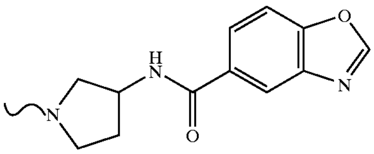 |

TABLE 3-continued
| | 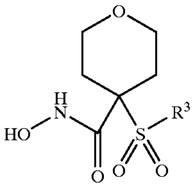 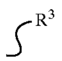 |
|---|---|
| 9 | 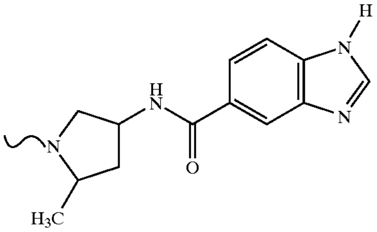 |
| 10 | 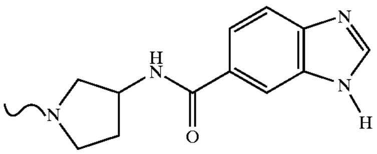 |
| 11 | 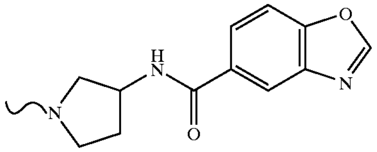 |
| 12 | 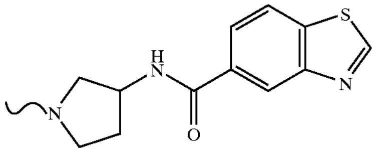 |
| 13 | 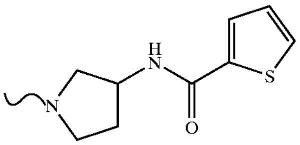 |
| 14 | 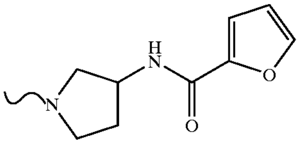 |
| 15 | 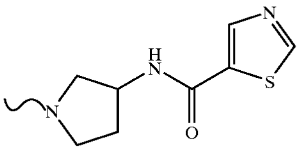 |
TABLE 3-continued
| | 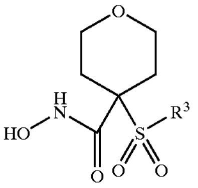 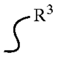 |
|---|---|
| 16 | 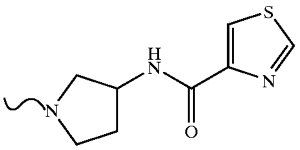 |
| 17 | 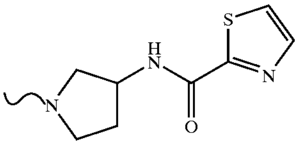 |
| 18 | 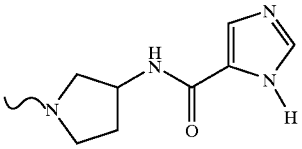 |
TABLE 4
| | 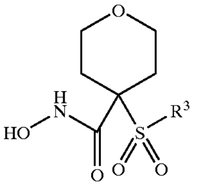 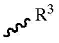 |
|---|---|
| 1 | 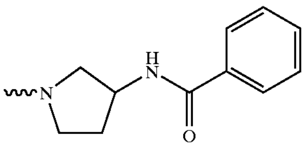 |
| 2 | 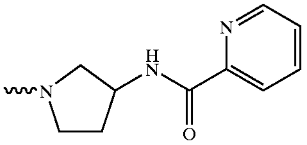 |
| 3 | 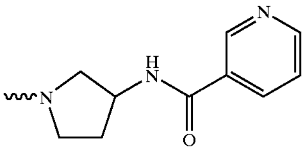 |

TABLE 4-continued
| | |
|---|---|
| | 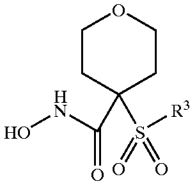 |
| | 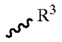 |
| 4 | 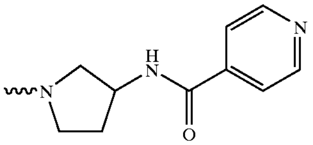 |
| 5 | 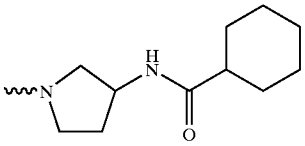 |
| 6 | 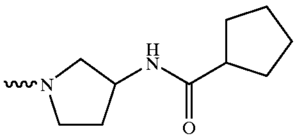 |
| 7 | 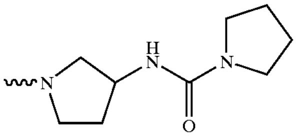 |
| 8 | 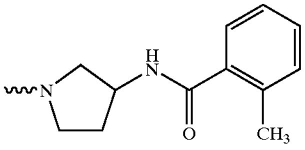 |
| 9 | 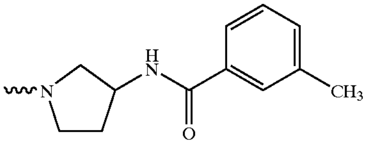 |
| 10 | 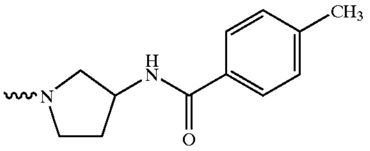 |
| 11 | 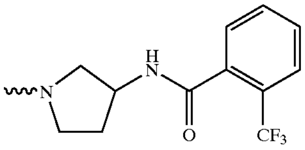 |
TABLE 4-continued
| | |
|---|---|
| | 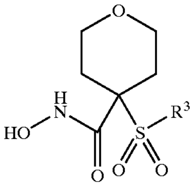 |
| | 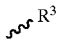 |
| 12 | 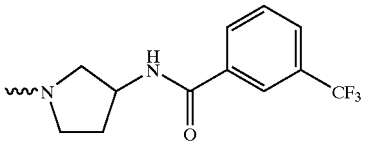 |
| 13 | 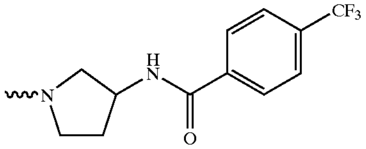 |
| 14 | 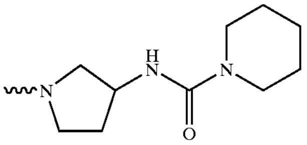 |
| 15 | 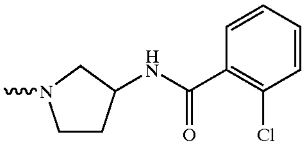 |
| 16 | 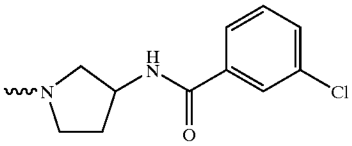 |
| 17 | 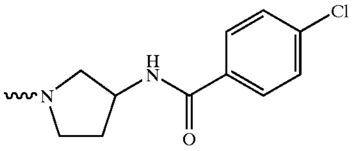 |
| 18 | 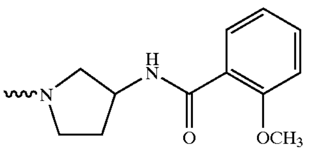 |
| 19 | 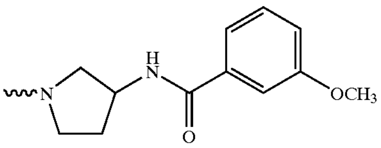 |

TABLE 4-continued
| | |
|---|---|
| | 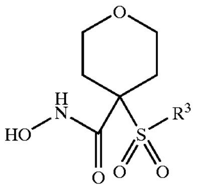 |
| | 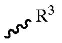 |
| 20 | 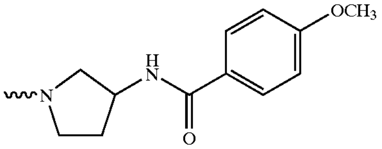 |
| 21 | 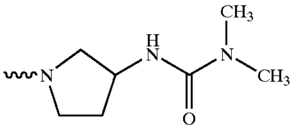 |
TABLE 5
| | |
|---|---|
| | 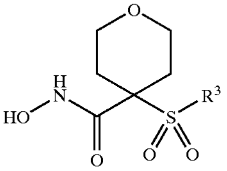 |
| | 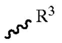 |
| 1 | 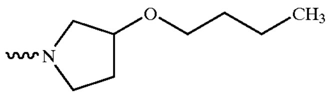 |
| 2 | 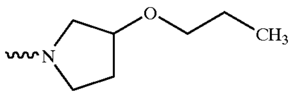 |
| 3 | 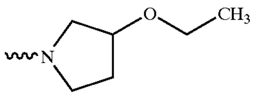 |
| 4 | 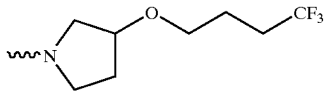 |
| 5 | 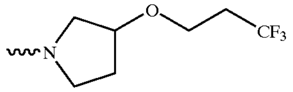 |
| 6 | 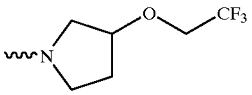 |
TABLE 5-continued
| | |
|---|---|
| | 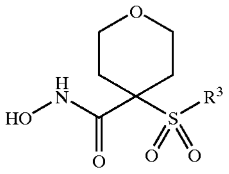 |
| | 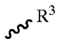 |
| 7 | 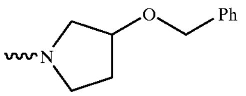 |
| 8 | 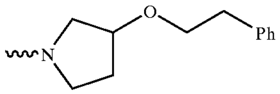 |
| 9 | 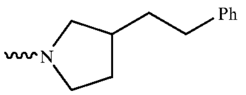 |
| 10 | 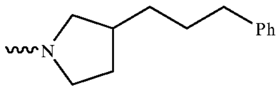 |
| 11 | 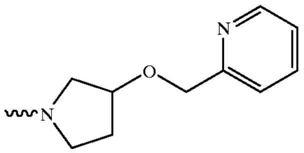 |
| 12 | 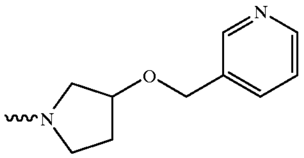 |
| 13 | 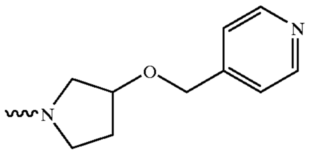 |
| 14 | 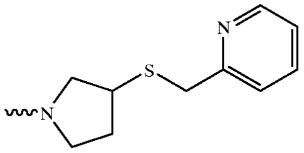 |
| 15 | 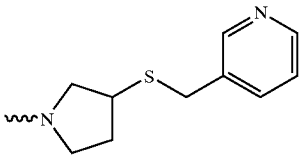 |

TABLE 5-continued
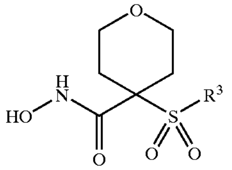
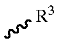
| | |
|---|---|
| 16 | 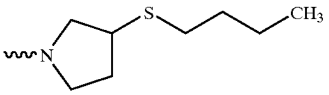 |
| 17 | 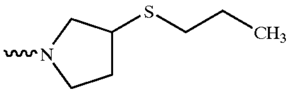 |
| 18 | 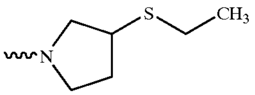 |
| 19 | 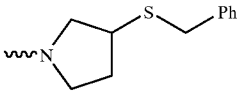 |
| 20 | 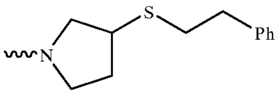 |
| 21 | 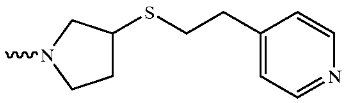 |
| 22 | 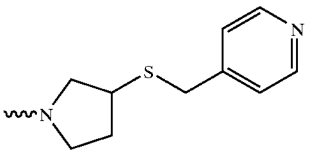 |
TABLE 6
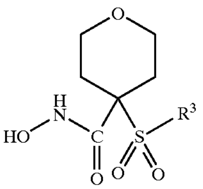
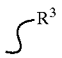
| | |
|---|---|
| 1 | 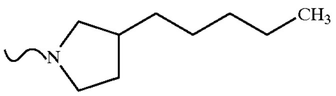 |
TABLE 6-continued
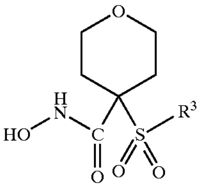
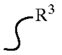
| | |
|---|---|
| 2 | 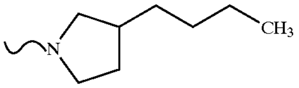 |
| 3 | 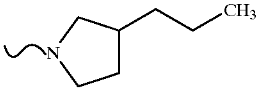 |
| 4 | 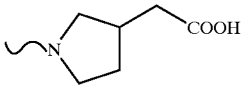 |
| 5 | 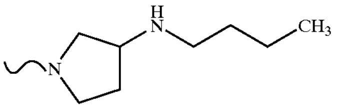 |
| 6 | 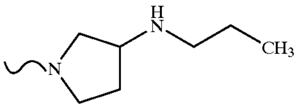 |
| 7 | 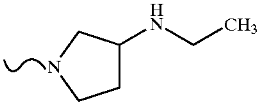 |
| 8 | 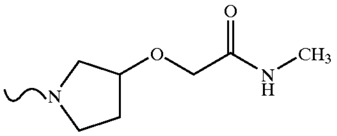 |
| 9 | 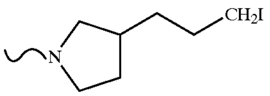 |
| 10 | 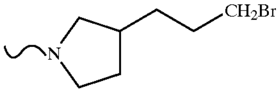 |
| 11 | 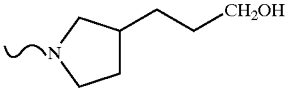 |
| 12 | 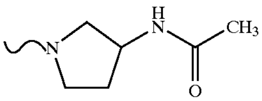 |

TABLE 6-continued
| | 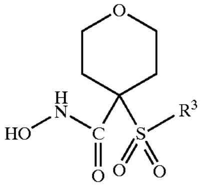 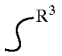 |
|---|---|
| 13 | 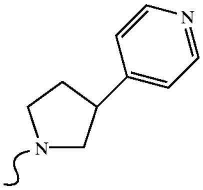 |
| 14 | 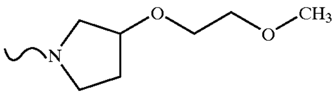 |
| 15 | 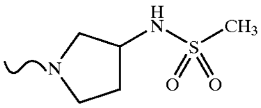 |
| 16 | 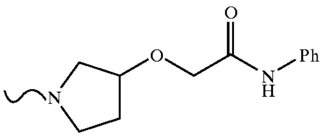 |
| 17 | 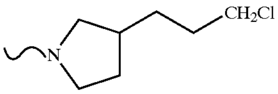 |
| 18 | 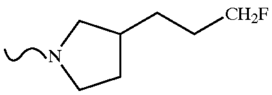 |
| 19 | 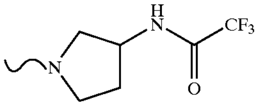 |
| 20 | 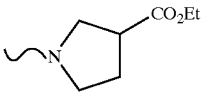 |
| 21 | 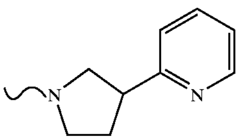 |
| 22 | 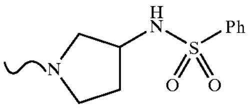 |
TABLE 6-continued
| | 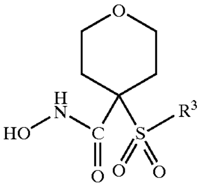 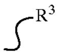 |
|---|---|
| 23 | 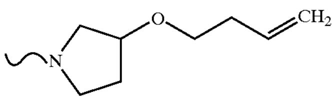 |
| 24 | 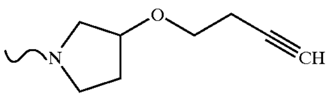 |
| 25 | 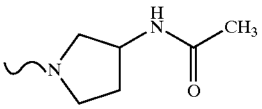 |
| 26 | 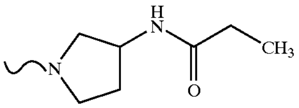 |
| 27 | 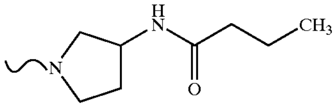 |
| 28 | 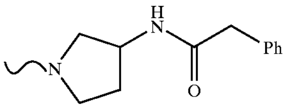 |
| 29 | 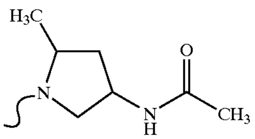 |
| 30 | 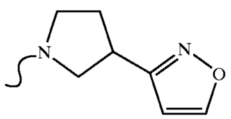 |

TABLE 7
| | 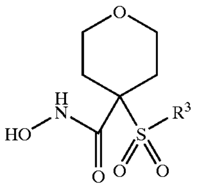<br>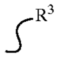 |
|---|---|
| 1 | 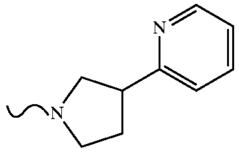 |
| 2 | 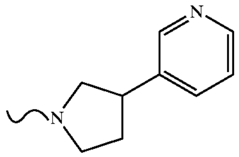 |
| 3 | 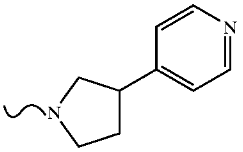 |
| 4 | 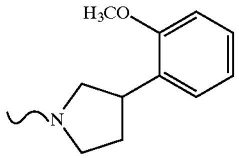 |
| 5 | 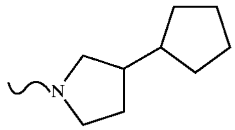 |
| 6 | 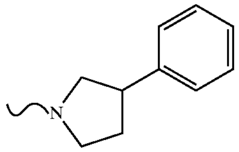 |
| 7 | 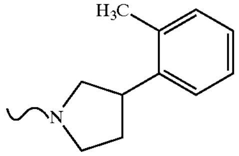 |
TABLE 7-continued
| | 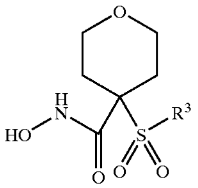<br>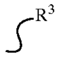 |
|---|---|
| 8 | 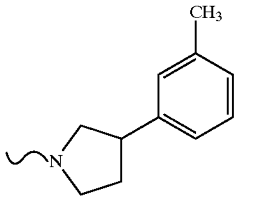 |
| 9 | 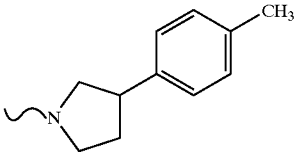 |
| 10 | 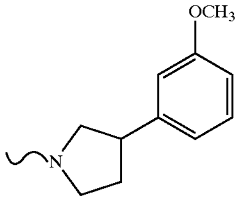 |
| 11 | 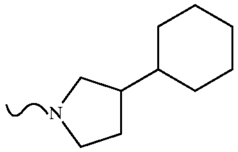 |
| 12 | 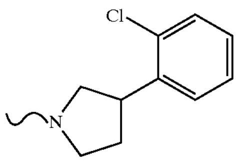 |
| 13 | 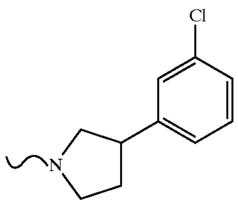 |
| 14 | 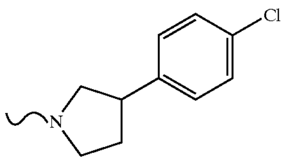 |

TABLE 7-continued
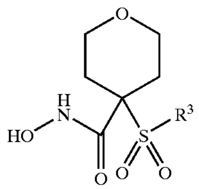
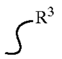
| | |
|---|---|
| 15 | 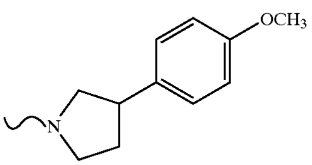 |
| 16 | 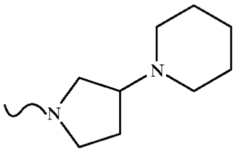 |
| 17 | 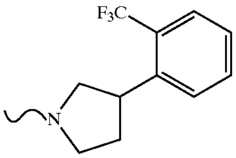 |
| 18 | 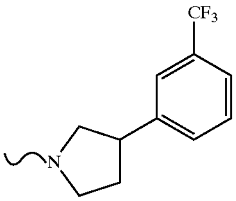 |
| 19 | 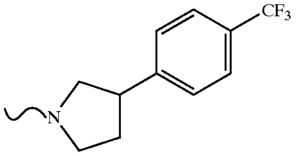 |
| 20 | 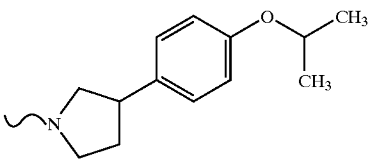 |
| 21 | 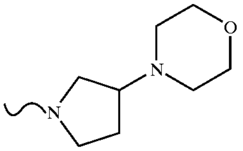 |
TABLE 8
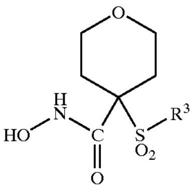
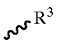
| | |
|---|---|
| 1 | 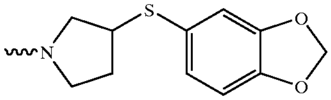 |
| 2 | 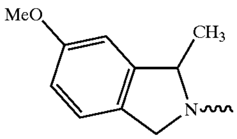 |
| 3 | 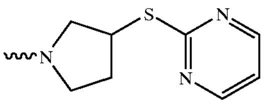 |
| 4 | 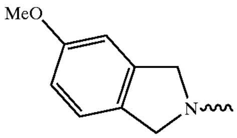 |
| 5 | 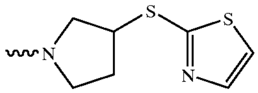 |
| 6 | 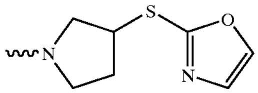 |
| 7 | 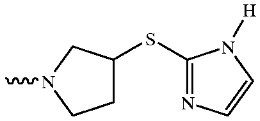 |
| 8 | 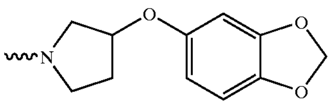 |
| 9 | 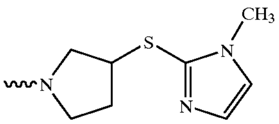 |
| 10 | 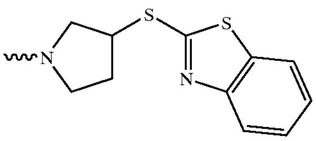 |

TABLE 8-continued
| | 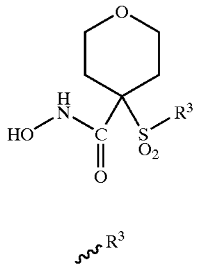 |
|---|---|
| 11 | 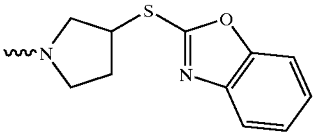 |
TABLE 9
| | 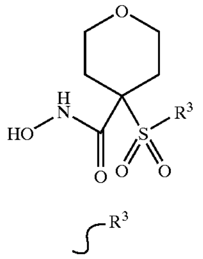 |
|---|---|
| 1 | 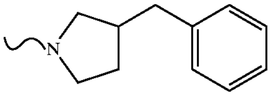 |
| 2 | 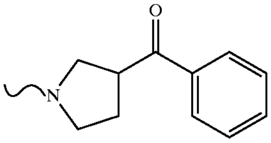 |
| 3 | 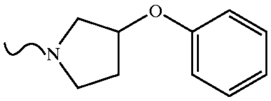 |
| 4 | 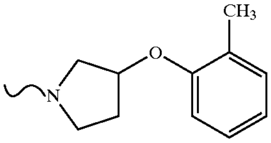 |
| 5 | 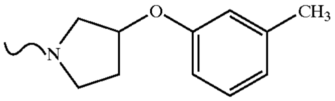 |
| 6 | 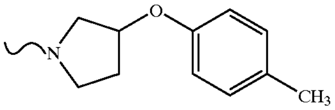 |
TABLE 9-continued
| | 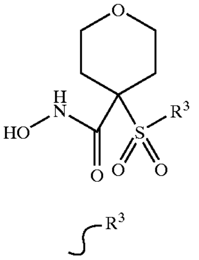 |
|---|---|
| 7 | 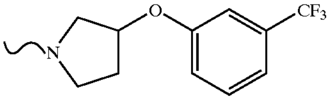 |
| 8 | 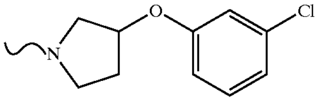 |
| 9 | 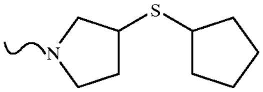 |
| 10 | 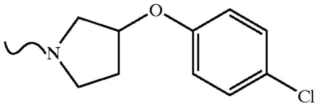 |
| 11 | 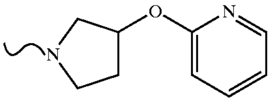 |
| 12 | 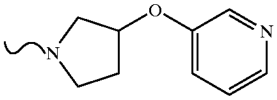 |
| 13 | 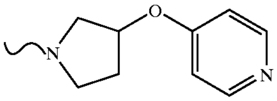 |
| 14 | 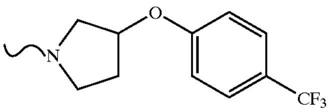 |
| 15 | 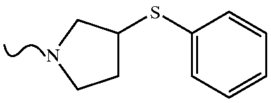 |
| 16 | 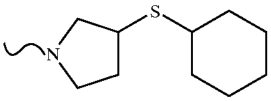 |
| 17 | 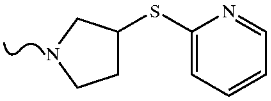 |

TABLE 9-continued
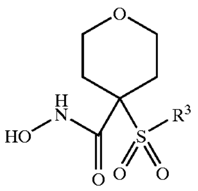
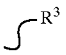
18 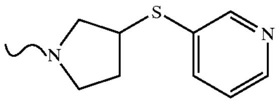
19 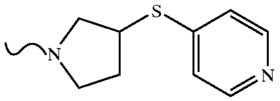
20 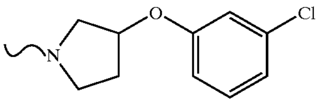
21 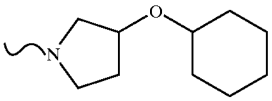
TABLE 10
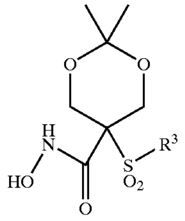
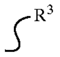
1 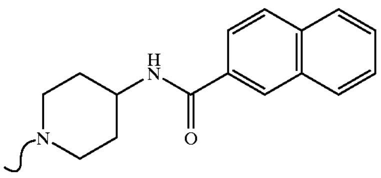
2 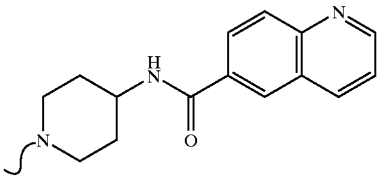
TABLE 10-continued
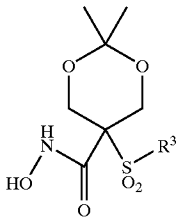
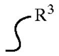
3 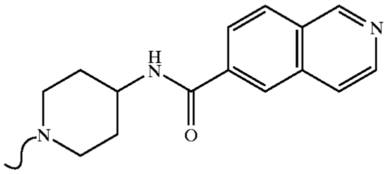
4 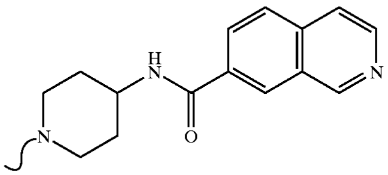
5 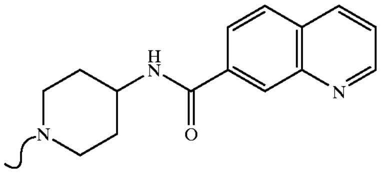
6 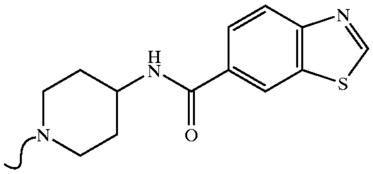
7 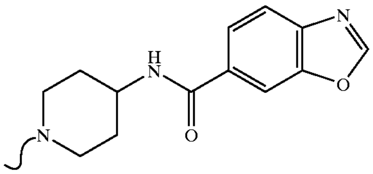
8 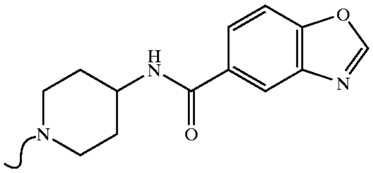

TABLE 10-continued
| | |
|---|---|
| | 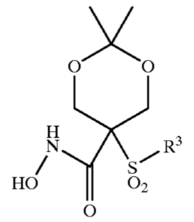 |
| | 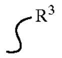 |
| 9 | 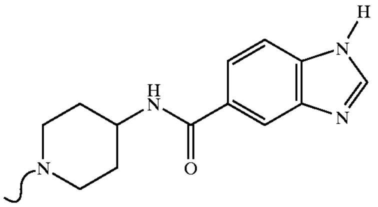 |
| 10 | 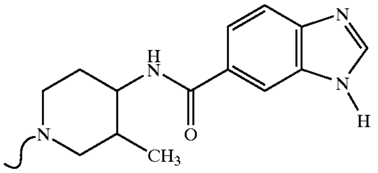 |
| 11 | 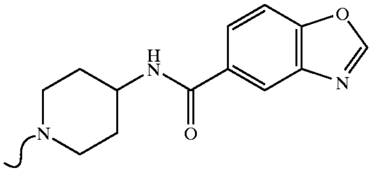 |
| 12 | 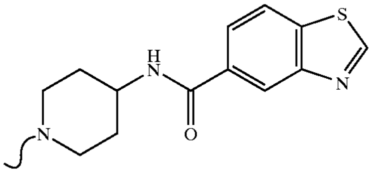 |
| 13 | 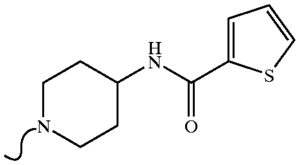 |
| 14 | 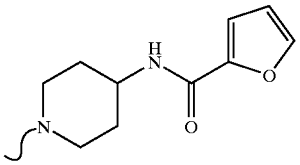 |
| 15 | 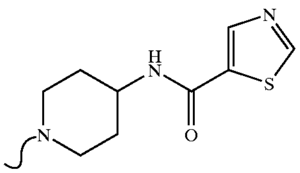 |
TABLE 10-continued
| | |
|---|---|
| | 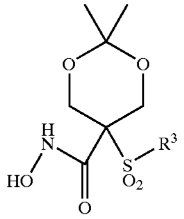 |
| | 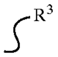 |
| 16 | 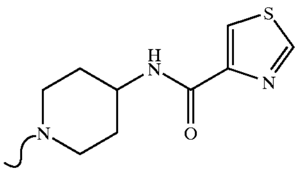 |
| 17 | 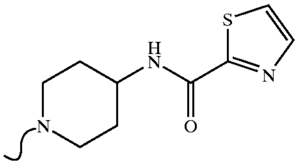 |
| 18 | 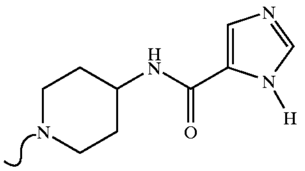 |
TABLE 11
| | |
|---|---|
| | 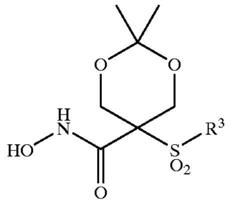 |
| | 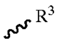 |
| 1 | 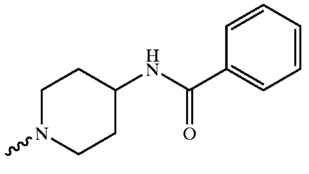 |
| 2 | 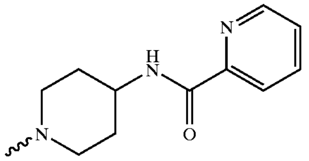 |

TABLE 11-continued
| | |
|---|---|
| | 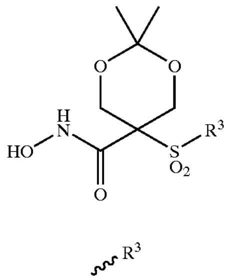 |
| 3 | 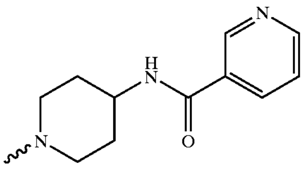 |
| 4 | 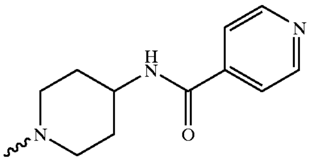 |
| 5 | 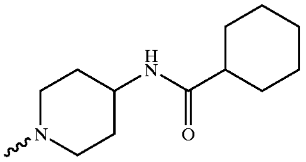 |
| 6 | 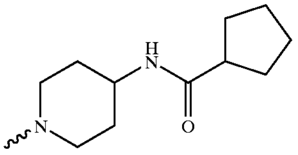 |
| 7 | 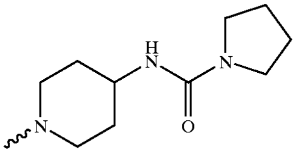 |
| 8 | 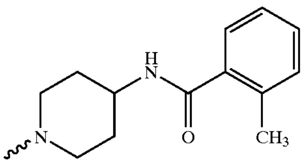 |
| 9 | 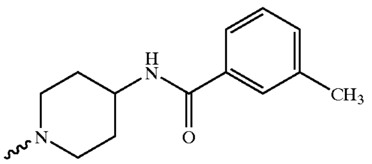 |
TABLE 11-continued
| | |
|---|---|
| | 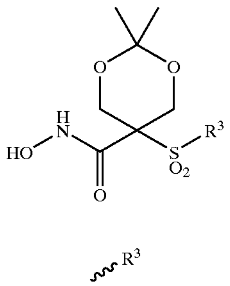 |
| 10 | 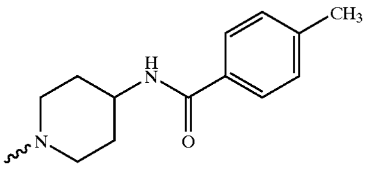 |
| 11 | 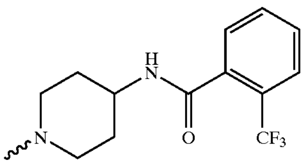 |
| 12 | 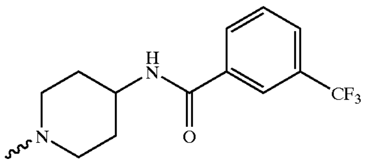 |
| 13 | 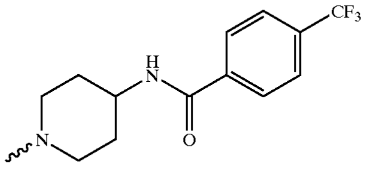 |
| 14 | 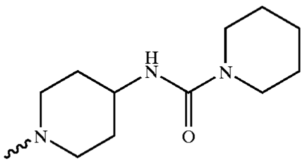 |
| 15 | 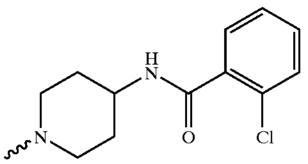 |

TABLE 11-continued
| | |
|---|---|
| | 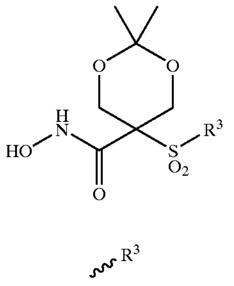 |
| 16 | 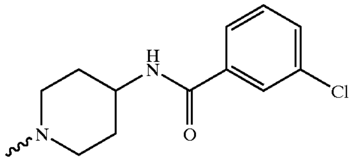 |
| 17 | 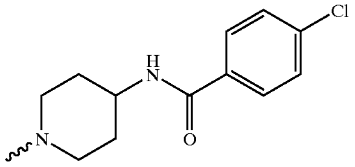 |
| 18 | 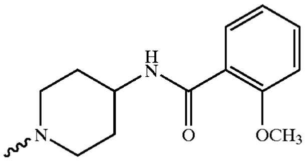 |
| 19 | 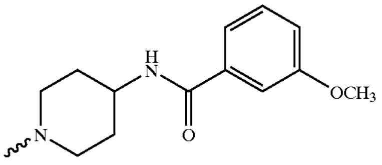 |
| 20 | 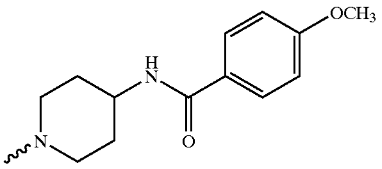 |
| 21 | 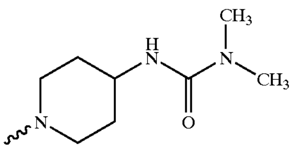 |
TABLE 12
| | |
|---|---|
| | 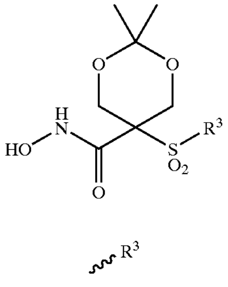 |
| 1 | 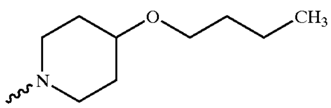 |
| 2 | 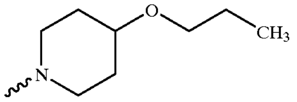 |
| 3 | 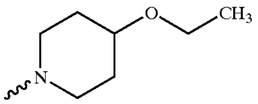 |
| 4 | 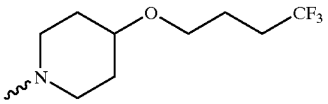 |
| 5 | 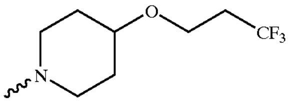 |
| 6 | 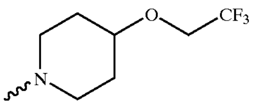 |
| 7 | 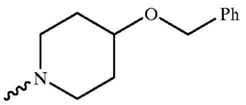 |
| 8 | 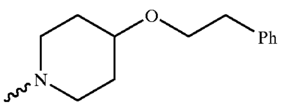 |
| 9 | 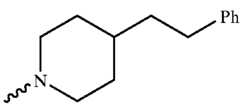 |
| 10 | 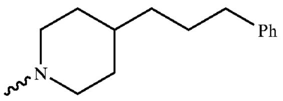 |

TABLE 12-continued
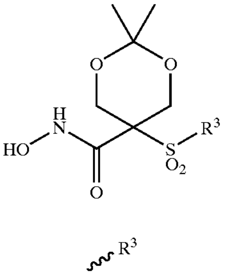
| | |
|---|---|
| 11 | 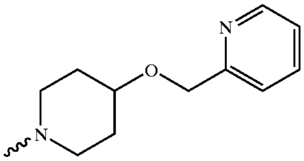 |
| 12 | 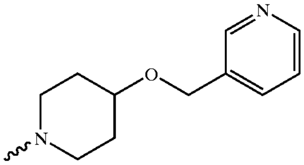 |
| 13 | 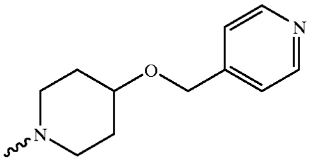 |
| 14 | 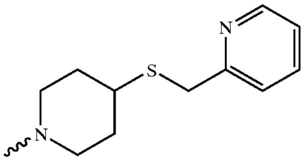 |
| 15 | 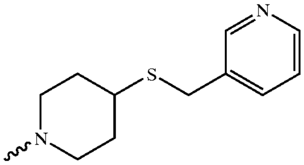 |
| 16 | 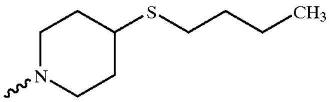 |
| 17 | 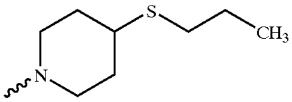 |
| 18 | 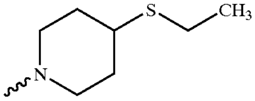 |
TABLE 12-continued
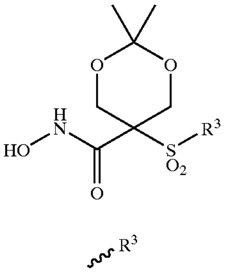
| | |
|---|---|
| 19 | 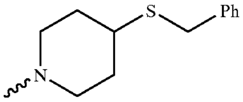 |
| 20 | 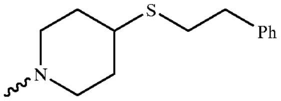 |
| 21 | 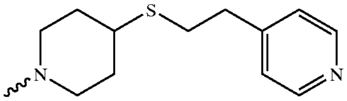 |
| 22 | 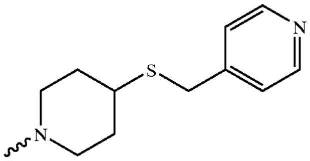 |
TABLE 13
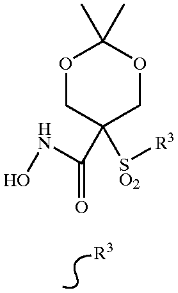
| | |
|---|---|
| 1 | 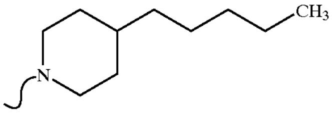 |
| 2 | 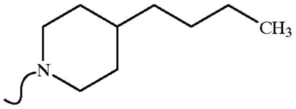 |
| 3 | 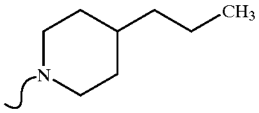 |

TABLE 13-continued
| 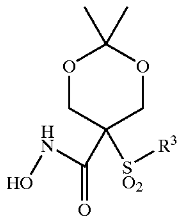 |  |
|---|---|
| 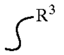 |  |
| 4 | 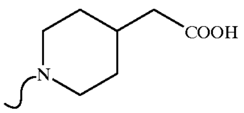 |
| 5 | 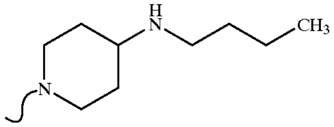 |
| 6 | 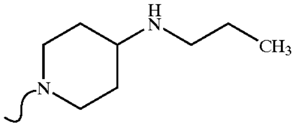 |
| 7 | 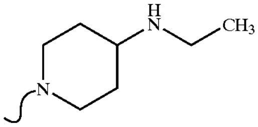 |
| 8 | 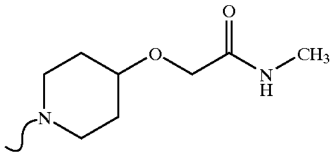 |
| 9 | 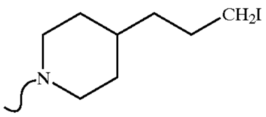 |
| 10 | 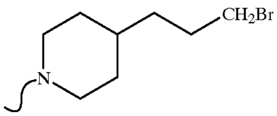 |
| 11 | 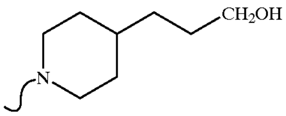 |
| 12 | 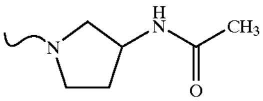 |
TABLE 13-continued
| 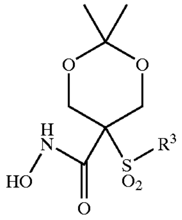 |  |
|---|---|
| 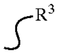 |  |
| 13 | 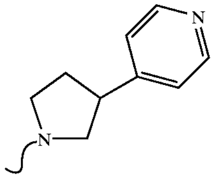 |
| 14 | 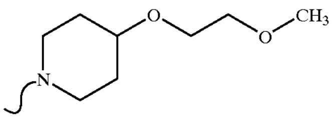 |
| 15 | 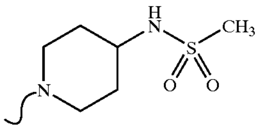 |
| 16 | 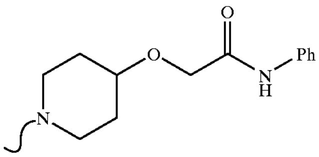 |
| 17 | 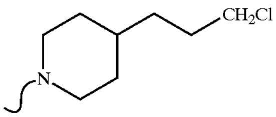 |
| 18 | 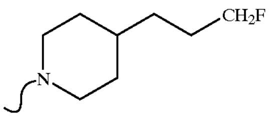 |
| 19 | 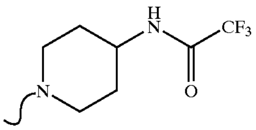 |
| 20 | 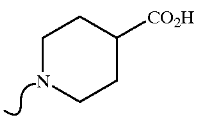 |
| 21 | 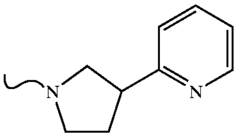 |

TABLE 13-continued
| | |
|---|---|
| | 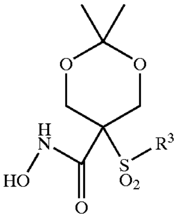 |
| | 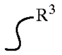 |
| 22 | 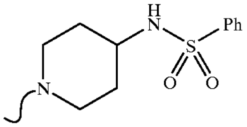 |
| 23 | 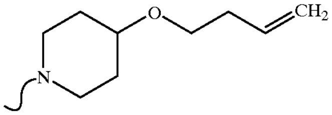 |
| 24 | 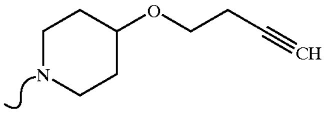 |
| 25 | 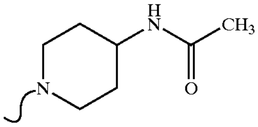 |
| 26 | 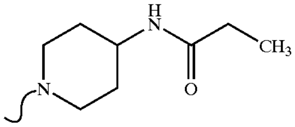 |
| 27 | 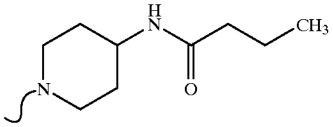 |
| 28 | 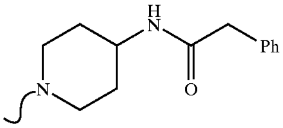 |
| 29 | 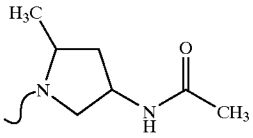 |
| 30 | 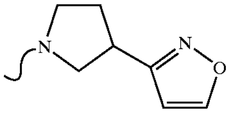 |
TABLE 13-continued
| | |
|---|---|
| | 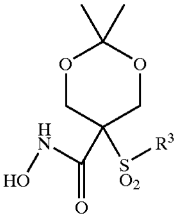 |
| | 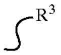 |
| 31 | 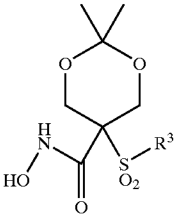 |
TABLE 14
| | |
|---|---|
| | 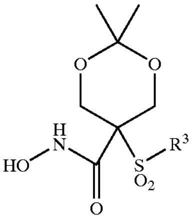 |
| | 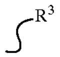 |
| 1 | 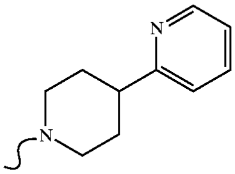 |
| 2 | 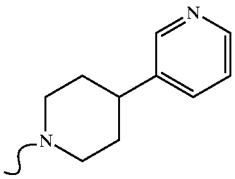 |
| 3 | 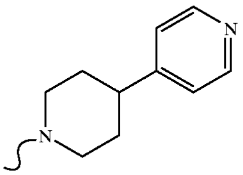 |

TABLE 14-continued
| | |
|---|---|
| | 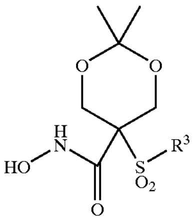 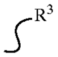 |
| 4 | 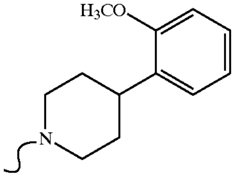 |
| 5 | 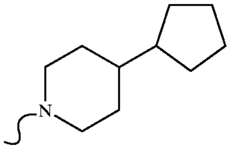 |
| 6 | 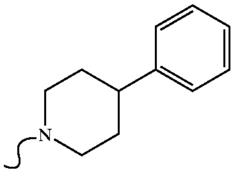 |
| 7 | 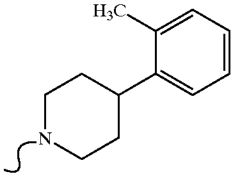 |
| 8 | 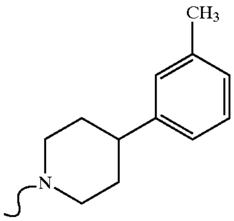 |
| 9 | 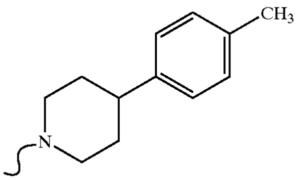 |
TABLE 14-continued
| | |
|---|---|
| | 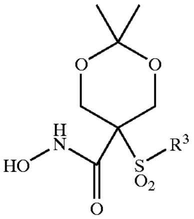 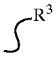 |
| 10 | 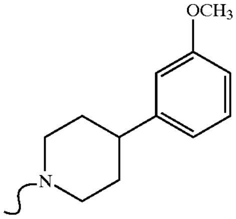 |
| 11 | 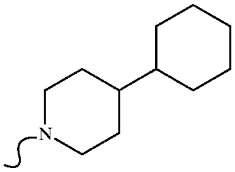 |
| 12 | 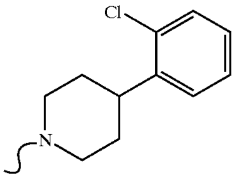 |
| 13 | 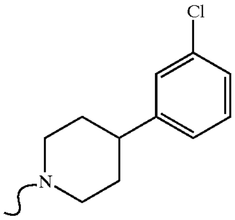 |
| 14 | 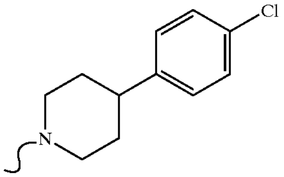 |
| 15 | 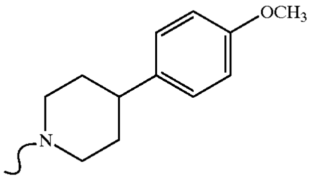 |

TABLE 14-continued
| | 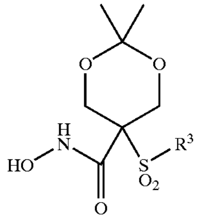 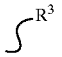 |
|---|---|
| 16 | 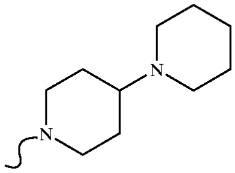 |
| 17 | 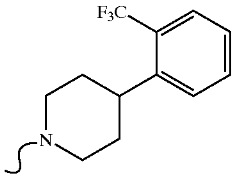 |
| 18 | 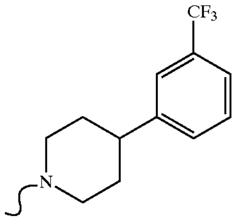 |
| 19 | 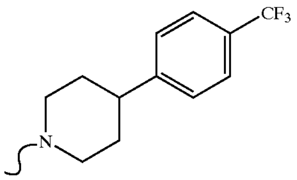 |
| 20 | 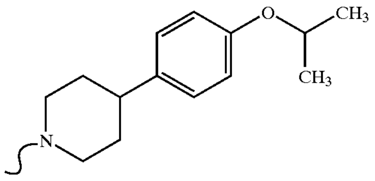 |
| 21 | 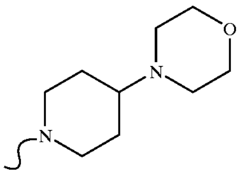 |
TABLE 15
| | 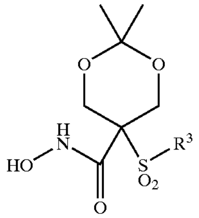 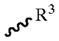 |
|---|---|
| 1 | 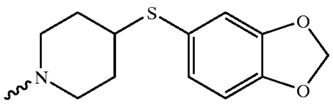 |
| 2 | 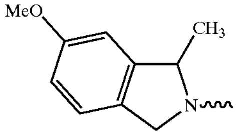 |
| 3 | 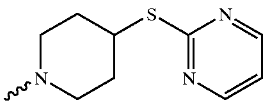 |
| 4 | 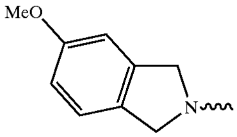 |
| 5 | 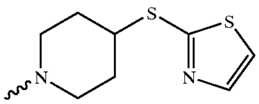 |
| 6 | 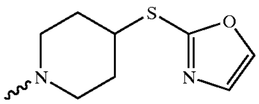 |
| 7 | 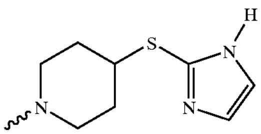 |
| 8 | 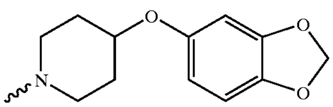 |
| 9 | 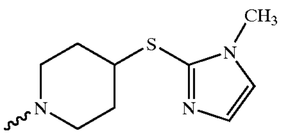 |

TABLE 15-continued
| | |
|---|---|
| | 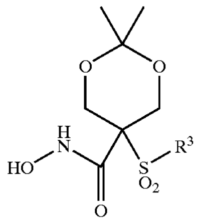 |
| | 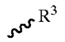 |
| 10 | 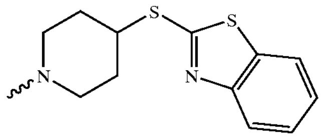 |
| 11 | 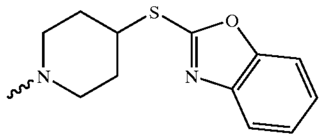 |
TABLE 16
| | |
|---|---|
| | 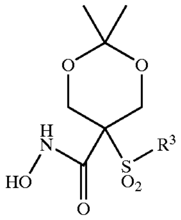 |
| | 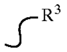 |
| 1 | 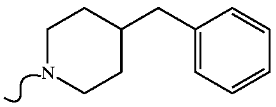 |
| 2 | 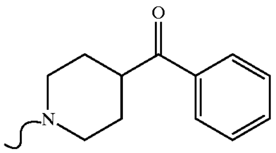 |
| 3 | 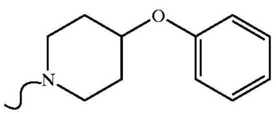 |
| 4 | 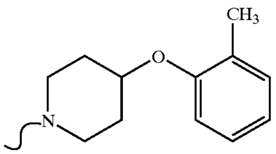 |
TABLE 16-continued
| | |
|---|---|
| | 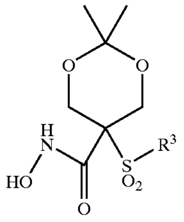 |
| | 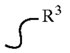 |
| 5 | 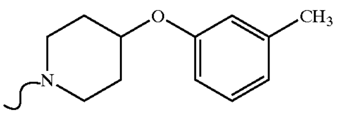 |
| 6 | 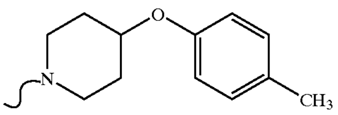 |
| 7 | 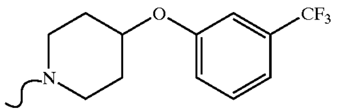 |
| 8 | 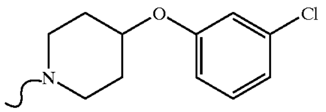 |
| 9 | 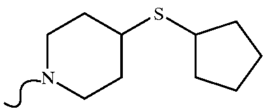 |
| 10 | 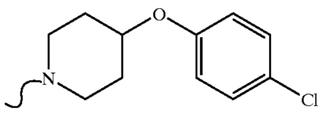 |
| 11 | 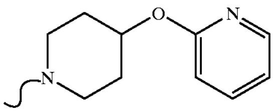 |
| 12 | 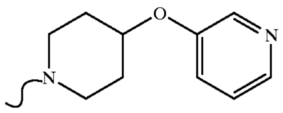 |
| 13 | 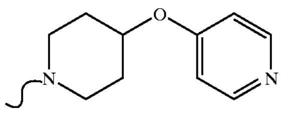 |
| 14 | 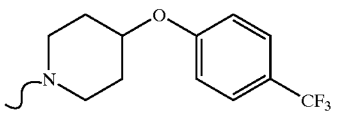 |

TABLE 16-continued
| 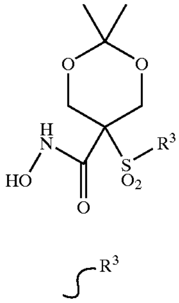 | |
|---|---|
| 15 | 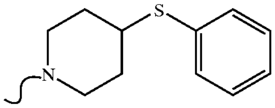 |
| 16 | 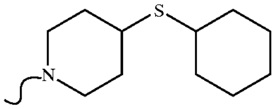 |
| 17 | 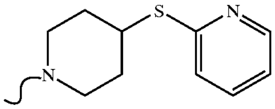 |
| 18 | 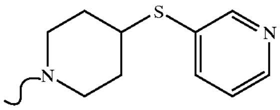 |
| 19 | 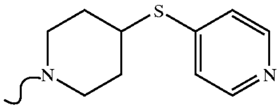 |
| 20 | 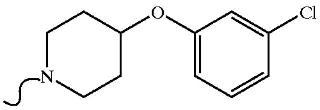 |
| 21 | 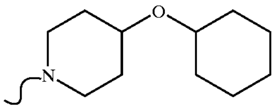 |
TABLE 17
| 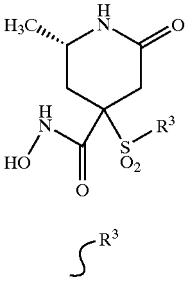 | |
|---|---|
| 1 | 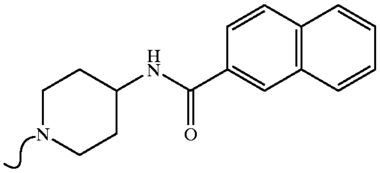 |
| 2 | 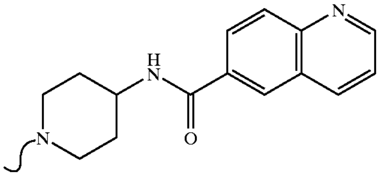 |
| 3 | 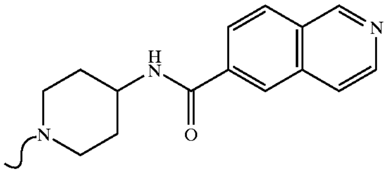 |
| 4 | 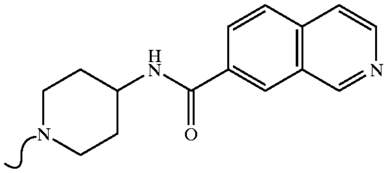 |
| 5 | 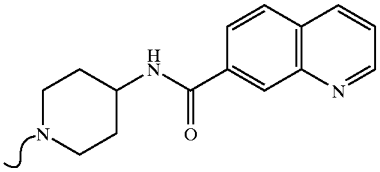 |
| 6 | 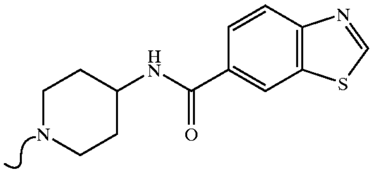 |
| 7 | 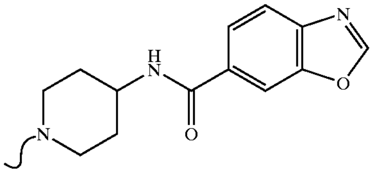 |

TABLE 17-continued
| | |
|---|---|
| 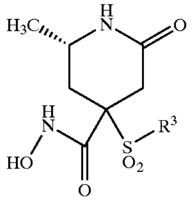 | |
| 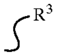 | |
| 8 | 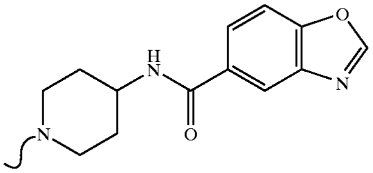 |
| 9 | 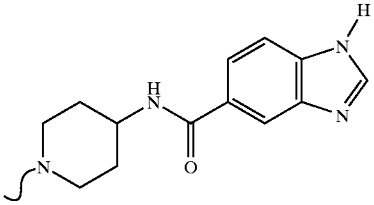 |
| 10 | 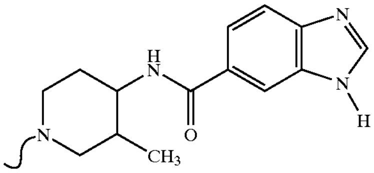 |
| 11 | 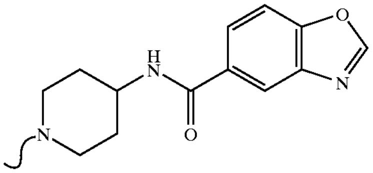 |
| 12 | 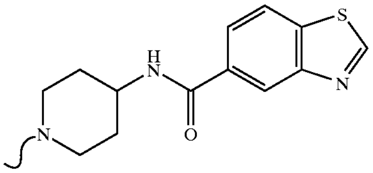 |
| 13 | 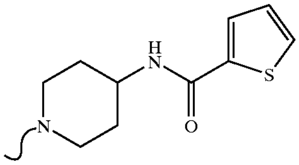 |
| 14 | 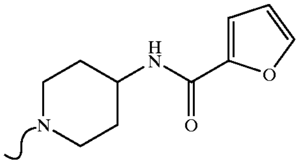 |
TABLE 17-continued
| | |
|---|---|
| 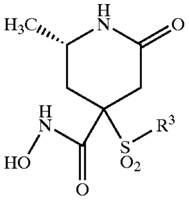 | |
| 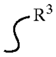 | |
| 15 | 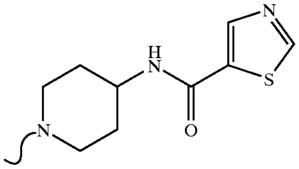 |
| 16 | 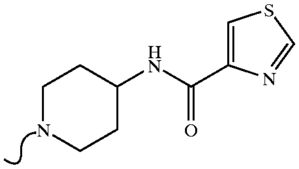 |
| 17 | 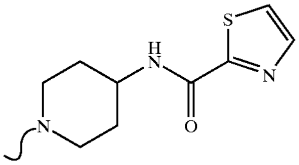 |
| 18 | 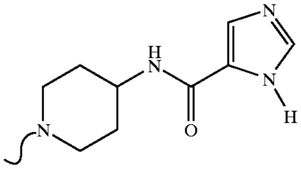 |
TABLE 18
| | |
|---|---|
| 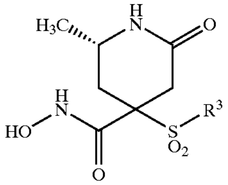 | |
| 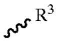 | |
| 1 | 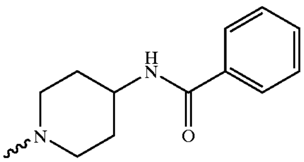 |

TABLE 18-continued
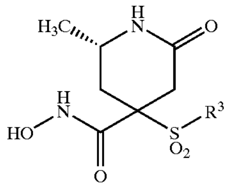
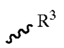
| | |
|---|---|
| 2 | 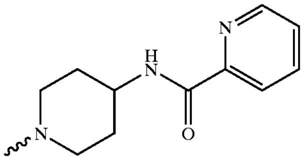 |
| 3 | 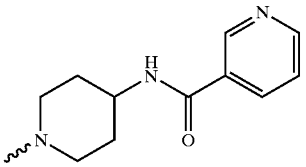 |
| 4 | 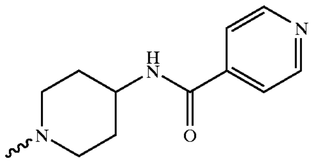 |
| 5 | 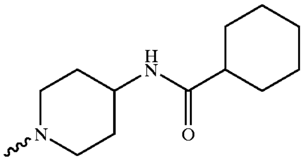 |
| 6 | 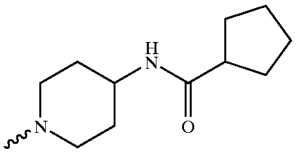 |
| 7 | 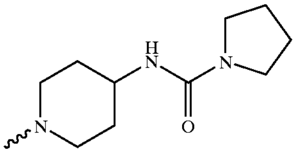 |
| 8 | 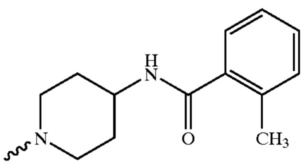 |
TABLE 18-continued
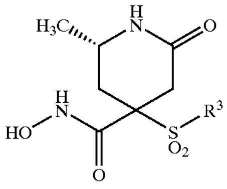
| | |
|---|---|
| 9 | 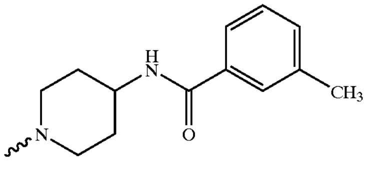 |
| 10 | 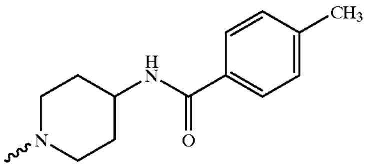 |
| 11 | 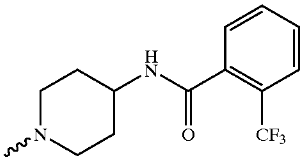 |
| 12 | 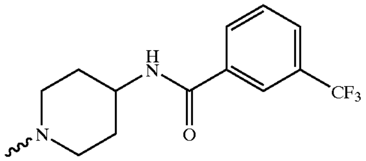 |
| 13 | 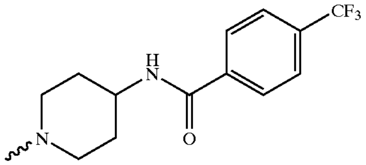 |
| 14 | 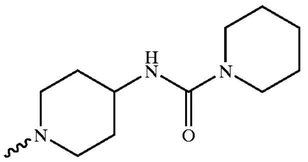 |
| 15 | 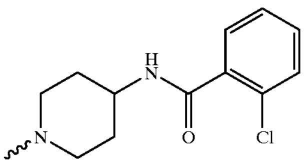 |

TABLE 18-continued
| | |
|---|---|
| | 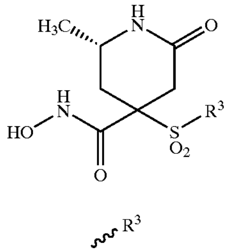 |
| 16 | 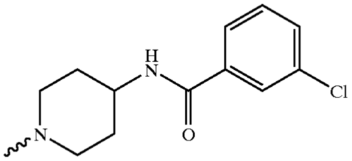 |
| 17 | 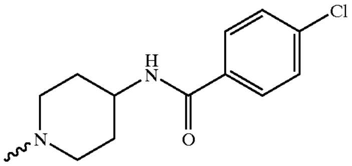 |
| 18 | 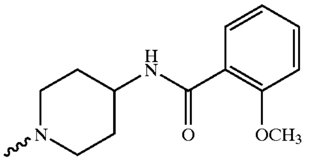 |
| 19 | 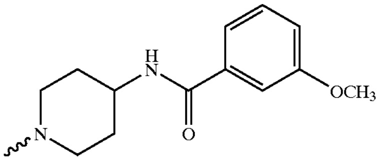 |
| 20 | 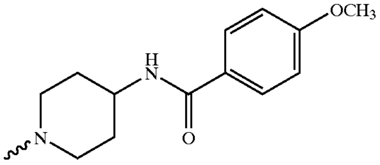 |
| 21 | 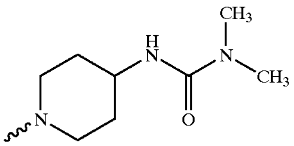 |
TABLE 19
| | |
|---|---|
| | 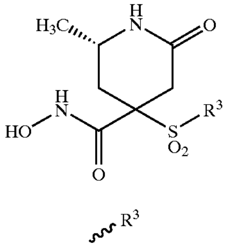 |
| 1 | 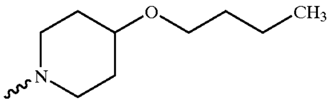 |
| 2 | 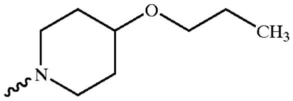 |
| 3 | 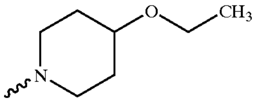 |
| 4 | 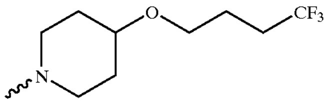 |
| 5 | 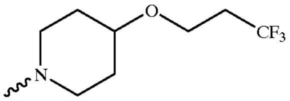 |
| 6 | 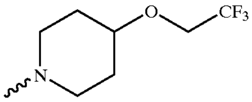 |
| 7 | 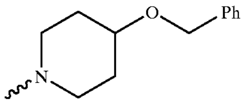 |
| 8 | 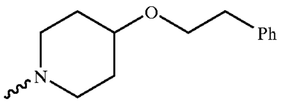 |
| 9 | 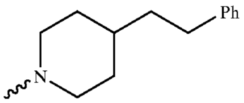 |
| 10 | 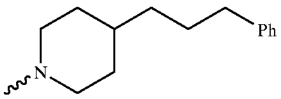 |
| 11 | 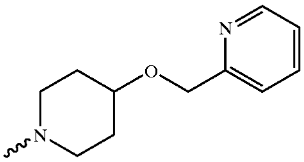 |

TABLE 19-continued
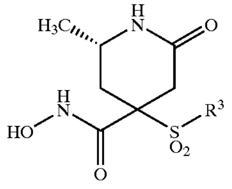
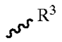
| | |
|---|---|
| 12 | 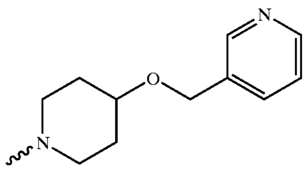 |
| 13 | 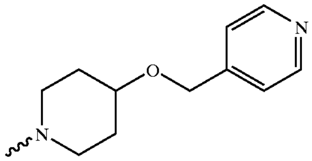 |
| 14 | 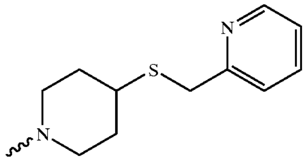 |
| 15 | 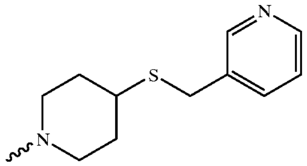 |
| 16 | 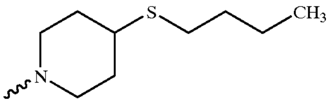 |
| 17 | 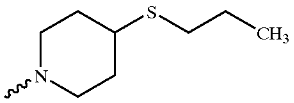 |
| 18 | 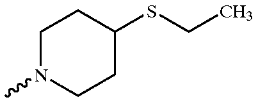 |
| 19 | 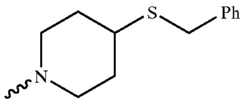 |
| 20 | 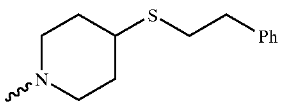 |
TABLE 19-continued
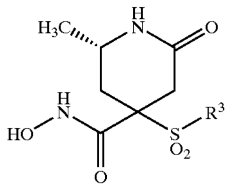
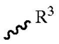
| | |
|---|---|
| 21 | 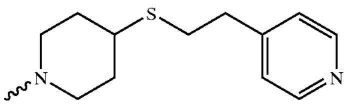 |
| 22 | 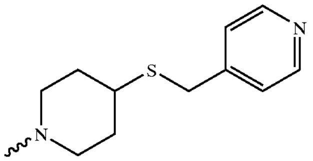 |
TABLE 20
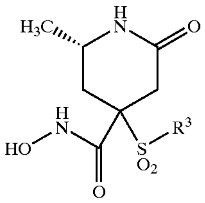
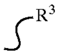
| | |
|---|---|
| 1 | 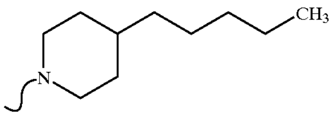 |
| 2 | 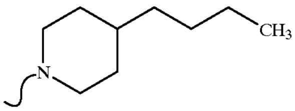 |
| 3 | 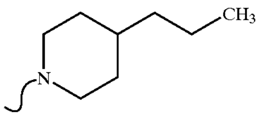 |
| 4 | 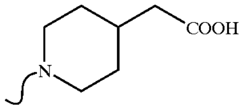 |
| 5 | 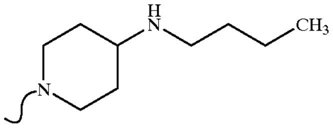 |

TABLE 20-continued
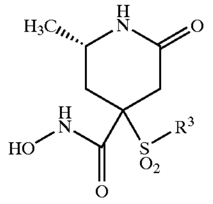
| | |
|---|---|
| | 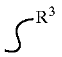 |
| 6 | 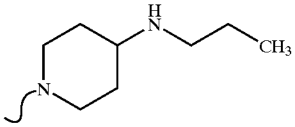 |
| 7 | 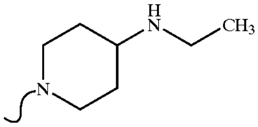 |
| 8 | 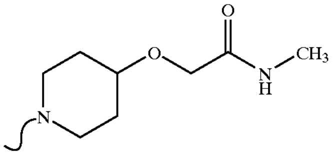 |
| 9 | 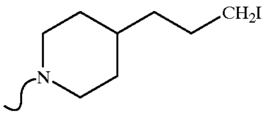 |
| 10 | 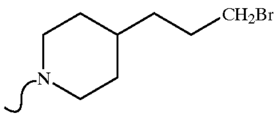 |
| 11 | 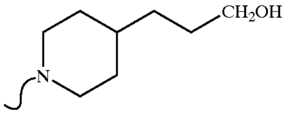 |
| 12 | 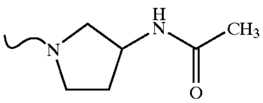 |
| 13 | 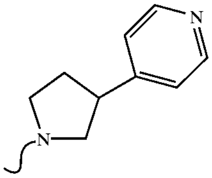 |
| 14 | 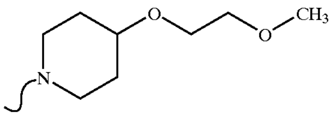 |
TABLE 20-continued
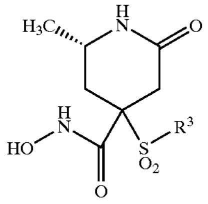
| | |
|---|---|
| | 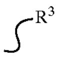 |
| 15 | 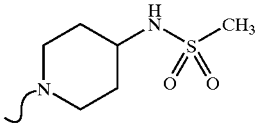 |
| 16 | 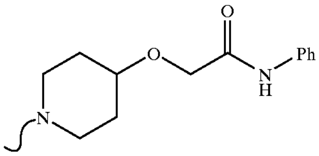 |
| 17 | 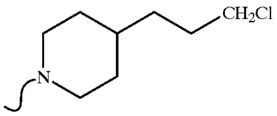 |
| 18 | 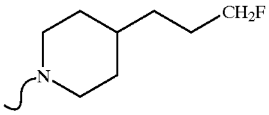 |
| 19 | 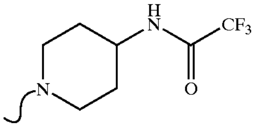 |
| 20 | 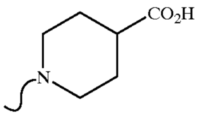 |
| 21 | 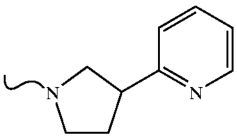 |
| 22 | 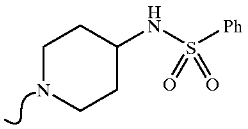 |
| 23 | 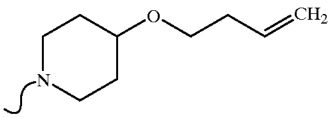 |

TABLE 20-continued
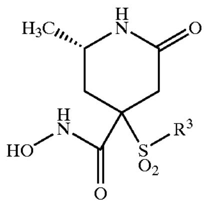
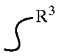
| | |
|---|---|
| 24 | 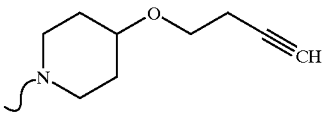 |
| 25 | 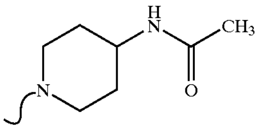 |
| 26 | 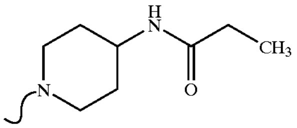 |
| 27 | 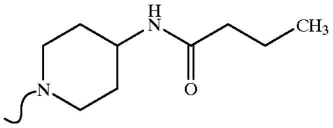 |
| 28 | 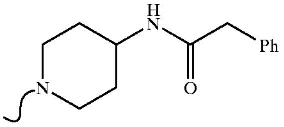 |
| 29 | 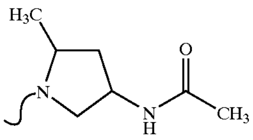 |
| 30 | 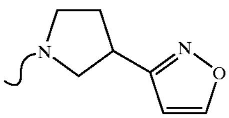 |
| 31 | 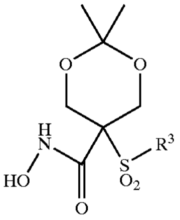 |
TABLE 14
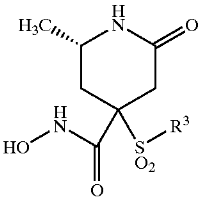
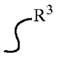
| | |
|---|---|
| 1 | 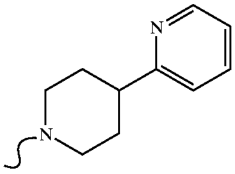 |
| 2 | 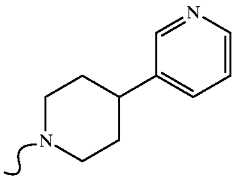 |
| 3 | 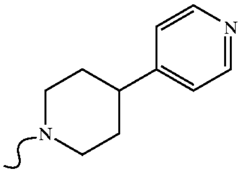 |
| 4 | 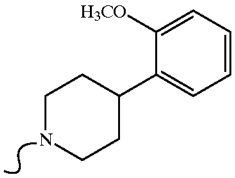 |
| 5 | 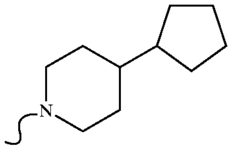 |
| 6 | 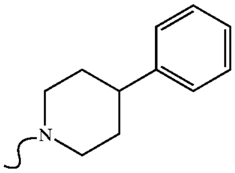 |
| 7 | 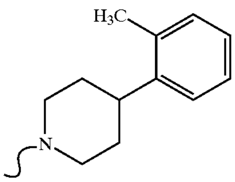 |

TABLE 14-continued
| | |
|---|---|
| | 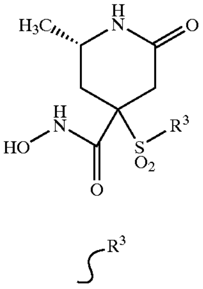 |
| 8 | 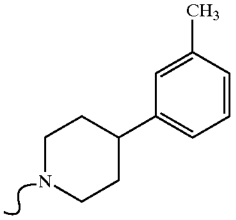 |
| 9 | 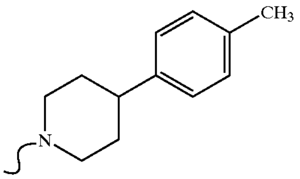 |
| 10 | 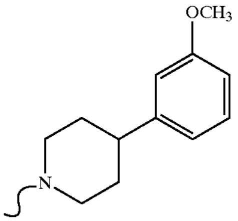 |
| 11 | 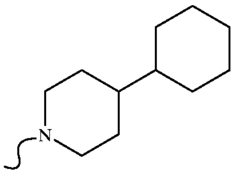 |
| 12 | 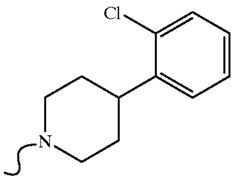 |
| 13 | 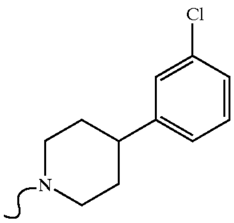 |
TABLE 14-continued
| | |
|---|---|
| | 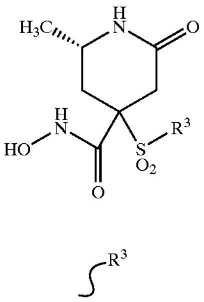 |
| 14 | 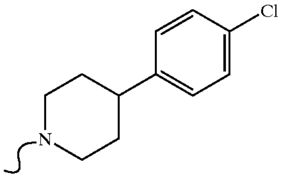 |
| 15 | 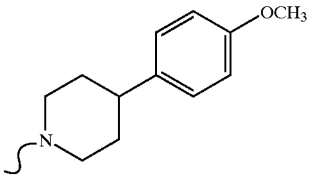 |
| 16 | 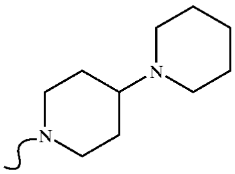 |
| 17 | 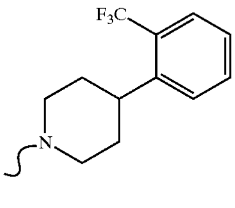 |
| 18 | 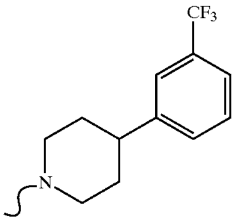 |
| 19 | 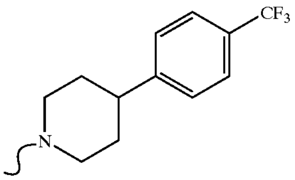 |

TABLE 14-continued
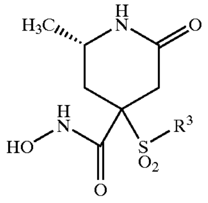
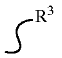
20 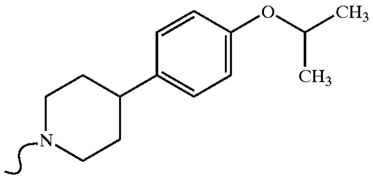
21 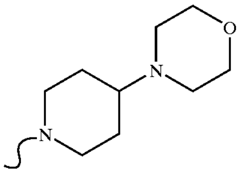
TABLE 22
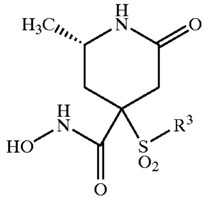
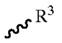
1 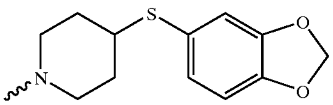
2 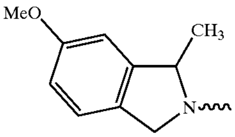
3 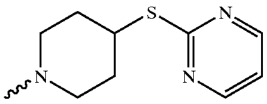
4 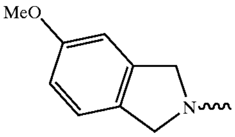
TABLE 22-continued
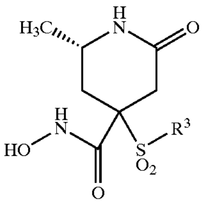
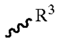
5 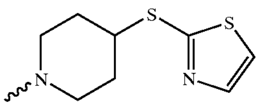
6 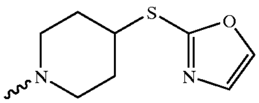
7 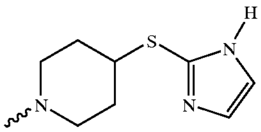
8 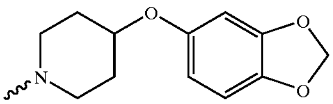
9 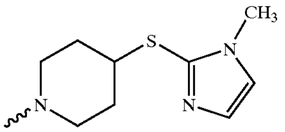
10 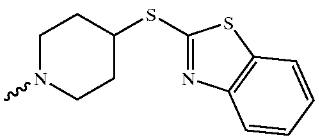
11 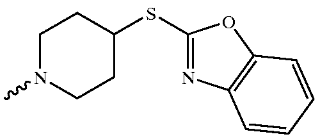

TABLE 23
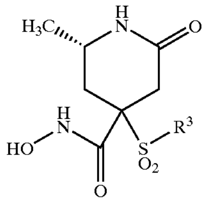
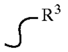
| | |
|---|---|
| 1 | 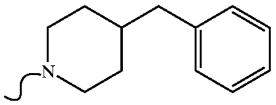 |
| 2 | 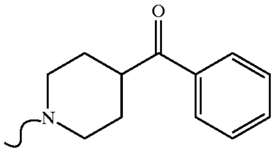 |
| 3 | 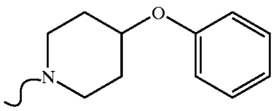 |
| 4 | 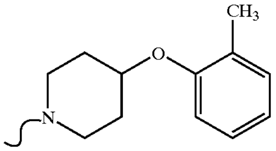 |
| 5 | 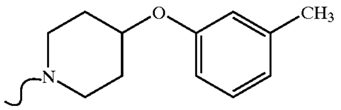 |
| 6 | 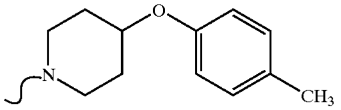 |
| 7 | 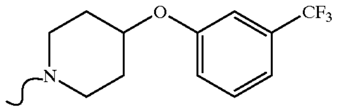 |
| 8 | 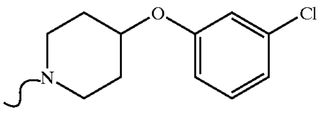 |
| 9 | 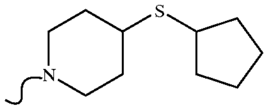 |
| 10 | 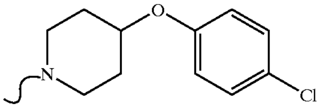 |
TABLE 23-continued
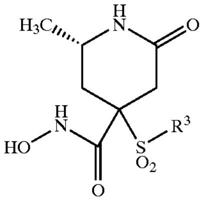
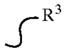
| | |
|---|---|
| 11 | 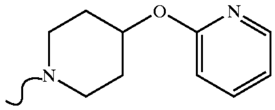 |
| 12 | 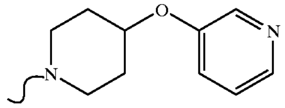 |
| 13 | 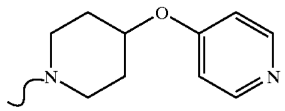 |
| 14 | 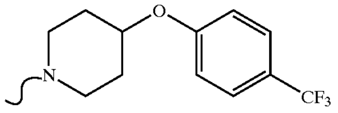 |
| 15 | 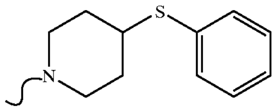 |
| 16 | 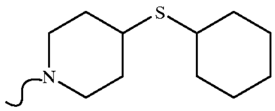 |
| 17 | 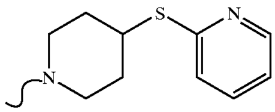 |
| 18 | 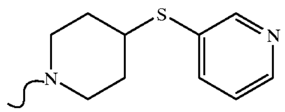 |
| 19 | 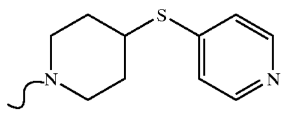 |
| 20 | 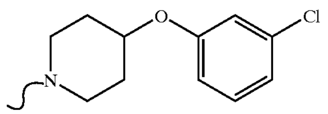 |

TABLE 23-continued
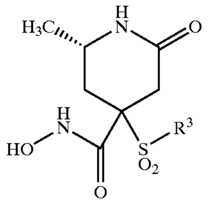
21 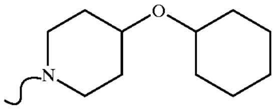
TABLE 24
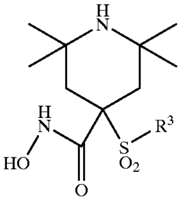
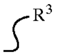
1 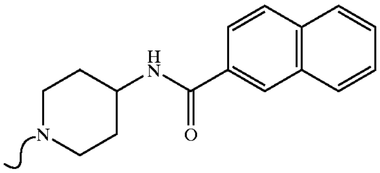
2 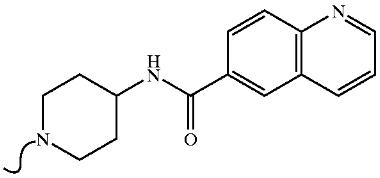
3 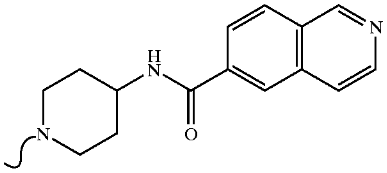
4 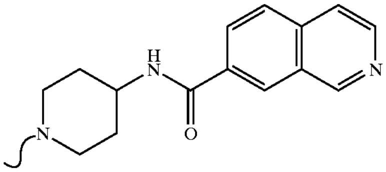
TABLE 24-continued
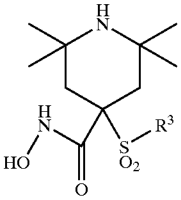
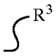
5 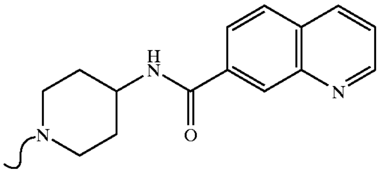
6 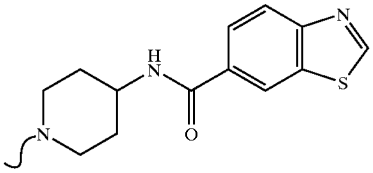
7 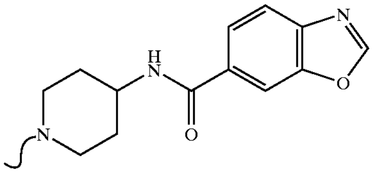
8 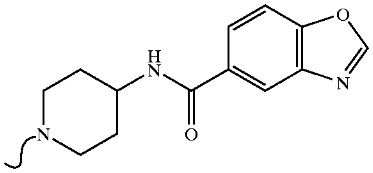
9 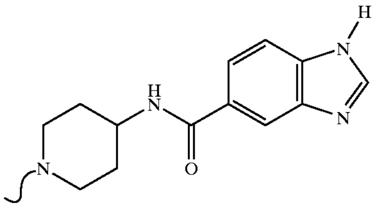
10 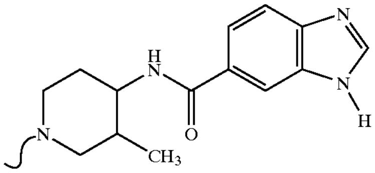
11 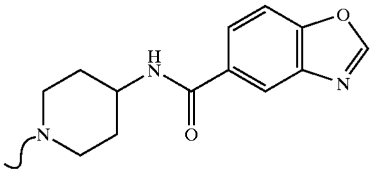

TABLE 24-continued
| | |
|---|---|
| 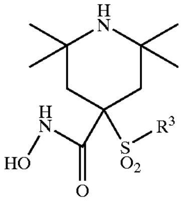 | |
| 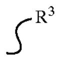 | |
| 12 | 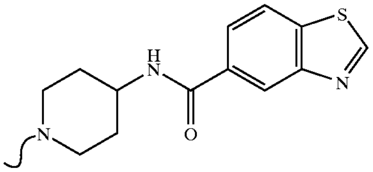 |
| 13 | 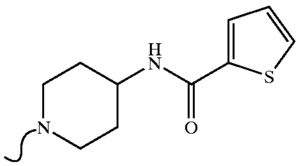 |
| 14 | 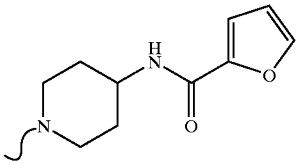 |
| 15 | 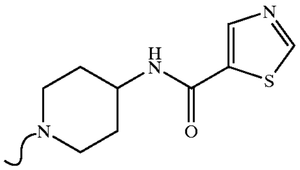 |
| 16 | 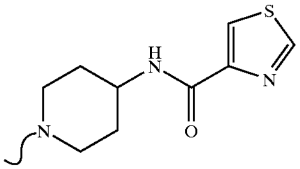 |
| 17 | 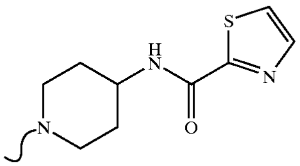 |
| 18 | 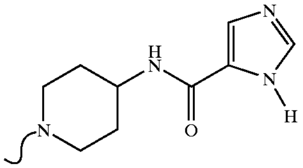 |
TABLE 25
| | |
|---|---|
| 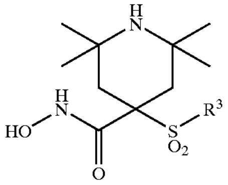 | |
| 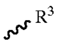 | |
| 1 | 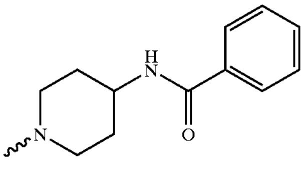 |
| 2 | 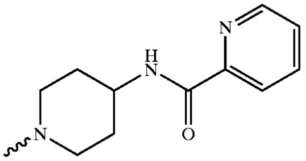 |
| 3 | 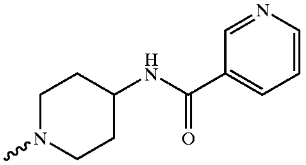 |
| 4 | 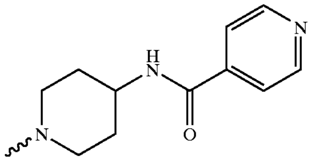 |
| 5 | 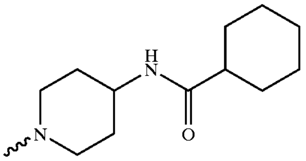 |
| 6 | 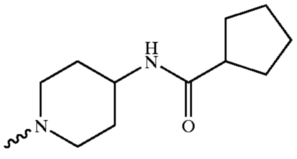 |
| 7 | 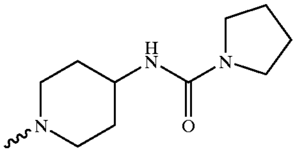 |

TABLE 25-continued
| | 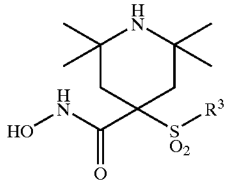<br>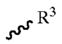 |
|---|---|
| 8 | 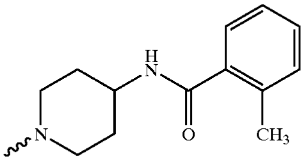 |
| 9 | 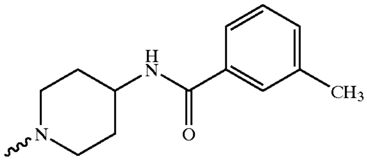 |
| 10 | 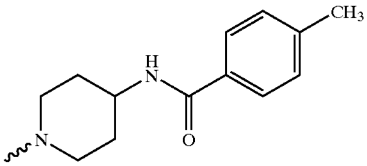 |
| 11 | 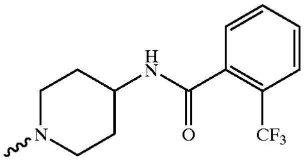 |
| 12 | 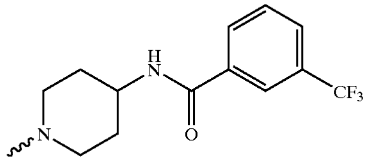 |
| 13 | 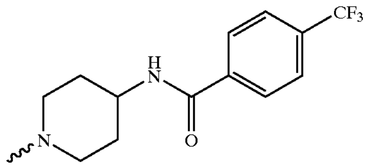 |
| 14 | 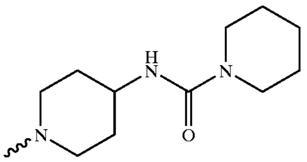 |
TABLE 25-continued
| | 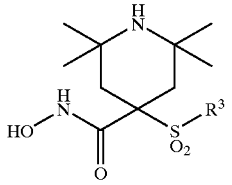<br>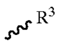 |
|---|---|
| 15 | 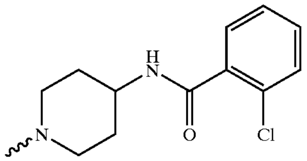 |
| 16 | 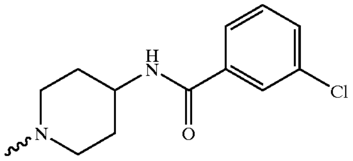 |
| 17 | 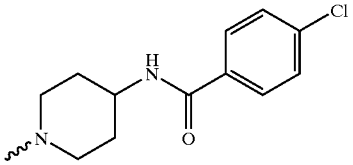 |
| 18 | 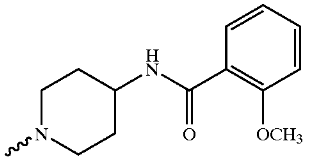 |
| 19 | 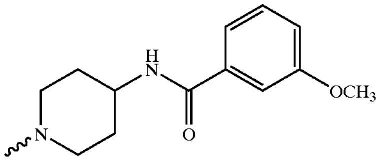 |
| 20 | 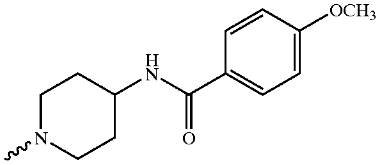 |
| 21 | 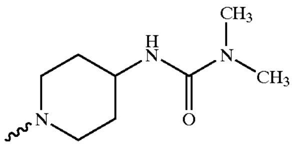 |

TABLE 26
| | |
|---|---|
| | 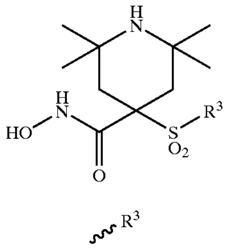 |
| 1 | 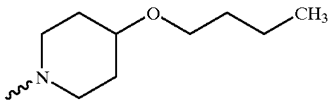 |
| 2 | 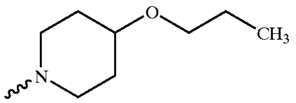 |
| 3 | 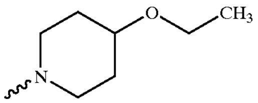 |
| 4 | 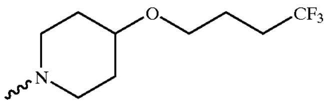 |
| 5 | 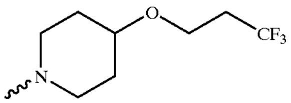 |
| 6 | 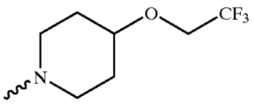 |
| 7 | 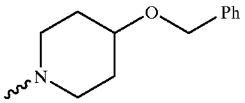 |
| 8 | 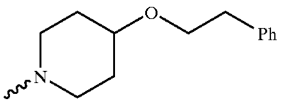 |
| 9 | 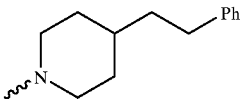 |
| 10 | 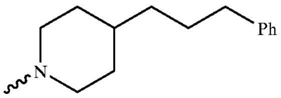 |
| 11 | 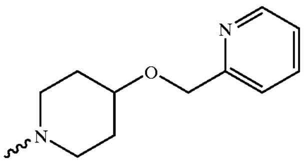 |
TABLE 26-continued
| | |
|---|---|
| | 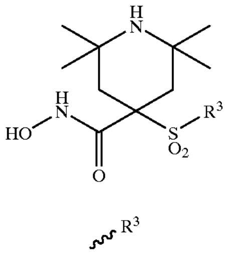 |
| 12 | 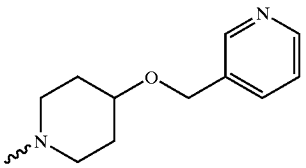 |
| 13 | 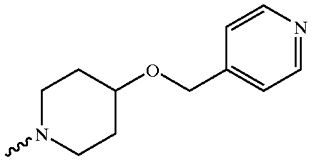 |
| 14 | 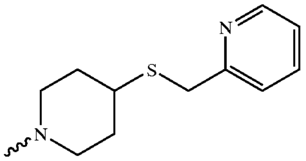 |
| 15 | 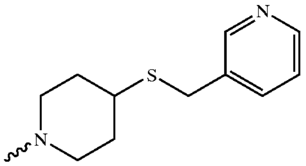 |
| 16 | 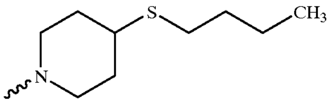 |
| 17 | 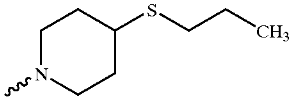 |
| 18 | 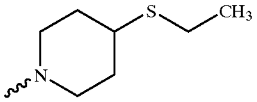 |
| 19 | 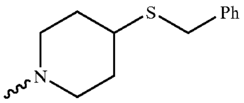 |
| 20 | 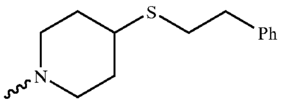 |

TABLE 26-continued
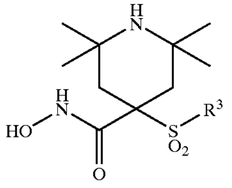
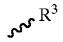
| | |
|---|---|
| 21 | 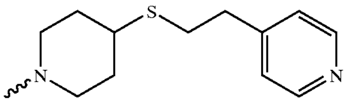 |
| 22 | 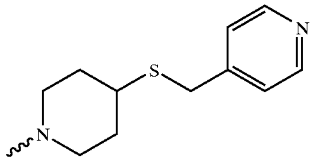 |
TABLE 27
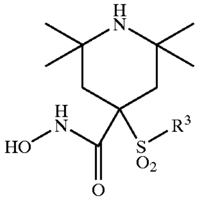
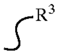
| | |
|---|---|
| 1 | 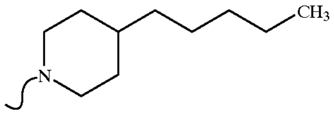 |
| 2 | 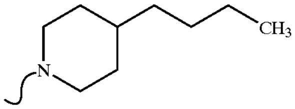 |
| 3 | 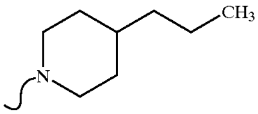 |
| 4 | 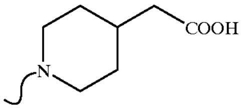 |
| 5 | 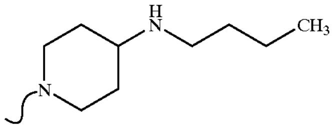 |
TABLE 27-continued
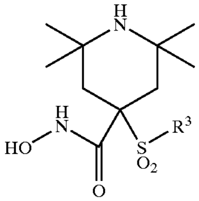
| | |
|---|---|
| 6 | 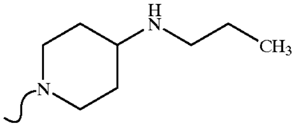 |
| 7 | 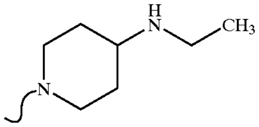 |
| 8 | 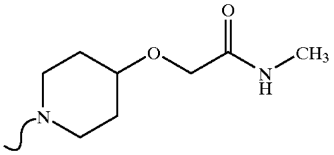 |
| 9 | 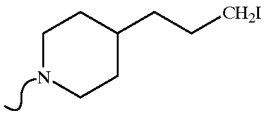 |
| 10 | 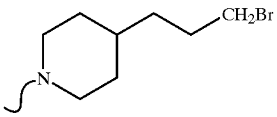 |
| 11 | 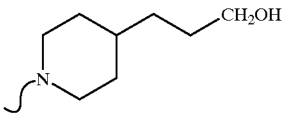 |
| 12 | 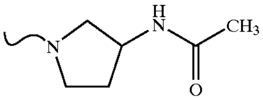 |
| 13 | 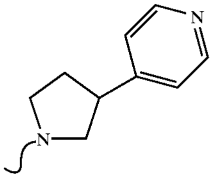 |
| 14 | 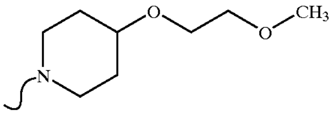 |

TABLE 27-continued
| | |
|---|---|
| | 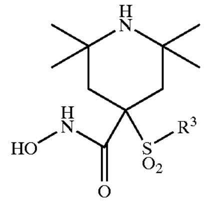 |
| | 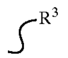 |
| 15 | 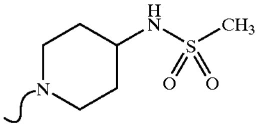 |
| 16 | 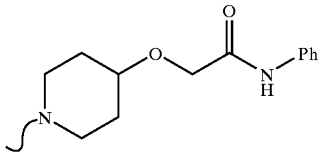 |
| 17 | 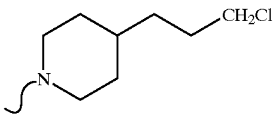 |
| 18 | 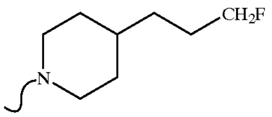 |
| 19 | 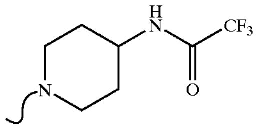 |
| 20 | 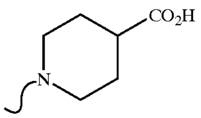 |
| 21 | 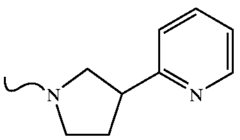 |
| 22 | 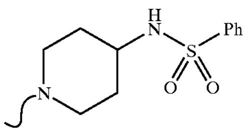 |
| 23 | 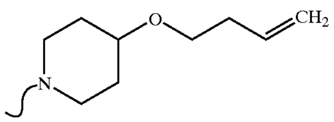 |
TABLE 27-continued
| | |
|---|---|
| | 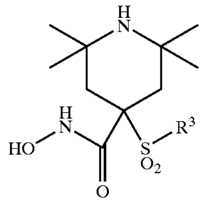 |
| | 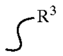 |
| 24 | 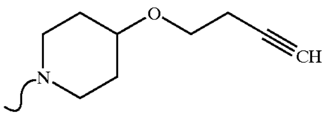 |
| 25 | 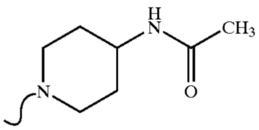 |
| 26 | 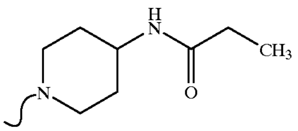 |
| 27 | 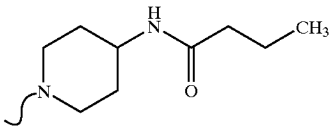 |
| 28 | 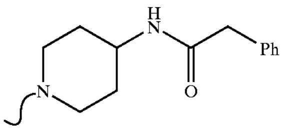 |
| 29 | 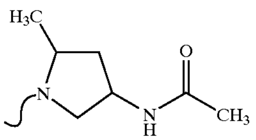 |
| 30 | 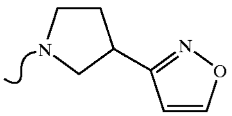 |
| 31 | 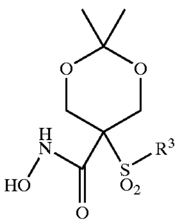 |

TABLE 28
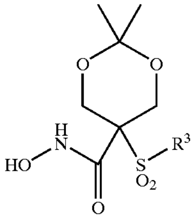
| | 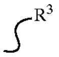 |
|---|---|
| 1 | 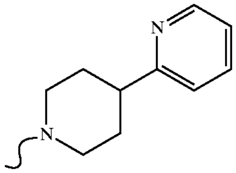 |
| 2 | 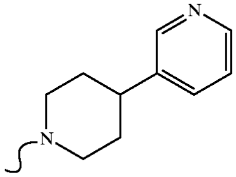 |
| 3 | 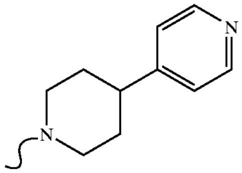 |
| 4 | 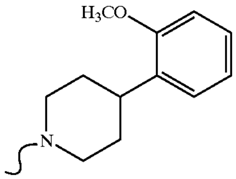 |
| 5 | 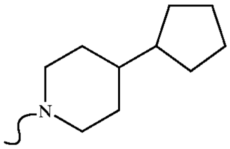 |
| 6 | 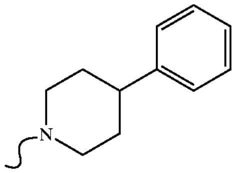 |
| 7 | 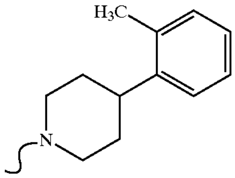 |
TABLE 28-continued
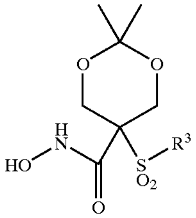
| | 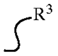 |
|---|---|
| 8 | 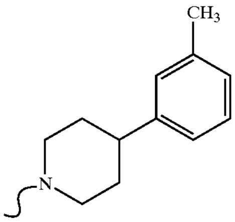 |
| 9 | 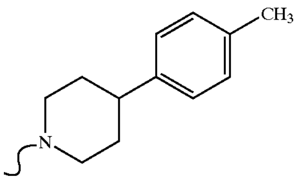 |
| 10 | 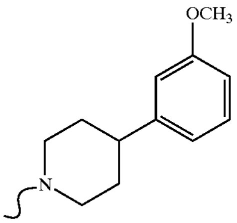 |
| 11 | 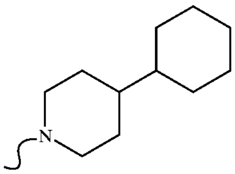 |
| 12 | 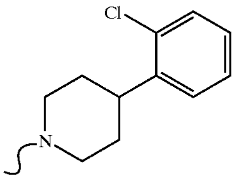 |
| 13 | 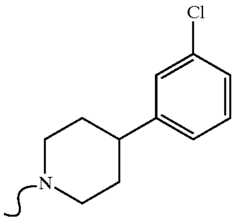 |

TABLE 28-continued
| | |
|---|---|
| | 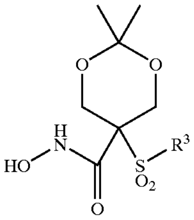 |
| | 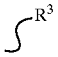 |
| 14 | 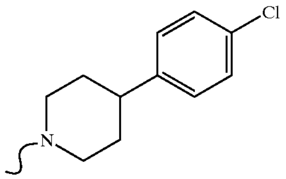 |
| 15 | 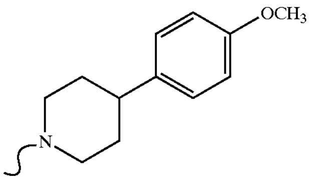 |
| 16 | 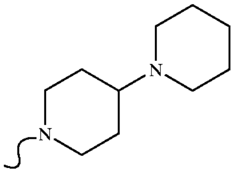 |
| 17 | 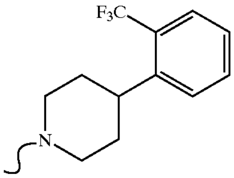 |
| 18 | 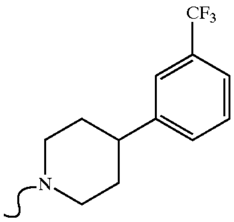 |
| 19 | 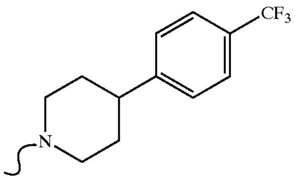 |
TABLE 28-continued
| | |
|---|---|
| | 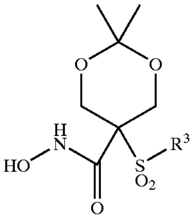 |
| | 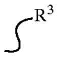 |
| 20 | 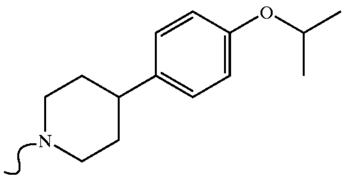 |
| 21 | 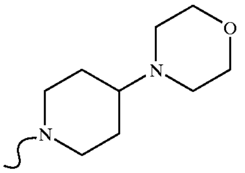 |
TABLE 29
| | |
|---|---|
| | 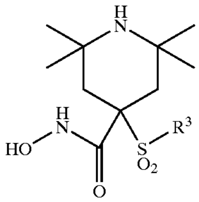 |
| | 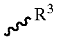 |
| 1 | 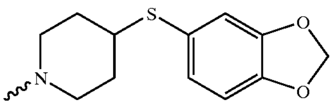 |
| 2 | 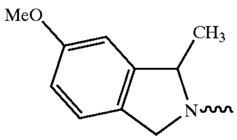 |
| 3 | 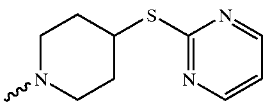 |
| 4 | 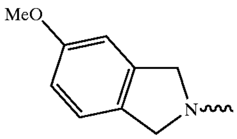 |

TABLE 29-continued
| 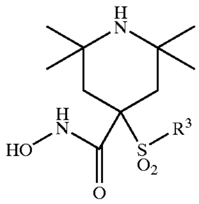 | 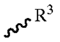 |
|---|---|
| 5 | 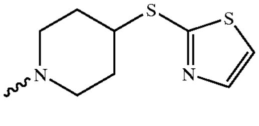 |
| 6 | 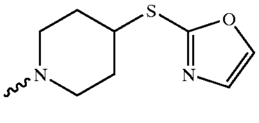 |
| 7 | 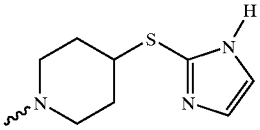 |
| 8 | 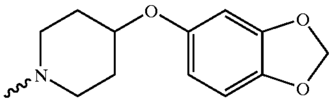 |
| 9 | 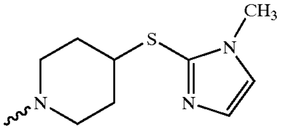 |
| 10 | 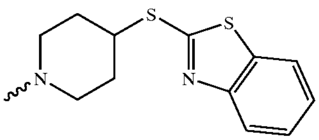 |
| 11 | 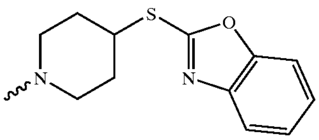 |
TABLE 30
| 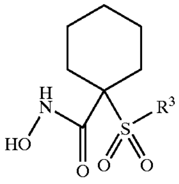 | 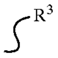 |
|---|---|
| 1 | 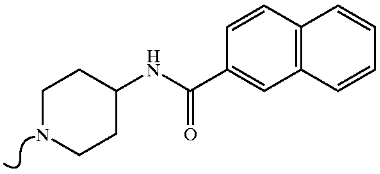 |
| 2 | 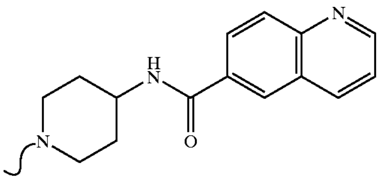 |
| 3 | 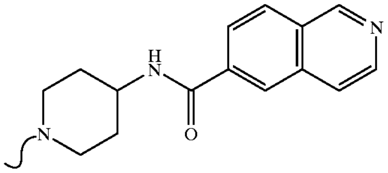 |
| 4 | 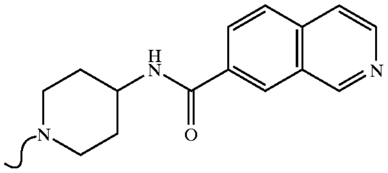 |
| 5 | 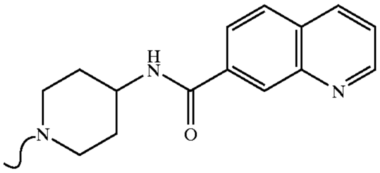 |
| 6 | 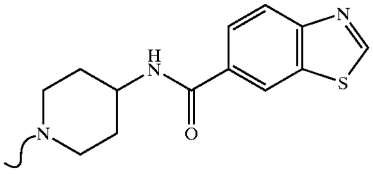 |
| 7 | 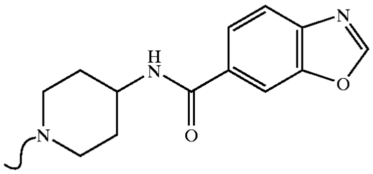 |

TABLE 30-continued
| | |
|---|---|
| 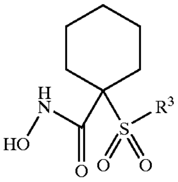 | |
| 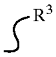 | |
| 8 | 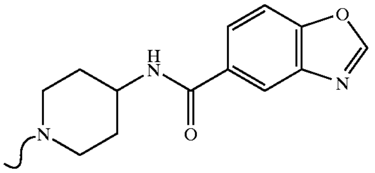 |
| 9 | 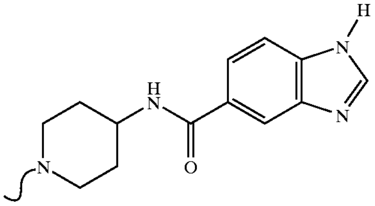 |
| 10 | 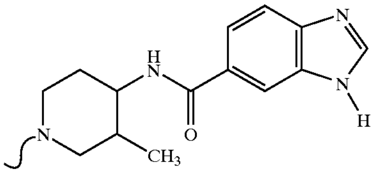 |
| 11 | 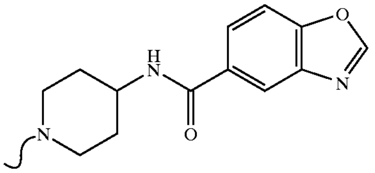 |
| 12 | 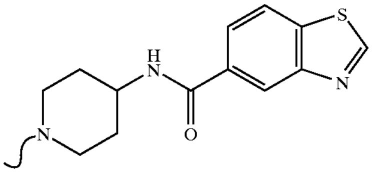 |
| 13 | 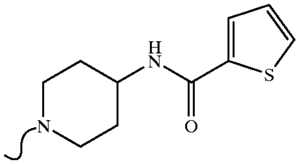 |
| 14 | 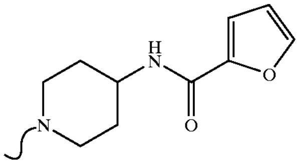 |
TABLE 30-continued
| | |
|---|---|
| 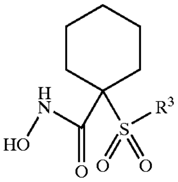 | |
| 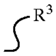 | |
| 15 | 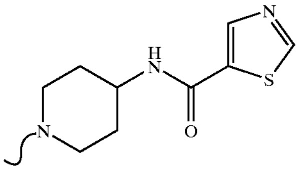 |
| 16 | 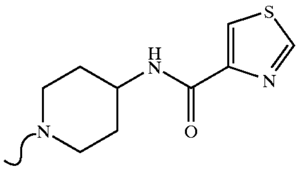 |
| 17 | 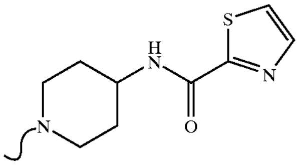 |
| 18 | 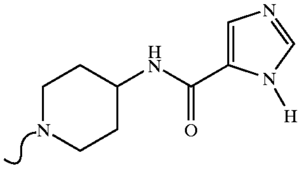 |
TABLE 31
| | |
|---|---|
| 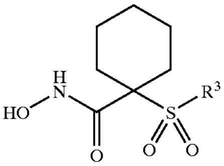 | |
| 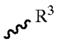 | |
| 1 | 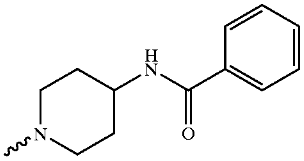 |

TABLE 31-continued
| | 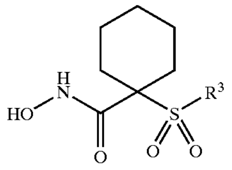<br>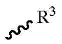 |
|---|---|
| 2 | 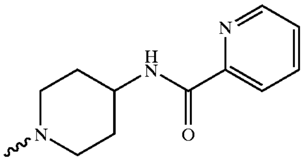 |
| 3 | 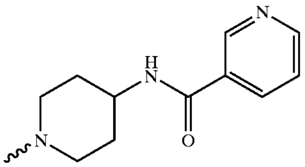 |
| 4 | 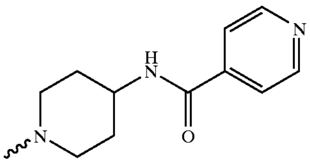 |
| 5 | 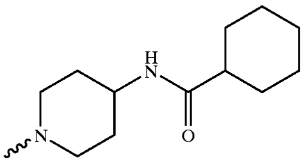 |
| 6 | 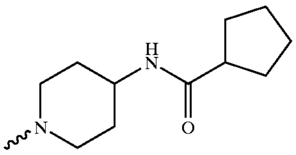 |
| 7 | 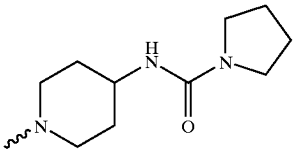 |
| 8 | 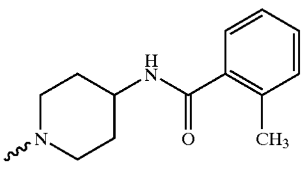 |
TABLE 31-continued
| | 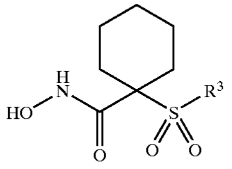<br>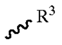 |
|---|---|
| 9 | 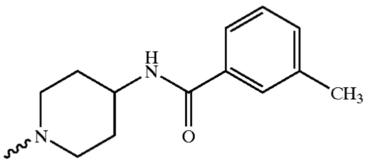 |
| 10 | 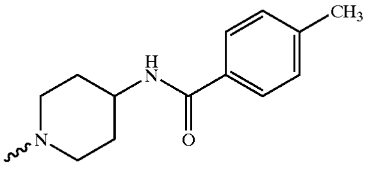 |
| 11 | 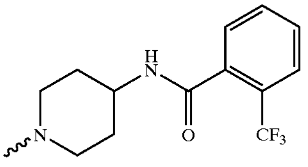 |
| 12 | 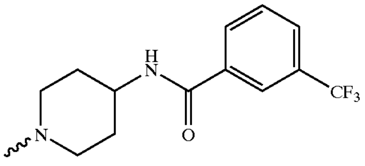 |
| 13 | 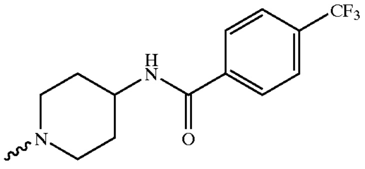 |
| 14 | 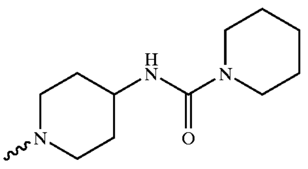 |
| 15 | 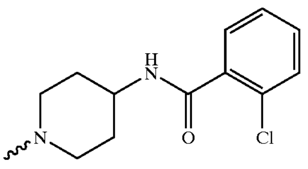 |

TABLE 31-continued
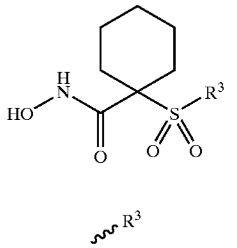
| | |
|---|---|
| 16 | 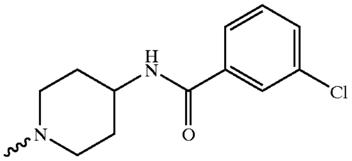 |
| 17 | 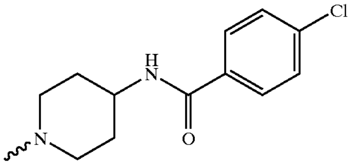 |
| 18 | 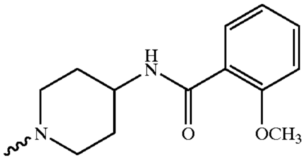 |
| 19 | 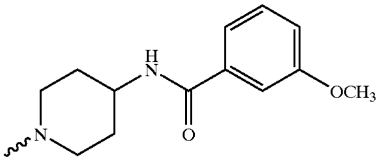 |
| 20 | 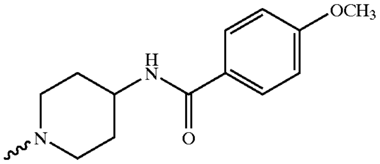 |
| 21 | 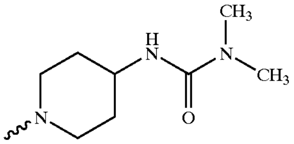 |
TABLE 32
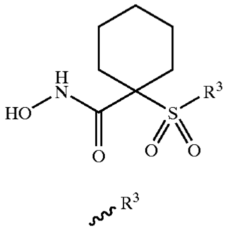
| | |
|---|---|
| 1 | 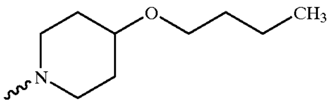 |
| 2 | 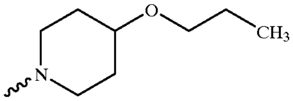 |
| 3 | 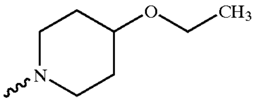 |
| 4 | 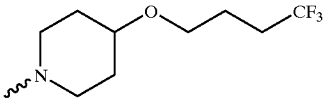 |
| 5 | 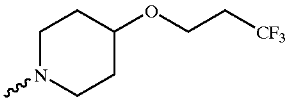 |
| 6 | 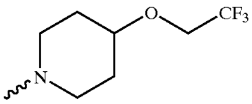 |
| 7 | 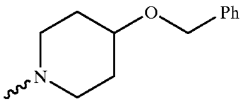 |
| 8 | 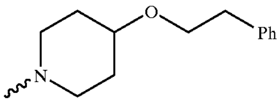 |
| 9 | 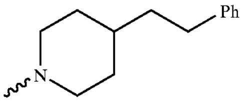 |
| 10 | 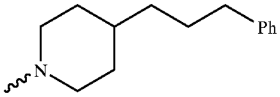 |
| 11 | 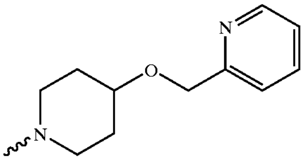 |

TABLE 32-continued
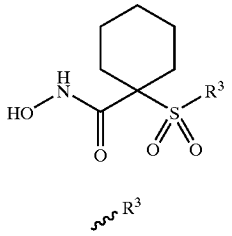
| | |
|---|---|
| 12 | 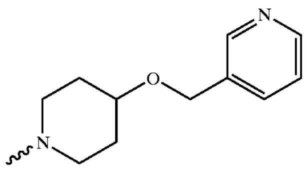 |
| 13 | 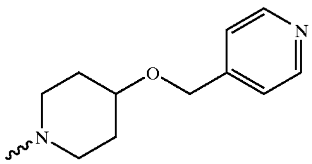 |
| 14 | 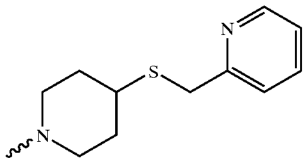 |
| 15 | 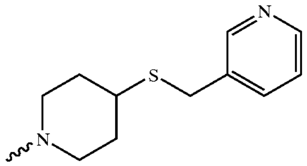 |
| 16 | 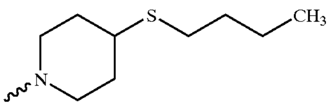 |
| 17 | 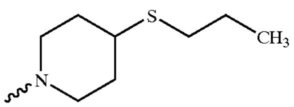 |
| 18 | 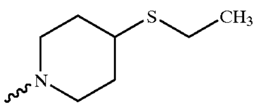 |
| 19 | 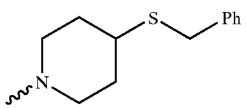 |
| 20 | 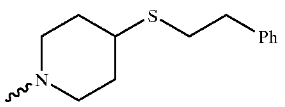 |
TABLE 32-continued
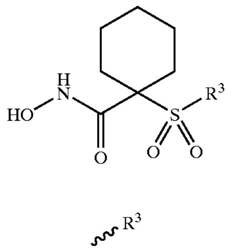
| | |
|---|---|
| 21 | 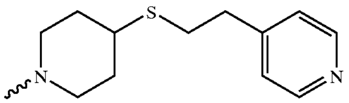 |
| 22 | 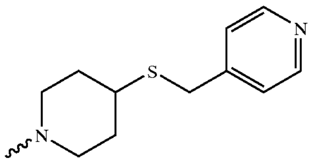 |
TABLE 33
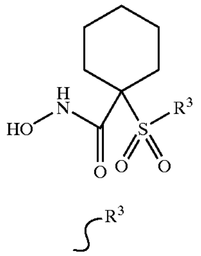
| | |
|---|---|
| 1 | 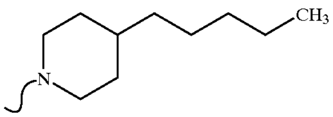 |
| 2 | 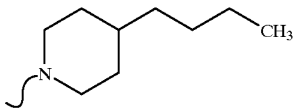 |
| 3 | 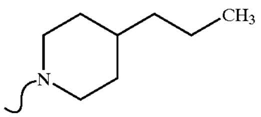 |
| 4 | 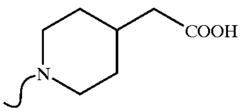 |
| 5 | 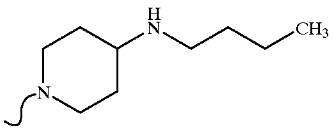 |

TABLE 33-continued
| | 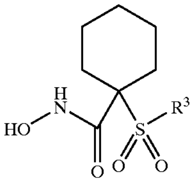 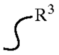 |
|---|---|
| 6 | 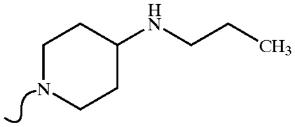 |
| 7 | 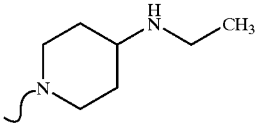 |
| 8 | 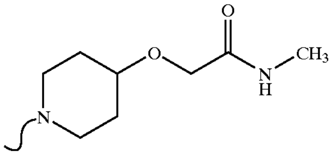 |
| 9 | 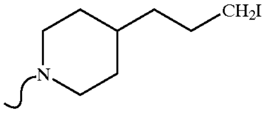 |
| 10 | 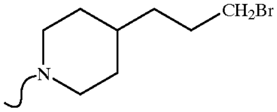 |
| 11 | 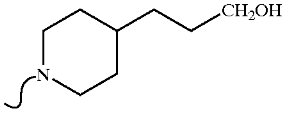 |
| 12 | 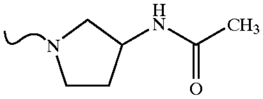 |
| 13 | 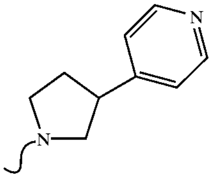 |
| 14 | 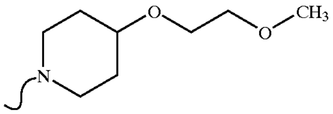 |
TABLE 33-continued
| | 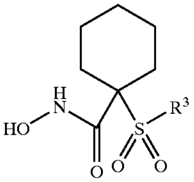 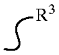 |
|---|---|
| 15 | 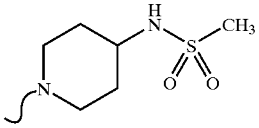 |
| 16 | 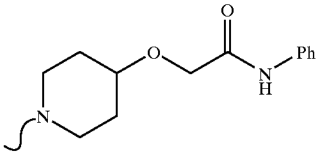 |
| 17 | 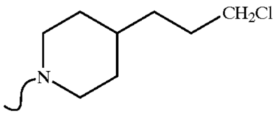 |
| 18 | 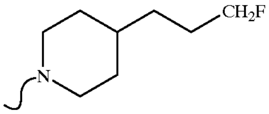 |
| 19 | 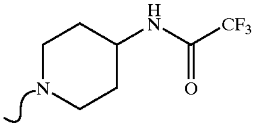 |
| 20 | 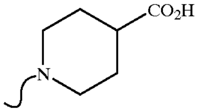 |
| 21 | 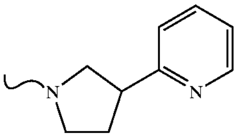 |
| 22 | 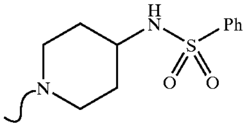 |
| 23 | 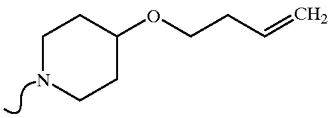 |

TABLE 33-continued
| | |
|---|---|
| | 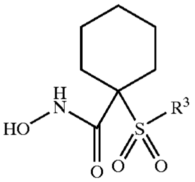 |
| | 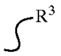 |
| 24 | 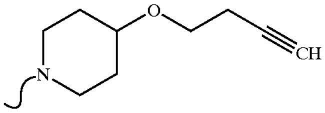 |
| 25 | 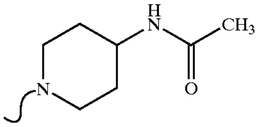 |
| 26 | 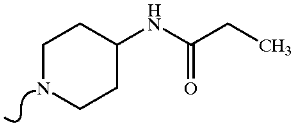 |
| 27 | 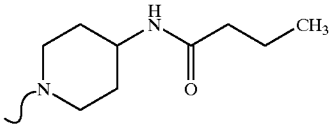 |
| 28 | 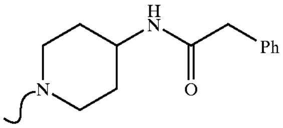 |
| 29 | 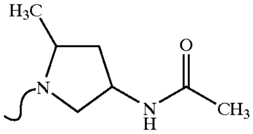 |
| 30 | 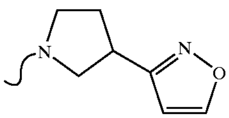 |
| 31 | 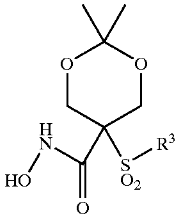 |
TABLE 34
| | |
|---|---|
| | 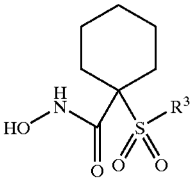 |
| | 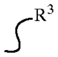 |
| 1 | 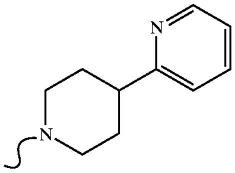 |
| 2 | 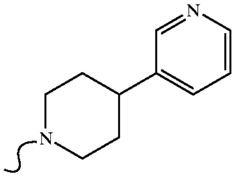 |
| 3 | 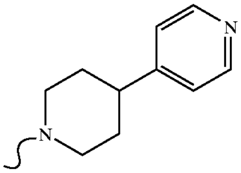 |
| 4 | 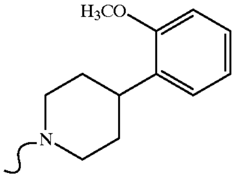 |
| 5 | 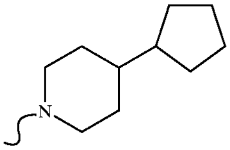 |
| 6 | 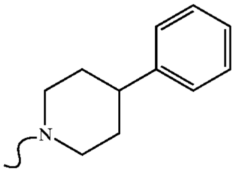 |
| 7 | 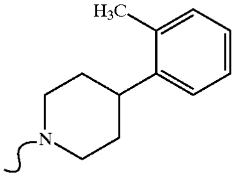 |

TABLE 34-continued
| | |
|---|---|
| | 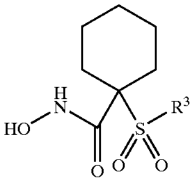 |
| | 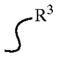 |
| 8 | 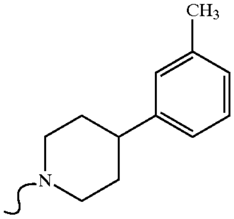 |
| 9 | 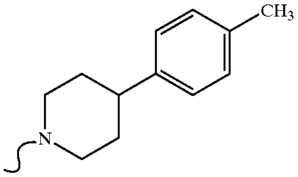 |
| 10 | 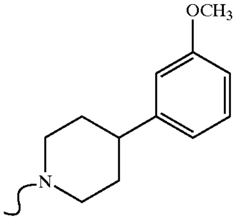 |
| 11 | 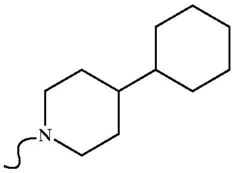 |
| 12 | 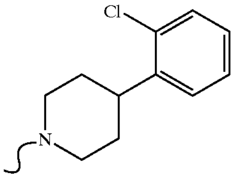 |
| 13 | 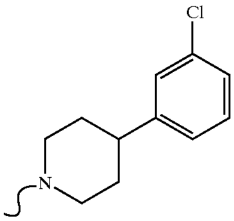 |
TABLE 34-continued
| | |
|---|---|
| | 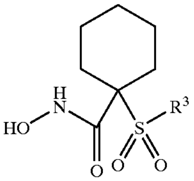 |
| | 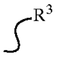 |
| 14 | 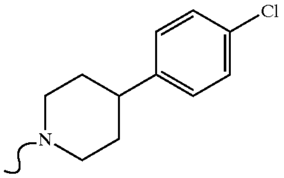 |
| 15 | 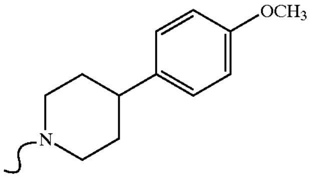 |
| 16 | 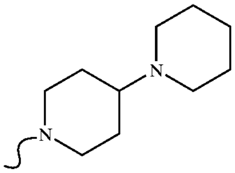 |
| 17 | 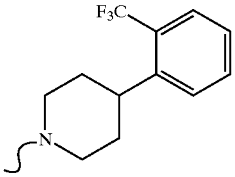 |
| 18 | 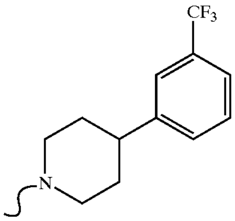 |
| 19 | 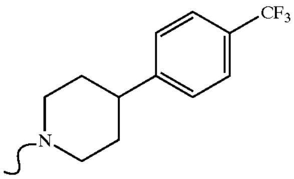 |

TABLE 34-continued
| | |
|---|---|
| | 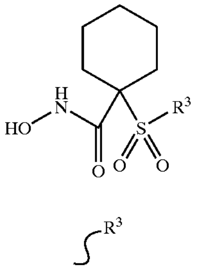 |
| 20 | 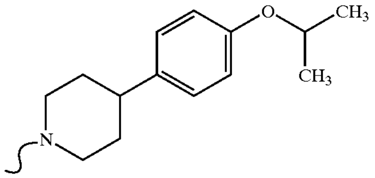 |
| 21 | 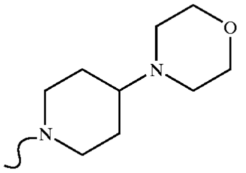 |
TABLE 35
| | |
|---|---|
| | 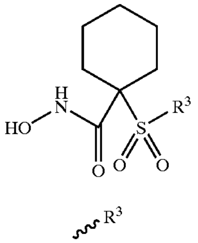 |
| 1 | 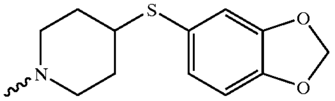 |
| 2 | 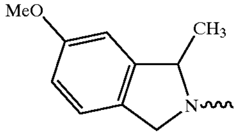 |
| 3 | 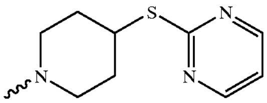 |
| 4 | 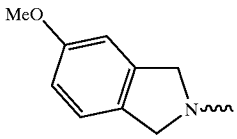 |
TABLE 35-continued
| | |
|---|---|
| | 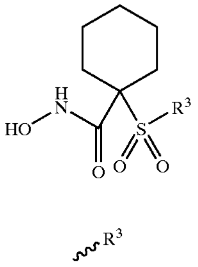 |
| 5 | 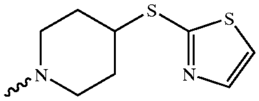 |
| 6 | 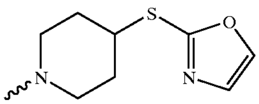 |
| 7 | 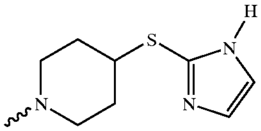 |
| 8 | 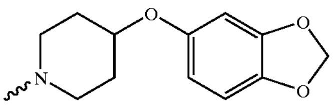 |
| 9 | 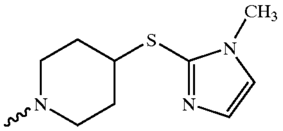 |
| 10 | 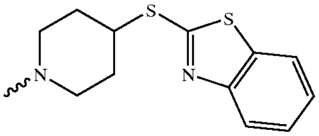 |
| 11 | 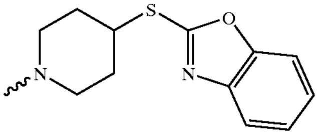 |

TABLE 36
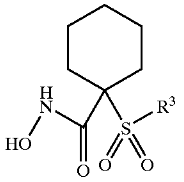
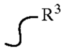
| | |
|---|---|
| 1 | 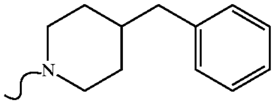 |
| 2 | 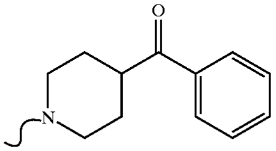 |
| 3 | 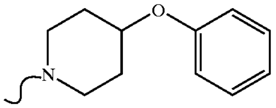 |
| 4 | 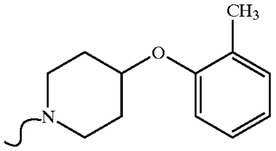 |
| 5 | 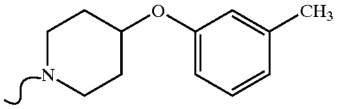 |
| 6 | 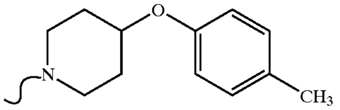 |
| 7 | 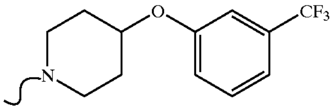 |
| 8 | 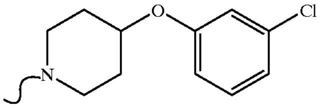 |
| 9 | 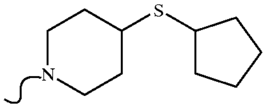 |
| 10 | 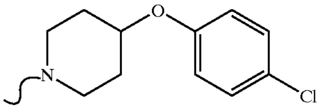 |
TABLE 36-continued
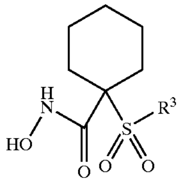
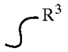
| | |
|---|---|
| 11 | 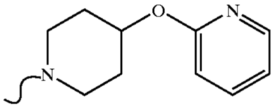 |
| 12 | 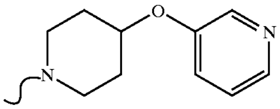 |
| 13 | 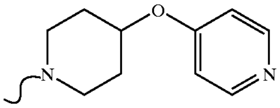 |
| 14 | 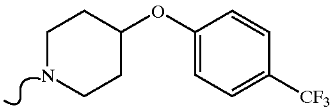 |
| 15 | 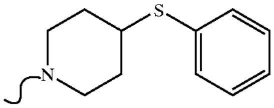 |
| 16 | 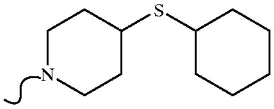 |
| 17 | 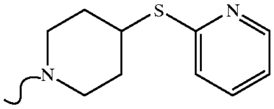 |
| 18 | 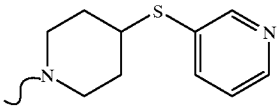 |
| 19 | 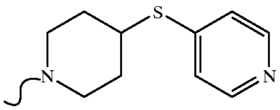 |
| 20 | 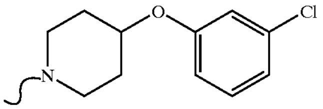 |

TABLE 36-continued
| | |
|---|---|
| | 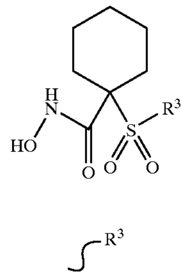 |
| 21 | 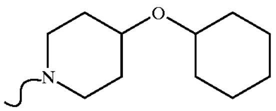 |
TABLE 37
| | |
|---|---|
| | 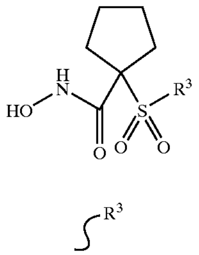 |
| 1 | 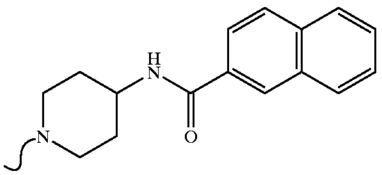 |
| 2 | 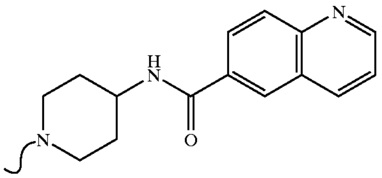 |
| 3 | 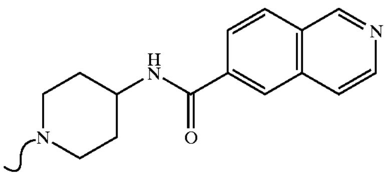 |
| 4 | 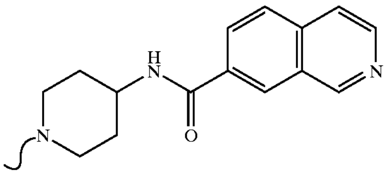 |
TABLE 37-continued
| | |
|---|---|
| | 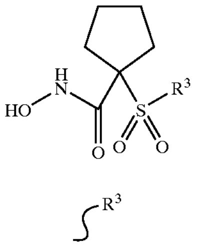 |
| 5 | 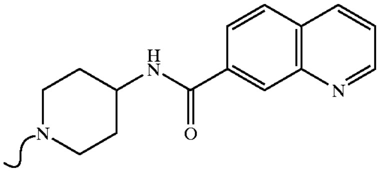 |
| 6 | 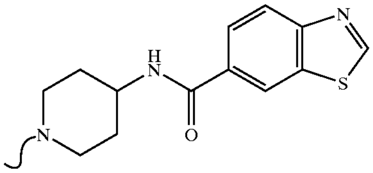 |
| 7 | 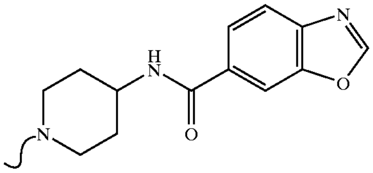 |
| 8 | 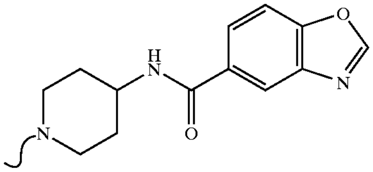 |
| 9 | 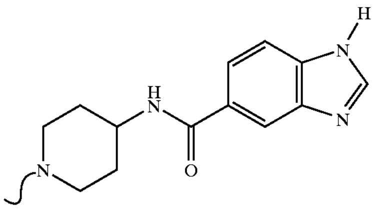 |
| 10 | 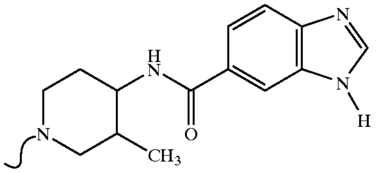 |
| 11 | 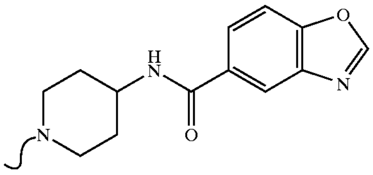 |

TABLE 37-continued
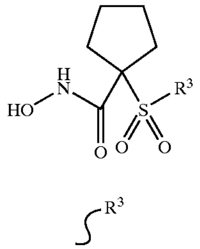
| | |
|---|---|
| 12 | 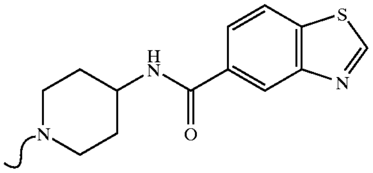 |
| 13 | 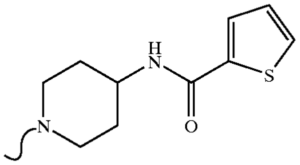 |
| 14 | 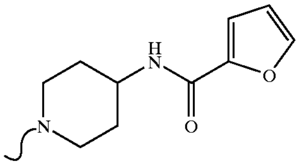 |
| 15 | 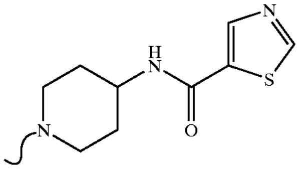 |
| 16 | 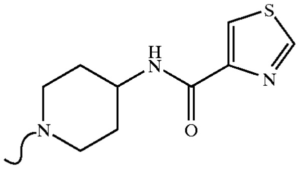 |
| 17 | 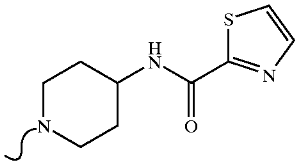 |
| 18 | 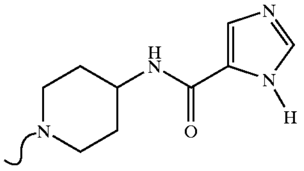 |
TABLE 38
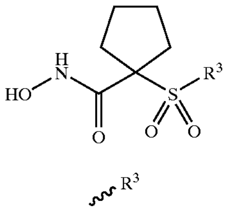
| | |
|---|---|
| 1 | 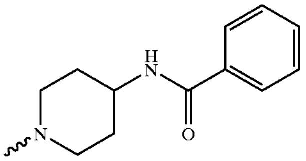 |
| 2 | 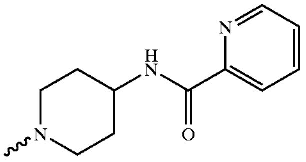 |
| 3 | 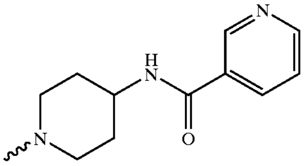 |
| 4 | 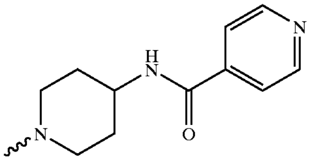 |
| 5 | 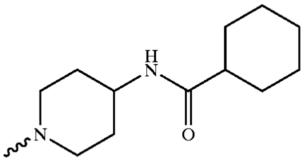 |
| 6 | 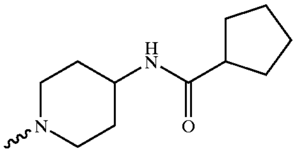 |
| 7 | 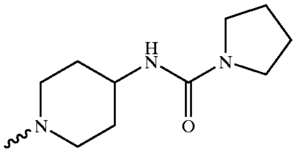 |
| 8 | 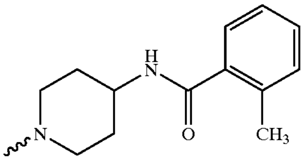 |

TABLE 38-continued
| | |
|---|---|
| | 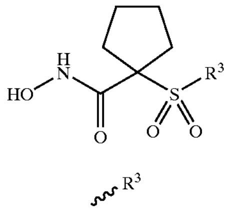 |
| 9 | 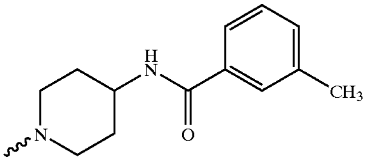 |
| 10 | 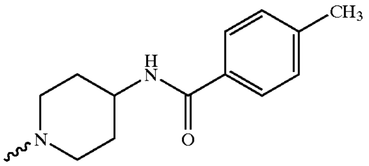 |
| 11 | 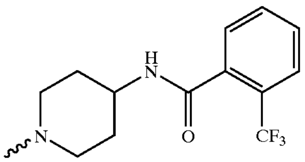 |
| 12 | 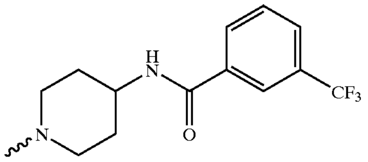 |
| 13 | 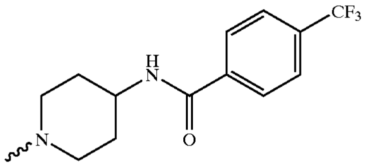 |
| 14 | 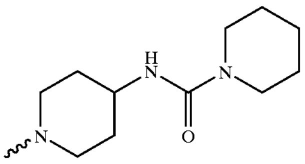 |
| 15 | 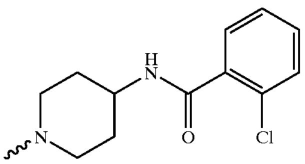 |
TABLE 38-continued
| | |
|---|---|
| | 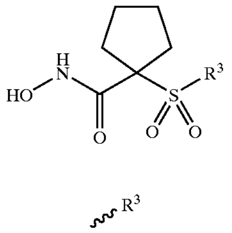 |
| 16 | 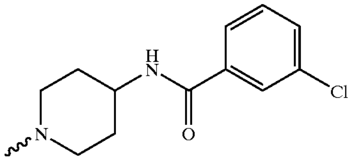 |
| 17 | 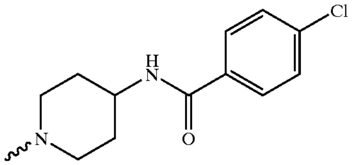 |
| 18 | 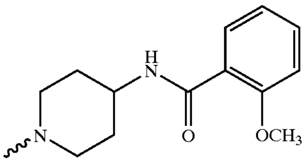 |
| 19 | 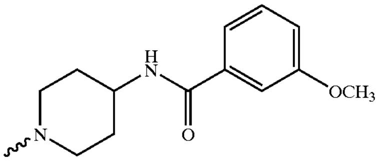 |
| 20 | 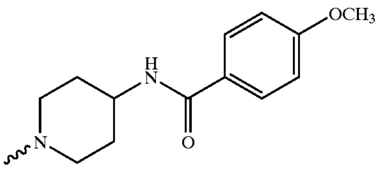 |
| 21 | 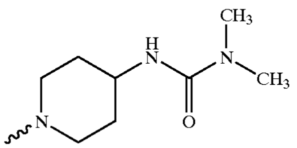 |

TABLE 39
| | 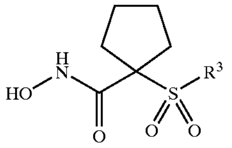<br>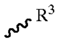 |
|---|---|
| 1 | 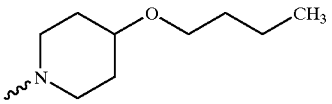 |
| 2 | 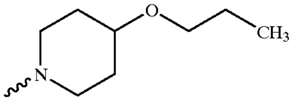 |
| 3 | 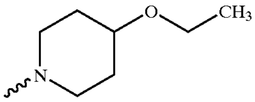 |
| 4 | 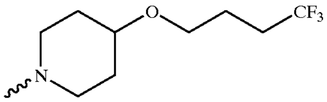 |
| 5 | 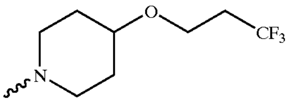 |
| 6 | 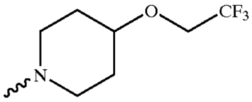 |
| 7 | 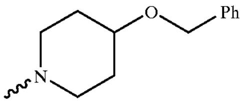 |
| 8 | 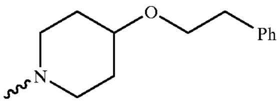 |
| 9 | 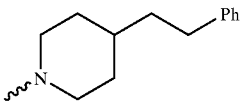 |
| 10 | 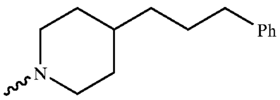 |
| 11 | 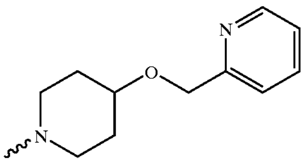 |
TABLE 39-continued
| | 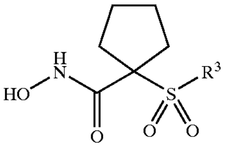<br>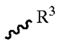 |
|---|---|
| 12 | 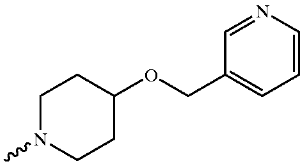 |
| 13 | 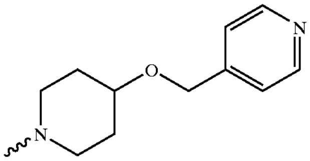 |
| 14 | 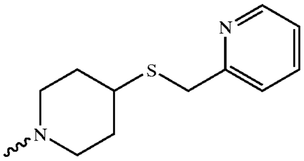 |
| 15 | 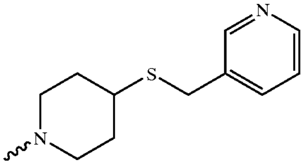 |
| 16 | 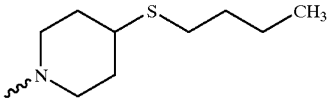 |
| 17 | 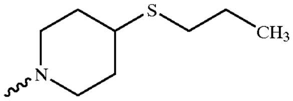 |
| 18 | 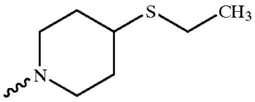 |
| 19 | 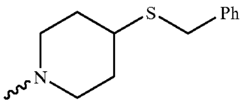 |
| 20 | 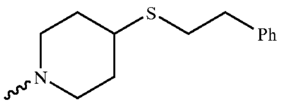 |

TABLE 39-continued
| | |
|---|---|
| | 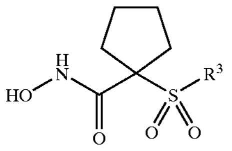 |
| | 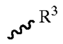 |
| 21 | 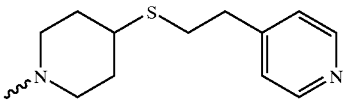 |
| 22 | 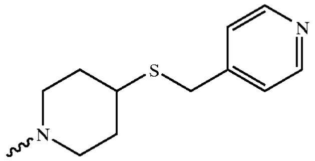 |
TABLE 40
| | |
|---|---|
| | 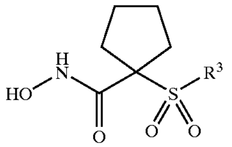 |
| | 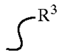 |
| 1 | 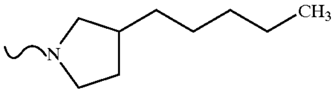 |
| 2 | 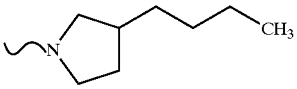 |
| 3 | 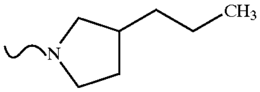 |
| 4 | 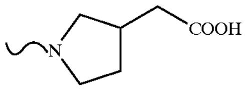 |
| 5 | 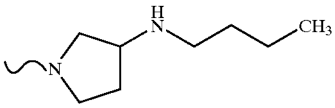 |
| 6 | 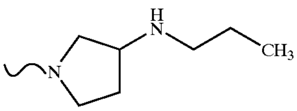 |
TABLE 40-continued
| | |
|---|---|
| | 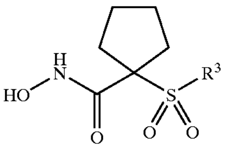 |
| | 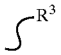 |
| 7 | 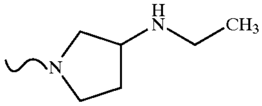 |
| 8 | 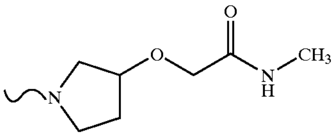 |
| 9 | 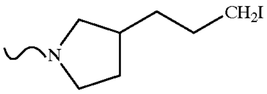 |
| 10 | 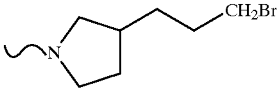 |
| 11 | 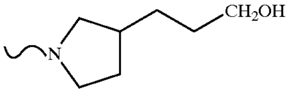 |
| 12 | 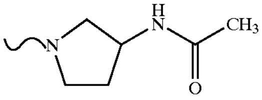 |
| 13 | 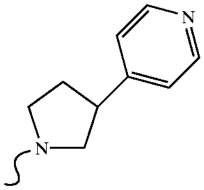 |
| 14 | 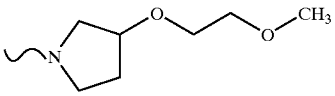 |
| 15 | 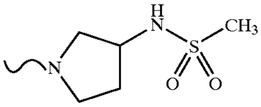 |
| 16 | 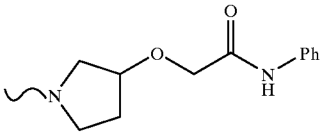 |

TABLE 40-continued
| | |
|---|---|
| | 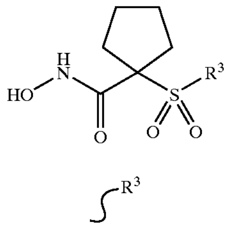 |
| 17 | 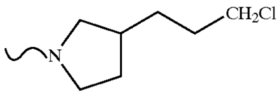 |
| 18 | 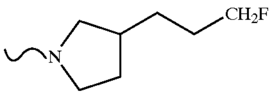 |
| 19 | 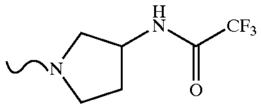 |
| 20 | 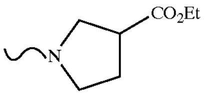 |
| 21 | 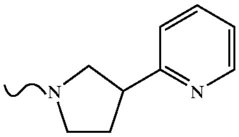 |
| 22 | 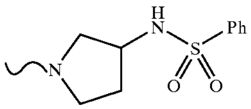 |
| 23 | 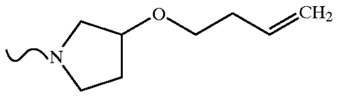 |
| 24 | 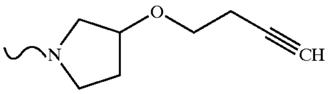 |
| 25 | 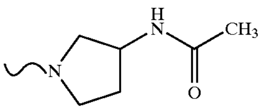 |
| 26 | 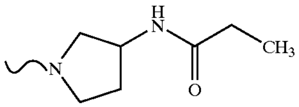 |
| 27 | 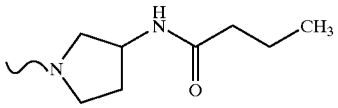 |
TABLE 40-continued
| | |
|---|---|
| | 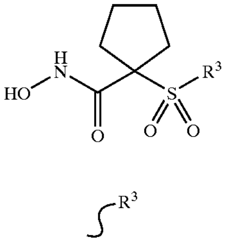 |
| 28 | 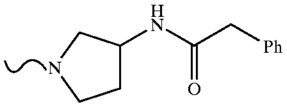 |
| 29 | 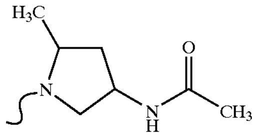 |
| 30 | 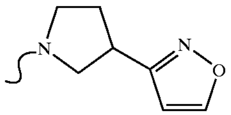 |
TABLE 41
| | |
|---|---|
| | 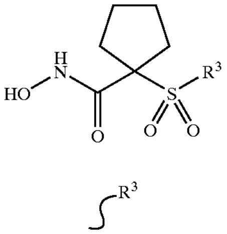 |
| 1 | 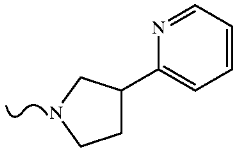 |
| 2 | 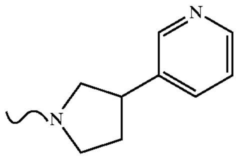 |
| 3 | 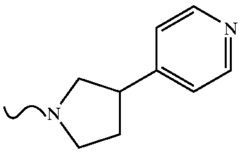 |

TABLE 41-continued
| 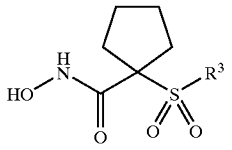 |
| --- |
| 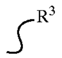 |
| | |
| --- | --- |
| 4 | 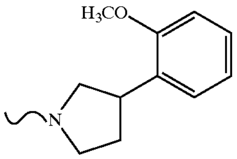 |
| 5 | 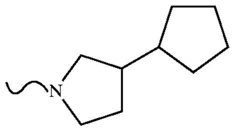 |
| 6 | 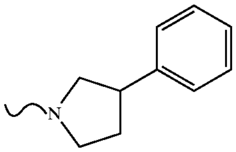 |
| 7 | 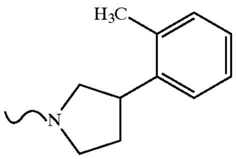 |
| 8 | 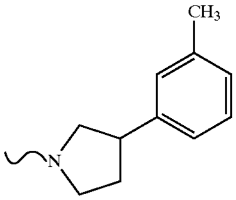 |
| 9 | 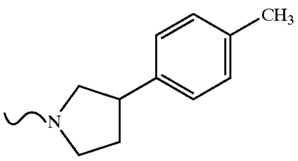 |
| 10 | 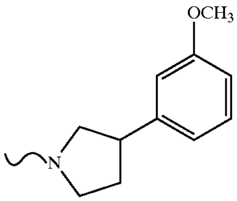 |
TABLE 41-continued
| 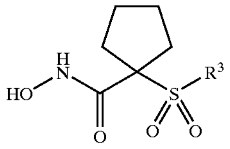 |
| --- |
| 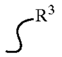 |
| | |
| --- | --- |
| 11 | 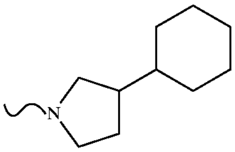 |
| 12 | 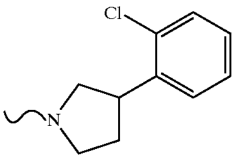 |
| 13 | 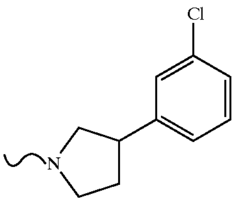 |
| 14 | 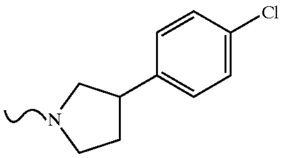 |
| 15 | 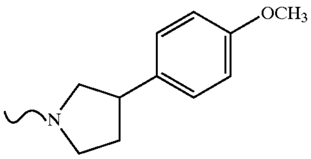 |
| 16 | 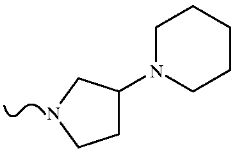 |
| 17 | 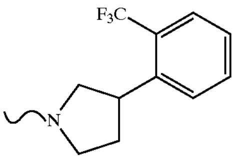 |

TABLE 41-continued
| | |
|---|---|
| | 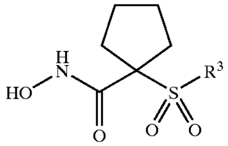 |
| | 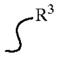 |
| 18 | 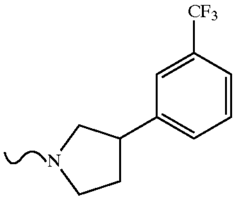 |
| 19 | 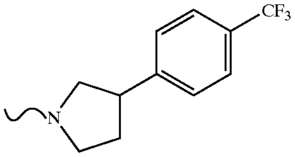 |
| 20 | 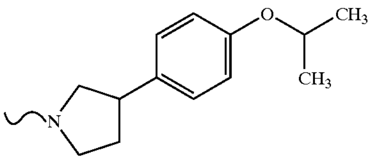 |
| 21 | 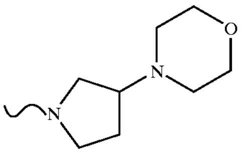 |
TABLE 42
| | |
|---|---|
| | 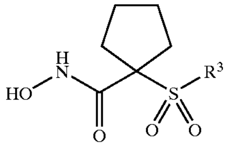 |
| | 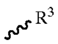 |
| 1 | 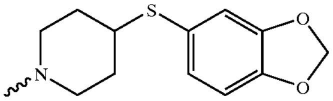 |
| 2 | 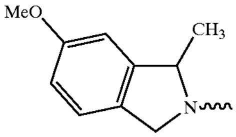 |
TABLE 42-continued
| | |
|---|---|
| | 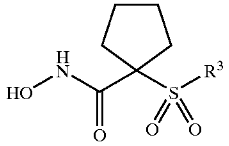 |
| | 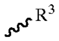 |
| 3 | 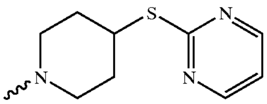 |
| 4 | 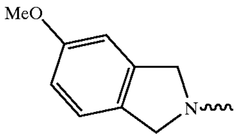 |
| 5 | 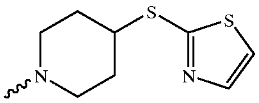 |
| 6 | 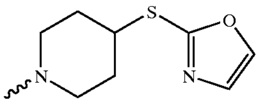 |
| 7 | 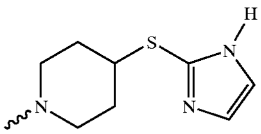 |
| 8 | 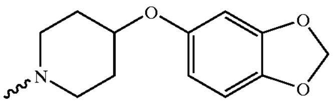 |
| 9 | 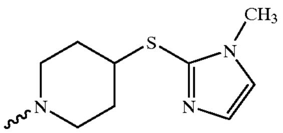 |
| 10 | 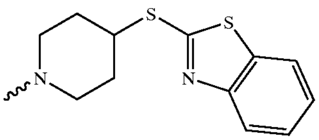 |
| 11 | 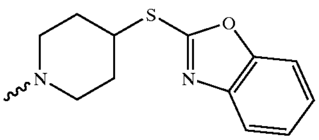 |

TABLE 43
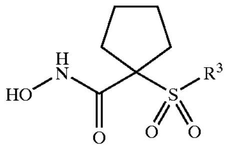
| | 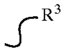 |
|---|---|
| 1 | 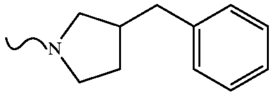 |
| 2 | 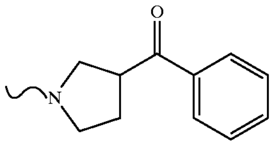 |
| 3 | 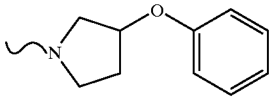 |
| 4 | 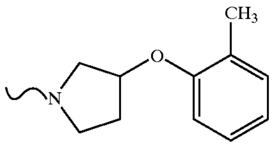 |
| 5 | 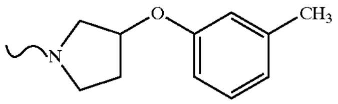 |
| 6 | 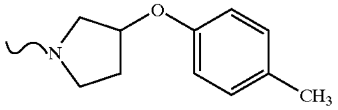 |
| 7 | 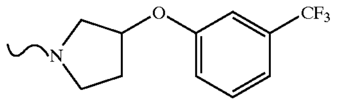 |
| 8 | 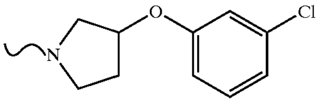 |
| 9 | 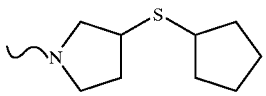 |
| 10 | 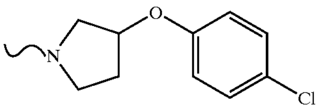 |
| 11 | 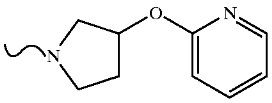 |
TABLE 43-continued
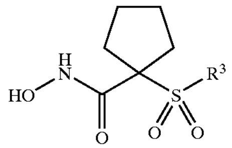
| | 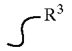 |
|---|---|
| 12 | 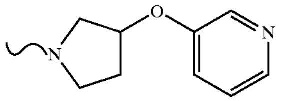 |
| 13 | 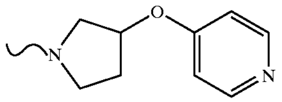 |
| 14 | 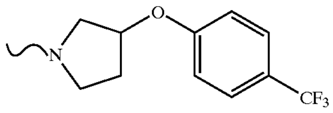 |
| 15 | 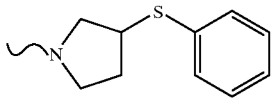 |
| 16 | 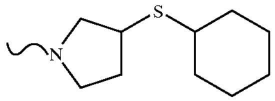 |
| 17 | 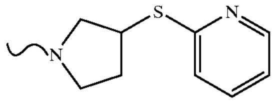 |
| 18 | 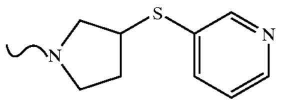 |
| 19 | 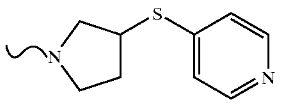 |
| 20 | 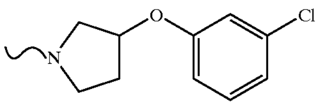 |
| 21 | 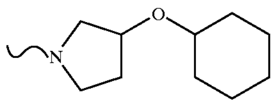 |

TABLE 44
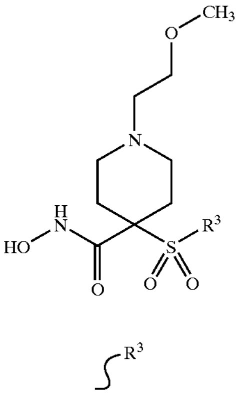
| | |
|---|---|
| 1 | 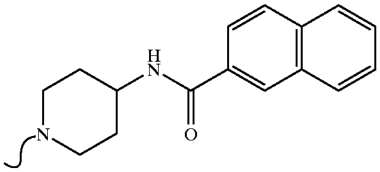 |
| 2 | 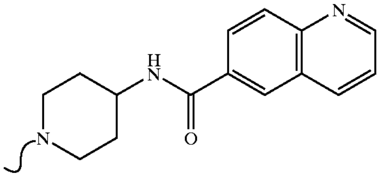 |
| 3 | 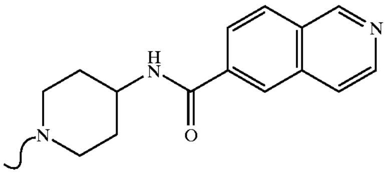 |
| 4 | 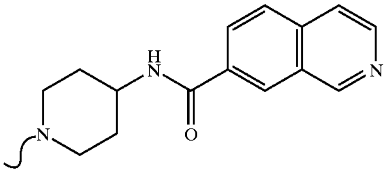 |
| 5 | 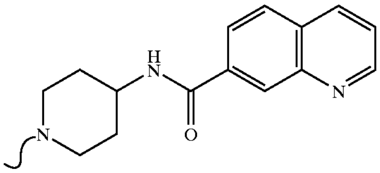 |
| 6 | 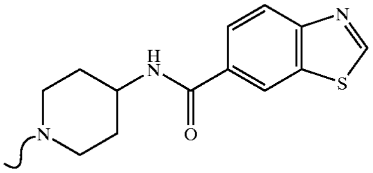 |
TABLE 44-continued
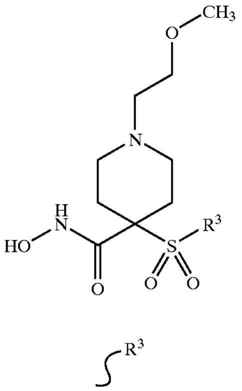
| | |
|---|---|
| 7 | 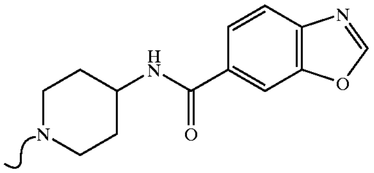 |
| 8 | 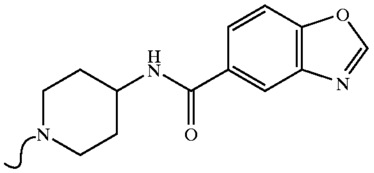 |
| 9 | 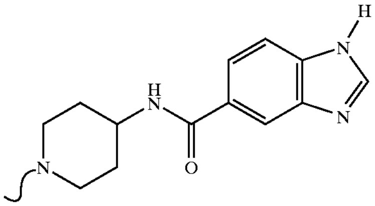 |
| 10 | 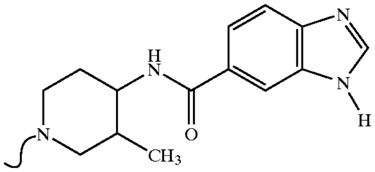 |
| 11 | 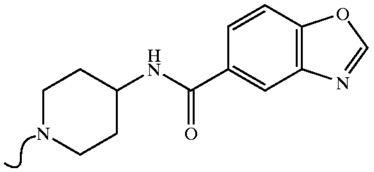 |
| 12 | 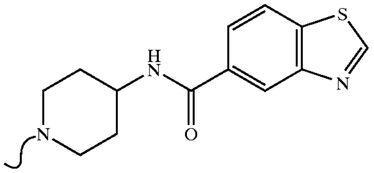 |

TABLE 44-continued
| | |
|---|---|
| 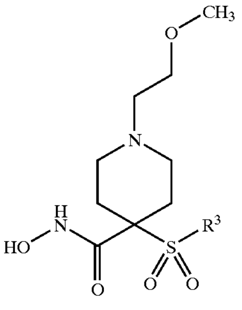 | |
| 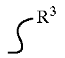 | |
| 13 | 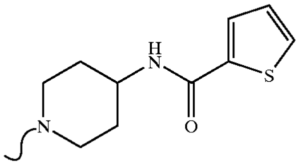 |
| 14 | 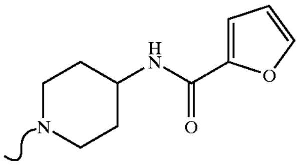 |
| 15 | 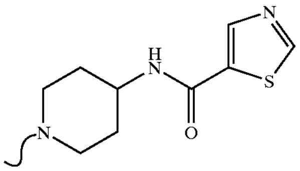 |
| 16 | 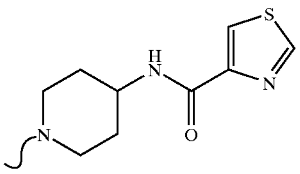 |
| 17 | 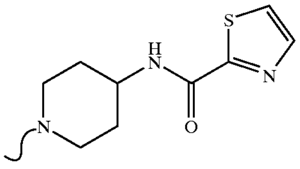 |
| 18 | 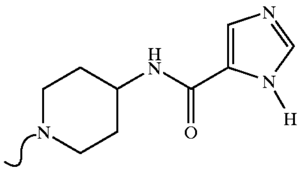 |
TABLE 45
| | |
|---|---|
| 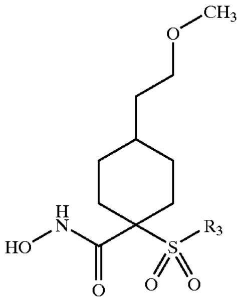 | |
| 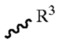 | |
| 1 | 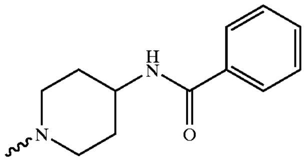 |
| 2 | 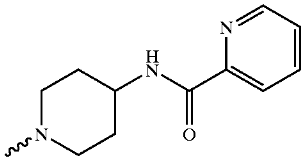 |
| 3 | 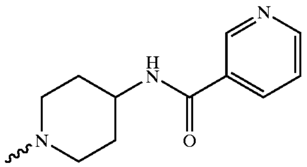 |
| 4 | 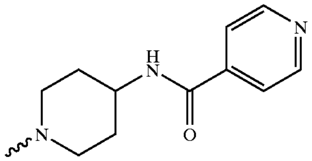 |
| 5 | 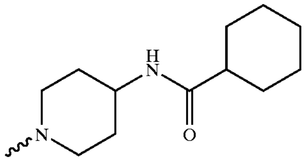 |
| 6 | 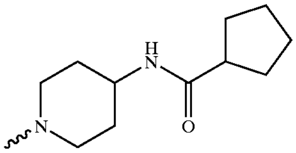 |
| 7 | 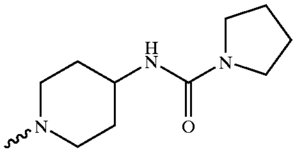 |

TABLE 45-continued
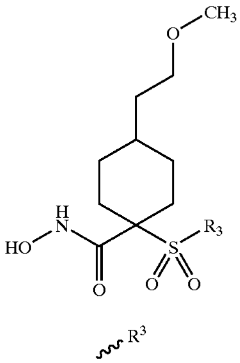
8
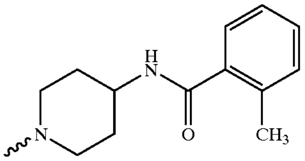
9
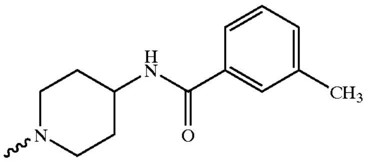
10
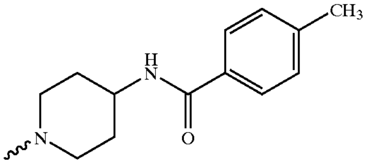
11
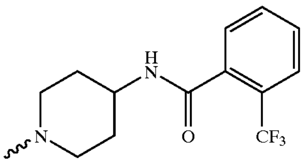
12
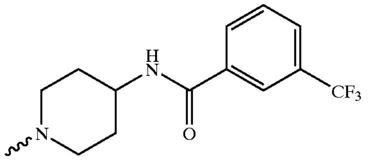
13
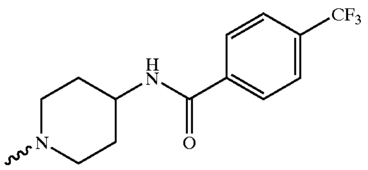
14
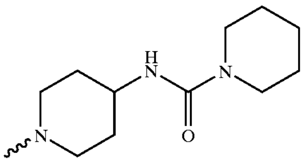
TABLE 45-continued
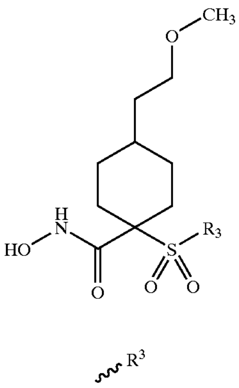
15
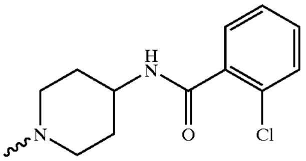
16
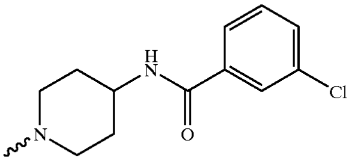
17
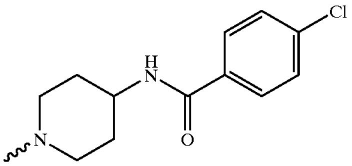
18
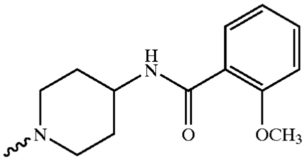
19
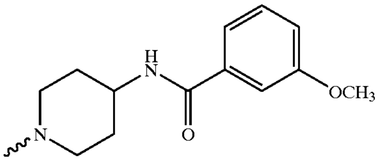
20
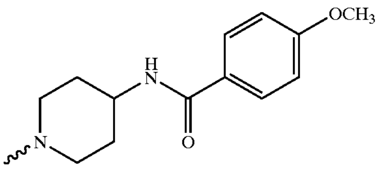

TABLE 45-continued
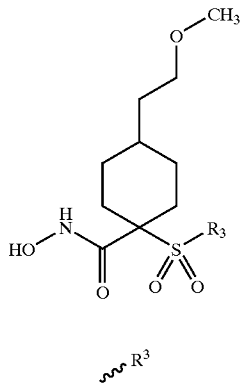
| | |
|---|---|
| 21 | 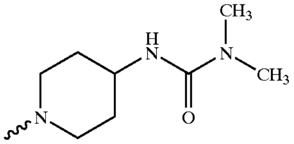 |
TABLE 46
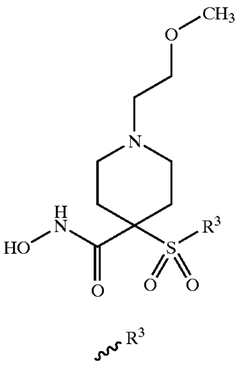
| | |
|---|---|
| 1 | 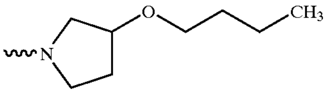 |
| 2 | 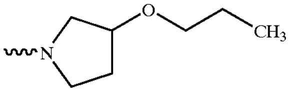 |
| 3 | 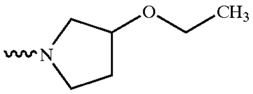 |
| 4 | 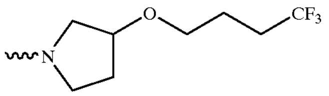 |
| 5 | 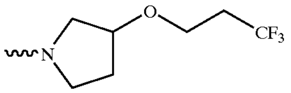 |
TABLE 46-continued
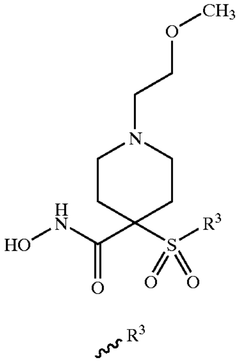
| | |
|---|---|
| 6 | 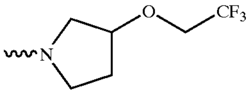 |
| 7 | 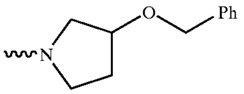 |
| 8 | 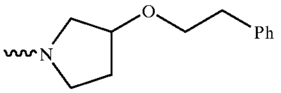 |
| 9 | 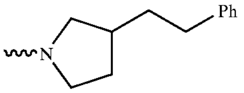 |
| 10 | 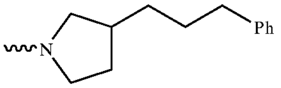 |
| 11 | 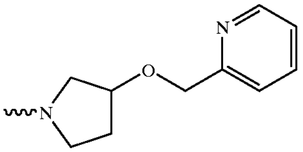 |
| 12 | 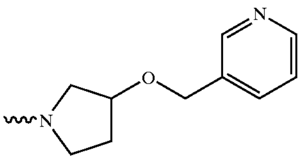 |
| 13 | 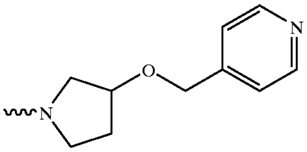 |
| 14 | 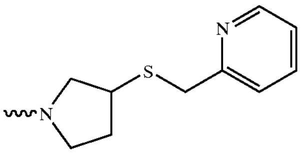 |

TABLE 46-continued
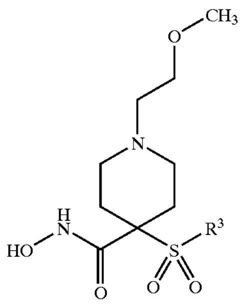
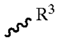
| | |
|---|---|
| 15 | 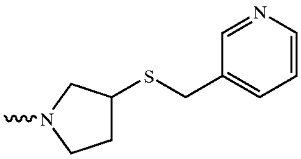 |
| 16 | 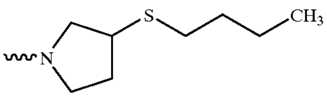 |
| 17 | 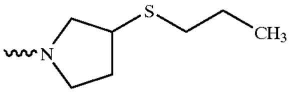 |
| 18 | 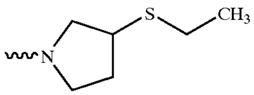 |
| 19 | 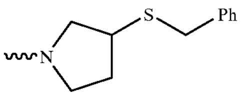 |
| 20 | 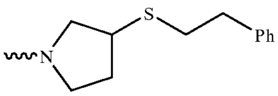 |
| 21 | 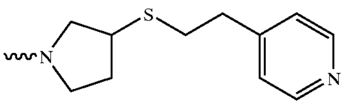 |
| 22 | 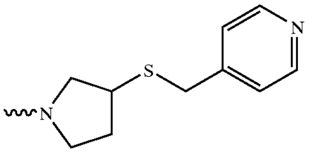 |
TABLE 47
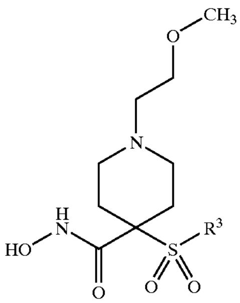
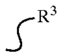
| | |
|---|---|
| 1 | 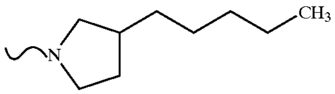 |
| 2 | 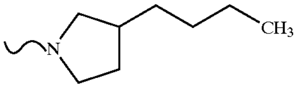 |
| 3 | 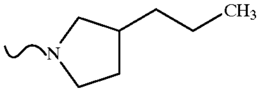 |
| 4 | 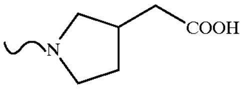 |
| 5 | 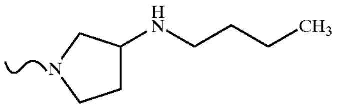 |
| 6 | 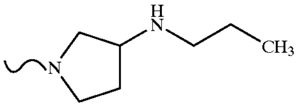 |
| 7 | 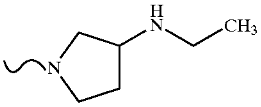 |
| 8 | 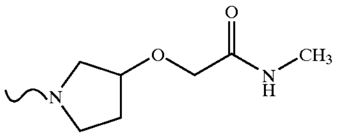 |
| 9 | 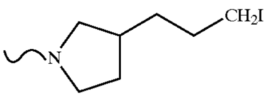 |
| 10 | 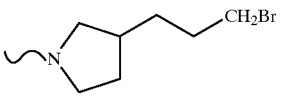 |

TABLE 47-continued
| 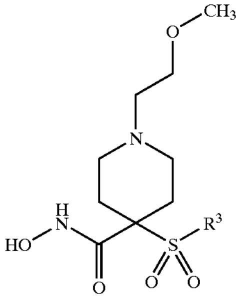 | |
|---|---|
| | 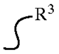 |
| 11 | 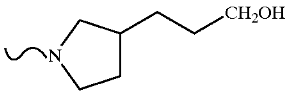 |
| 12 | 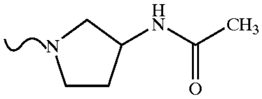 |
| 13 | 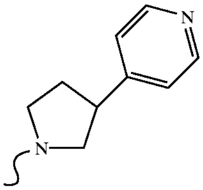 |
| 14 | 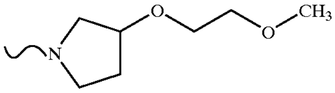 |
| 15 | 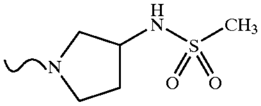 |
| 16 | 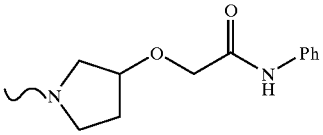 |
| 17 | 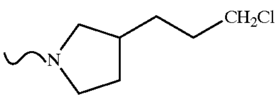 |
| 18 | 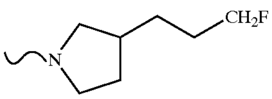 |
| 19 | 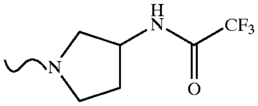 |
TABLE 47-continued
| 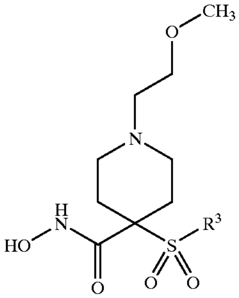 | |
|---|---|
| | 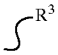 |
| 20 | 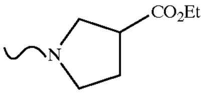 |
| 21 | 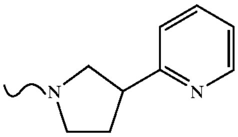 |
| 22 | 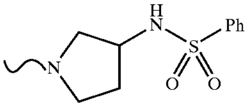 |
| 23 | 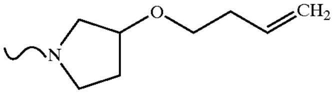 |
| 24 | 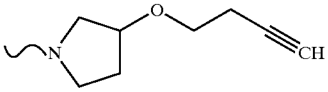 |
| 25 | 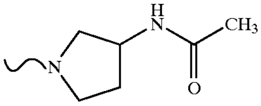 |
| 26 | 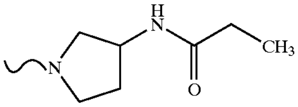 |
| 27 | 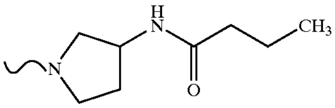 |
| 28 | 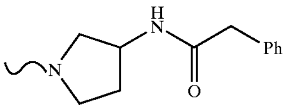 |

TABLE 47-continued
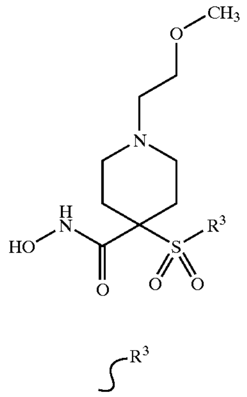
| | |
|---|---|
| 29 | 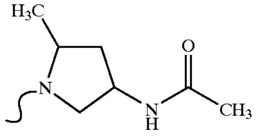 |
| 30 | 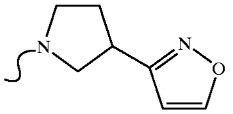 |
TABLE 48
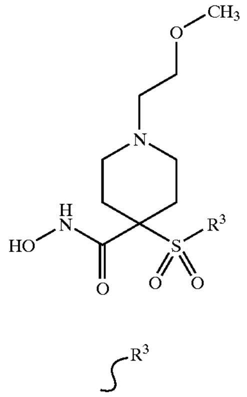
| | |
|---|---|
| 1 | 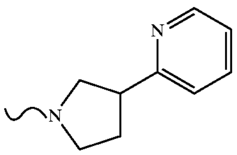 |
| 2 | 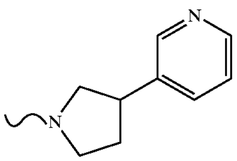 |
TABLE 48-continued
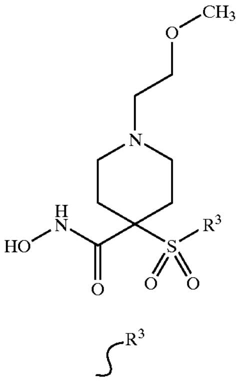
| | |
|---|---|
| 3 | 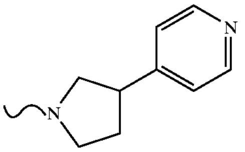 |
| 4 | 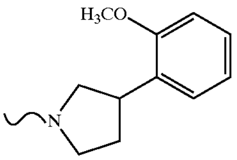 |
| 5 | 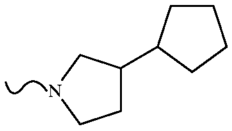 |
| 6 | 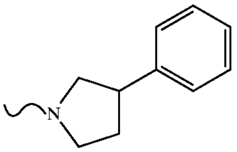 |
| 7 | 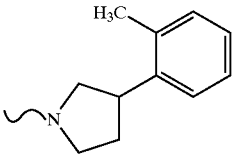 |
| 8 | 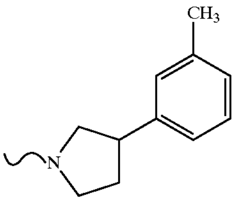 |
| 9 | 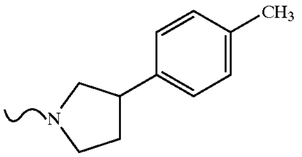 |

TABLE 48-continued
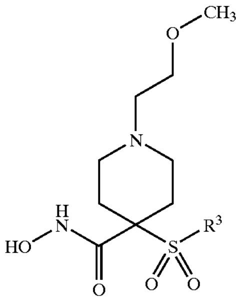
| | 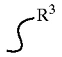 |
|---|---|
| 10 | 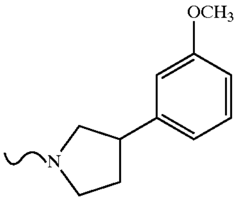 |
| 11 | 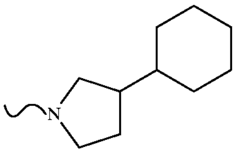 |
| 12 | 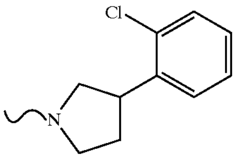 |
| 13 | 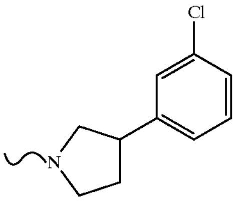 |
| 14 | 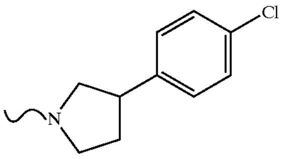 |
| 15 | 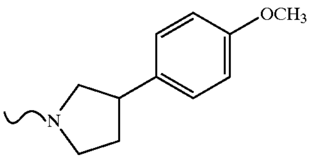 |
TABLE 48-continued
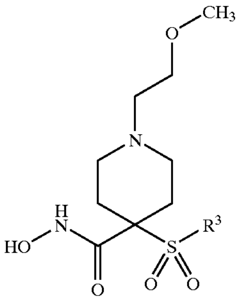
| | 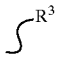 |
|---|---|
| 16 | 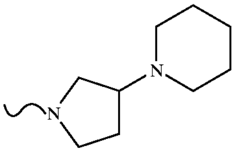 |
| 17 | 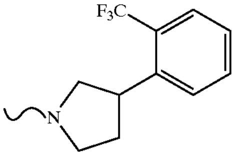 |
| 18 | 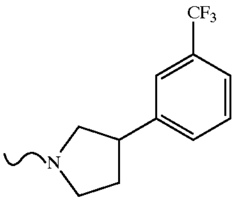 |
| 19 | 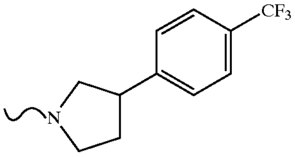 |
| 20 | 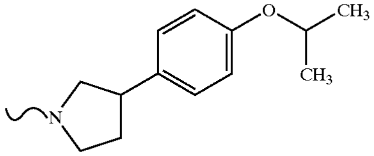 |
| 21 | 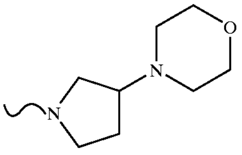 |

TABLE 49
| 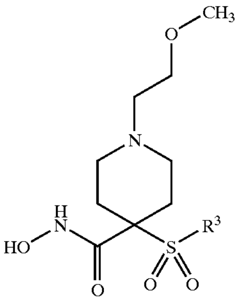 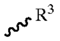 | |
|---|---|
| 1 | 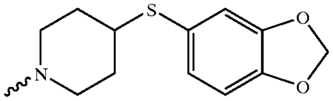 |
| 2 | 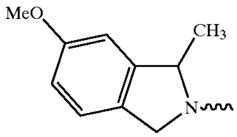 |
| 3 | 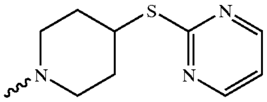 |
| 4 | 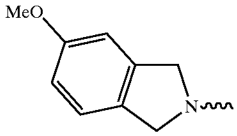 |
| 5 | 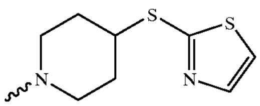 |
| 6 | 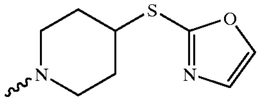 |
| 7 | 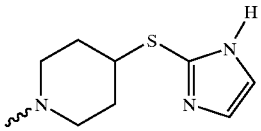 |
| 8 | 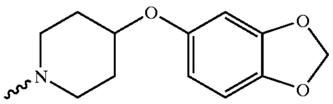 |
| 9 | 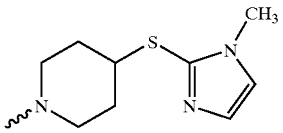 |
TABLE 49-continued
| 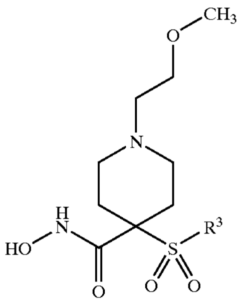 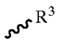 | |
|---|---|
| 10 | 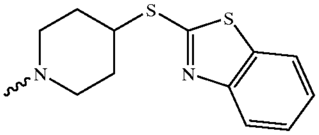 |
| 11 | 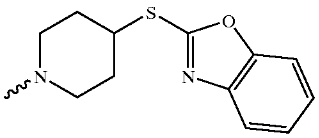 |
TABLE 50
| 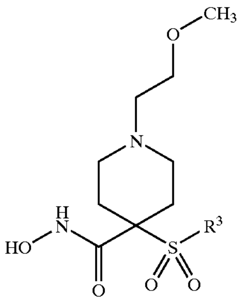 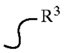 | |
|---|---|
| 1 | 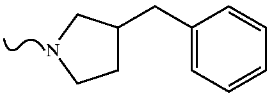 |
| 2 | 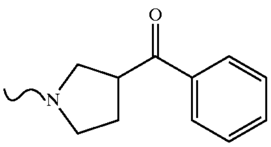 |
| 3 | 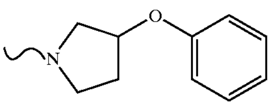 |

TABLE 50-continued
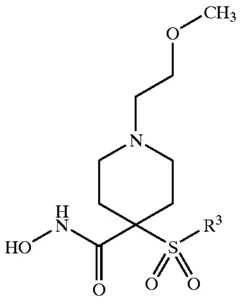
| | |
|---|---|
| | 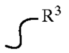 |
| 4 | 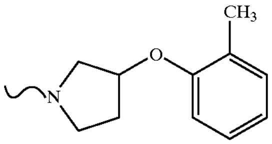 |
| 5 | 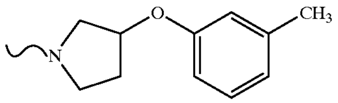 |
| 6 | 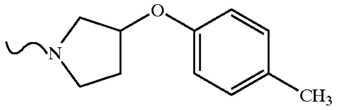 |
| 7 | 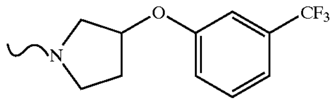 |
| 8 | 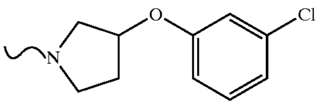 |
| 9 | 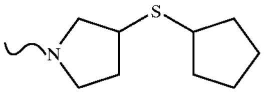 |
| 10 | 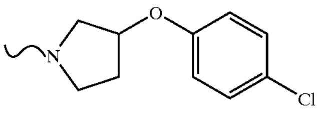 |
| 11 | 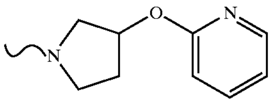 |
| 12 | 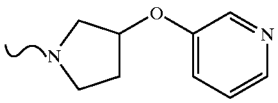 |
| 13 | 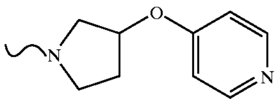 |
TABLE 50-continued
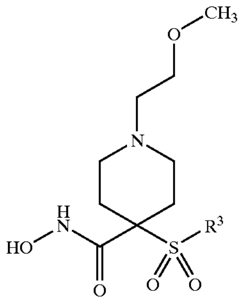
| | |
|---|---|
| |  |
| 14 | 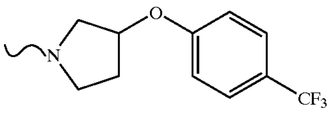 |
| 15 | 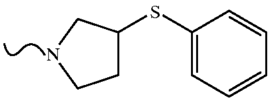 |
| 16 | 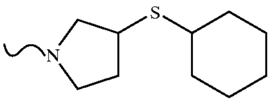 |
| 17 | 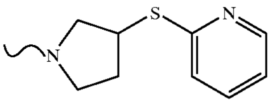 |
| 18 | 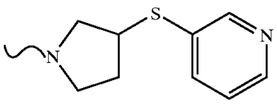 |
| 19 | 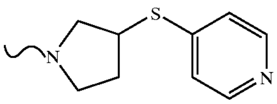 |
| 20 | 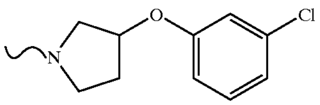 |
| 21 | 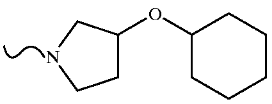 |

TABLE 51
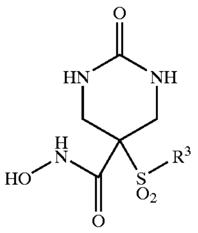
| | 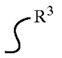 |
|---|---|
| 1 | 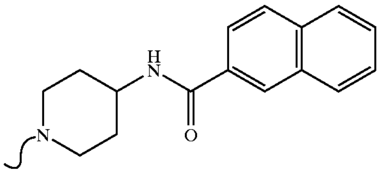 |
| 2 | 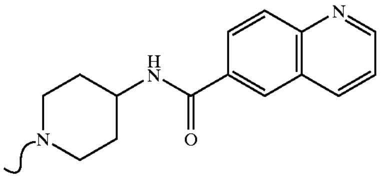 |
| 3 | 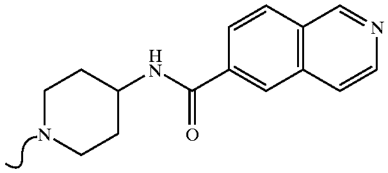 |
| 4 | 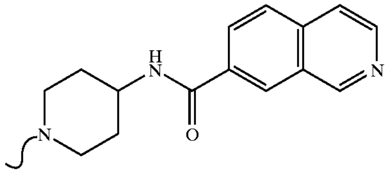 |
| 5 | 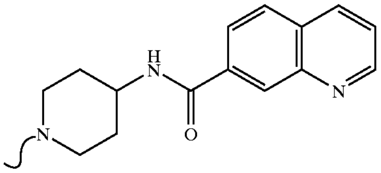 |
| 6 | 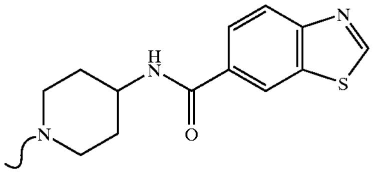 |
| 7 | 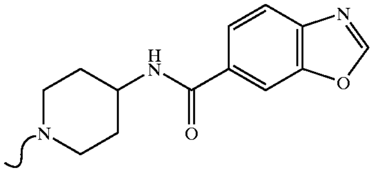 |
TABLE 51-continued
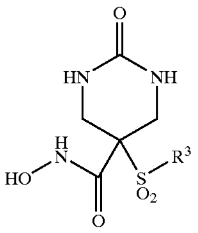
| | 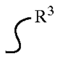 |
|---|---|
| 8 | 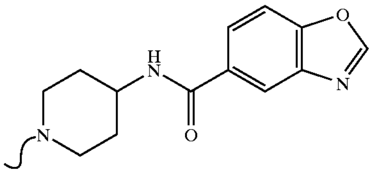 |
| 9 | 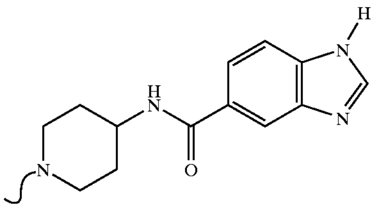 |
| 10 | 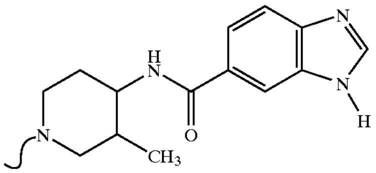 |
| 11 | 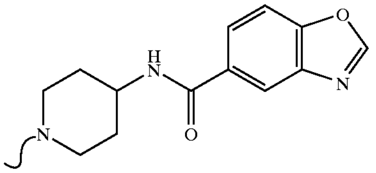 |
| 12 | 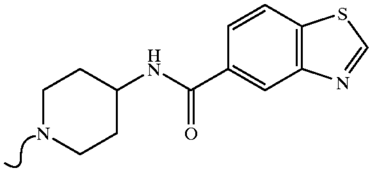 |
| 13 | 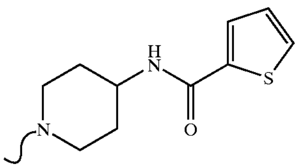 |
| 14 | 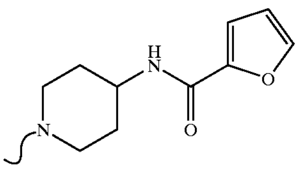 |

TABLE 51-continued
| | 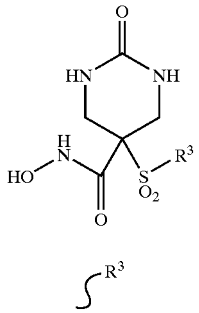 |
|---|---|
| 15 | 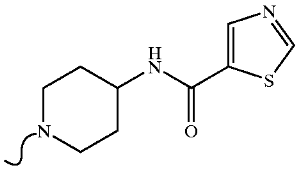 |
| 16 | 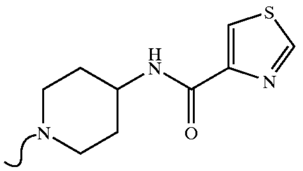 |
| 17 | 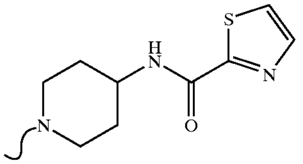 |
| 18 | 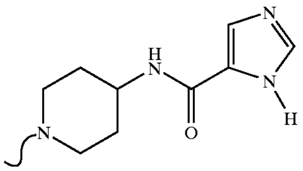 |
TABLE 52
| | 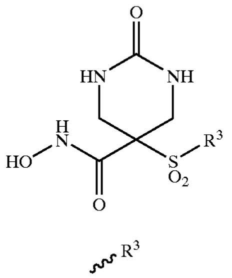 |
|---|---|
| 1 | 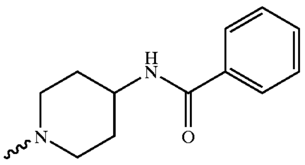 |
TABLE 52-continued
| | 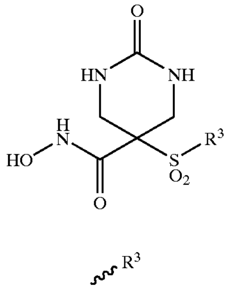 |
|---|---|
| 2 | 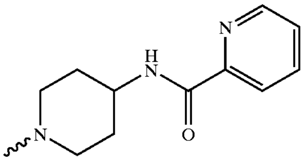 |
| 3 | 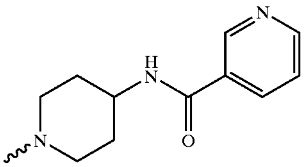 |
| 4 | 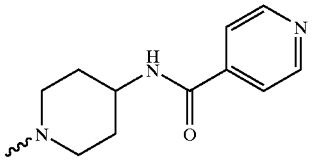 |
| 5 | 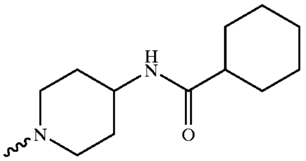 |
| 6 | 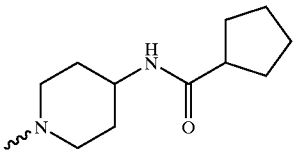 |
| 7 | 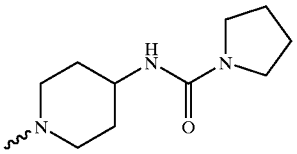 |
| 8 | 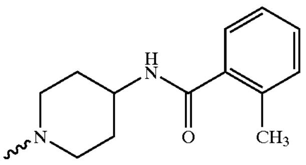 |

TABLE 52-continued
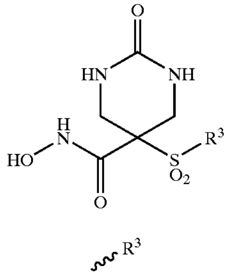
9
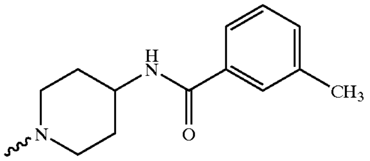
10
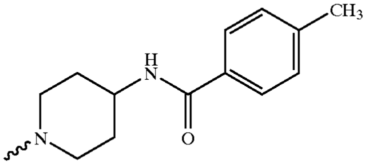
11
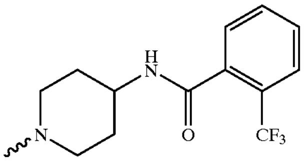
12
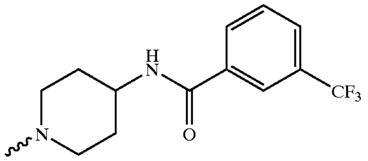
13
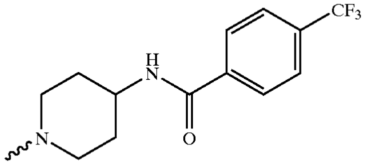
14
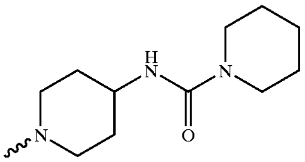
15
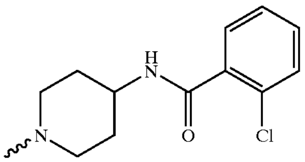
TABLE 52-continued
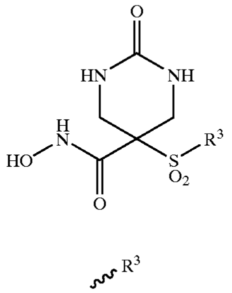
16
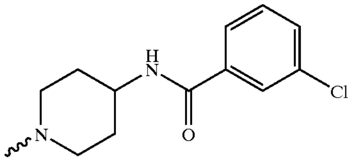
17
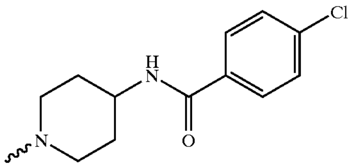
18
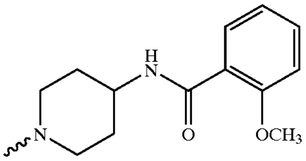
19
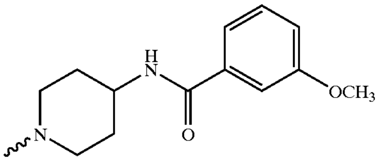
20
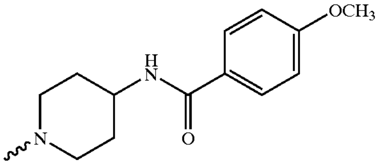
21
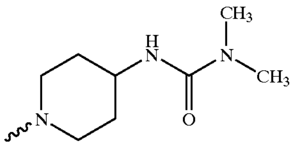

TABLE 53
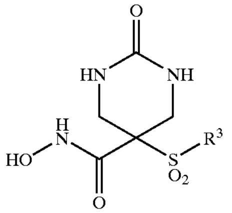
| | 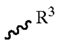 |
|---|---|
| 1 | 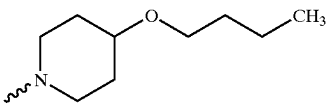 |
| 2 | 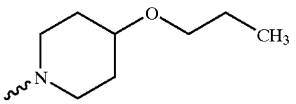 |
| 3 | 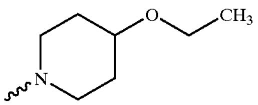 |
| 4 | 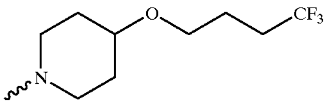 |
| 5 | 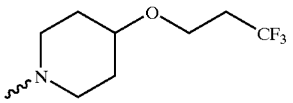 |
| 6 | 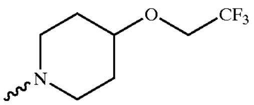 |
| 7 | 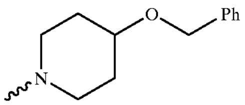 |
| 8 | 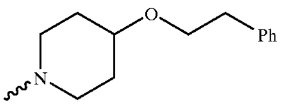 |
| 9 | 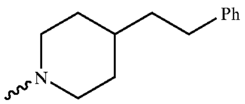 |
| 10 | 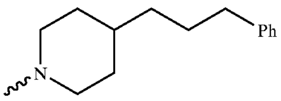 |
TABLE 53-continued
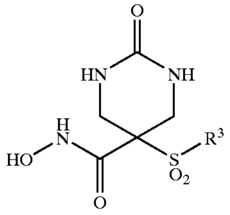
| | 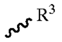 |
|---|---|
| 11 | 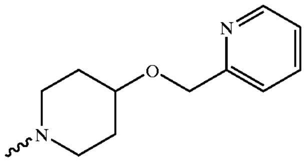 |
| 12 | 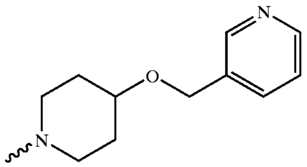 |
| 13 | 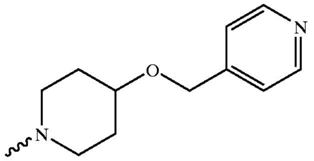 |
| 14 | 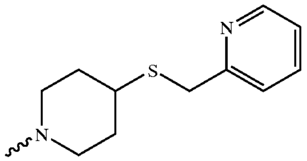 |
| 15 | 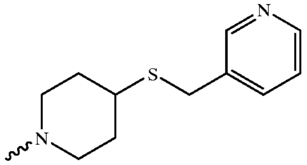 |
| 16 | 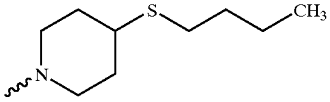 |
| 17 | 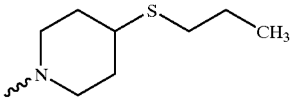 |
| 18 | 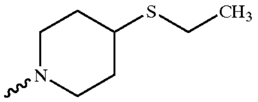 |

TABLE 53-continued
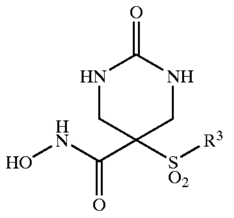
| | 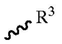 |
|---|---|
| 19 | 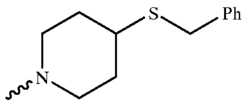 |
| 20 | 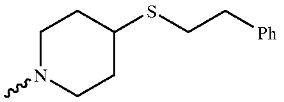 |
| 21 | 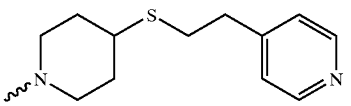 |
| 22 | 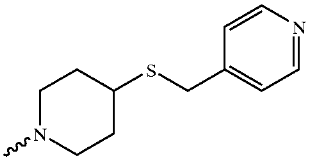 |
TABLE 54
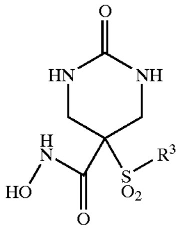
| | 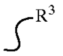 |
|---|---|
| 1 | 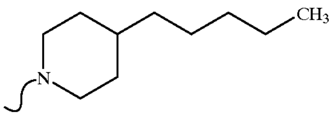 |
| 2 | 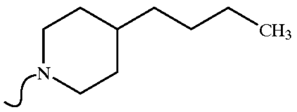 |
| 3 | 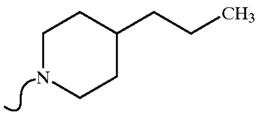 |
TABLE 54-continued
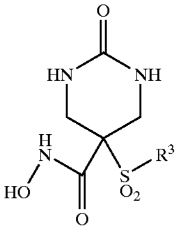
| | 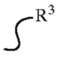 |
|---|---|
| 4 | 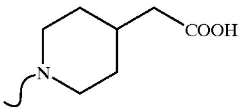 |
| 5 | 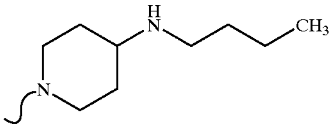 |
| 6 | 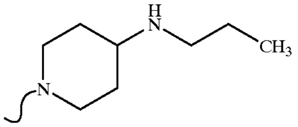 |
| 7 | 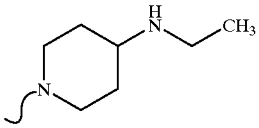 |
| 8 | 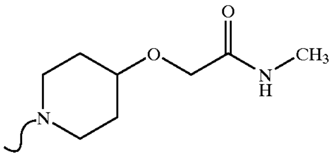 |
| 9 | 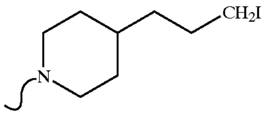 |
| 10 | 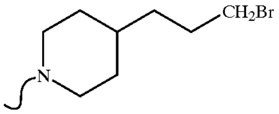 |
| 11 | 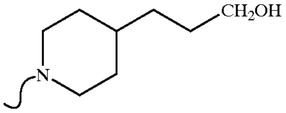 |
| 12 | 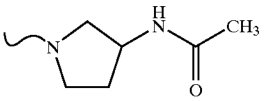 |

TABLE 54-continued
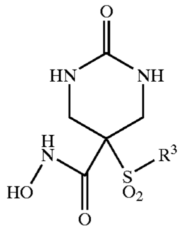
| | 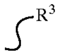 |
|---|---|
| 13 | 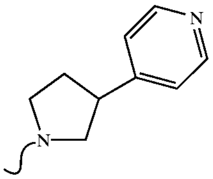 |
| 14 | 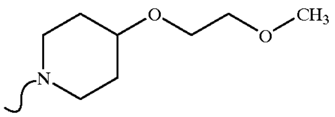 |
| 15 | 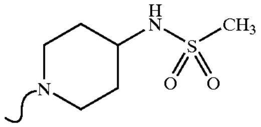 |
| 16 | 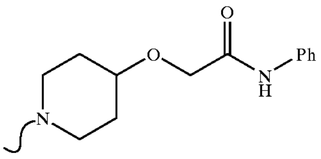 |
| 17 | 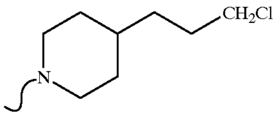 |
| 18 | 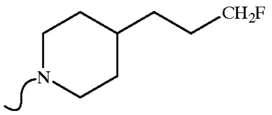 |
| 19 | 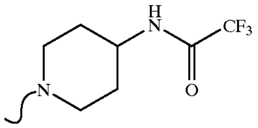 |
| 20 | 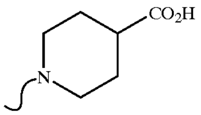 |
TABLE 54-continued
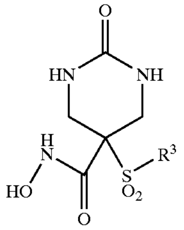
| | 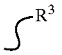 |
|---|---|
| 21 | 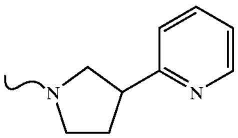 |
| 22 | 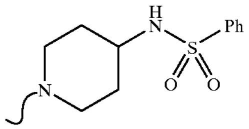 |
| 23 | 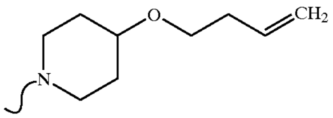 |
| 24 | 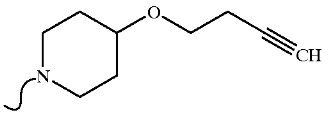 |
| 25 | 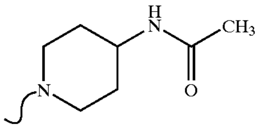 |
| 26 | 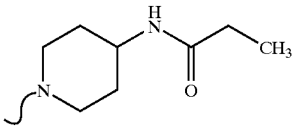 |
| 27 | 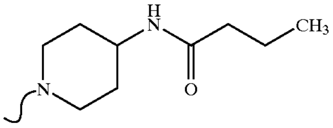 |
| 28 | 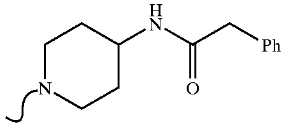 |
| 29 | 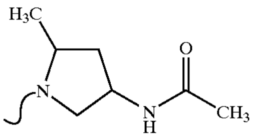 |

TABLE 54-continued
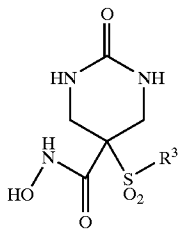
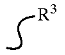
| | |
|---|---|
| 30 | 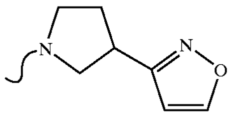 |
| 31 | 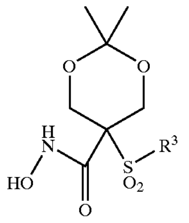 |
TABLE 55
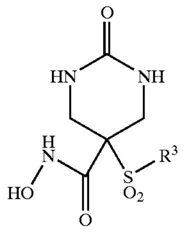
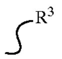
| | |
|---|---|
| 1 | 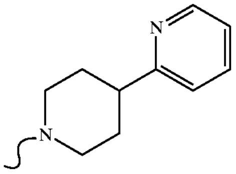 |
| 2 | 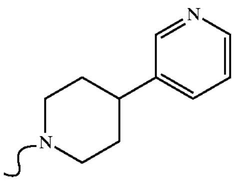 |
TABLE 55-continued
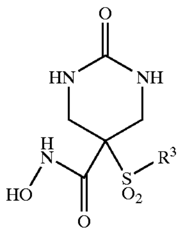
| | |
|---|---|
| 3 | 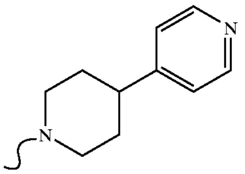 |
| 4 | 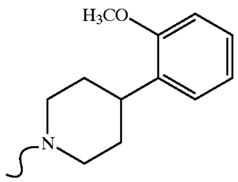 |
| 5 | 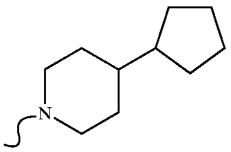 |
| 6 | 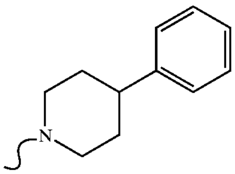 |
| 7 | 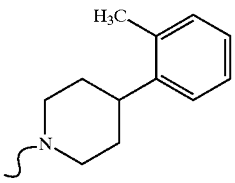 |
| 8 | 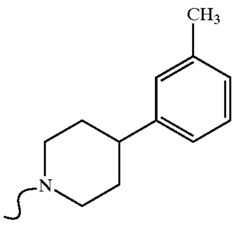 |

TABLE 55-continued
| 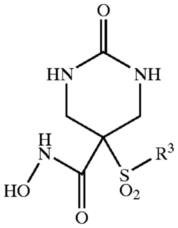 | |
|---|---|
| | 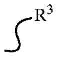 |
| 9 | 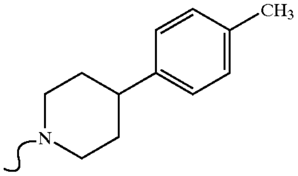 |
| 10 | 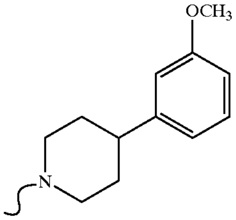 |
| 11 | 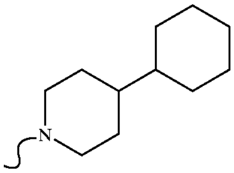 |
| 12 | 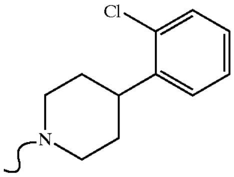 |
| 13 | 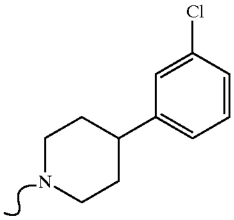 |
| 14 | 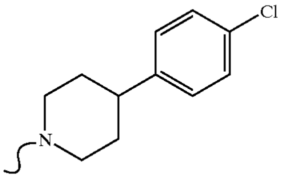 |
TABLE 55-continued
| 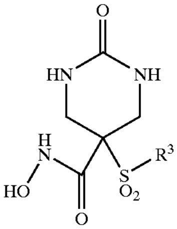 | |
|---|---|
| |  |
| 15 | 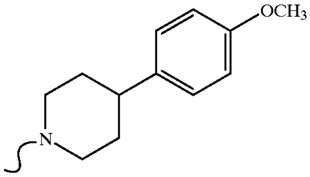 |
| 16 | 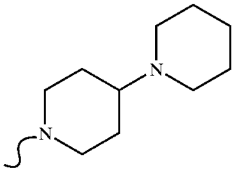 |
| 17 | 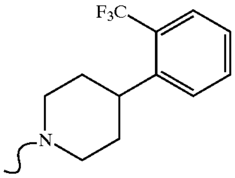 |
| 18 | 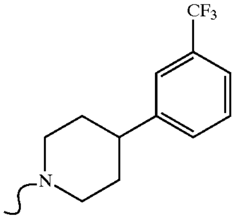 |
| 19 | 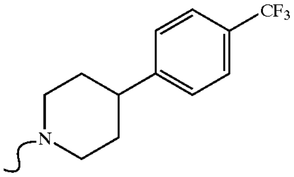 |
| 20 | 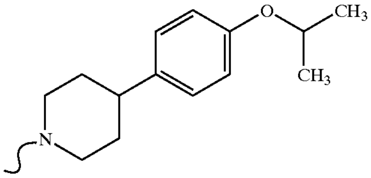 |

TABLE 55-continued
| 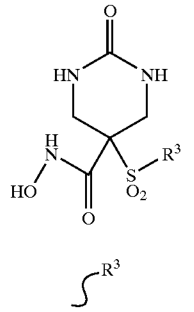 | |
|---|---|
| 21 | 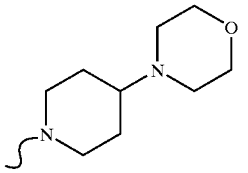 |
TABLE 56
| 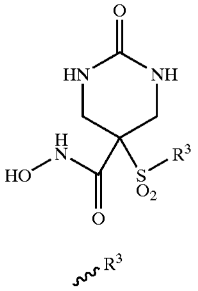 | |
|---|---|
| 1 | 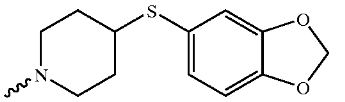 |
| 2 | 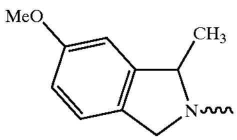 |
| 3 | 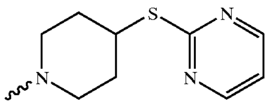 |
| 4 | 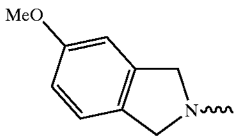 |
| 5 | 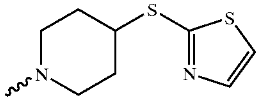 |
TABLE 56-continued
| 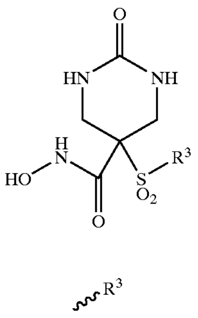 | |
|---|---|
| 6 | 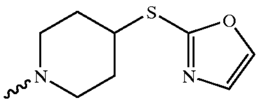 |
| 7 | 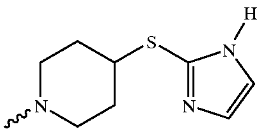 |
| 8 | 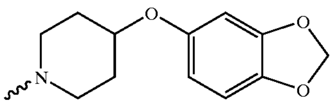 |
| 9 | 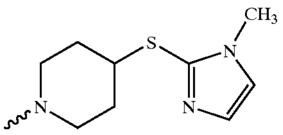 |
| 10 | 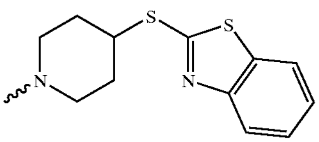 |
| 11 | 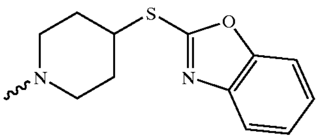 |

TABLE 59
| | 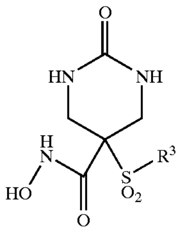 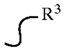 |
|---|---|
| 1 | 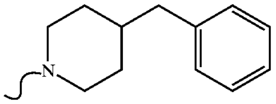 |
| 2 | 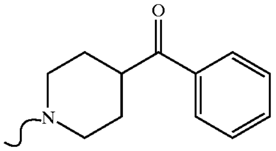 |
| 3 | 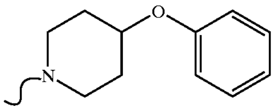 |
| 4 | 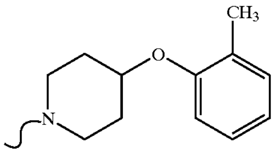 |
| 5 | 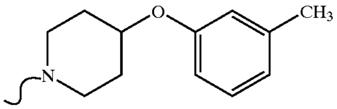 |
| 6 | 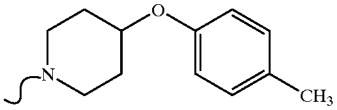 |
| 7 | 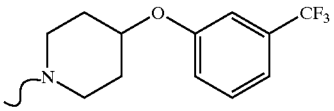 |
| 8 | 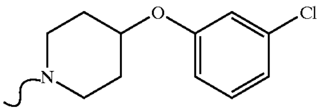 |
| 9 | 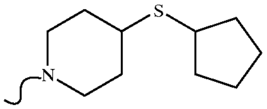 |
TABLE 59-continued
| | 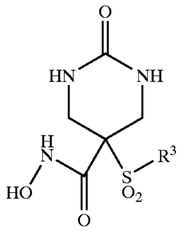 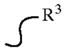 |
|---|---|
| 10 | 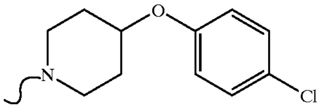 |
| 11 | 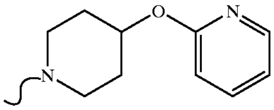 |
| 12 | 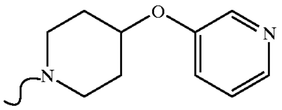 |
| 13 | 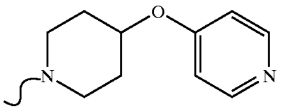 |
| 14 | 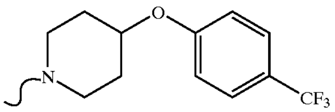 |
| 15 | 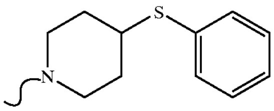 |
| 16 | 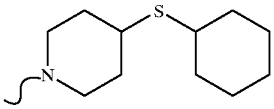 |
| 17 | 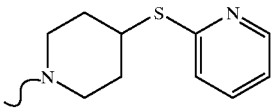 |
| 18 | 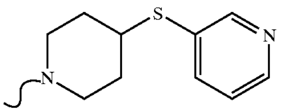 |
| 19 | 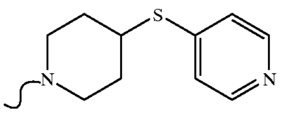 |

TABLE 59-continued
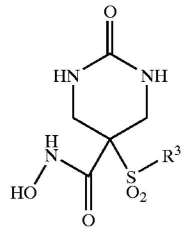
| 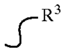 |
|---|
| 20 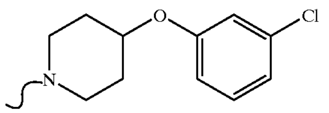 |
| 21 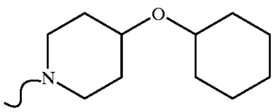 |
TABLE 58
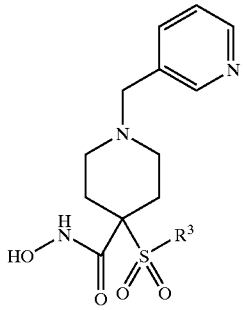
| 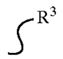 |
|---|
| 1 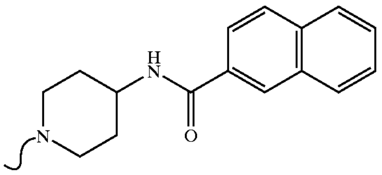 |
| 2 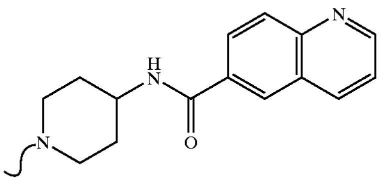 |
| 3 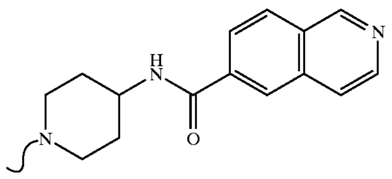 |
TABLE 58-continued
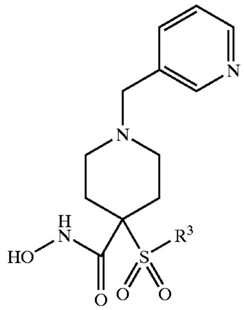
| 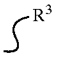 |
|---|
| 4 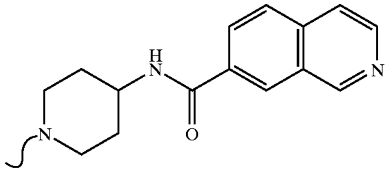 |
| 5 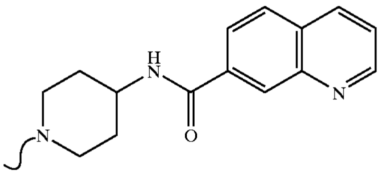 |
| 6 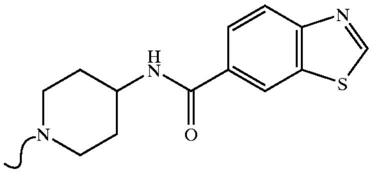 |
| 7 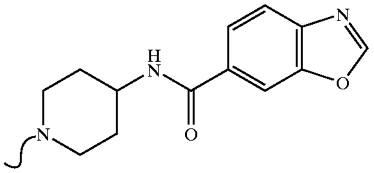 |
| 8 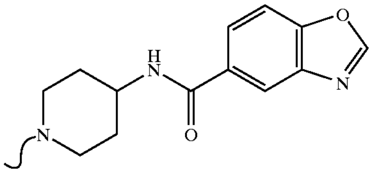 |
| 9 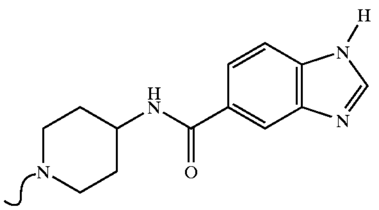 |

TABLE 58-continued
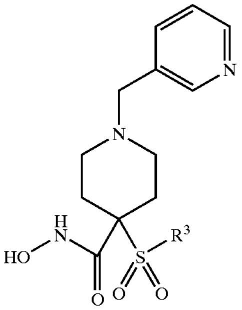
| 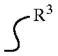 |  |
|---|---|
| 10 | 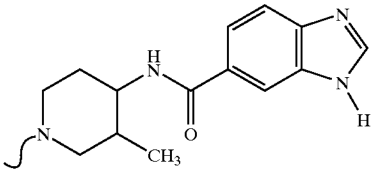 |
| 11 | 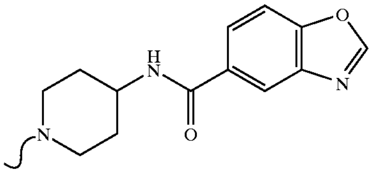 |
| 12 | 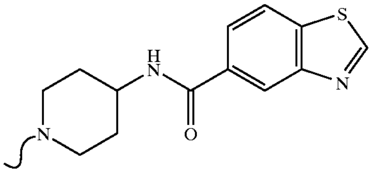 |
| 13 | 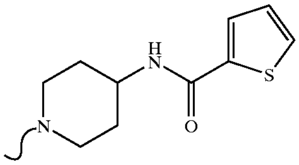 |
| 14 | 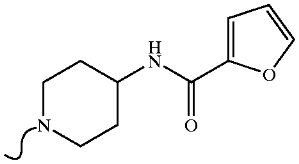 |
| 15 | 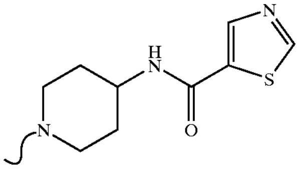 |
TABLE 58-continued
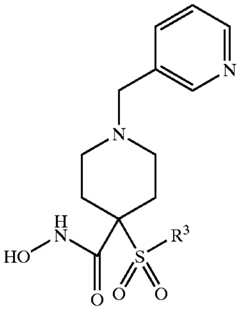
| 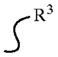 |  |
|---|---|
| 16 | 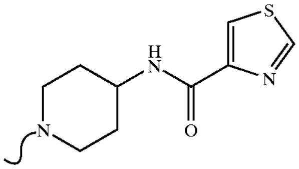 |
| 17 | 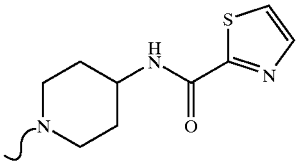 |
| 18 | 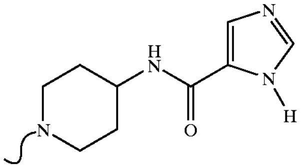 |
TABLE 59
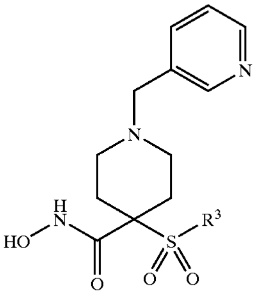
| 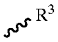 |  |
|---|---|
| 1 | 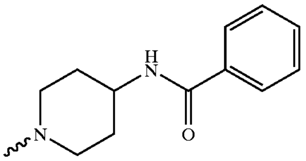 |

TABLE 59-continued
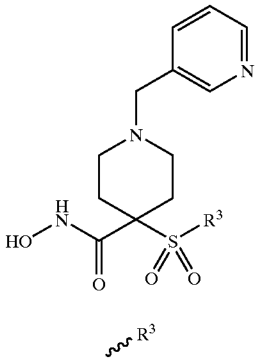
| | |
|---|---|
| 2 | 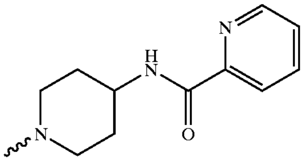 |
| 3 | 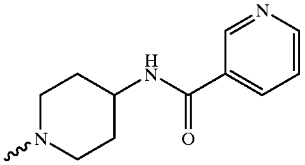 |
| 4 | 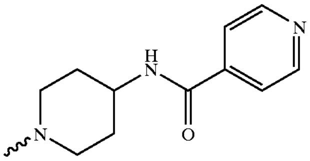 |
| 5 | 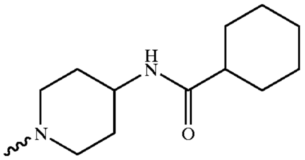 |
| 6 | 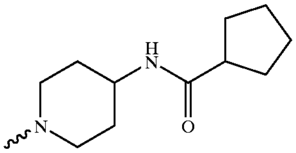 |
| 7 | 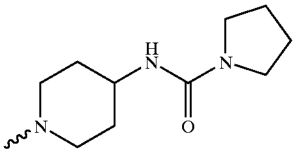 |
| 8 | 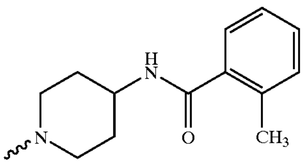 |
TABLE 59-continued
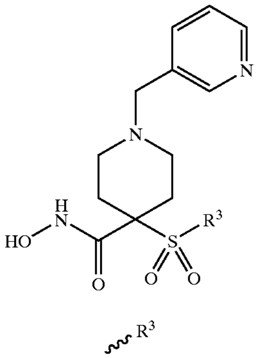
| | |
|---|---|
| 9 | 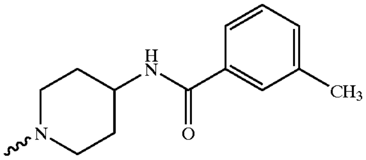 |
| 10 | 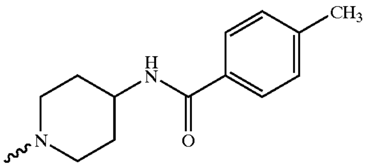 |
| 11 | 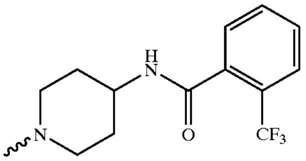 |
| 12 | 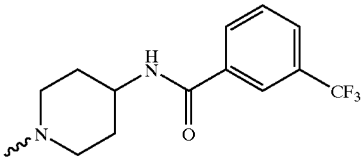 |
| 13 | 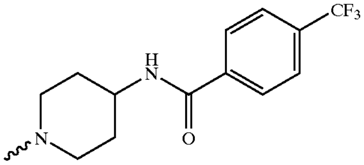 |
| 14 | 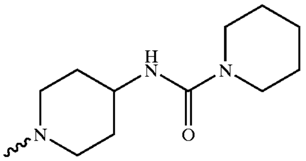 |
| 15 | 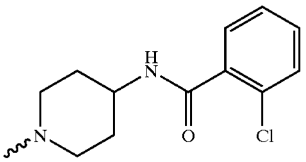 |

TABLE 59-continued
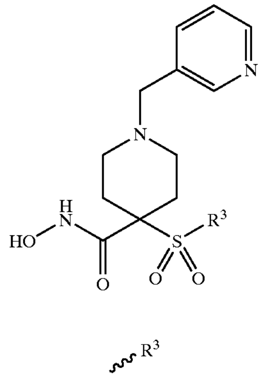
| | |
|---|---|
| 16 | 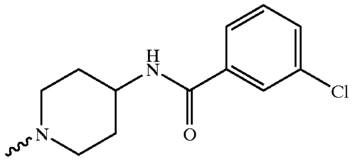 |
| 17 | 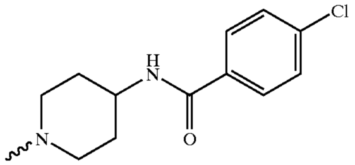 |
| 18 | 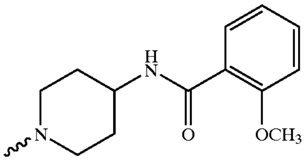 |
| 19 | 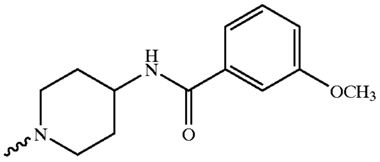 |
| 20 | 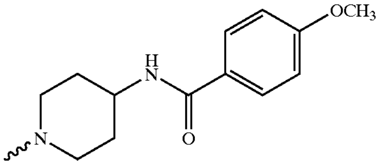 |
| 21 | 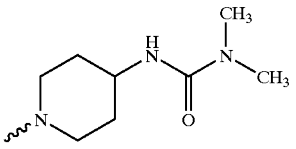 |
TABLE 60
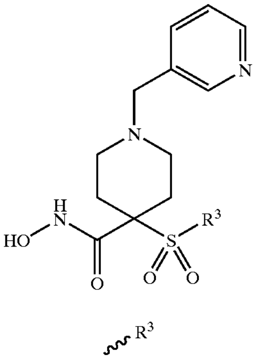
| | |
|---|---|
| 1 | 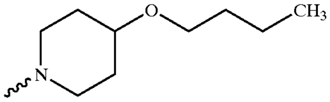 |
| 2 | 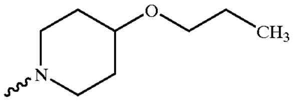 |
| 3 | 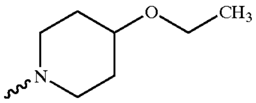 |
| 4 | 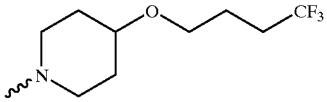 |
| 5 | 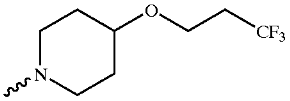 |
| 6 | 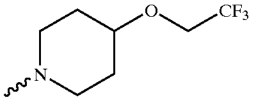 |
| 7 | 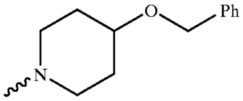 |
| 8 | 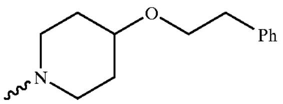 |
| 9 | 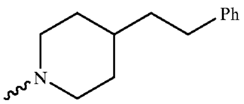 |
| 10 | 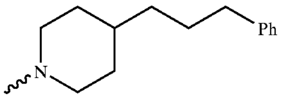 |

TABLE 60-continued
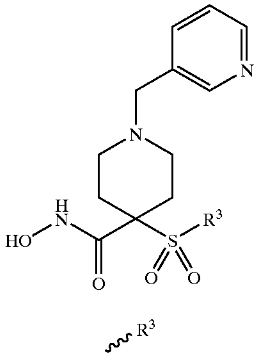
11
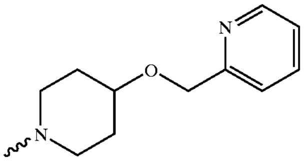
12
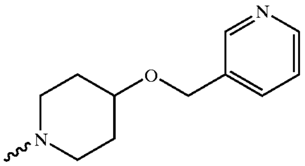
13
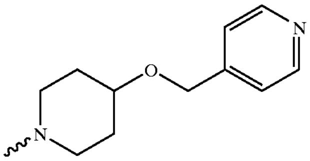
14
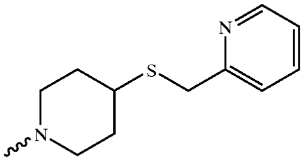
15
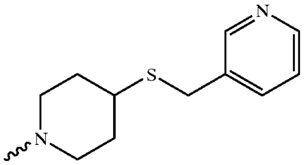
16
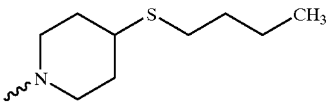
17
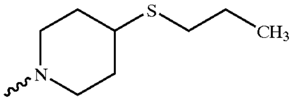
18
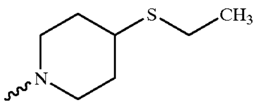
TABLE 60-continued
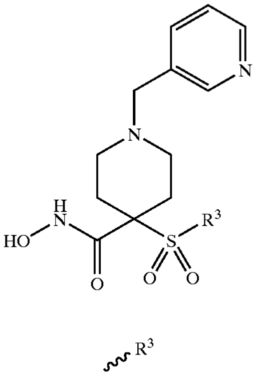
19
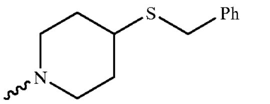
20
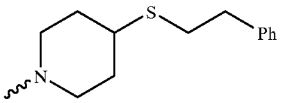
21
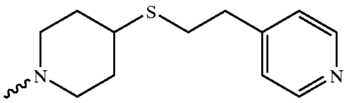
22
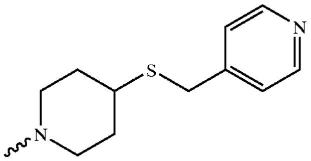
TABLE 61
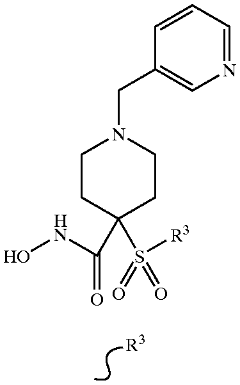
1
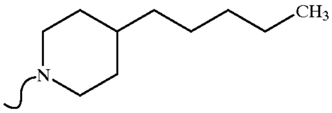

TABLE 61-continued
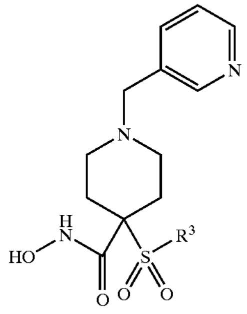
| | 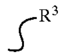 |
|---|---|
| 2 | 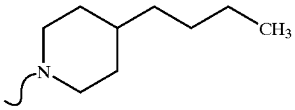 |
| 3 | 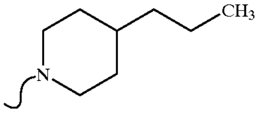 |
| 4 | 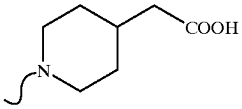 |
| 5 | 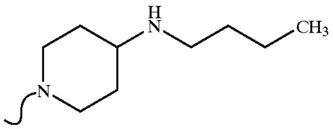 |
| 6 | 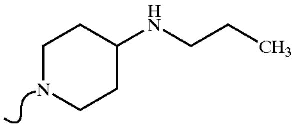 |
| 7 | 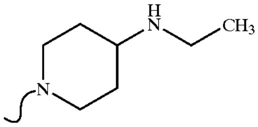 |
| 8 | 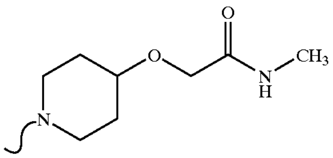 |
| 9 | 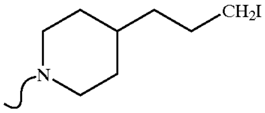 |
| 10 | 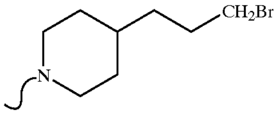 |
TABLE 61-continued
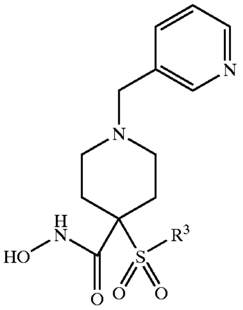
| | 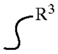 |
|---|---|
| 11 | 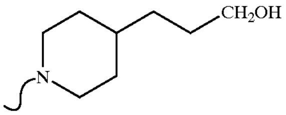 |
| 12 | 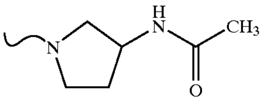 |
| 13 | 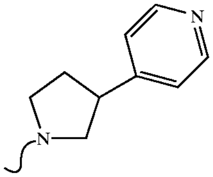 |
| 14 | 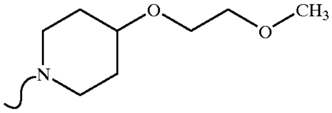 |
| 15 | 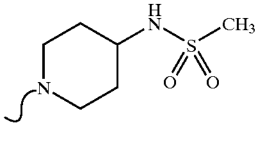 |
| 16 | 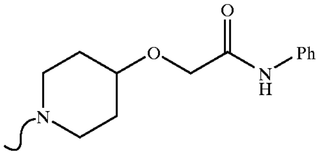 |
| 17 | 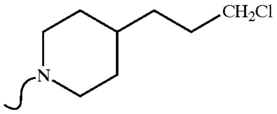 |
| 18 | 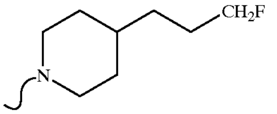 |

TABLE 61-continued
| | |
|---|---|
| | 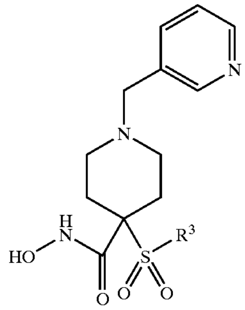 |
| | 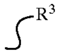 |
| 19 | 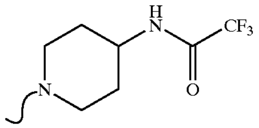 |
| 20 | 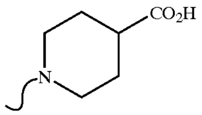 |
| 21 | 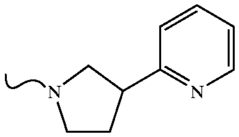 |
| 22 | 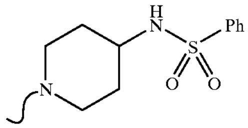 |
| 23 | 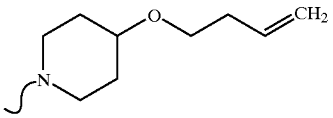 |
| 24 | 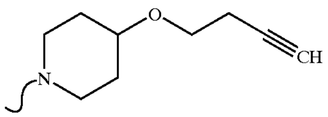 |
| 25 | 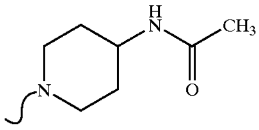 |
TABLE 61-continued
| | |
|---|---|
| | 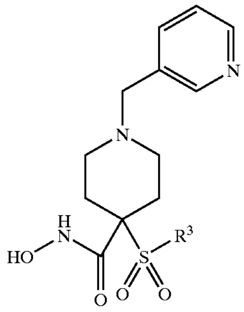 |
| | 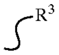 |
| 26 | 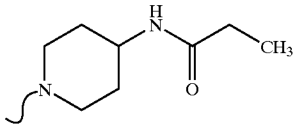 |
| 27 | 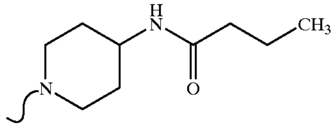 |
| 28 | 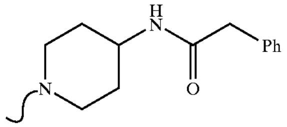 |
| 29 | 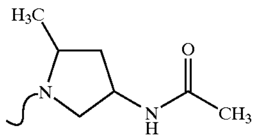 |
| 30 | 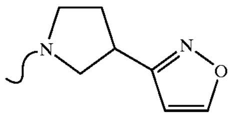 |
| 31 | 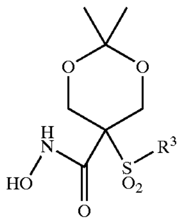 |

TABLE 62
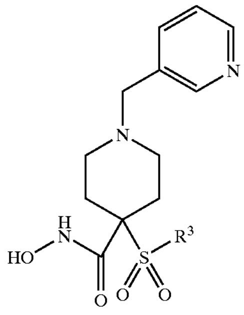
| | |
|---|---|
| 1 | 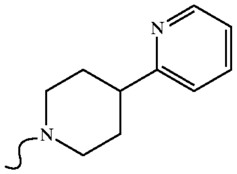 |
| 2 | 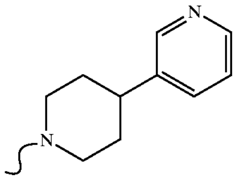 |
| 3 | 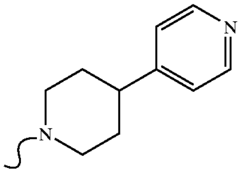 |
| 4 | 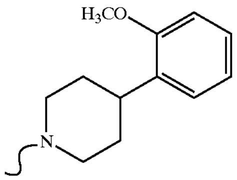 |
| 5 | 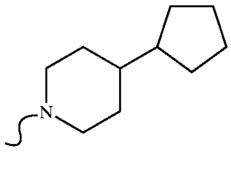 |
TABLE 62-continued
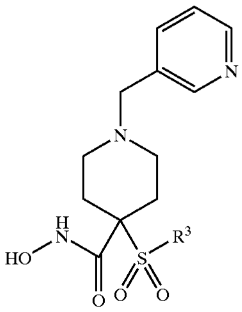
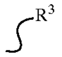
| | |
|---|---|
| 6 | 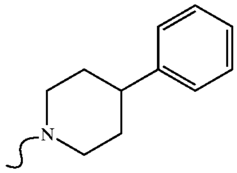 |
| 7 | 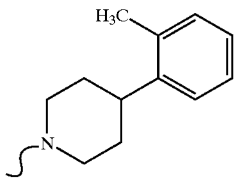 |
| 8 | 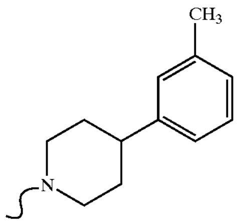 |
| 9 | 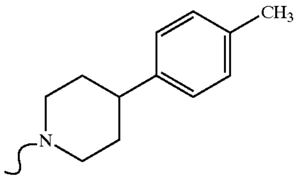 |
| 10 | 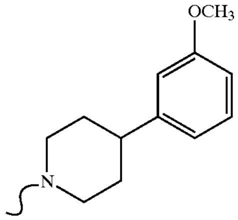 |

TABLE 62-continued
| | 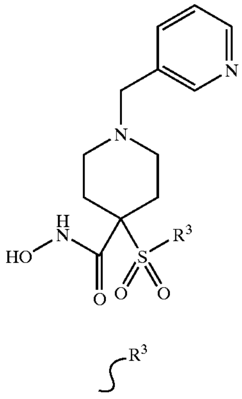 |
|---|---|
| 11 | 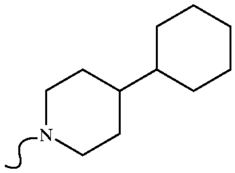 |
| 12 | 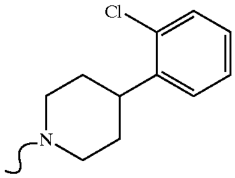 |
| 13 | 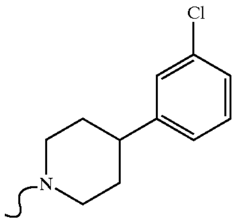 |
| 14 | 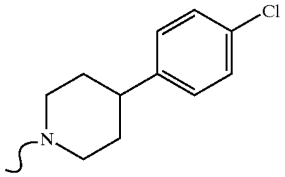 |
| 15 | 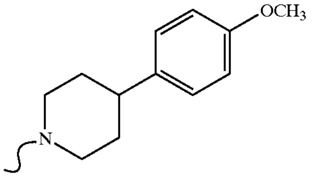 |
| 16 | 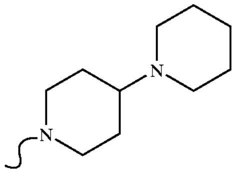 |
TABLE 62-continued
| | 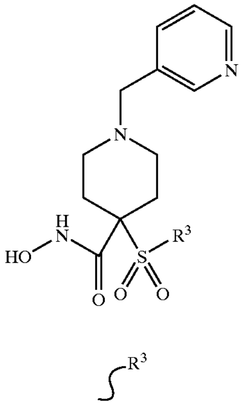 |
|---|---|
| 17 | 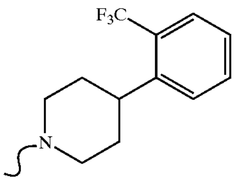 |
| 18 | 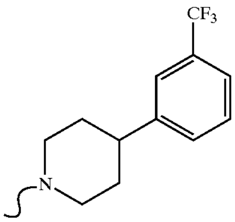 |
| 19 | 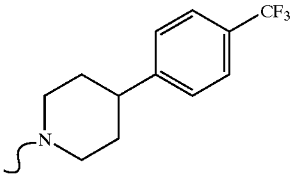 |
| 20 | 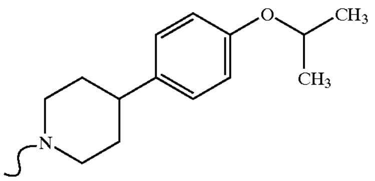 |
| 21 | 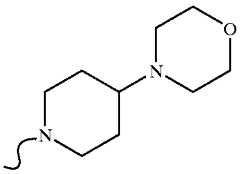 |

TABLE 63
| | |
|---|---|
| | 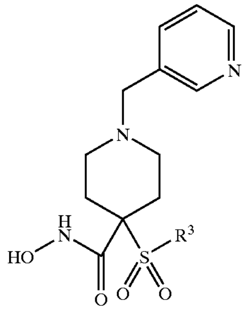 |
| | 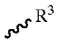 |
| 1 | 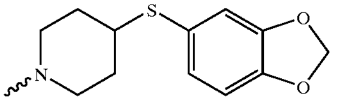 |
| 2 | 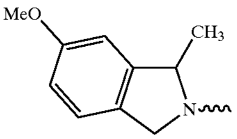 |
| 3 | 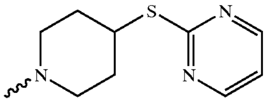 |
| 4 | 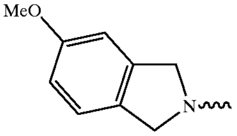 |
| 5 | 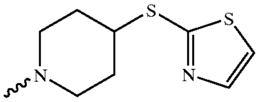 |
| 6 | 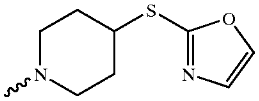 |
| 7 | 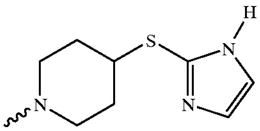 |
| 8 | 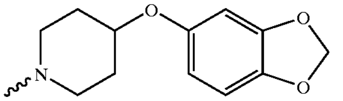 |
| 9 | 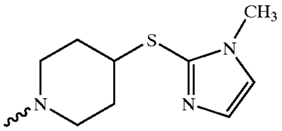 |
TABLE 63-continued
| | |
|---|---|
| | 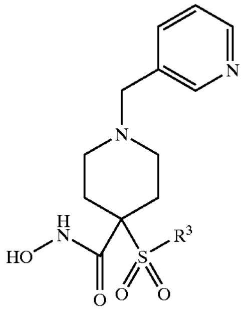 |
| | 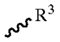 |
| 10 | 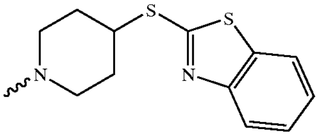 |
| 11 | 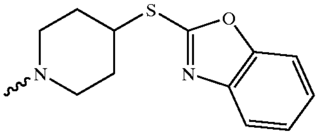 |
TABLE 64
| | |
|---|---|
| | 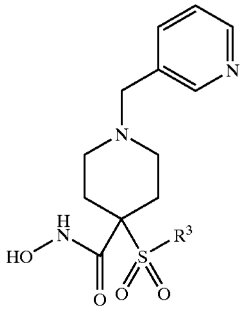 |
| | 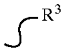 |
| 1 | 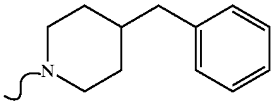 |
| 2 | 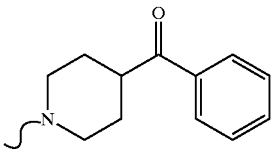 |
| 3 | 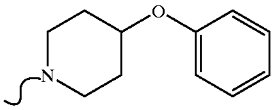 |

TABLE 64-continued
| | |
|---|---|
| | 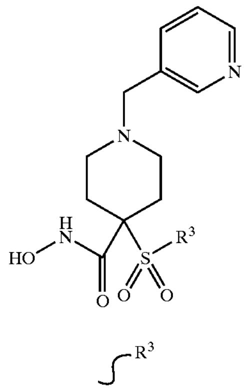 |
| 4 | 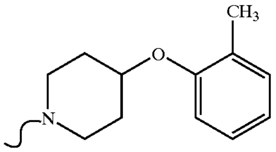 |
| 5 | 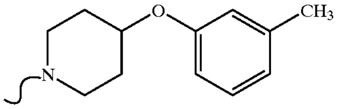 |
| 6 | 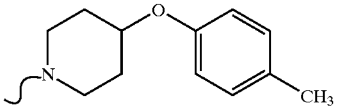 |
| 7 | 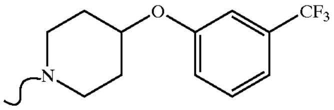 |
| 8 | 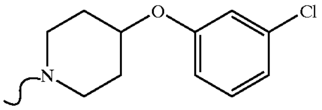 |
| 9 | 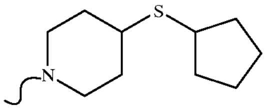 |
| 10 | 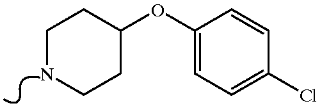 |
| 11 | 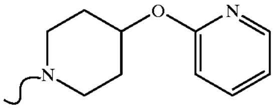 |
| 12 | 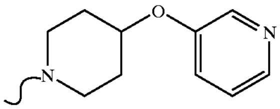 |
| | 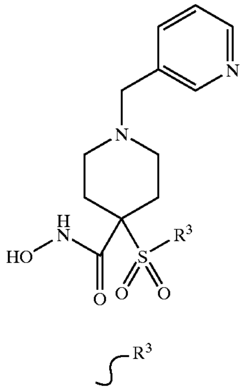 |
| 13 | 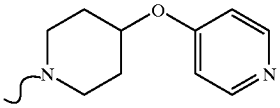 |
| 14 | 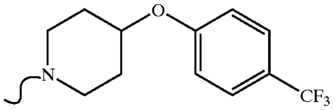 |
| 15 | 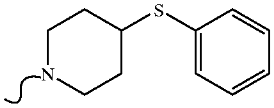 |
| 16 | 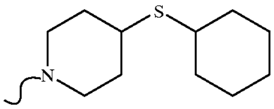 |
| 17 | 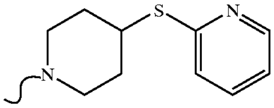 |
| 18 | 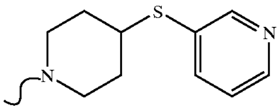 |
| 19 | 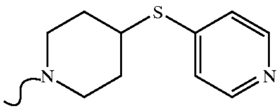 |
| 20 | 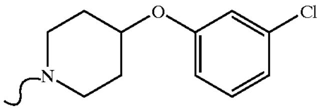 |
| 21 | 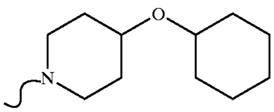 |

TABLE 65
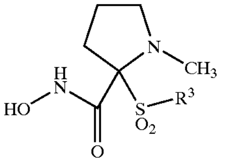
| | 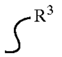 |
|---|---|
| 1 | 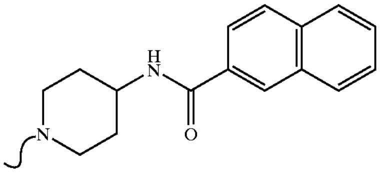 |
| 2 | 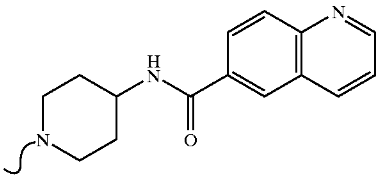 |
| 3 | 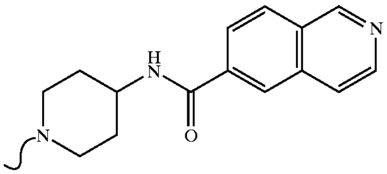 |
| 4 | 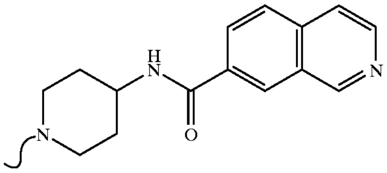 |
| 5 | 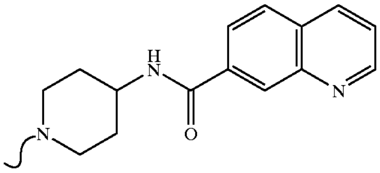 |
| 6 | 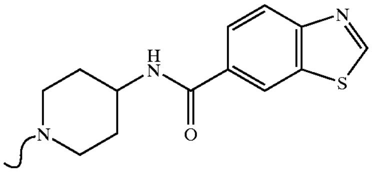 |
| 7 | 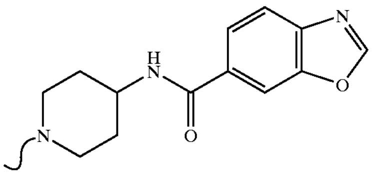 |
TABLE 65-continued
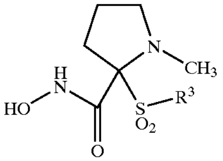
| | 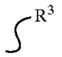 |
|---|---|
| 8 | 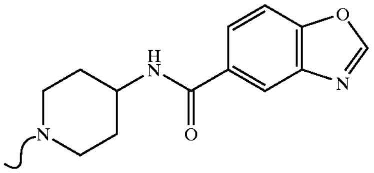 |
| 9 | 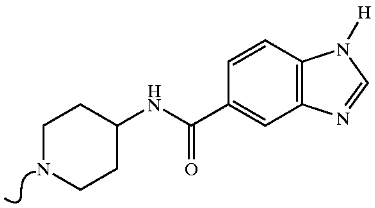 |
| 10 | 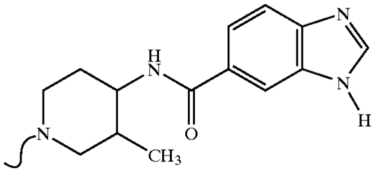 |
| 11 | 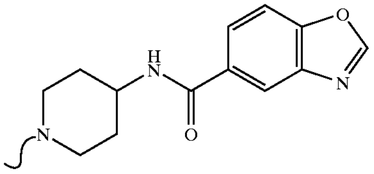 |
| 12 | 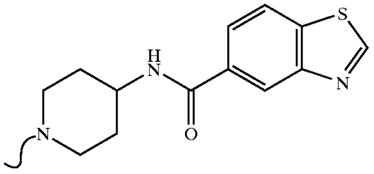 |
| 13 | 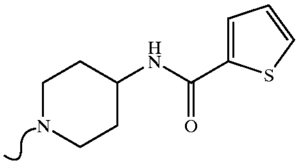 |
| 14 | 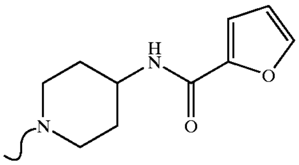 |

TABLE 65-continued
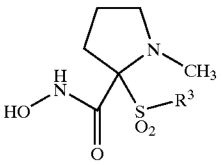
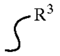
| | |
|---|---|
| 15 | 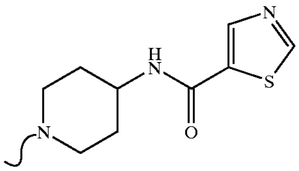 |
| 16 | 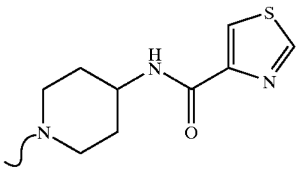 |
| 17 | 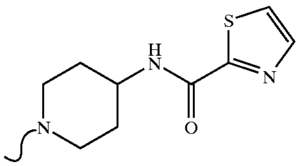 |
| 18 | 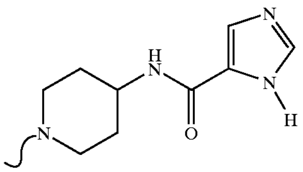 |
TABLE 66
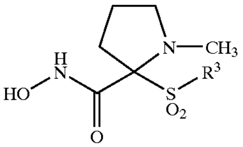
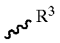
| | |
|---|---|
| 1 | 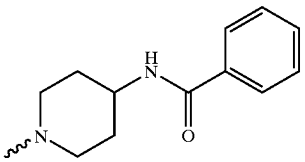 |
TABLE 66-continued
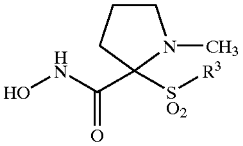
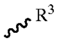
| | |
|---|---|
| 2 | 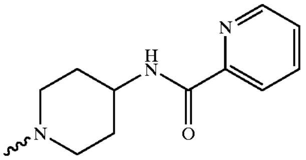 |
| 3 | 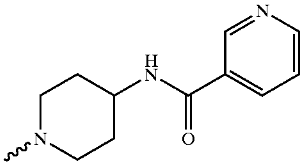 |
| 4 | 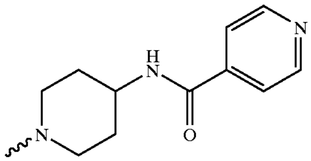 |
| 5 | 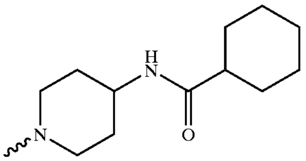 |
| 6 | 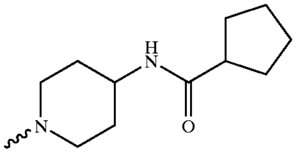 |
| 7 | 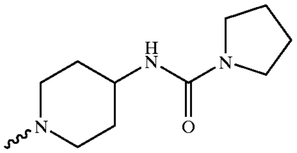 |
| 8 | 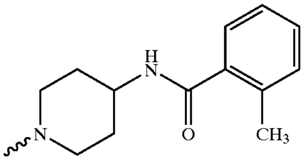 |
| 9 | 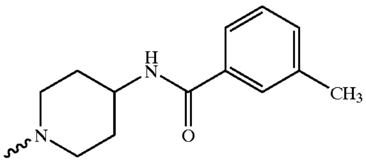 |

TABLE 66-continued
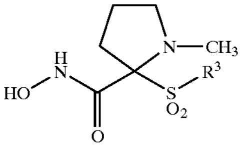
| | 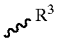 |
|---|---|
| 10 | 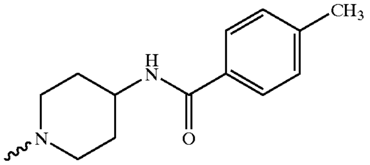 |
| 11 | 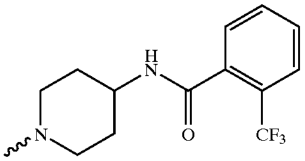 |
| 12 | 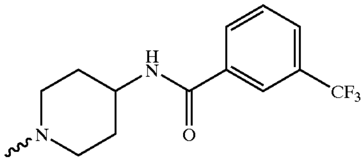 |
| 13 | 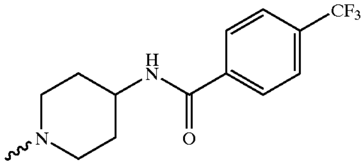 |
| 14 | 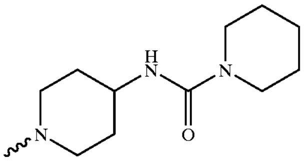 |
| 15 | 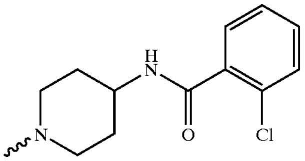 |
| 16 | 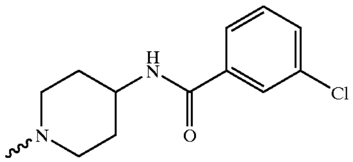 |
TABLE 66-continued
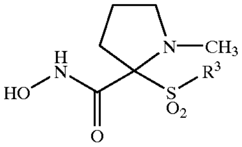
| | 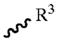 |
|---|---|
| 17 | 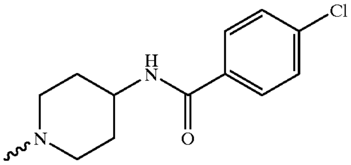 |
| 18 | 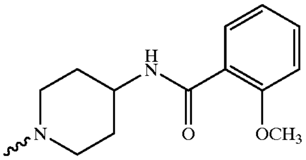 |
| 19 | 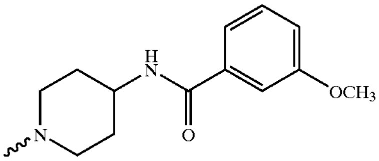 |
| 20 | 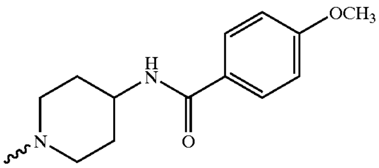 |
| 21 | 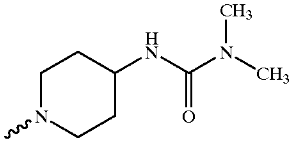 |
TABLE 67
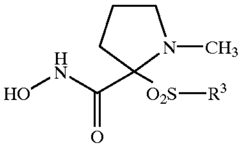
| | 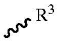 |
|---|---|
| 1 | 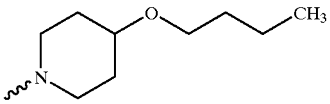 |

TABLE 67-continued
| | 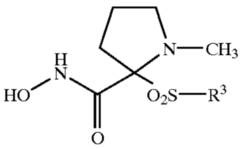<br>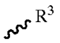 |
|---|---|
| 2 | 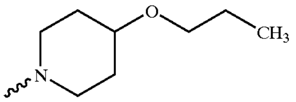 |
| 3 | 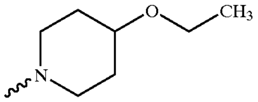 |
| 4 | 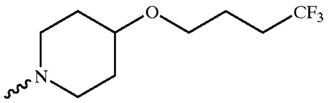 |
| 5 | 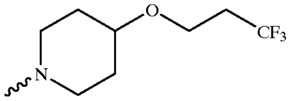 |
| 6 | 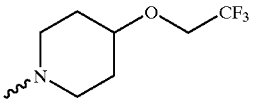 |
| 7 | 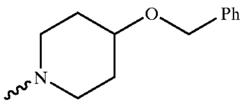 |
| 8 | 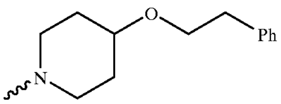 |
| 9 | 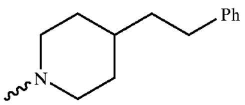 |
| 10 | 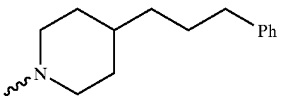 |
| 11 | 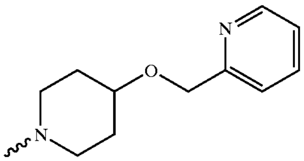 |
TABLE 67-continued
| | 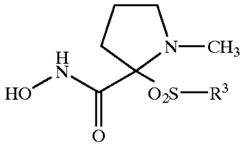<br>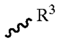 |
|---|---|
| 12 | 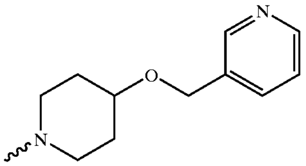 |
| 13 | 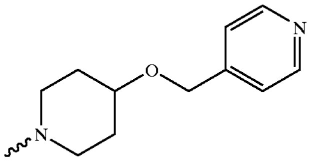 |
| 14 | 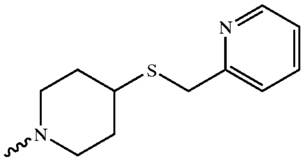 |
| 15 | 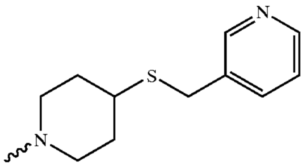 |
| 16 | 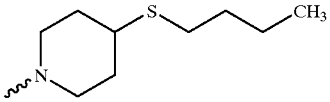 |
| 17 | 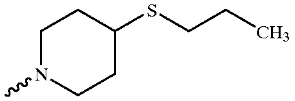 |
| 18 | 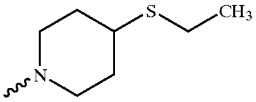 |
| 19 | 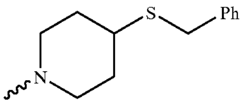 |
| 20 | 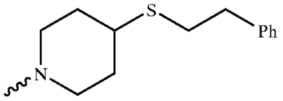 |

TABLE 67-continued
| | |
|---|---|
| | 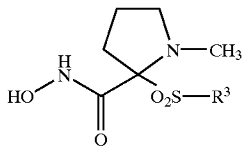 |
| | 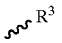 |
| 21 | 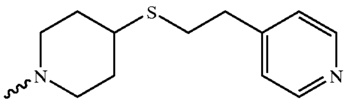 |
| 22 | 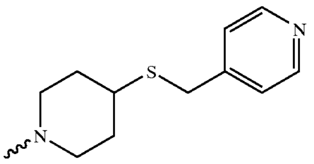 |
TABLE 68
| | |
|---|---|
| | 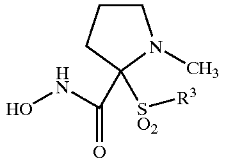 |
| | 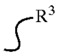 |
| 1 | 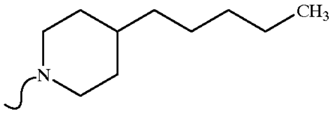 |
| 2 | 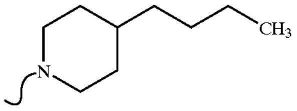 |
| 3 | 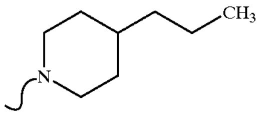 |
| 4 | 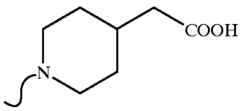 |
| 5 | 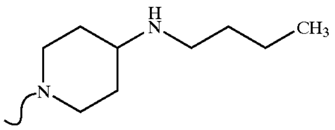 |
TABLE 68-continued
| | |
|---|---|
| | 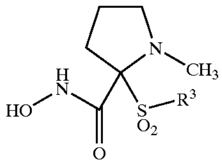 |
| | 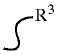 |
| 6 | 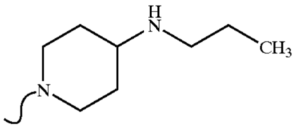 |
| 7 | 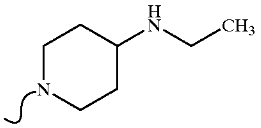 |
| 8 | 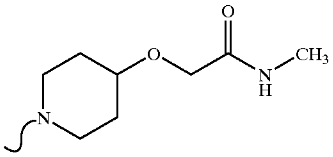 |
| 9 | 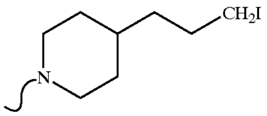 |
| 10 | 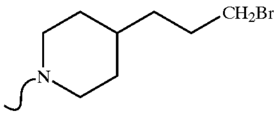 |
| 11 | 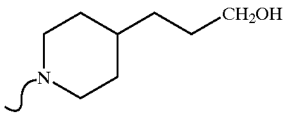 |
| 12 | 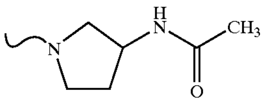 |
| 13 | 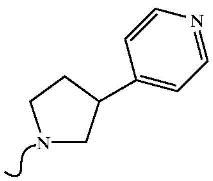 |
| 14 | 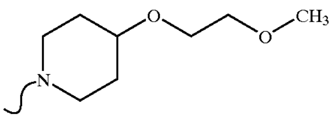 |

TABLE 68-continued
| 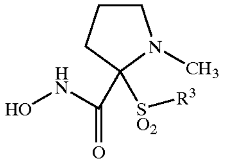 |
| --- |
| 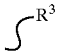 |
| | |
| --- | --- |
| 15 | 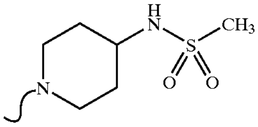 |
| 16 | 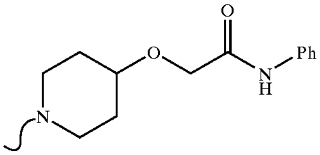 |
| 17 | 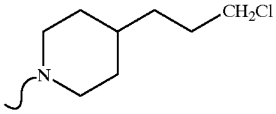 |
| 18 | 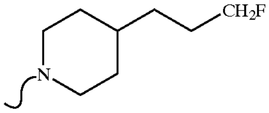 |
| 19 | 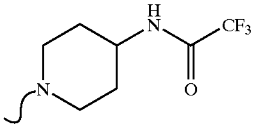 |
| 20 | 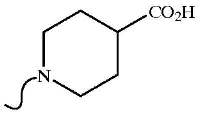 |
| 21 | 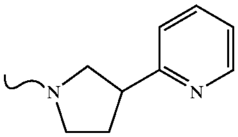 |
| 22 | 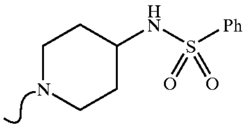 |
| 23 | 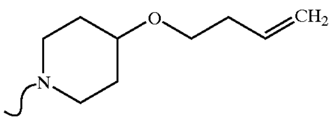 |
TABLE 68-continued
| 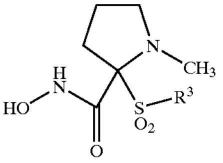 |
| --- |
| 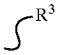 |
| | |
| --- | --- |
| 24 | 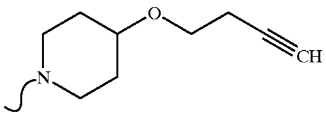 |
| 25 | 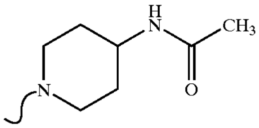 |
| 26 | 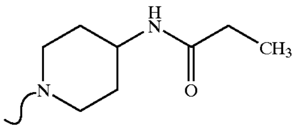 |
| 27 | 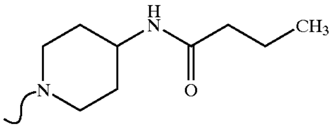 |
| 28 | 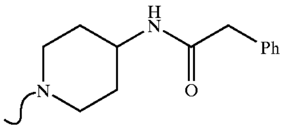 |
| 29 | 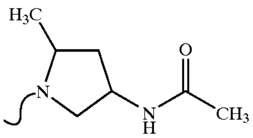 |
| 30 | 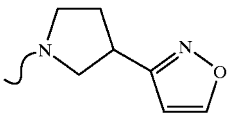 |
| 31 | 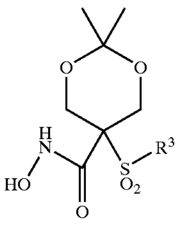 |

TABLE 69
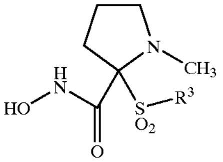
| | 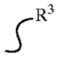 |
|---|---|
| 1 | 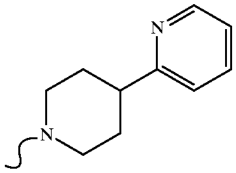 |
| 2 | 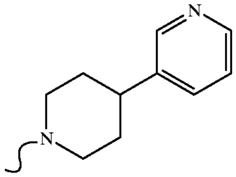 |
| 3 | 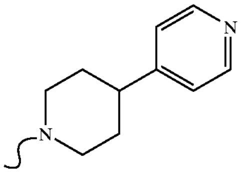 |
| 4 | 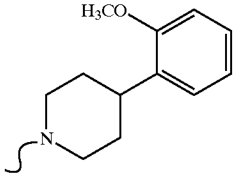 |
| 5 | 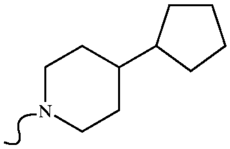 |
| 6 | 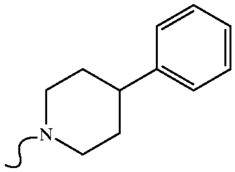 |
| 7 | 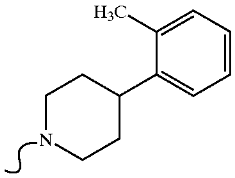 |
TABLE 69-continued
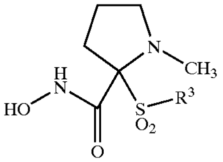
| | 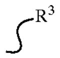 |
|---|---|
| 8 | 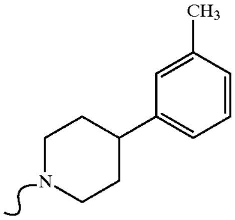 |
| 9 | 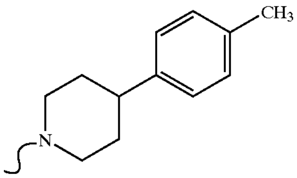 |
| 10 | 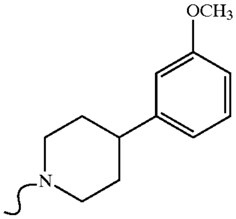 |
| 11 | 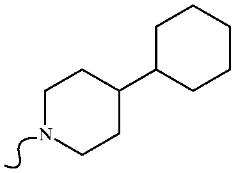 |
| 12 | 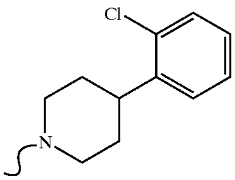 |
| 13 | 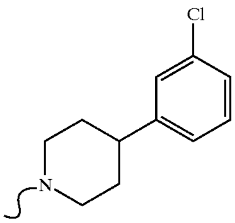 |

TABLE 69-continued
| | |
|---|---|
| | 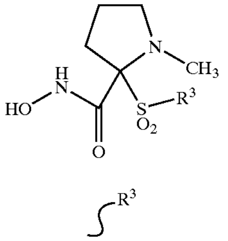 |
| 14 | 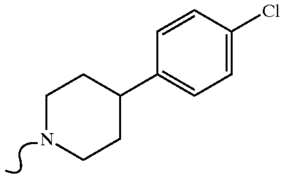 |
| 15 | 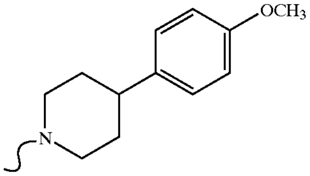 |
| 16 | 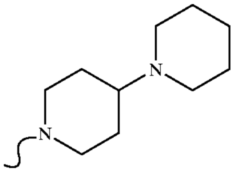 |
| 17 | 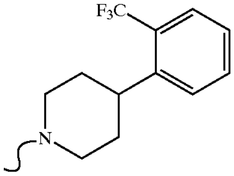 |
| 18 | 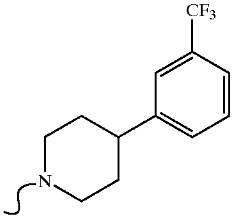 |
| 19 | 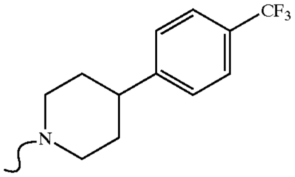 |
| 20 | 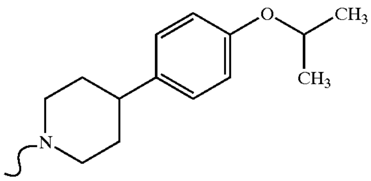 |
TABLE 69-continued
| | |
|---|---|
| | 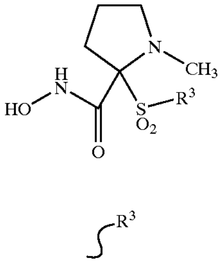 |
| 21 | 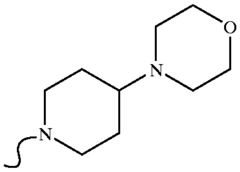 |
TABLE 70
| | |
|---|---|
| | 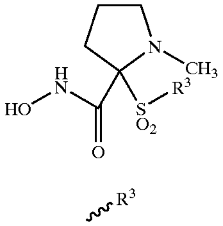 |
| 1 | 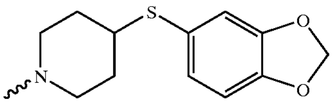 |
| 2 | 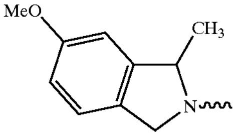 |
| 3 | 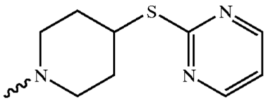 |
| 4 | 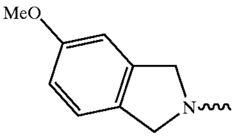 |
| 5 | 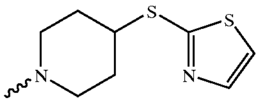 |
| 6 | 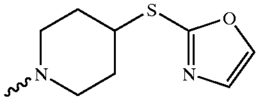 |

TABLE 70-continued
| | 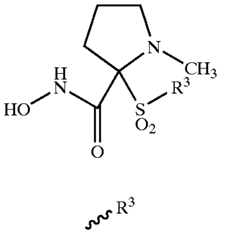 |
|---|---|
| 7 | 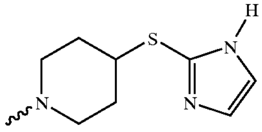 |
| 8 | 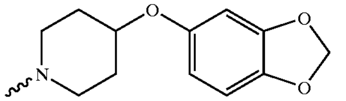 |
| 9 | 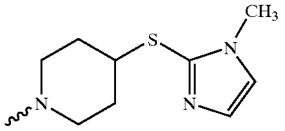 |
| 10 | 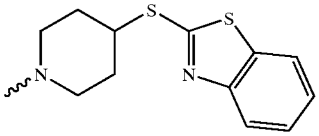 |
| 11 | 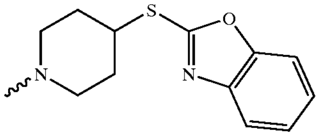 |
TABLE 71
| | 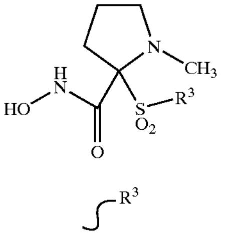 |
|---|---|
| 1 | 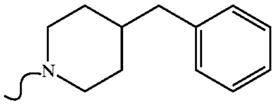 |
| 2 | 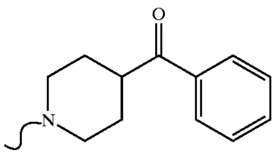 |
TABLE 71-continued
| | 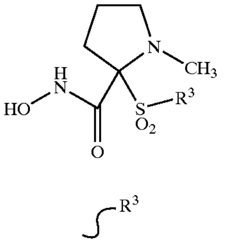 |
|---|---|
| 3 | 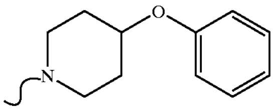 |
| 4 | 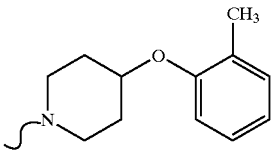 |
| 5 | 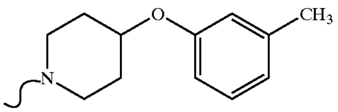 |
| 6 | 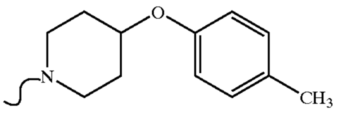 |
| 7 | 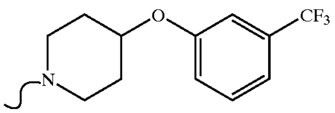 |
| 8 | 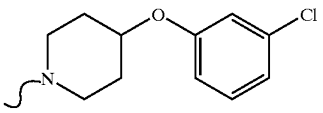 |
| 9 | 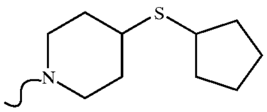 |
| 10 | 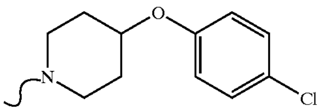 |
| 11 | 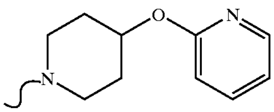 |
| 12 | 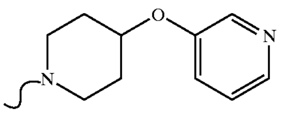 |

TABLE 71-continued
| | |
|---|---|
| 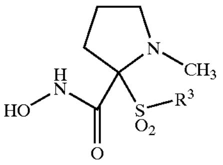 | |
| 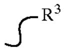 | |
| 13 | 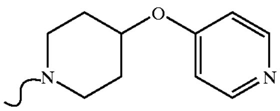 |
| 14 | 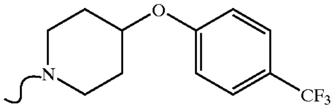 |
| 15 | 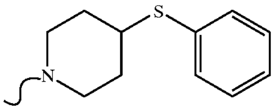 |
| 16 | 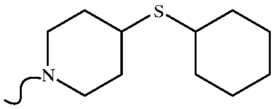 |
| 17 | 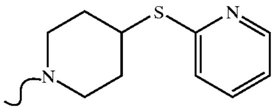 |
| 18 | 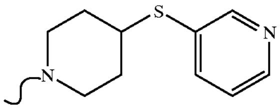 |
| 19 | 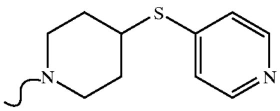 |
| 20 | 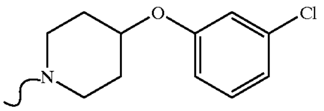 |
| 21 | 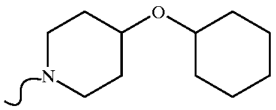 |
TABLE 72
| | |
|---|---|
| 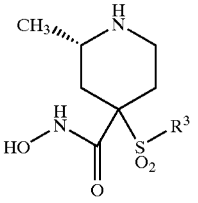 | |
| 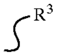 | |
| 1 | 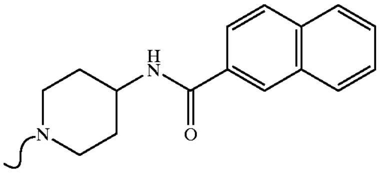 |
| 2 | 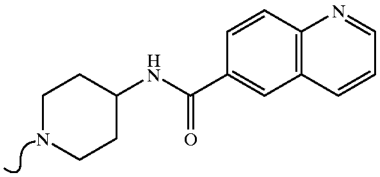 |
| 3 | 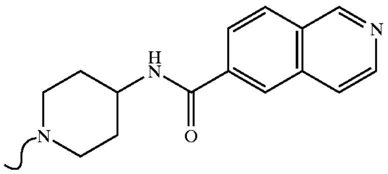 |
| 4 | 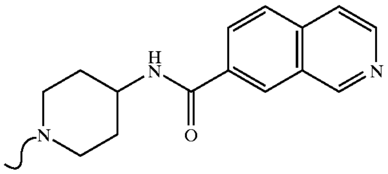 |
| 5 | 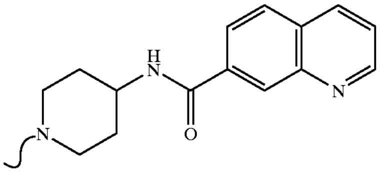 |
| 6 | 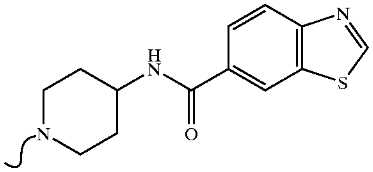 |
| 7 | 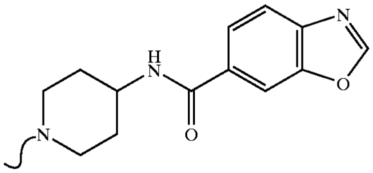 |

TABLE 72-continued
| 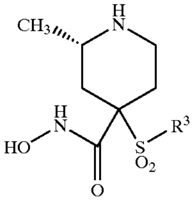 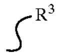 | |
|---|---|
| 8 | 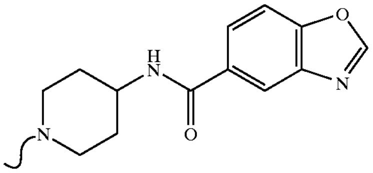 |
| 9 | 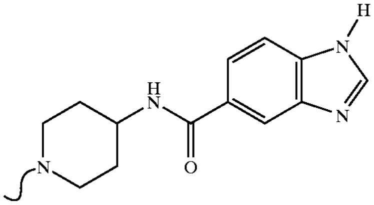 |
| 10 | 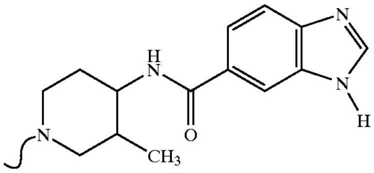 |
| 11 | 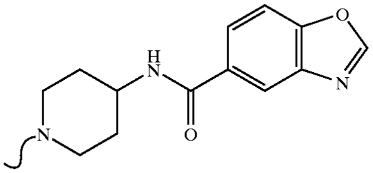 |
| 12 | 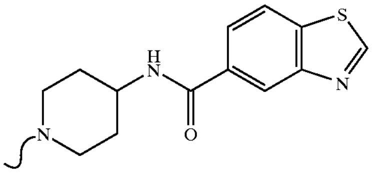 |
| 13 | 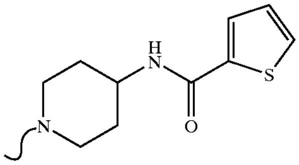 |
| 14 | 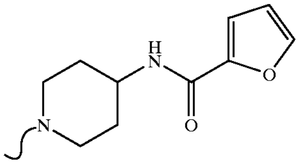 |
TABLE 72-continued
| 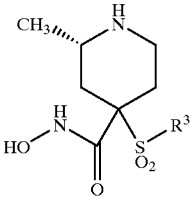 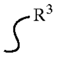 | |
|---|---|
| 15 | 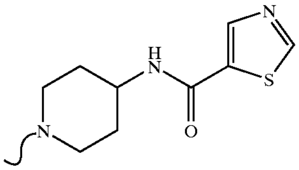 |
| 16 | 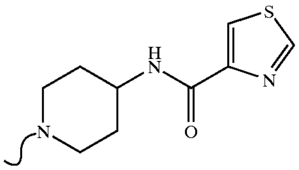 |
| 17 | 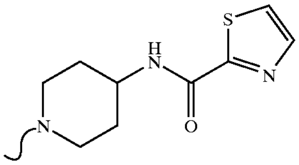 |
| 18 | 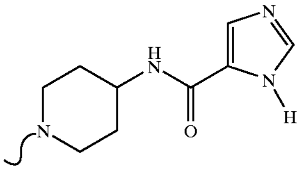 |
TABLE 73
| 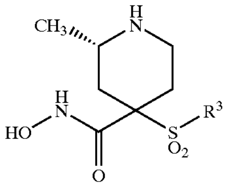 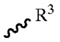 | |
|---|---|
| 1 | 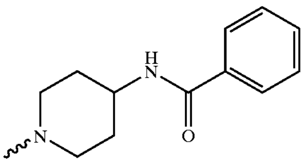 |

TABLE 73-continued
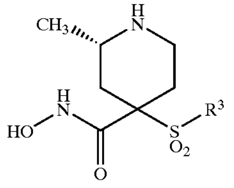
| | 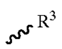 |
|---|---|
| 2 | 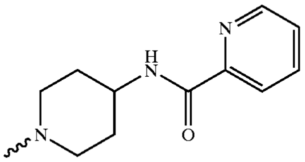 |
| 3 | 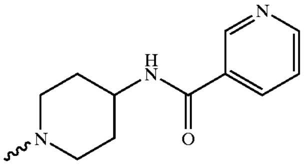 |
| 4 | 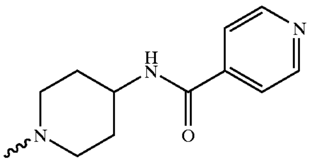 |
| 5 | 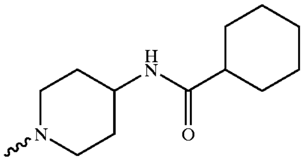 |
| 6 | 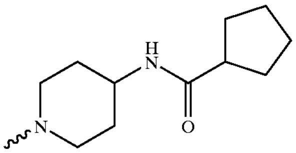 |
| 7 | 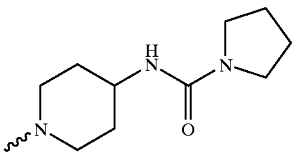 |
| 8 | 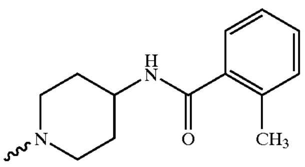 |
TABLE 73-continued
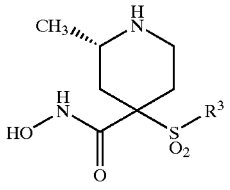
| | 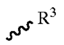 |
|---|---|
| 9 | 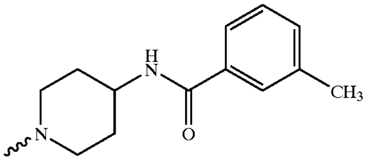 |
| 10 | 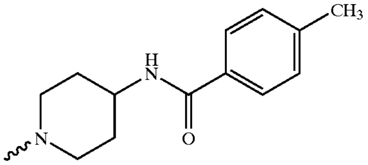 |
| 11 | 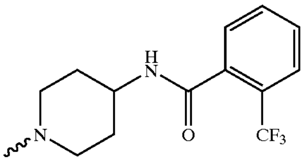 |
| 12 | 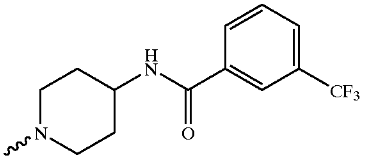 |
| 13 | 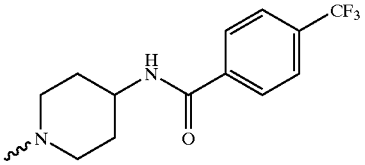 |
| 14 | 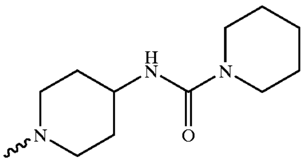 |
| 15 | 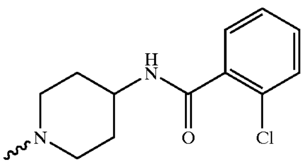 |

TABLE 73-continued
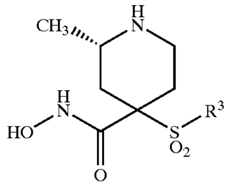
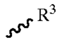
| | |
|---|---|
| 16 | 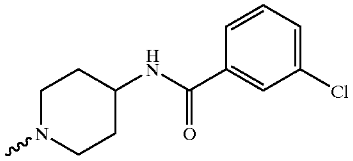 |
| 17 | 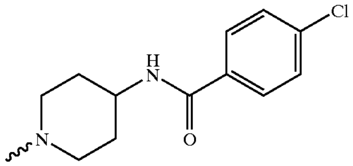 |
| 18 | 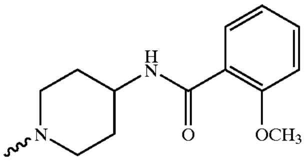 |
| 19 | 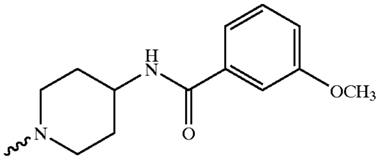 |
| 20 | 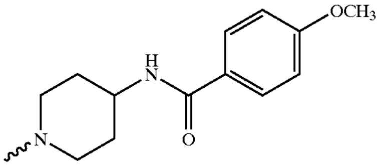 |
| 21 | 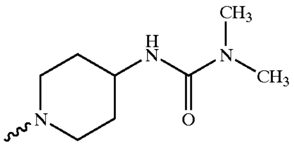 |
TABLE 74
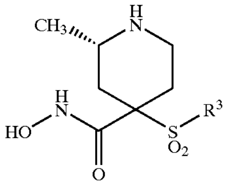
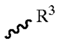
| | |
|---|---|
| 1 | 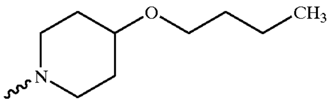 |
| 2 | 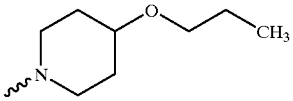 |
| 3 | 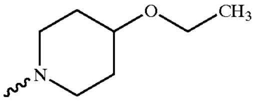 |
| 4 | 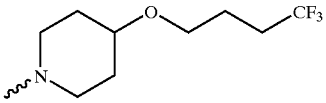 |
| 5 | 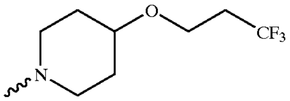 |
| 6 | 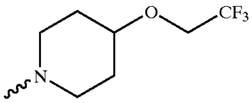 |
| 7 | 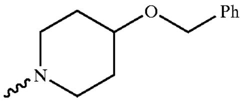 |
| 8 | 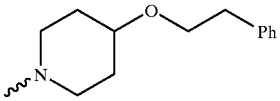 |
| 9 | 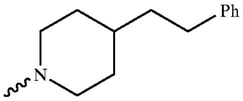 |
| 10 | 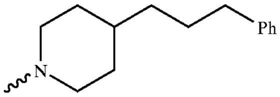 |
| 11 | 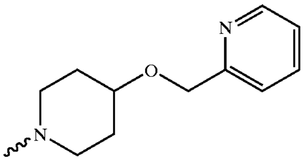 |

TABLE 74-continued
| | 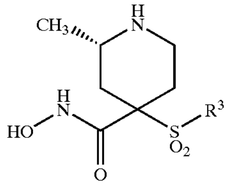 |
|---|---|
| | 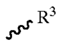 |
| 12 | 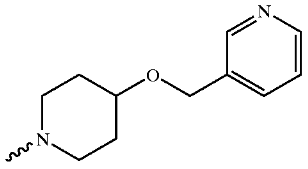 |
| 13 | 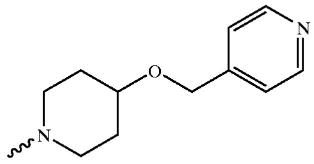 |
| 14 | 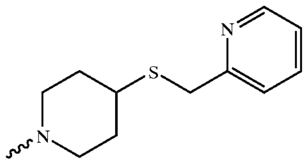 |
| 15 | 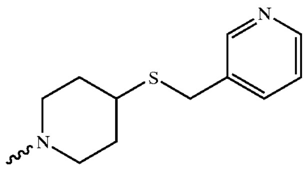 |
| 16 | 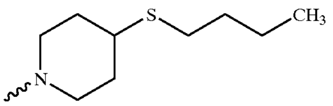 |
| 17 | 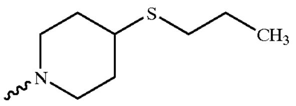 |
| 18 | 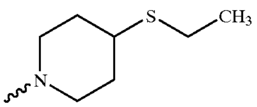 |
| 19 | 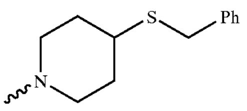 |
| 20 | 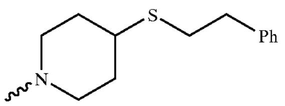 |
TABLE 74-continued
| | 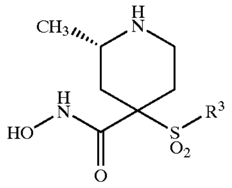 |
|---|---|
| | 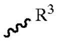 |
| 21 | 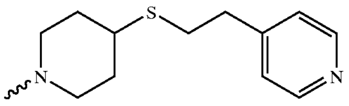 |
| 22 | 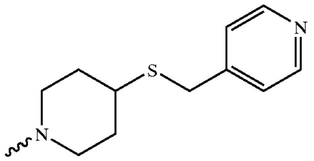 |
TABLE 75
| | 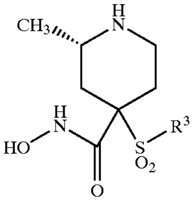 |
|---|---|
| | 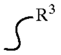 |
| 1 | 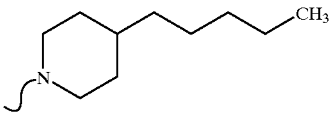 |
| 2 | 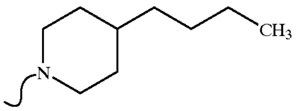 |
| 3 | 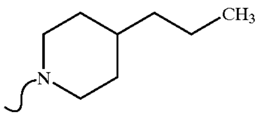 |
| 4 | 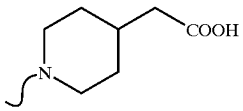 |
| 5 | 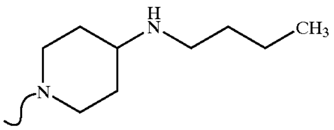 |

TABLE 75-continued
| | |
|---|---|
| | 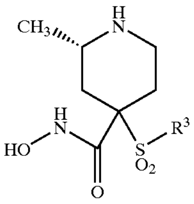 |
| | 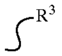 |
| 6 | 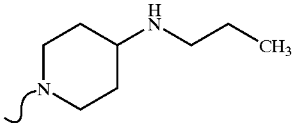 |
| 7 | 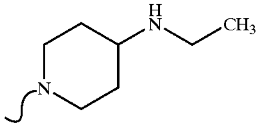 |
| 8 | 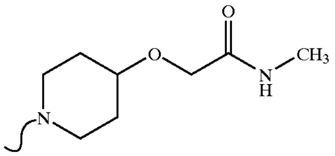 |
| 9 | 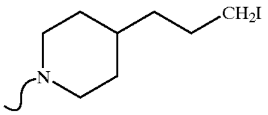 |
| 10 | 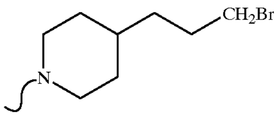 |
| 11 | 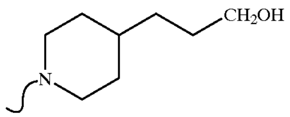 |
| 12 | 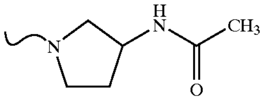 |
| 13 | 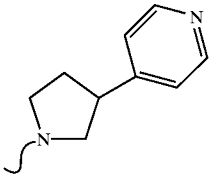 |
| 14 | 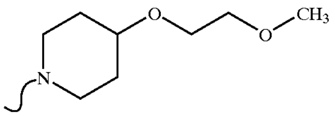 |
TABLE 75-continued
| | |
|---|---|
| | 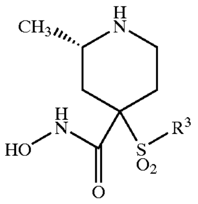 |
| | 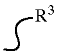 |
| 15 | 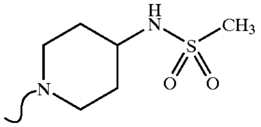 |
| 16 | 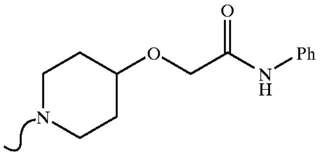 |
| 17 | 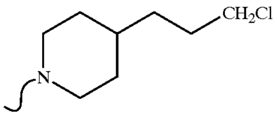 |
| 18 | 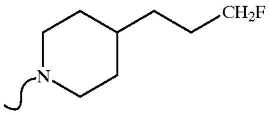 |
| 19 | 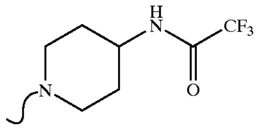 |
| 20 | 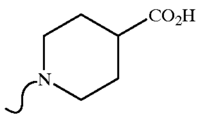 |
| 21 | 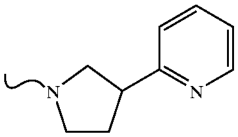 |
| 22 | 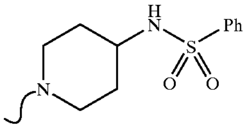 |
| 23 | 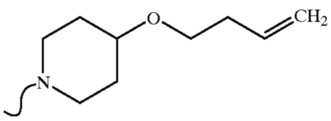 |

TABLE 75-continued
| 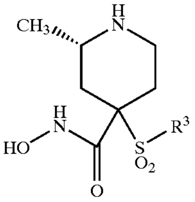 | 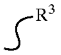 |
|---|---|
| 24 | 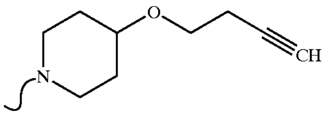 |
| 25 | 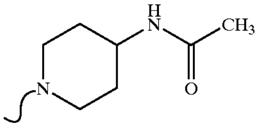 |
| 26 | 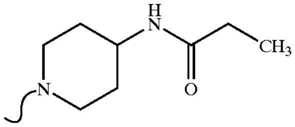 |
| 27 | 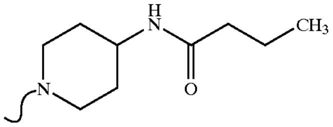 |
| 28 | 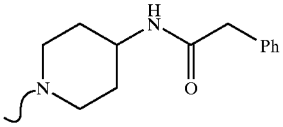 |
| 29 | 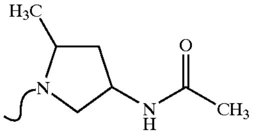 |
| 30 | 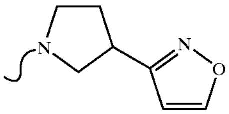 |
| 31 | 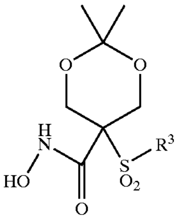 |
TABLE 76
| 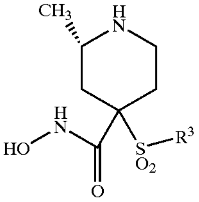 | 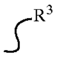 |
|---|---|
| 1 | 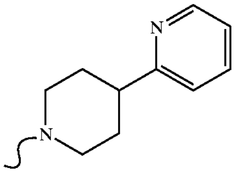 |
| 2 | 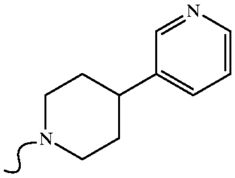 |
| 3 | 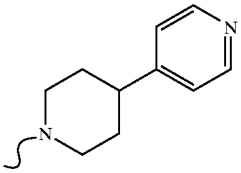 |
| 4 | 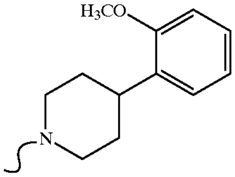 |
| 5 | 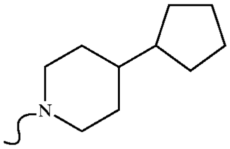 |
| 6 | 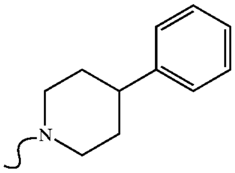 |
| 7 | 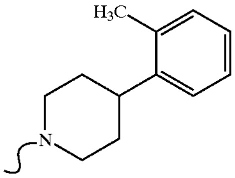 |

TABLE 76-continued
| | 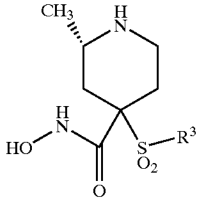 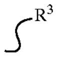 |
|---|---|
| 8 | 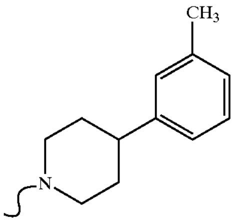 |
| 9 | 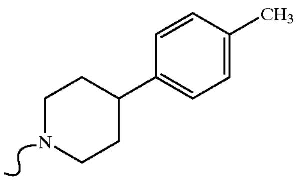 |
| 10 | 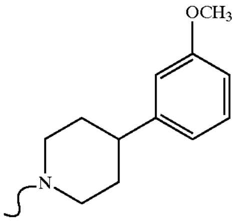 |
| 11 | 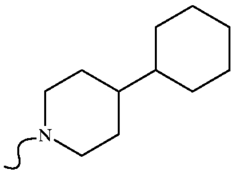 |
| 12 | 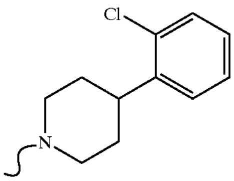 |
| 13 | 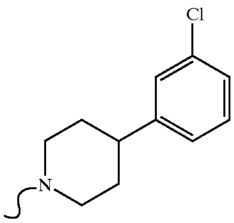 |
TABLE 76-continued
| | 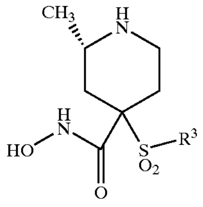 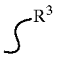 |
|---|---|
| 14 | 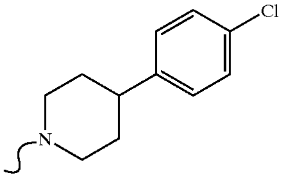 |
| 15 | 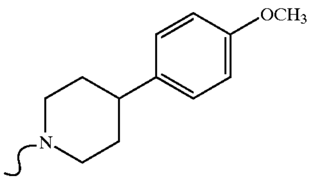 |
| 16 | 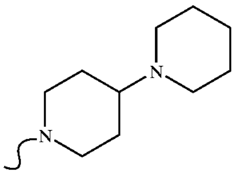 |
| 17 | 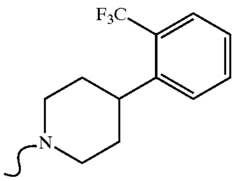 |
| 18 | 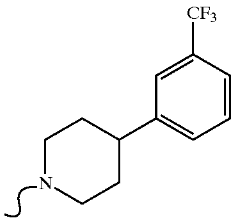 |
| 19 | 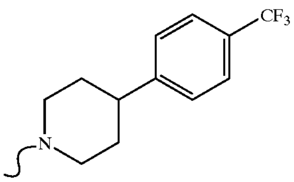 |

TABLE 76-continued
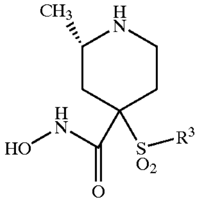
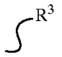
20 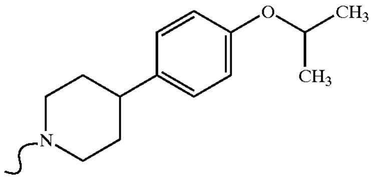
21 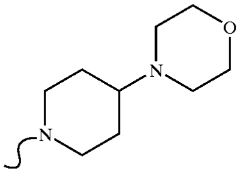
TABLE 77
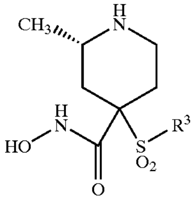
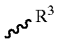
1 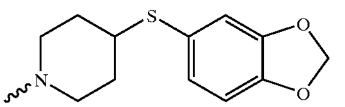
2 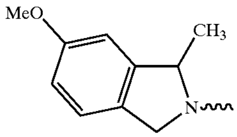
3 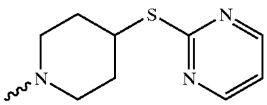
4 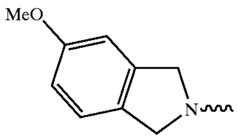
TABLE 77-continued
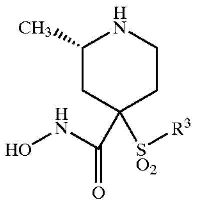
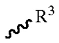
5 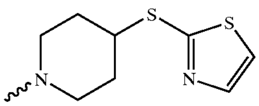
6 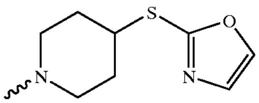
7 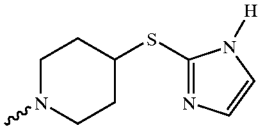
8 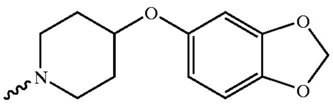
9 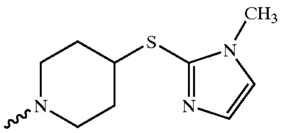
10 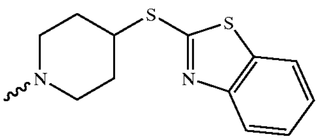
11 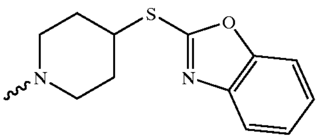

TABLE 78
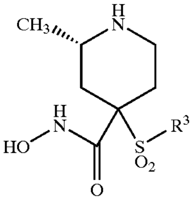
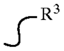
| | |
|---|---|
| 1 | 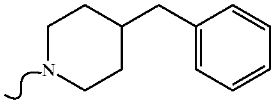 |
| 2 | 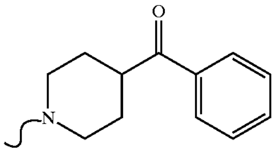 |
| 3 | 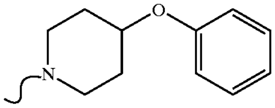 |
| 4 | 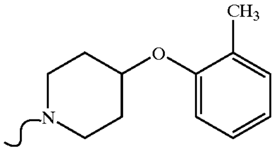 |
| 5 | 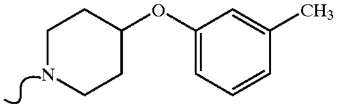 |
| 6 | 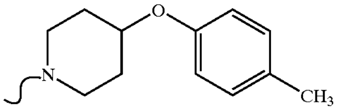 |
| 7 | 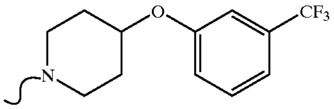 |
| 8 | 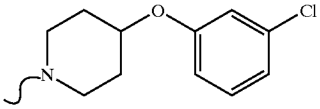 |
| 9 | 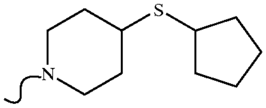 |
| 10 | 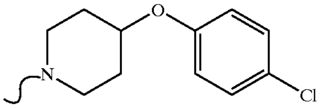 |
TABLE 78-continued
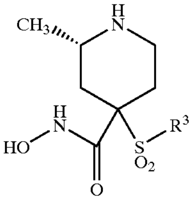
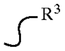
| | |
|---|---|
| 11 | 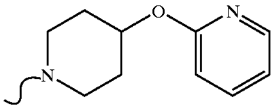 |
| 12 | 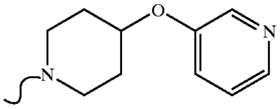 |
| 13 | 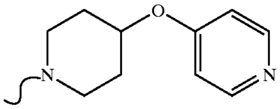 |
| 14 | 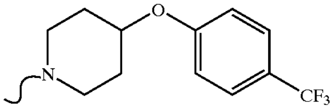 |
| 15 | 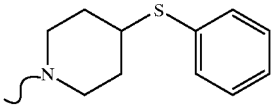 |
| 16 | 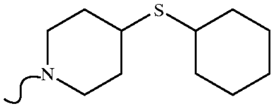 |
| 17 | 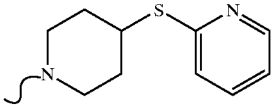 |
| 18 | 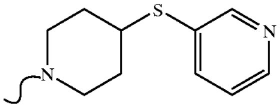 |
| 19 | 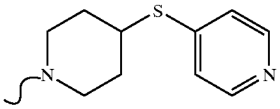 |
| 20 | 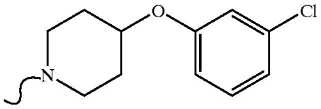 |

TABLE 78-continued
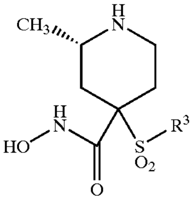
| | 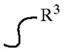 |
|---|---|
| 21 | 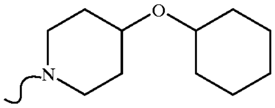 |
TABLE 79
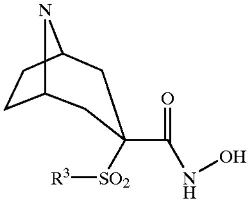
| | 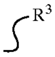 |
|---|---|
| 1 | 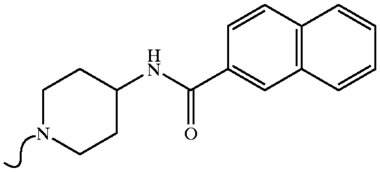 |
| 2 | 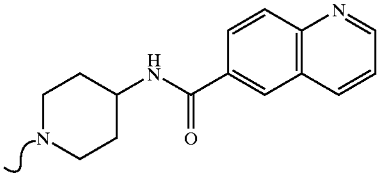 |
| 3 | 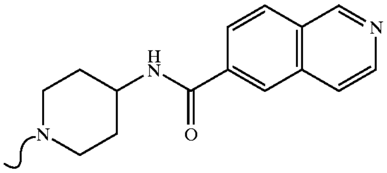 |
| 4 | 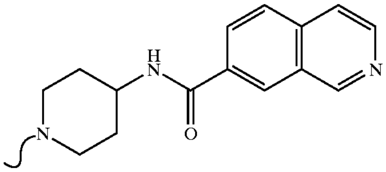 |
TABLE 79-continued
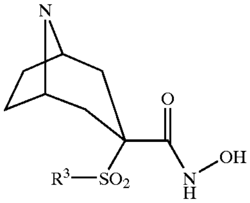
| | 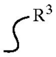 |
|---|---|
| 5 | 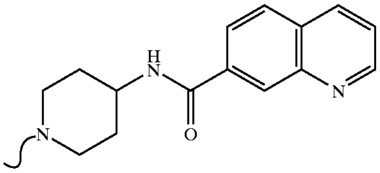 |
| 6 | 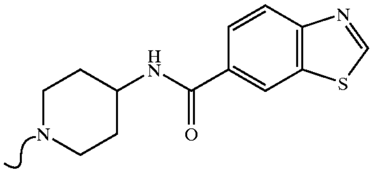 |
| 7 | 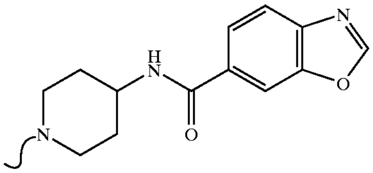 |
| 8 | 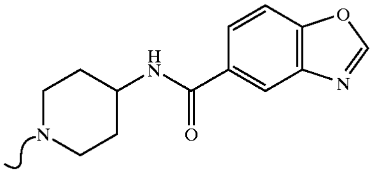 |
| 9 | 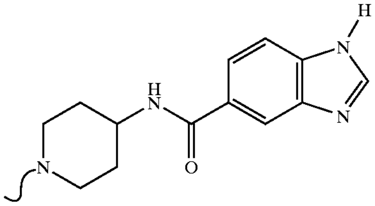 |
| 10 | 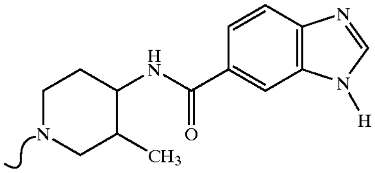 |
| 11 | 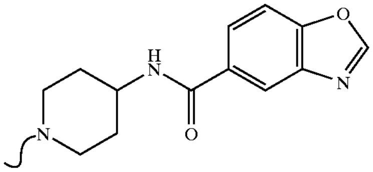 |

TABLE 79-continued
| | |
|---|---|
| | 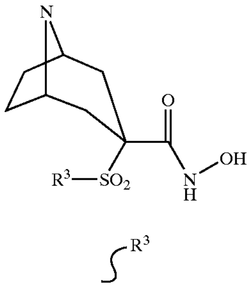 |
| 12 | 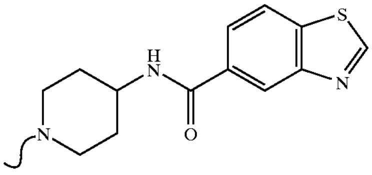 |
| 13 | 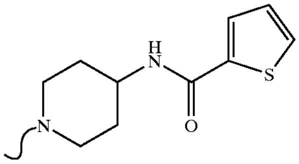 |
| 14 | 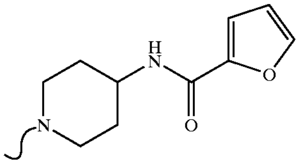 |
| 15 | 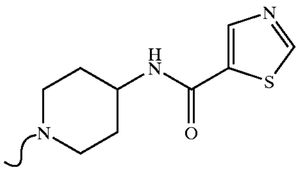 |
| 16 | 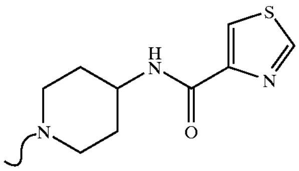 |
| 17 | 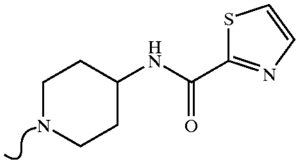 |
| 18 | 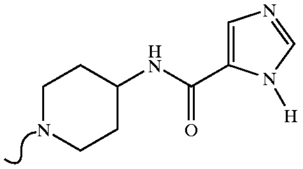 |
TABLE 80
| | |
|---|---|
| | 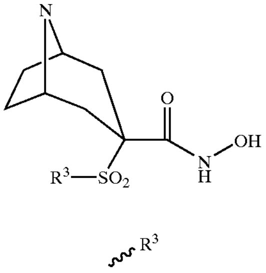 |
| 1 | 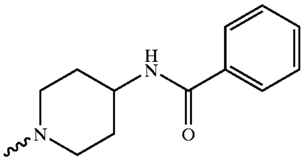 |
| 2 | 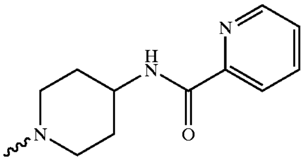 |
| 3 | 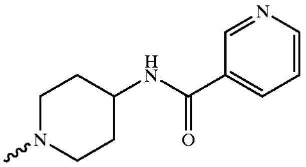 |
| 4 | 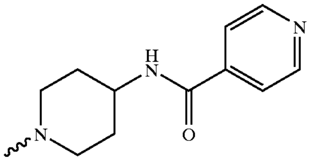 |
| 5 | 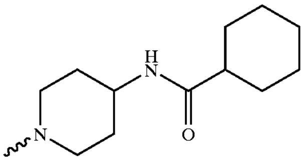 |
| 6 | 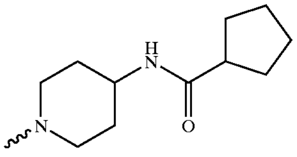 |
| 7 | 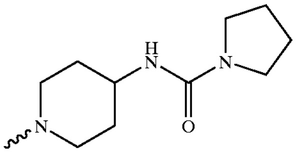 |

TABLE 80-continued
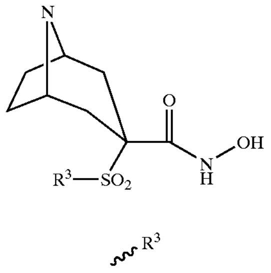
| | |
|---|---|
| 8 | 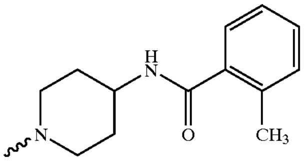 |
| 9 | 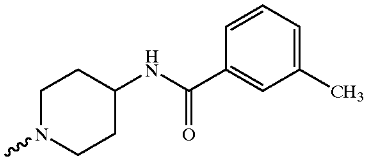 |
| 10 | 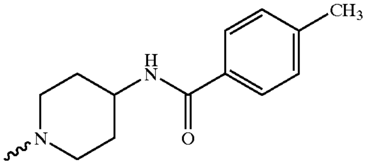 |
| 11 | 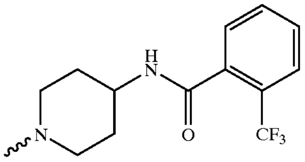 |
| 12 | 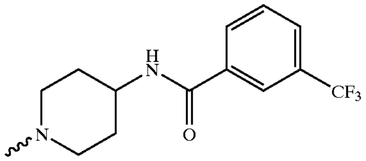 |
| 13 | 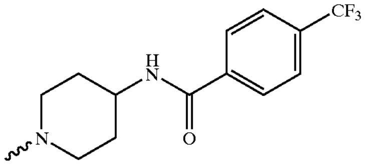 |
| 14 | 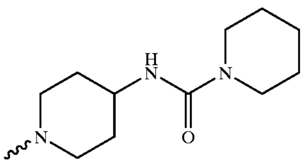 |
TABLE 80-continued
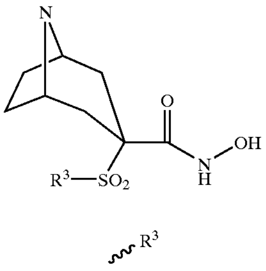
| | |
|---|---|
| 15 | 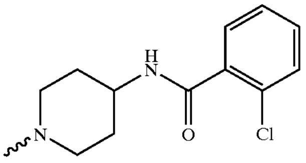 |
| 16 | 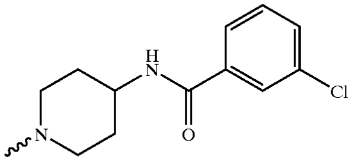 |
| 17 | 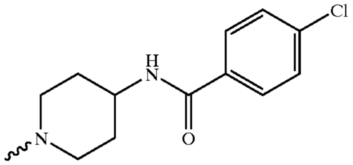 |
| 18 | 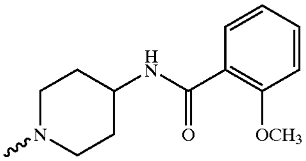 |
| 19 | 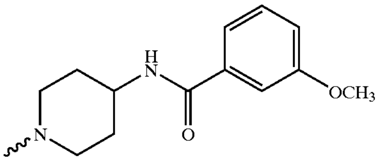 |
| 20 | 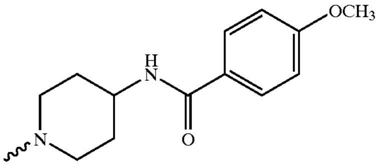 |
| 21 | 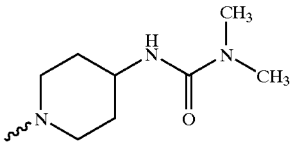 |

TABLE 81
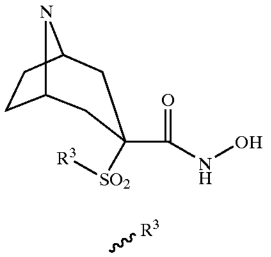
| | |
|---|---|
| 1 | 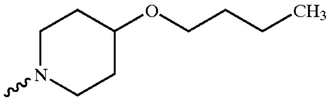 |
| 2 | 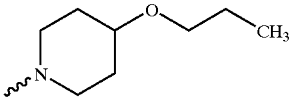 |
| 3 | 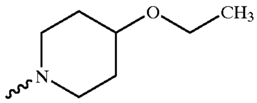 |
| 4 | 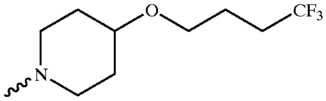 |
| 5 | 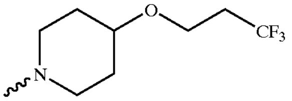 |
| 6 | 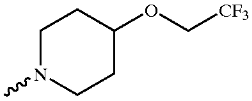 |
| 7 | 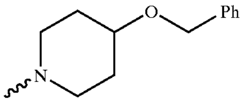 |
| 8 | 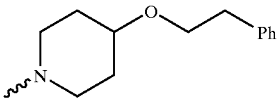 |
| 9 | 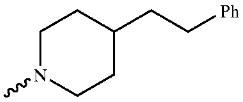 |
| 10 | 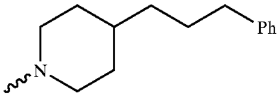 |
| 11 | 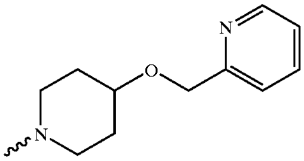 |
TABLE 81-continued
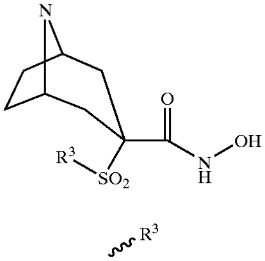
| | |
|---|---|
| 12 | 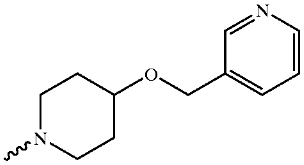 |
| 13 | 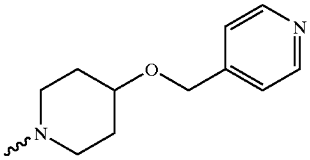 |
| 14 | 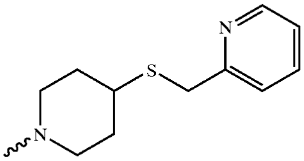 |
| 15 | 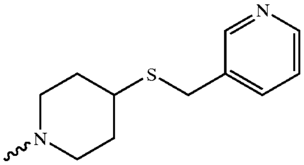 |
| 16 | 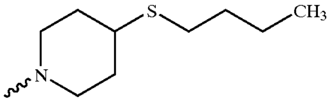 |
| 17 | 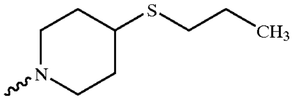 |
| 18 | 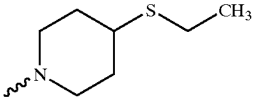 |
| 19 | 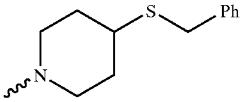 |
| 20 | 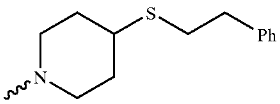 |

TABLE 81-continued
| | |
|---|---|
| 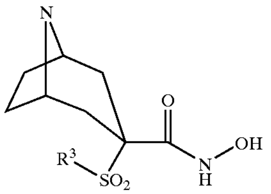 | |
| 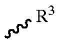 | |
| 21 | 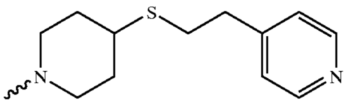 |
| 22 | 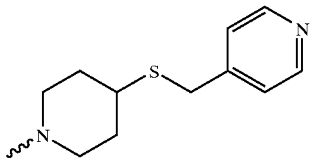 |
TABLE 82
| | |
|---|---|
| 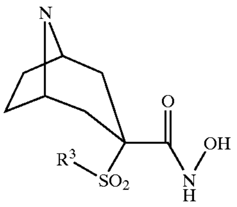 | |
| 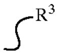 | |
| 1 | 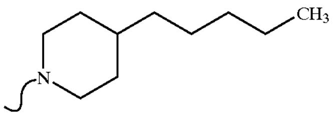 |
| 2 | 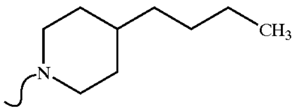 |
| 3 | 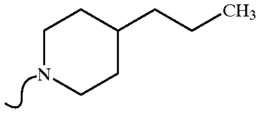 |
| 4 | 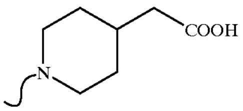 |
| 5 | 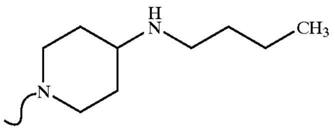 |
TABLE 82-continued
| | |
|---|---|
| 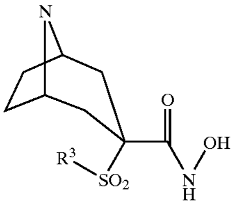 | |
| 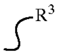 | |
| 6 | 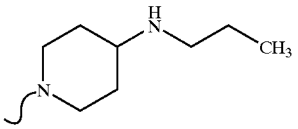 |
| 7 | 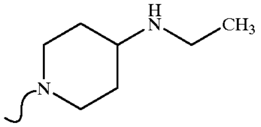 |
| 8 | 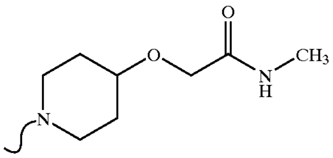 |
| 9 | 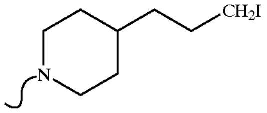 |
| 10 | 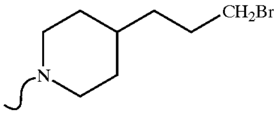 |
| 11 | 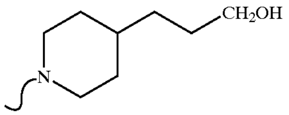 |
| 12 | 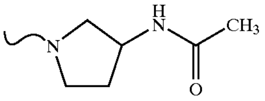 |
| 13 | 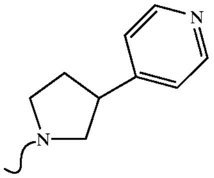 |
| 14 | 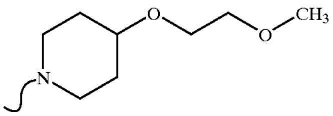 |

TABLE 82-continued
| | 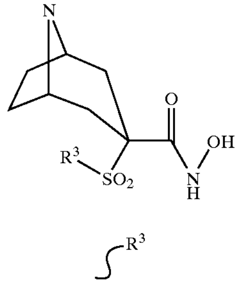 |
|---|---|
| 15 | 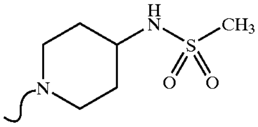 |
| 16 | 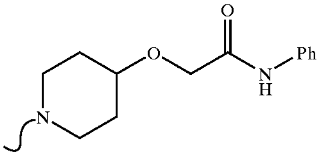 |
| 17 | 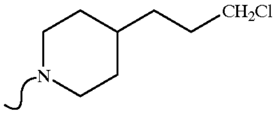 |
| 18 | 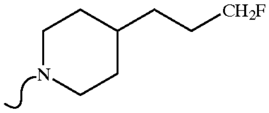 |
| 19 | 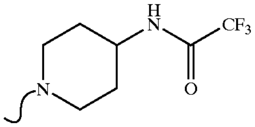 |
| 20 | 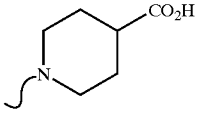 |
| 21 | 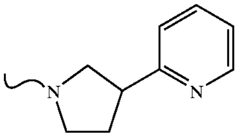 |
| 22 | 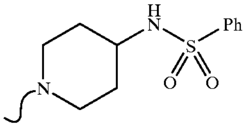 |
| 23 | 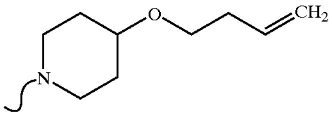 |
TABLE 82-continued
| | 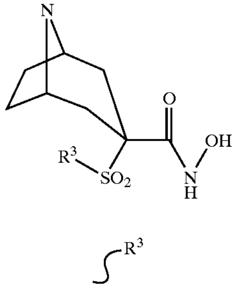 |
|---|---|
| 24 | 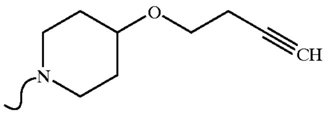 |
| 25 | 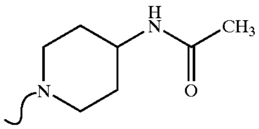 |
| 26 | 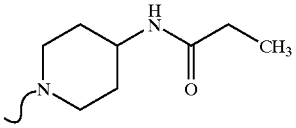 |
| 27 | 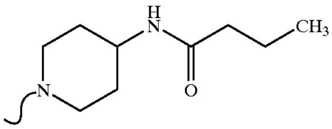 |
| 28 | 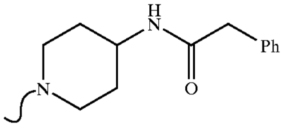 |
| 29 | 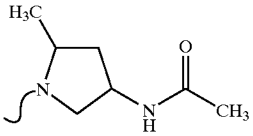 |
| 30 | 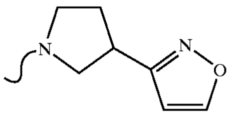 |
| 31 | 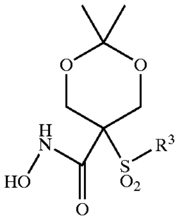 |

TABLE 83
| 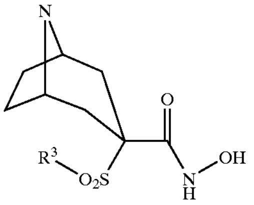 | |
|---|---|
| | 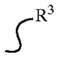 |
| 1 | 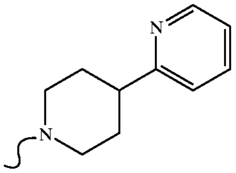 |
| 2 | 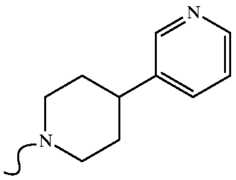 |
| 3 | 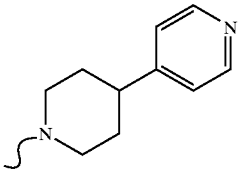 |
| 4 | 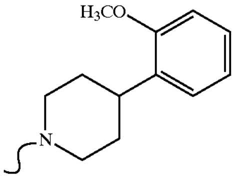 |
| 5 | 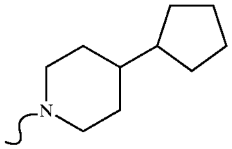 |
| 6 | 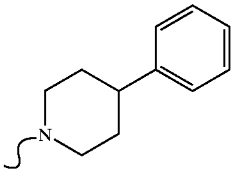 |
| 7 | 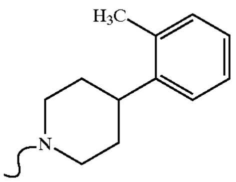 |
TABLE 83-continued
| 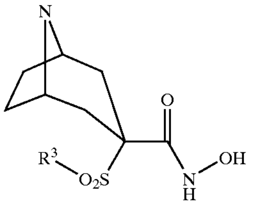 | |
|---|---|
| | 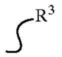 |
| 8 | 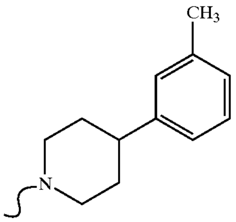 |
| 9 | 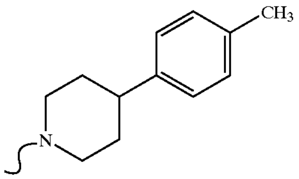 |
| 10 | 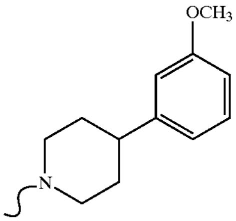 |
| 11 | 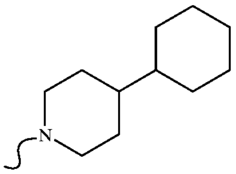 |
| 12 | 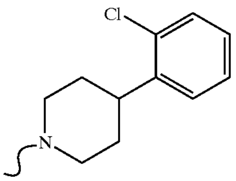 |
| 13 | 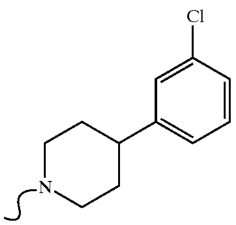 |

TABLE 83-continued
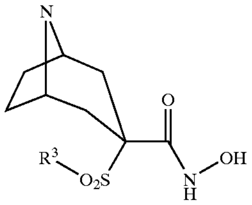
| | 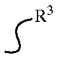 |
|---|---|
| 14 | 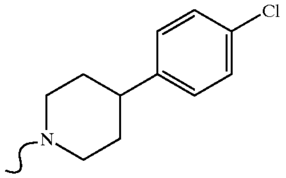 |
| 15 | 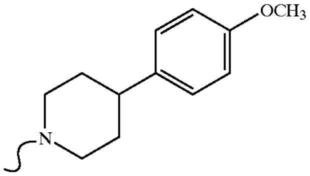 |
| 16 | 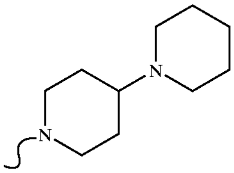 |
| 17 | 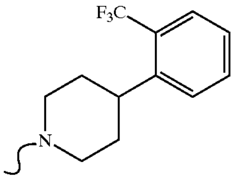 |
| 18 | 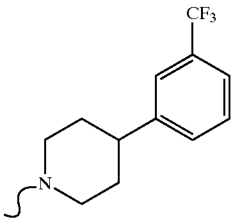 |
| 19 | 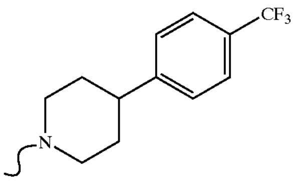 |
TABLE 83-continued
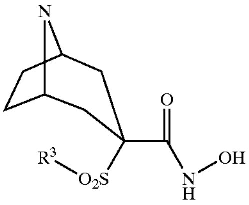
| | 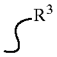 |
|---|---|
| 20 | 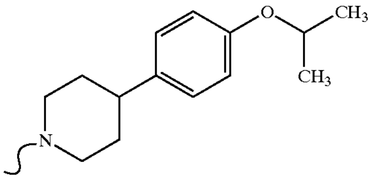 |
| 21 | 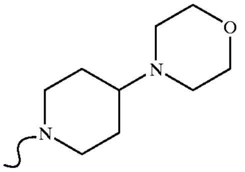 |
TABLE 84
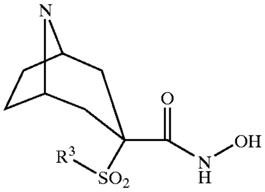
| | 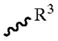 |
|---|---|
| 1 | 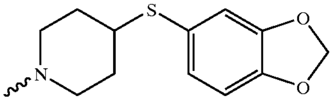 |
| 2 | 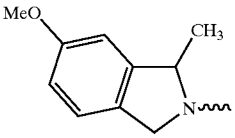 |
| 3 | 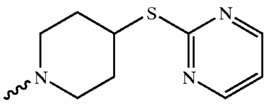 |
| 4 | 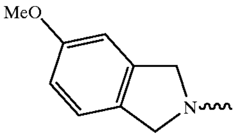 |

TABLE 84-continued
| | 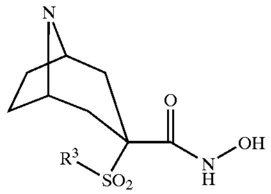 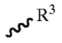 |
|---|---|
| 5 | 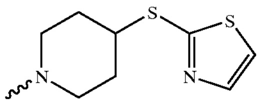 |
| 6 | 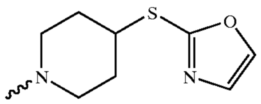 |
| 7 | 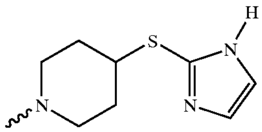 |
| 8 | 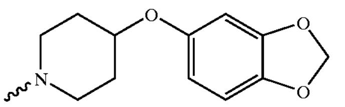 |
| 9 | 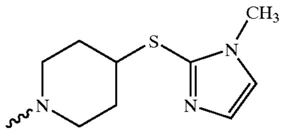 |
| 10 | 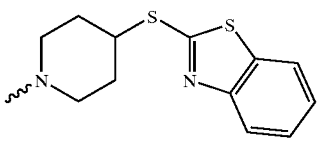 |
| 11 | 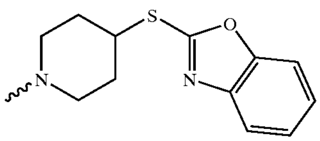 |
TABLE 85
| | 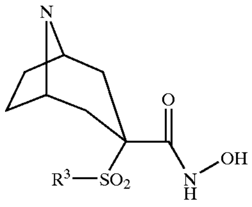 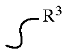 |
|---|---|
| 1 | 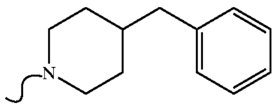 |
| 2 | 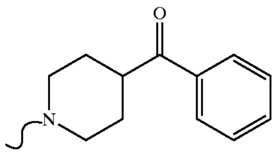 |
| 3 | 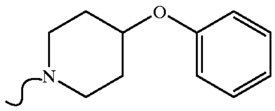 |
| 4 | 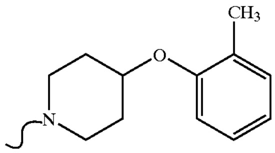 |
| 5 | 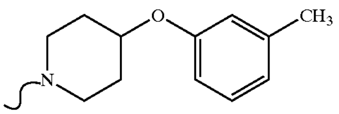 |
| 6 | 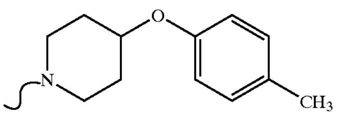 |
| 7 | 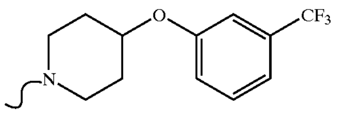 |
| 8 | 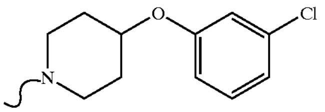 |
| 9 | 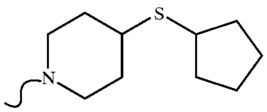 |
| 10 | 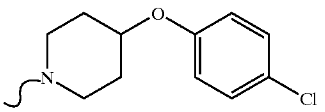 |

TABLE 85-continued
| | |
|---|---|
| | 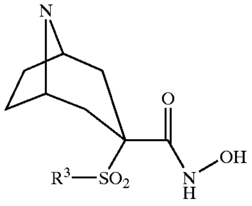 |
| | 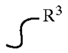 |
| 11 | 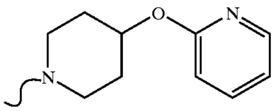 |
| 12 | 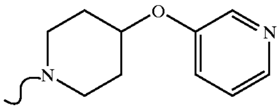 |
| 13 | 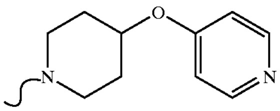 |
| 14 | 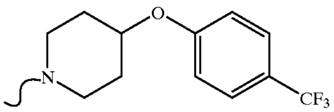 |
| 15 | 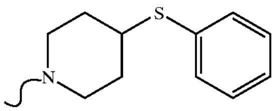 |
| 16 | 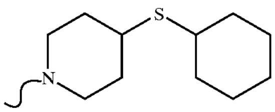 |
| 17 | 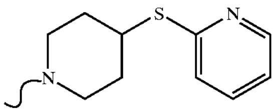 |
| 18 | 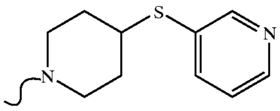 |
| 19 | 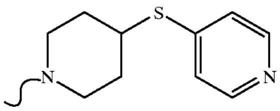 |
| 20 | 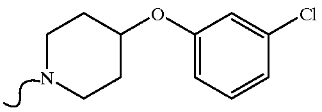 |
TABLE 85-continued
| | |
|---|---|
| | 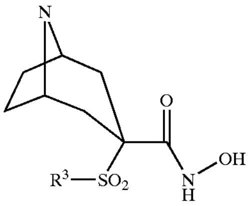 |
| | 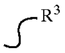 |
| 21 | 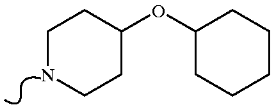 |
TABLE 86
| | |
|---|---|
| | 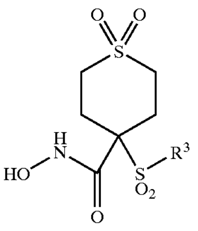 |
| | 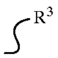 |
| 1 | 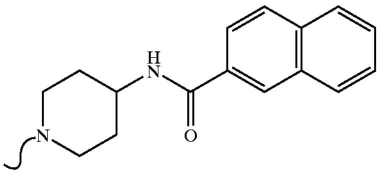 |
| 2 | 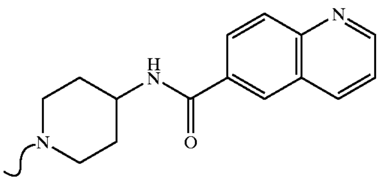 |
| 3 | 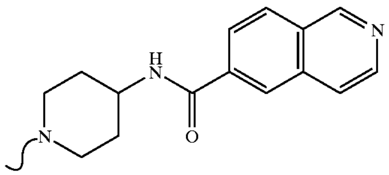 |
| 4 | 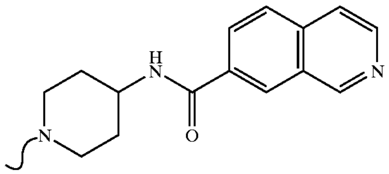 |

TABLE 86-continued
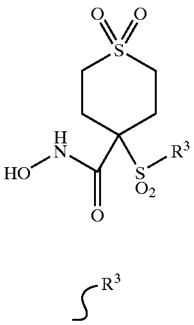
| | |
|---|---|
| 5 | 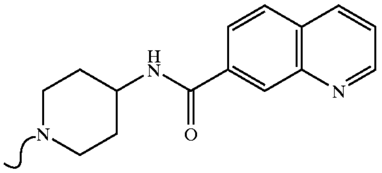 |
| 6 | 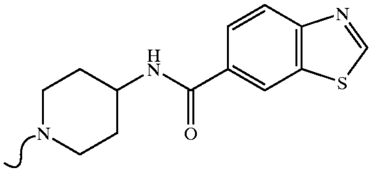 |
| 7 | 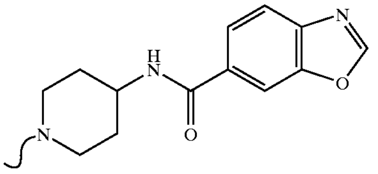 |
| 8 | 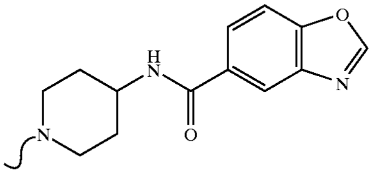 |
| 9 | 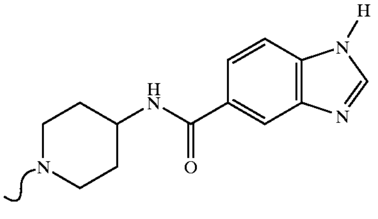 |
| 10 | 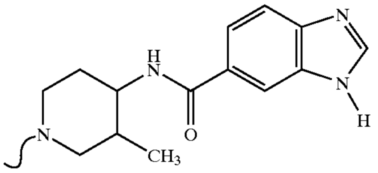 |
TABLE 86-continued
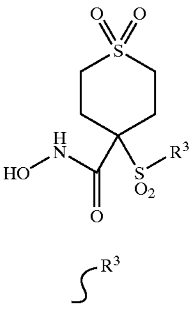
| | |
|---|---|
| 11 | 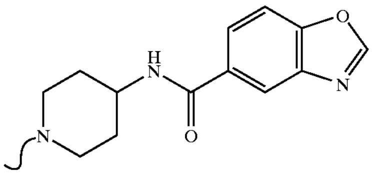 |
| 12 | 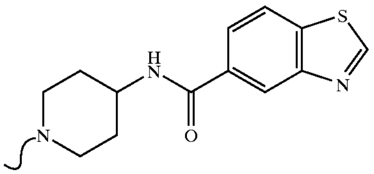 |
| 13 | 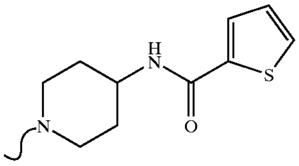 |
| 14 | 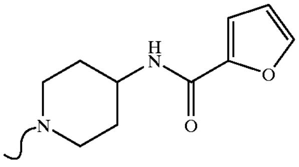 |
| 15 | 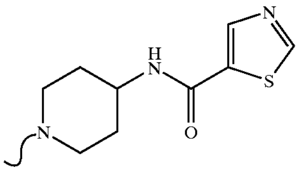 |
| 16 | 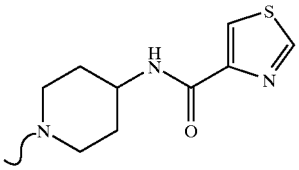 |
| 17 | 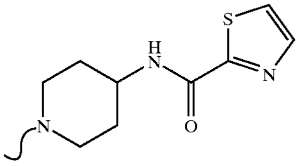 |

TABLE 86-continued
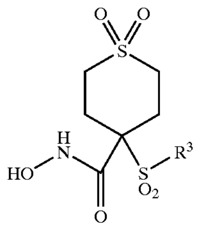
18 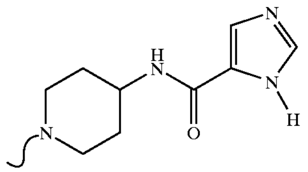
TABLE 87
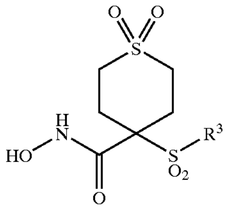
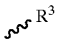
1 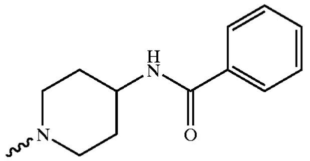
2 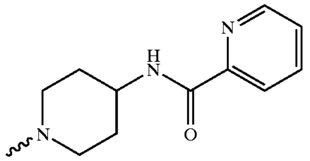
3 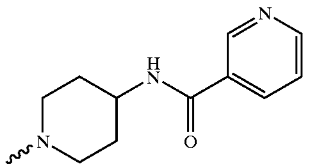
4 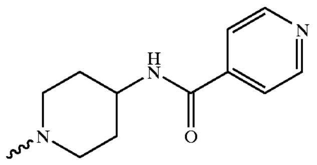
TABLE 87-continued
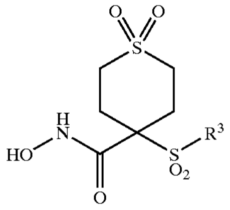
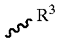
5 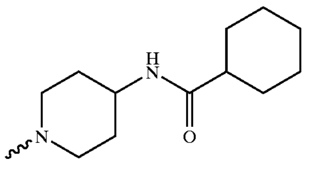
6 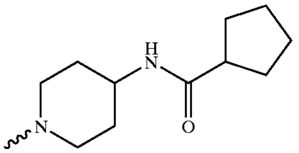
7 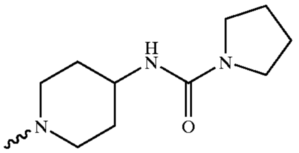
8 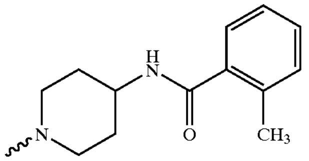
9 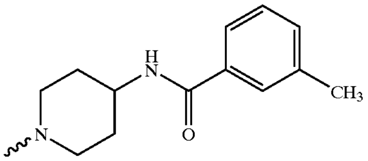
10 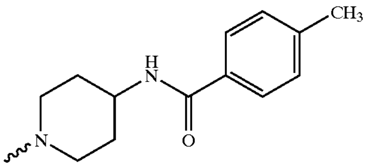
11 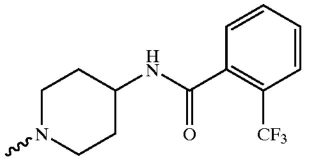

TABLE 87-continued
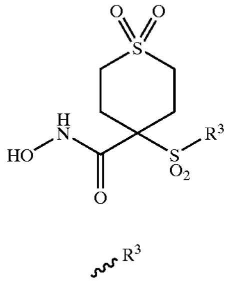
| | |
|---|---|
| 12 | 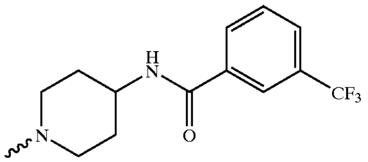 |
| 13 | 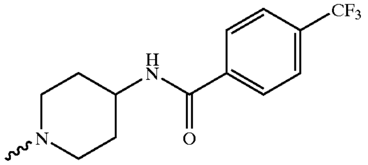 |
| 14 | 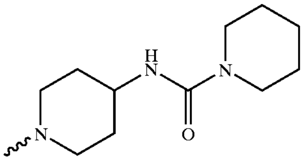 |
| 15 | 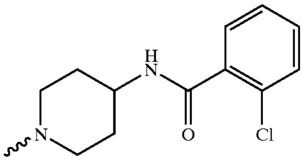 |
| 16 | 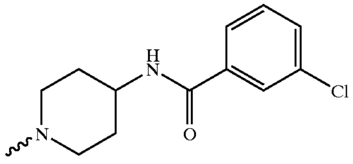 |
| 17 | 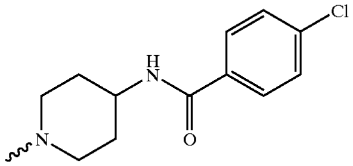 |
| 18 | 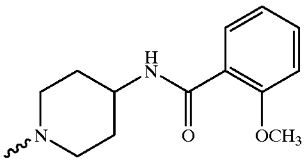 |
TABLE 87-continued
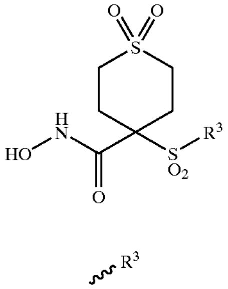
| | |
|---|---|
| 19 | 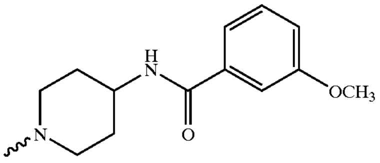 |
| 20 | 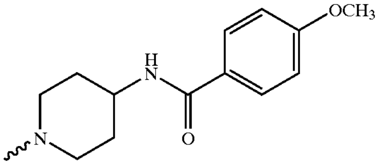 |
| 21 | 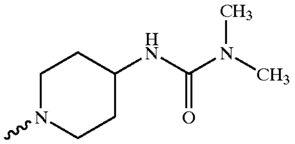 |
TABLE 88
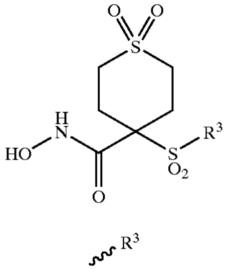
| | |
|---|---|
| 1 | 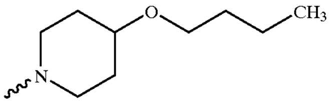 |
| 2 | 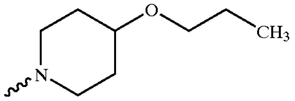 |
| 3 | 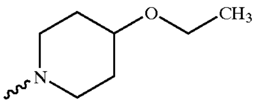 |

TABLE 88-continued
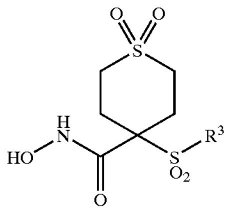
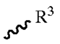
4
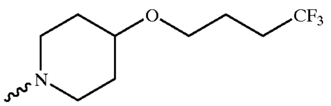
5
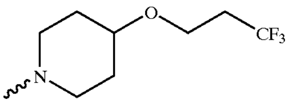
6
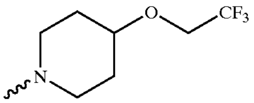
7
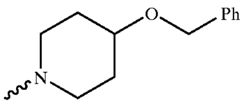
8
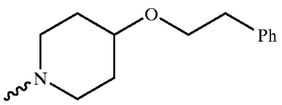
9
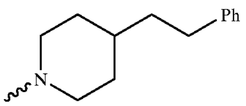
10
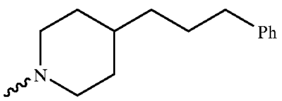
11
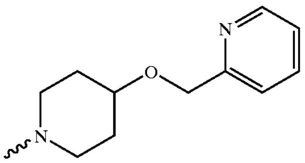
12
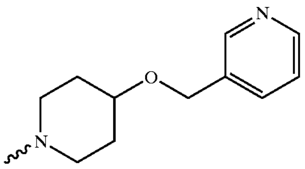
TABLE 88-continued
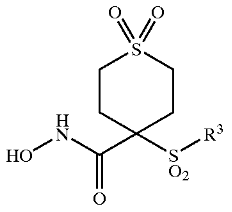
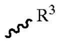
13
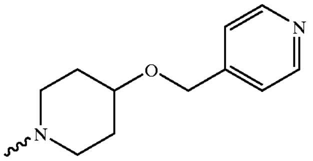
14
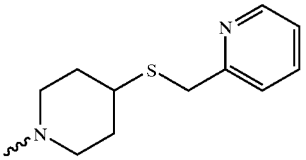
15
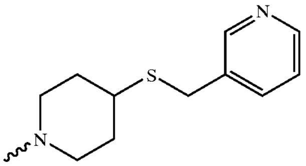
16
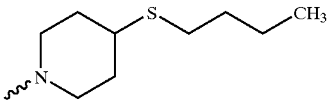
17
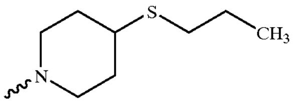
18
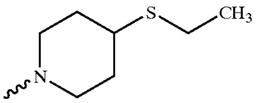
19
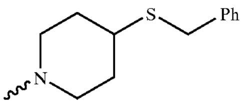
20
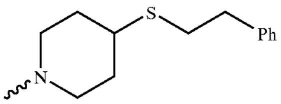
21
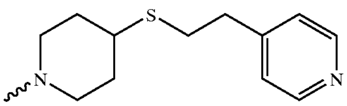

TABLE 88-continued
| 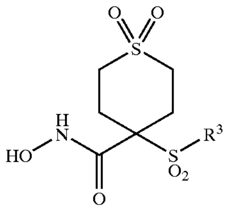 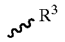 | |
|---|---|
| 22 | 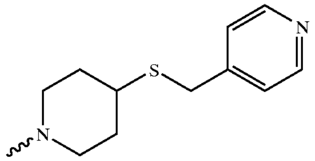 |
TABLE 89
| 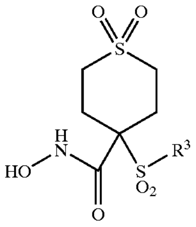 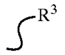 | |
|---|---|
| 1 | 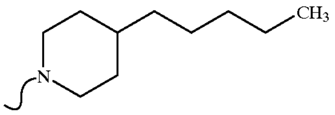 |
| 2 | 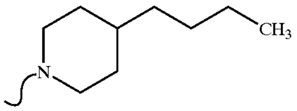 |
| 3 | 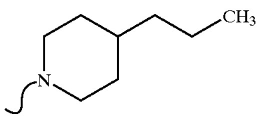 |
| 4 | 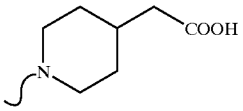 |
| 5 | 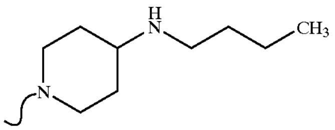 |
TABLE 89-continued
| 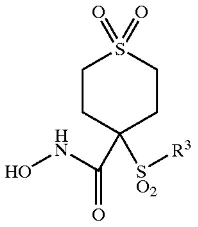 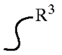 | |
|---|---|
| 6 | 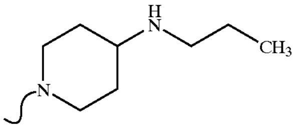 |
| 7 | 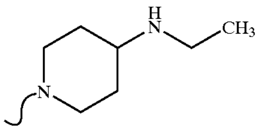 |
| 8 | 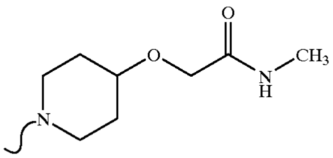 |
| 9 | 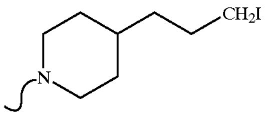 |
| 10 | 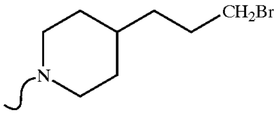 |
| 11 | 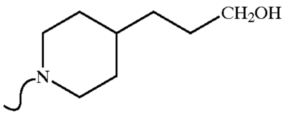 |
| 12 | 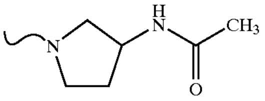 |
| 13 | 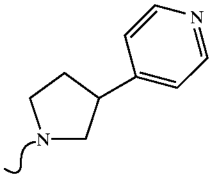 |
| 14 | 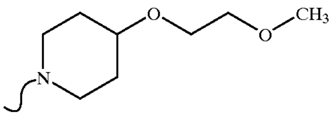 |

TABLE 89-continued
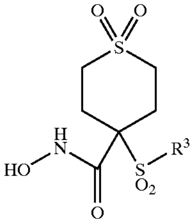
| | 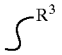 |
|---|---|
| 15 | 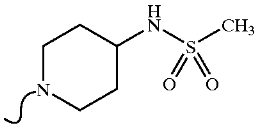 |
| 16 | 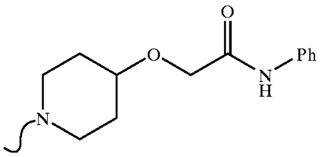 |
| 17 | 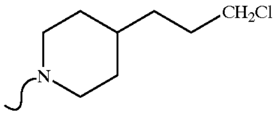 |
| 18 | 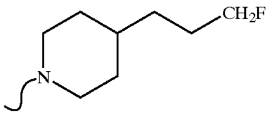 |
| 19 | 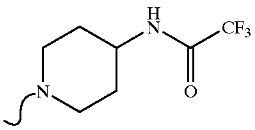 |
| 20 | 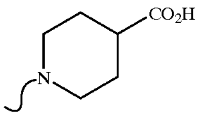 |
| 21 | 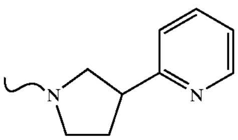 |
| 22 | 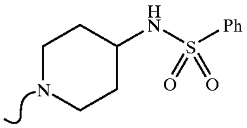 |
| 23 | 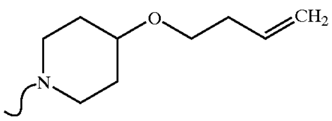 |
TABLE 89-continued
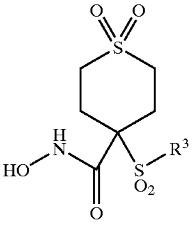
| | 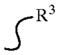 |
|---|---|
| 24 | 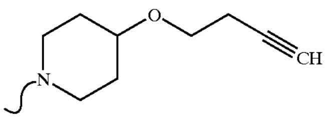 |
| 25 | 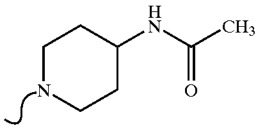 |
| 26 | 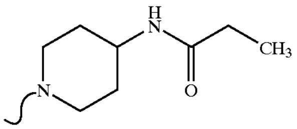 |
| 27 | 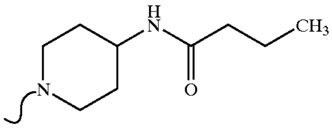 |
| 28 | 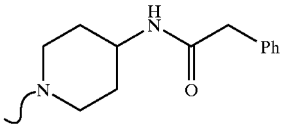 |
| 29 | 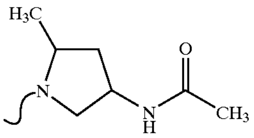 |
| 30 | 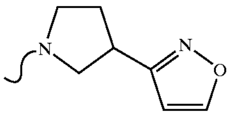 |
| 31 | 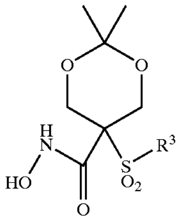 |

TABLE 90
| | |
|---|---|
| | 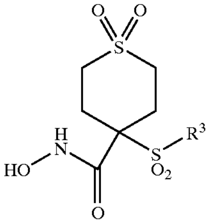 |
| | 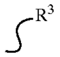 |
| 1 | 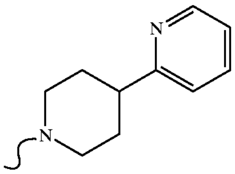 |
| 2 | 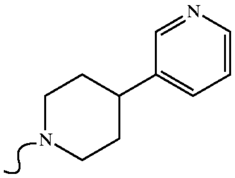 |
| 3 | 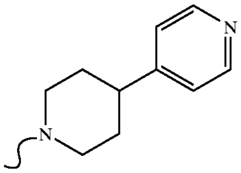 |
| 4 | 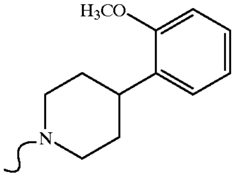 |
| 5 | 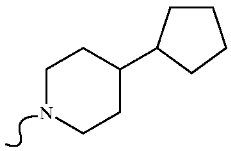 |
| 6 | 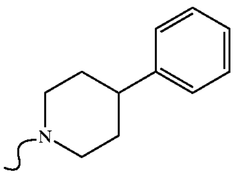 |
| 7 | 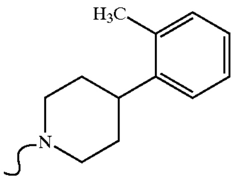 |
TABLE 90-continued
| | |
|---|---|
| | 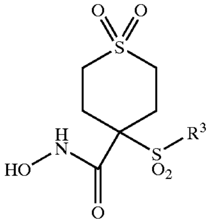 |
| | 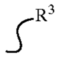 |
| 8 | 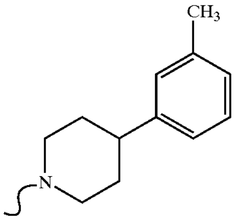 |
| 9 | 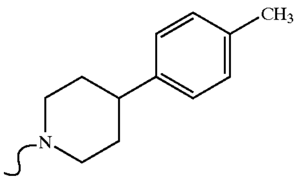 |
| 10 | 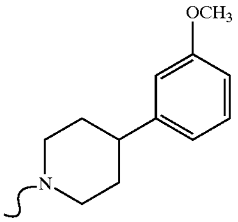 |
| 11 | 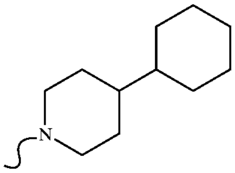 |
| 12 | 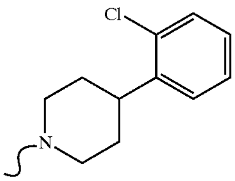 |
| 13 | 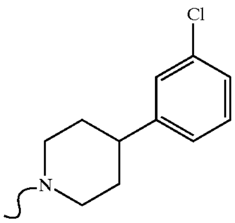 |

TABLE 90-continued
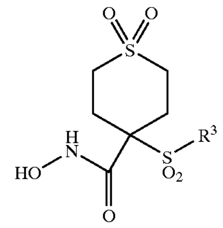
14 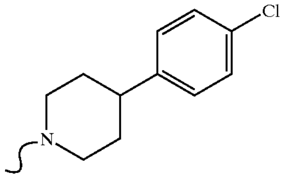
15 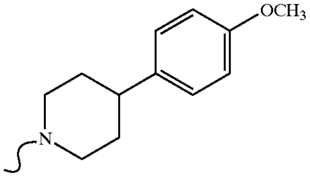
16 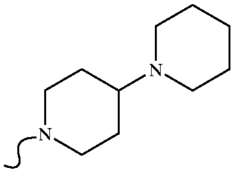
17 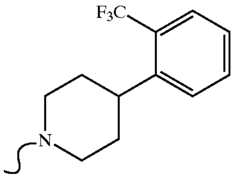
18 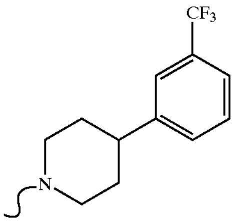
19 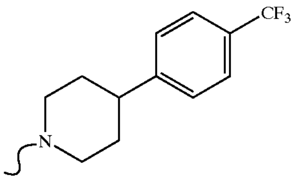
TABLE 90-continued
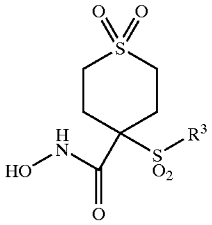
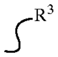
20 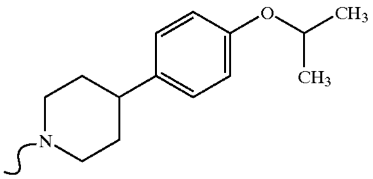
21 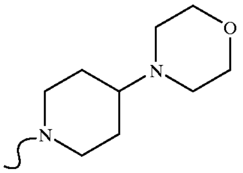
TABLE 91
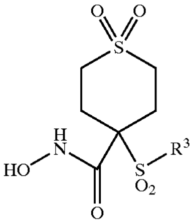
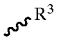
1 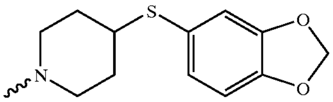
2 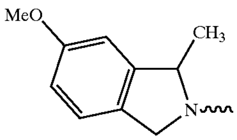
3 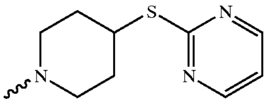
4 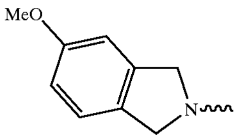

TABLE 91-continued
| | |
|---|---|
| | 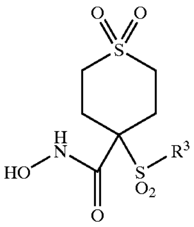 |
| | 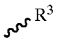 |
| 5 | 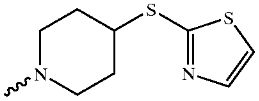 |
| 6 | 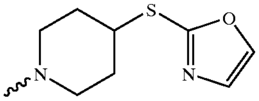 |
| 7 | 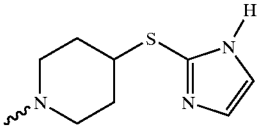 |
| 8 | 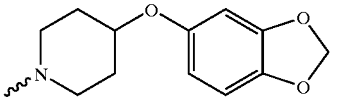 |
| 9 | 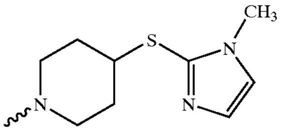 |
| 10 | 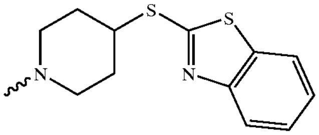 |
| 11 | 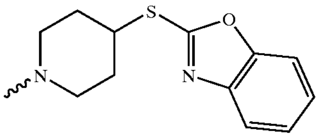 |
TABLE 92
| | |
|---|---|
| | 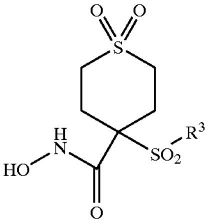 |
| | 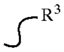 |
| 1 | 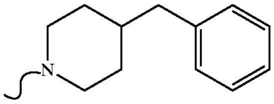 |
| 2 | 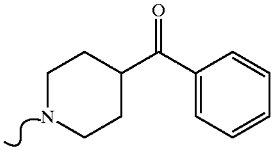 |
| 3 | 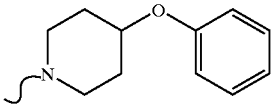 |
| 4 | 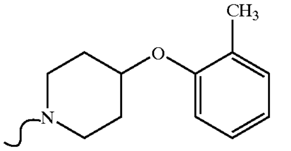 |
| 5 | 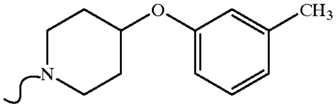 |
| 6 | 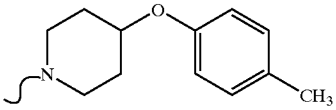 |
| 7 | 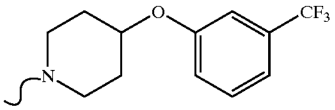 |
| 8 | 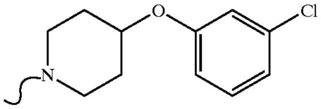 |
| 9 | 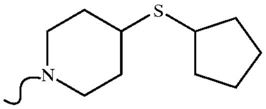 |

TABLE 92-continued
| | 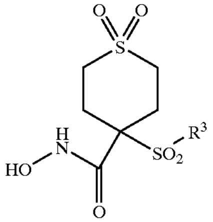 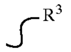 |
|---|---|
| 10 | 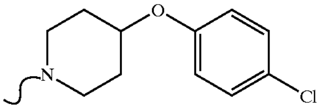 |
| 11 | 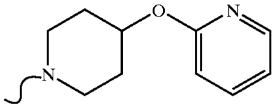 |
| 12 | 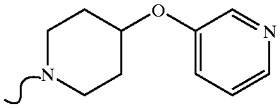 |
| 13 | 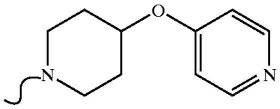 |
| 14 | 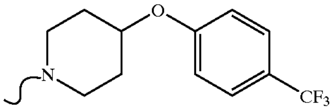 |
| 15 | 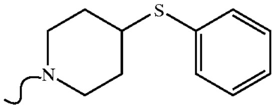 |
| 16 | 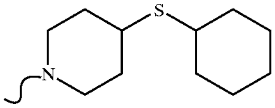 |
| 17 | 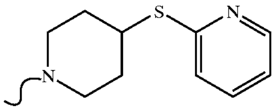 |
| 18 | 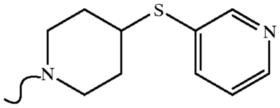 |
| 19 | 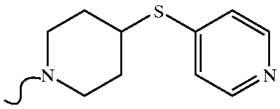 |
TABLE 92-continued
| | 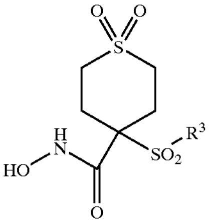  |
|---|---|
| 20 | 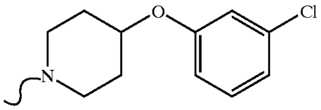 |
| 21 | 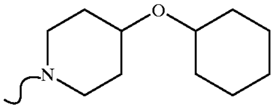 |
TABLE 93
| | 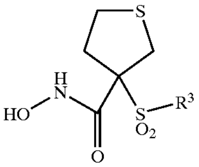 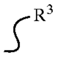 |
|---|---|
| 1 | 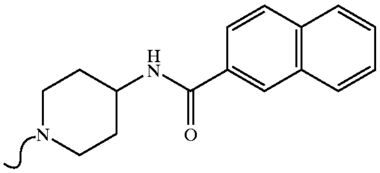 |
| 2 | 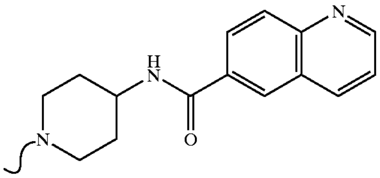 |
| 3 | 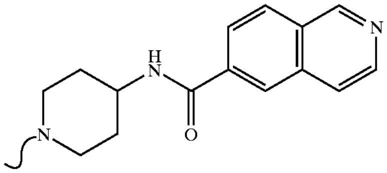 |

TABLE 93-continued
| 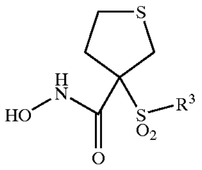 | |
|---|---|
| 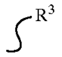 | |
| 4 | 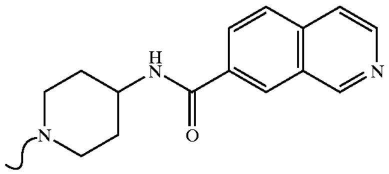 |
| 5 | 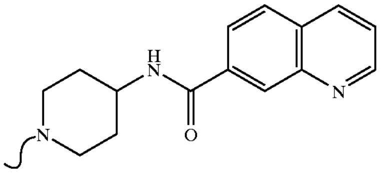 |
| 6 | 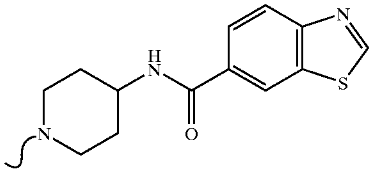 |
| 7 | 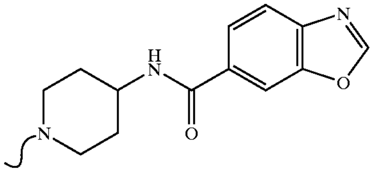 |
| 8 | 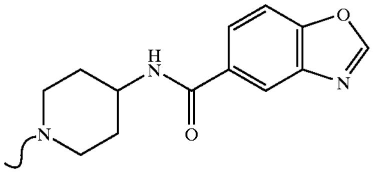 |
| 9 | 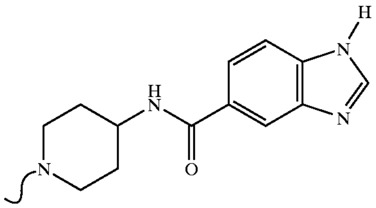 |
| 10 | 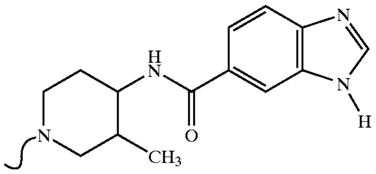 |
TABLE 93-continued
| 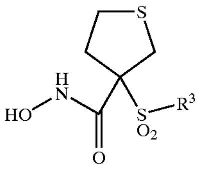 | |
|---|---|
| 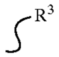 | |
| 11 | 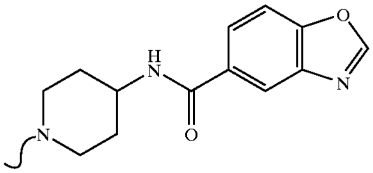 |
| 12 | 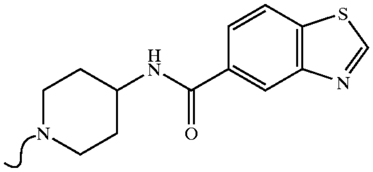 |
| 13 | 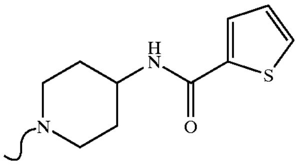 |
| 14 | 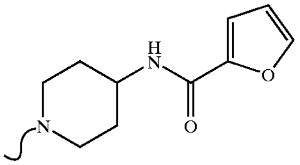 |
| 15 | 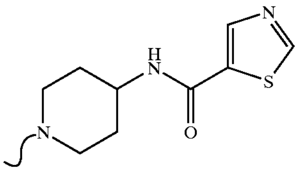 |
| 16 | 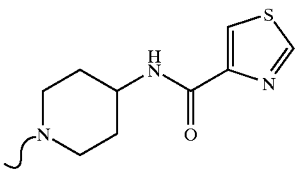 |
| 17 | 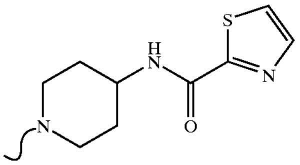 |

TABLE 93-continued
| |
|---|
| 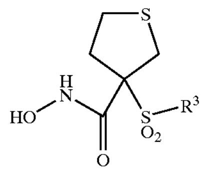 |
|  |
| 18 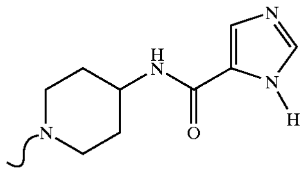 |
TABLE 94
| |
|---|
| 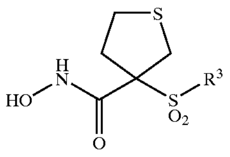 |
| 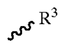 |
| 1 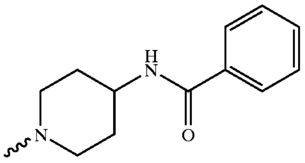 |
| 2 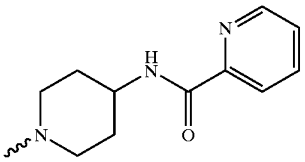 |
| 3 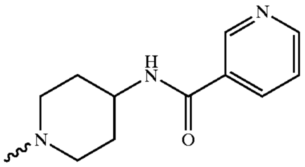 |
| 4 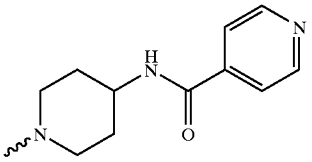 |
TABLE 94-continued
| |
|---|
| 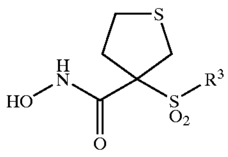 |
| 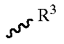 |
| 5 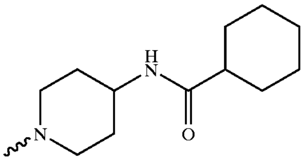 |
| 6 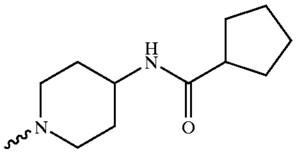 |
| 7 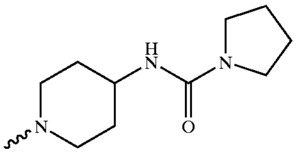 |
| 8 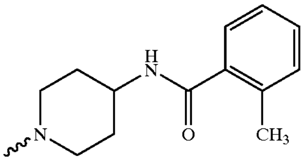 |
| 9 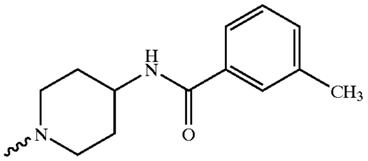 |
| 10 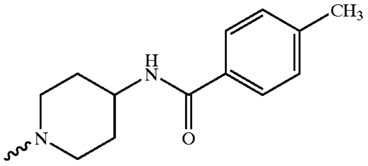 |
| 11 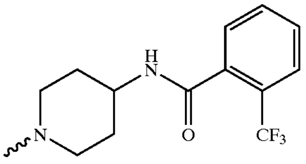 |
| 12 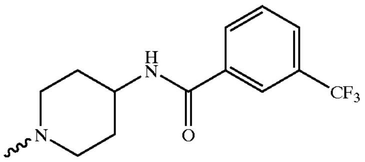 |

TABLE 94-continued
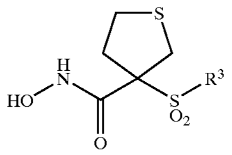
| | 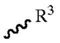 |
|---|---|
| 13 | 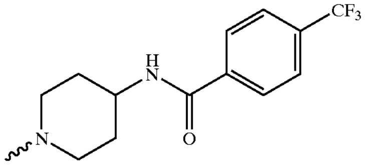 |
| 14 | 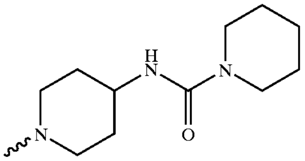 |
| 15 | 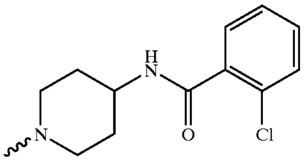 |
| 16 | 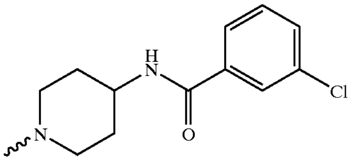 |
| 17 | 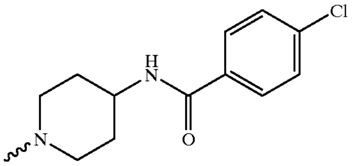 |
| 18 | 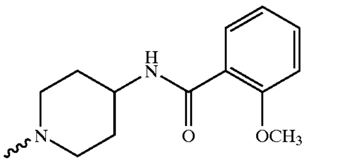 |
| 19 | 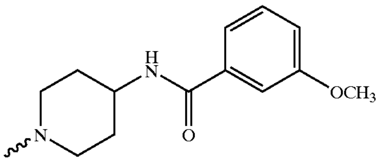 |
TABLE 94-continued
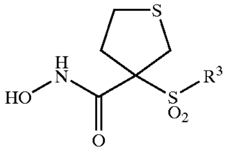
| | 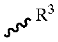 |
|---|---|
| 20 | 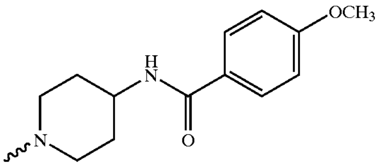 |
| 21 | 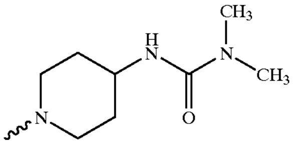 |
TABLE 95
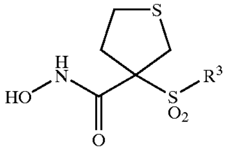
| | 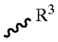 |
|---|---|
| 1 | 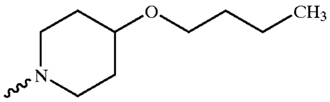 |
| 2 | 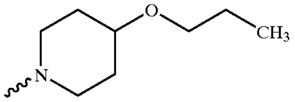 |
| 3 | 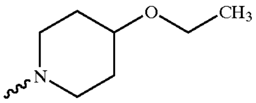 |
| 4 | 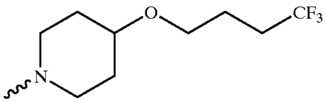 |
| 5 | 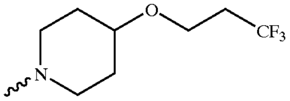 |
| 6 | 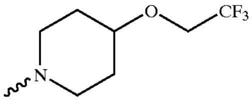 |

TABLE 95-continued
| | |
|---|---|
| | 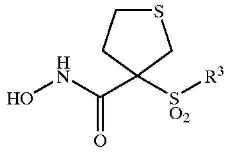 |
| | 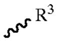 |
| 7 | 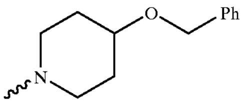 |
| 8 | 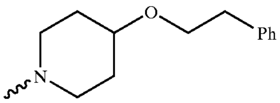 |
| 9 | 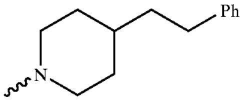 |
| 10 | 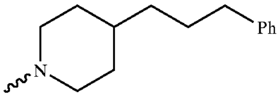 |
| 11 | 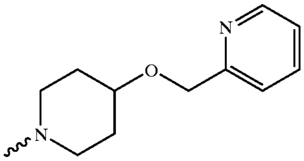 |
| 12 | 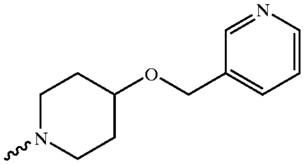 |
| 13 | 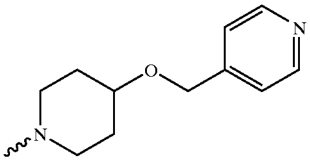 |
| 14 | 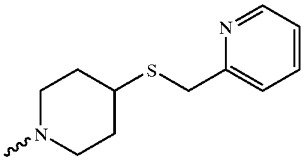 |
| 15 | 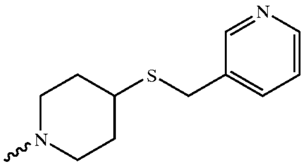 |
TABLE 95-continued
| | |
|---|---|
| | 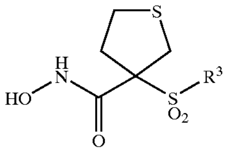 |
| | 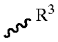 |
| 16 | 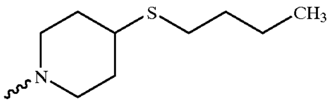 |
| 17 | 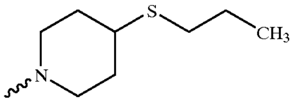 |
| 18 | 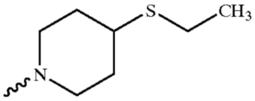 |
| 19 | 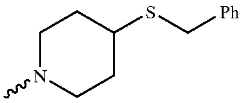 |
| 20 | 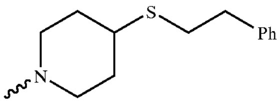 |
| 21 | 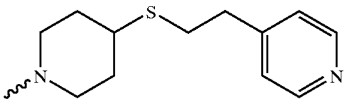 |
| 22 | 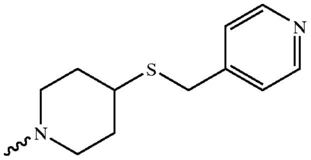 |
TABLE 96
| | |
|---|---|
| | 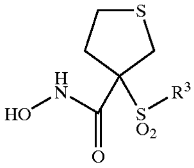 |
| | 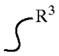 |
| 1 | 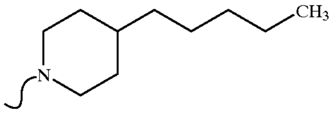 |

TABLE 96-continued
| | |
|---|---|
| | 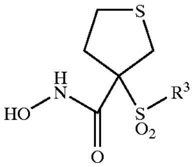<br> |
| 2 | 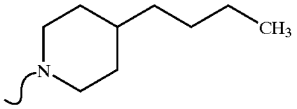 |
| 3 | 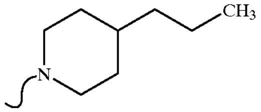 |
| 4 | 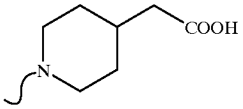 |
| 5 | 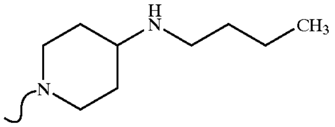 |
| 6 | 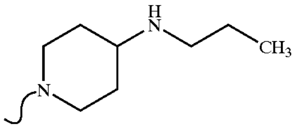 |
| 7 | 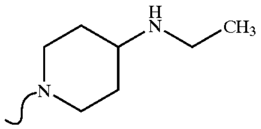 |
| 8 | 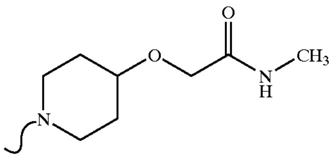 |
| 9 | 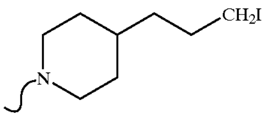 |
| 10 | 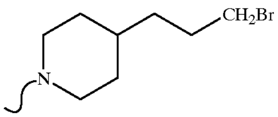 |
| 11 | 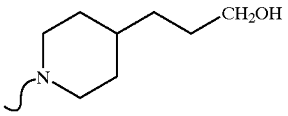 |
TABLE 96-continued
| | |
|---|---|
| | 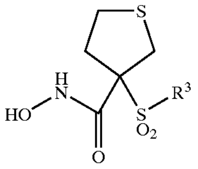<br> |
| 12 | 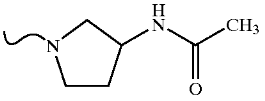 |
| 13 | 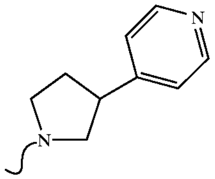 |
| 14 | 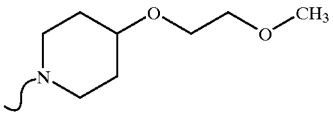 |
| 15 | 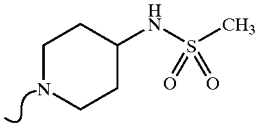 |
| 16 | 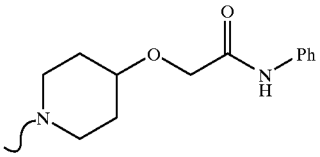 |
| 17 | 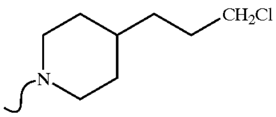 |
| 18 | 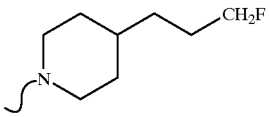 |
| 19 | 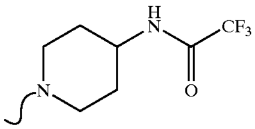 |
| 20 | 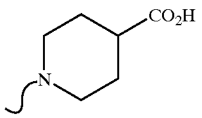 |

TABLE 96-continued
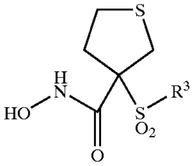
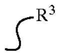
21 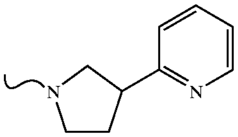
22 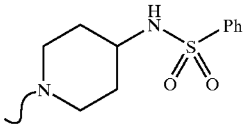
23 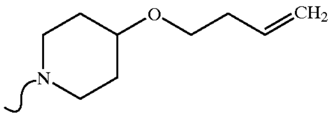
24 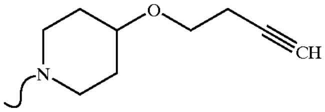
25 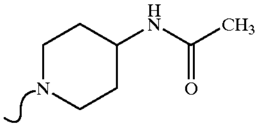
26 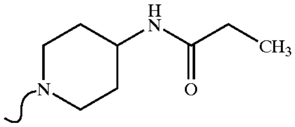
27 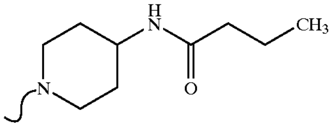
28 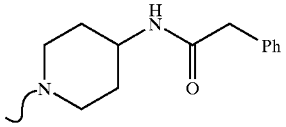
29 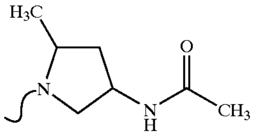
TABLE 96-continued
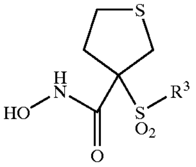
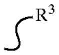
30 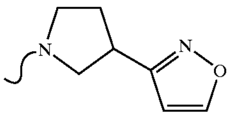
31 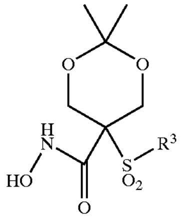
TABLE 97
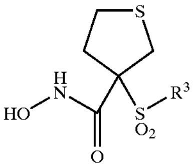
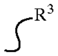
1 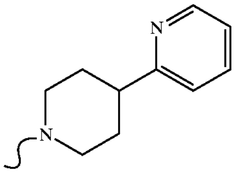
2 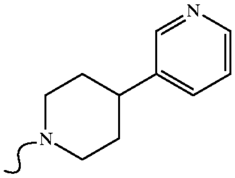
3 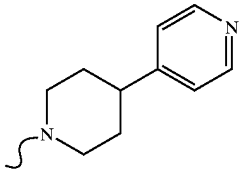

TABLE 97-continued
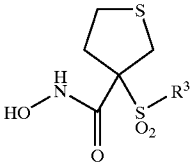
| | 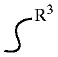 |
|---|---|
| 4 | 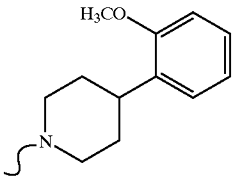 |
| 5 | 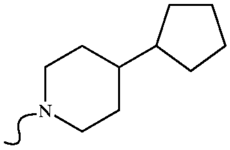 |
| 6 | 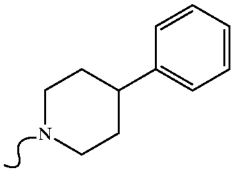 |
| 7 | 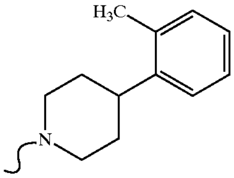 |
| 8 | 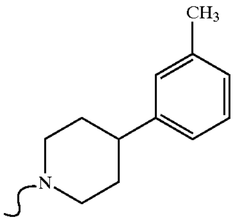 |
| 9 | 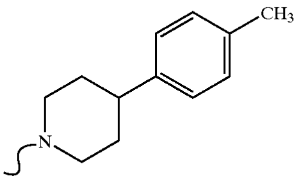 |
TABLE 97-continued
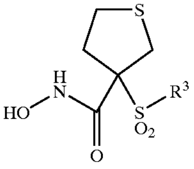
| | 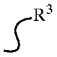 |
|---|---|
| 10 | 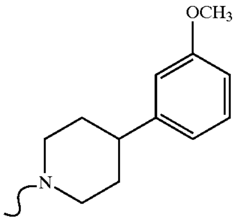 |
| 11 | 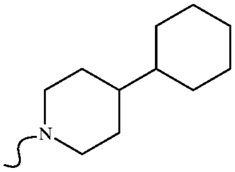 |
| 12 | 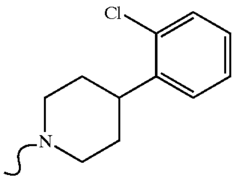 |
| 13 | 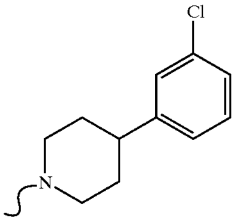 |
| 14 | 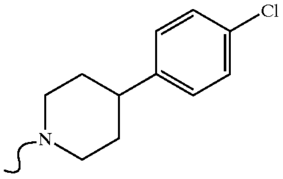 |
| 15 | 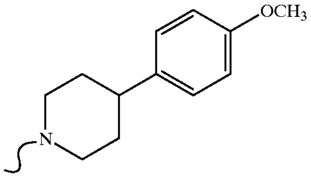 |

TABLE 97-continued
| | |
|---|---|
| | 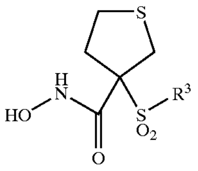 |
| | 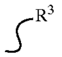 |
| 16 | 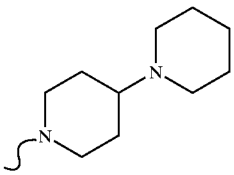 |
| 17 | 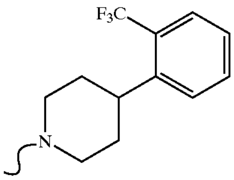 |
| 18 | 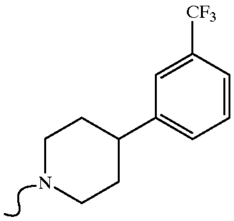 |
| 19 | 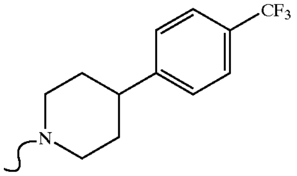 |
| 20 | 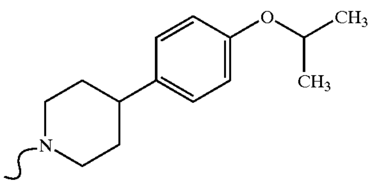 |
| 21 | 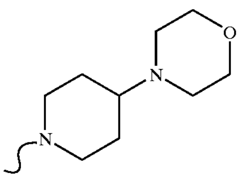 |
TABLE 98
| | |
|---|---|
| | 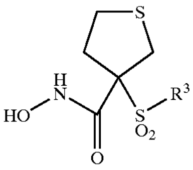 |
| | 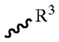 |
| 1 | 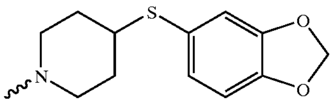 |
| 2 | 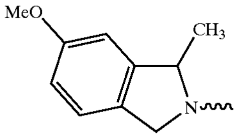 |
| 3 | 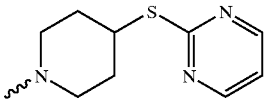 |
| 4 | 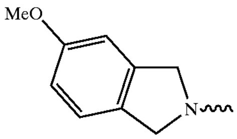 |
| 5 | 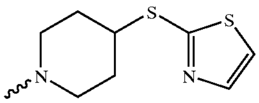 |
| 6 | 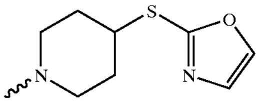 |
| 7 | 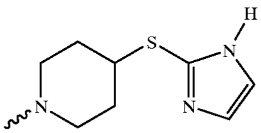 |
| 8 | 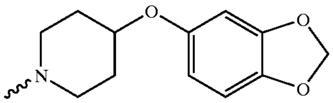 |
| 9 | 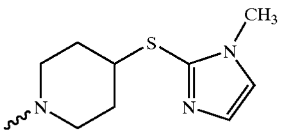 |
| 10 | 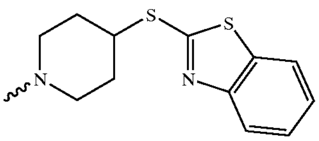 |

TABLE 98-continued
| | 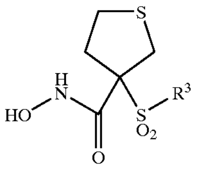 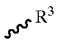 |
|---|---|
| 11 | 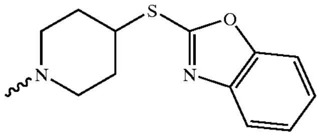 |
TABLE 99
| | 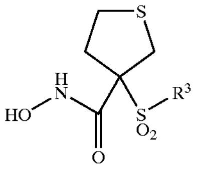 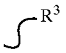 |
|---|---|
| 1 | 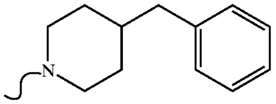 |
| 2 | 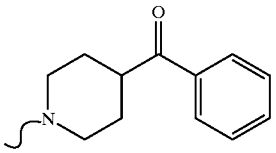 |
| 3 | 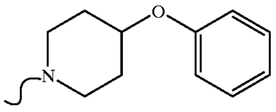 |
| 4 | 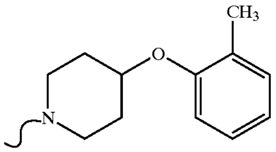 |
| 5 | 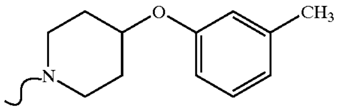 |
| 6 | 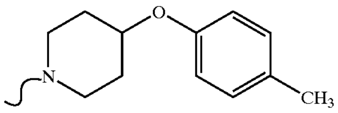 |
TABLE 99-continued
| | 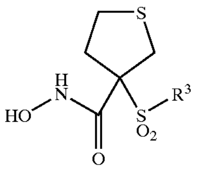 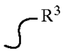 |
|---|---|
| 7 | 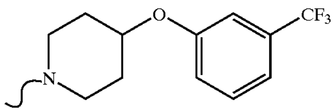 |
| 8 | 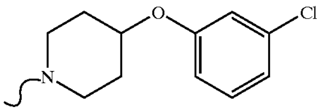 |
| 9 | 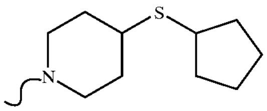 |
| 10 | 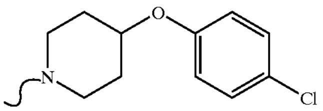 |
| 11 | 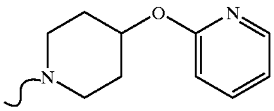 |
| 12 | 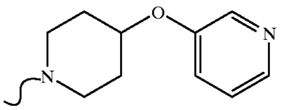 |
| 13 | 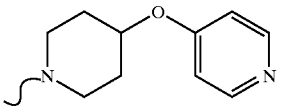 |
| 14 | 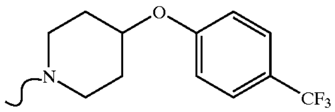 |
| 15 | 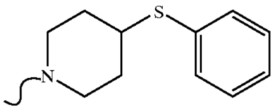 |
| 16 | 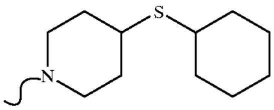 |
| 17 | 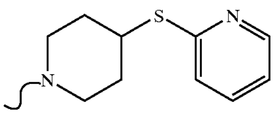 |

TABLE 99-continued
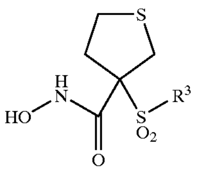
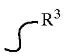
| | |
|---|---|
| 18 | 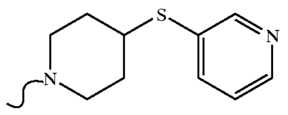 |
| 19 | 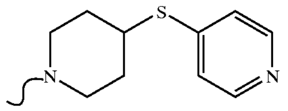 |
| 20 | 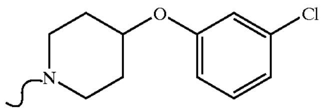 |
| 21 | 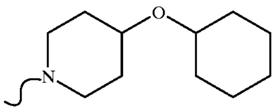 |
TABLE 100
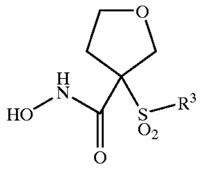
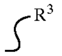
| | |
|---|---|
| 1 | 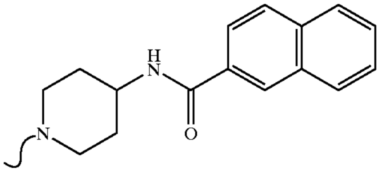 |
| 2 | 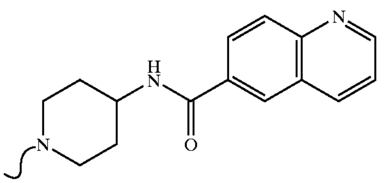 |
TABLE 100-continued
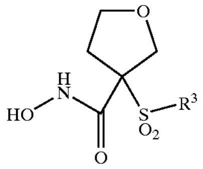
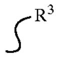
| | |
|---|---|
| 3 | 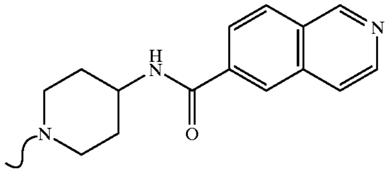 |
| 4 | 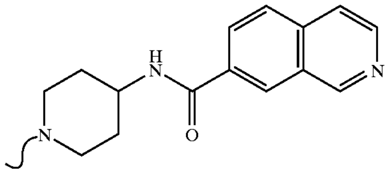 |
| 5 | 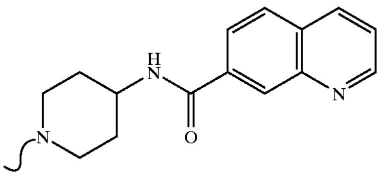 |
| 6 | 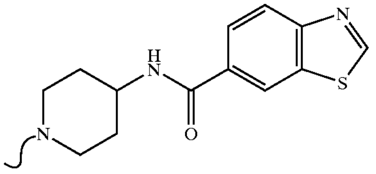 |
| 7 | 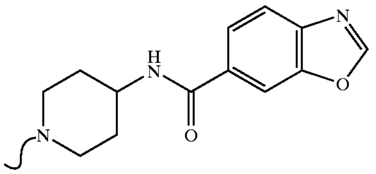 |
| 8 | 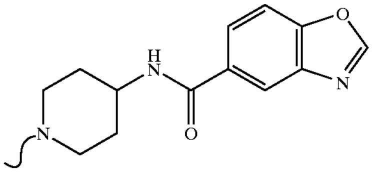 |
| 9 | 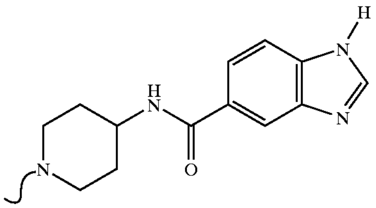 |

TABLE 100-continued
| 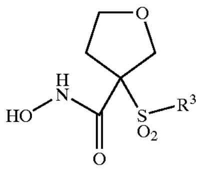 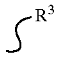 | |
|---|---|
| 10 | 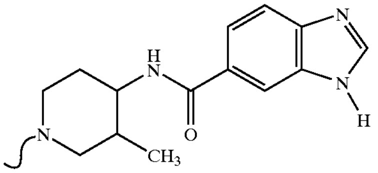 |
| 11 | 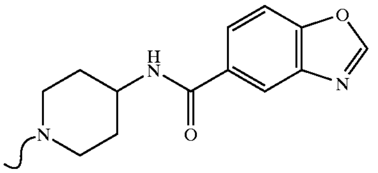 |
| 12 | 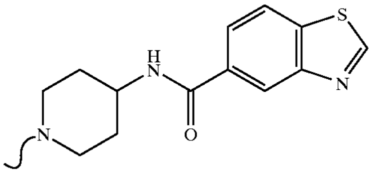 |
| 13 | 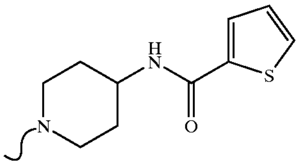 |
| 14 | 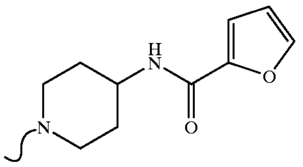 |
| 15 | 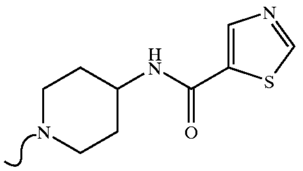 |
| 16 | 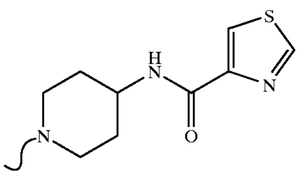 |
TABLE 100-continued
| 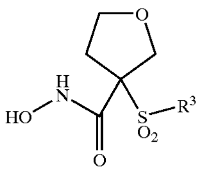 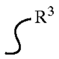 | |
|---|---|
| 17 | 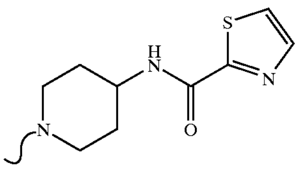 |
| 18 | 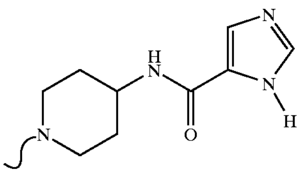 |
TABLE 101
| 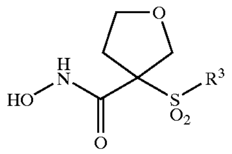 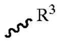 | |
|---|---|
| 1 | 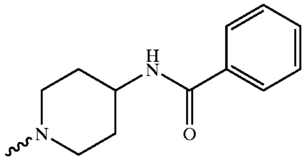 |
| 2 | 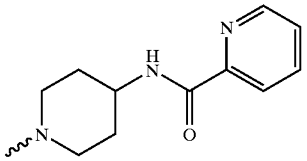 |
| 3 | 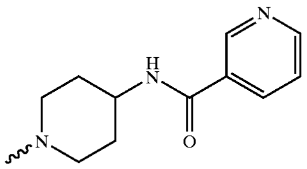 |

TABLE 101-continued
| | |
|---|---|
| | 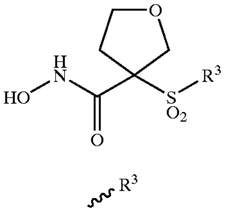 |
| 4 | 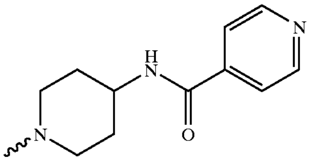 |
| 5 | 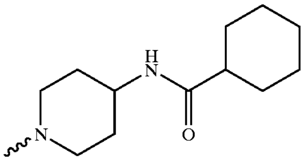 |
| 6 | 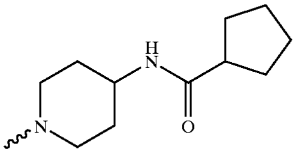 |
| 7 | 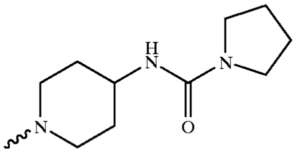 |
| 8 | 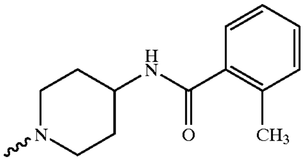 |
| 9 | 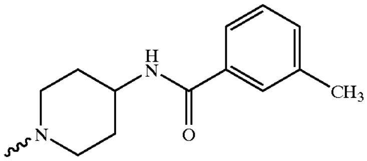 |
| 10 | 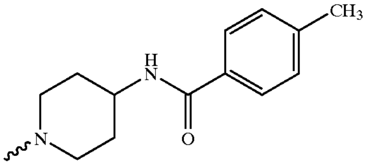 |
| 11 | 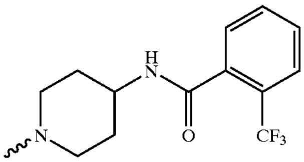 |
TABLE 101-continued
| | |
|---|---|
| | 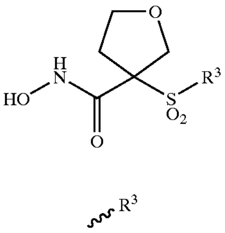 |
| 12 | 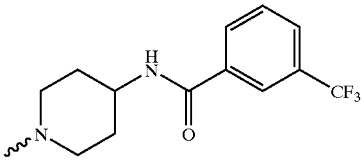 |
| 13 | 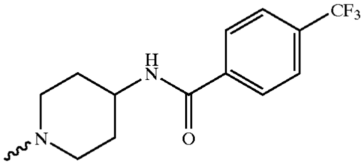 |
| 14 | 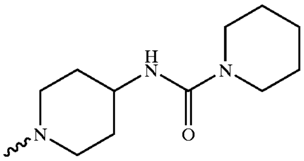 |
| 15 | 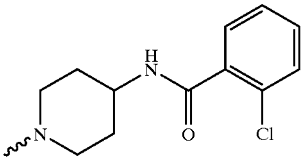 |
| 16 | 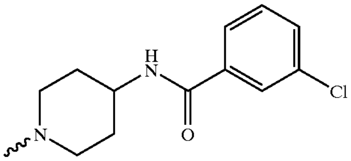 |
| 17 | 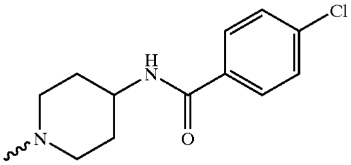 |
| 18 | 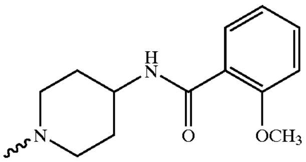 |

TABLE 101-continued
| | |
|---|---|
| | 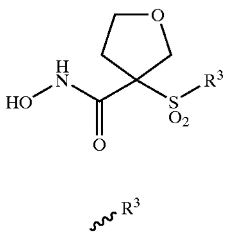 |
| 19 | 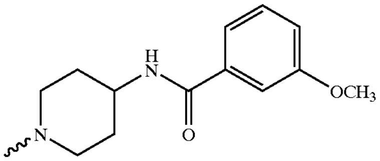 |
| 20 | 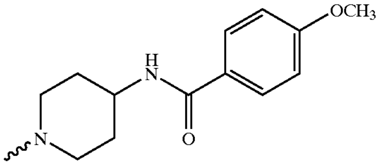 |
| 21 | 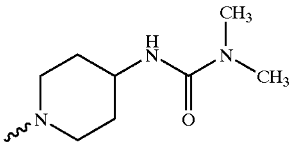 |
TABLE 102
| | |
|---|---|
| | 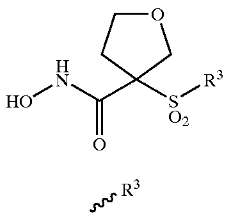 |
| 1 | 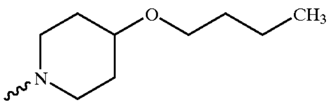 |
| 2 | 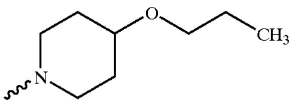 |
| 3 | 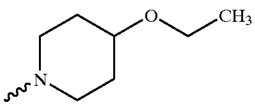 |
| 4 | 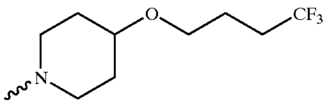 |
TABLE 102-continued
| | |
|---|---|
| | 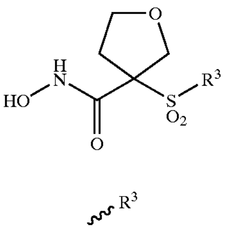 |
| 5 | 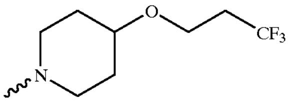 |
| 6 | 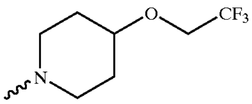 |
| 7 | 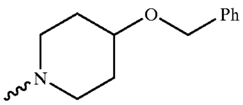 |
| 8 | 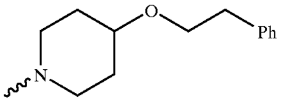 |
| 9 | 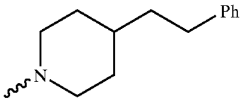 |
| 10 | 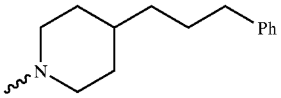 |
| 11 | 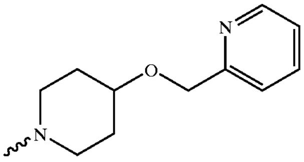 |
| 12 | 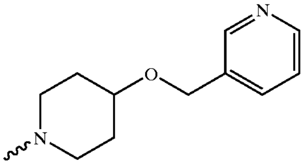 |
| 13 | 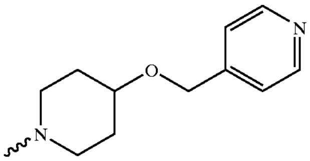 |

TABLE 102-continued
| | |
|---|---|
| 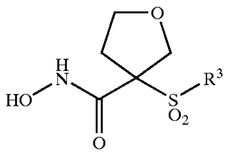 | |
| 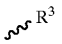 | |
| 14 | 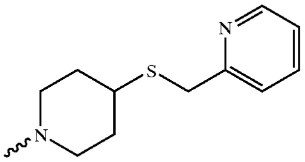 |
| 15 | 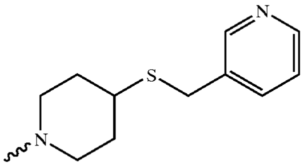 |
| 16 | 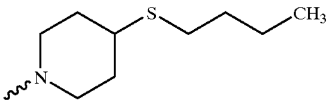 |
| 17 | 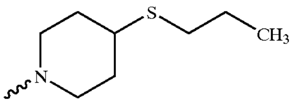 |
| 18 | 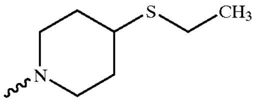 |
| 19 | 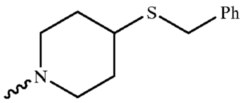 |
| 20 | 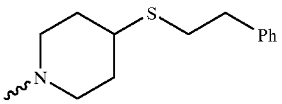 |
| 21 | 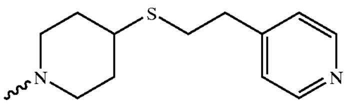 |
| 22 | 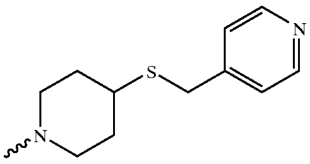 |
TABLE 103
| | |
|---|---|
| 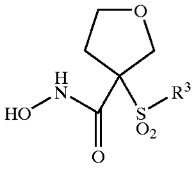 | |
| 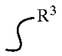 | |
| 1 | 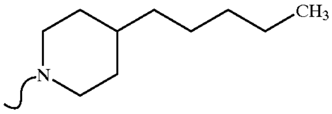 |
| 2 | 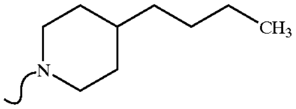 |
| 3 | 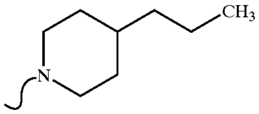 |
| 4 | 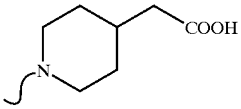 |
| 5 | 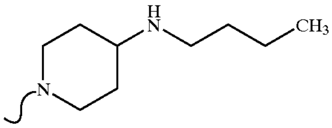 |
| 6 | 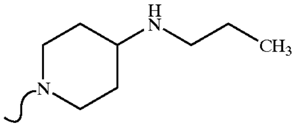 |
| 7 | 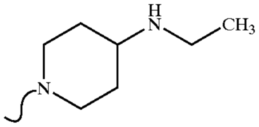 |
| 8 | 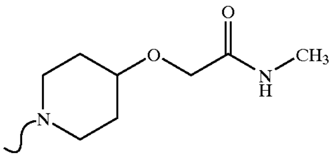 |
| 9 | 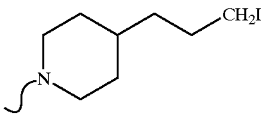 |
| 10 | 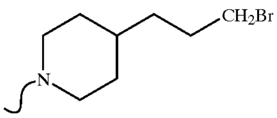 |

TABLE 103-continued
| 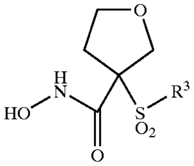 | |
|---|---|
| | 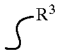 |
| 11 | 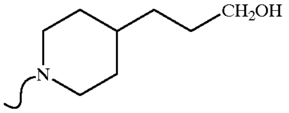 |
| 12 | 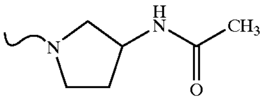 |
| 13 | 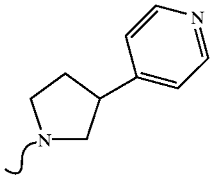 |
| 14 | 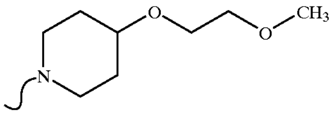 |
| 15 | 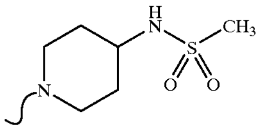 |
| 16 | 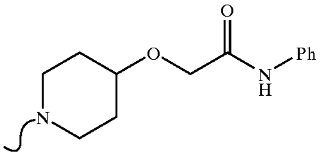 |
| 17 | 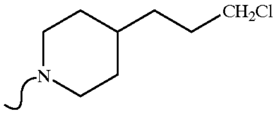 |
| 18 | 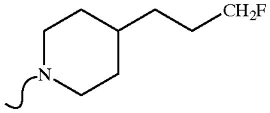 |
| 19 | 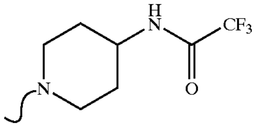 |
TABLE 103-continued
| 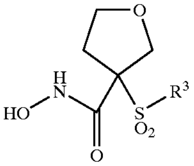 | |
|---|---|
| | 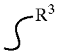 |
| 20 | 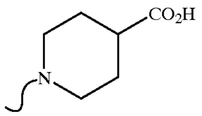 |
| 21 | 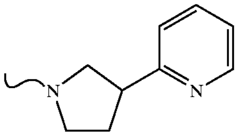 |
| 22 | 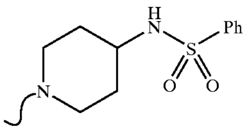 |
| 23 | 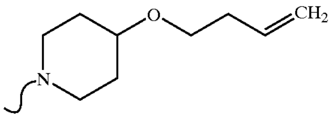 |
| 24 | 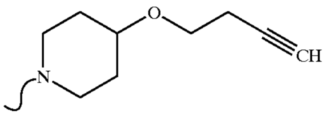 |
| 25 | 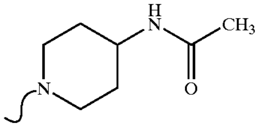 |
| 26 | 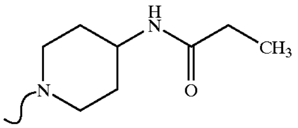 |
| 27 | 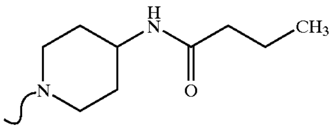 |
| 28 | 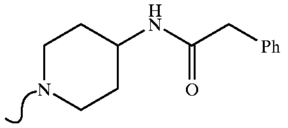 |

TABLE 103-continued
| | 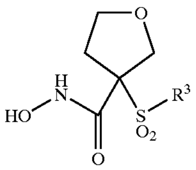 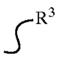 |
|---|---|
| 29 | 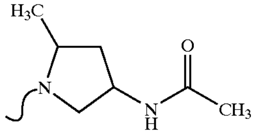 |
| 30 | 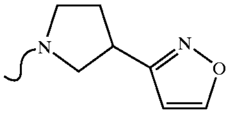 |
| 31 | 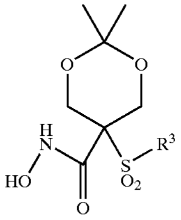 |
TABLE 104
| | 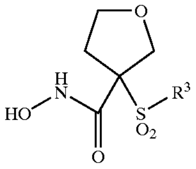 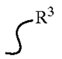 |
|---|---|
| 1 | 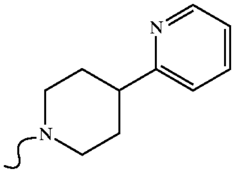 |
| 2 | 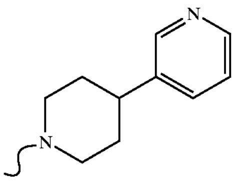 |
TABLE 104-continued
| | 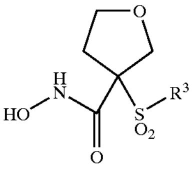 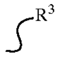 |
|---|---|
| 3 | 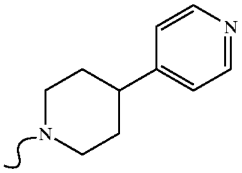 |
| 4 | 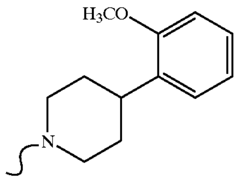 |
| 5 | 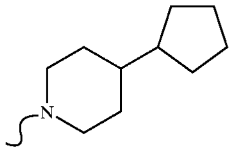 |
| 6 | 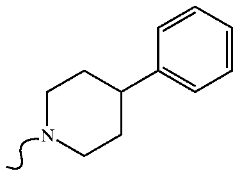 |
| 7 | 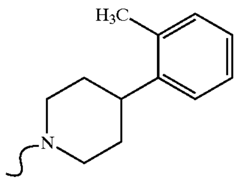 |
| 8 | 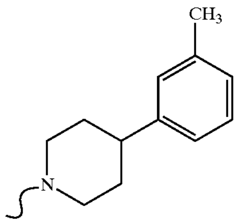 |
| 9 | 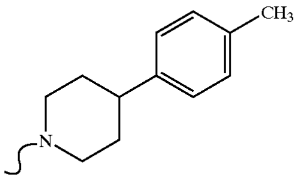 |

TABLE 104-continued
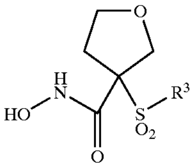
| | 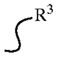 |
|---|---|
| 10 | 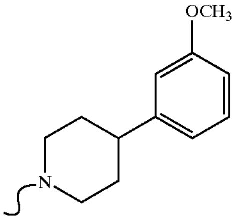 |
| 11 | 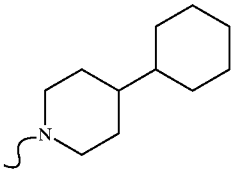 |
| 12 | 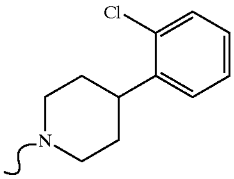 |
| 13 | 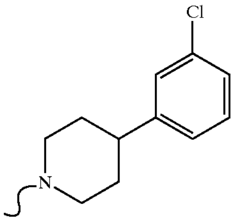 |
| 14 | 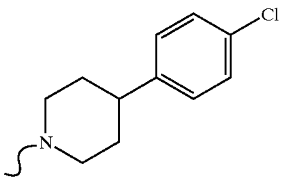 |
| 15 | 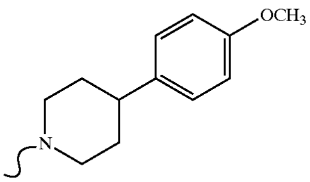 |
TABLE 104-continued
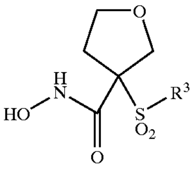
| | 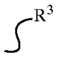 |
|---|---|
| 16 | 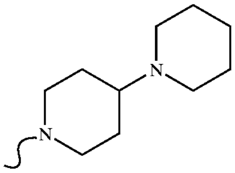 |
| 17 | 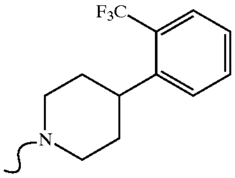 |
| 18 | 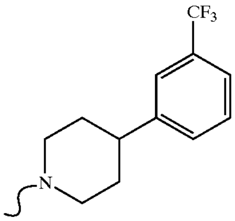 |
| 19 | 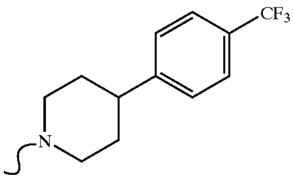 |
| 20 | 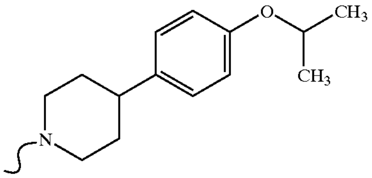 |
| 21 | 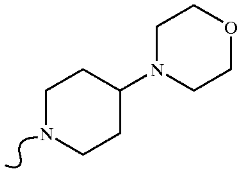 |

TABLE 105
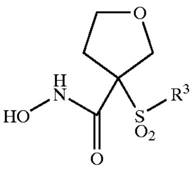
| | 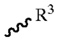 |
|---|---|
| 1 | 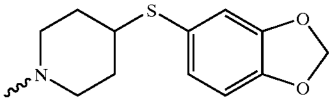 |
| 2 | 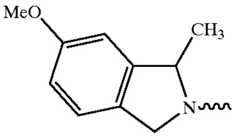 |
| 3 | 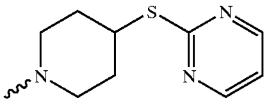 |
| 4 | 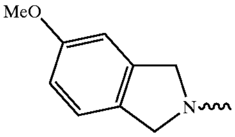 |
| 5 | 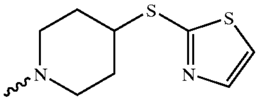 |
| 6 | 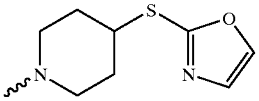 |
| 7 | 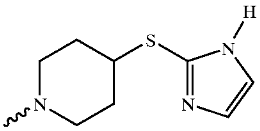 |
| 8 | 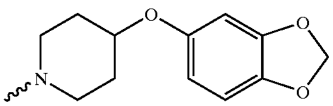 |
| 9 | 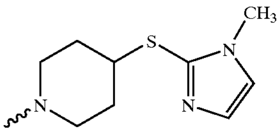 |
| 10 | 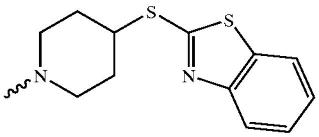 |
TABLE 105-continued
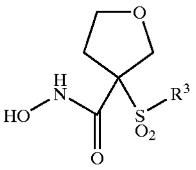
| | 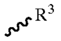 |
|---|---|
| 11 | 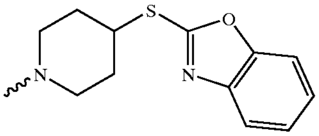 |
TABLE 106
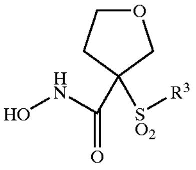
| | 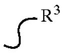 |
|---|---|
| 1 | 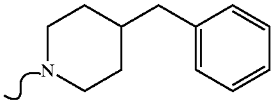 |
| 2 | 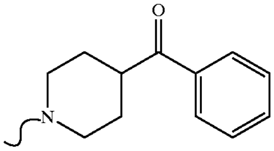 |
| 3 | 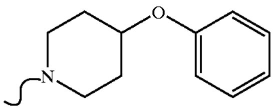 |
| 4 | 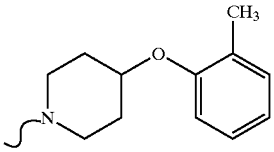 |
| 5 | 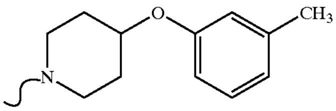 |
| 6 | 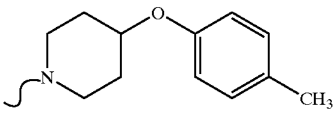 |

TABLE 106-continued
| 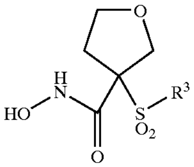 | 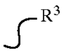 |
|---|---|
| 7 | 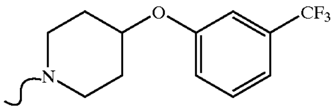 |
| 8 | 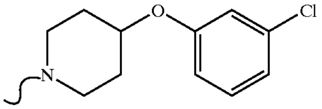 |
| 9 | 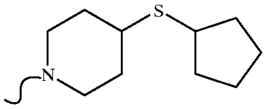 |
| 10 | 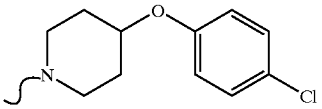 |
| 11 | 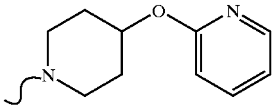 |
| 12 | 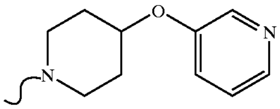 |
| 13 | 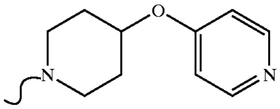 |
| 14 | 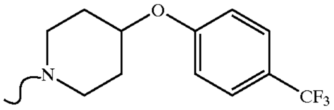 |
| 15 | 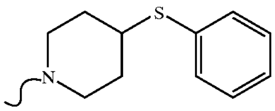 |
| 16 | 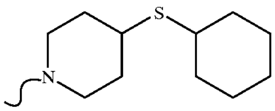 |
| 17 | 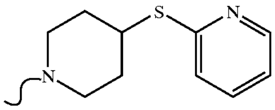 |
TABLE 106-continued
| 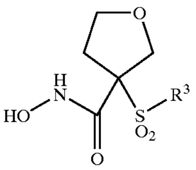 | 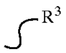 |
|---|---|
| 18 | 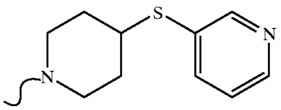 |
| 19 | 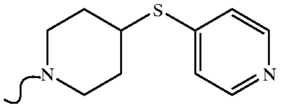 |
| 20 | 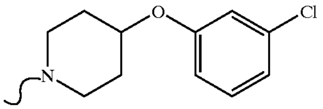 |
| 21 | 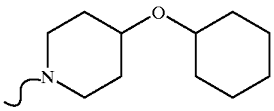 |
TABLE 107
| 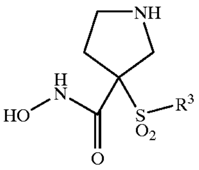 | 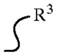 |
|---|---|
| 1 | 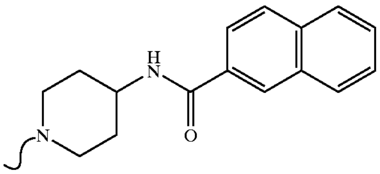 |
| 2 | 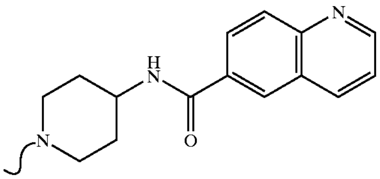 |

TABLE 107-continued
| 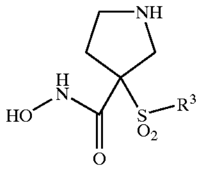 | 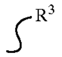 |
|---|---|
| 3 | 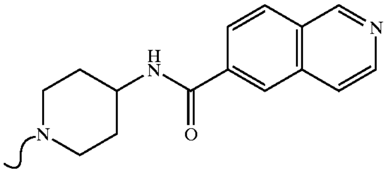 |
| 4 | 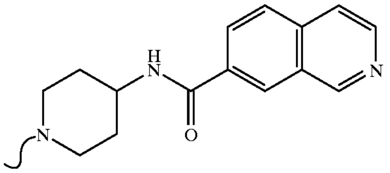 |
| 5 | 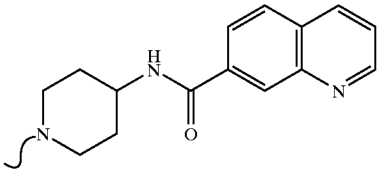 |
| 6 | 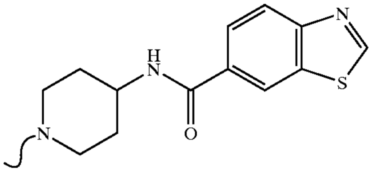 |
| 7 | 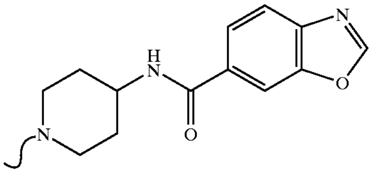 |
| 8 | 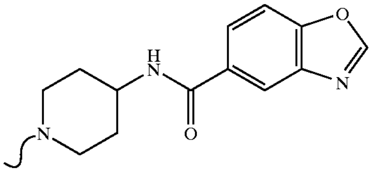 |
| 9 | 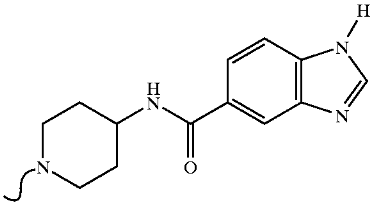 |
TABLE 107-continued
| 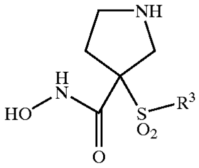 | 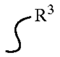 |
|---|---|
| 10 | 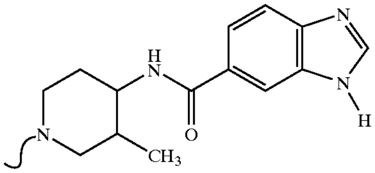 |
| 11 | 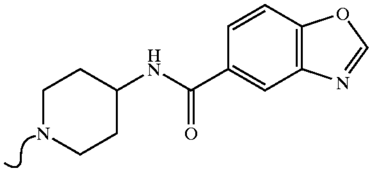 |
| 12 | 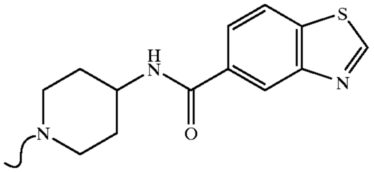 |
| 13 | 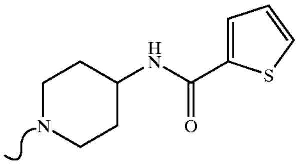 |
| 14 | 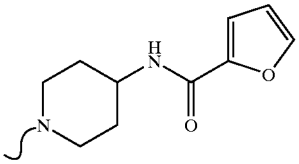 |
| 15 | 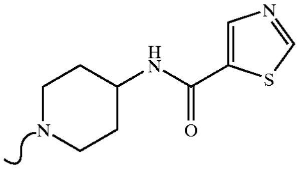 |
| 16 | 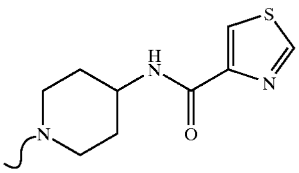 |

TABLE 107-continued
| | |
|---|---|
| | 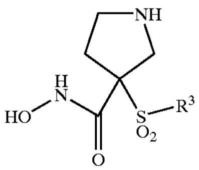 |
| | 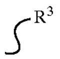 |
| 17 | 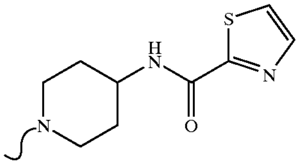 |
| 18 | 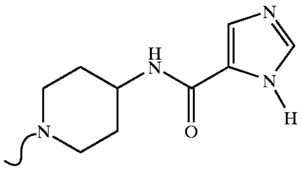 |
TABLE 108
| | |
|---|---|
| | 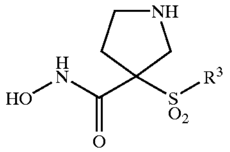 |
| | 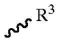 |
| 1 | 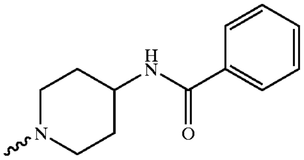 |
| 2 | 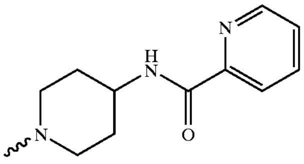 |
| 3 | 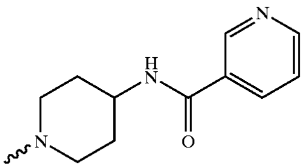 |
TABLE 108-continued
| | |
|---|---|
| | 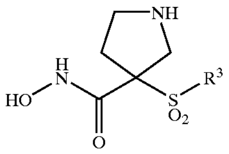 |
| | 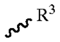 |
| 4 | 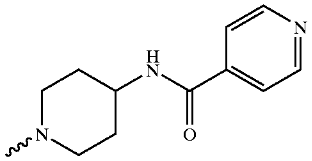 |
| 5 | 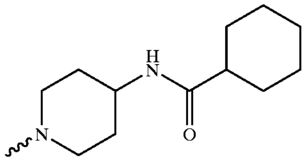 |
| 6 | 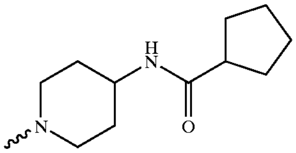 |
| 7 | 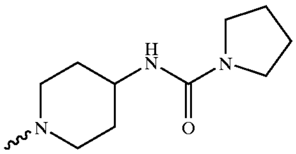 |
| 8 | 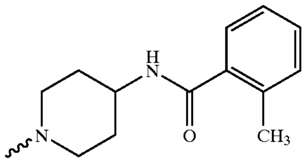 |
| 9 | 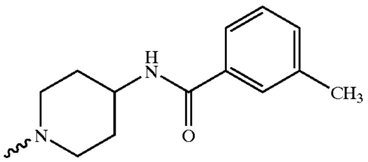 |
| 10 | 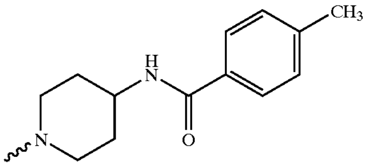 |
| 11 | 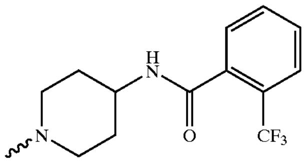 |

TABLE 108-continued
| | |
|---|---|
| | 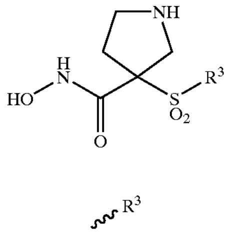 |
| 12 | 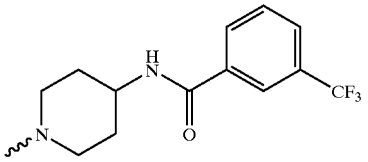 |
| 13 | 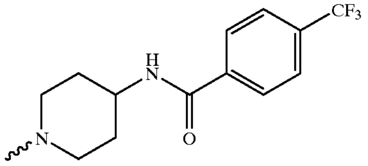 |
| 14 | 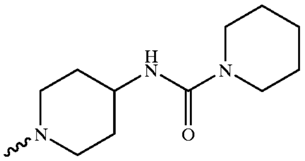 |
| 15 | 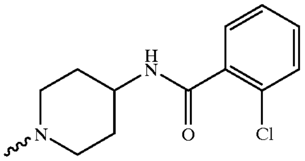 |
| 16 | 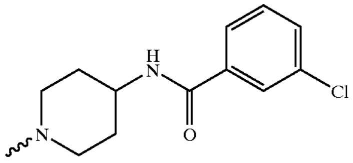 |
| 17 | 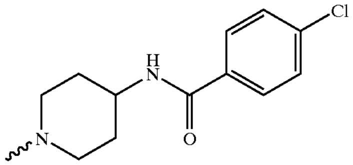 |
| 18 | 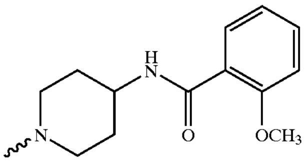 |
TABLE 108-continued
| | |
|---|---|
| | 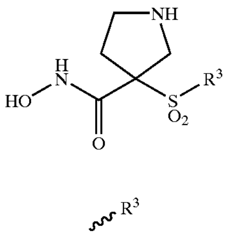 |
| 19 | 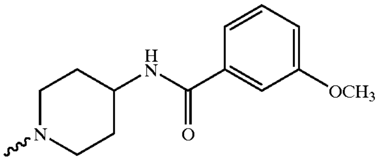 |
| 20 | 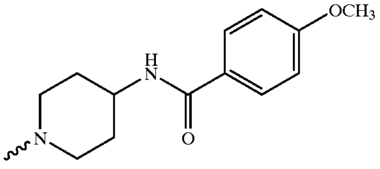 |
| 21 | 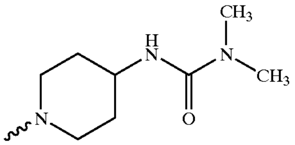 |
TABLE 109
| | |
|---|---|
| | 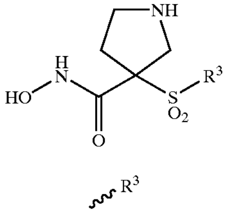 |
| 1 | 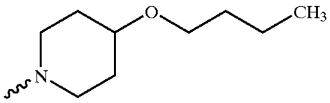 |
| 2 | 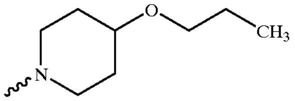 |
| 3 | 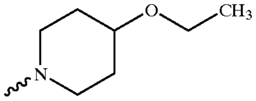 |
| 4 | 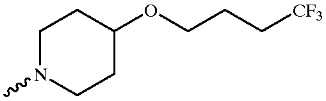 |

TABLE 109-continued
| | 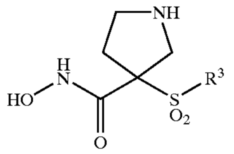<br>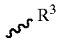 |
|---|---|
| 5 | 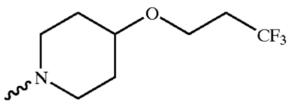 |
| 6 | 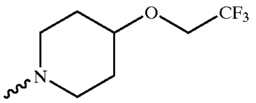 |
| 7 | 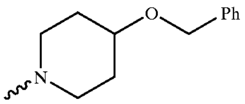 |
| 8 | 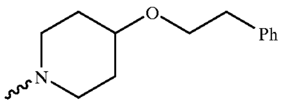 |
| 9 | 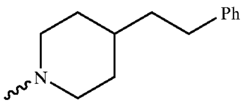 |
| 10 | 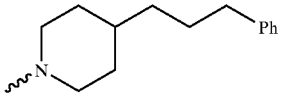 |
| 11 | 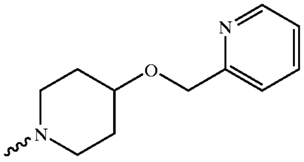 |
| 12 | 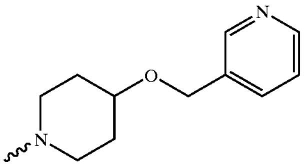 |
| 13 | 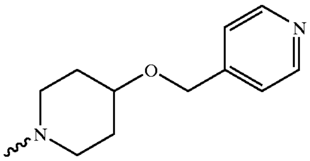 |
TABLE 109-continued
| | 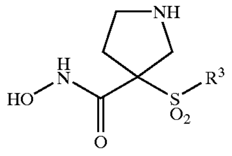<br>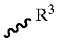 |
|---|---|
| 14 | 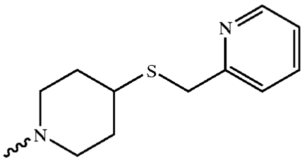 |
| 15 | 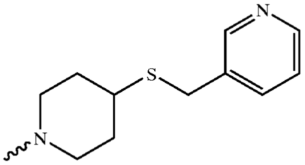 |
| 16 | 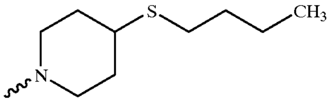 |
| 17 | 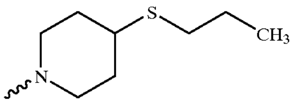 |
| 18 | 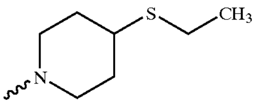 |
| 19 | 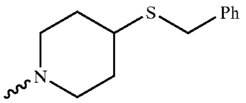 |
| 20 | 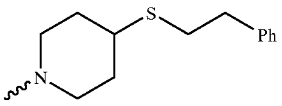 |
| 21 | 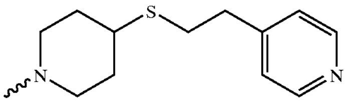 |
| 22 | 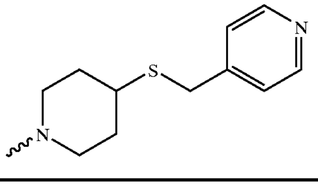 |

TABLE 110
| | 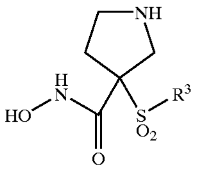<br>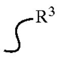 |
|---|---|
| 1 | 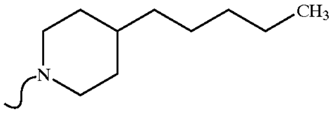 |
| 2 | 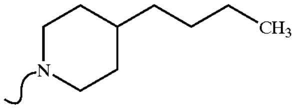 |
| 3 | 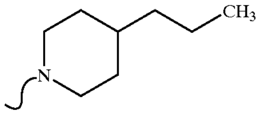 |
| 4 | 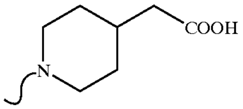 |
| 5 | 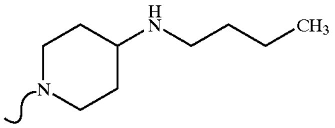 |
| 6 | 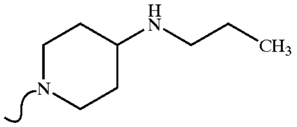 |
| 7 | 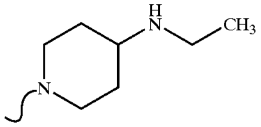 |
| 8 | 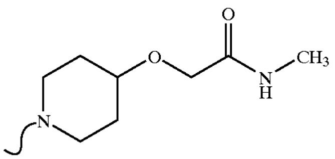 |
| 9 | 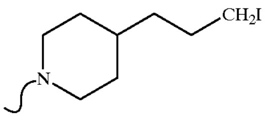 |
| 10 | 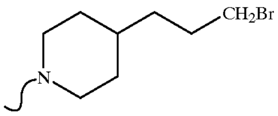 |
TABLE 110-continued
| | 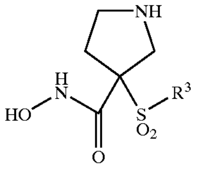<br>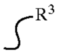 |
|---|---|
| 11 | 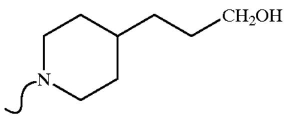 |
| 12 | 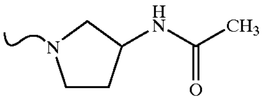 |
| 13 | 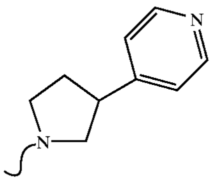 |
| 14 | 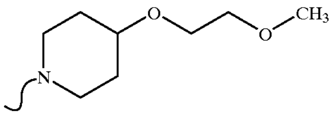 |
| 15 | 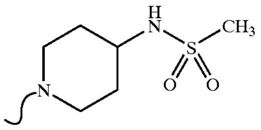 |
| 16 | 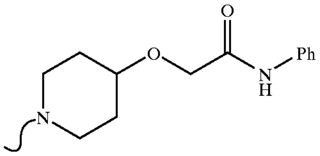 |
| 17 | 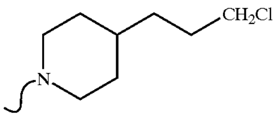 |
| 18 | 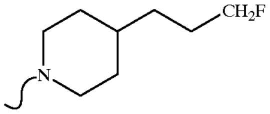 |
| 19 | 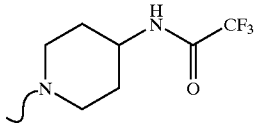 |

TABLE 110-continued
| | 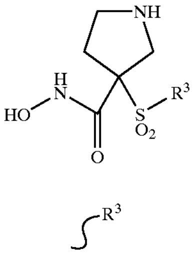 |
|---|---|
| 20 | 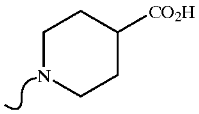 |
| 21 | 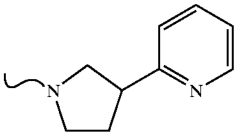 |
| 22 | 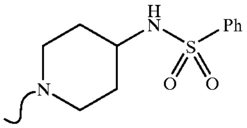 |
| 23 | 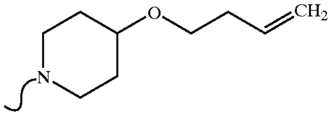 |
| 24 | 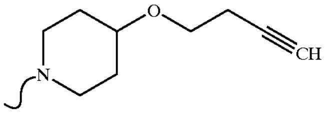 |
| 25 | 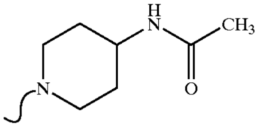 |
| 26 | 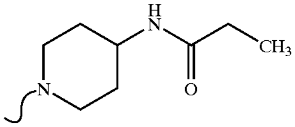 |
| 27 | 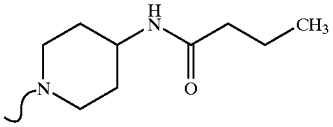 |
| 28 | 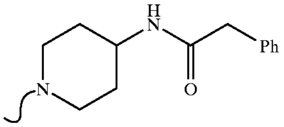 |
TABLE 110-continued
| | 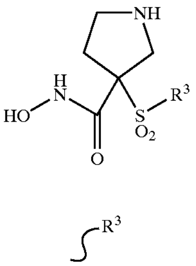 |
|---|---|
| 29 | 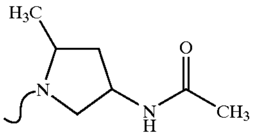 |
| 30 | 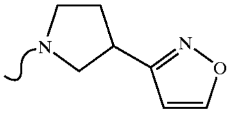 |
| 31 | 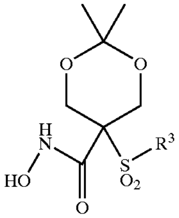 |
TABLE 111
| | 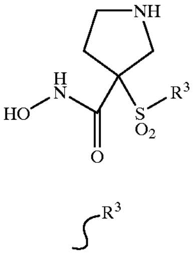 |
|---|---|
| 1 | 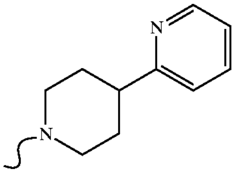 |
| 2 | 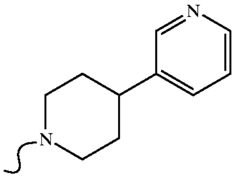 |

TABLE 111-continued
| 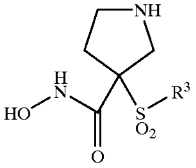 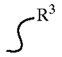 |  |
| --- | --- |
| 3 | 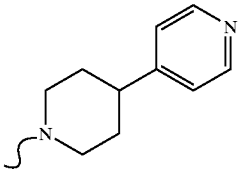 |
| 4 | 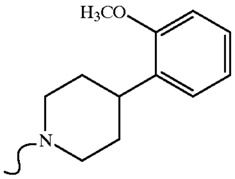 |
| 5 | 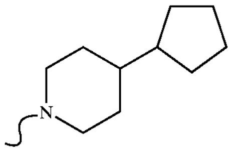 |
| 6 | 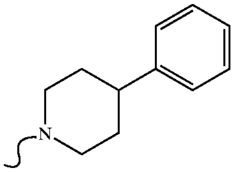 |
| 7 | 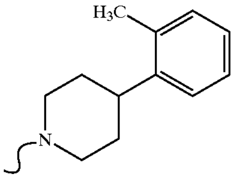 |
| 8 | 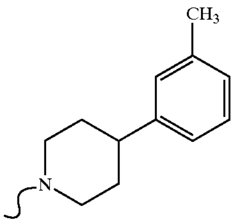 |
| 9 | 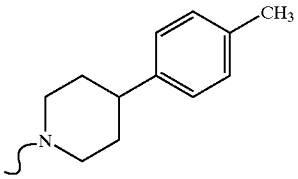 |
TABLE 111-continued
| 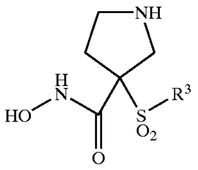 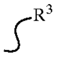 |  |
| --- | --- |
| 10 | 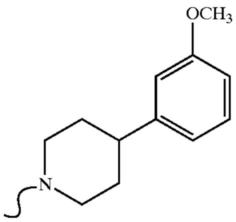 |
| 11 | 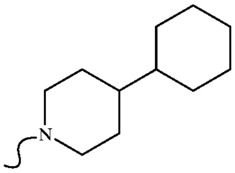 |
| 12 | 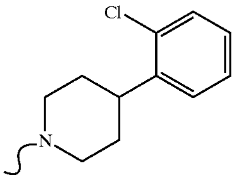 |
| 13 | 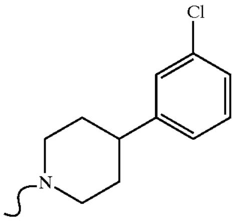 |
| 14 | 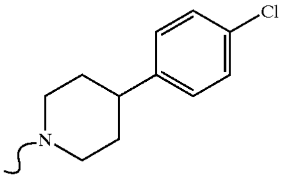 |
| 15 | 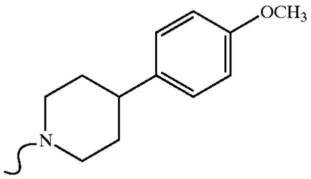 |

TABLE 111-continued
| | |
|---|---|
| 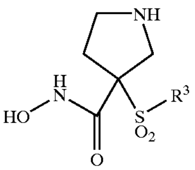 | |
| 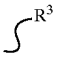 | |
| 16 | 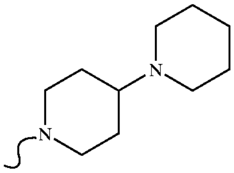 |
| 17 | 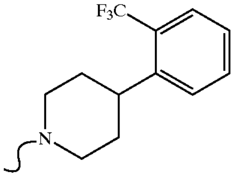 |
| 18 | 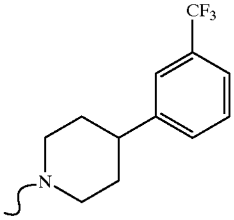 |
| 19 | 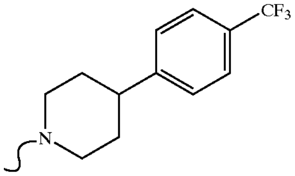 |
| 20 | 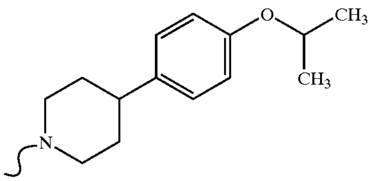 |
| 21 | 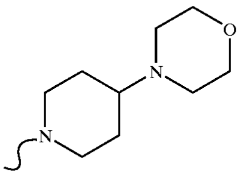 |
TABLE 112
| | |
|---|---|
| 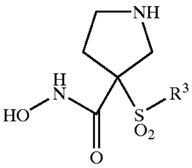 | |
| 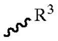 | |
| 1 | 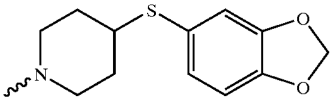 |
| 2 | 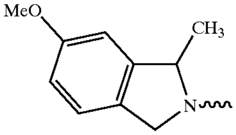 |
| 3 | 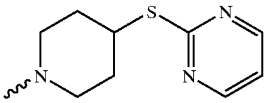 |
| 4 | 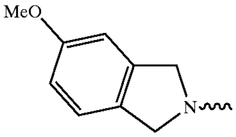 |
| 5 | 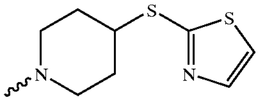 |
| 6 | 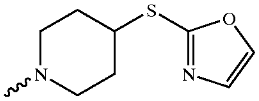 |
| 7 | 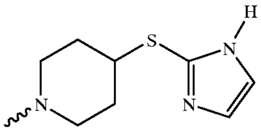 |
| 8 | 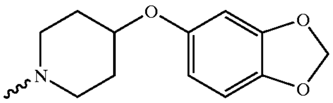 |
| 9 | 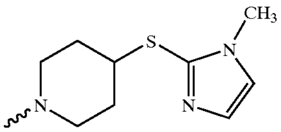 |
| 10 | 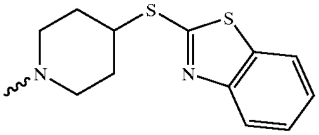 |

TABLE 112-continued
| 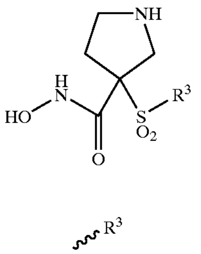 | |
| --- | --- |
| 11 | 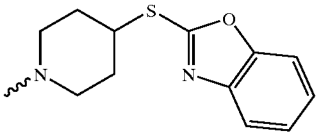 |
TABLE 113
| 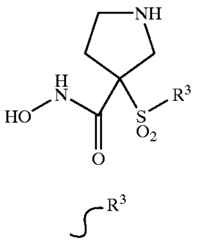 | |
| --- | --- |
| 1 | 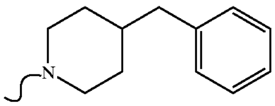 |
| 2 | 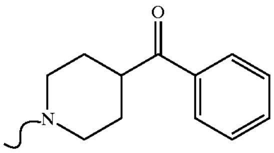 |
| 3 | 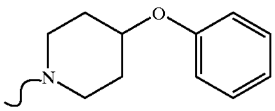 |
| 4 | 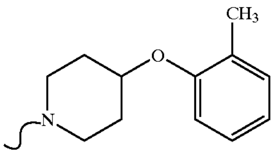 |
| 5 | 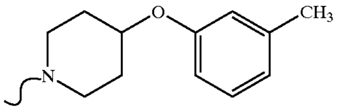 |
| 6 | 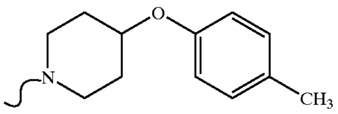 |
TABLE 113-continued
| 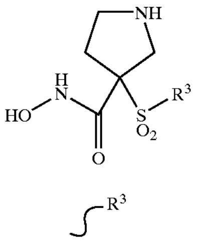 | |
| --- | --- |
| 7 | 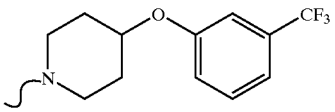 |
| 8 | 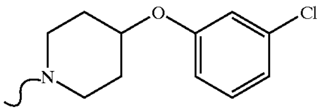 |
| 9 | 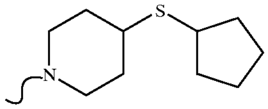 |
| 10 | 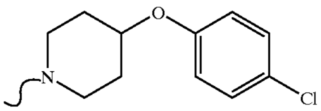 |
| 11 | 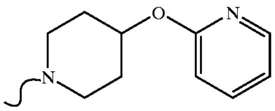 |
| 12 | 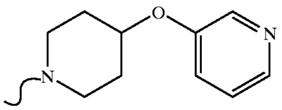 |
| 13 | 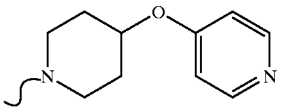 |
| 14 | 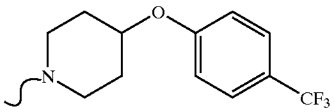 |
| 15 | 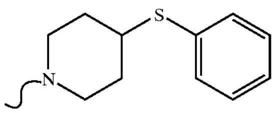 |
| 16 | 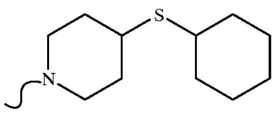 |
| 17 | 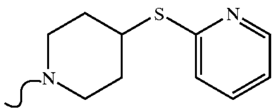 |

TABLE 113-continued
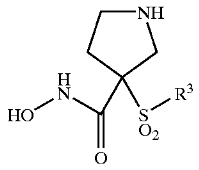
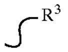
18 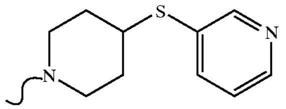
19 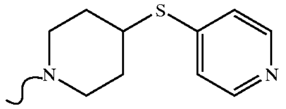
20 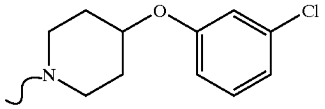
21 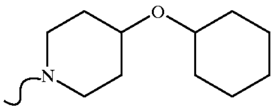
TABLE 114
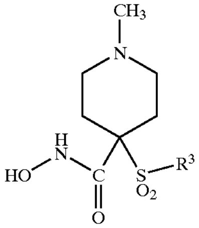
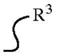
1 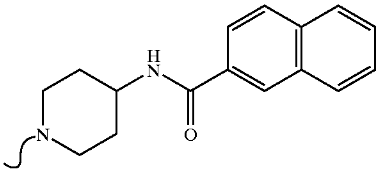
2 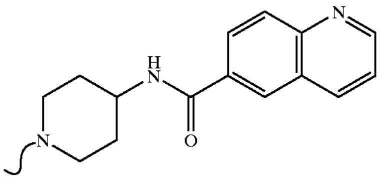
TABLE 114-continued
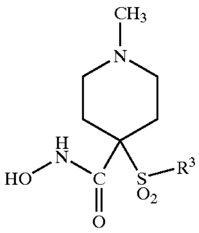
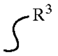
3 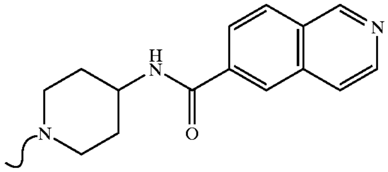
4 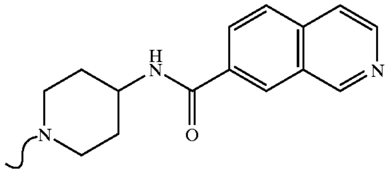
5 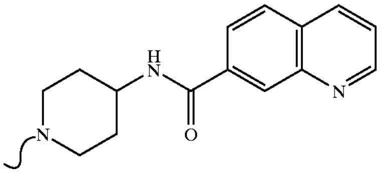
6 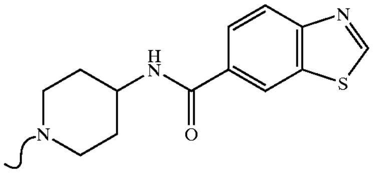
7 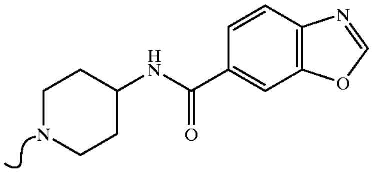
8 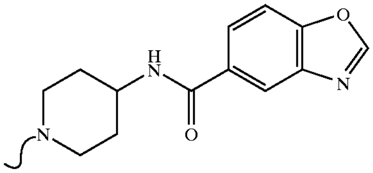

TABLE 114-continued
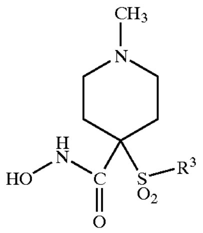
| | 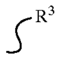 |
|---|---|
| 9 | 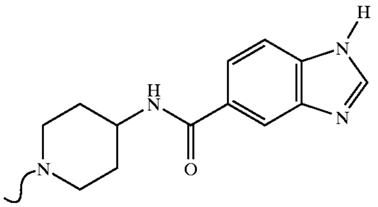 |
| 10 | 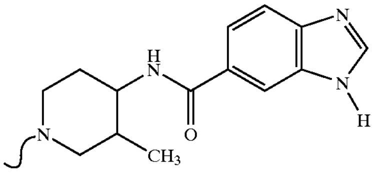 |
| 11 | 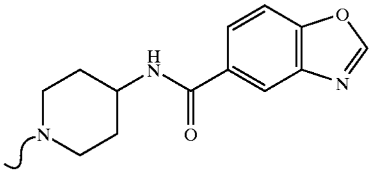 |
| 12 | 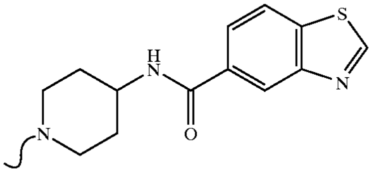 |
| 13 | 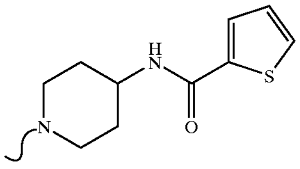 |
| 14 | 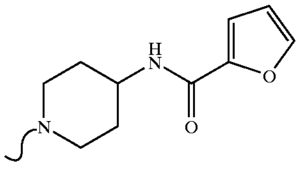 |
TABLE 114-continued
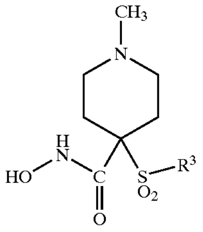
| | 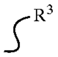 |
|---|---|
| 15 | 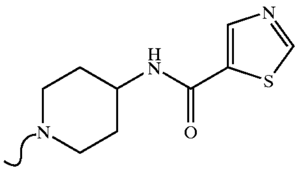 |
| 16 | 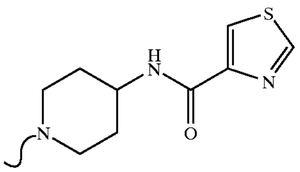 |
| 17 | 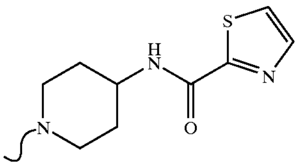 |
| 18 | 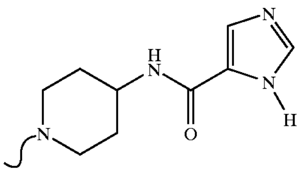 |
TABLE 115
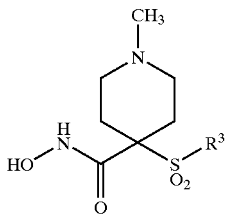
| | 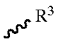 |
|---|---|
| 1 | 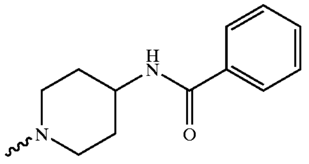 |

TABLE 115-continued
| | 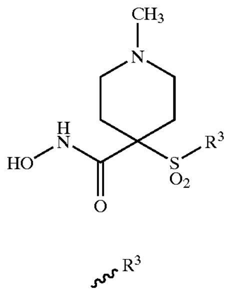 |
|---|---|
| 2 | 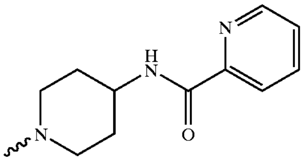 |
| 3 | 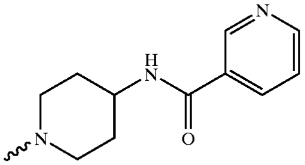 |
| 4 | 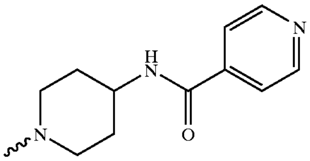 |
| 5 | 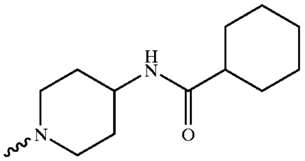 |
| 6 | 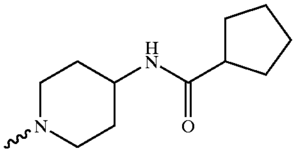 |
| 7 | 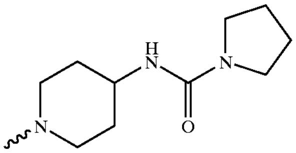 |
| 8 | 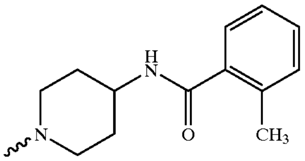 |
TABLE 115-continued
| | 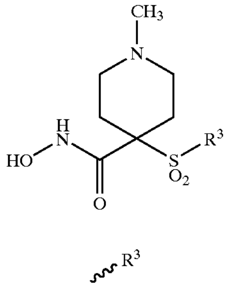 |
|---|---|
| 9 | 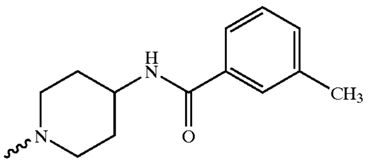 |
| 10 | 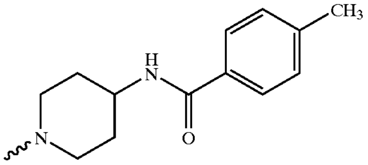 |
| 11 | 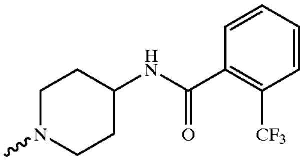 |
| 12 | 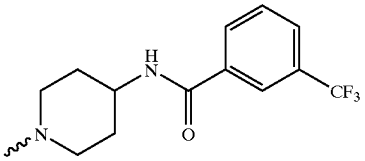 |
| 13 | 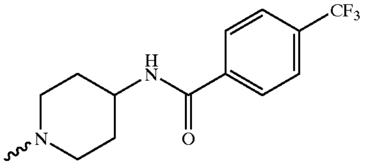 |
| 14 | 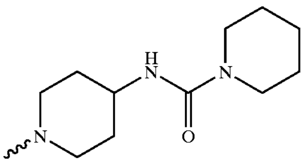 |
| 15 | 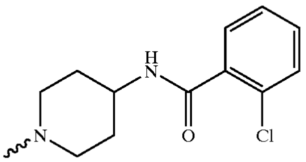 |

TABLE 115-continued
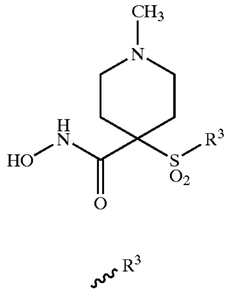
| | |
|---|---|
| 16 | 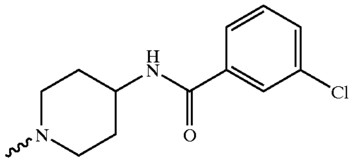 |
| 17 | 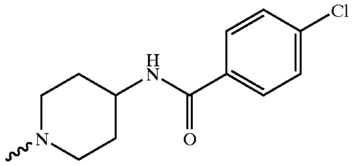 |
| 18 | 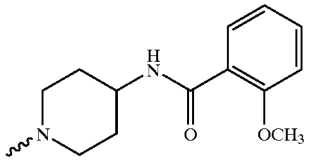 |
| 19 | 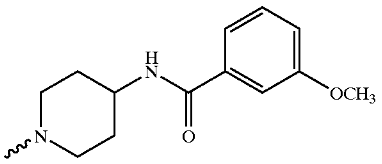 |
| 20 | 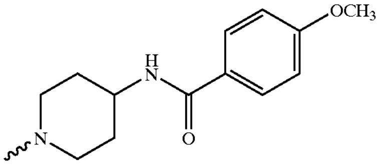 |
| 21 | 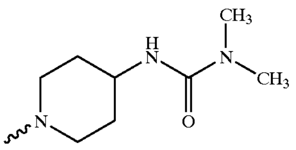 |
TABLE 116
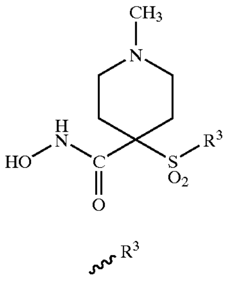
| | |
|---|---|
| 1 | 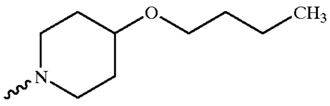 |
| 2 | 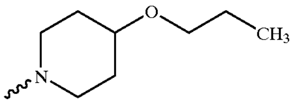 |
| 3 | 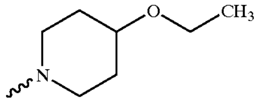 |
| 4 | 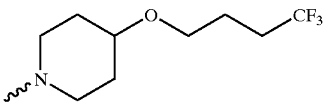 |
| 5 | 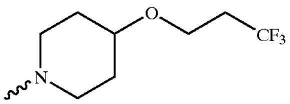 |
| 6 | 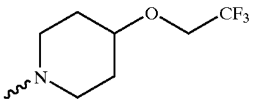 |
| 7 | 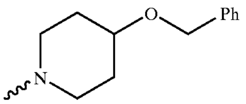 |
| 8 | 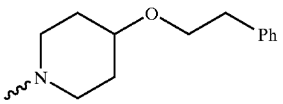 |
| 9 | 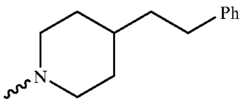 |
| 10 | 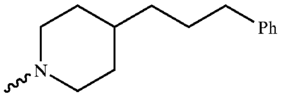 |

TABLE 116-continued
| | |
|---|---|
| | 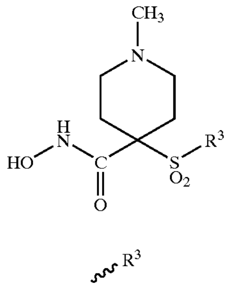 |
| 11 | 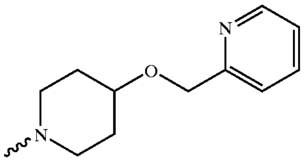 |
| 12 | 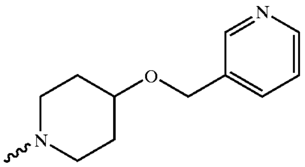 |
| 13 | 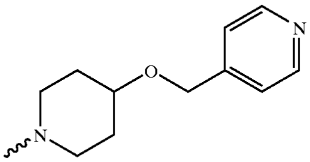 |
| 14 | 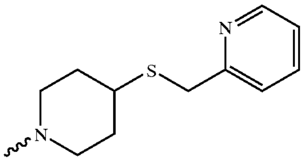 |
| 15 | 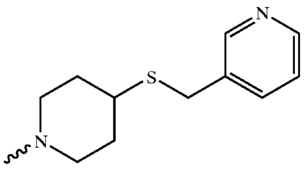 |
| 16 | 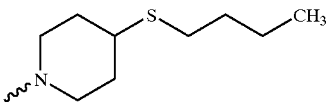 |
| 17 | 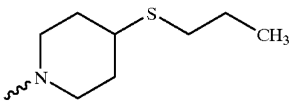 |
| 18 | 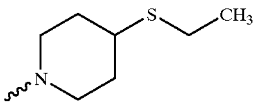 |
TABLE 116-continued
| | |
|---|---|
| | 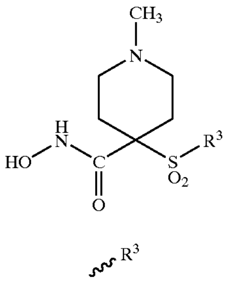 |
| 19 | 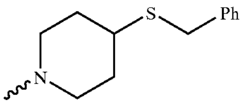 |
| 20 | 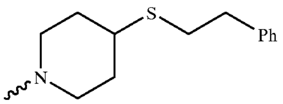 |
| 21 | 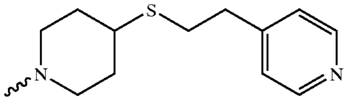 |
| 22 | 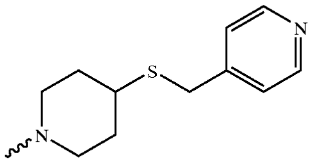 |
TABLE 117
| | |
|---|---|
| | 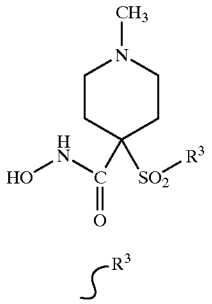 |
| 1 | 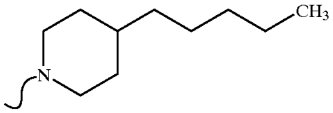 |
| 2 | 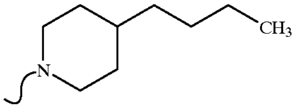 |
| 3 | 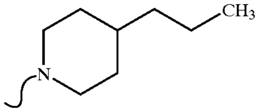 |

TABLE 117-continued
| | 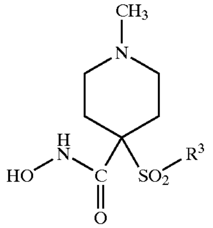 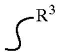 |
|---|---|
| 4 | 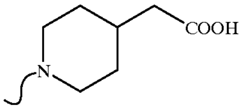 |
| 5 | 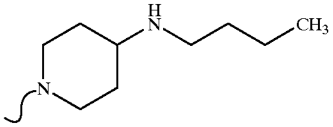 |
| 6 | 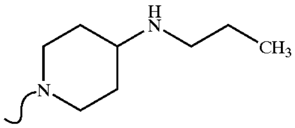 |
| 7 | 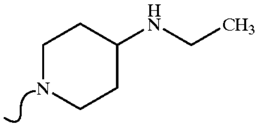 |
| 8 | 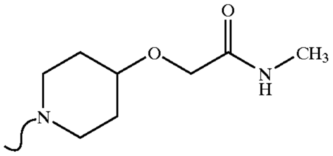 |
| 9 | 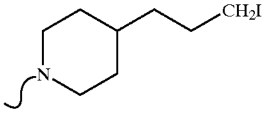 |
| 10 | 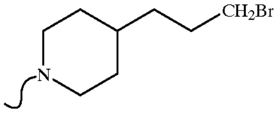 |
| 11 | 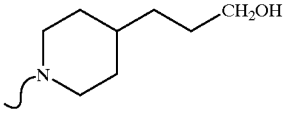 |
| 12 | 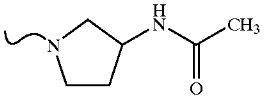 |
TABLE 117-continued
| | 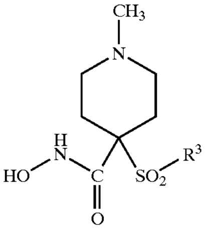 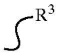 |
|---|---|
| 13 | 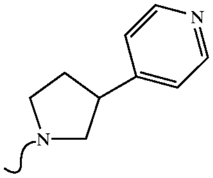 |
| 14 | 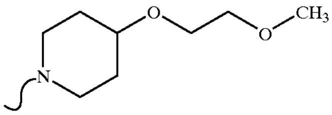 |
| 15 | 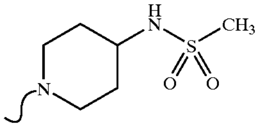 |
| 16 | 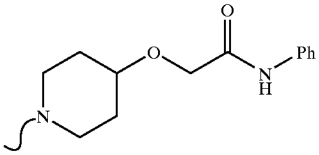 |
| 17 | 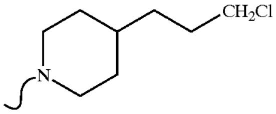 |
| 18 | 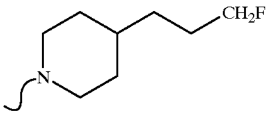 |
| 19 | 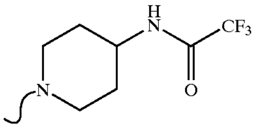 |
| 20 | 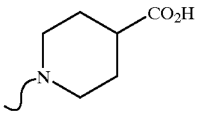 |

TABLE 117-continued
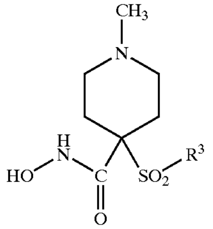
| | 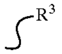 |
|---|---|
| 21 | 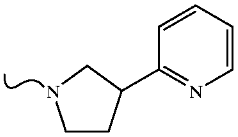 |
| 22 | 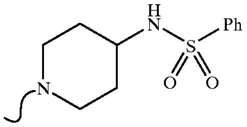 |
| 23 | 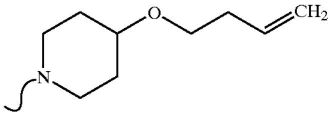 |
| 24 | 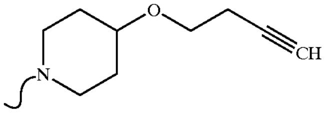 |
| 25 | 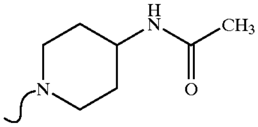 |
| 26 | 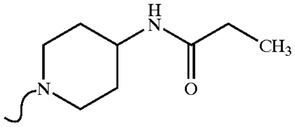 |
| 27 | 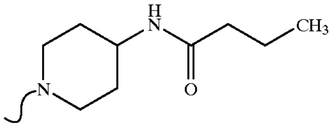 |
| 28 | 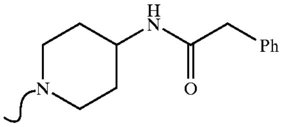 |
| 29 | 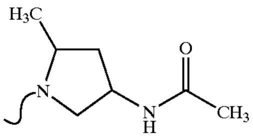 |
TABLE 117-continued
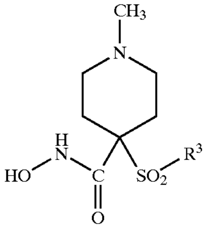
| | 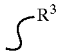 |
|---|---|
| 30 | 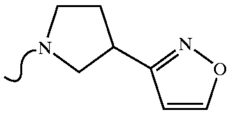 |
| 31 | 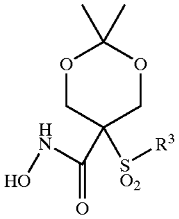 |
TABLE 118
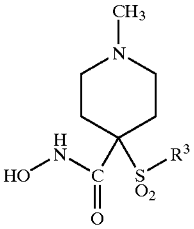
| | 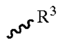 |
|---|---|
| 1 | 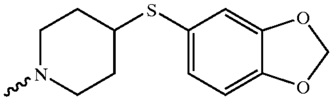 |
| 2 | 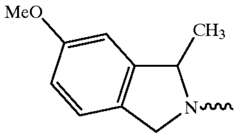 |
| 3 | 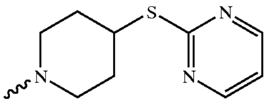 |
| 4 | 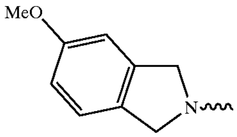 |

TABLE 118-continued
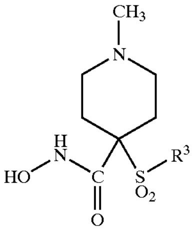
| 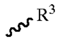 | |
|---|---|
| 5 | 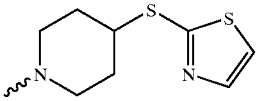 |
| 6 | 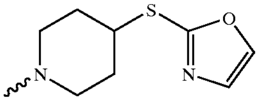 |
| 7 | 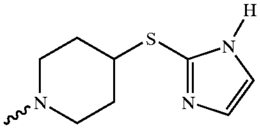 |
| 8 | 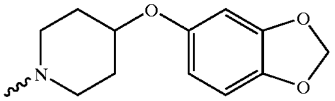 |
| 9 | 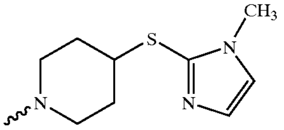 |
| 10 | 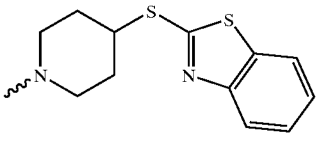 |
| 11 | 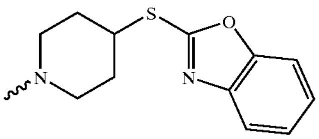 |
TABLE 119
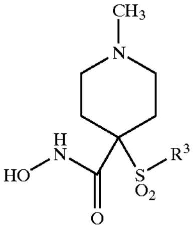
| 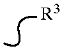 | |
|---|---|
| 1 | 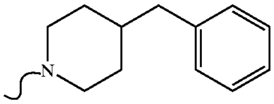 |
| 2 | 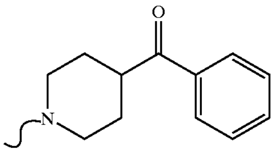 |
| 3 | 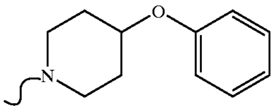 |
| 4 | 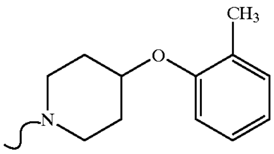 |
| 5 | 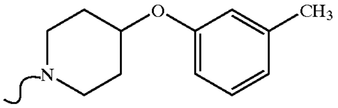 |
| 6 | 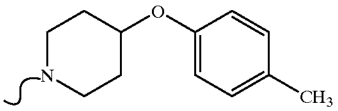 |
| 7 | 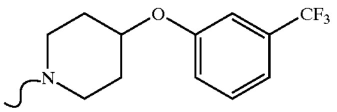 |
| 8 | 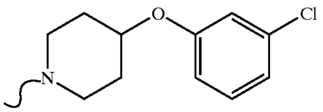 |
| 9 | 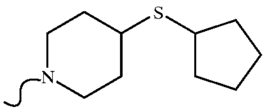 |

TABLE 119-continued
| | 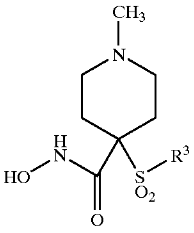 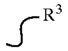 |
|---|---|
| 10 | 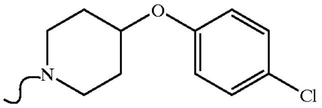 |
| 11 | 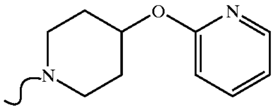 |
| 12 | 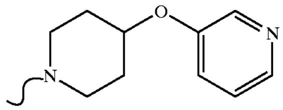 |
| 13 | 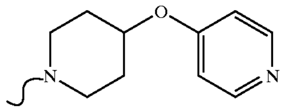 |
| 14 | 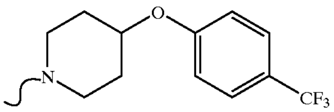 |
| 15 | 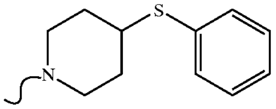 |
| 16 | 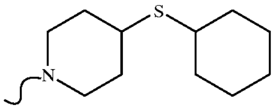 |
| 17 | 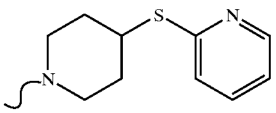 |
| 18 | 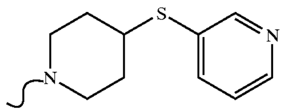 |
| 19 | 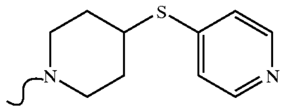 |
TABLE 119-continued
| | 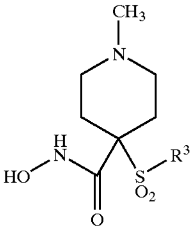 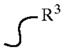 |
|---|---|
| 20 | 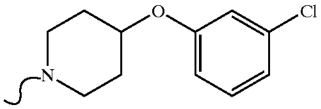 |
| 21 | 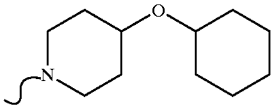 |
TABLE 120
| | 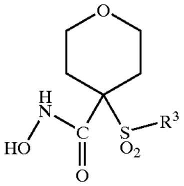 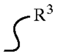 |
|---|---|
| 1 | 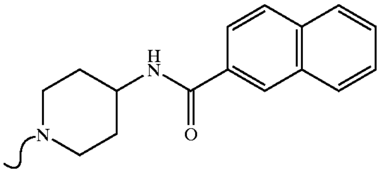 |
| 2 | 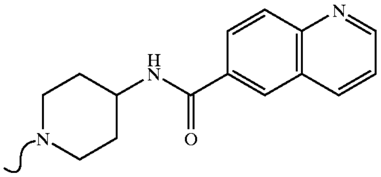 |
| 3 | 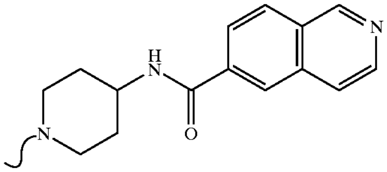 |

TABLE 120-continued
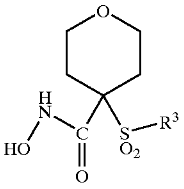
| | 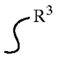 |
|---|---|
| 4 | 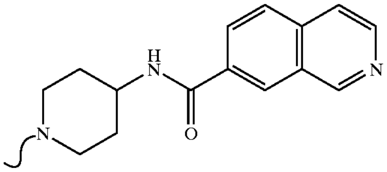 |
| 5 | 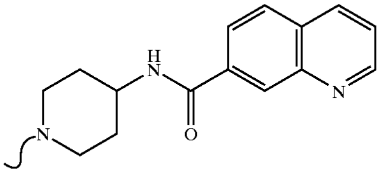 |
| 6 | 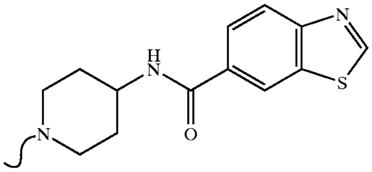 |
| 7 | 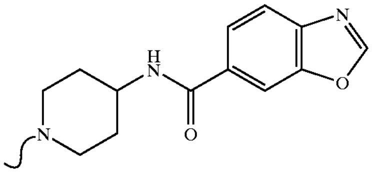 |
| 8 | 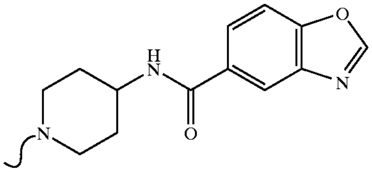 |
| 9 | 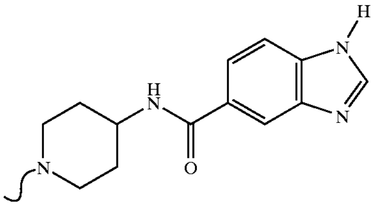 |
| 10 | 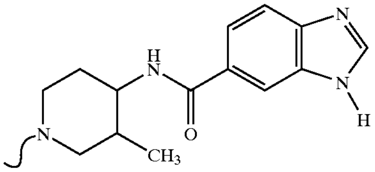 |
TABLE 120-continued
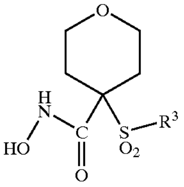
| | 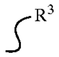 |
|---|---|
| 11 | 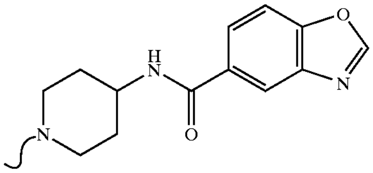 |
| 12 | 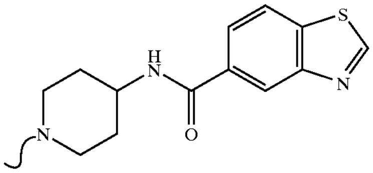 |
| 13 | 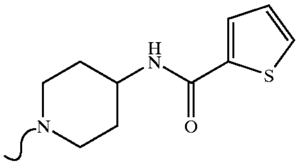 |
| 14 | 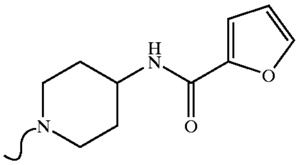 |
| 15 | 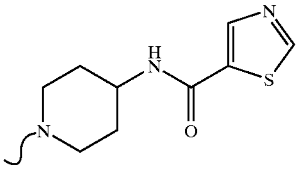 |
| 16 | 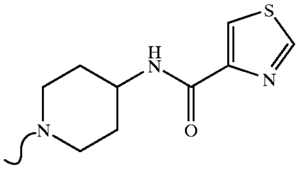 |
| 17 | 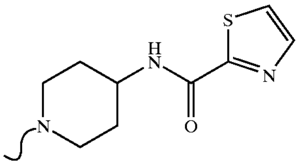 |

TABLE 120-continued
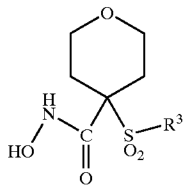
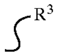
18
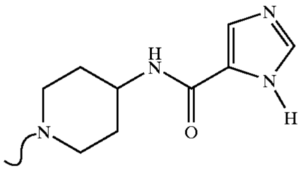
TABLE 121
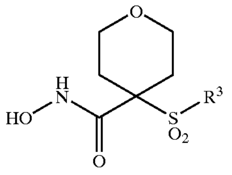
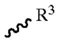
1
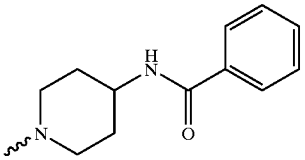
2
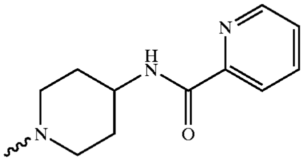
3
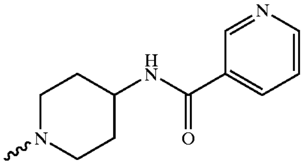
4
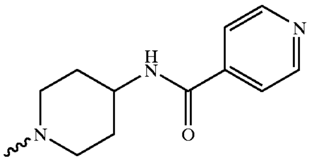
TABLE 121-continued
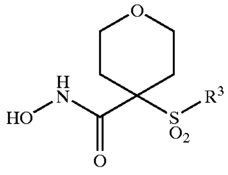
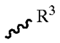
5
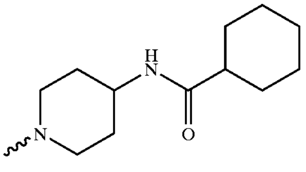
6
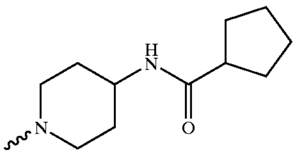
7
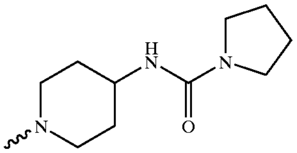
8
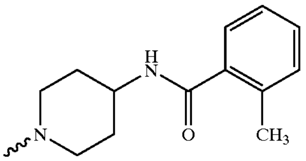
9
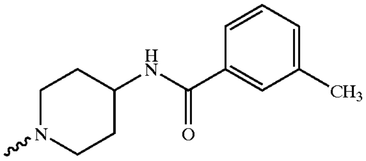
10
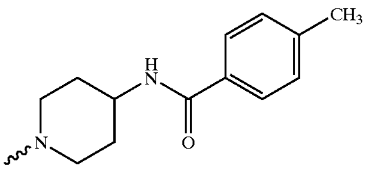
11
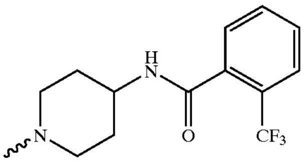

TABLE 121-continued
| | |
|---|---|
| | 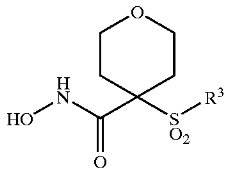 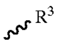 |
| 12 | 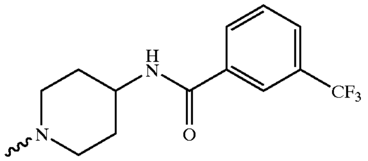 |
| 13 | 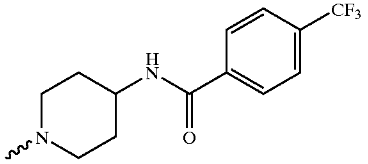 |
| 14 | 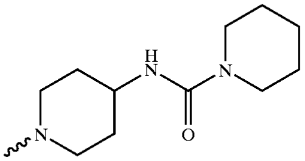 |
| 15 | 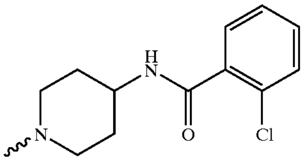 |
| 16 | 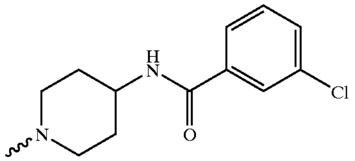 |
| 17 | 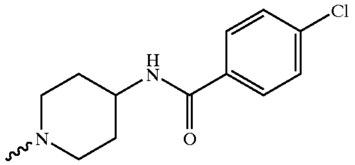 |
| 18 | 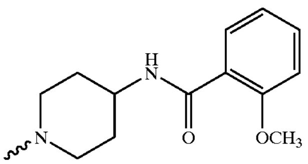 |
| 19 | 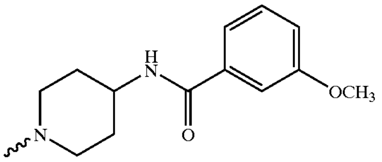 |
| 20 | 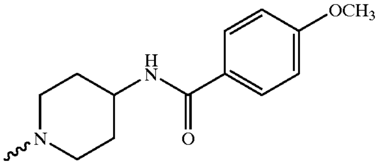 |
| 21 | 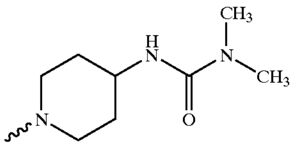 |
TABLE 122
| | |
|---|---|
| | 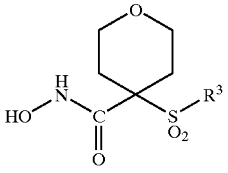 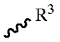 |
| 1 | 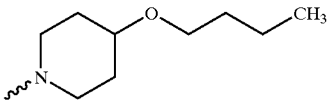 |
| 2 | 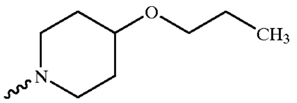 |
| 3 | 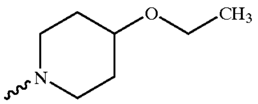 |
| 4 | 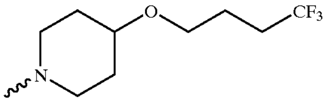 |

TABLE 122-continued
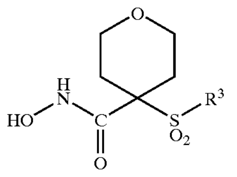
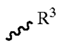
| | |
|---|---|
| 5 | 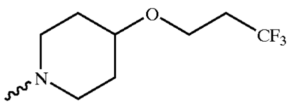 |
| 6 | 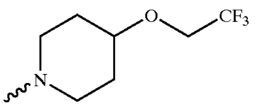 |
| 7 | 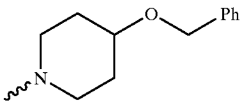 |
| 8 | 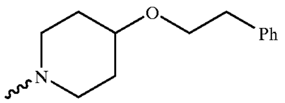 |
| 9 | 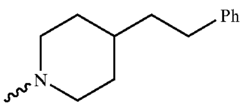 |
| 10 | 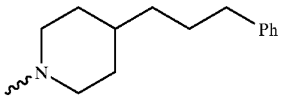 |
| 11 | 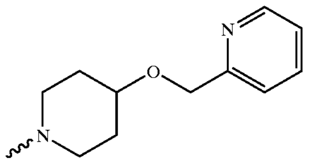 |
| 12 | 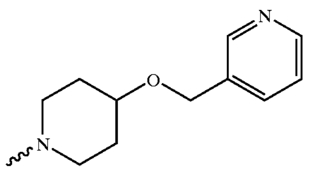 |
| 13 | 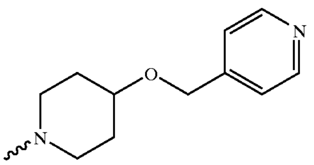 |
TABLE 122-continued
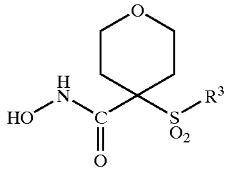
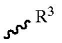
| | |
|---|---|
| 14 | 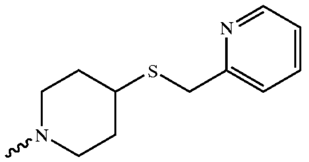 |
| 15 | 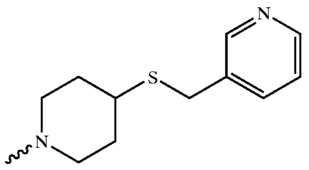 |
| 16 | 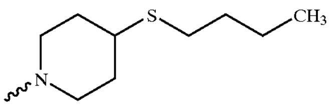 |
| 17 | 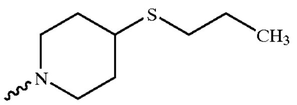 |
| 18 | 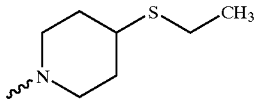 |
| 19 | 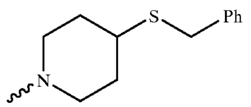 |
| 20 | 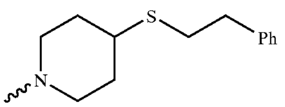 |
| 21 | 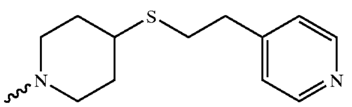 |
| 22 | 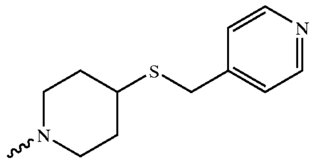 |

TABLE 123
| | 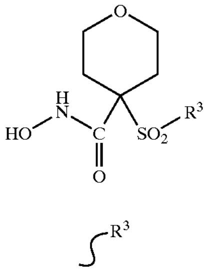 |
|---|---|
| 1 | 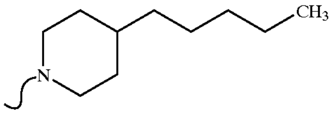 |
| 2 | 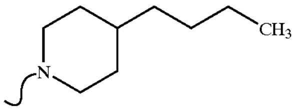 |
| 3 | 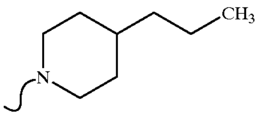 |
| 4 | 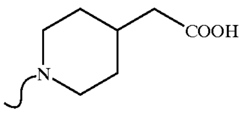 |
| 5 | 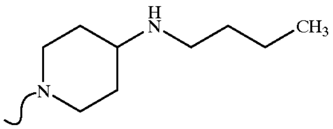 |
| 6 | 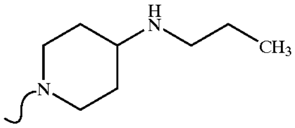 |
| 7 | 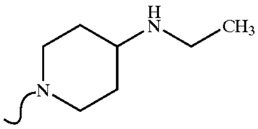 |
| 8 | 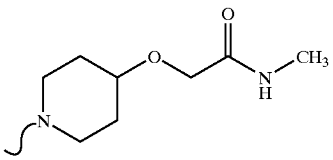 |
| 9 | 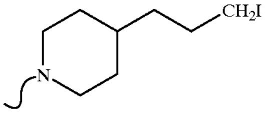 |
TABLE 123-continued
| | 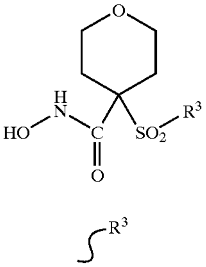 |
|---|---|
| 10 | 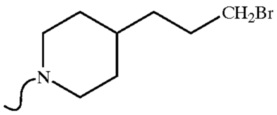 |
| 11 | 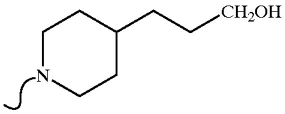 |
| 12 | 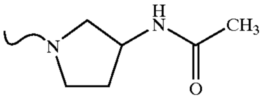 |
| 13 | 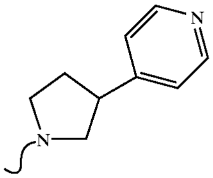 |
| 14 | 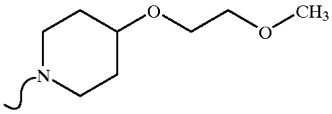 |
| 15 | 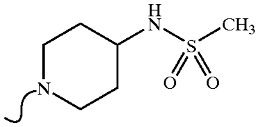 |
| 16 | 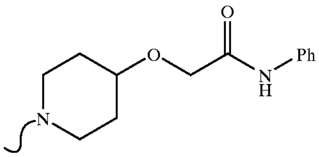 |
| 17 | 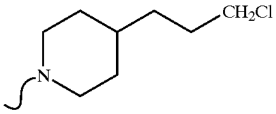 |
| 18 | 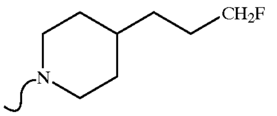 |

TABLE 123-continued
| | 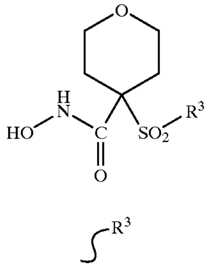 |
|---|---|
| 19 | 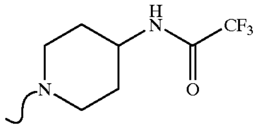 |
| 20 | 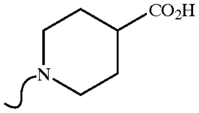 |
| 21 | 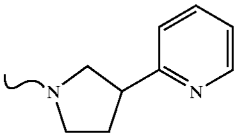 |
| 22 | 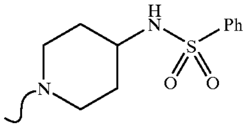 |
| 23 | 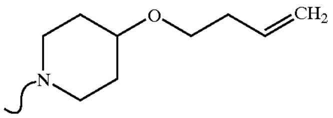 |
| 24 | 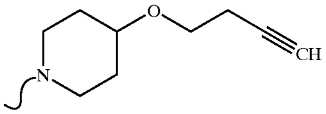 |
| 25 | 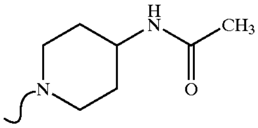 |
| 26 | 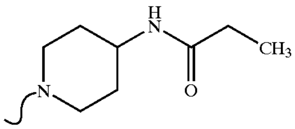 |
| 27 | 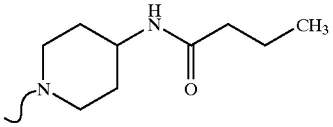 |
TABLE 123-continued
| | 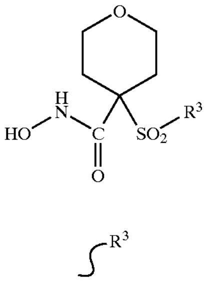 |
|---|---|
| 28 | 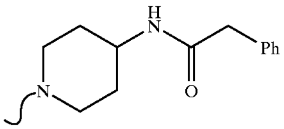 |
| 29 | 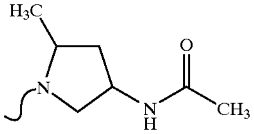 |
| 30 | 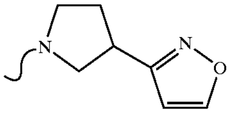 |
| 31 | 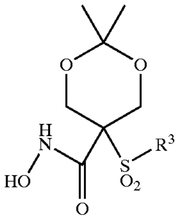 |
TABLE 124
| | 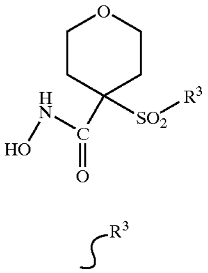 |
|---|---|
| 1 | 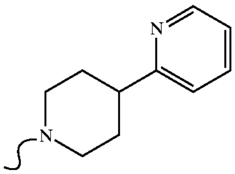 |

TABLE 124-continued
| | 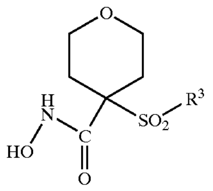 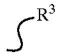 |
|---|---|
| 2 | 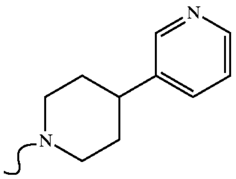 |
| 3 | 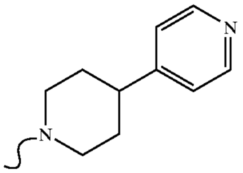 |
| 4 | 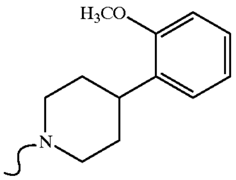 |
| 5 | 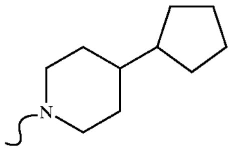 |
| 6 | 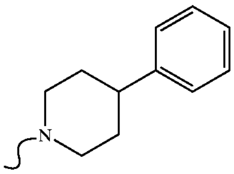 |
| 7 | 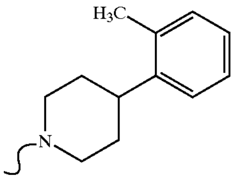 |
| 8 | 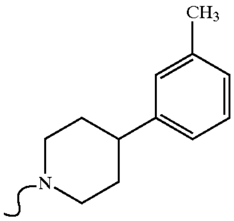 |
TABLE 124-continued
| | 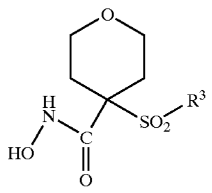 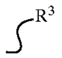 |
|---|---|
| 9 | 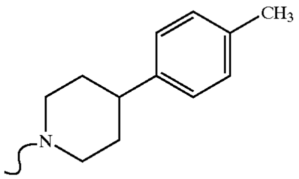 |
| 10 | 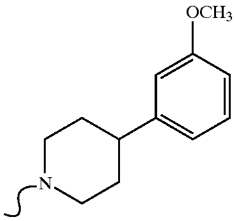 |
| 11 | 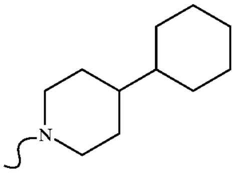 |
| 12 | 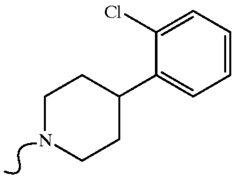 |
| 13 | 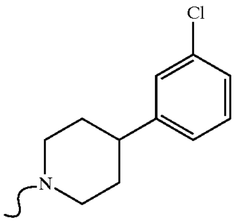 |
| 14 | 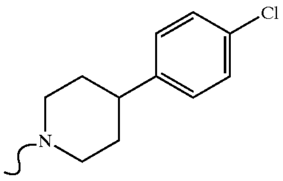 |

TABLE 124-continued
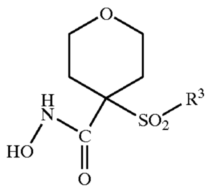
15 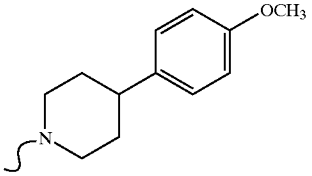
16 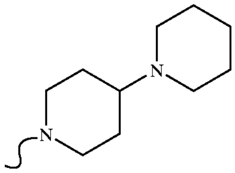
17 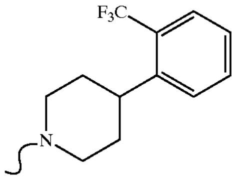
18 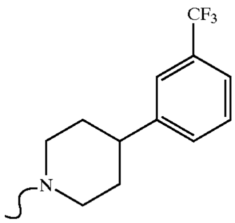
19 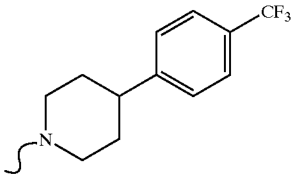
20 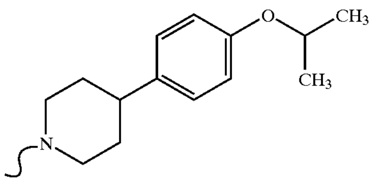
TABLE 124-continued
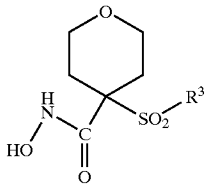
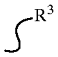
21 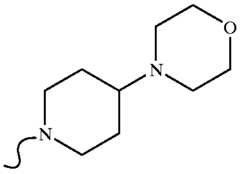
TABLE 125
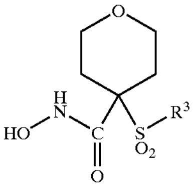
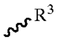
1 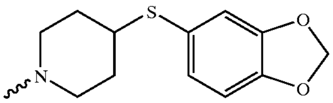
2 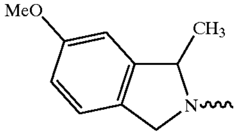
3 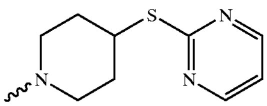
4 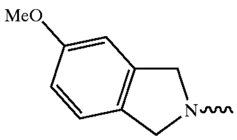
5 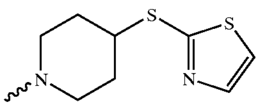
6 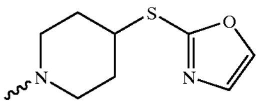

TABLE 125-continued
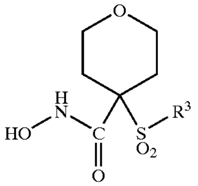
| 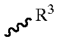 | |
|---|---|
| 7 | 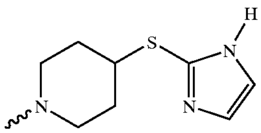 |
| 8 | 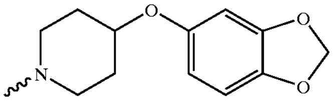 |
| 9 | 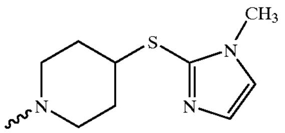 |
| 10 | 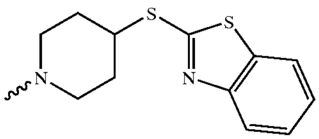 |
| 11 | 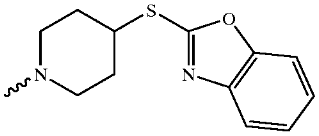 |
TABLE 126
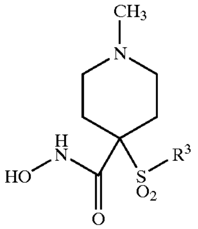
| 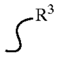 | |
|---|---|
| 1 | 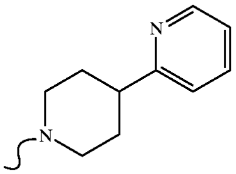 |
TABLE 126-continued
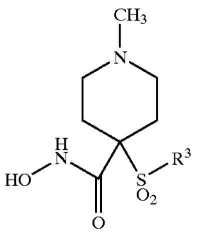
| 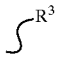 | |
|---|---|
| 2 | 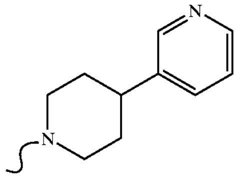 |
| 3 | 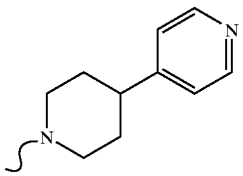 |
| 4 | 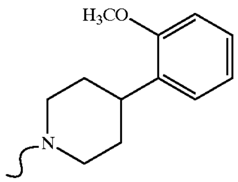 |
| 5 | 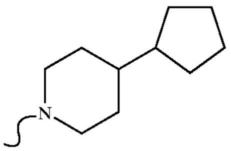 |
| 6 | 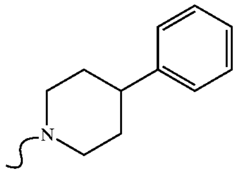 |
| 7 | 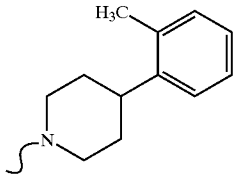 |

TABLE 126-continued
| | |
|---|---|
| 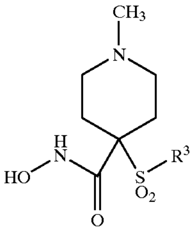 | |
| 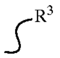 | |
| 8 | 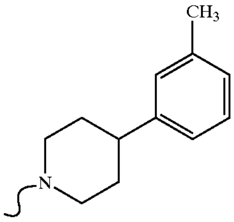 |
| 9 | 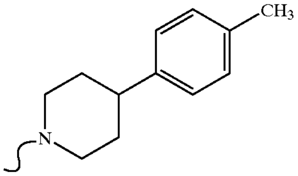 |
| 10 | 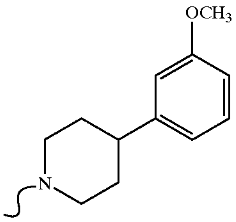 |
| 11 | 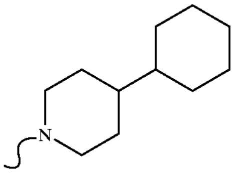 |
| 12 | 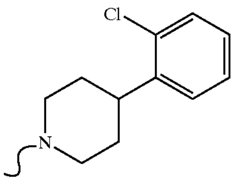 |
| 13 | 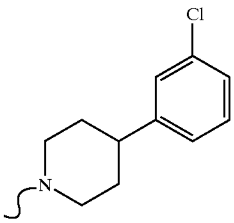 |
TABLE 126-continued
| | |
|---|---|
| 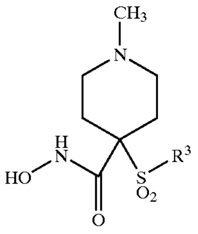 | |
| 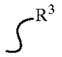 | |
| 14 | 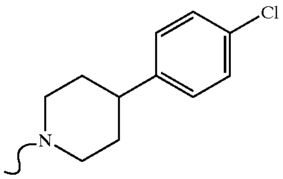 |
| 15 | 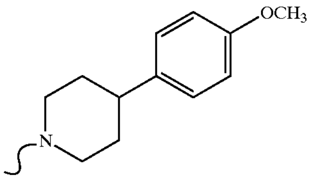 |
| 16 | 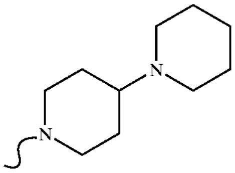 |
| 17 | 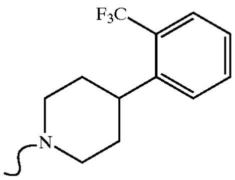 |
| 18 | 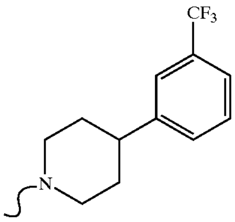 |
| 19 | 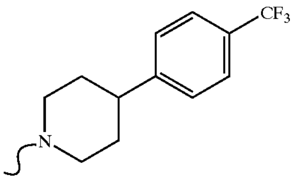 |

TABLE 126-continued
| | |
|---|---|
| 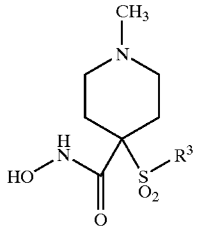 | |
|  | |
| 20 | 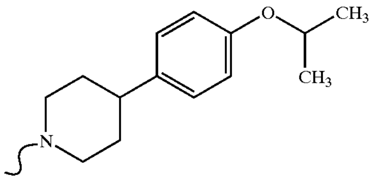 |
| 21 | 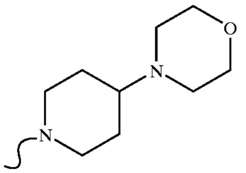 |
TABLE 127
| | |
|---|---|
| 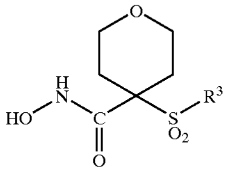 | |
| 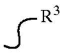 | |
| 1 | 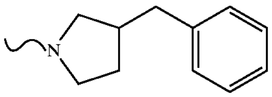 |
| 2 | 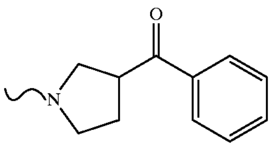 |
| 3 | 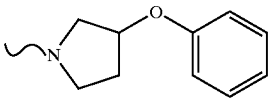 |
| 4 | 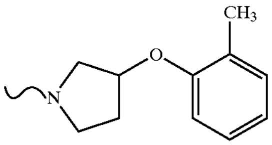 |
TABLE 127-continued
| | |
|---|---|
| 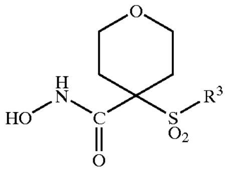 | |
| 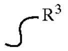 | |
| 5 | 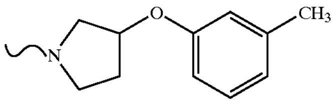 |
| 6 | 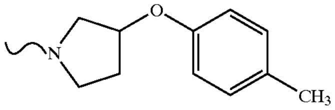 |
| 7 | 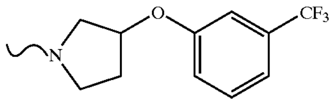 |
| 8 | 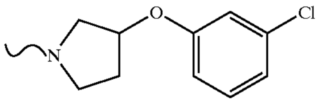 |
| 9 | 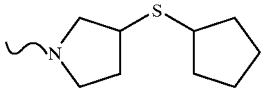 |
| 10 | 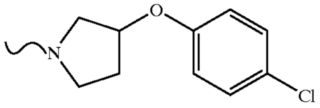 |
| 11 | 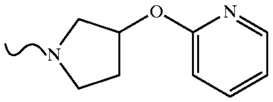 |
| 12 | 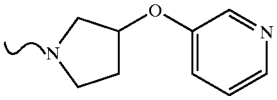 |
| 13 | 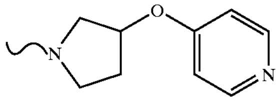 |
| 14 | 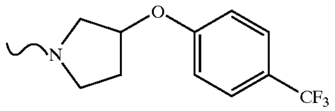 |
| 15 | 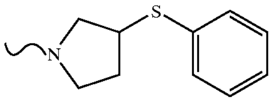 |

TABLE 127-continued
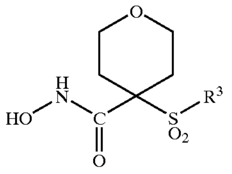
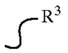
16 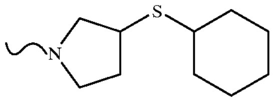
17 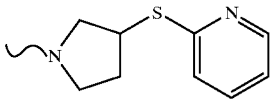
18 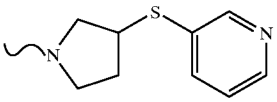
19 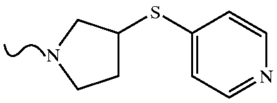
20 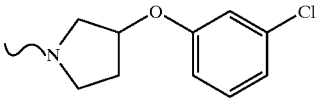
21 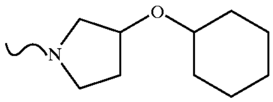
TABLE 128
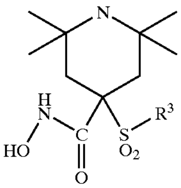
1 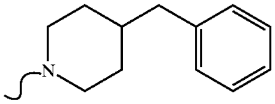
2 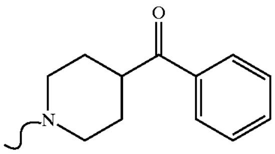
TABLE 128-continued
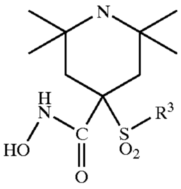
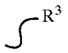
3 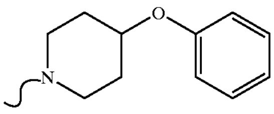
4 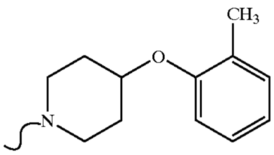
5 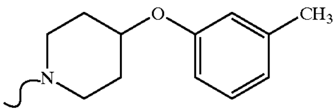
6 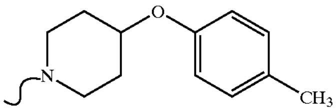
7 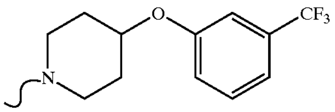
8 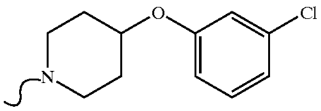
9 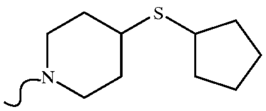
10 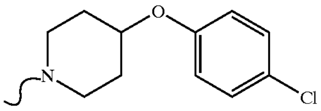
11 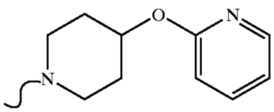
12 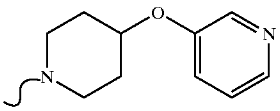

TABLE 128-continued
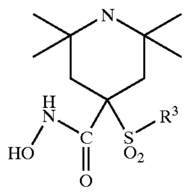
| | 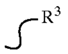 |
|---|---|
| 13 | 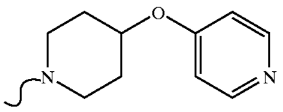 |
| 14 | 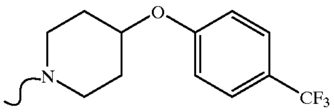 |
| 15 | 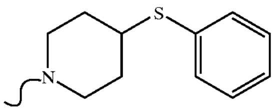 |
| 16 | 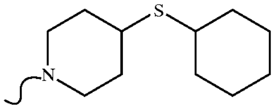 |
| 17 | 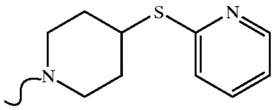 |
| 18 | 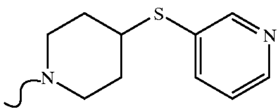 |
| 19 | 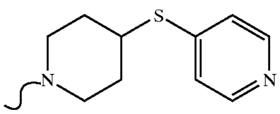 |
| 20 | 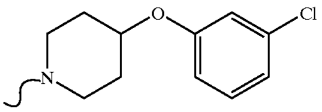 |
| 21 | 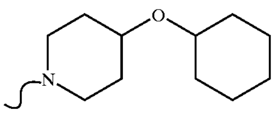 |
TABLE 129
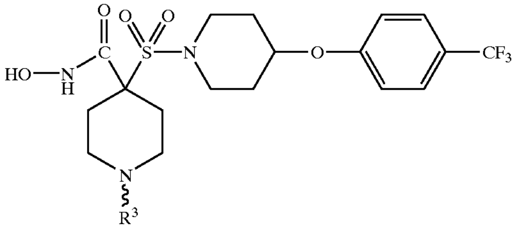
| | 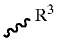 |
|---|---|
| 1 | 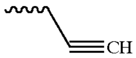 |
| 2 | 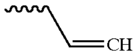 |
| 3 | 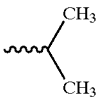 |
| 4 | 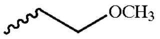 |
| 5 | 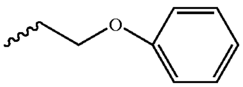 |
| 6 | 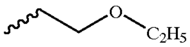 |
| 7 | 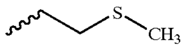 |
| 8 | 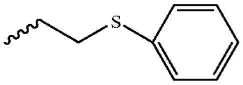 |
| 9 | 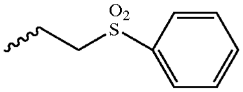 |
| 10 | 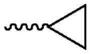 |
| 11 | 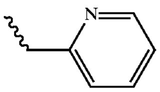 |
| 12 | 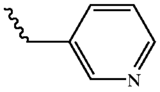 |
| 13 | 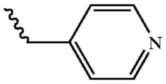 |
| 14 | 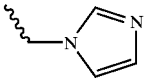 |

TABLE 129-continued
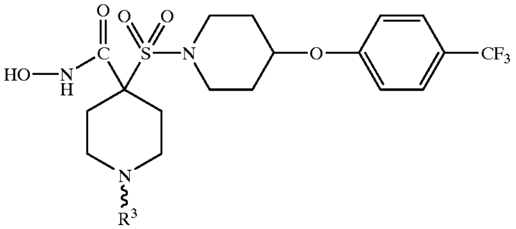
| | 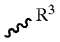 |
|---|---|
| 15 | 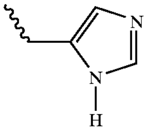 |
| 16 | 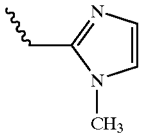 |
| 17 | 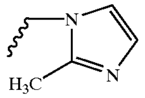 |
| 18 | 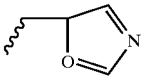 |
| 19 | 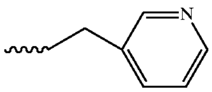 |
| 20 | 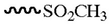 |
| 21 | 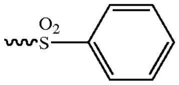 |
| 22 | 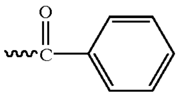 |
| 23 | 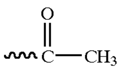 |
| 25 | 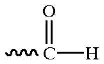 |
| 25 | 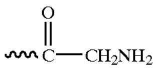 |
| 26 | 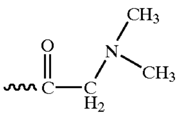 |
TABLE 130
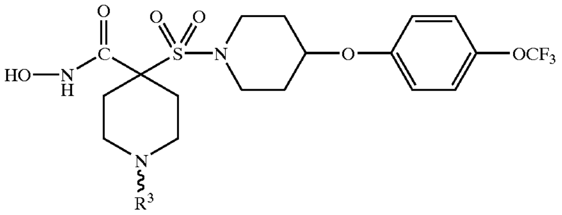
| | 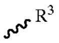 |
|---|---|
| 1 | 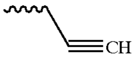 |
| 2 | 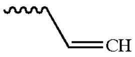 |
| 3 | 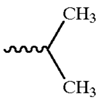 |
| 4 | 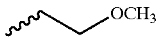 |
| 5 | 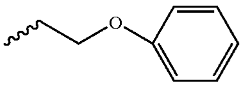 |
| 6 | 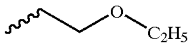 |
| 7 | 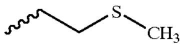 |
| 8 | 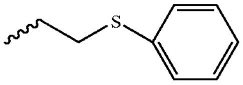 |
| 9 | 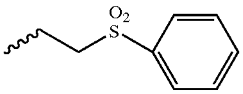 |
| 10 | 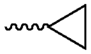 |
| 11 | 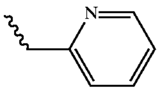 |
| 12 | 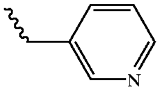 |
| 13 | 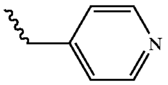 |
| 14 | 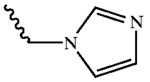 |

TABLE 130-continued
| | |
|---|---|
| 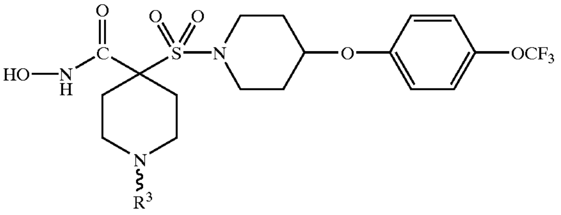 | 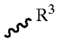 |
| 15 | 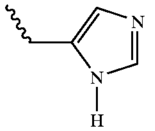 |
| 16 | 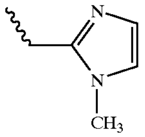 |
| 17 | 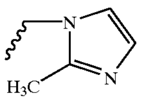 |
| 18 | 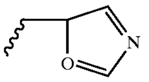 |
| 19 | 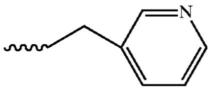 |
| 20 | 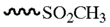 |
| 21 | 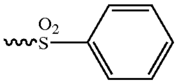 |
| 22 | 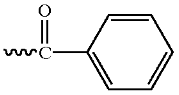 |
| 23 | 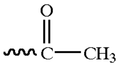 |
| 25 | 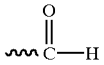 |
| 25 | 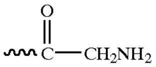 |
| 26 | 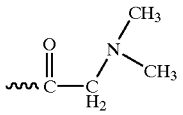 |
TABLE 131
| | |
|---|---|
| 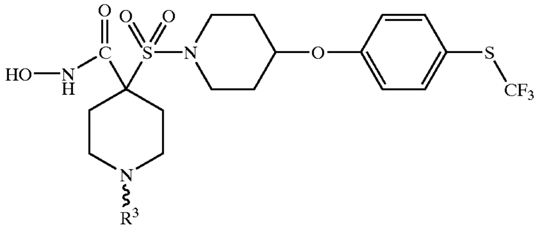 | 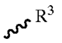 |
| 1 | 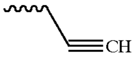 |
| 2 | 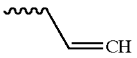 |
| 3 | 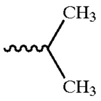 |
| 4 | 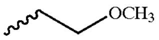 |
| 5 | 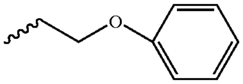 |
| 6 | 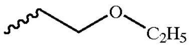 |
| 7 | 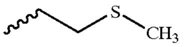 |
| 8 | 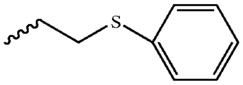 |
| 9 | 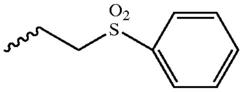 |
| 10 | 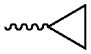 |
| 11 | 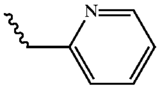 |
| 12 | 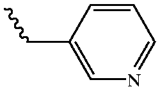 |
| 13 | 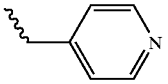 |
| 14 | 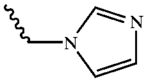 |

TABLE 131-continued
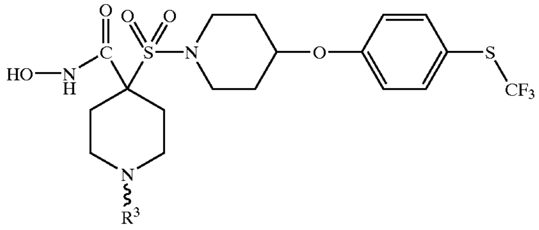
| | 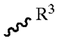 |
|---|---|
| 15 | 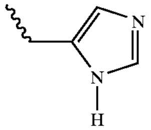 |
| 16 | 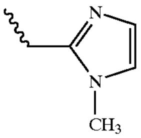 |
| 17 | 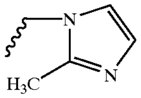 |
| 18 | 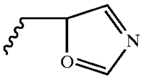 |
| 19 | 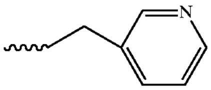 |
| 20 | 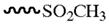 |
| 21 | 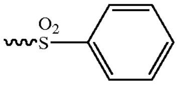 |
| 22 | 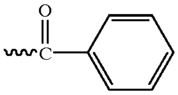 |
| 23 | 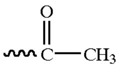 |
| 25 | 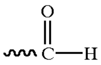 |
| 25 | 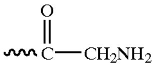 |
| 26 | 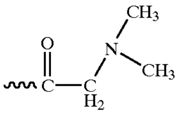 |
TABLE 132
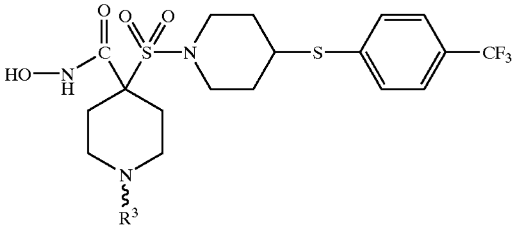
| | 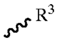 |
|---|---|
| 1 | 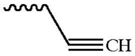 |
| 2 | 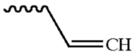 |
| 3 | 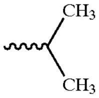 |
| 4 | 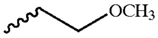 |
| 5 | 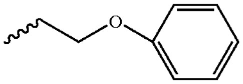 |
| 6 | 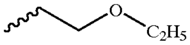 |
| 7 | 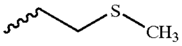 |
| 8 | 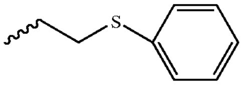 |
| 9 | 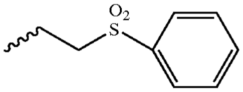 |
| 10 | 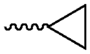 |
| 11 | 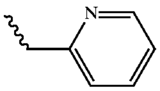 |
| 12 | 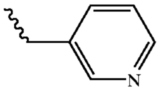 |
| 13 | 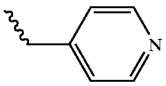 |
| 14 | 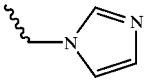 |

TABLE 132-continued
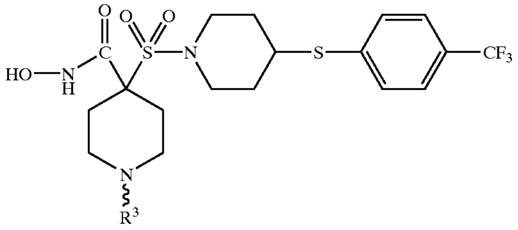
| | 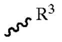 |
|---|---|
| 15 | 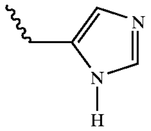 |
| 16 | 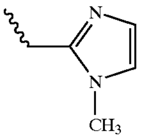 |
| 17 | 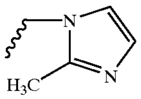 |
| 18 | 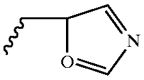 |
| 19 | 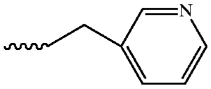 |
| 20 | 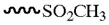 |
| 21 | 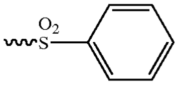 |
| 22 | 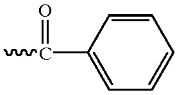 |
| 23 | 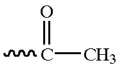 |
| 25 | 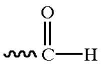 |
| 25 | 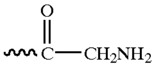 |
| 26 | 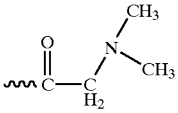 |
TABLE 133
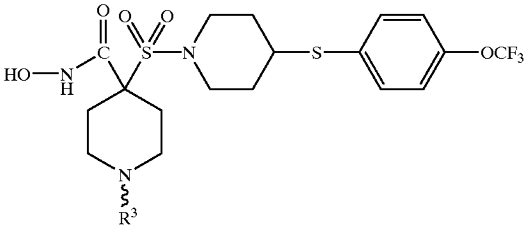
| | 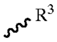 |
|---|---|
| 1 | 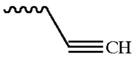 |
| 2 | 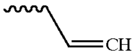 |
| 3 | 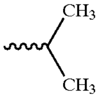 |
| 4 | 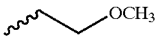 |
| 5 | 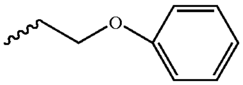 |
| 6 | 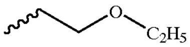 |
| 7 | 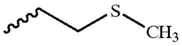 |
| 8 | 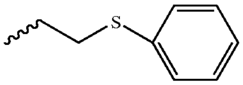 |
| 9 | 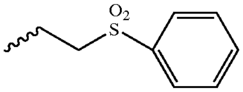 |
| 10 | 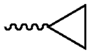 |
| 11 | 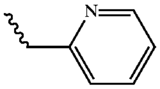 |
| 12 | 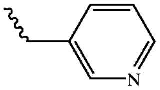 |
| 13 | 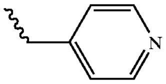 |
| 14 | 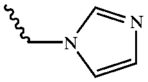 |

TABLE 133-continued
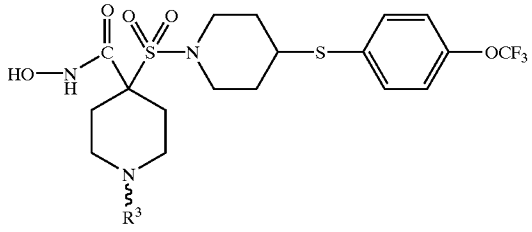
| | 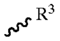 |
|---|---|
| 15 | 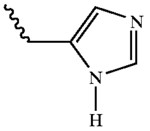 |
| 16 | 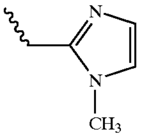 |
| 17 | 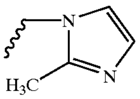 |
| 18 | 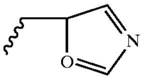 |
| 19 | 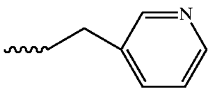 |
| 20 | 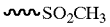 |
| 21 | 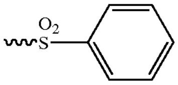 |
| 22 | 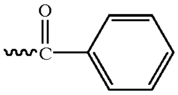 |
| 23 | 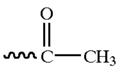 |
| 25 | 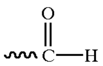 |
| 25 | 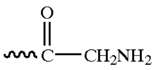 |
| 26 | 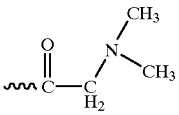 |
TABLE 134
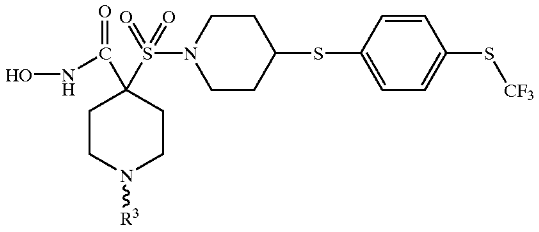
| | 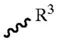 |
|---|---|
| 1 | 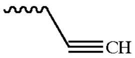 |
| 2 | 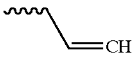 |
| 3 | 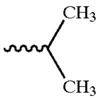 |
| 4 | 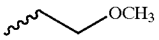 |
| 5 | 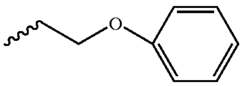 |
| 6 | 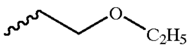 |
| 7 | 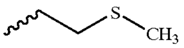 |
| 8 | 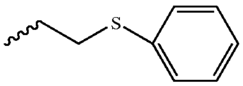 |
| 9 | 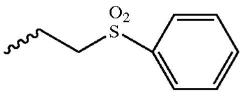 |
| 10 | 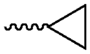 |
| 11 | 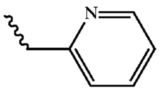 |
| 12 | 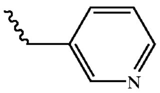 |
| 13 | 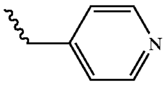 |
| 14 | 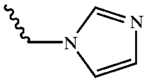 |

TABLE 134-continued
| | |
|---|---|
| 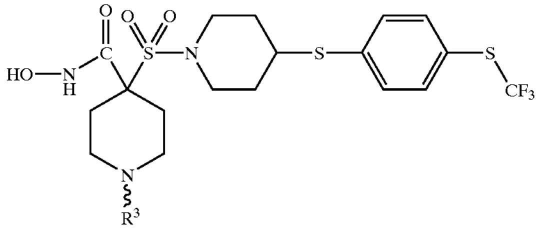 | |
| 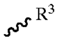 | |
| 15 | 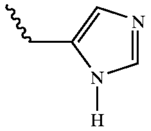 |
| 16 | 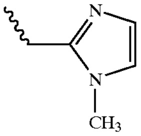 |
| 17 | 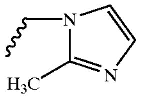 |
| 18 | 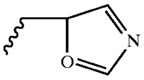 |
| 19 | 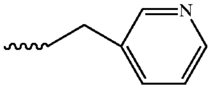 |
| 20 | $SO_2CH_3$ |
| 21 | 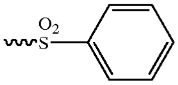 |
| 22 | 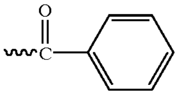 |
| 23 | 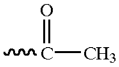 |
| 25 | 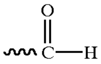 |
| 25 | 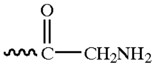 |
| 26 | 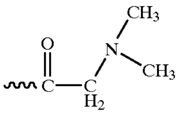 |
TABLE 135
| | |
|---|---|
| 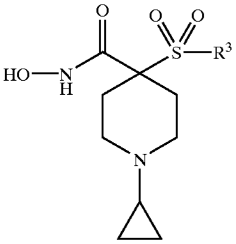 | |
| 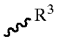 | |
| 1 | 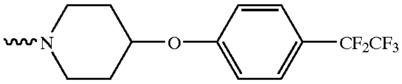 |
| 2 | 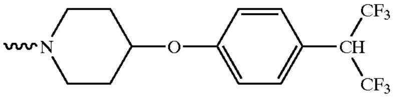 |
| 3 | 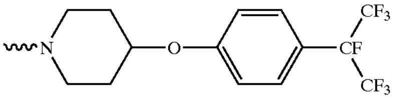 |
| 4 | 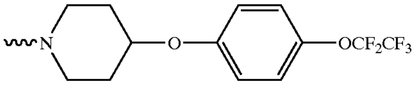 |
| 5 | 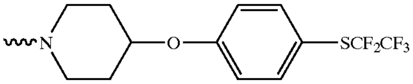 |
| 6 | 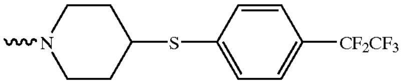 |
| 7 | 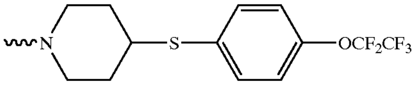 |
| 8 | 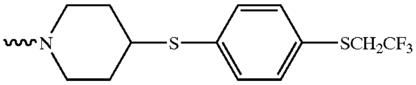 |
| 9 | 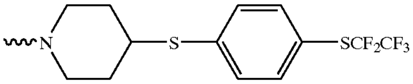 |
| 10 | 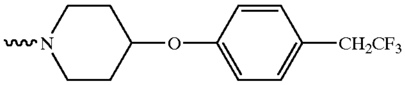 |
| 11 | 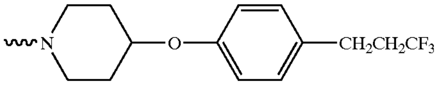 |
| 12 | 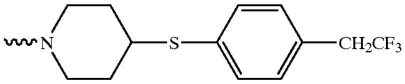 |

TABLE 135-continued
| | |
|---|---|
| | 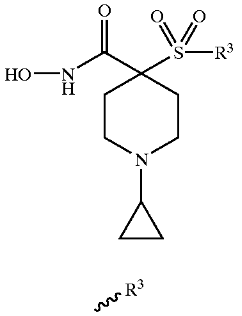 |
| 13 | 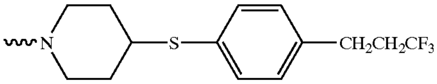 |
| 14 | 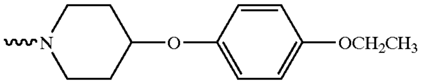 |
| 15 | 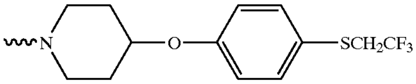 |
| 16 | 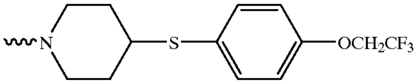 |
TABLE 136
| | |
|---|---|
| | 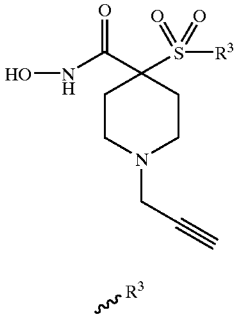 |
| 1 | 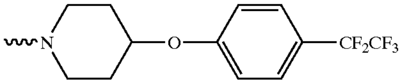 |
| 2 | 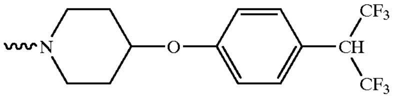 |
| 3 | 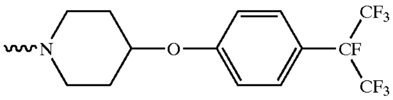 |
| 4 | 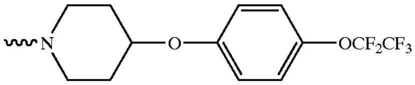 |
TABLE 136-continued
| | |
|---|---|
| | 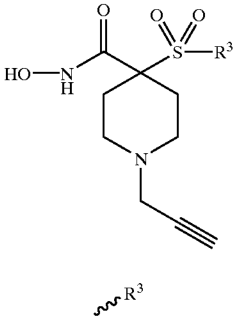 |
| 5 | 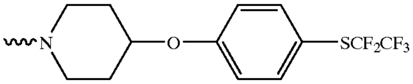 |
| 6 | 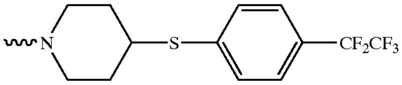 |
| 7 | 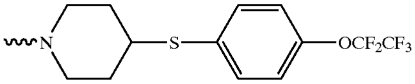 |
| 8 | 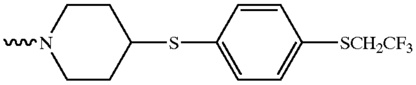 |
| 9 | 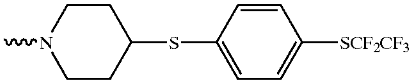 |
| 10 | 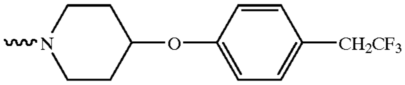 |
| 11 | 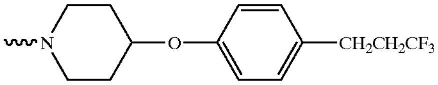 |
| 12 | 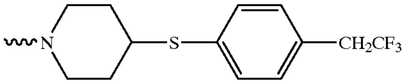 |
| 13 | 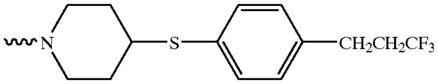 |
| 14 | 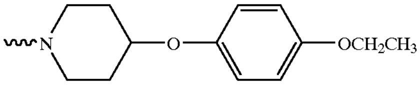 |
| 15 | 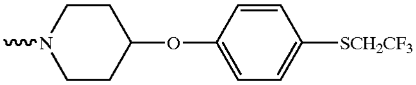 |
| 16 | 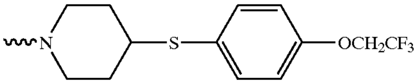 |

TABLE 137
| | |
|---|---|
| | 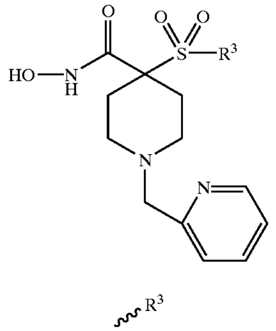 |
| 1 | 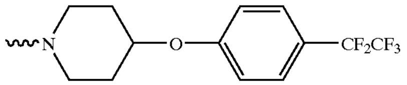 |
| 2 | 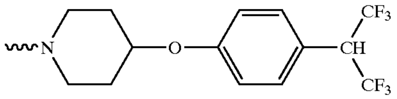 |
| 3 | 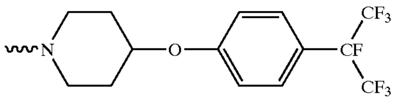 |
| 4 | 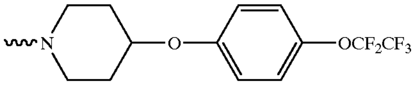 |
| 5 | 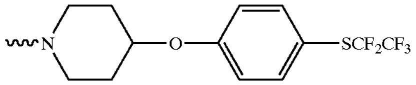 |
| 6 | 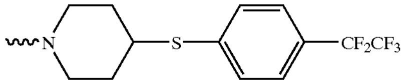 |
| 7 | 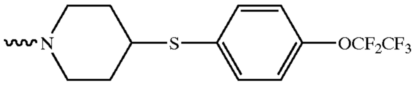 |
| 8 | 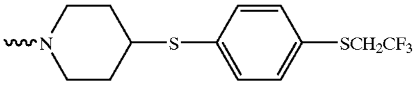 |
| 9 | 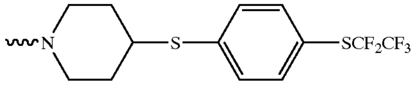 |
| 10 | 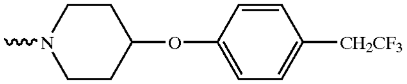 |
| 11 | 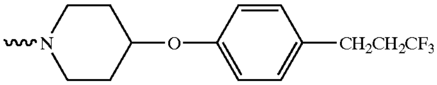 |
| 12 | 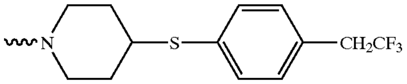 |
TABLE 137-continued
| | |
|---|---|
| | 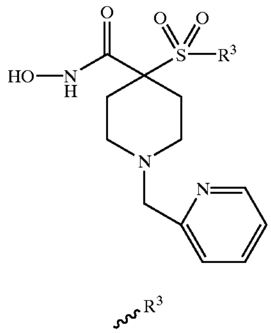 |
| 13 | 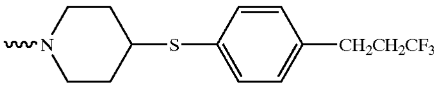 |
| 14 | 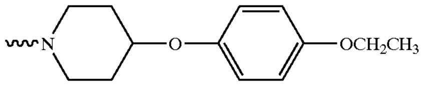 |
| 15 | 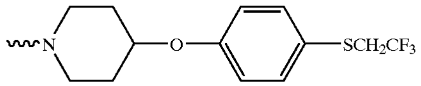 |
| 16 | 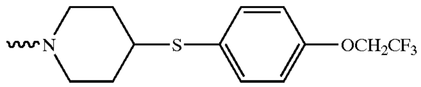 |
TABLE 138
| | |
|---|---|
| | 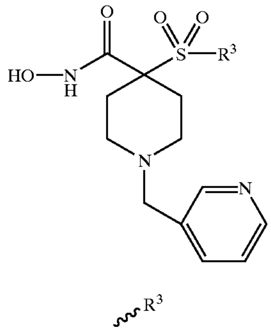 |
| 1 | 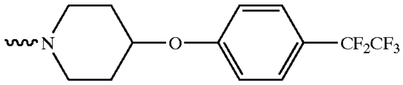 |
| 2 | 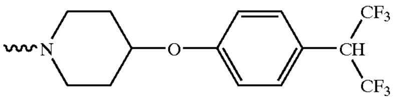 |
| 3 | 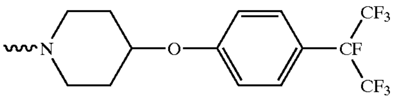 |
| 4 | 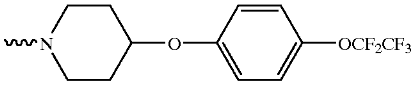 |

TABLE 138-continued
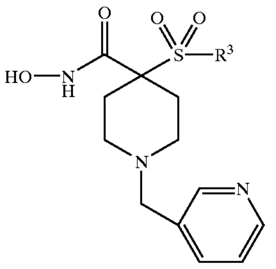
| | |
|---|---|
| | 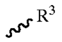 |
| 5 | 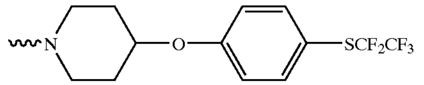 |
| 6 | 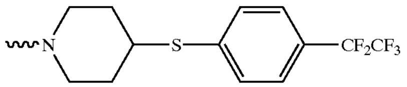 |
| 7 | 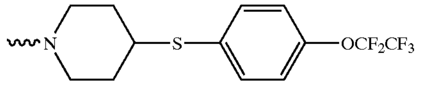 |
| 8 | 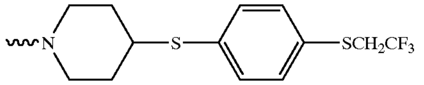 |
| 9 | 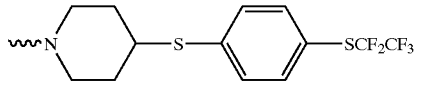 |
| 10 | 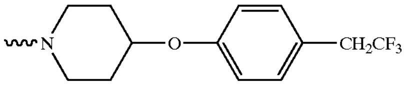 |
| 11 | 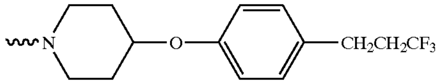 |
| 12 | 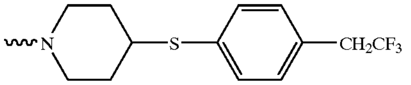 |
| 13 | 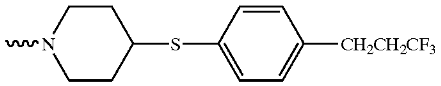 |
| 14 | 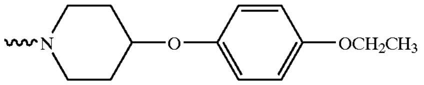 |
| 15 | 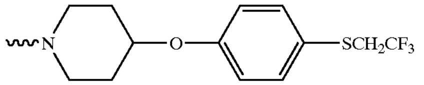 |
| 16 | 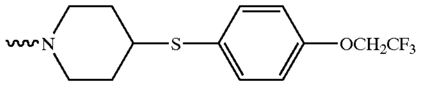 |
TABLE 139
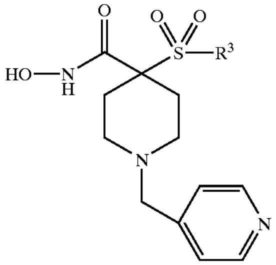
| | |
|---|---|
| | 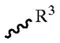 |
| 1 | 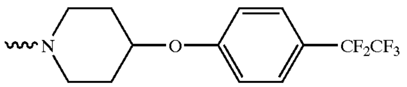 |
| 2 | 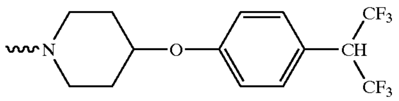 |
| 3 | 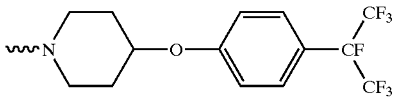 |
| 4 | 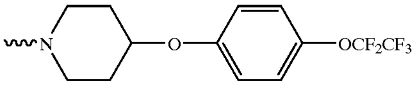 |
| 5 | 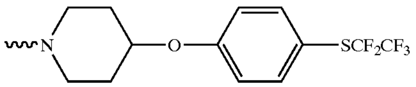 |
| 6 | 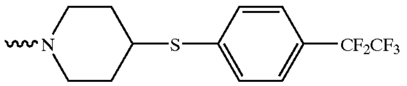 |
| 7 | 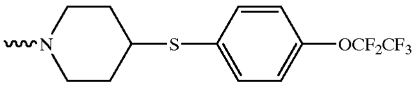 |
| 8 | 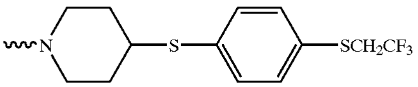 |
| 9 | 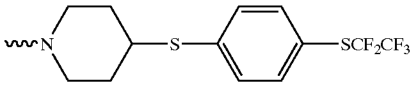 |
| 10 | 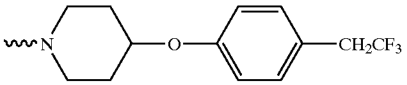 |
| 11 | 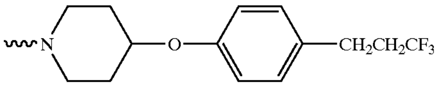 |
| 12 | 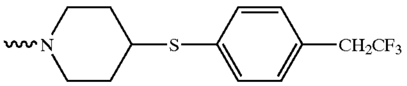 |

TABLE 139-continued
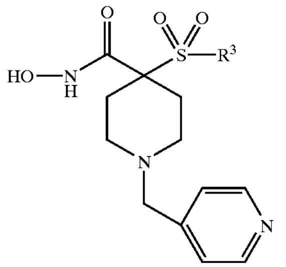
| | 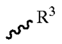 |
|---|---|
| 13 | 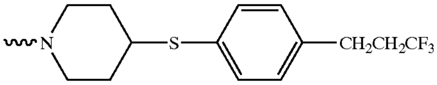 |
| 14 | 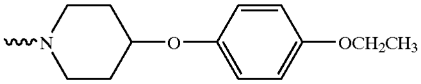 |
| 15 | 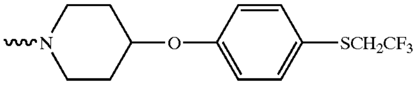 |
| 16 | 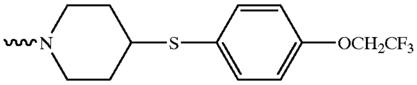 |
TABLE 140
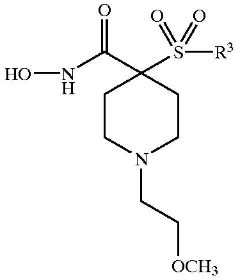
| | 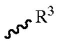 |
|---|---|
| 1 | 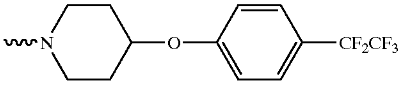 |
| 2 | 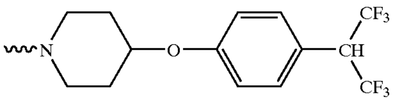 |
| 3 | 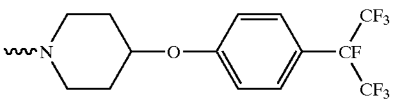 |
| 4 | 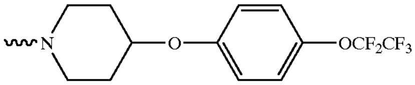 |
TABLE 140-continued
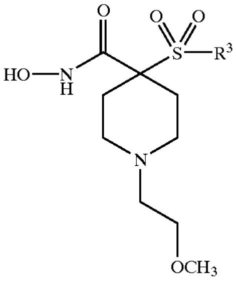
| | 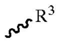 |
|---|---|
| 5 | 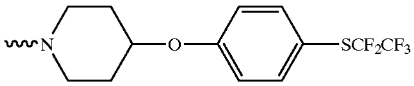 |
| 6 | 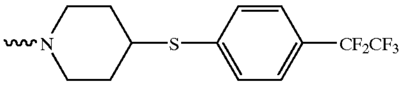 |
| 7 | 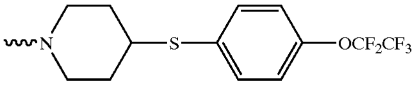 |
| 8 | 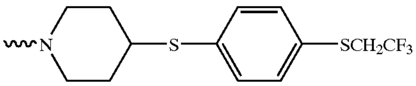 |
| 9 | 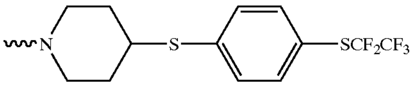 |
| 10 | 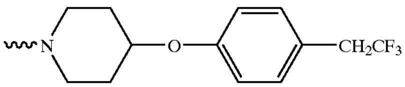 |
| 11 | 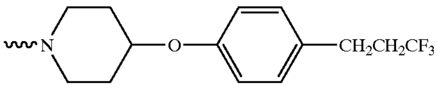 |
| 12 | 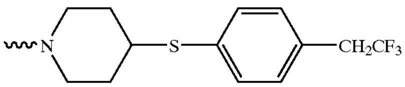 |
| 13 | 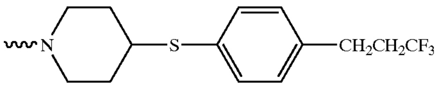 |
| 14 | 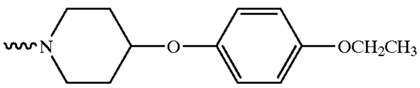 |
| 15 | 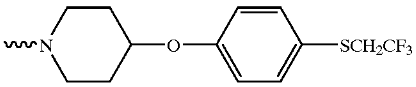 |
| 16 | 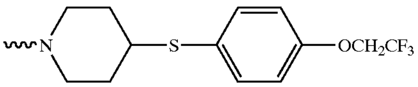 |

TABLE 141
| | |
|---|---|
| | 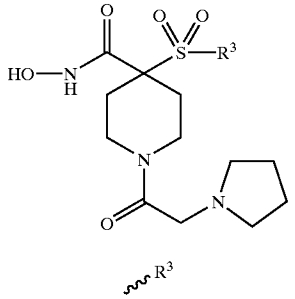 |
| 1 | 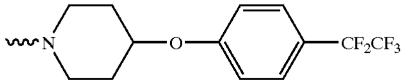 |
| 2 | 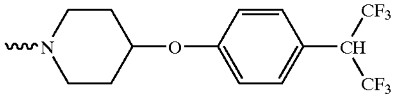 |
| 3 | 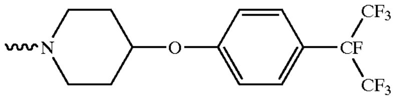 |
| 4 | 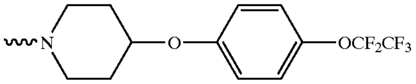 |
| 5 | 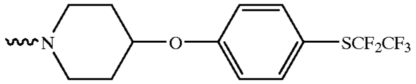 |
| 6 | 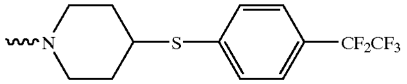 |
| 7 | 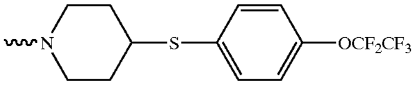 |
| 8 | 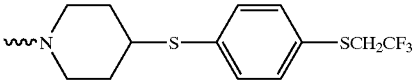 |
| 9 | 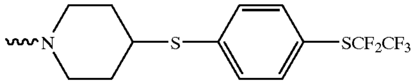 |
| 10 | 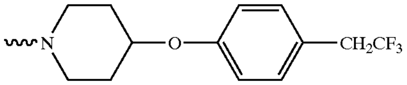 |
| 11 | 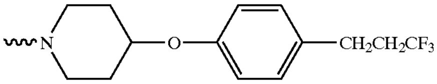 |
| 12 | 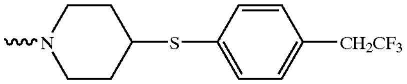 |
TABLE 141-continued
| | |
|---|---|
| | 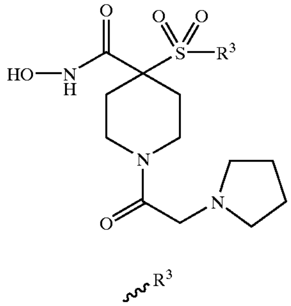 |
| 13 | 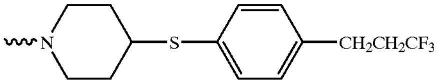 |
| 14 | 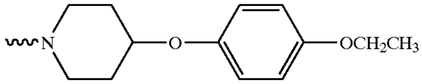 |
| 15 | 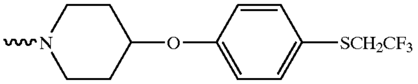 |
| 16 | 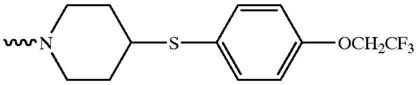 |
TABLE 142
| | |
|---|---|
| | 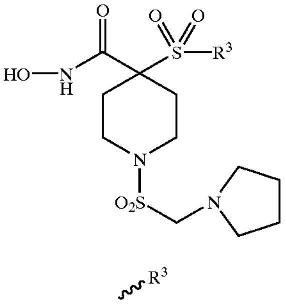 |
| 1 | 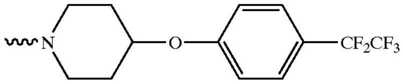 |
| 2 | 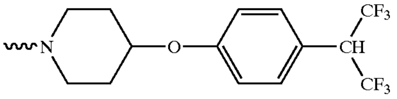 |
| 3 | 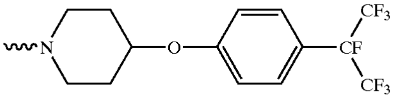 |
| 4 | 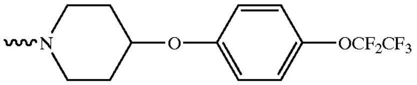 |

TABLE 142-continued
| | |
|---|---|
| | 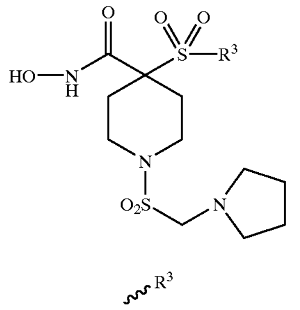 |
| 5 | 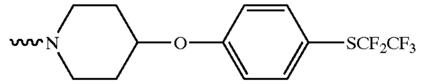 |
| 6 | 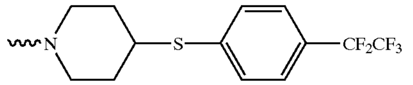 |
| 7 | 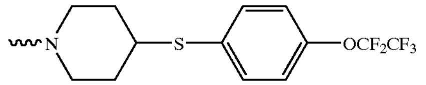 |
| 8 | 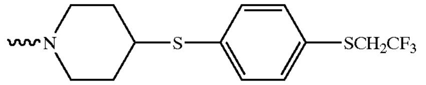 |
| 9 | 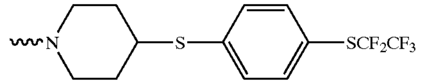 |
| 10 | 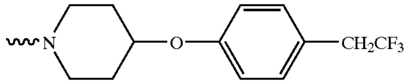 |
| 11 | 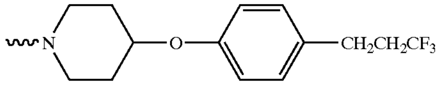 |
| 12 | 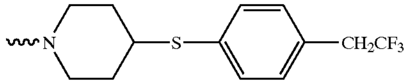 |
| 13 | 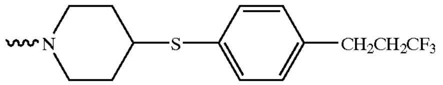 |
| 14 | 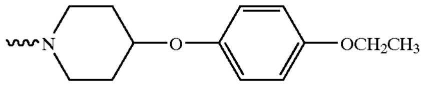 |
| 15 | 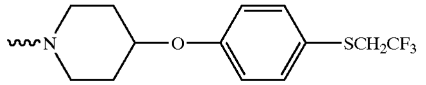 |
| 16 | 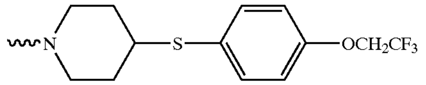 |
TABLE 143
| | |
|---|---|
| | 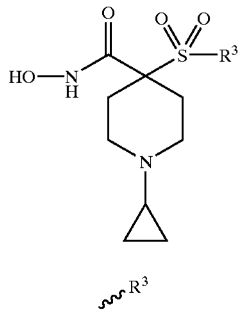 |
| 1 | 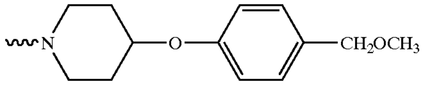 |
| 2 | 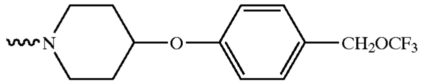 |
| 3 | 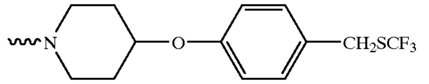 |
| 4 | 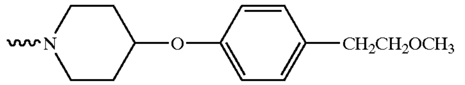 |
| 5 | 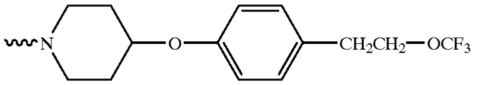 |
| 6 | 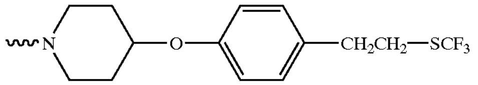 |
| 7 | 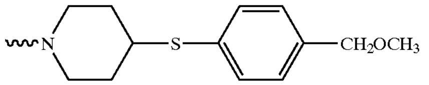 |
| 8 | 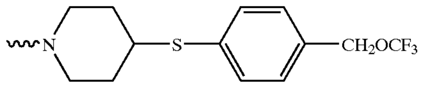 |
| 9 | 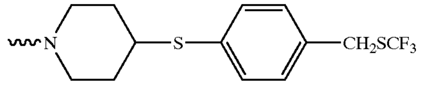 |
| 10 | 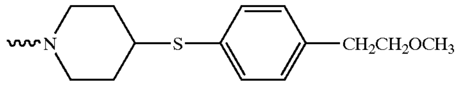 |
| 11 | 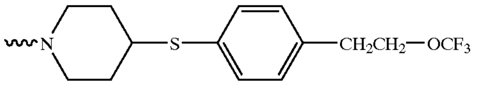 |
| 12 | 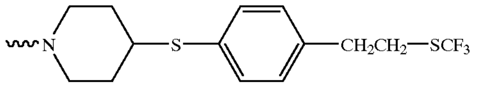 |

TABLE 144
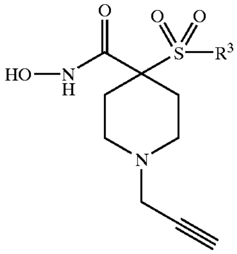
| | 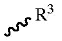 |
|---|---|
| 1 | 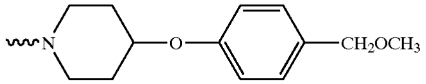 |
| 2 | 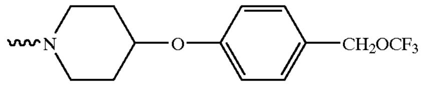 |
| 3 | 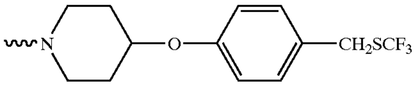 |
| 4 | 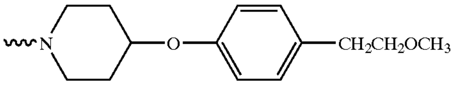 |
| 5 | 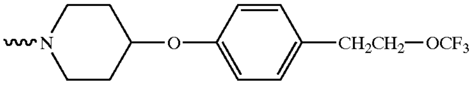 |
| 6 | 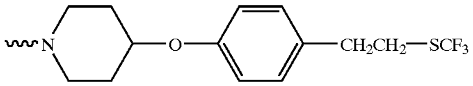 |
| 7 | 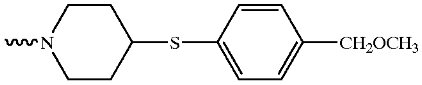 |
| 8 | 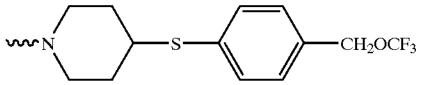 |
| 9 | 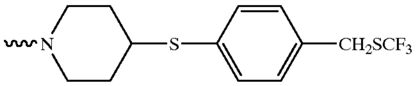 |
| 10 | 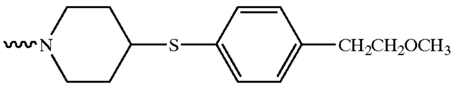 |
| 11 | 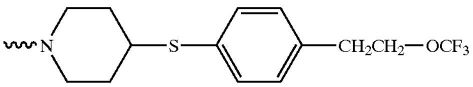 |
| 12 | 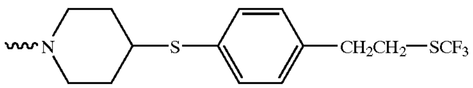 |
TABLE 145
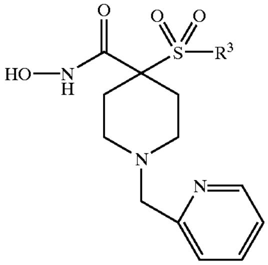
| | 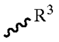 |
|---|---|
| 1 | 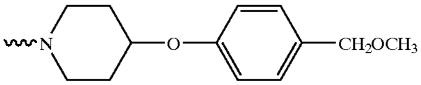 |
| 2 | 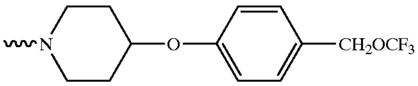 |
| 3 | 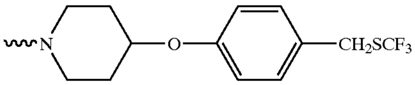 |
| 4 | 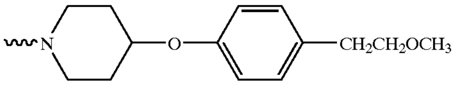 |
| 5 | 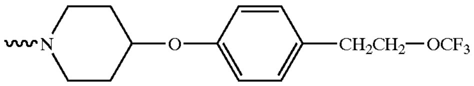 |
| 6 | 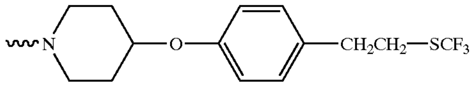 |
| 7 | 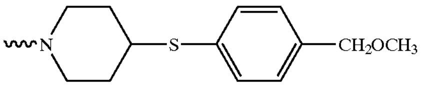 |
| 8 | 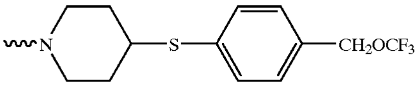 |
| 9 | 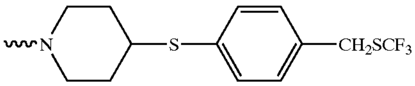 |
| 10 | 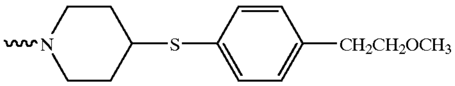 |
| 11 | 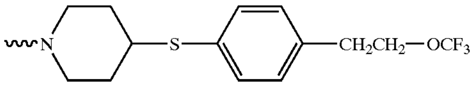 |
| 12 | 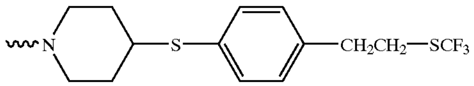 |

TABLE 146
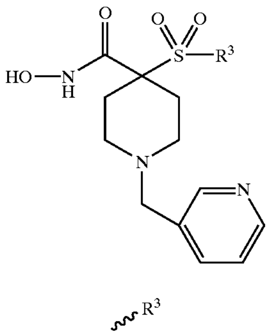
| | |
|---|---|
| 1 | 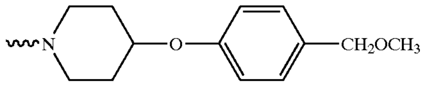 |
| 2 | 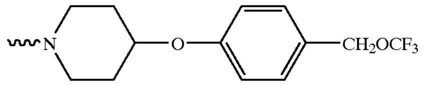 |
| 3 | 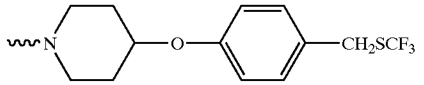 |
| 4 | 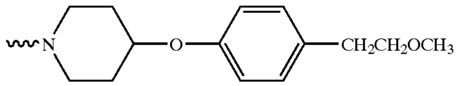 |
| 5 | 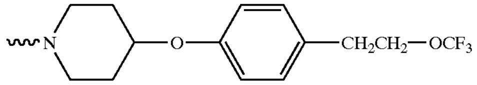 |
| 6 | 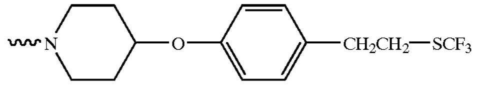 |
| 7 | 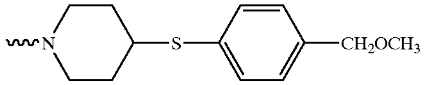 |
| 8 | 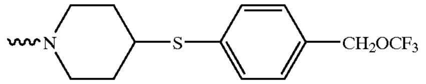 |
| 9 | 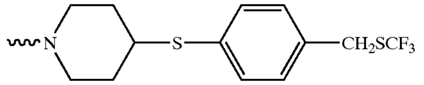 |
| 10 | 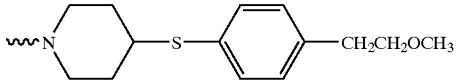 |
| 11 | 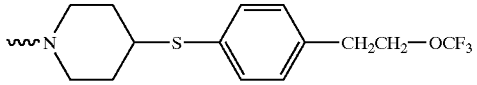 |
| 12 | 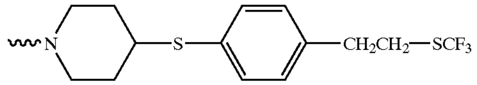 |
TABLE 147
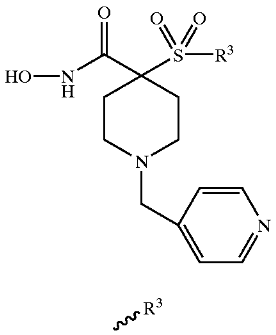
| | |
|---|---|
| 1 | 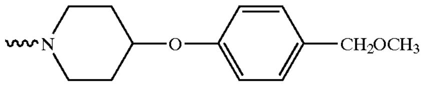 |
| 2 | 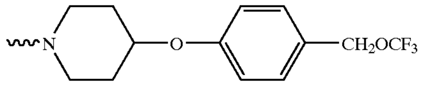 |
| 3 | 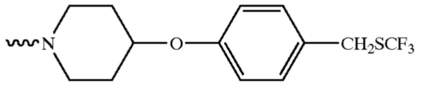 |
| 4 | 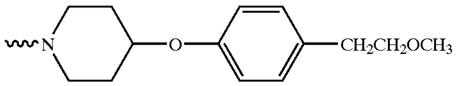 |
| 5 | 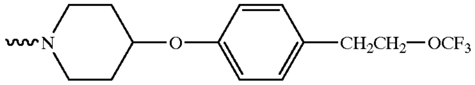 |
| 6 | 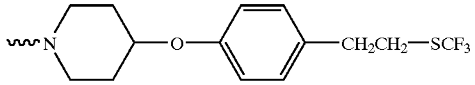 |
| 7 | 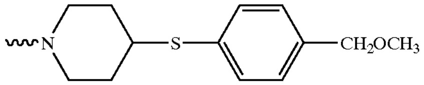 |
| 8 | 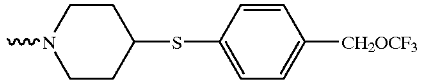 |
| 9 | 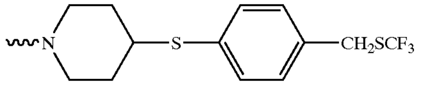 |
| 10 | 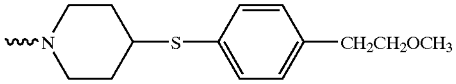 |
| 11 | 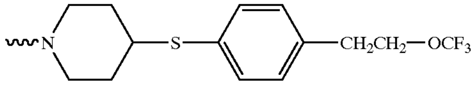 |
| 12 | 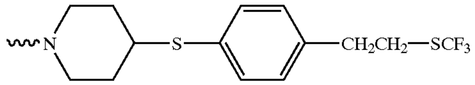 |

TABLE 148
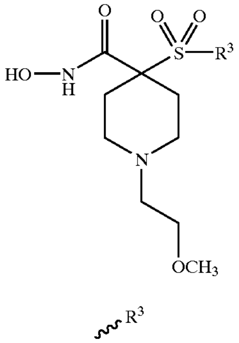
| | |
|---|---|
| 1 | 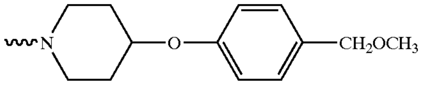 |
| 2 | 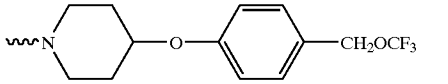 |
| 3 | 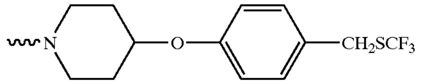 |
| 4 | 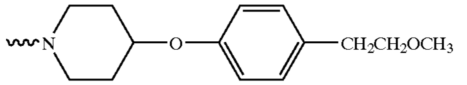 |
| 5 | 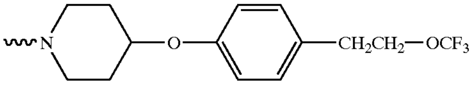 |
| 6 | 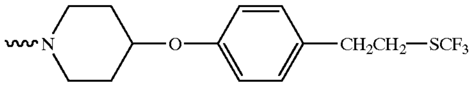 |
| 7 | 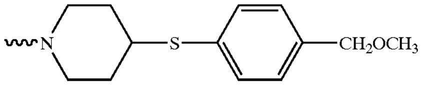 |
| 8 | 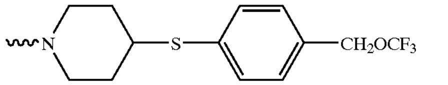 |
| 9 | 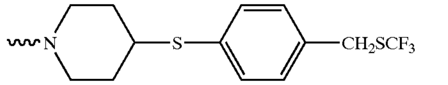 |
| 10 | 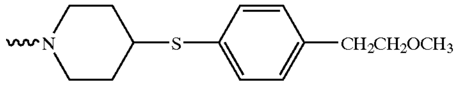 |
| 11 | 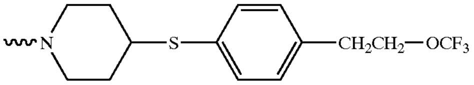 |
| 12 | 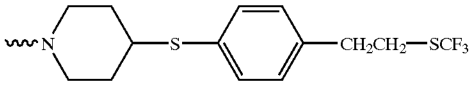 |
TABLE 149
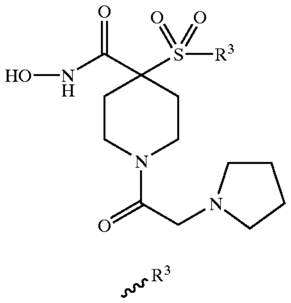
| | |
|---|---|
| 1 | 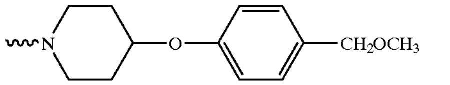 |
| 2 | 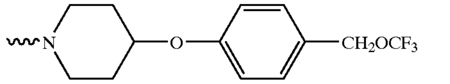 |
| 3 | 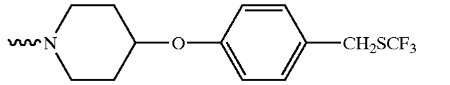 |
| 4 | 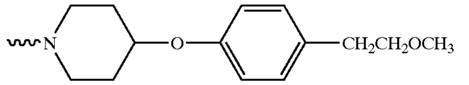 |
| 5 | 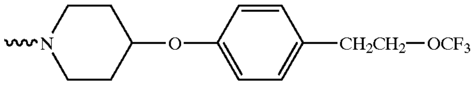 |
| 6 | 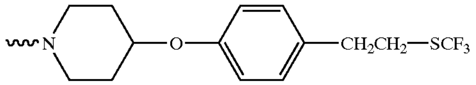 |
| 7 | 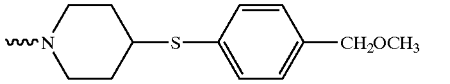 |
| 8 | 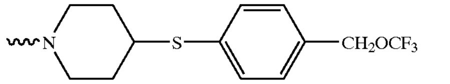 |
| 9 | 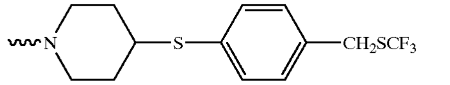 |
| 10 | 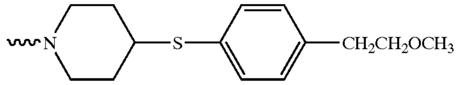 |
| 11 | 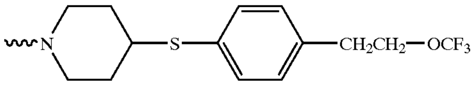 |
| 12 | 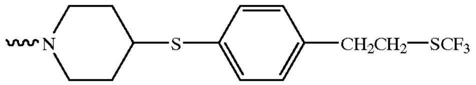 |

TABLE 150
| | 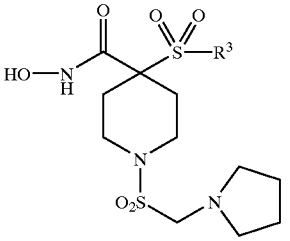 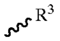 |
|---|---|
| 1 | 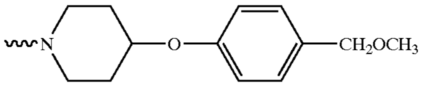 |
| 2 | 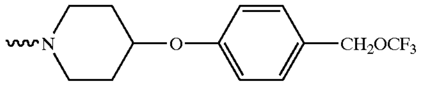 |
| 3 | 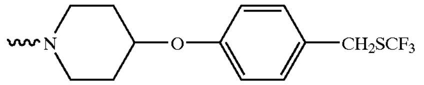 |
| 4 | 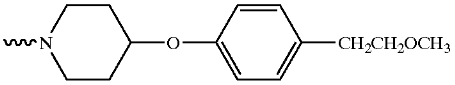 |
| 5 | 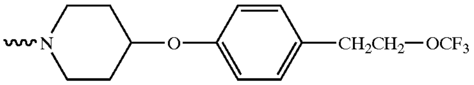 |
| 6 | 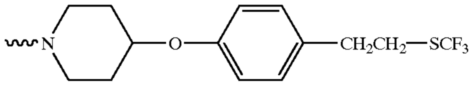 |
| 7 | 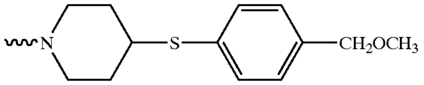 |
| 8 | 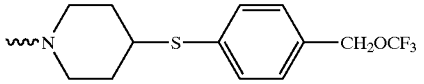 |
| 9 | 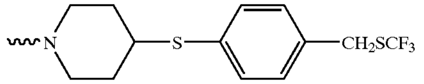 |
| 10 | 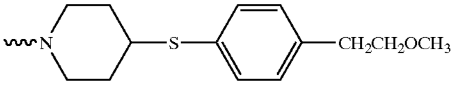 |
| 11 | 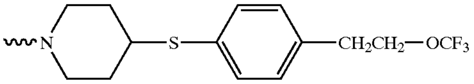 |
| 12 | 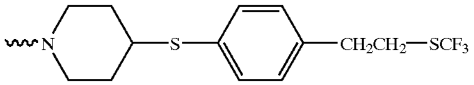 |
TABLE 151
| | 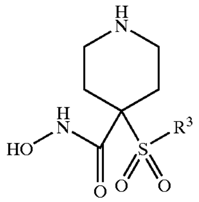 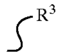 |
|---|---|
| 1 | 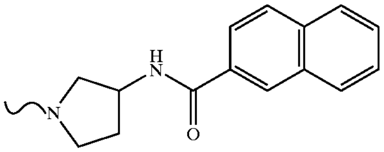 |
| 2 | 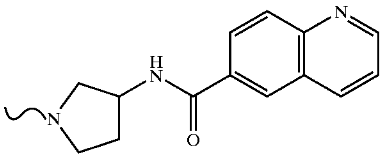 |
| 3 | 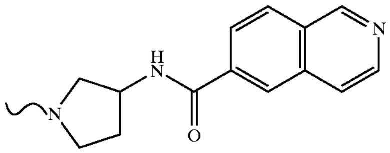 |
| 4 | 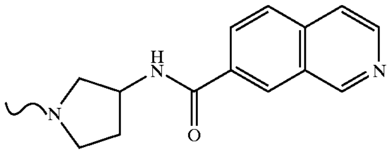 |
| 5 | 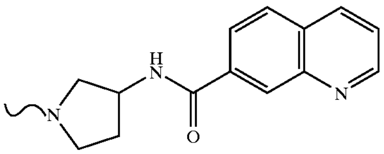 |
| 6 | 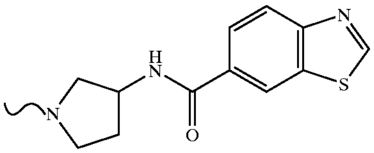 |
| 7 | 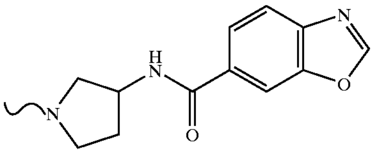 |
| 8 | 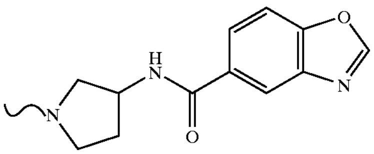 |

TABLE 151-continued
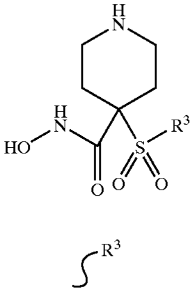
| | |
|---|---|
| 9 | 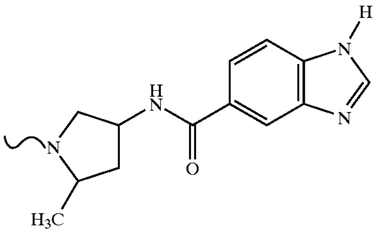 |
| 10 | 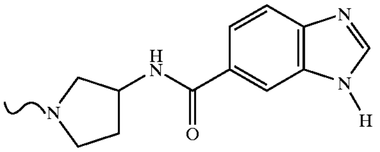 |
| 11 | 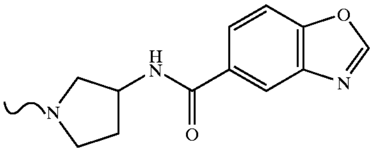 |
| 12 | 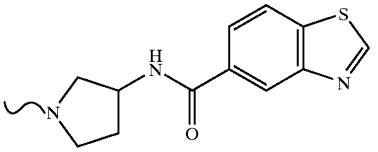 |
| 13 | 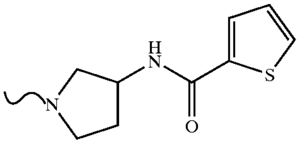 |
| 14 | 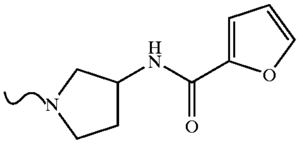 |
| 15 | 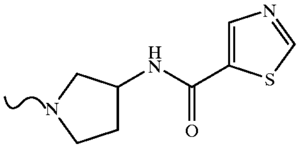 |
TABLE 151-continued
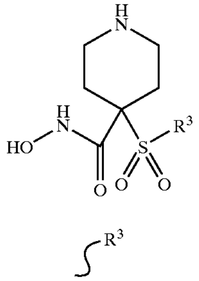
| | |
|---|---|
| 16 | 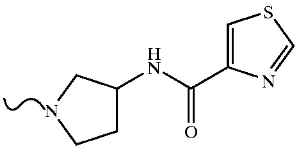 |
| 17 | 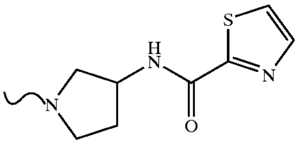 |
| 18 | 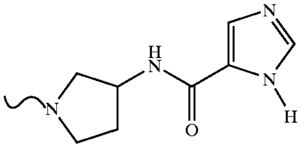 |
TABLE 152
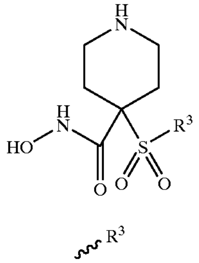
| | |
|---|---|
| 1 | 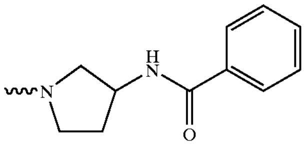 |
| 2 | 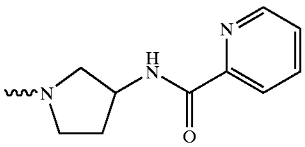 |
| 3 | 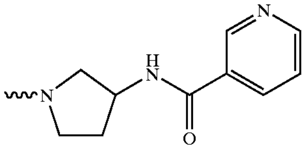 |

TABLE 152-continued
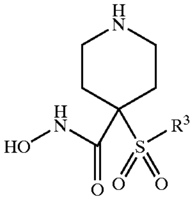
| | 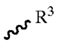 |
|---|---|
| 4 | 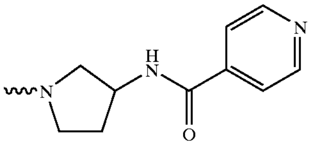 |
| 5 | 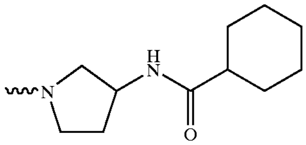 |
| 6 | 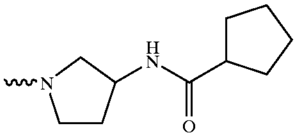 |
| 7 | 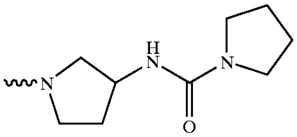 |
| 8 | 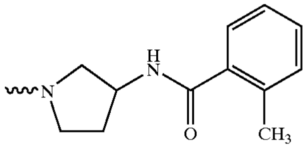 |
| 9 | 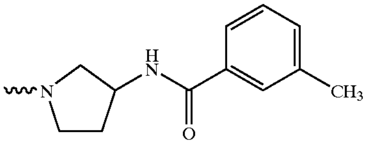 |
| 10 | 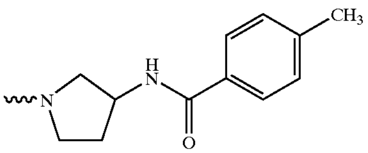 |
| 11 | 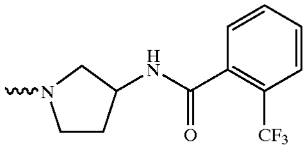 |
TABLE 152-continued
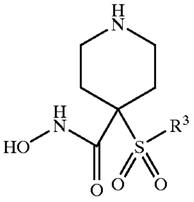
| | 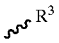 |
|---|---|
| 12 | 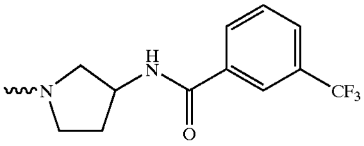 |
| 13 | 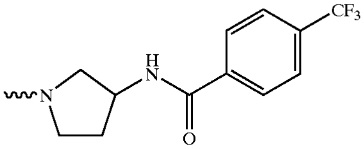 |
| 14 | 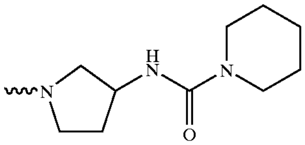 |
| 15 | 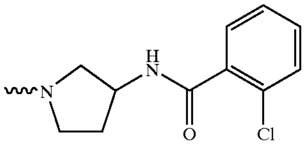 |
| 16 | 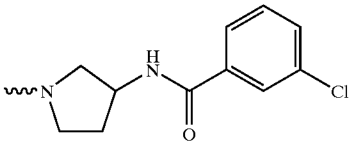 |
| 17 | 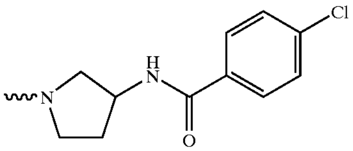 |
| 18 | 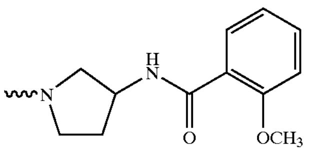 |
| 19 | 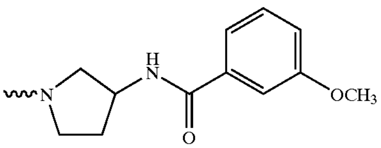 |

TABLE 152-continued
| | |
|---|---|
| 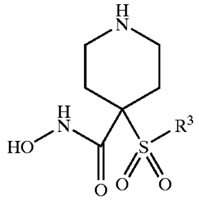 | |
| 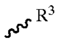 | |
| 20 | 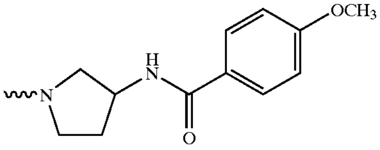 |
| 21 | 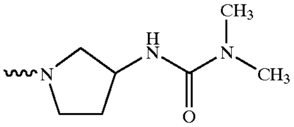 |
TABLE 153
| | |
|---|---|
| 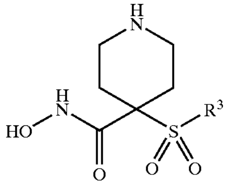 | |
| 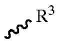 | |
| 1 | 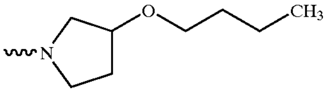 |
| 2 | 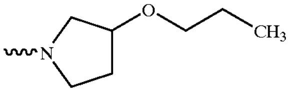 |
| 3 | 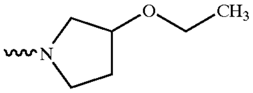 |
| 4 | 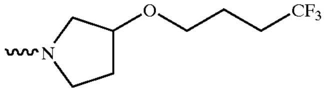 |
| 5 | 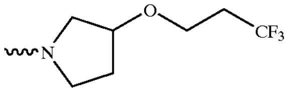 |
| 6 | 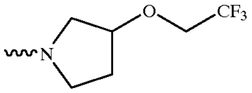 |
TABLE 153-continued
| | |
|---|---|
| 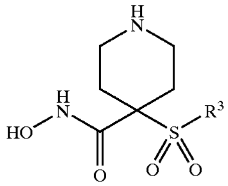 | |
| 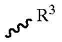 | |
| 7 | 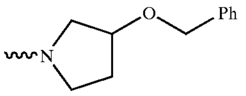 |
| 8 | 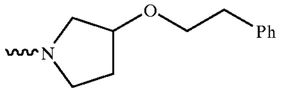 |
| 9 | 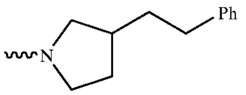 |
| 10 | 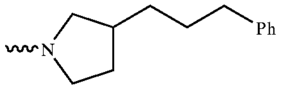 |
| 11 | 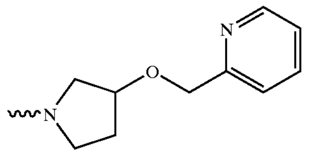 |
| 12 | 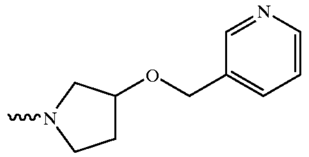 |
| 13 | 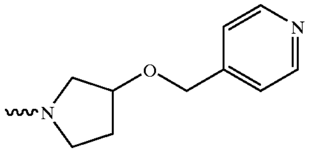 |
| 14 | 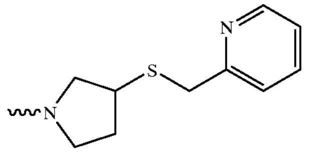 |
| 15 | 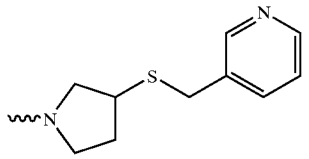 |

TABLE 153-continued
| | |
|---|---|
| | 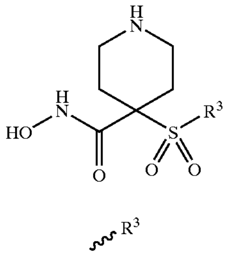 |
| 16 | 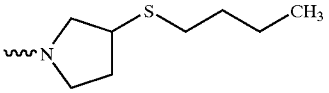 |
| 17 | 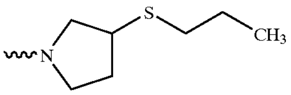 |
| 18 | 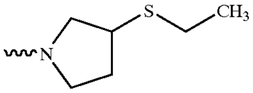 |
| 19 | 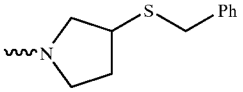 |
| 20 | 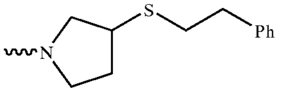 |
| 21 | 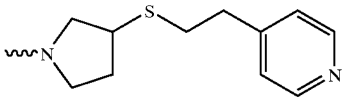 |
| 22 | 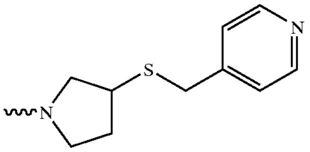 |
TABLE 154
| | |
|---|---|
| | 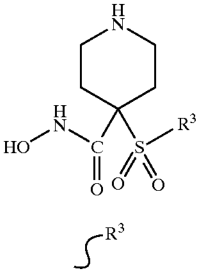 |
| 1 | 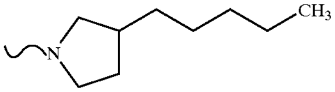 |
TABLE 154-continued
| | |
|---|---|
| | 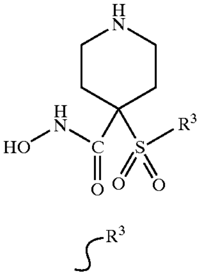 |
| 2 | 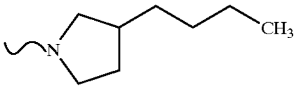 |
| 3 | 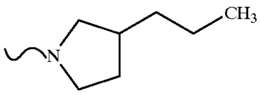 |
| 4 | 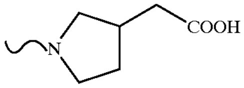 |
| 5 | 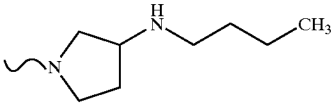 |
| 6 | 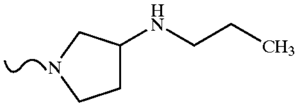 |
| 7 | 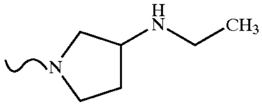 |
| 8 | 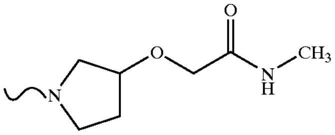 |
| 9 | 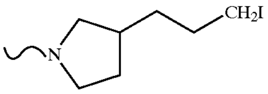 |
| 10 | 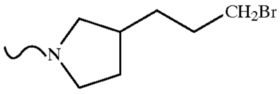 |
| 11 | 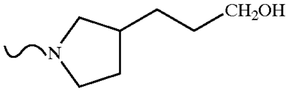 |
| 12 | 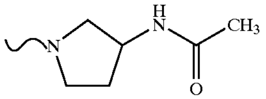 |

TABLE 154-continued
| | |
|---|---|
| | 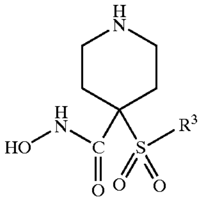 |
| | 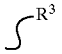 |
| 13 | 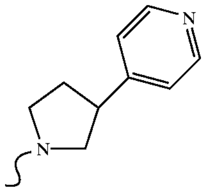 |
| 14 | 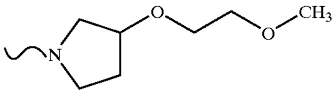 |
| 15 | 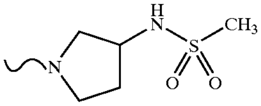 |
| 16 | 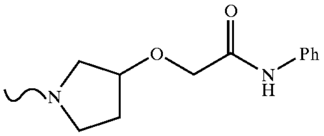 |
| 17 | 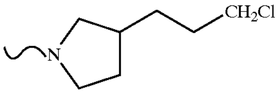 |
| 18 | 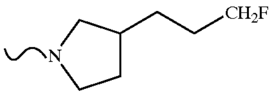 |
| 19 | 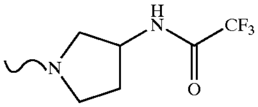 |
| 20 | 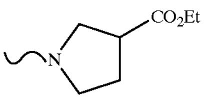 |
| 21 | 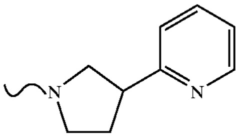 |
| 22 | 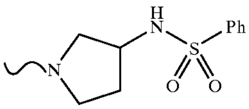 |
TABLE 154-continued
| | |
|---|---|
| | 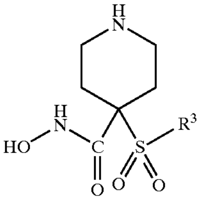 |
| | 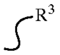 |
| 23 | 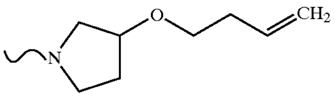 |
| 24 | 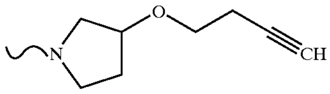 |
| 25 | 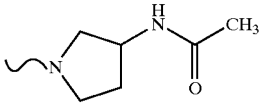 |
| 26 | 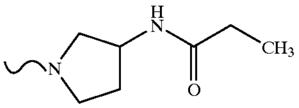 |
| 27 | 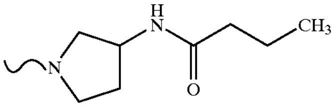 |
| 28 | 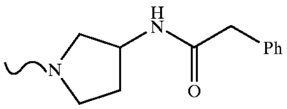 |
| 29 | 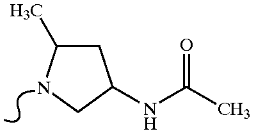 |
| 30 | 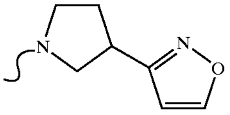 |

TABLE 155
| | 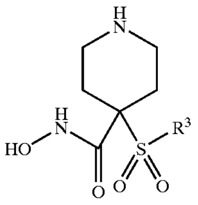<br>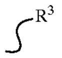 |
|---|---|
| 1 | 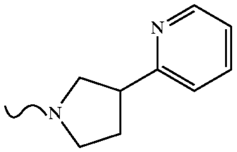 |
| 2 | 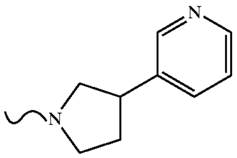 |
| 3 | 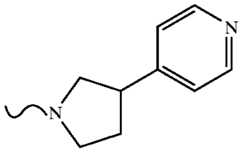 |
| 4 | 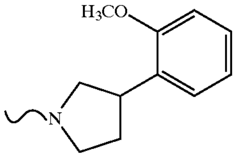 |
| 5 | 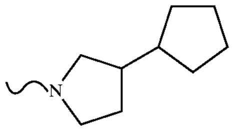 |
| 6 | 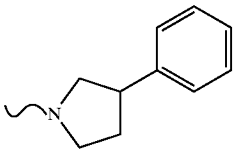 |
| 7 | 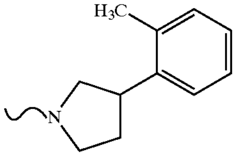 |
TABLE 155-continued
| | 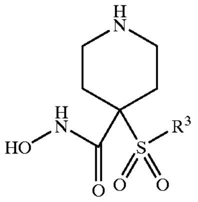<br>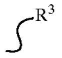 |
|---|---|
| 8 | 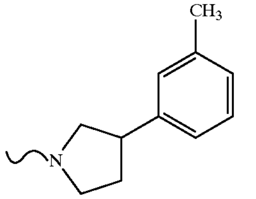 |
| 9 | 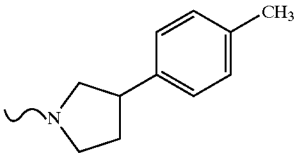 |
| 10 | 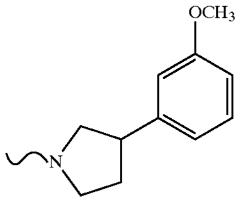 |
| 11 | 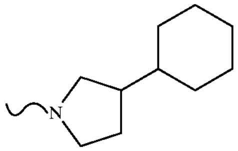 |
| 12 | 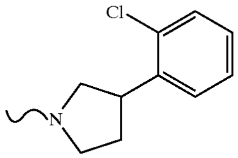 |
| 13 | 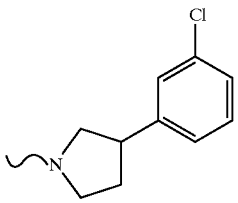 |
| 14 | 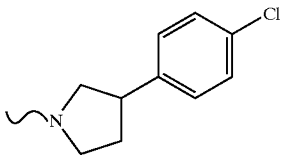 |

TABLE 155-continued
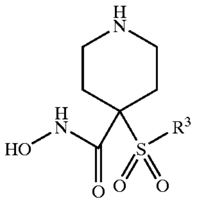
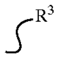
| | |
|---|---|
| 15 | 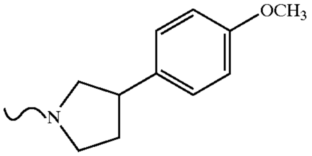 |
| 16 | 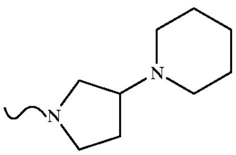 |
| 17 | 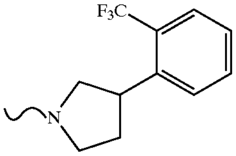 |
| 18 | 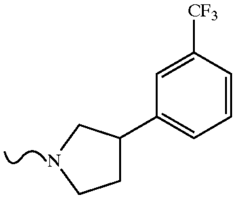 |
| 19 | 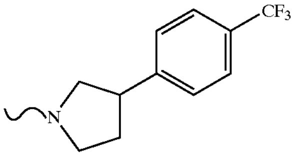 |
| 20 | 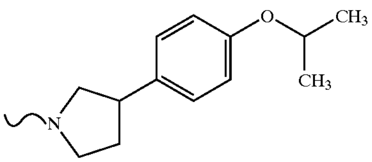 |
| 21 | 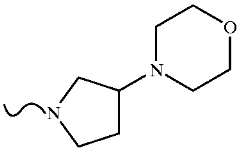 |
TABLE 156
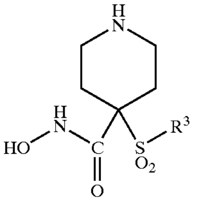
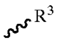
| | |
|---|---|
| 1 | 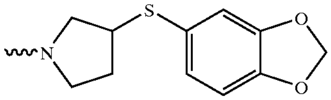 |
| 2 | 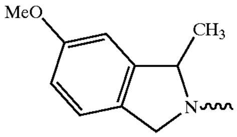 |
| 3 | 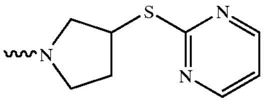 |
| 4 | 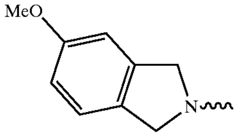 |
| 5 | 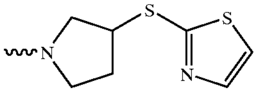 |
| 6 | 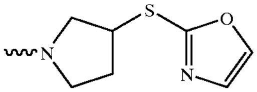 |
| 7 | 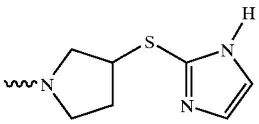 |
| 8 | 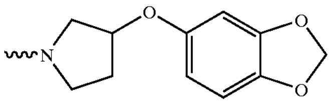 |
| 9 | 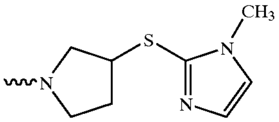 |
| 10 | 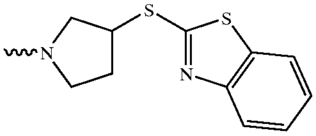 |

TABLE 156-continued
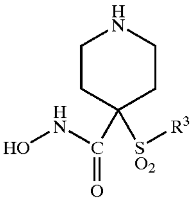
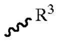
| | |
|---|---|
| 11 | 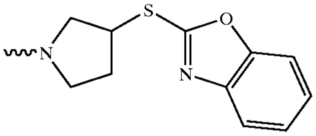 |
TABLE 157
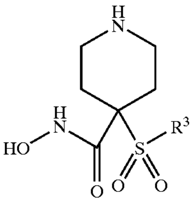
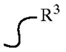
| | |
|---|---|
| 1 | 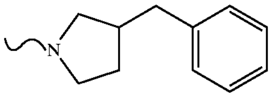 |
| 2 | 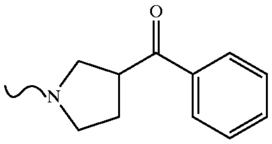 |
| 3 | 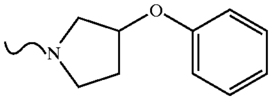 |
| 4 | 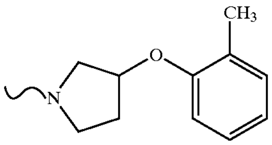 |
| 5 | 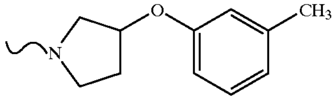 |
| 6 | 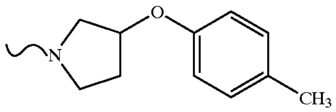 |
TABLE 157-continued
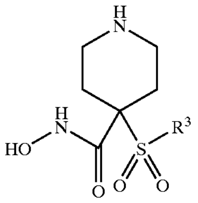
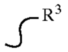
| | |
|---|---|
| 7 | 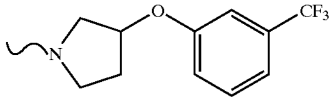 |
| 8 | 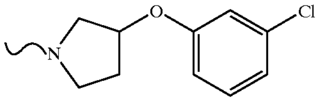 |
| 9 | 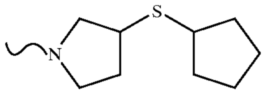 |
| 10 | 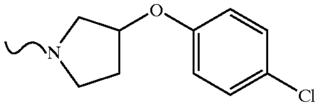 |
| 11 | 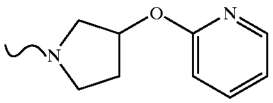 |
| 12 | 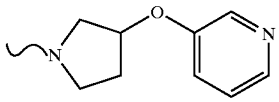 |
| 13 | 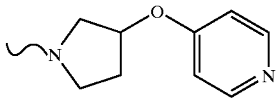 |
| 14 | 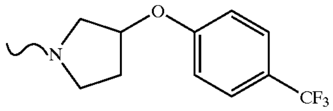 |
| 15 | 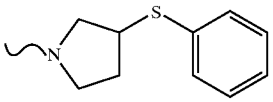 |
| 16 | 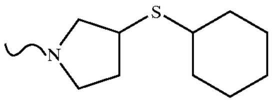 |
| 17 | 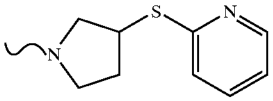 |

TABLE 157-continued
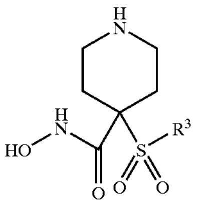
18 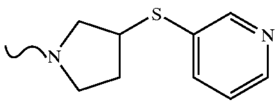
19 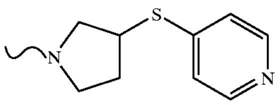
20 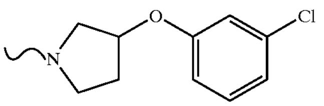
21 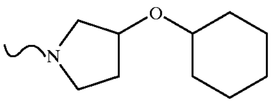
TABLE 158
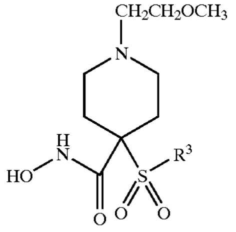
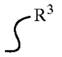
1 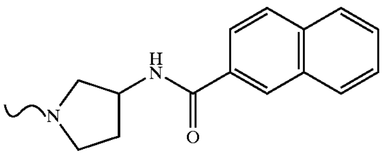
2 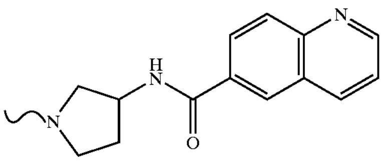
TABLE 158-continued
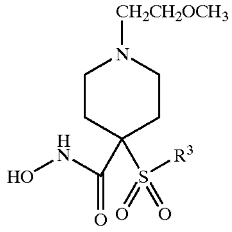
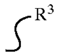
3 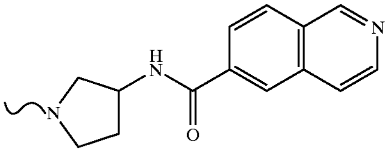
4 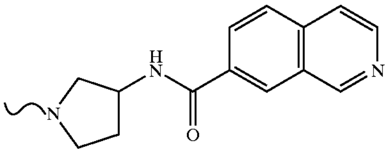
5 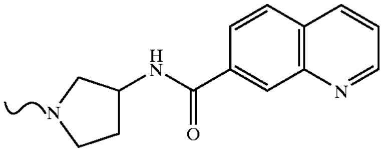
6 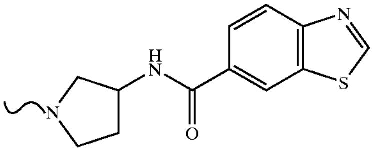
7 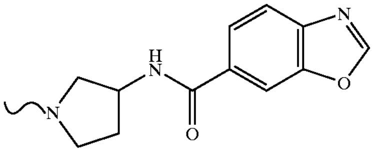
8 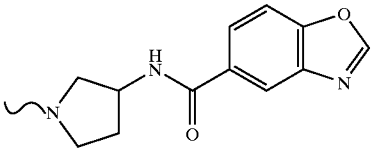
9 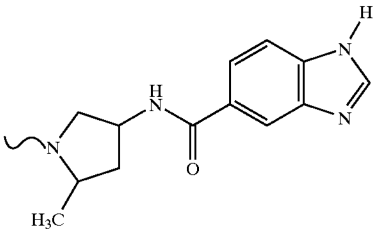

TABLE 158-continued
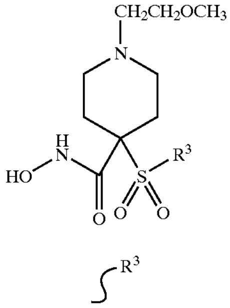
| | |
|---|---|
| 10 | 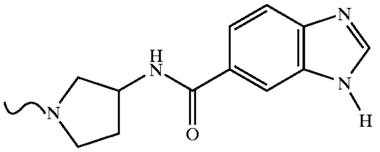 |
| 11 | 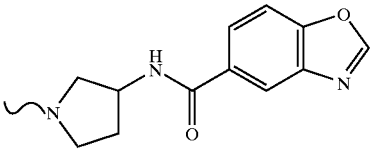 |
| 12 | 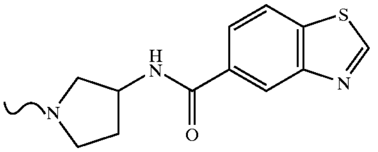 |
| 13 | 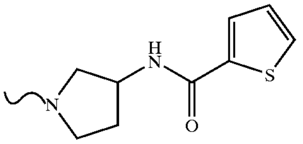 |
| 14 | 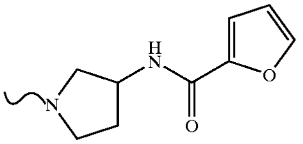 |
| 15 | 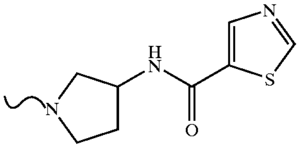 |
| 16 | 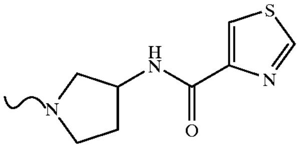 |
| 17 | 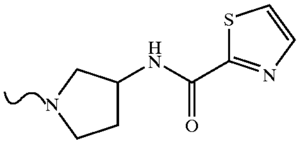 |
TABLE 158-continued
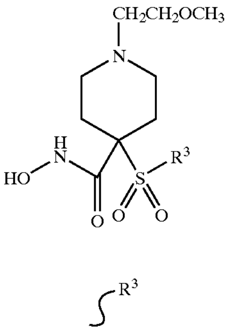
| | |
|---|---|
| 18 | 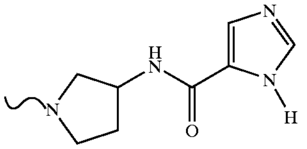 |
TABLE 159
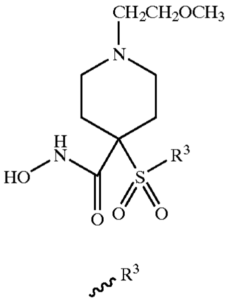
| | |
|---|---|
| 1 | 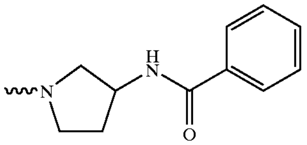 |
| 2 | 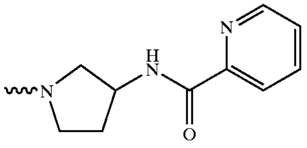 |
| 3 | 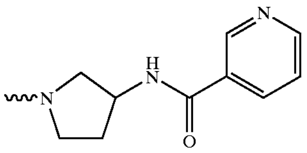 |
| 4 | 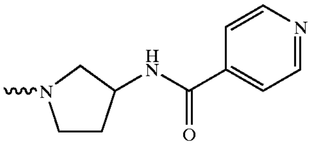 |

TABLE 159-continued
| | 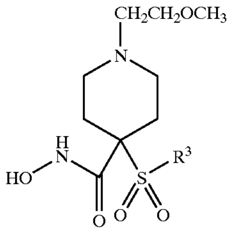 |
|---|---|
| | 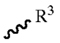 |
| 5 | 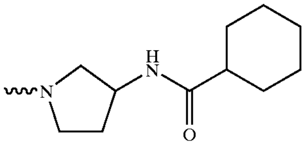 |
| 6 | 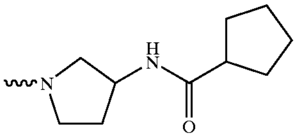 |
| 7 | 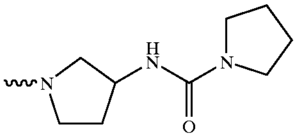 |
| 8 | 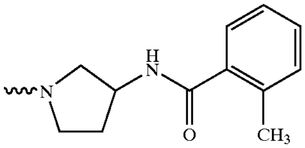 |
| 9 | 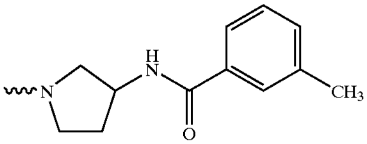 |
| 10 | 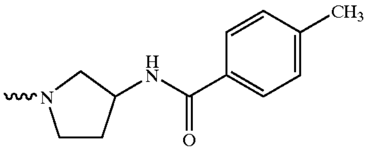 |
| 11 | 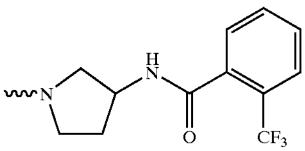 |
| 12 | 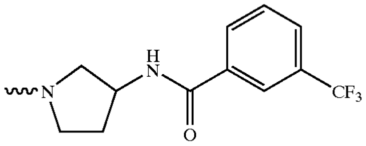 |
TABLE 159-continued
| | 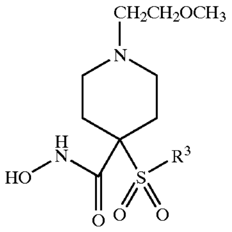 |
|---|---|
| | 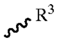 |
| 13 | 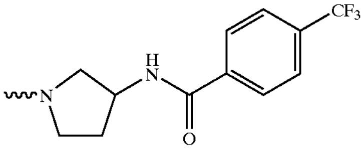 |
| 14 | 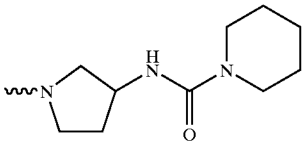 |
| 15 | 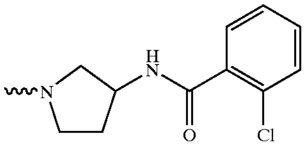 |
| 16 | 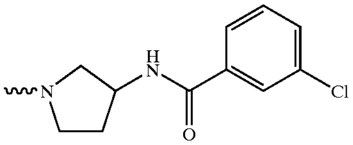 |
| 17 | 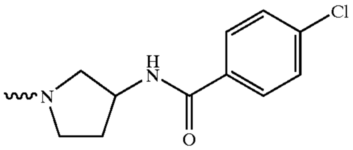 |
| 18 | 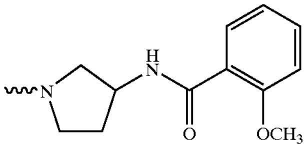 |
| 19 | 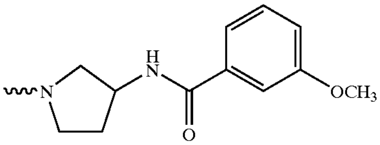 |
| 20 | 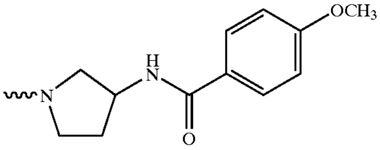 |

TABLE 159-continued
| | |
|---|---|
| | 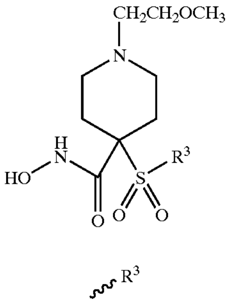 |
| 21 | 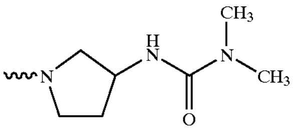 |
TABLE 160
| | |
|---|---|
| | 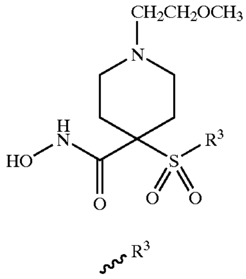 |
| 1 | 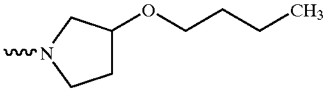 |
| 2 | 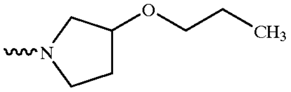 |
| 3 | 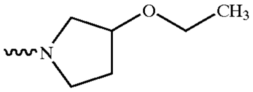 |
| 4 | 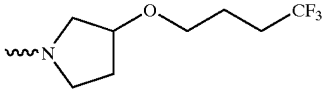 |
| 5 | 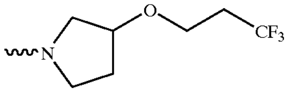 |
| 6 | 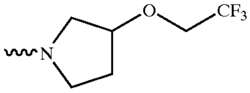 |
| 7 | 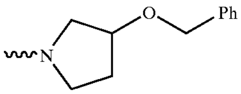 |
TABLE 160-continued
| | |
|---|---|
| | 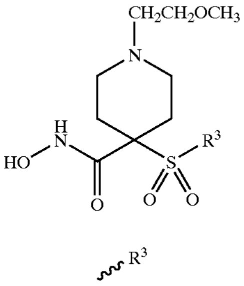 |
| 8 | 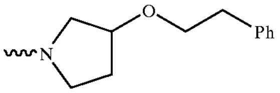 |
| 9 | 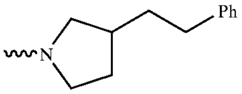 |
| 10 | 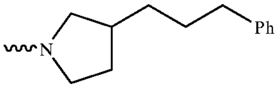 |
| 11 | 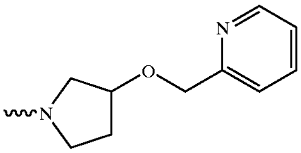 |
| 12 | 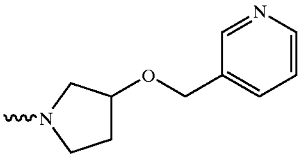 |
| 13 | 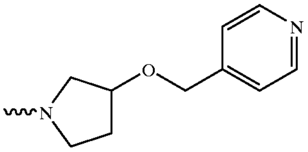 |
| 14 | 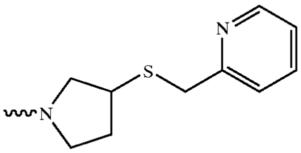 |
| 15 | 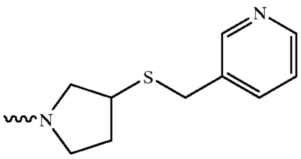 |
| 16 | 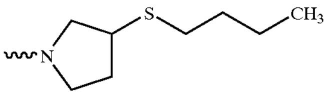 |

TABLE 160-continued
| | 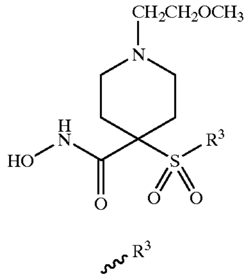 |
|---|---|
| 17 | 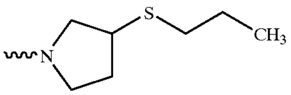 |
| 18 | 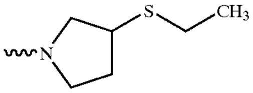 |
| 19 | 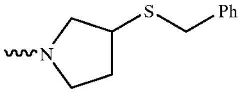 |
| 20 | 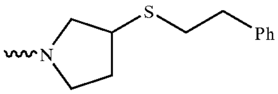 |
| 21 | 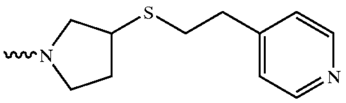 |
| 22 | 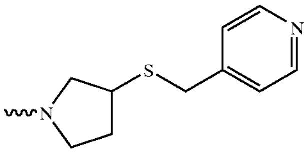 |
TABLE 161
| | 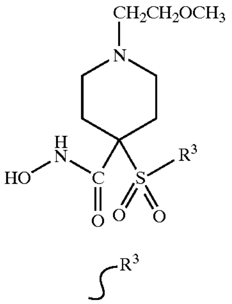 |
|---|---|
| 1 | 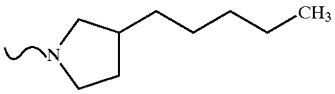 |
| 2 | 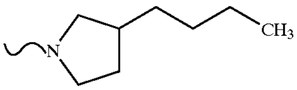 |
TABLE 161-continued
| | 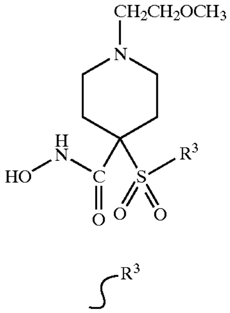 |
|---|---|
| 3 | 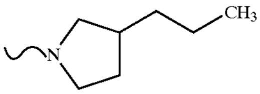 |
| 4 | 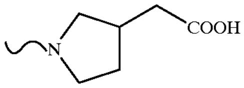 |
| 5 | 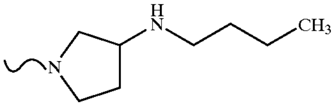 |
| 6 | 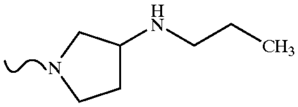 |
| 7 | 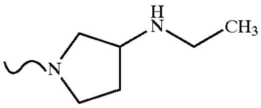 |
| 8 | 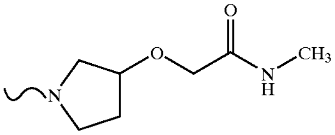 |
| 9 | 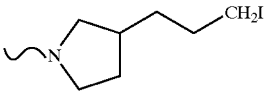 |
| 10 | 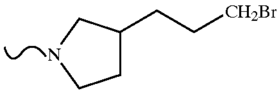 |
| 11 | 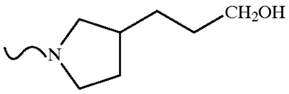 |
| 12 | 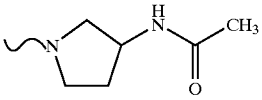 |

TABLE 161-continued
| | |
|---|---|
| | 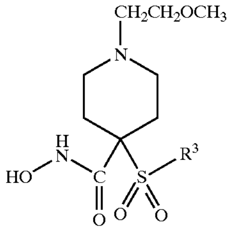 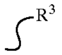 |
| 13 | 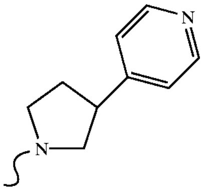 |
| 14 | 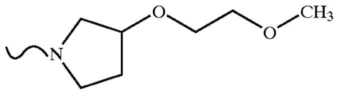 |
| 15 | 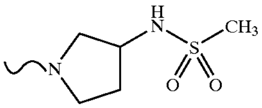 |
| 16 | 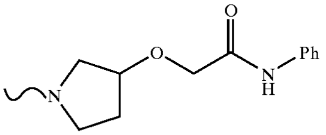 |
| 17 | 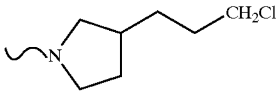 |
| 18 | 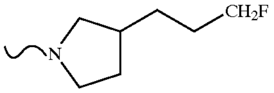 |
| 19 | 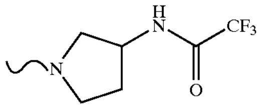 |
| 20 | 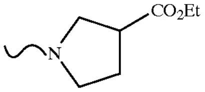 |
| 21 | 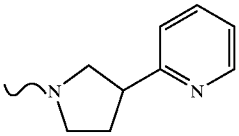 |
| 22 | 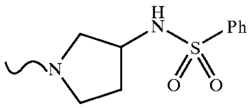 |
TABLE 161-continued
| | |
|---|---|
| | 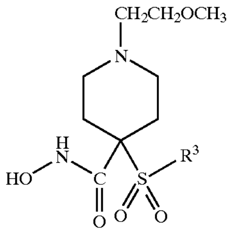 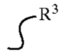 |
| 23 | 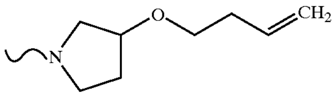 |
| 24 | 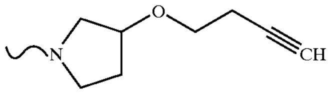 |
| 25 | 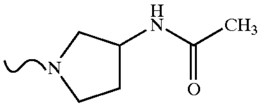 |
| 26 | 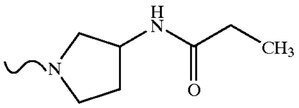 |
| 27 | 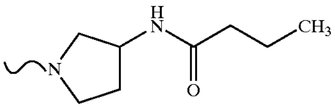 |
| 28 | 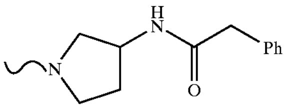 |
| 29 | 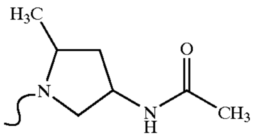 |
| 30 | 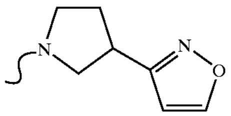 |

TABLE 162
| 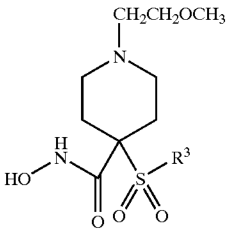 |  |
|---|---|
| 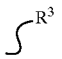 |  |
| 1 | 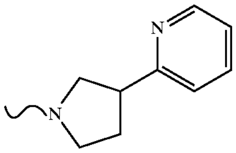 |
| 2 | 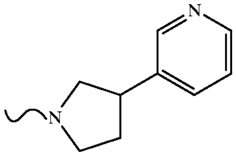 |
| 3 | 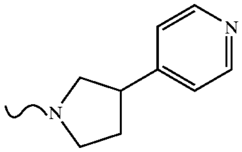 |
| 4 | 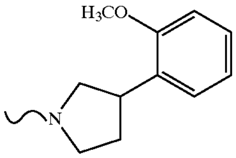 |
| 5 | 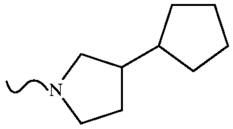 |
| 6 | 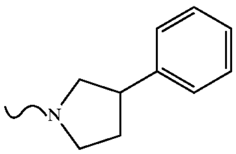 |
| 7 | 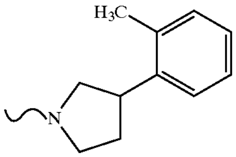 |
TABLE 162-continued
| 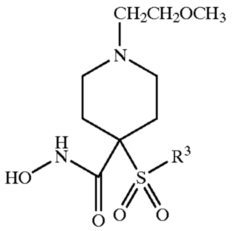 |  |
|---|---|
| 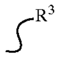 |  |
| 8 | 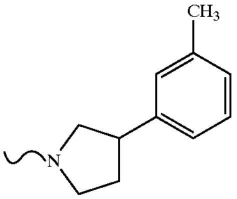 |
| 9 | 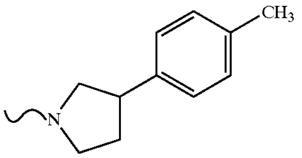 |
| 10 | 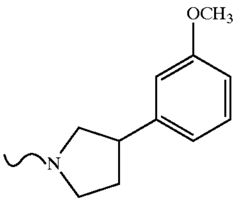 |
| 11 | 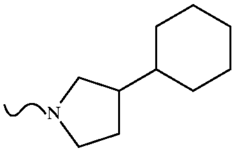 |
| 12 | 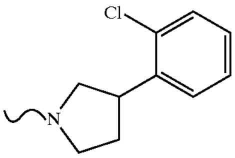 |
| 13 | 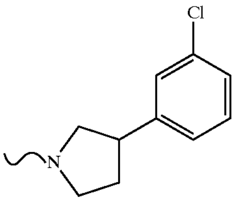 |

TABLE 162-continued
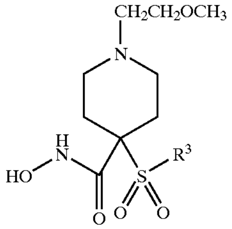
| | 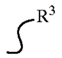 |
|---|---|
| 14 | 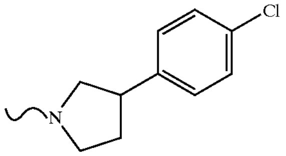 |
| 15 | 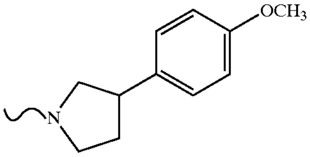 |
| 16 | 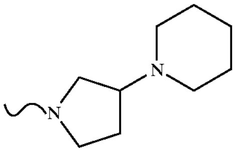 |
| 17 | 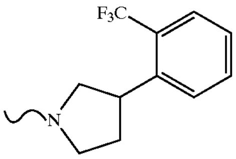 |
| 18 | 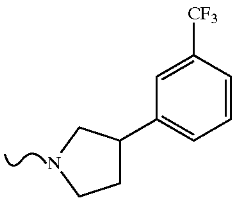 |
| 19 | 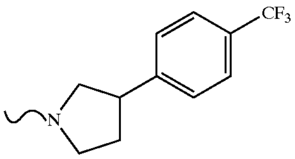 |
| 20 | 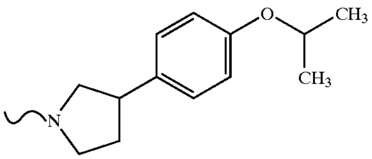 |
TABLE 162-continued
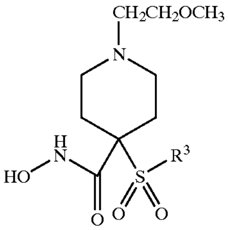
| | 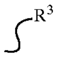 |
|---|---|
| 21 | 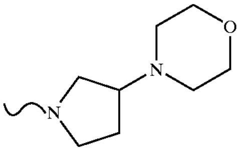 |
TABLE 163
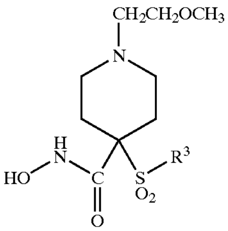
| | 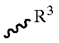 |
|---|---|
| 1 | 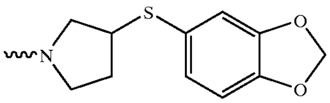 |
| 2 | 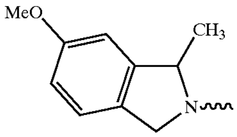 |
| 3 | 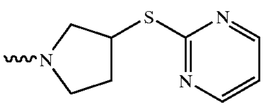 |
| 4 | 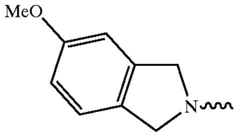 |
| 5 | 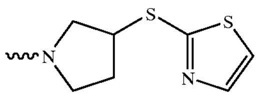 |

TABLE 163-continued
| | |
|---|---|
| 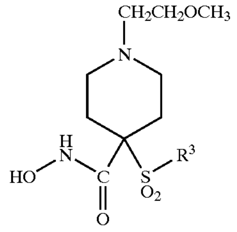 | |
| 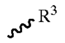 | |
| 6 | 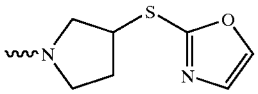 |
| 7 | 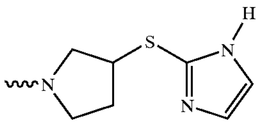 |
| 8 | 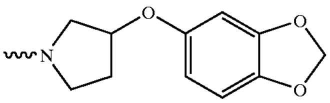 |
| 9 | 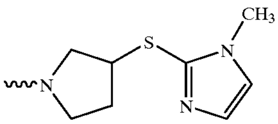 |
| 10 | 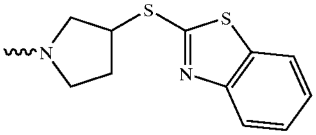 |
| 11 | 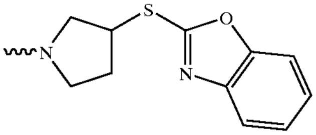 |
TABLE 164
| | |
|---|---|
| 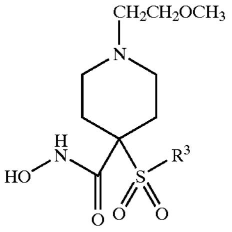 | |
| 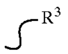 | |
| 1 | 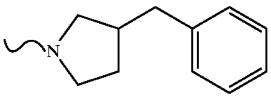 |
TABLE 164-continued
| | |
|---|---|
| 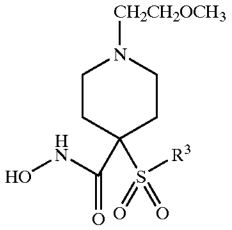 | |
| 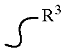 | |
| 2 | 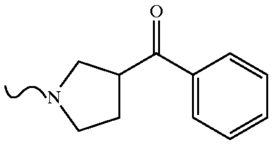 |
| 3 | 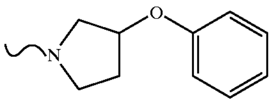 |
| 4 | 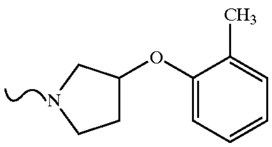 |
| 5 | 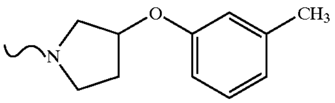 |
| 6 | 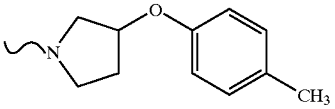 |
| 7 | 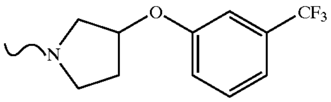 |
| 8 | 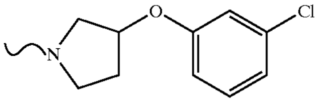 |
| 9 | 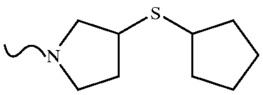 |
| 10 | 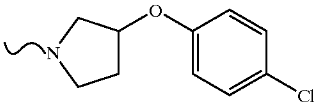 |
| 11 | 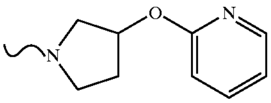 |

TABLE 164-continued
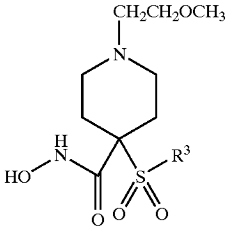
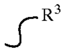
| | |
|---|---|
| 12 | 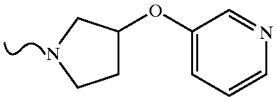 |
| 13 | 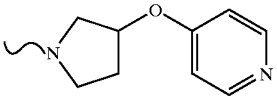 |
| 14 | 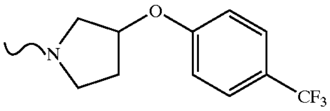 |
| 15 | 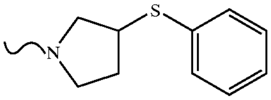 |
| 16 | 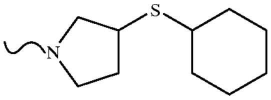 |
| 17 | 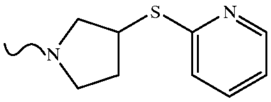 |
| 18 | 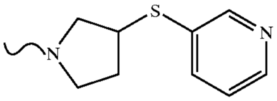 |
| 19 | 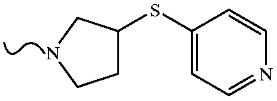 |
| 20 | 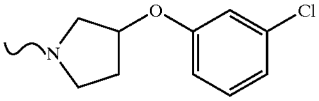 |
| 21 | 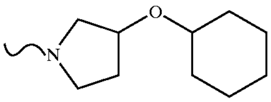 |
TABLE 165
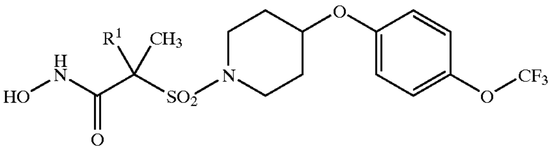
| | |
|---|---|
| 1 | $-CH_3$ |
| 2 | $-CH_2CH_3$ |
| 3 | $-CH(CH_3)_2$ |
| 4 | 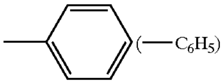 |
| 5 | 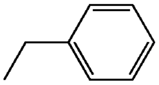 |
| 6 | 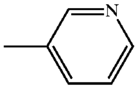 |
| 7 | 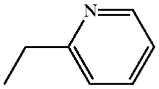 |
| 8 | $-CH_2-N(CH_3)_2$ |
| 9 | $-CH_2-N(CH_3)CH_2C_6H_5$ |
| 10 | 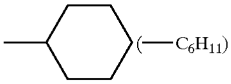 |
| 11 | 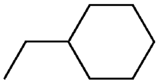 |
| 12 | 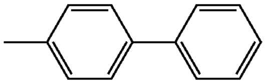 |
| 13 | 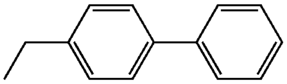 |
| 14 | $-CH_2CH{=}CHCH_3$ |
| 15 | 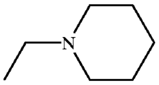 |
| 16 | 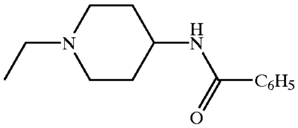 |
| 17 | 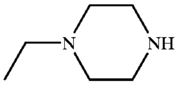 |

TABLE 165-continued
| | |
|---|---|
| 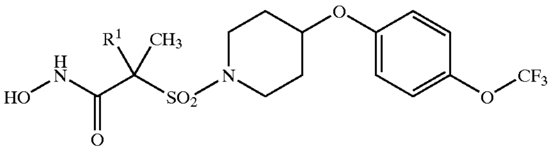 | |
| | 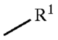 |
| 18 | 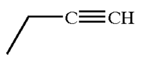 |
| 19 | 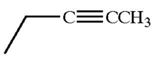 |
| 20 | 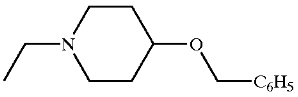 |
| 21 | 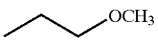 |
| 22 | 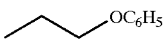 |
| 23 | 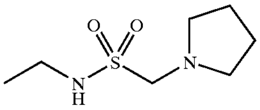 |
| 24 | 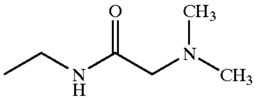 |
| 25 | 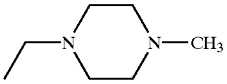 |
| 26 | 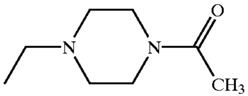 |
| 27 | 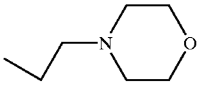 |
| 28 | 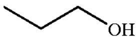 |
| 29 | 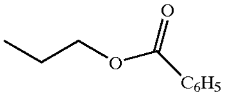 |
| 30 | 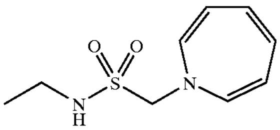 |
| 30 | 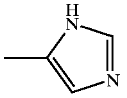 |
TABLE 165-continued
| | |
|---|---|
| 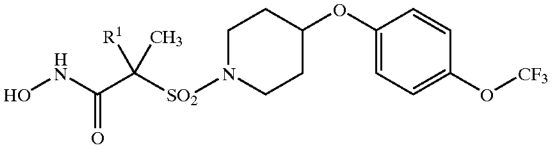 | |
| | 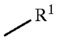 |
| 31 | 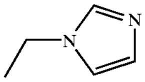 |
| 32 | 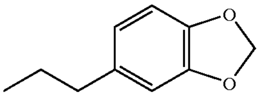 |
| 33 | 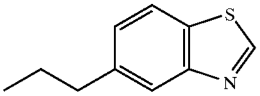 |
| 34 | 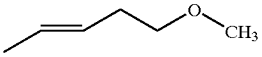 |
| 35 | 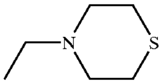 |
| 36 | 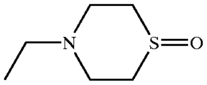 |
| 37 | 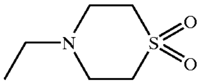 |
| 38 | 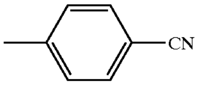 |
| 39 | 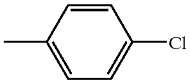 |
| 40 | 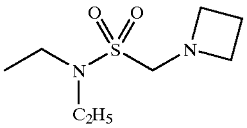 |
| 41 | 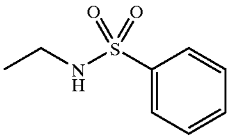 |
| 42 | 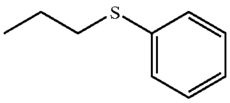 |

TABLE 165-continued
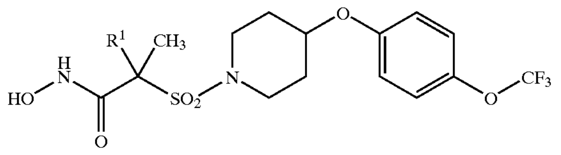
| 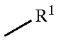 | |
|---|---|
| 43 | 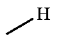 |
TABLE 166
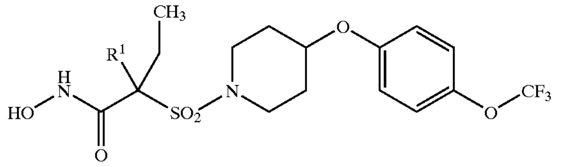
| 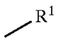 | |
|---|---|
| 1 | $-CH_3$ |
| 2 | $-CH_2CH_3$ |
| 3 | $-CH(CH_3)_2$ |
| 4 | 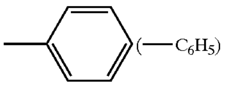 |
| 5 | 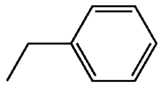 |
| 6 | 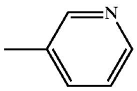 |
| 7 | 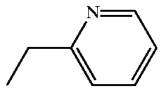 |
| 8 | $-CH_2-N(CH_3)_2$ |
| 9 | $-CH_2-N(CH_3)CH_2C_6H_5$ |
| 10 | 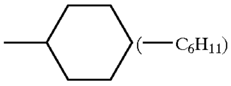 |
| 11 | 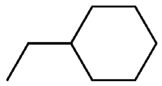 |
| 12 | 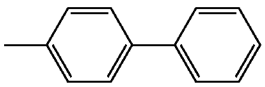 |
| 13 | 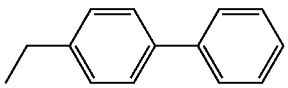 |
| 14 | $-CH_2CH{=}CHCH_3$ |
TABLE 166-continued
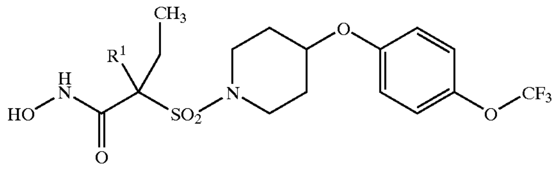
| 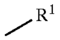 | |
|---|---|
| 15 | 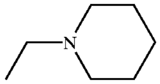 |
| 16 | 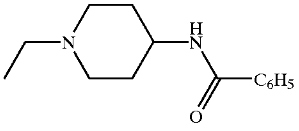 |
| 17 | 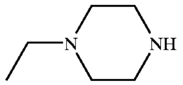 |
| 18 | 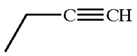 |
| 19 | 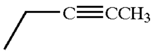 |
| 20 | 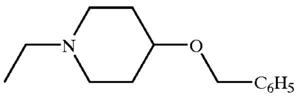 |
| 21 | 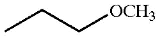 |
| 22 | 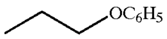 |
| 23 | 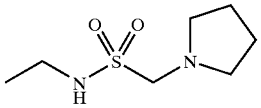 |
| 24 | 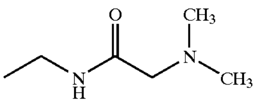 |
| 25 | 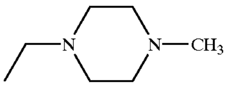 |
| 26 | 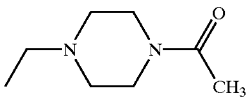 |
| 27 | 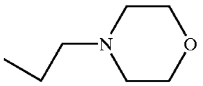 |
| 28 | 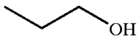 |

TABLE 166-continued
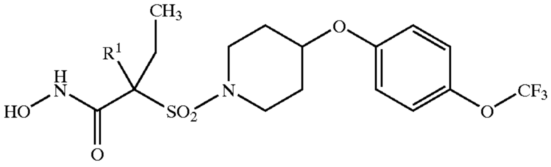
| | 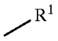 |
|---|---|
| 29 | 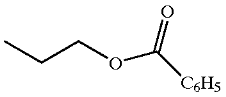 |
| 30 | 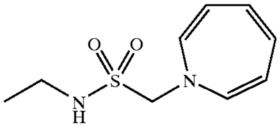 |
| 30 | 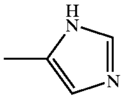 |
| 31 | 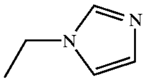 |
| 32 | 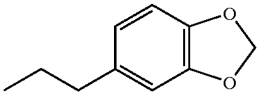 |
| 33 | 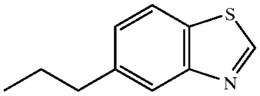 |
| 34 | 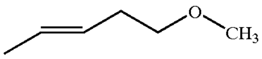 |
| 35 | 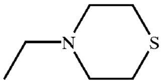 |
| 36 | 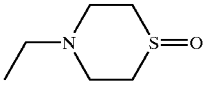 |
| 37 | 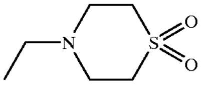 |
| 38 | 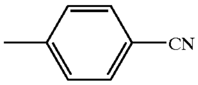 |
| 39 | 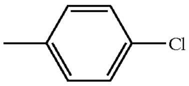 |
TABLE 166-continued
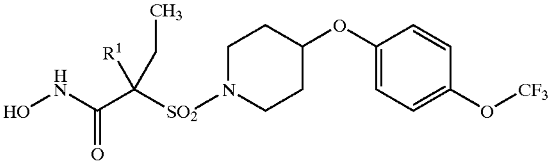
| | 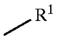 |
|---|---|
| 40 | 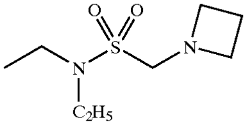 |
| 41 | 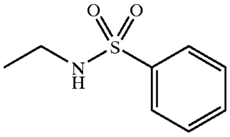 |
| 42 | 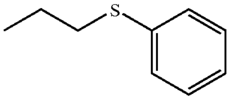 |
| 43 | 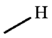 |
TABLE 167
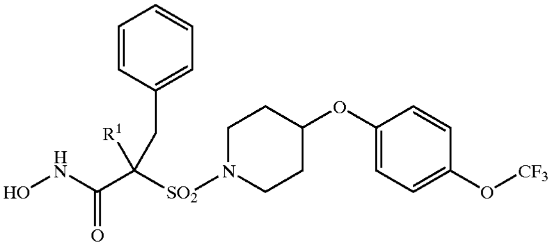
| | 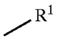 |
|---|---|
| 1 | —$CH_3$ |
| 2 | —$CH_2CH_3$ |
| 3 | —$CH(CH_3)_2$ |
| 4 | 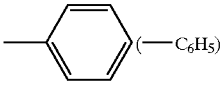 |
| 5 | 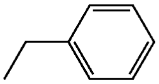 |
| 6 | 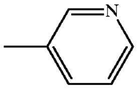 |
| 7 | 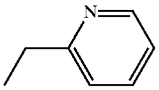 |

TABLE 167-continued
| | 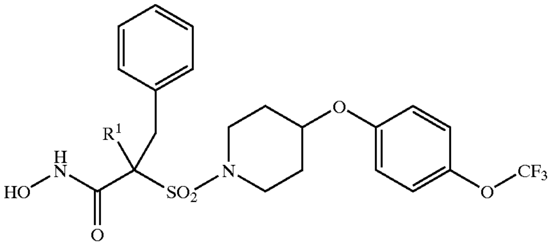 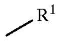 |
|---|---|
| 8 | $—CH_2—N(CH_3)_2$ |
| 9 | $—CH_2—N(CH_3)CH_2C_6H_5$ |
| 10 | 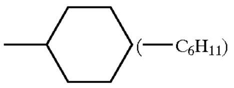 |
| 11 | 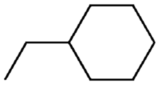 |
| 12 | 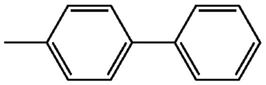 |
| 13 | 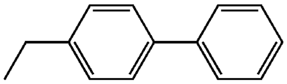 |
| 14 | $—CH_2CH{=}CHCH_3$ |
| 15 | 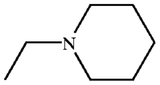 |
| 16 | 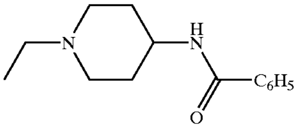 |
| 17 | 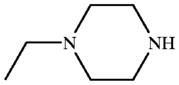 |
| 18 | 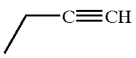 |
| 19 | 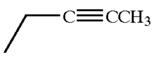 |
| 20 | 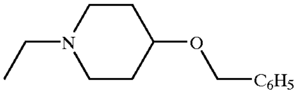 |
| 21 | 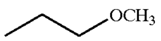 |
| 22 | 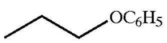 |
TABLE 167-continued
| | 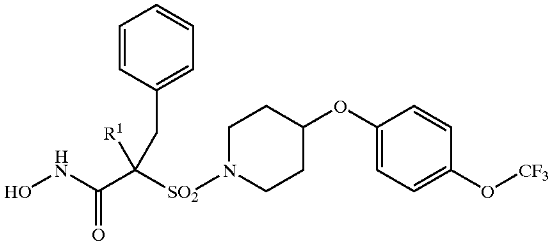 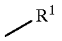 |
|---|---|
| 23 | 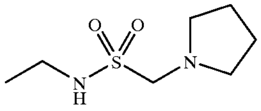 |
| 24 | 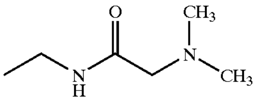 |
| 25 | 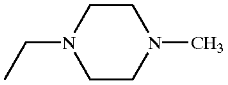 |
| 26 | 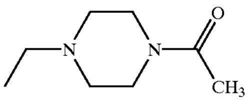 |
| 27 | 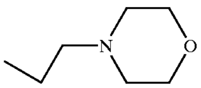 |
| 28 | 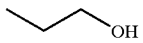 |
| 29 | 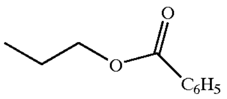 |
| 30 | 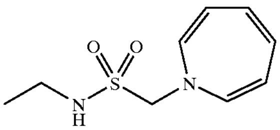 |
| 30 | 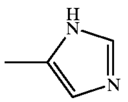 |
| 31 | 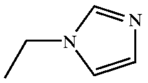 |
| 32 | 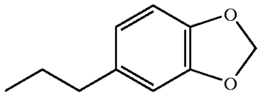 |

TABLE 167-continued
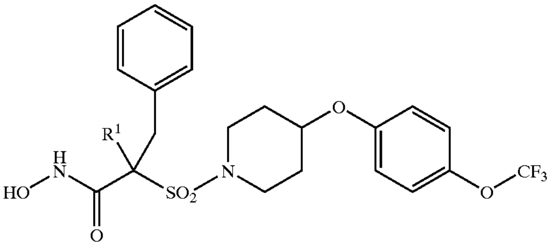
| | |
|---|---|
| 33 | 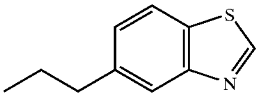 |
| 34 | 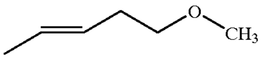 |
| 35 | 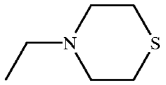 |
| 36 | 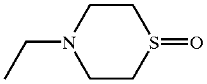 |
| 37 | 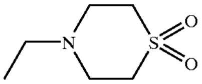 |
| 38 | 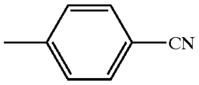 |
| 39 | 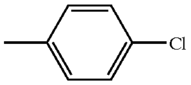 |
| 40 | 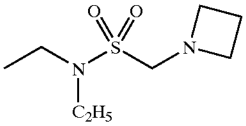 |
| 41 | 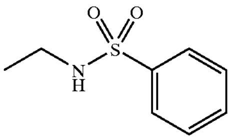 |
| 42 | 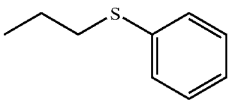 |
| 43 | 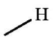 |
TABLE 168
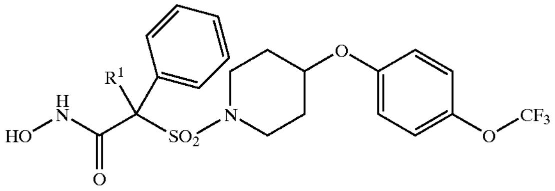
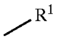
| | |
|---|---|
| 1 | $—CH_3$ |
| 2 | $—CH_2CH_3$ |
| 3 | $—CH(CH_3)_2$ |
| 4 | 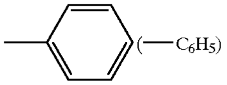 |
| 5 | 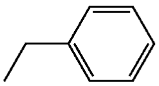 |
| 6 | 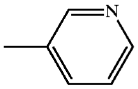 |
| 7 | 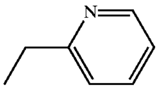 |
| 8 | $—CH_2—N(CH_3)_2$ |
| 9 | $—CH_2—N(CH_3)CH_2C_6H_5$ |
| 10 | 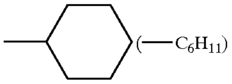 |
| 11 | 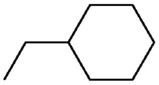 |
| 12 | 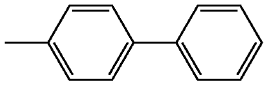 |
| 13 | 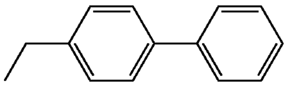 |
| 14 | $—CH_2CH{=}CHCH_3$ |
| 15 | 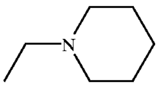 |
| 16 | 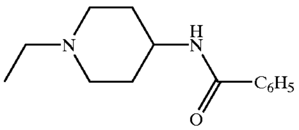 |
| 17 | 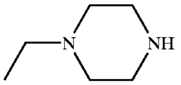 |

TABLE 168-continued
| | 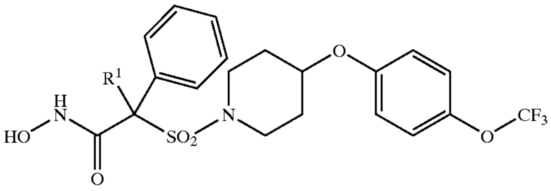 |
|---|---|
| | 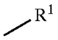 |
| 18 | 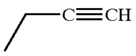 |
| 19 | 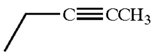 |
| 20 | 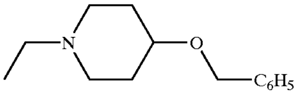 |
| 21 | 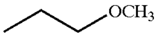 |
| 22 | 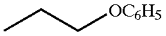 |
| 23 | 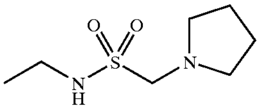 |
| 24 | 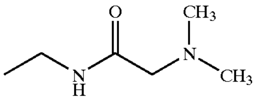 |
| 25 | 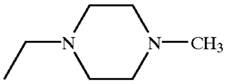 |
| 26 | 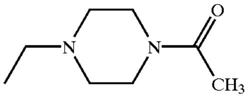 |
| 27 | 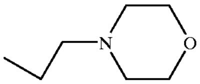 |
| 28 | 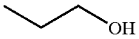 |
| 29 | 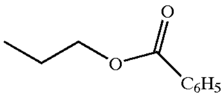 |
| 30 | 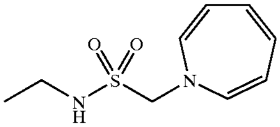 |
TABLE 168-continued
| | 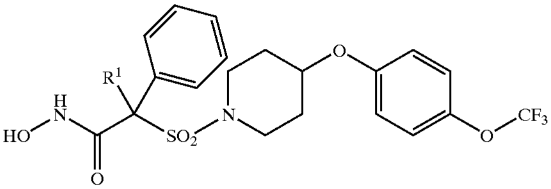 |
|---|---|
| | 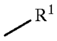 |
| 30 | 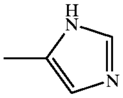 |
| 31 | 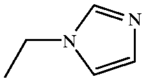 |
| 32 | 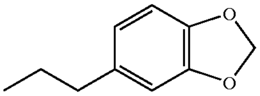 |
| 33 | 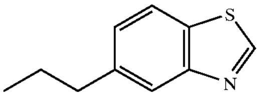 |
| 34 | 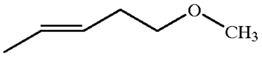 |
| 35 | 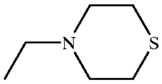 |
| 36 | 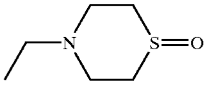 |
| 37 | 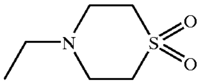 |
| 38 | 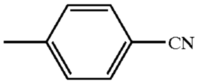 |
| 39 | 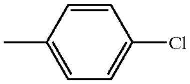 |
| 40 | 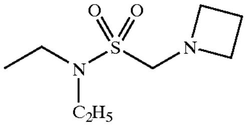 |
| 41 | 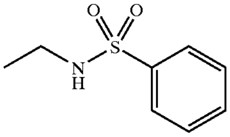 |

TABLE 168-continued
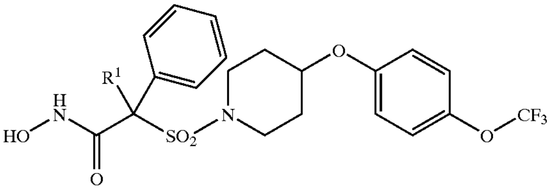
| | 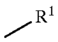 |
|---|---|
| 42 | 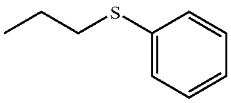 |
| 43 | 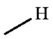 |
TABLE 169
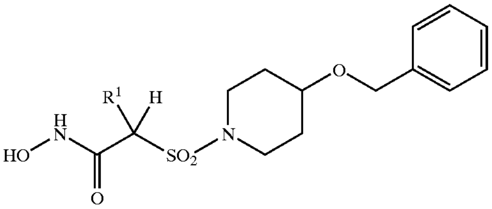
| | 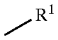 |
|---|---|
| 1 | $—CH_3$ |
| 2 | $—CH_2CH_3$ |
| 3 | $—CH(CH_3)_2$ |
| 4 | 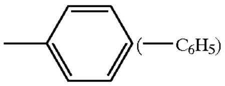 |
| 5 | 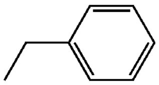 |
| 6 | 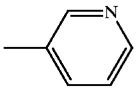 |
| 7 | 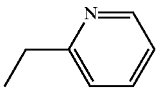 |
| 8 | $—CH_2—N(CH_3)_2$ |
| 9 | $—CH_2—N(CH_3)CH_2C_6H_5$ |
| 10 | 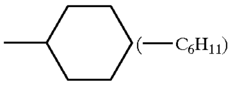 |
| 11 | 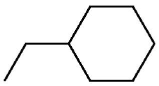 |
TABLE 169-continued
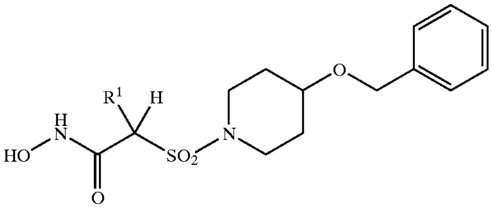
| | 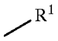 |
|---|---|
| 12 | 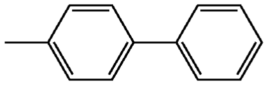 |
| 13 | 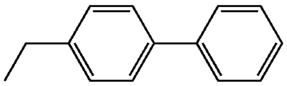 |
| 14 | $—CH_2CH{=}CHCH_3$ |
| 15 | 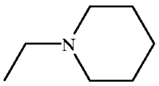 |
| 16 | 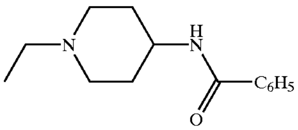 |
| 17 | 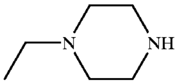 |
| 18 | 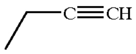 |
| 19 | 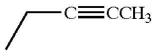 |
| 20 | 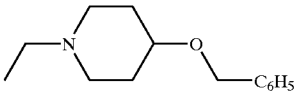 |
| 21 | 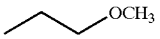 |
| 22 | 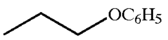 |
| 23 | 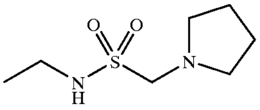 |
| 24 | 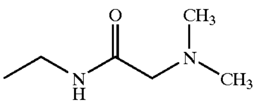 |
| 25 | 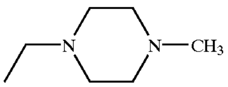 |

TABLE 169-continued
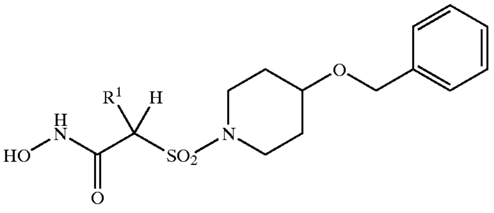
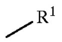
| | |
|---|---|
| 26 | 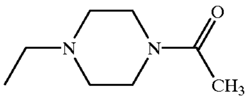 |
| 27 | 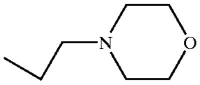 |
| 28 | 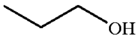 |
| 29 | 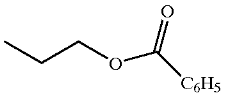 |
| 30 | 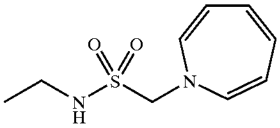 |
| 30 | 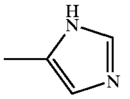 |
| 31 | 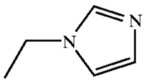 |
| 32 | 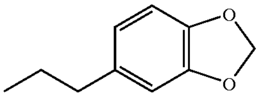 |
| 33 | 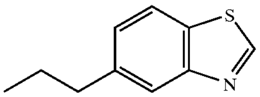 |
| 34 | 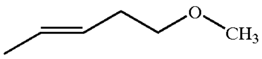 |
| 35 | 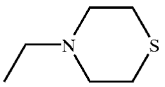 |
| 36 | 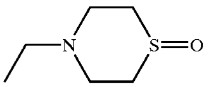 |
TABLE 169-continued
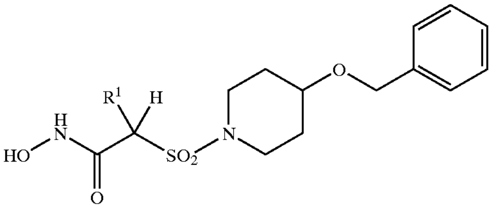
| | |
|---|---|
| 37 | 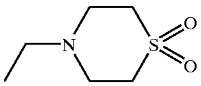 |
| 38 | 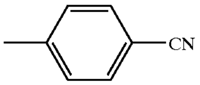 |
| 39 | 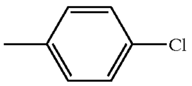 |
| 40 | 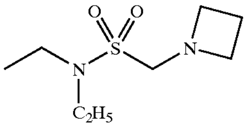 |
| 41 | 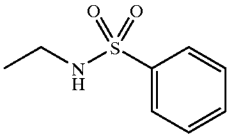 |
| 42 | 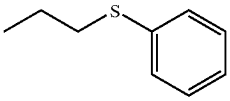 |
| 43 | 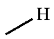 |
TABLE 170
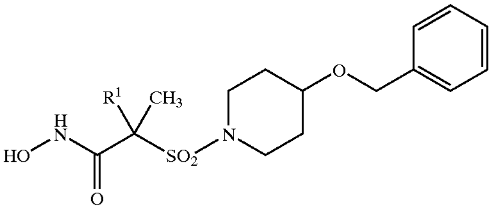
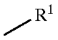
| | |
|---|---|
| 1 | $-CH_3$ |
| 2 | $-CH_2CH_3$ |
| 3 | $-CH(CH_3)_2$ |
| 4 | 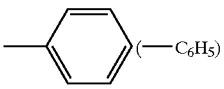 |

TABLE 170-continued
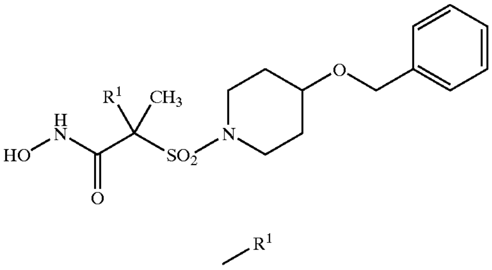
| | |
|---|---|
| 5 | 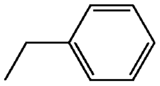 |
| 6 | 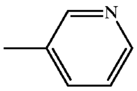 |
| 7 | 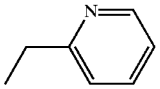 |
| 8 | $-CH_2-N(CH_3)_2$ |
| 9 | $-CH_2-N(CH_3)CH_2C_6H_5$ |
| 10 | 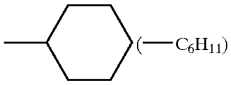 |
| 11 | 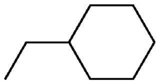 |
| 12 | 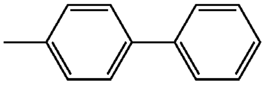 |
| 13 | 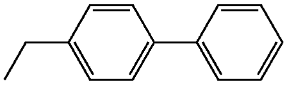 |
| 14 | $-CH_2CH{=}CHCH_3$ |
| 15 | 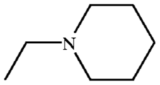 |
| 16 | 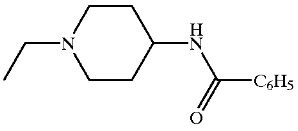 |
| 17 | 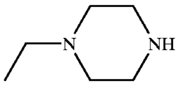 |
| 18 | 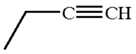 |
| 19 | 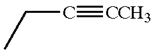 |
TABLE 170-continued
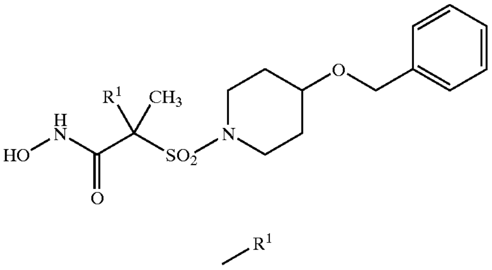
| | |
|---|---|
| 20 | 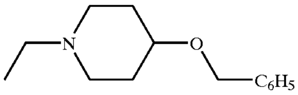 |
| 21 | 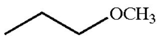 |
| 22 | 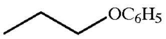 |
| 23 | 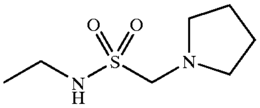 |
| 24 | 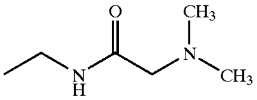 |
| 25 | 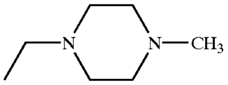 |
| 26 | 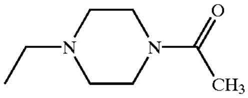 |
| 27 | 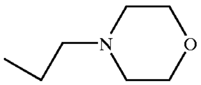 |
| 28 | 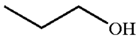 |
| 29 | 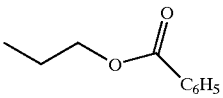 |
| 30 | 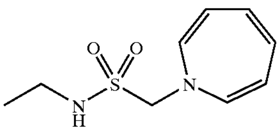 |
| 30 | 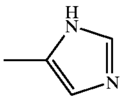 |
| 31 | 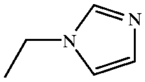 |

TABLE 170-continued
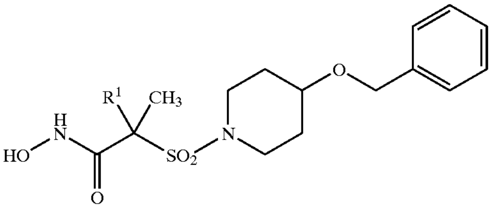
| | 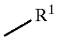 |
|---|---|
| 32 | 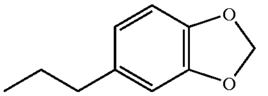 |
| 33 | 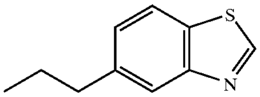 |
| 34 | 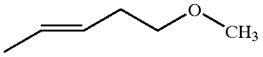 |
| 35 | 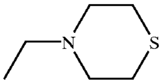 |
| 36 | 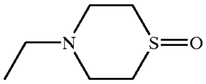 |
| 37 | 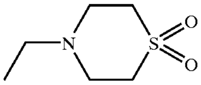 |
| 38 | 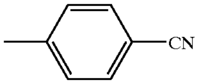 |
| 39 | 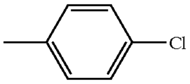 |
| 40 | 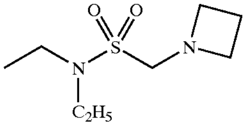 |
| 41 | 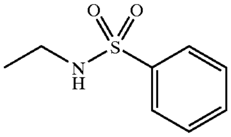 |
| 42 | 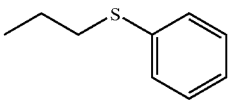 |
| 43 | 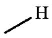 |
TABLE 171
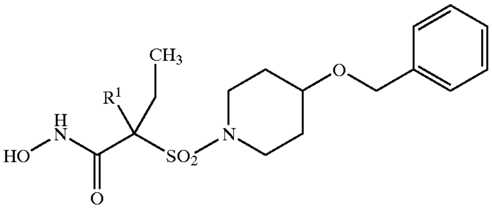
| | 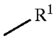 |
|---|---|
| 1 | $—CH_3$ |
| 2 | $—CH_2CH_3$ |
| 3 | $—CH(CH_3)_2$ |
| 4 | 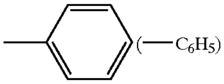 |
| 5 | 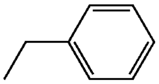 |
| 6 | 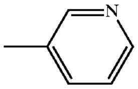 |
| 7 | 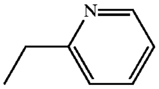 |
| 8 | $—CH_2—N(CH_3)_2$ |
| 9 | $—CH_2—N(CH_3)CH_2C_6H_5$ |
| 10 | 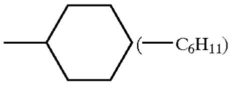 |
| 11 | 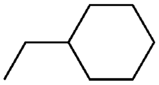 |
| 12 | 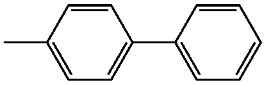 |
| 13 | 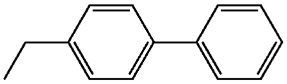 |
| 14 | $—CH_2CH{=}CHCH_3$ |
| 15 | 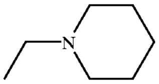 |
| 16 | 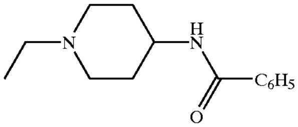 |

TABLE 171-continued
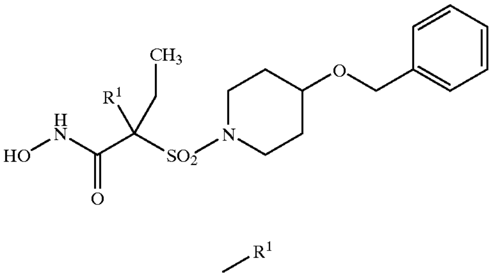
| | |
|---|---|
| 17 | 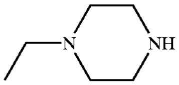 |
| 18 | 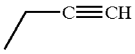 |
| 19 | 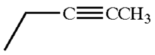 |
| 20 | 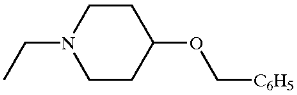 |
| 21 | 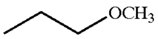 |
| 22 | 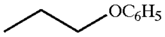 |
| 23 | 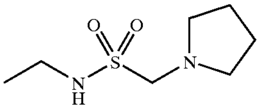 |
| 24 | 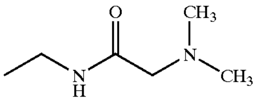 |
| 25 | 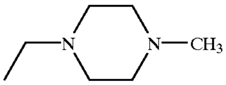 |
| 26 | 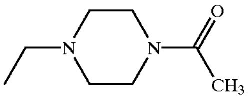 |
| 27 | 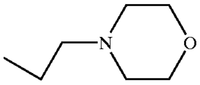 |
| 28 | 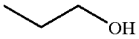 |
| 29 | 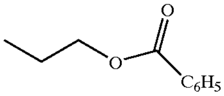 |
TABLE 171-continued
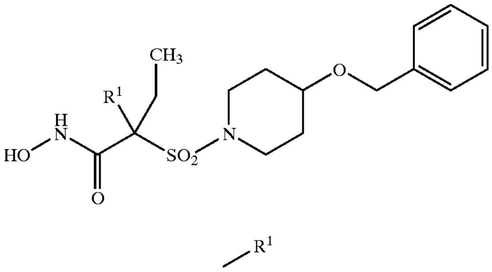
| | |
|---|---|
| 30 | 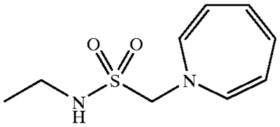 |
| 30 | 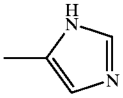 |
| 31 | 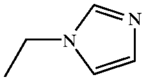 |
| 32 | 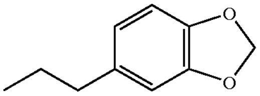 |
| 33 | 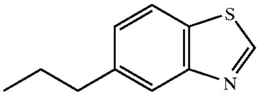 |
| 34 | 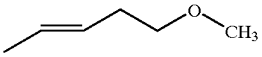 |
| 35 | 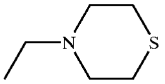 |
| 36 | 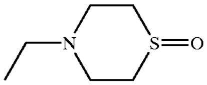 |
| 37 | 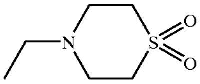 |
| 38 | 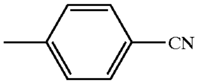 |
| 39 | 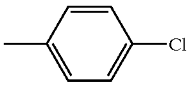 |
| 40 | 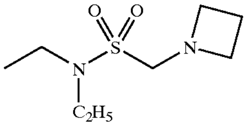 |

TABLE 171-continued
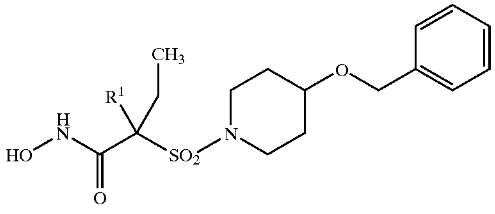
| | 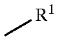 |
|---|---|
| 41 | 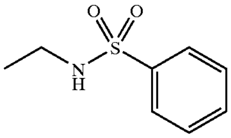 |
| 42 | 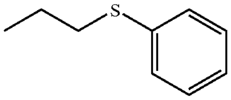 |
| 43 | 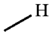 |
TABLE 172
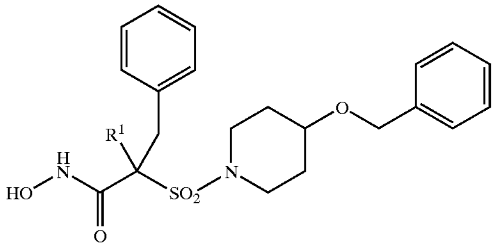
| | 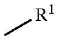 |
|---|---|
| 1 | —$CH_3$ |
| 2 | —$CH_2CH_3$ |
| 3 | —$CH(CH_3)_2$ |
| 4 | 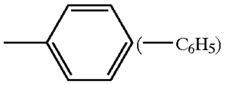 |
| 5 | 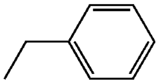 |
| 6 | 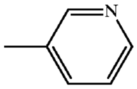 |
| 7 | 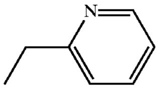 |
| 8 | —$CH_2$—$N(CH_3)_2$ |
| 9 | —$CH_2$—$N(CH_3)CH_2C_6H_5$ |
TABLE 172-continued
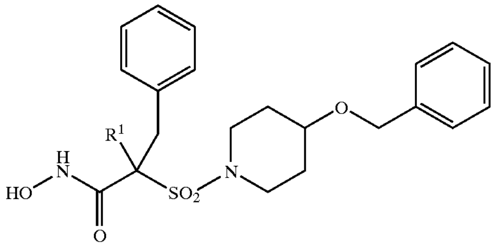
| | 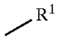 |
|---|---|
| 10 | 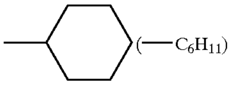 |
| 11 | 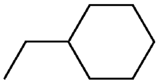 |
| 12 | 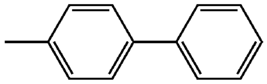 |
| 13 | 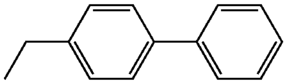 |
| 14 | —$CH_2CH{=}CHCH_3$ |
| 15 | 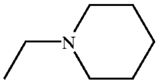 |
| 16 | 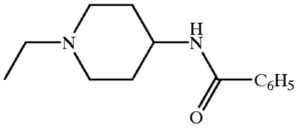 |
| 17 | 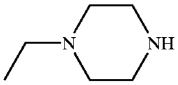 |
| 18 | 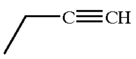 |
| 19 | 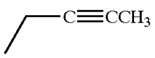 |
| 20 | 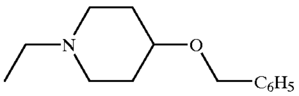 |
| 21 | 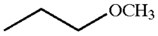 |
| 22 | 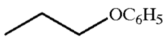 |
| 23 | 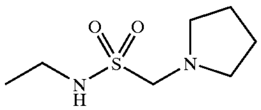 |

TABLE 172-continued
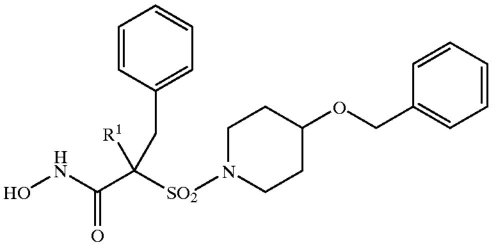
| | 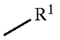 |
|---|---|
| 24 | 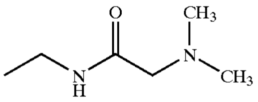 |
| 25 | 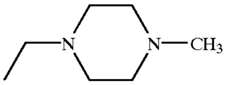 |
| 26 | 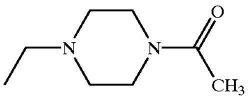 |
| 27 | 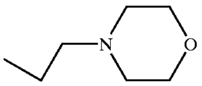 |
| 28 | 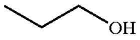 |
| 29 | 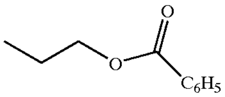 |
| 30 | 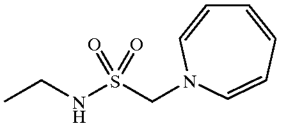 |
| 30 | 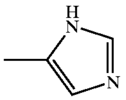 |
| 31 | 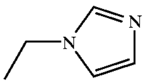 |
| 32 | 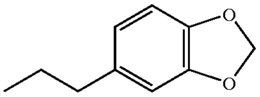 |
| 33 | 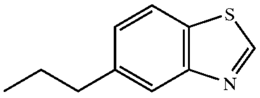 |
| 34 | 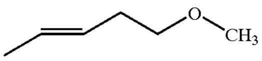 |
TABLE 172-continued
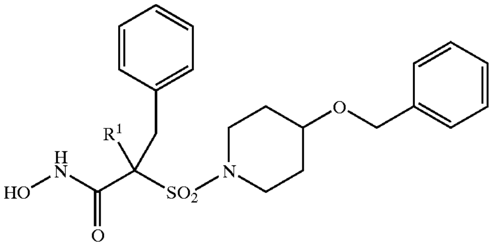
| | 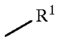 |
|---|---|
| 35 | 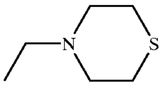 |
| 36 | 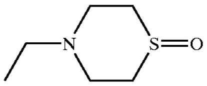 |
| 37 | 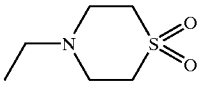 |
| 38 | 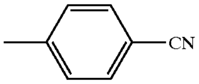 |
| 39 | 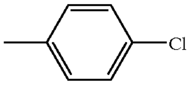 |
| 40 | 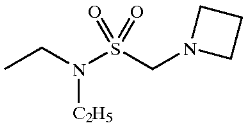 |
| 41 | 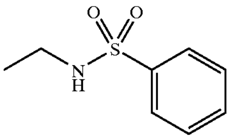 |
| 42 | 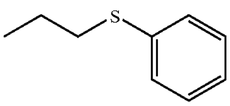 |
| 43 | 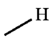 |

TABLE 173
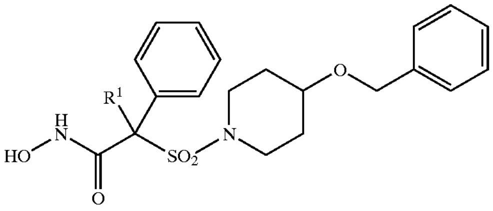
| | 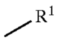 |
|---|---|
| 1 | $—CH_3$ |
| 2 | $—CH_2CH_3$ |
| 3 | $—CH(CH_3)_2$ |
| 4 | 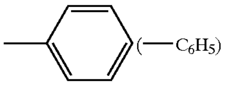 |
| 5 | 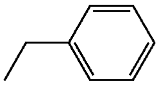 |
| 6 | 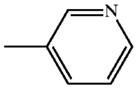 |
| 7 | 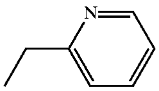 |
| 8 | $—CH_2—N(CH_3)_2$ |
| 9 | $—CH_2—N(CH_3)CH_2C_6H_5$ |
| 10 | 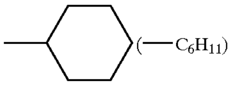 |
| 11 | 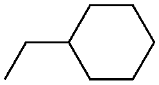 |
| 12 | 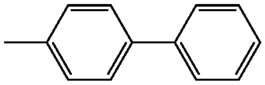 |
| 13 | 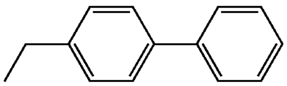 |
| 14 | $—CH_2CH{=}CHCH_3$ |
| 15 | 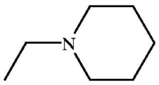 |
| 16 | 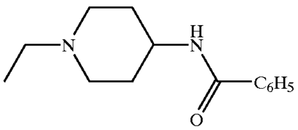 |
TABLE 173-continued
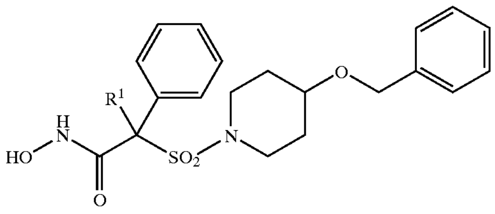
| | 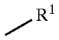 |
|---|---|
| 17 | 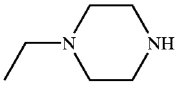 |
| 18 | 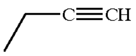 |
| 19 | 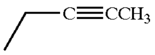 |
| 20 | 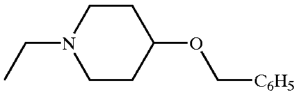 |
| 21 | 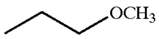 |
| 22 | 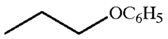 |
| 23 | 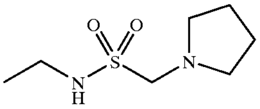 |
| 24 | 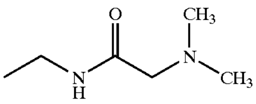 |
| 25 | 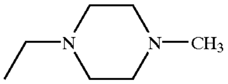 |
| 26 | 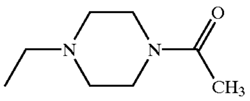 |
| 27 | 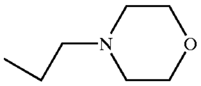 |
| 28 | 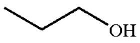 |
| 29 | 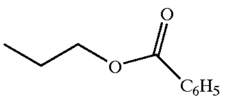 |

TABLE 173-continued
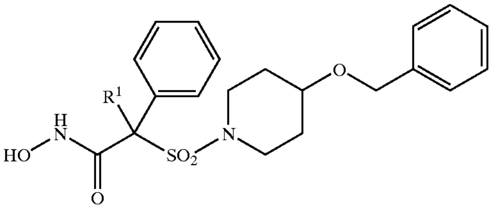
| | 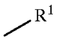 |
|---|---|
| 30 | 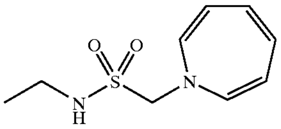 |
| 30 | 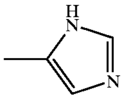 |
| 31 | 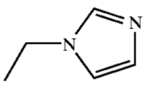 |
| 32 | 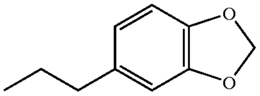 |
| 33 | 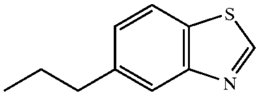 |
| 34 | 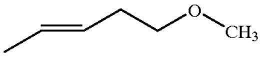 |
| 35 | 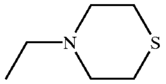 |
| 36 | 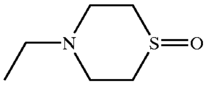 |
| 37 | 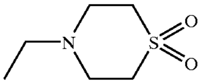 |
| 38 | 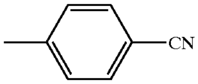 |
| 39 | 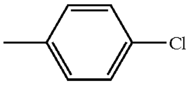 |
| 40 | 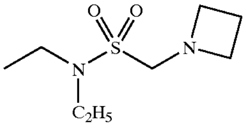 |
TABLE 173-continued
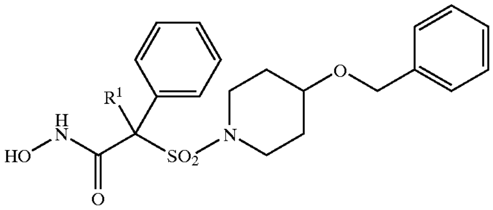
| | 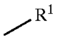 |
|---|---|
| 41 | 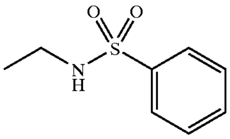 |
| 42 | 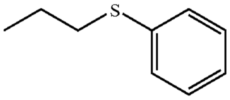 |
| 43 | 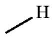 |
TABLE 174
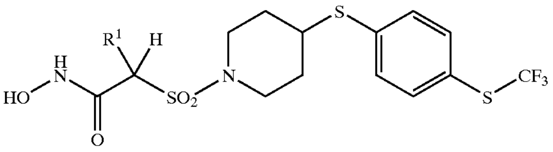
| | 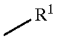 |
|---|---|
| 1 | $—CH_3$ |
| 2 | $—CH_2CH_3$ |
| 3 | $—CH(CH_3)_2$ |
| 4 | 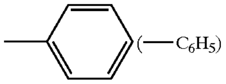 |
| 5 | 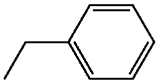 |
| 6 | 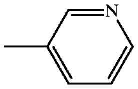 |
| 7 | 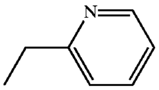 |
| 8 | $—CH_2—N(CH_3)_2$ |
| 9 | $—CH_2—N(CH_3)CH_2C_6H_5$ |
| 10 | 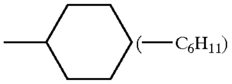 |

TABLE 174-continued
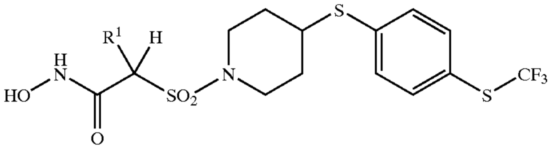
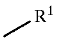
| | |
|---|---|
| 11 | 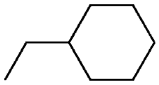 |
| 12 | 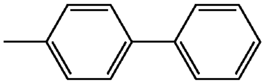 |
| 13 | 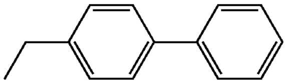 |
| 14 | $—CH_2CH═CHCH_3$ |
| 15 | 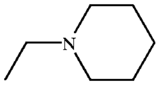 |
| 16 | 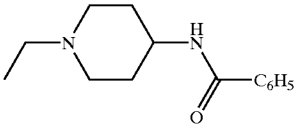 |
| 17 | 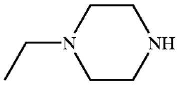 |
| 18 | 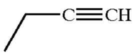 |
| 19 | 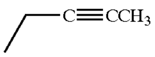 |
| 20 | 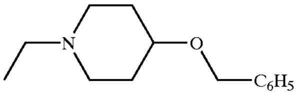 |
| 21 | 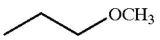 |
| 22 | 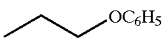 |
| 23 | 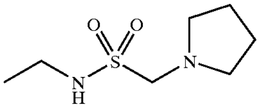 |
| 24 | 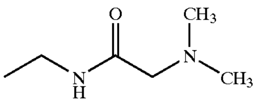 |
TABLE 174-continued
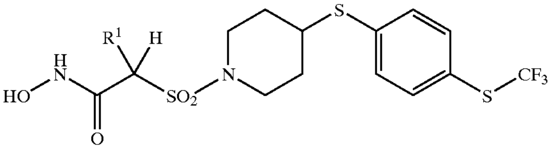
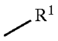
| | |
|---|---|
| 25 | 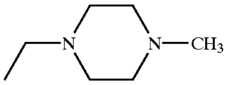 |
| 26 | 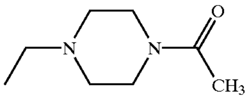 |
| 27 | 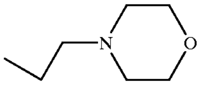 |
| 28 | 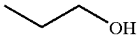 |
| 29 | 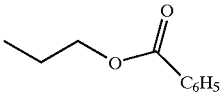 |
| 30 | 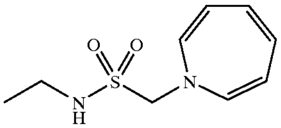 |
| 30 | 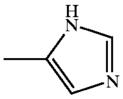 |
| 31 | 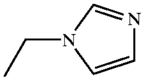 |
| 32 | 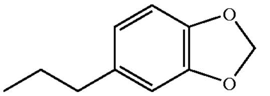 |
| 33 | 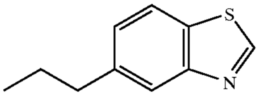 |
| 34 | 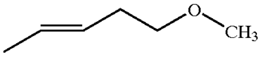 |
| 35 | 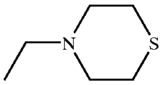 |
| 36 | 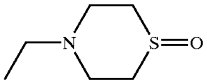 |

TABLE 174-continued
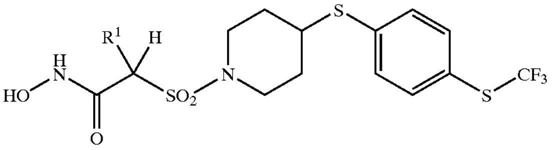
| 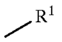 | |
|---|---|
| 37 | 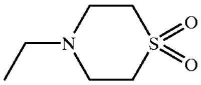 |
| 38 | 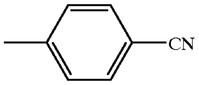 |
| 39 | 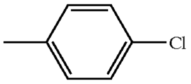 |
| 40 | 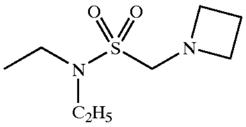 |
| 41 | 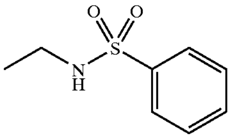 |
| 42 | 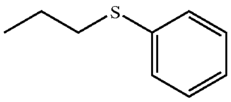 |
| 43 | 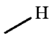 |
TABLE 175
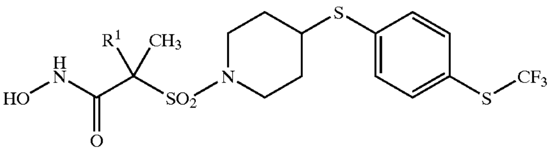
| 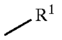 | |
|---|---|
| 1 | $—CH_3$ |
| 2 | $—CH_2CH_3$ |
| 3 | $—CH(CH_3)_2$ |
| 4 | 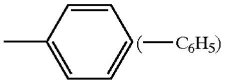 |
| 5 | 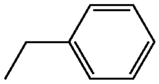 |
TABLE 175-continued
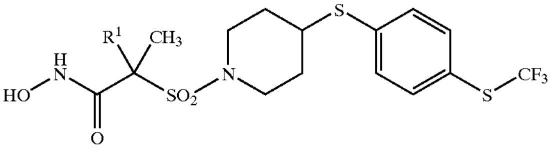
| 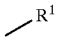 | |
|---|---|
| 6 | 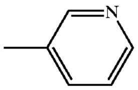 |
| 7 | 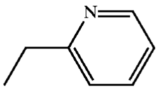 |
| 8 | $—CH_2—N(CH_3)_2$ |
| 9 | $—CH_2—N(CH_3)CH_2C_6H_5$ |
| 10 | 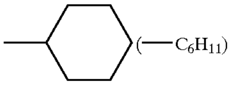 |
| 11 | 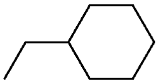 |
| 12 | 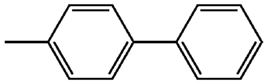 |
| 13 | 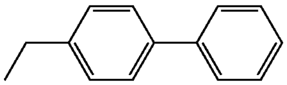 |
| 14 | $—CH_2CH{=}CHCH_3$ |
| 15 | 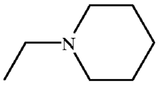 |
| 16 | 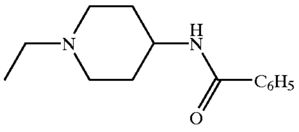 |
| 17 | 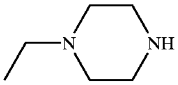 |
| 18 | 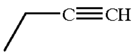 |
| 19 | 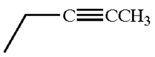 |
| 20 | 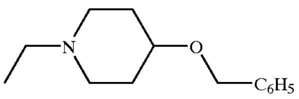 |
| 21 | 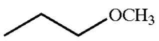 |
| 22 | 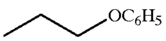 |
| 23 | 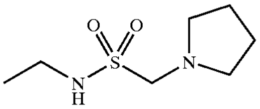 |
| 24 | 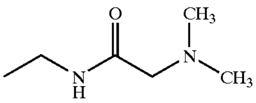 |

TABLE 175-continued
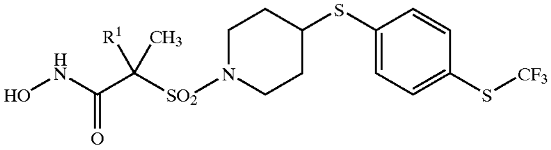
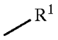
| | |
|---|---|
| 25 | 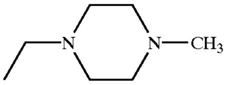 |
| 26 | 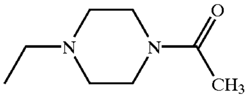 |
| 27 | 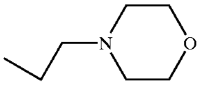 |
| 28 | 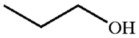 |
| 29 | 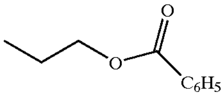 |
| 30 | 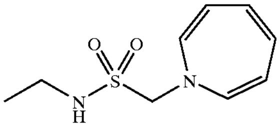 |
| 30 | 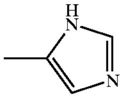 |
| 31 | 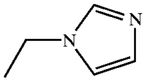 |
| 32 | 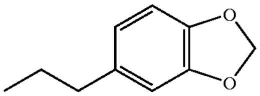 |
| 33 | 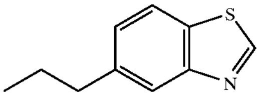 |
| 34 | 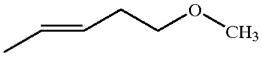 |
| 35 | 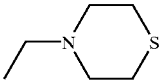 |
| 36 | 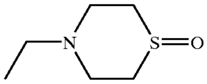 |
| 37 | 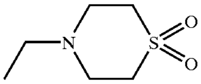 |
| 38 | 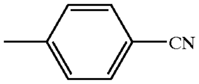 |
| 39 | 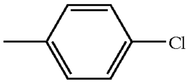 |
TABLE 175-continued
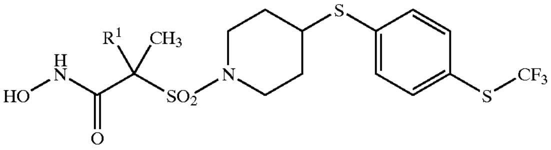
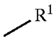
| | |
|---|---|
| 40 | 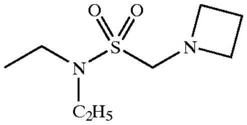 |
| 41 | 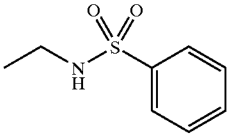 |
| 42 | 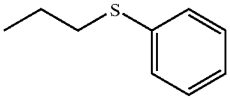 |
| 43 | 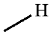 |
TABLE 176
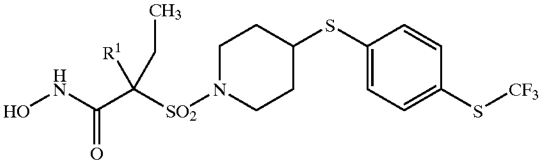
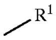
| | |
|---|---|
| 1 | $—CH_3$ |
| 2 | $—CH_2CH_3$ |
| 3 | $—CH(CH_3)_2$ |
| 4 | 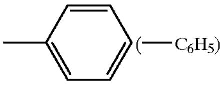 |
| 5 | 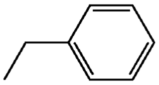 |
| 6 | 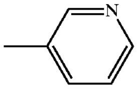 |
| 7 | 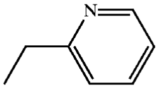 |
| 8 | $—CH_2—N(CH_3)_2$ |
| 9 | $—CH_2—N(CH_3)CH_2C_6H_5$ |
| 10 | 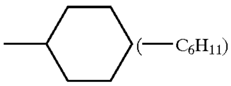 |

TABLE 176-continued
| | |
|---|---|
| 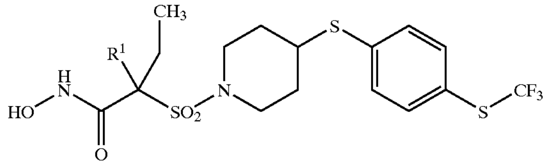 | |
| | 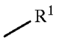 |
| 11 | 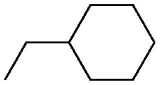 |
| 12 | 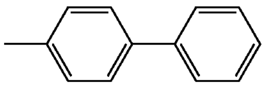 |
| 13 | 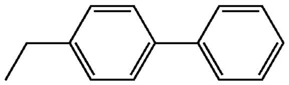 |
| 14 | $-CH_2CH{=}CHCH_3$ |
| 15 | 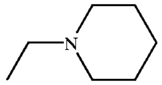 |
| 16 | 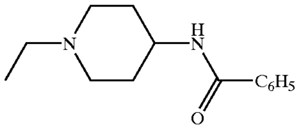 |
| 17 | 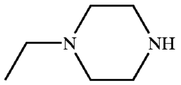 |
| 18 | 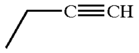 |
| 19 | 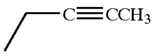 |
| 20 | 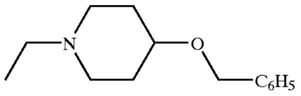 |
| 21 | 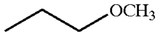 |
| 22 | 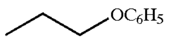 |
| 23 | 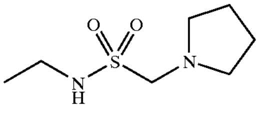 |
| 24 | 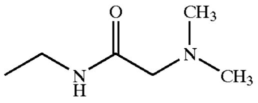 |
TABLE 176-continued
| | |
|---|---|
| 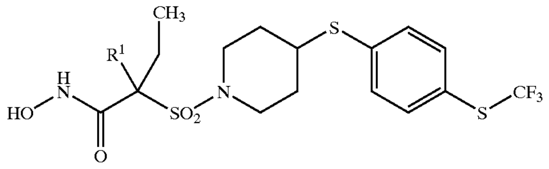 | |
| | 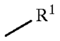 |
| 25 | 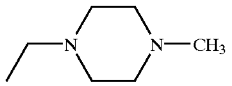 |
| 26 | 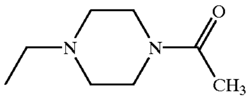 |
| 27 | 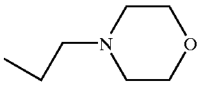 |
| 28 | 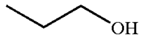 |
| 29 | 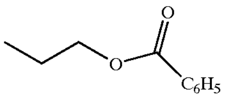 |
| 30 | 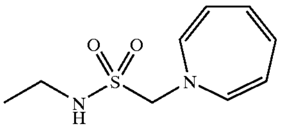 |
| 30 | 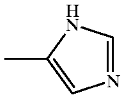 |
| 31 | 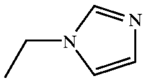 |
| 32 | 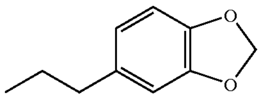 |
| 33 | 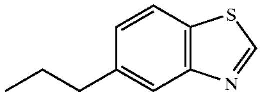 |
| 34 | 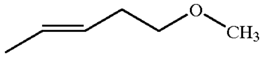 |
| 35 | 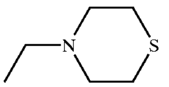 |
| 36 | 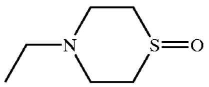 |

TABLE 176-continued
| 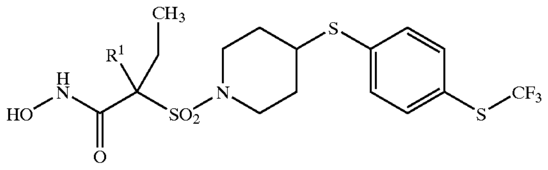 | |
|---|---|
| | 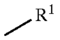 |
| 37 | 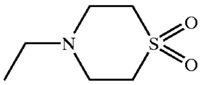 |
| 38 | 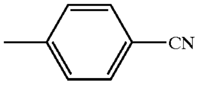 |
| 39 | 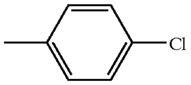 |
| 40 | 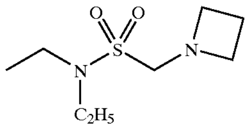 |
| 41 | 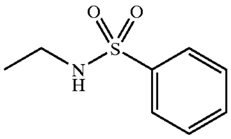 |
| 42 | 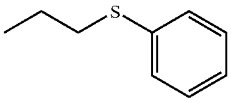 |
| 43 | 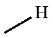 |
TABLE 177
| 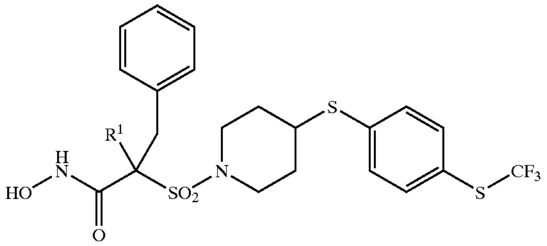 | |
|---|---|
| | 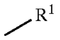 |
| 1 | $—CH_3$ |
| 2 | $—CH_2CH_3$ |
| 3 | $—CH(CH_3)_2$ |
| 4 | 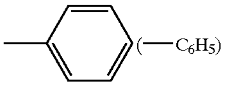 |
TABLE 177-continued
| 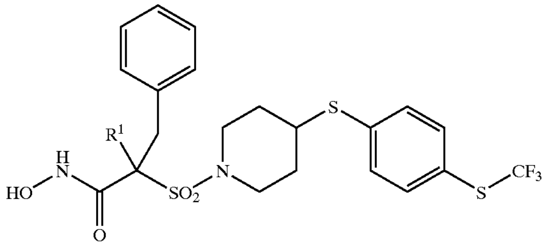 | |
|---|---|
| | 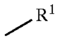 |
| 5 | 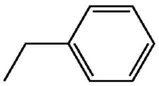 |
| 6 | 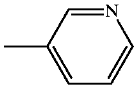 |
| 7 | 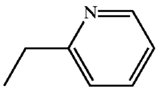 |
| 8 | $—CH_2—N(CH_3)_2$ |
| 9 | $—CH_2—N(CH_3)CH_2C_6H_5$ |
| 10 | 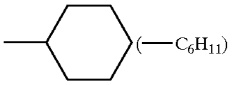 |
| 11 | 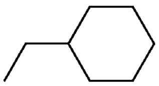 |
| 12 | 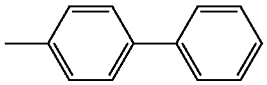 |
| 13 | 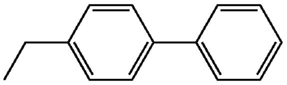 |
| 14 | $—CH_2CH{=}CHCH_3$ |
| 15 | 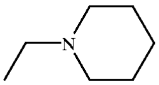 |
| 16 | 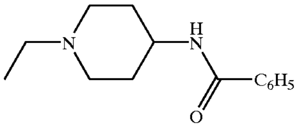 |
| 17 | 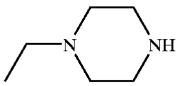 |
| 18 | 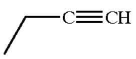 |

TABLE 177-continued
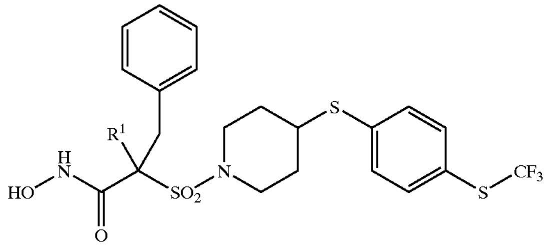
| | 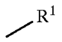 |
|---|---|
| 19 | 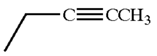 |
| 20 | 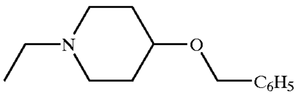 |
| 21 | 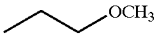 |
| 22 | 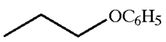 |
| 23 | 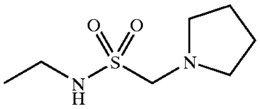 |
| 24 | 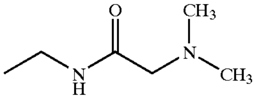 |
| 25 | 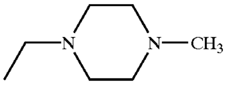 |
| 26 | 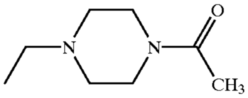 |
| 27 | 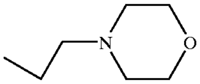 |
| 28 | 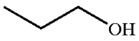 |
| 29 | 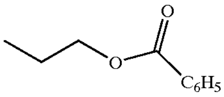 |
| 30 | 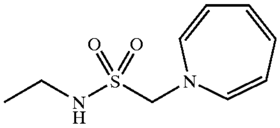 |
| 30 | 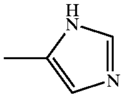 |
TABLE 177-continued
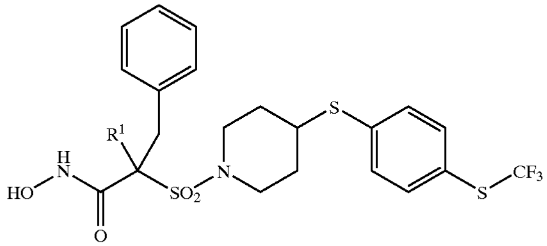
| | 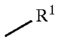 |
|---|---|
| 31 | 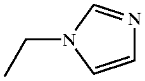 |
| 32 | 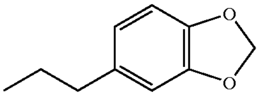 |
| 33 | 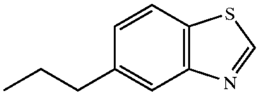 |
| 34 | 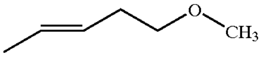 |
| 35 | 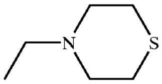 |
| 36 | 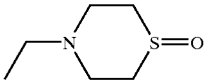 |
| 37 | 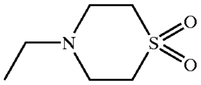 |
| 38 | 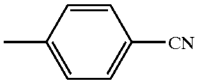 |
| 39 | 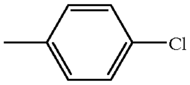 |
| 40 | 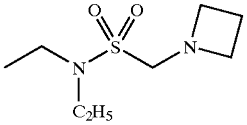 |
| 41 | 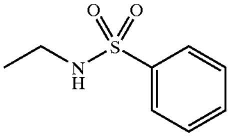 |

TABLE 177-continued
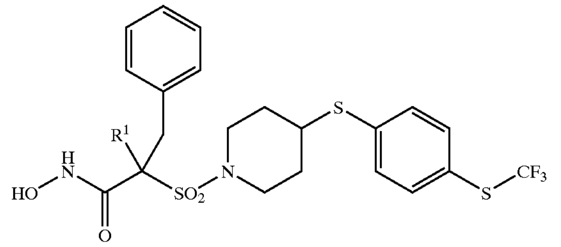
| 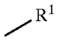 | |
|---|---|
| 42 | 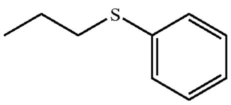 |
| 43 | 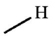 |
TABLE 178
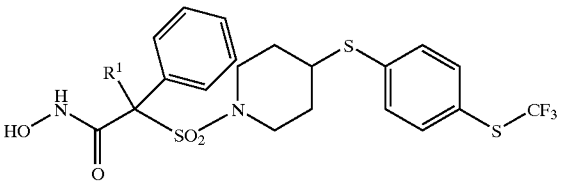
| 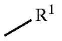 | |
|---|---|
| 1 | $—CH_3$ |
| 2 | $—CH_2CH_3$ |
| 3 | $—CH(CH_3)_2$ |
| 4 | 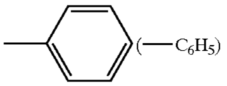 |
| 5 | 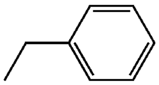 |
| 6 | 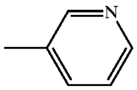 |
| 7 | 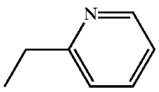 |
| 8 | $—CH_2—N(CH_3)_2$ |
| 9 | $—CH_2—N(CH_3)CH_2C_6H_5$ |
| 10 | 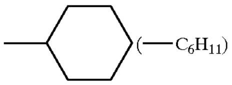 |
| 11 | 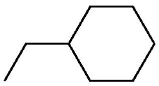 |
TABLE 178-continued
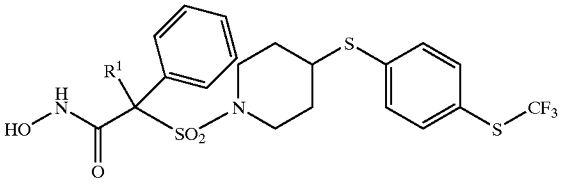
| 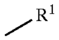 | |
|---|---|
| 12 | 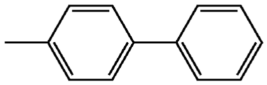 |
| 13 | 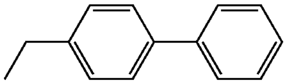 |
| 14 | $—CH_2CH{=}CHCH_3$ |
| 15 | 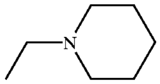 |
| 16 | 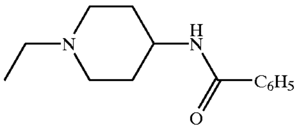 |
| 17 | 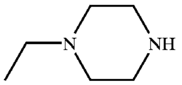 |
| 18 | 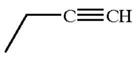 |
| 19 | 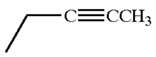 |
| 20 | 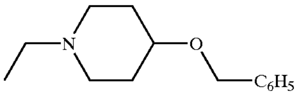 |
| 21 | 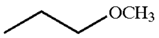 |
| 22 | 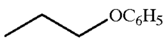 |
| 23 | 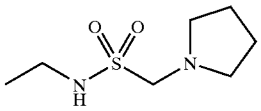 |
| 24 | 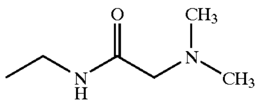 |
| 25 | 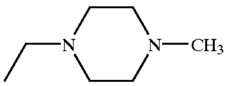 |

TABLE 178-continued
| 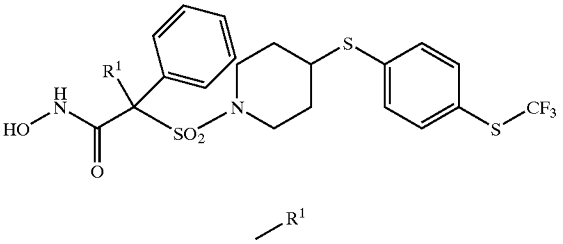 | |
|---|---|
| 26 | 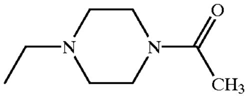 |
| 27 | 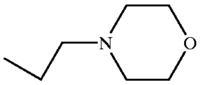 |
| 28 | 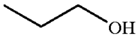 |
| 29 | 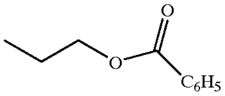 |
| 30 | 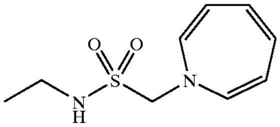 |
| 30 | 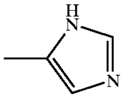 |
| 31 | 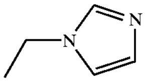 |
| 32 | 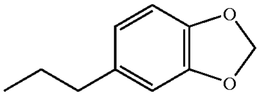 |
| 33 | 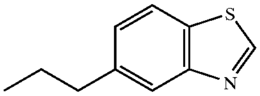 |
| 34 | 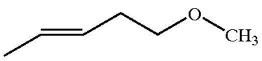 |
| 35 | 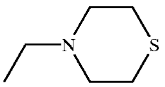 |
| 36 | 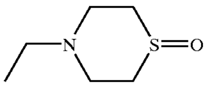 |
| 37 | 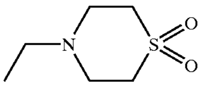 |
TABLE 178-continued
| 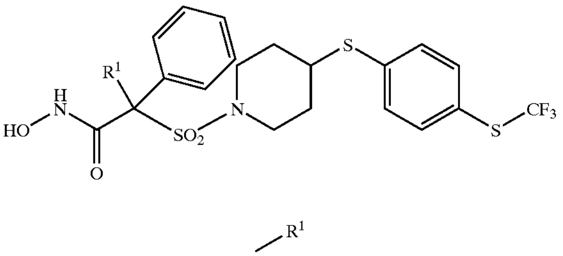 | |
|---|---|
| 38 | 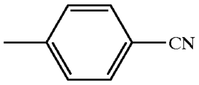 |
| 39 | 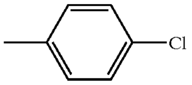 |
| 40 | 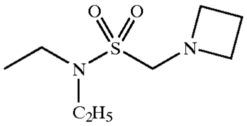 |
| 41 | 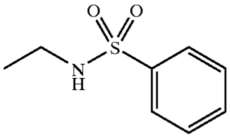 |
| 42 | 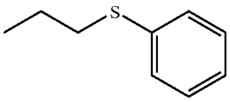 |
| 43 | 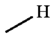 |
TABLE 179
| 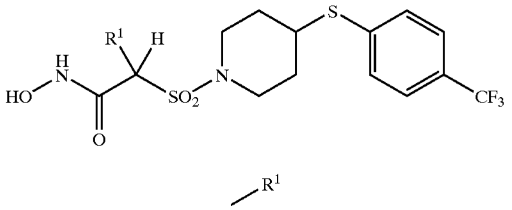 | |
|---|---|
| 1 | $—CH_3$ |
| 2 | $—CH_2CH_3$ |
| 3 | $—CH(CH_3)_2$ |
| 4 | 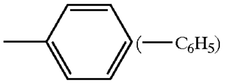 |
| 5 | 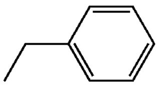 |

TABLE 179-continued
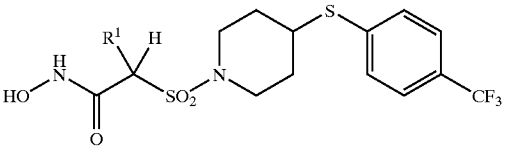
| | 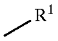 |
|---|---|
| 6 | 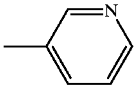 |
| 7 | 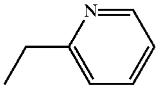 |
| 8 | —$CH_2$—$N(CH_3)_2$ |
| 9 | —$CH_2$—$N(CH_3)CH_2C_6H_5$ |
| 10 | 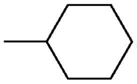 (—$C_6H_{11}$) |
| 11 | 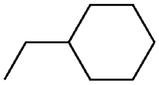 |
| 12 | 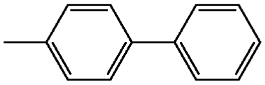 |
| 13 | 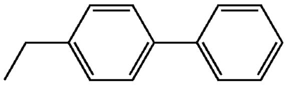 |
| 14 | —$CH_2CH$═$CHCH_3$ |
| 15 | 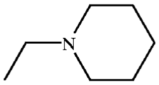 |
| 16 | 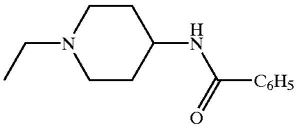 |
| 17 | 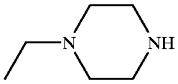 |
| 18 | 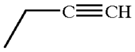 |
| 19 | 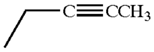 |
| 20 | 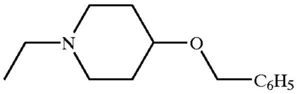 |
| 21 | 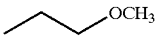 |
TABLE 179-continued
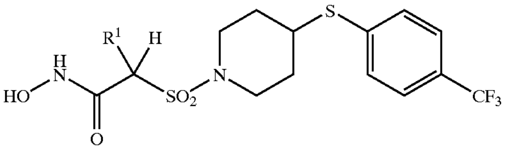
| | 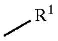 |
|---|---|
| 22 | 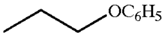 |
| 23 | 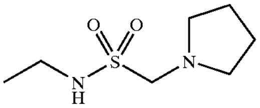 |
| 24 | 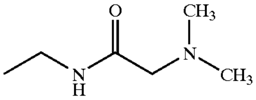 |
| 25 | 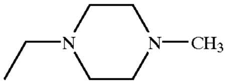 |
| 26 | 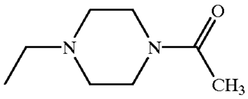 |
| 27 | 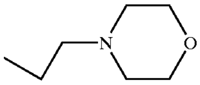 |
| 28 | 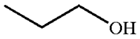 |
| 29 | 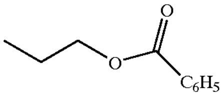 |
| 30 | 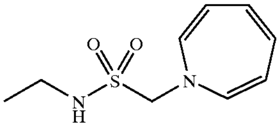 |
| 30 | 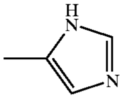 |
| 31 | 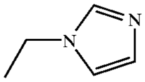 |
| 32 | 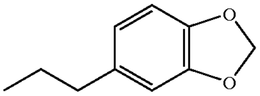 |
| 33 | 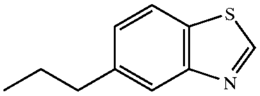 |

TABLE 179-continued
| | |
|---|---|
| 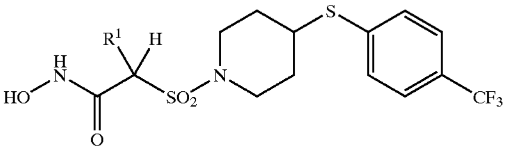 | |
| | 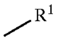 |
| 34 | 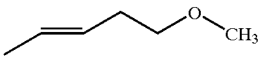 |
| 35 | 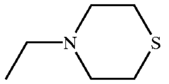 |
| 36 | 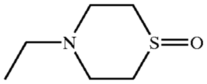 |
| 37 | 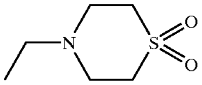 |
| 38 | 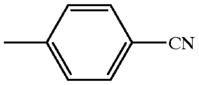 |
| 39 | 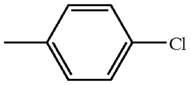 |
| 40 | 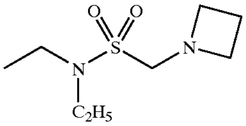 |
| 41 | 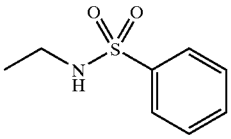 |
| 42 | 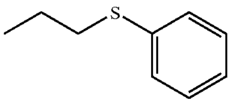 |
| 43 | 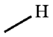 |
TABLE 180
| | |
|---|---|
| 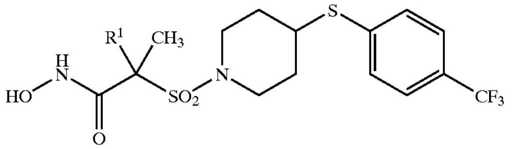 | |
| | 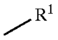 |
| 1 | $—CH_3$ |
| 2 | $—CH_2CH_3$ |
| 3 | $—CH(CH_3)_2$ |
| 4 | 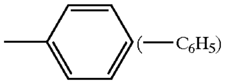 |
| 5 | 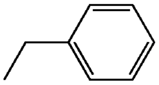 |
| 6 | 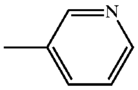 |
| 7 | 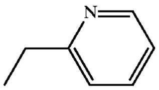 |
| 8 | $—CH_2—N(CH_3)_2$ |
| 9 | $—CH_2—N(CH_3)CH_2C_6H_5$ |
| 10 | 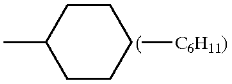 |
| 11 | 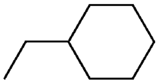 |
| 12 | 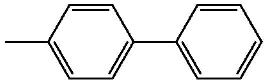 |
| 13 | 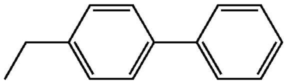 |
| 14 | $—CH_2CH═CHCH_3$ |
| 15 | 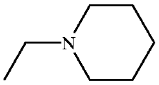 |
| 16 | 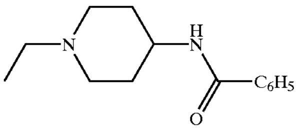 |
| 17 | 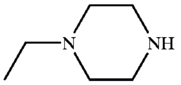 |

TABLE 180-continued
| | |
|---|---|
| 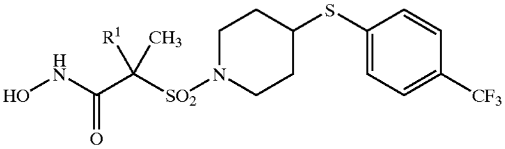 | |
| | 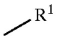 |
| 18 | 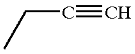 |
| 19 | 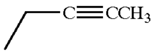 |
| 20 | 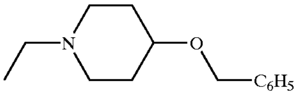 |
| 21 | 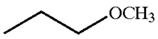 |
| 22 | 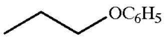 |
| 23 | 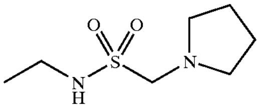 |
| 24 | 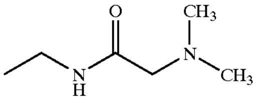 |
| 25 | 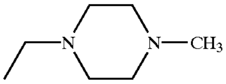 |
| 26 | 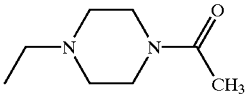 |
| 27 | 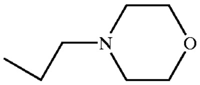 |
| 28 | 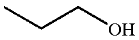 |
| 29 | 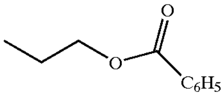 |
| 30 | 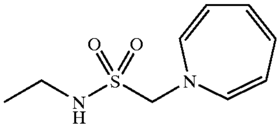 |
| 30 | 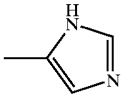 |
TABLE 180-continued
| | |
|---|---|
| 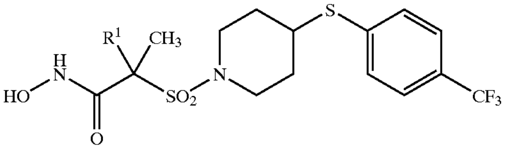 | |
| | 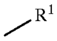 |
| 31 | 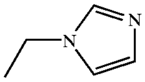 |
| 32 | 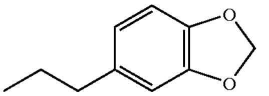 |
| 33 | 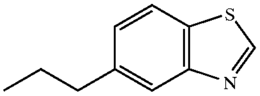 |
| 34 | 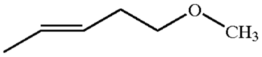 |
| 35 | 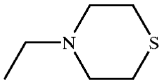 |
| 36 | 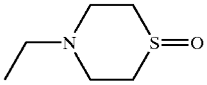 |
| 37 | 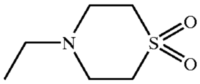 |
| 38 | 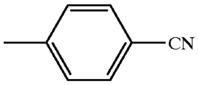 |
| 39 | 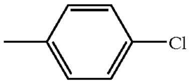 |
| 40 | 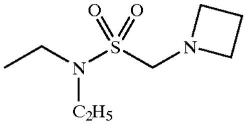 |
| 41 | 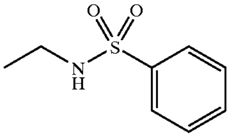 |
| 42 | 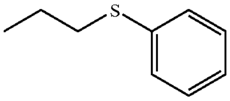 |

TABLE 180-continued
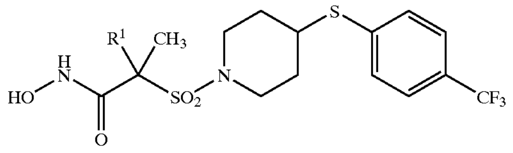
| | 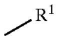 |
|---|---|
| 43 | 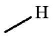 |
TABLE 181
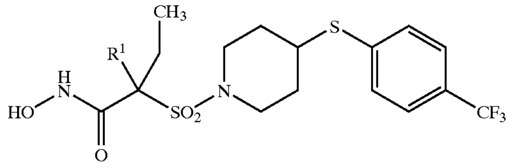
| | 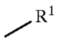 |
|---|---|
| 1 | $—CH_3$ |
| 2 | $—CH_2CH_3$ |
| 3 | $—CH(CH_3)_2$ |
| 4 | 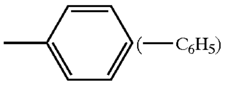 |
| 5 | 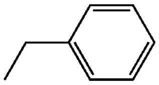 |
| 6 | 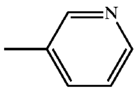 |
| 7 | 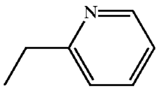 |
| 8 | $—CH_2—N(CH_3)_2$ |
| 9 | $—CH_2—N(CH_3)CH_2C_6H_5$ |
| 10 | 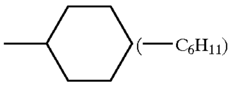 |
| 11 | 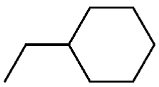 |
| 12 | 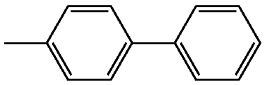 |
| 13 | 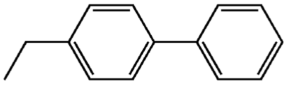 |
| 14 | $—CH_2CH═CHCH_3$ |
TABLE 181-continued
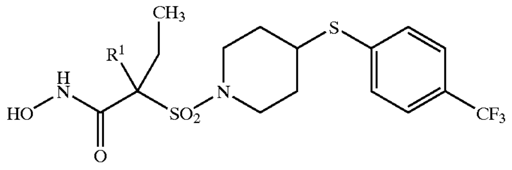
| | 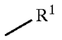 |
|---|---|
| 15 | 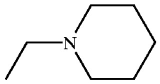 |
| 16 | 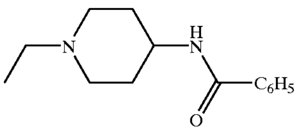 |
| 17 | 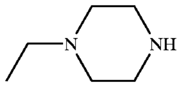 |
| 18 | 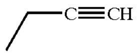 |
| 19 | 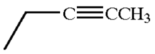 |
| 20 | 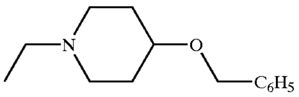 |
| 21 | 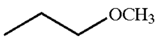 |
| 22 | 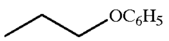 |
| 23 | 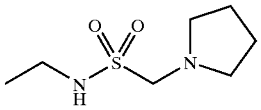 |
| 24 | 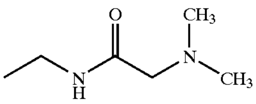 |
| 25 | 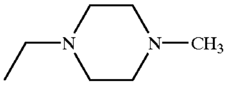 |
| 26 | 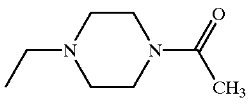 |
| 27 | 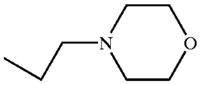 |
| 28 | 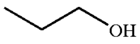 |

TABLE 181-continued
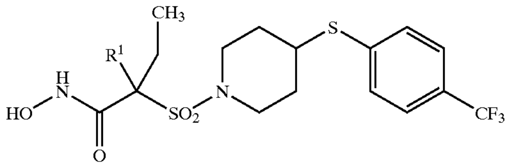
| | 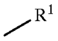 |
|---|---|
| 29 | 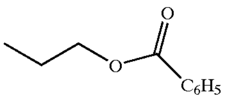 |
| 30 | 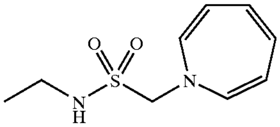 |
| 30 | 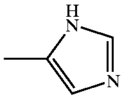 |
| 31 | 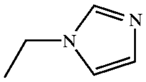 |
| 32 | 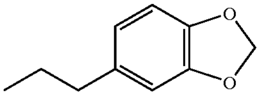 |
| 33 | 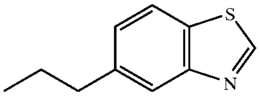 |
| 34 | 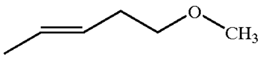 |
| 35 | 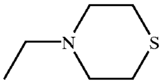 |
| 36 | 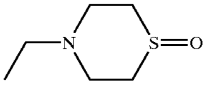 |
| 37 | 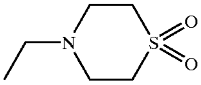 |
| 38 | 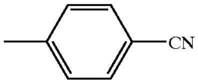 |
| 39 | 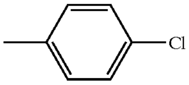 |
TABLE 181-continued
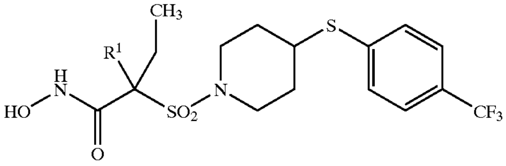
| | 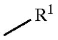 |
|---|---|
| 40 | 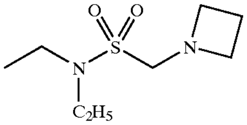 |
| 41 | 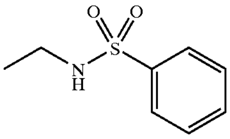 |
| 42 | 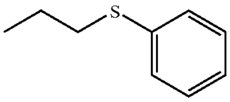 |
| 43 | 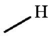 |
TABLE 182
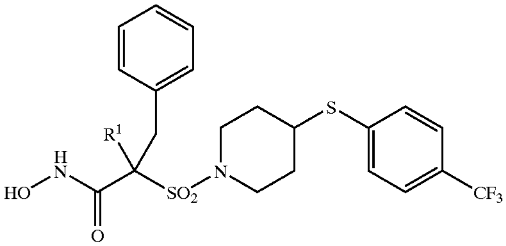
| | 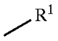 |
|---|---|
| 1 | $—CH_3$ |
| 2 | $—CH_2CH_3$ |
| 3 | $—CH(CH_3)_2$ |
| 4 | 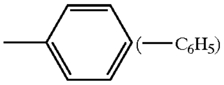 |
| 5 | 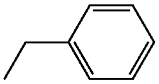 |
| 6 | 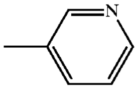 |
| 7 | 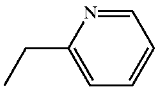 |

TABLE 182-continued
| | 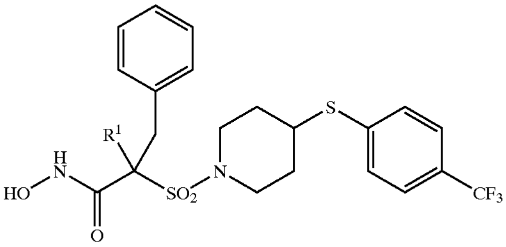 |
|---|---|
| | 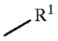 |
| 8 | $—CH_2—N(CH_3)_2$ |
| 9 | $—CH_2—N(CH_3)CH_2C_6H_5$ |
| 10 | 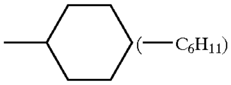 |
| 11 | 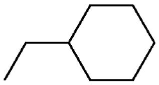 |
| 12 | 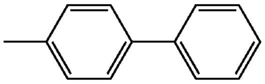 |
| 13 | 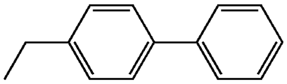 |
| 14 | $—CH_2CH═CHCH_3$ |
| 15 | 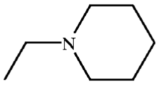 |
| 16 | 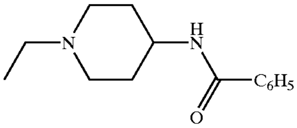 |
| 17 | 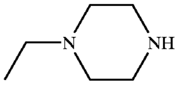 |
| 18 | 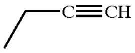 |
| 19 | 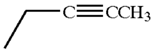 |
| 20 | 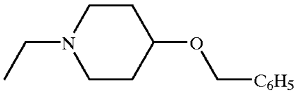 |
| 21 | 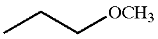 |
| 22 | 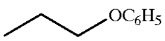 |
TABLE 182-continued
| | 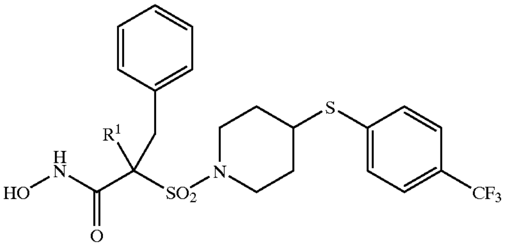 |
|---|---|
| | 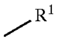 |
| 23 | 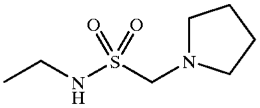 |
| 24 | 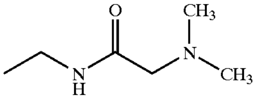 |
| 25 | 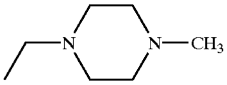 |
| 26 | 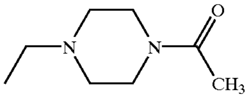 |
| 27 | 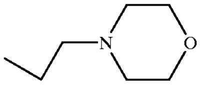 |
| 28 | 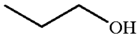 |
| 29 | 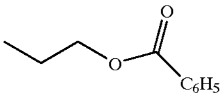 |
| 30 | 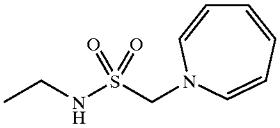 |
| 30 | 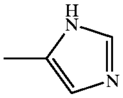 |
| 31 | 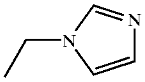 |
| 32 | 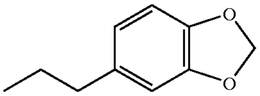 |

TABLE 182-continued
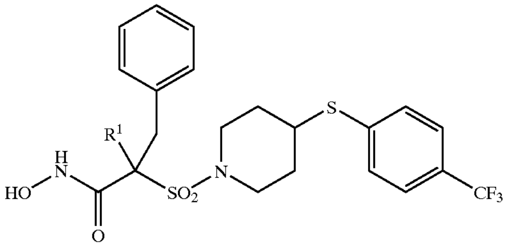
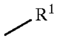
| | |
|---|---|
| 33 | 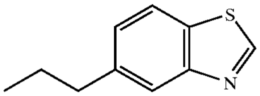 |
| 34 | 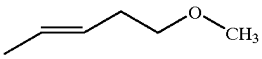 |
| 35 | 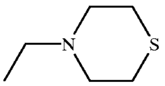 |
| 36 | 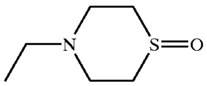 |
| 37 | 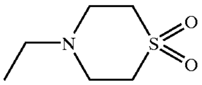 |
| 38 | 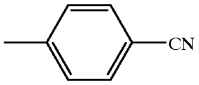 |
| 39 | 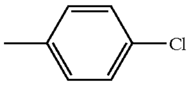 |
| 40 | 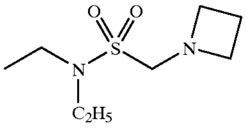 |
| 41 | 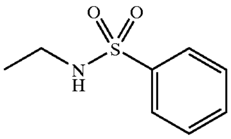 |
| 42 | 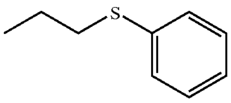 |
| 43 | 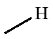 |
TABLE 183
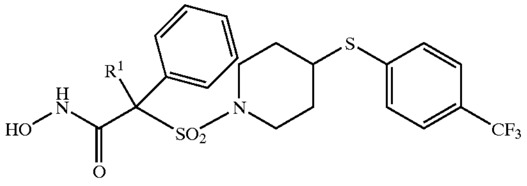
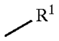
| | |
|---|---|
| 1 | $—CH_3$ |
| 2 | $—CH_2CH_3$ |
| 3 | $—CH(CH_3)_2$ |
| 4 | 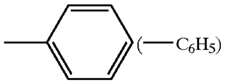 |
| 5 | 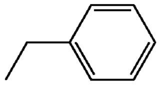 |
| 6 | 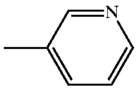 |
| 7 | 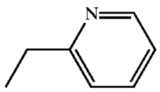 |
| 8 | $—CH_2—N(CH_3)_2$ |
| 9 | $—CH_2—N(CH_3)CH_2C_6H_5$ |
| 10 | 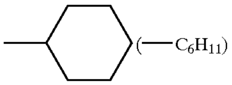 |
| 11 | 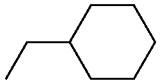 |
| 12 | 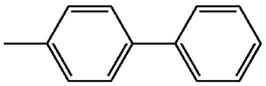 |
| 13 | 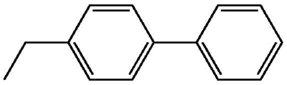 |
| 14 | $—CH_2CH{=}CHCH_3$ |
| 15 | 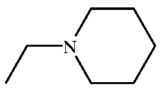 |
| 16 | 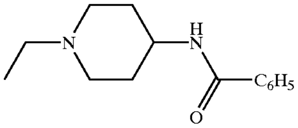 |
| 17 | 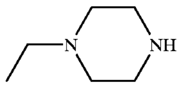 |

TABLE 183-continued
| | |
|---|---|
| 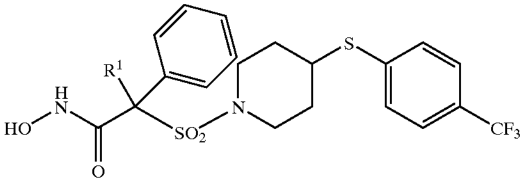 | |
| | 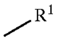 |
| 18 | 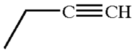 |
| 19 | 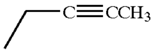 |
| 20 | 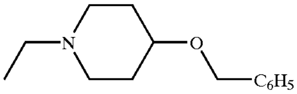 |
| 21 | 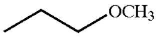 |
| 22 | 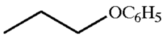 |
| 23 | 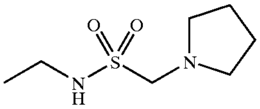 |
| 24 | 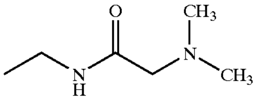 |
| 25 | 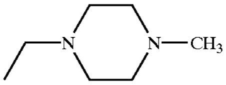 |
| 26 | 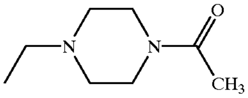 |
| 27 | 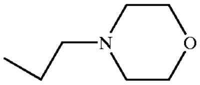 |
| 28 | 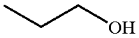 |
| 29 | 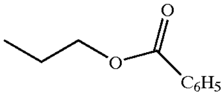 |
| 30 | 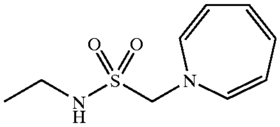 |
TABLE 183-continued
| | |
|---|---|
| 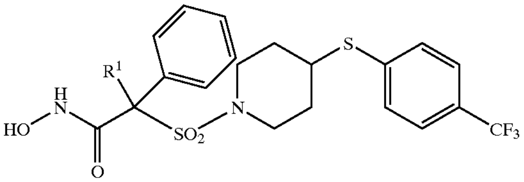 | |
| | 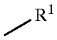 |
| 30 | 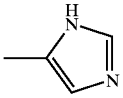 |
| 31 | 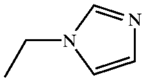 |
| 32 | 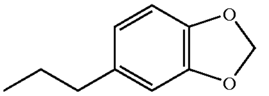 |
| 33 | 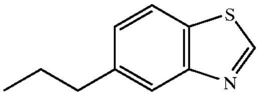 |
| 34 | 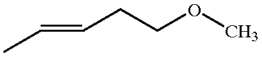 |
| 35 | 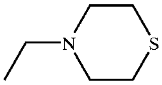 |
| 36 | 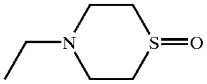 |
| 37 | 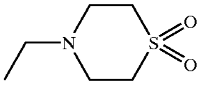 |
| 38 | 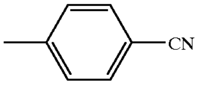 |
| 39 | 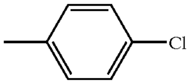 |
| 40 | 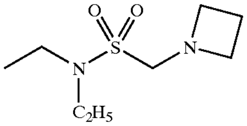 |
| 41 | 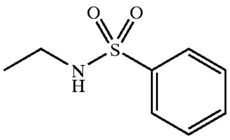 |

TABLE 183-continued
| | |
|---|---|
| 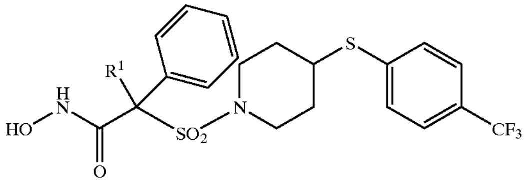 | |
| | 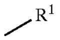 |
| 42 | 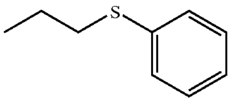 |
| 43 | 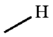 |
TABLE 184
| | |
|---|---|
| 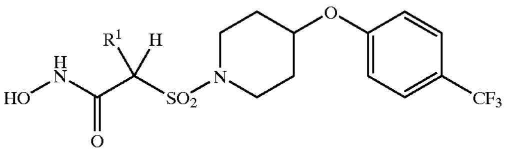 | |
| | 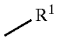 |
| 1 | —$CH_3$ |
| 2 | —$CH_2CH_3$ |
| 3 | —$CH(CH_3)_2$ |
| 4 | 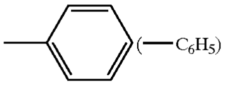 |
| 5 | 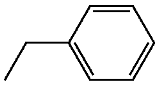 |
| 6 | 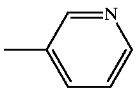 |
| 7 | 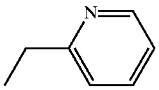 |
| 8 | —$CH_2$—$N(CH_3)_2$ |
| 9 | —$CH_2$—$N(CH_3)CH_2C_6H_5$ |
| 10 | 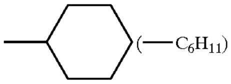 |
| 11 | 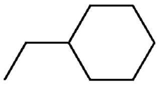 |
| 12 | 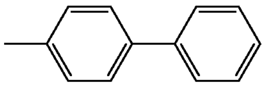 |
TABLE 184-continued
| | |
|---|---|
| 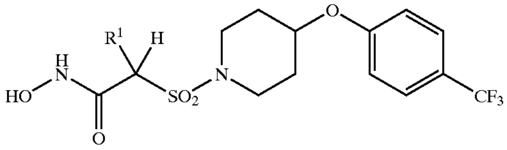 | |
| | 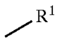 |
| 13 | 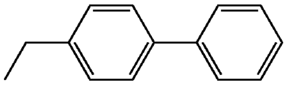 |
| 14 | —$CH_2CH{=}CHCH_3$ |
| 15 | 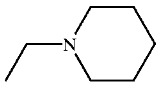 |
| 16 | 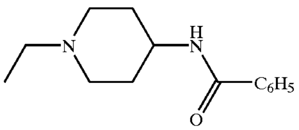 |
| 17 | 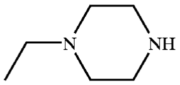 |
| 18 | 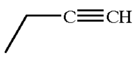 |
| 19 | 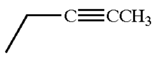 |
| 20 | 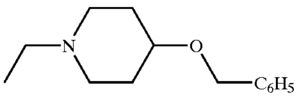 |
| 21 | 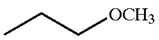 |
| 22 | 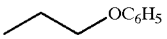 |
| 23 | 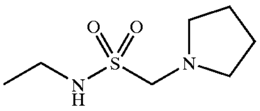 |
| 24 | 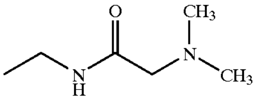 |
| 25 | 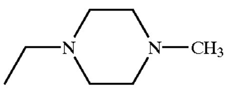 |
| 26 | 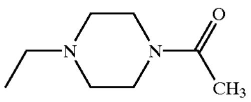 |

TABLE 184-continued
| | |
|---|---|
| | 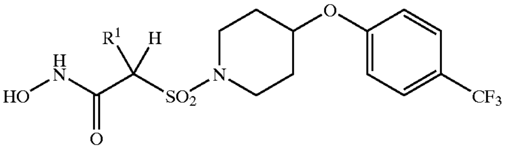 |
| | 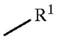 |
| 27 | 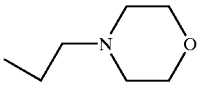 |
| 28 | 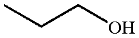 |
| 29 | 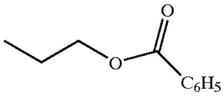 |
| 30 | 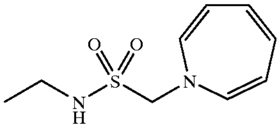 |
| 30 | 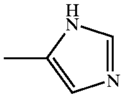 |
| 31 | 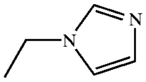 |
| 32 | 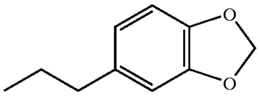 |
| 33 | 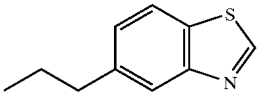 |
| 34 | 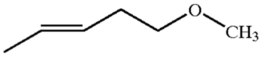 |
| 35 | 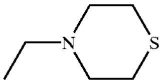 |
| 36 | 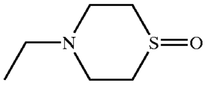 |
| 37 | 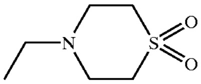 |
| 38 | 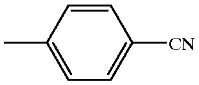 |
| 39 | 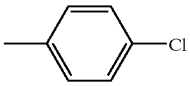 |
| 40 | 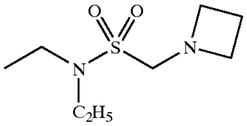 |
| 41 | 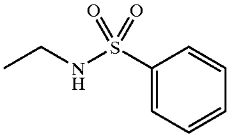 |
| 42 | 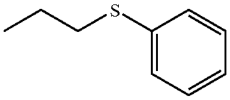 |
| 43 | 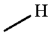 |
TABLE 185
| | |
|---|---|
| | 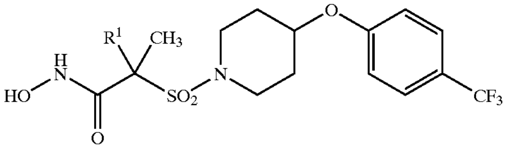 |
| | 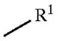 |
| 1 | $-CH_3$ |
| 2 | $-CH_2CH_3$ |
| 3 | $-CH(CH_3)_2$ |
| 4 | 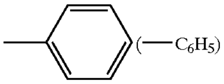 |
| 5 | 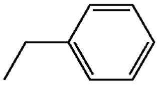 |
| 6 | 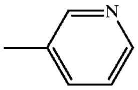 |
| 7 | 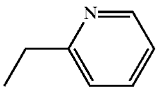 |

TABLE 185-continued
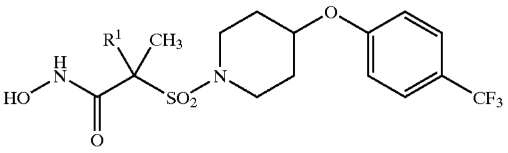
| | 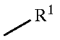 |
|---|---|
| 8 | —$CH_2$—$N(CH_3)_2$ |
| 9 | —$CH_2$—$N(CH_3)CH_2C_6H_5$ |
| 10 | 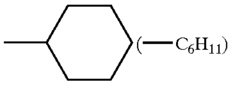 |
| 11 | 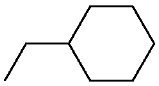 |
| 12 | 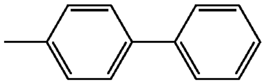 |
| 13 | 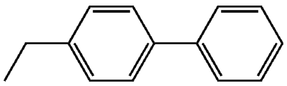 |
| 14 | —$CH_2CH{=}CHCH_3$ |
| 15 | 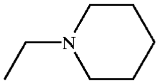 |
| 16 | 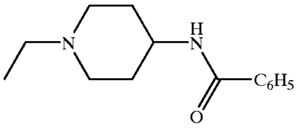 |
| 17 | 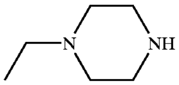 |
| 18 | 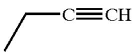 |
| 19 | 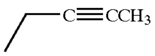 |
| 20 | 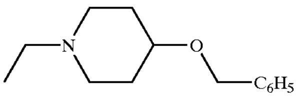 |
| 21 | 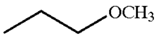 |
| 22 | 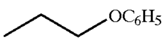 |
| 23 | 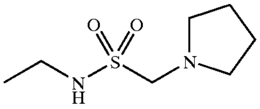 |
TABLE 185-continued
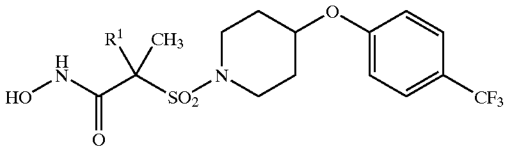
| | 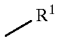 |
|---|---|
| 24 | 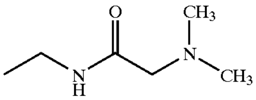 |
| 25 | 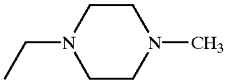 |
| 26 | 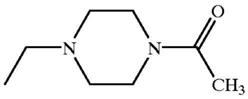 |
| 27 | 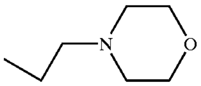 |
| 28 | 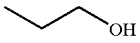 |
| 29 | 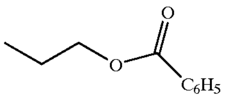 |
| 30 | 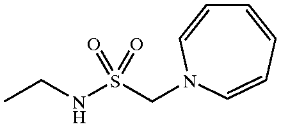 |
| 30 | 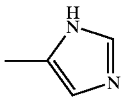 |
| 31 | 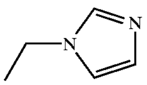 |
| 32 | 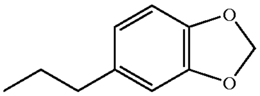 |
| 33 | 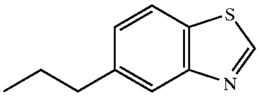 |
| 34 | 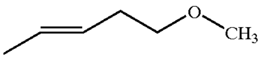 |
| 35 | 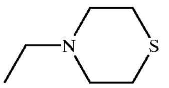 |

TABLE 185-continued
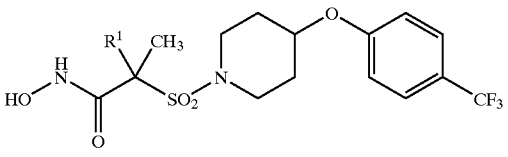
| | 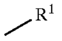 |
|---|---|
| 36 | 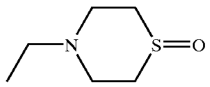 |
| 37 | 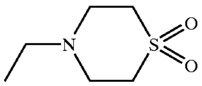 |
| 38 | 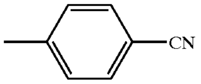 |
| 39 | 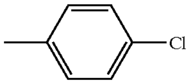 |
| 40 | 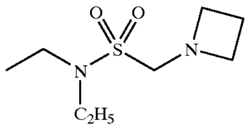 |
| 41 | 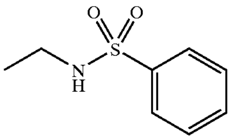 |
| 42 | 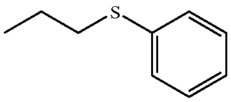 |
| 43 | 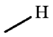 |
TABLE 186
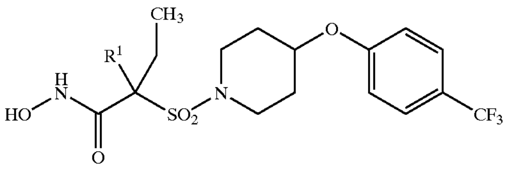
| | 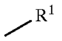 |
|---|---|
| 1 | $—CH_3$ |
| 2 | $—CH_2CH_3$ |
| 3 | $—CH(CH_3)_2$ |
| 4 | 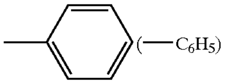 |
TABLE 186-continued
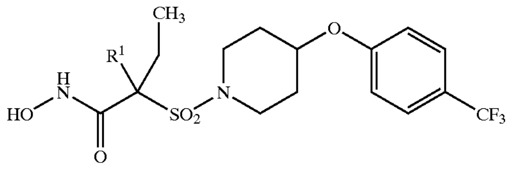
| | 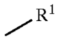 |
|---|---|
| 5 | 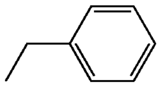 |
| 6 | 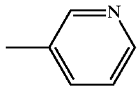 |
| 7 | 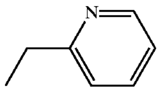 |
| 8 | $—CH_2—N(CH_3)_2$ |
| 9 | $—CH_2—N(CH_3)CH_2C_6H_5$ |
| 10 | 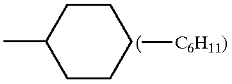 |
| 11 | 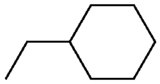 |
| 12 | 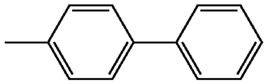 |
| 13 | 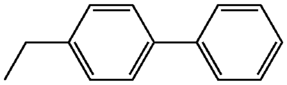 |
| 14 | $—CH_2CH{=}CHCH_3$ |
| 15 | 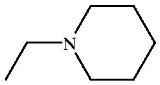 |
| 16 | 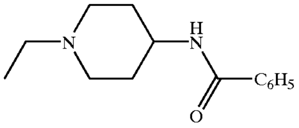 |
| 17 | 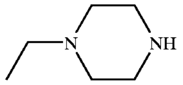 |
| 18 | 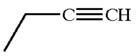 |
| 19 | 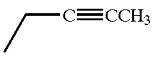 |

TABLE 186-continued
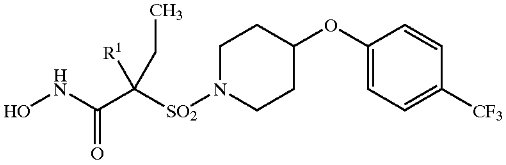
| | 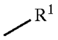 |
|---|---|
| 20 | 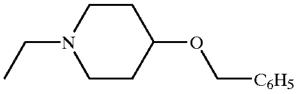 |
| 21 | 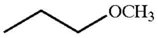 |
| 22 | 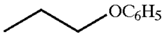 |
| 23 | 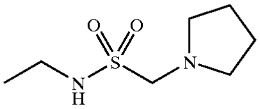 |
| 24 | 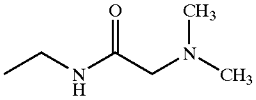 |
| 25 | 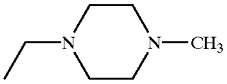 |
| 26 | 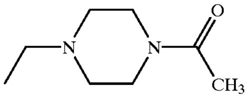 |
| 27 | 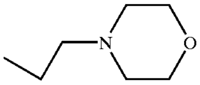 |
| 28 | 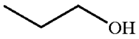 |
| 29 | 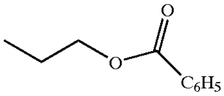 |
| 30 | 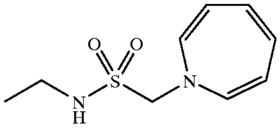 |
| 30 | 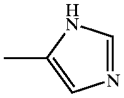 |
| 31 | 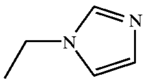 |
TABLE 186-continued
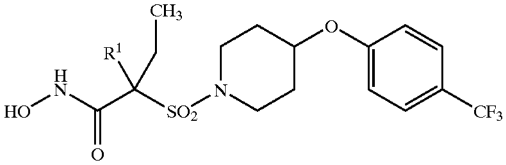
| | 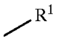 |
|---|---|
| 32 | 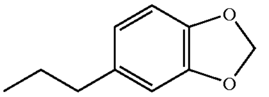 |
| 33 | 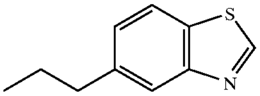 |
| 34 | 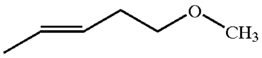 |
| 35 | 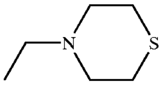 |
| 36 | 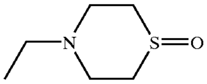 |
| 37 | 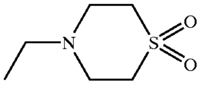 |
| 38 | 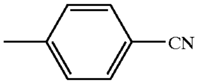 |
| 39 | 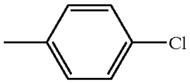 |
| 40 | 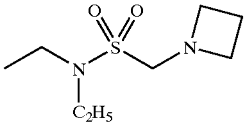 |
| 41 | 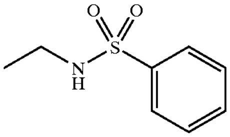 |
| 42 | 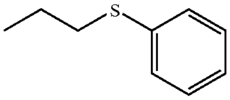 |
| 43 | 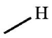 |

TABLE 187
| | |
|---|---|
| 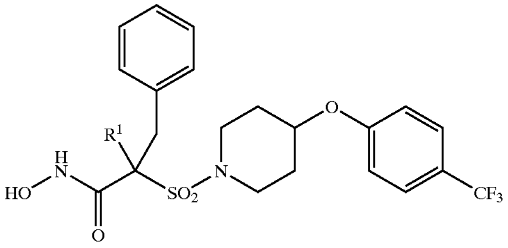 | |
| | 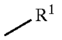 |
| 1 | $-CH_3$ |
| 2 | $-CH_2CH_3$ |
| 3 | $-CH(CH_3)_2$ |
| 4 | 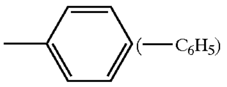 |
| 5 | 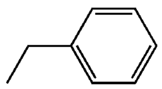 |
| 6 | 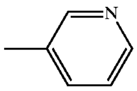 |
| 7 | 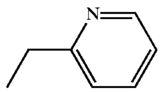 |
| 8 | $-CH_2-N(CH_3)_2$ |
| 9 | $-CH_2-N(CH_3)CH_2C_6H_5$ |
| 10 | 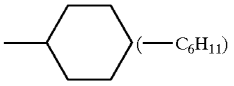 |
| 11 | 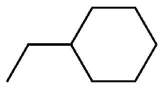 |
| 12 | 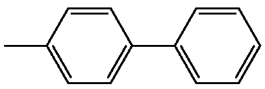 |
| 13 | 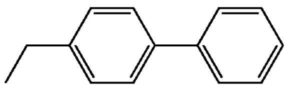 |
| 14 | $-CH_2CH=CHCH_3$ |
| 15 | 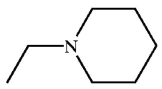 |
| 16 | 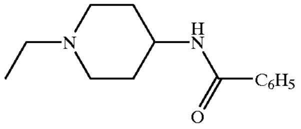 |
TABLE 187-continued
| | |
|---|---|
| 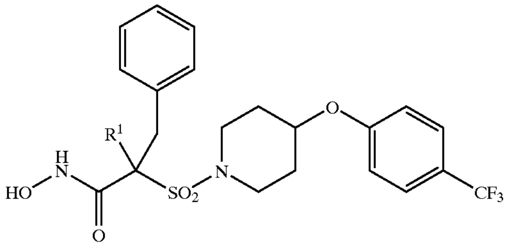 | |
| | 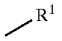 |
| 17 | 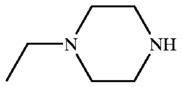 |
| 18 | 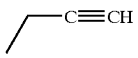 |
| 19 | 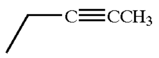 |
| 20 | 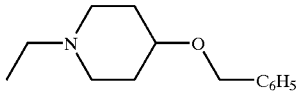 |
| 21 | 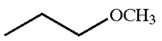 |
| 22 | 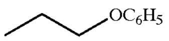 |
| 23 | 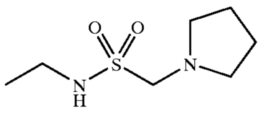 |
| 24 | 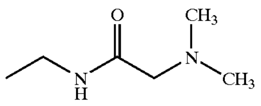 |
| 25 | 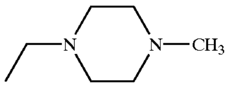 |
| 26 | 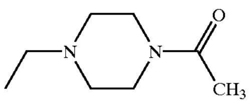 |
| 27 | 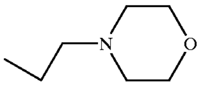 |
| 28 | 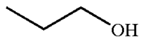 |
| 29 | 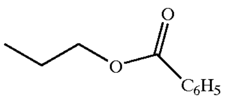 |

TABLE 187-continued
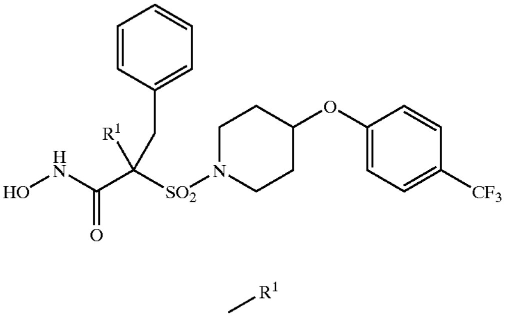
| | |
|---|---|
| 30 | 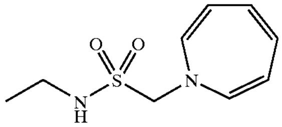 |
| 30 | 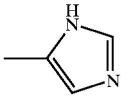 |
| 31 | 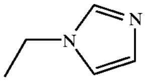 |
| 32 | 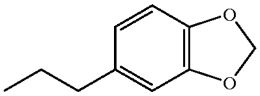 |
| 33 | 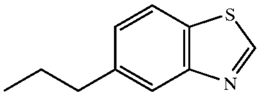 |
| 34 | 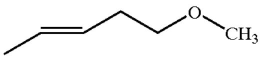 |
| 35 | 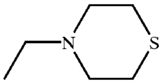 |
| 36 | 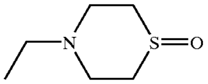 |
| 37 | 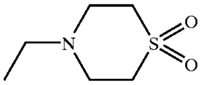 |
| 38 | 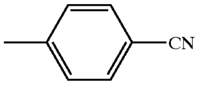 |
| 39 | 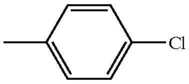 |
TABLE 187-continued
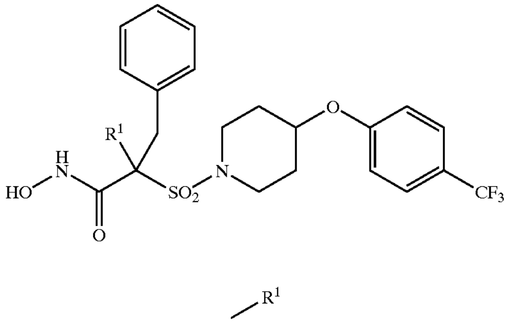
| | |
|---|---|
| 40 | 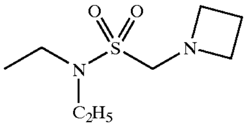 |
| 41 | 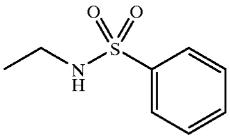 |
| 42 | 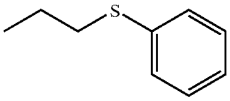 |
| 43 | 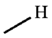 |
TABLE 188
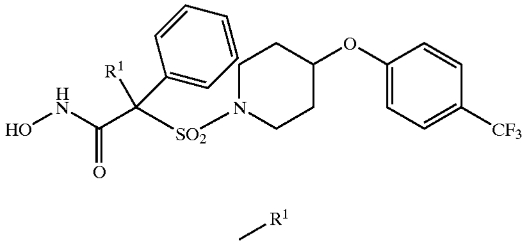
| | |
|---|---|
| 1 | $—CH_3$ |
| 2 | $—CH_2CH_3$ |
| 3 | $—CH(CH_3)_2$ |
| 4 | 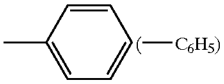 |
| 5 | 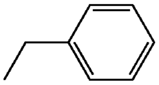 |
| 6 | 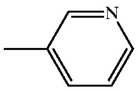 |

TABLE 188-continued
| | |
|---|---|
| | 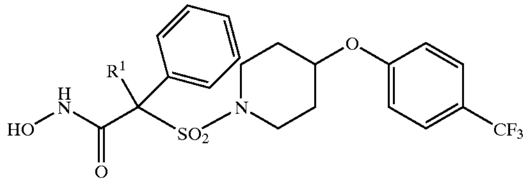 |
| | 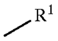 |
| 7 | 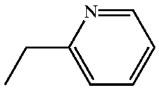 |
| 8 | —$CH_2$—$N(CH_3)_2$ |
| 9 | —$CH_2$—$N(CH_3)CH_2C_6H_5$ |
| 10 | 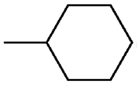 (—$C_6H_{11}$) |
| 11 | 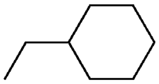 |
| 12 | 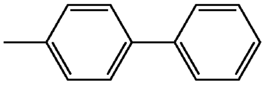 |
| 13 | 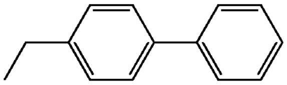 |
| 14 | —$CH_2CH$═$CHCH_3$ |
| 15 | 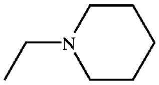 |
| 16 | 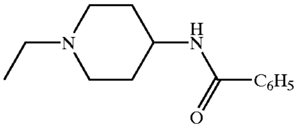 |
| 17 | 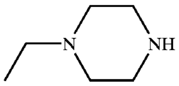 |
| 18 | 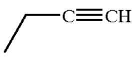 |
| 19 | 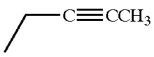 |
| 20 | 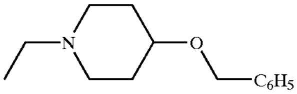 |
| 21 | 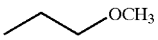 |
| 22 | 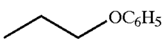 |
TABLE 188-continued
| | |
|---|---|
| | 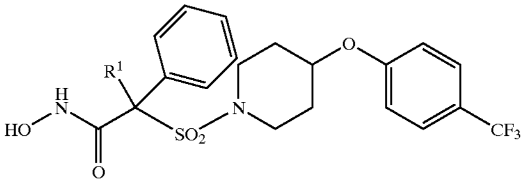 |
| | 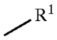 |
| 23 | 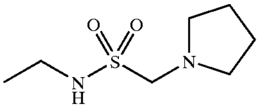 |
| 24 | 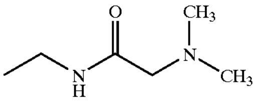 |
| 25 | 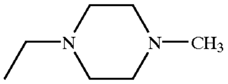 |
| 26 | 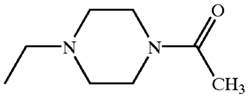 |
| 27 | 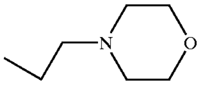 |
| 28 | 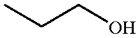 |
| 29 | 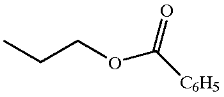 |
| 30 | 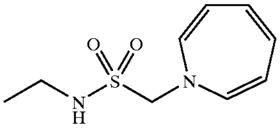 |
| 30 | 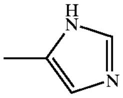 |
| 31 | 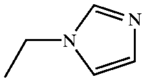 |
| 32 | 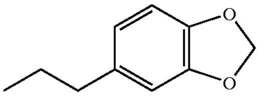 |
| 33 | 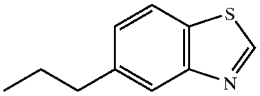 |

TABLE 188-continued
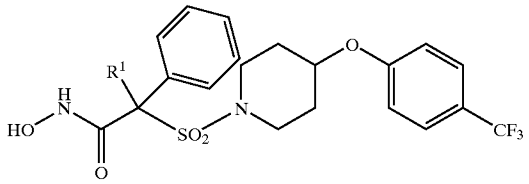
| | |
|---|---|
| 34 | 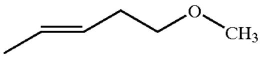 |
| 35 | 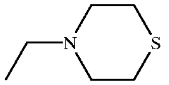 |
| 36 | 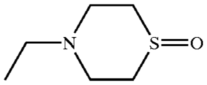 |
| 37 | 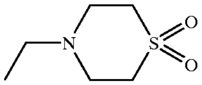 |
| 38 | 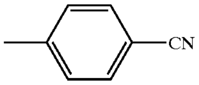 |
| 39 | 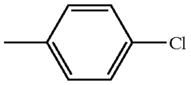 |
| 40 | 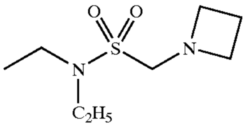 |
| 41 | 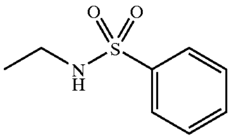 |
| 42 | 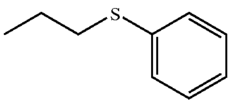 |
| 43 | 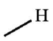 |
TABLE 189
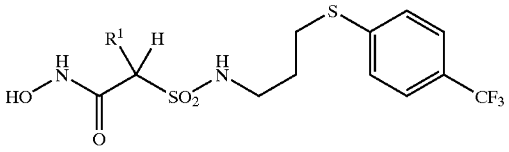
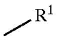
| | |
|---|---|
| 1 | $-CH_3$ |
| 2 | $-CH_2CH_3$ |
| 3 | $-CH(CH_3)_2$ |
| 4 | 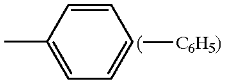 |
| 5 | 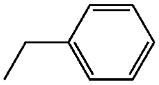 |
| 6 | 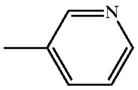 |
| 7 | 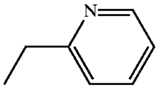 |
| 8 | $-CH_2-N(CH_3)_2$ |
| 9 | $-CH_2-N(CH_3)CH_2C_6H_5$ |
| 10 | 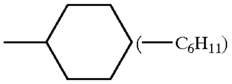 |
| 11 | 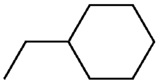 |
| 12 | 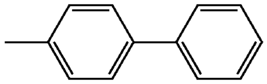 |
| 13 | 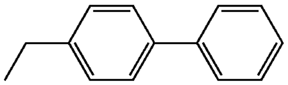 |
| 14 | $-CH_2CH{=}CHCH_3$ |
| 15 | 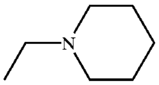 |
| 16 | 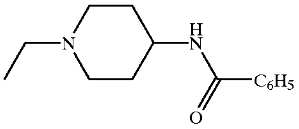 |
| 17 | 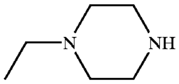 |

TABLE 189-continued
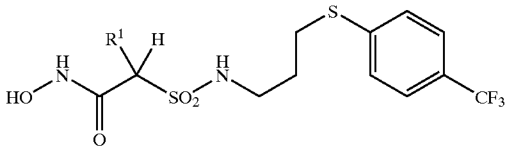
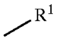
| | |
|---|---|
| 18 | 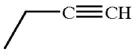 |
| 19 | 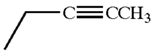 |
| 20 | 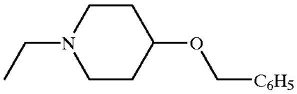 |
| 21 | 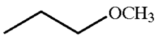 |
| 22 | 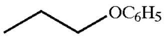 |
| 23 | 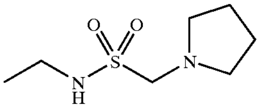 |
| 24 | 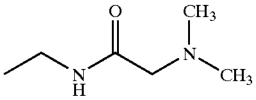 |
| 25 | 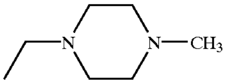 |
| 26 | 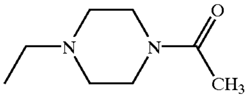 |
| 27 | 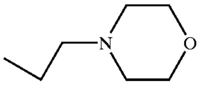 |
| 28 | 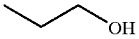 |
| 29 | 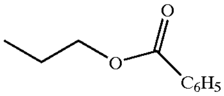 |
| 30 | 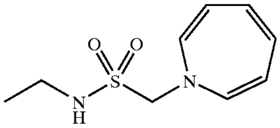 |
| 30 | 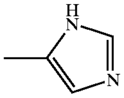 |
TABLE 189-continued
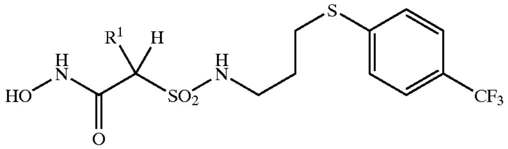
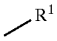
| | |
|---|---|
| 31 | 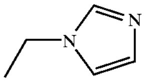 |
| 32 | 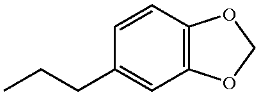 |
| 33 | 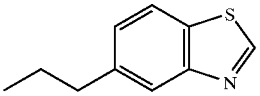 |
| 34 | 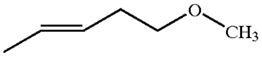 |
| 35 | 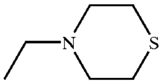 |
| 36 | 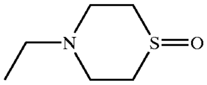 |
| 37 | 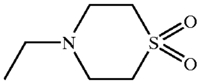 |
| 38 | 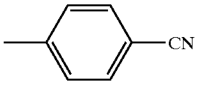 |
| 39 | 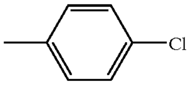 |
| 40 | 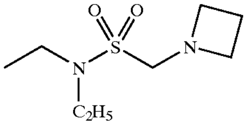 |
| 41 | 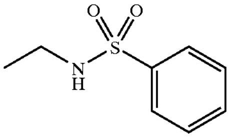 |
| 42 | 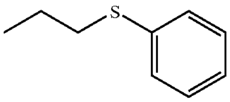 |

TABLE 189-continued
| | 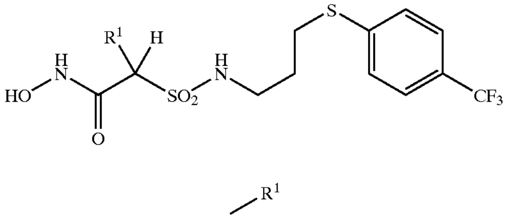 |
|---|---|
| 43 | 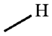 |
TABLE 190
| | 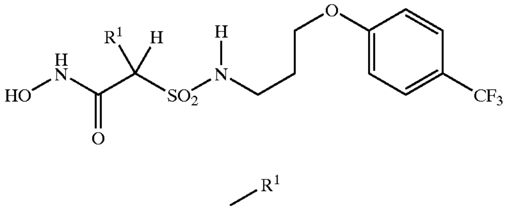 |
|---|---|
| 1 | —$CH_3$ |
| 2 | —$CH_2CH_3$ |
| 3 | —$CH(CH_3)_2$ |
| 4 | 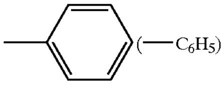 |
| 5 | 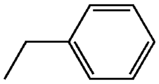 |
| 6 | 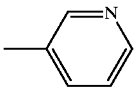 |
| 7 | 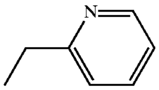 |
| 8 | —$CH_2$—$N(CH_3)_2$ |
| 9 | —$CH_2$—$N(CH_3)CH_2C_6H_5$ |
| 10 | 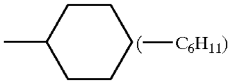 |
| 11 | 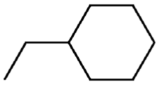 |
| 12 | 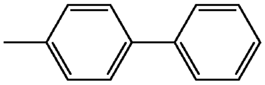 |
| 13 | 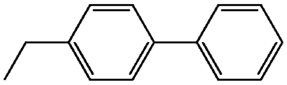 |
| 14 | —$CH_2CH$=$CHCH_3$ |
TABLE 190-continued
| | 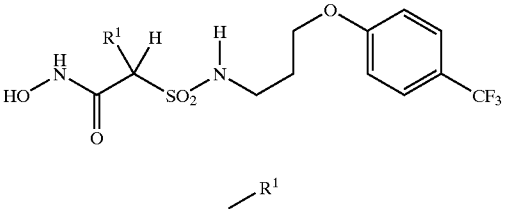 |
|---|---|
| 15 | 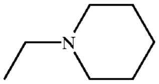 |
| 16 | 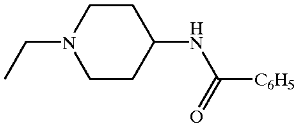 |
| 17 | 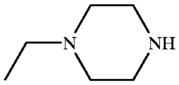 |
| 18 | 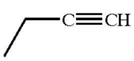 |
| 19 | 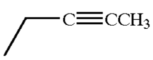 |
| 20 | 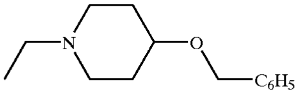 |
| 21 | 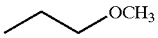 |
| 22 | 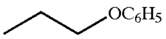 |
| 23 | 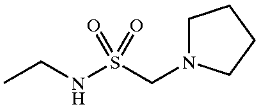 |
| 24 | 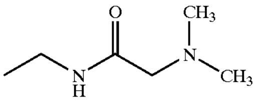 |
| 25 | 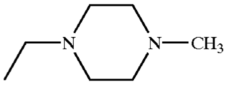 |
| 26 | 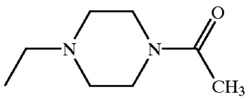 |
| 27 | 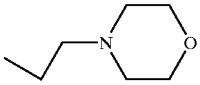 |
| 28 | 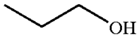 |

TABLE 190-continued
| 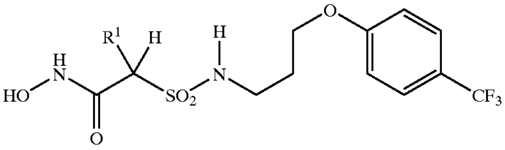 | |
|---|---|
| | 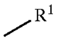 |
| 29 | 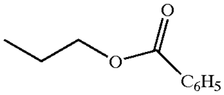 |
| 30 | 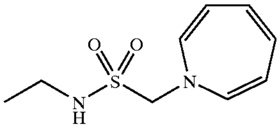 |
| 30 | 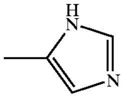 |
| 31 | 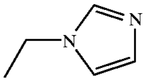 |
| 32 | 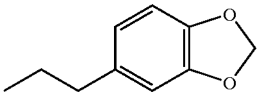 |
| 33 | 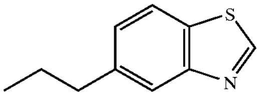 |
| 34 | 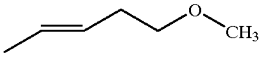 |
| 35 | 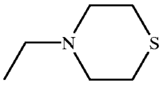 |
| 36 | 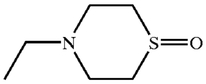 |
| 37 | 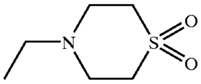 |
| 38 | 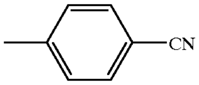 |
| 39 | 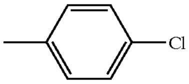 |
TABLE 190-continued
| 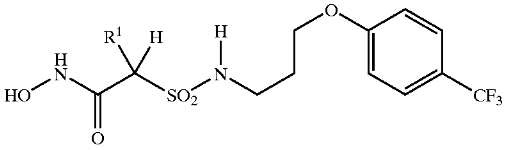 | |
|---|---|
| | 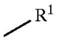 |
| 40 | 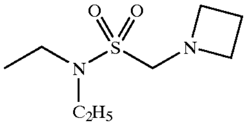 |
| 41 | 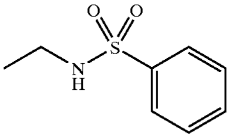 |
| 42 | 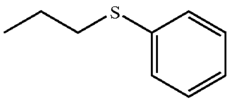 |
| 43 | 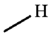 |
TABLE 191
| 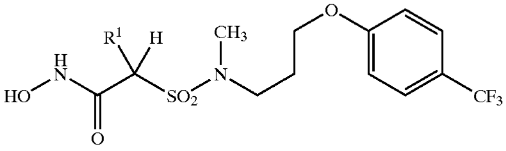 | |
|---|---|
| | 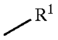 |
| 1 | $—CH_3$ |
| 2 | $—CH_2CH_3$ |
| 3 | $—CH(CH_3)_2$ |
| 4 | 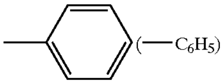 |
| 5 | 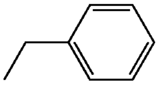 |
| 6 | 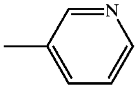 |
| 7 | 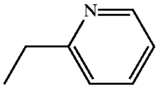 |
| 8 | $—CH_2—N(CH_3)_2$ |
| 9 | $—CH_2—N(CH_3)CH_2C_6H_5$ |

TABLE 191-continued
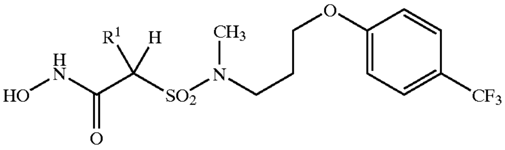
| | 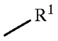 |
|---|---|
| 10 | 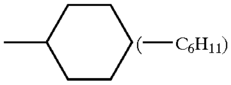 |
| 11 | 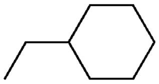 |
| 12 | 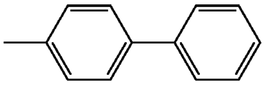 |
| 13 | 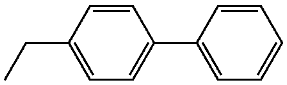 |
| 14 | $—CH_2CH{=}CHCH_3$ |
| 15 | 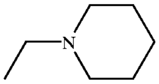 |
| 16 | 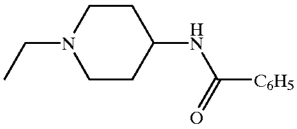 |
| 17 | 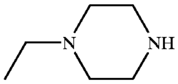 |
| 18 | 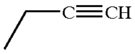 |
| 19 | 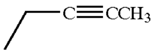 |
| 20 | 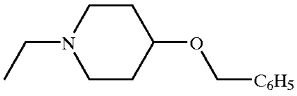 |
| 21 | 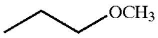 |
| 22 | 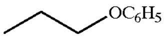 |
| 23 | 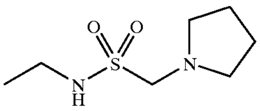 |
TABLE 191-continued
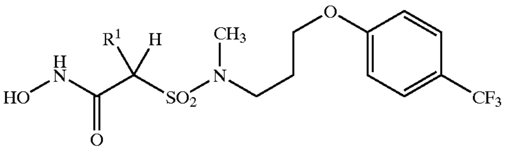
| | 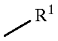 |
|---|---|
| 24 | 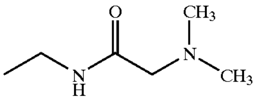 |
| 25 | 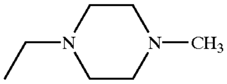 |
| 26 | 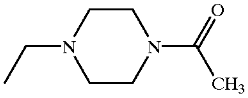 |
| 27 | 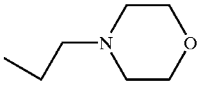 |
| 28 | 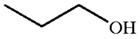 |
| 29 | 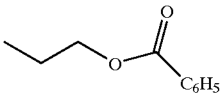 |
| 30 | 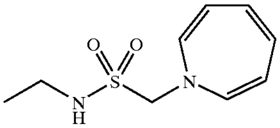 |
| 30 | 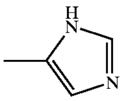 |
| 31 | 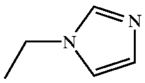 |
| 32 | 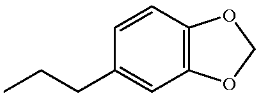 |
| 33 | 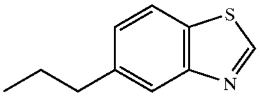 |
| 34 | 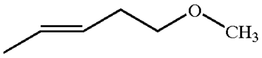 |
| 35 | 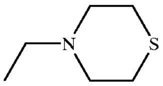 |

TABLE 191-continued
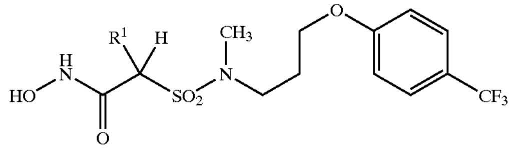
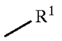
| | |
|---|---|
| 36 | 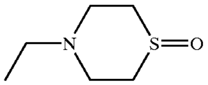 |
| 37 | 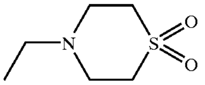 |
| 38 | 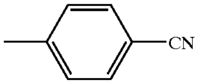 |
| 39 | 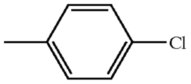 |
| 40 | 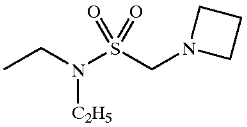 |
| 41 | 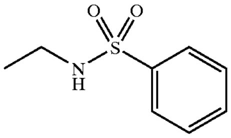 |
| 42 | 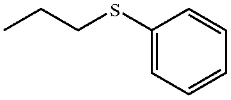 |
| 43 | 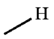 |
TABLE 192
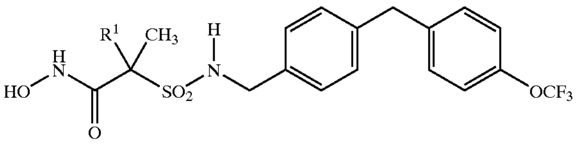
| | |
|---|---|
| 1 | $—CH_3$ |
| 2 | $—CH_2CH_3$ |
| 3 | $—CH(CH_3)_2$ |
| 4 | 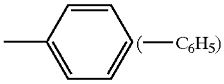 |
TABLE 192-continued
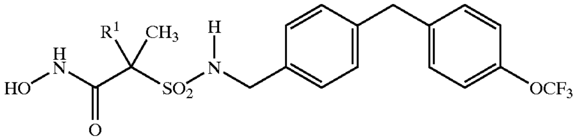
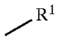
| | |
|---|---|
| 5 | 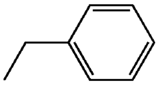 |
| 6 | 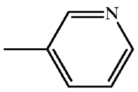 |
| 7 | 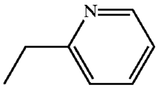 |
| 8 | $—CH_2—N(CH_3)_2$ |
| 9 | $—CH_2—N(CH_3)CH_2C_6H_5$ |
| 10 | 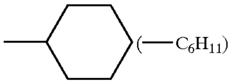 |
| 11 | 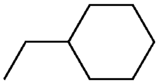 |
| 12 | 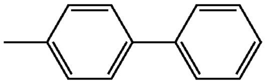 |
| 13 | 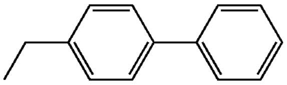 |
| 14 | $—CH_2CH{=}CHCH_3$ |
| 15 | 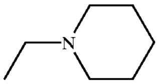 |
| 16 | 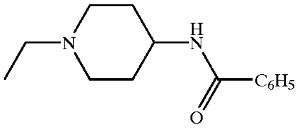 |
| 17 | 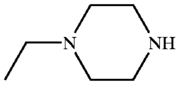 |
| 18 | 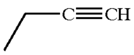 |
| 19 | 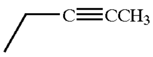 |

TABLE 192-continued
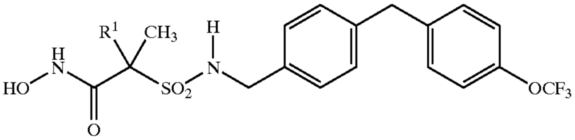
| | 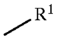 |
|---|---|
| 20 | 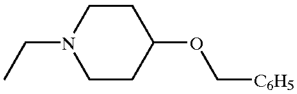 |
| 21 | 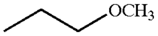 |
| 22 | 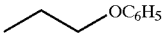 |
| 23 | 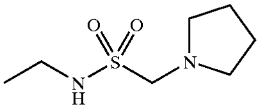 |
| 24 | 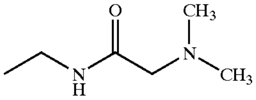 |
| 25 | 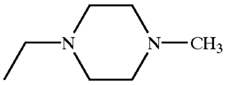 |
| 26 | 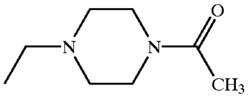 |
| 27 | 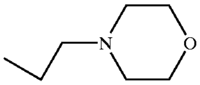 |
| 28 | 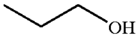 |
| 29 | 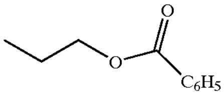 |
| 30 | 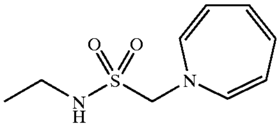 |
| 30 | 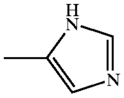 |
| 31 | 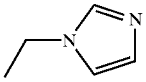 |
TABLE 192-continued
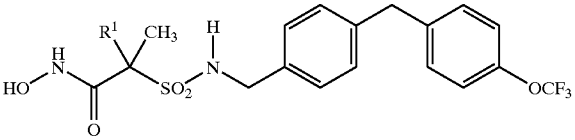
| | 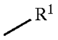 |
|---|---|
| 32 | 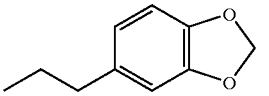 |
| 33 | 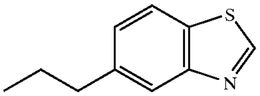 |
| 34 | 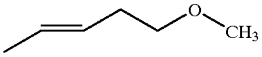 |
| 35 | 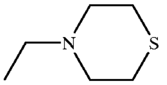 |
| 36 | 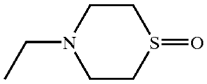 |
| 37 | 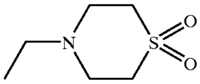 |
| 38 | 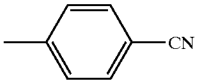 |
| 39 | 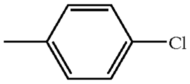 |
| 40 | 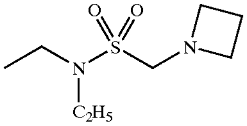 |
| 41 | 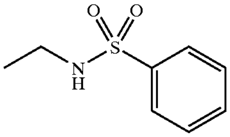 |
| 42 | 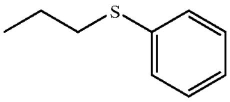 |
| 43 | 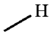 |

TABLE 193
| | 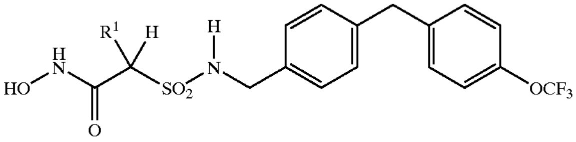<br>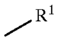 |
|---|---|
| 1 | $—CH_3$ |
| 2 | $—CH_2CH_3$ |
| 3 | $—CH(CH_3)_2$ |
| 4 | 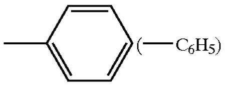 |
| 5 | 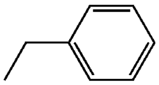 |
| 6 | 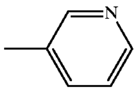 |
| 7 | 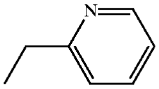 |
| 8 | $—CH_2—N(CH_3)_2$ |
| 9 | $—CH_2—N(CH_3)CH_2C_6H_5$ |
| 10 | 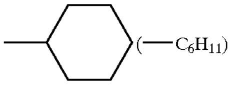 |
| 11 | 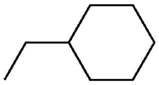 |
| 12 | 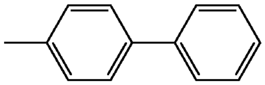 |
| 13 | 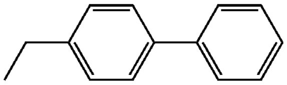 |
| 14 | $—CH_2CH=CHCH_3$ |
| 15 | 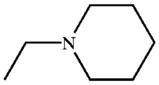 |
| 16 | 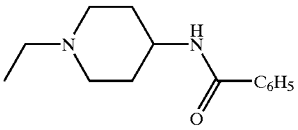 |
| 17 | 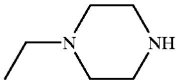 |
TABLE 193-continued
| | 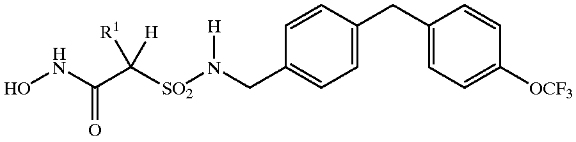<br>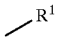 |
|---|---|
| 18 | 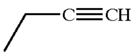 |
| 19 | 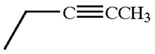 |
| 20 | 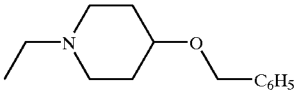 |
| 21 | 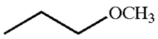 |
| 22 | 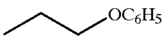 |
| 23 | 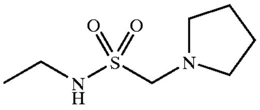 |
| 24 | 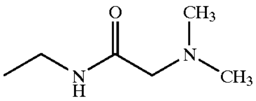 |
| 25 | 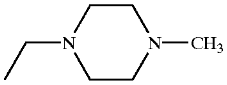 |
| 26 | 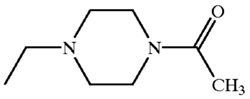 |
| 27 | 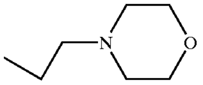 |
| 28 | 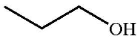 |
| 29 | 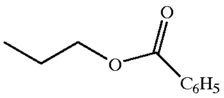 |
| 30 | 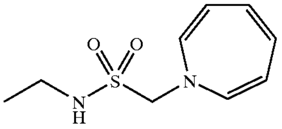 |
| 30 | 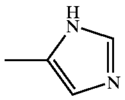 |

TABLE 193-continued
| 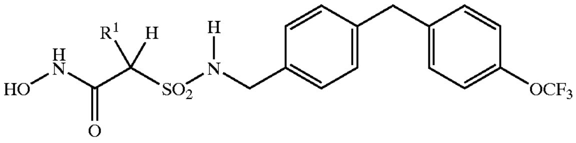 |  |
|---|---|
| 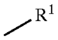 |  |
| 31 | 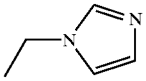 |
| 32 | 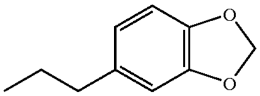 |
| 33 | 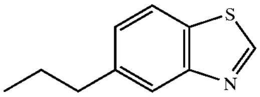 |
| 34 | 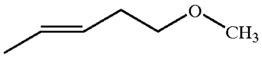 |
| 35 | 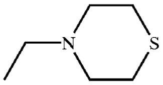 |
| 36 | 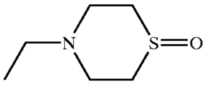 |
| 37 | 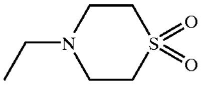 |
| 38 | 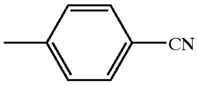 |
| 39 | 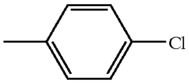 |
| 40 | 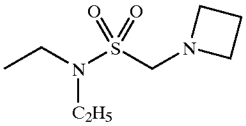 |
| 41 | 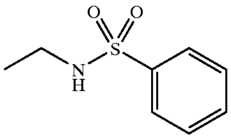 |
| 42 | 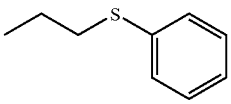 |
| 43 | 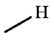 |
TABLE 194
| 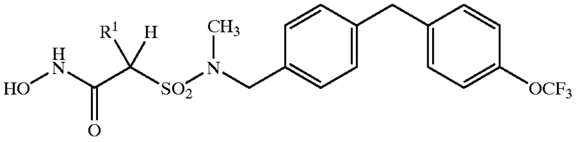 |  |
|---|---|
| 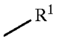 |  |
| 1 | $—CH_3$ |
| 2 | $—CH_2CH_3$ |
| 3 | $—CH(CH_3)_2$ |
| 4 | 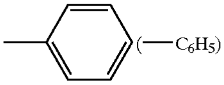 |
| 5 | 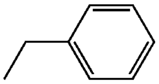 |
| 6 | 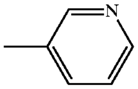 |
| 7 | 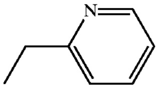 |
| 8 | $—CH_2—N(CH_3)_2$ |
| 9 | $—CH_2—N(CH_3)CH_2C_6H_5$ |
| 10 | 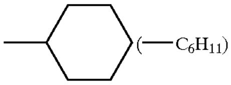 |
| 11 | 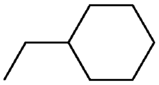 |
| 12 | 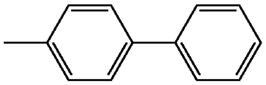 |
| 13 | 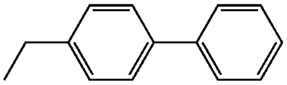 |
| 14 | $—CH_2CH{=}CHCH_3$ |
| 15 | 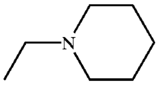 |
| 16 | 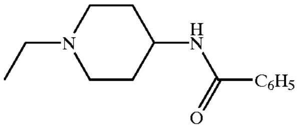 |
| 17 | 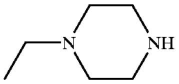 |

TABLE 194-continued
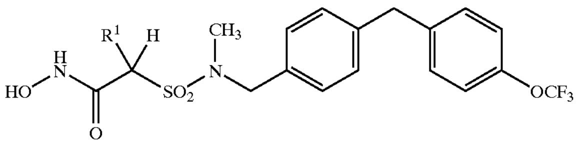
| | 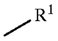 |
|---|---|
| 18 | 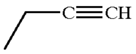 |
| 19 | 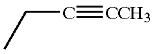 |
| 20 | 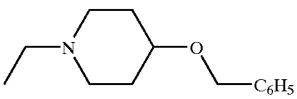 |
| 21 | 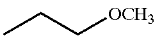 |
| 22 | 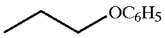 |
| 23 | 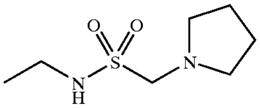 |
| 24 | 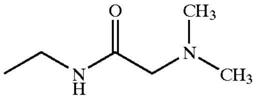 |
| 25 | 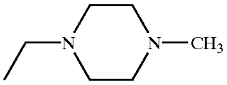 |
| 26 | 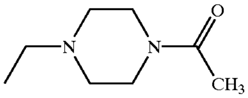 |
| 27 | 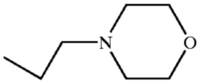 |
| 28 | 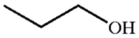 |
| 29 | 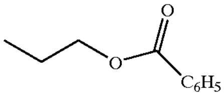 |
| 30 | 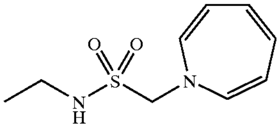 |
| 30 | 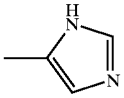 |
TABLE 194-continued
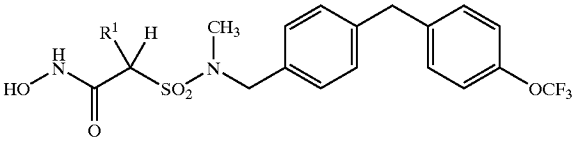
| | 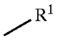 |
|---|---|
| 31 | 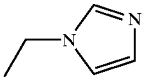 |
| 32 | 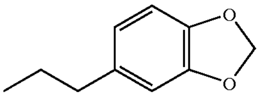 |
| 33 | 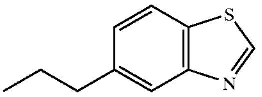 |
| 34 | 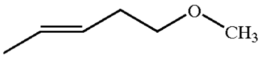 |
| 35 | 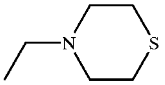 |
| 36 | 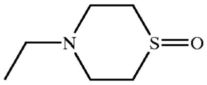 |
| 37 | 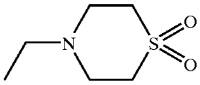 |
| 38 | 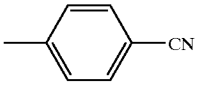 |
| 39 | 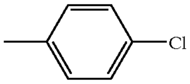 |
| 40 | 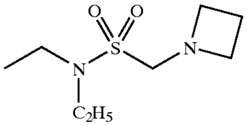 |
| 41 | 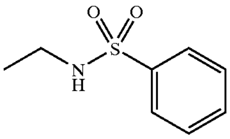 |
| 42 | 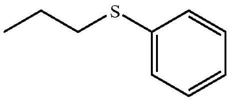 |
| 43 | 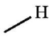 |

TABLE 195
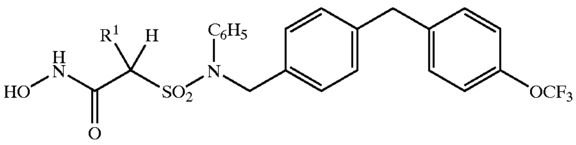
| # | 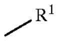 |
|---|---|
| 1 | $—CH_3$ |
| 2 | $—CH_2CH_3$ |
| 3 | $—CH(CH_3)_2$ |
| 4 | 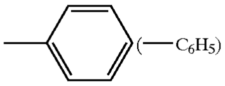 |
| 5 | 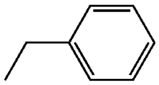 |
| 6 | 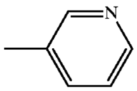 |
| 7 | 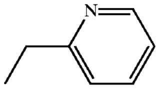 |
| 8 | $—CH_2—N(CH_3)_2$ |
| 9 | $—CH_2—N(CH_3)CH_2C_6H_5$ |
| 10 | 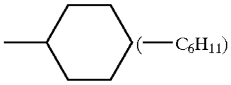 |
| 11 | 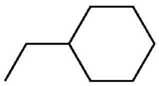 |
| 12 | 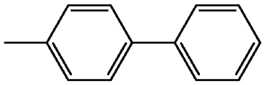 |
| 13 | 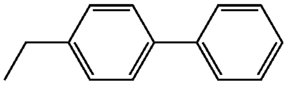 |
| 14 | $—CH_2CH{=}CHCH_3$ |
| 15 | 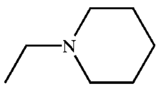 |
| 16 | 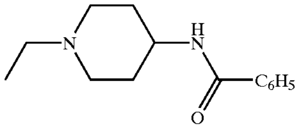 |
| 17 | 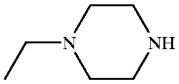 |
TABLE 195-continued
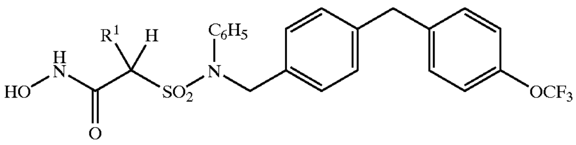
| # | 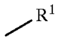 |
|---|---|
| 18 | 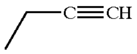 |
| 19 | 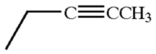 |
| 20 | 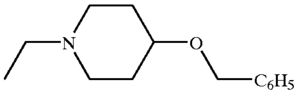 |
| 21 | 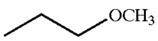 |
| 22 | 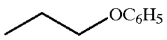 |
| 23 | 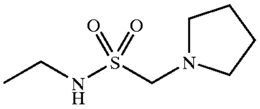 |
| 24 | 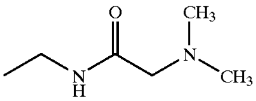 |
| 25 | 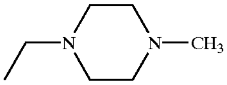 |
| 26 | 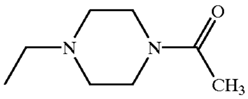 |
| 27 | 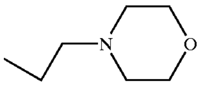 |
| 28 | 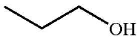 |
| 29 | 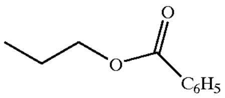 |
| 30 | 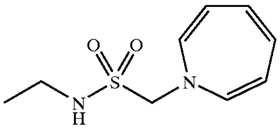 |
| 30 | 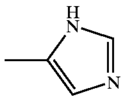 |

TABLE 195-continued
| | |
|---|---|
| 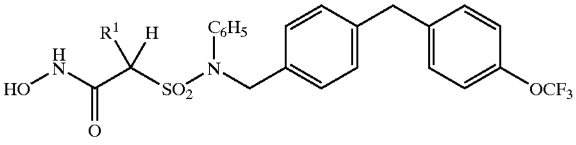 | |
| | 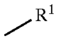 |
| 31 | 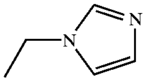 |
| 32 | 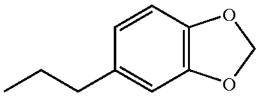 |
| 33 | 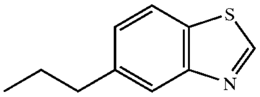 |
| 34 | 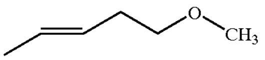 |
| 35 | 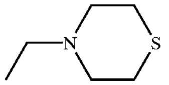 |
| 36 | 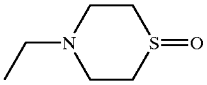 |
| 37 | 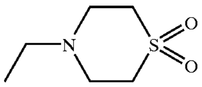 |
| 38 | 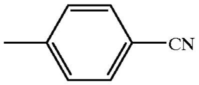 |
| 39 | 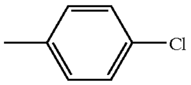 |
| 40 | 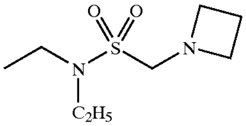 |
| 41 | 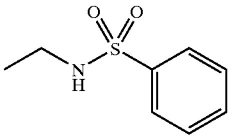 |
| 42 | 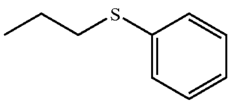 |
| 43 | 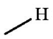 |
TABLE 196
| | |
|---|---|
| 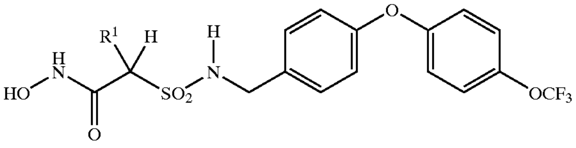 | |
| | 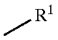 |
| 1 | $-CH_3$ |
| 2 | $-CH_2CH_3$ |
| 3 | $-CH(CH_3)_2$ |
| 4 | 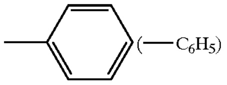 |
| 5 | 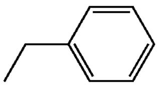 |
| 6 | 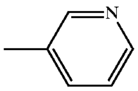 |
| 7 | 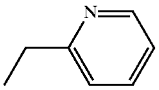 |
| 8 | $-CH_2-N(CH_3)_2$ |
| 9 | $-CH_2-N(CH_3)CH_2C_6H_5$ |
| 10 | 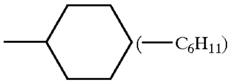 |
| 11 | 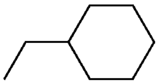 |
| 12 | 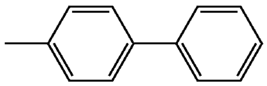 |
| 13 | 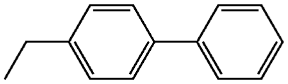 |
| 14 | $-CH_2CH{=}CHCH_3$ |
| 15 | 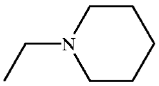 |
| 16 | 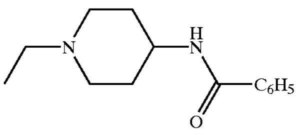 |
| 17 | 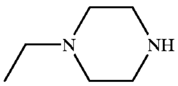 |

TABLE 196-continued
| | |
|---|---|
| 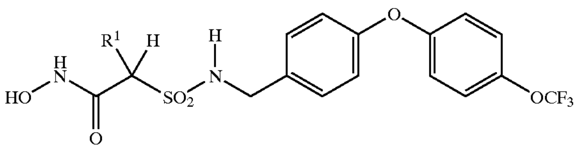 | |
| 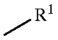 | |
| 18 | 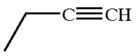 |
| 19 | 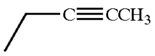 |
| 20 | 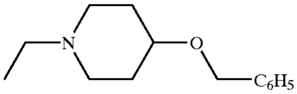 |
| 21 | 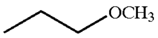 |
| 22 | 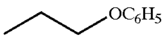 |
| 23 | 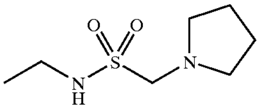 |
| 24 | 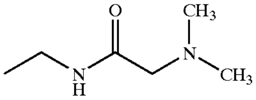 |
| 25 | 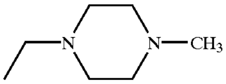 |
| 26 | 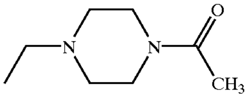 |
| 27 | 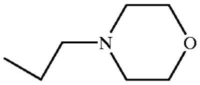 |
| 28 | 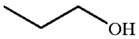 |
| 29 | 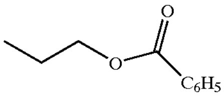 |
| 30 | 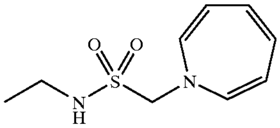 |
| 30 | 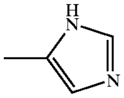 |
TABLE 196-continued
| | |
|---|---|
| 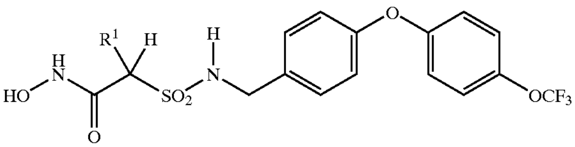 | |
| 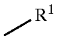 | |
| 31 | 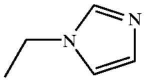 |
| 32 | 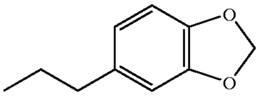 |
| 33 | 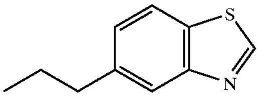 |
| 34 | 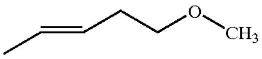 |
| 35 | 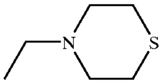 |
| 36 | 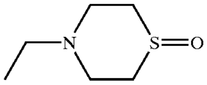 |
| 37 | 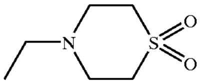 |
| 38 | 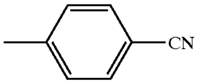 |
| 39 | 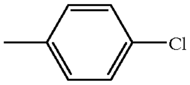 |
| 40 | 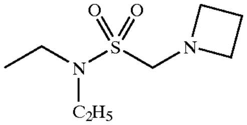 |
| 41 | 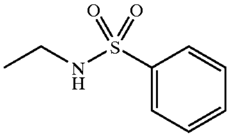 |
| 42 | 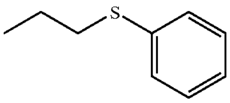 |

TABLE 196-continued
| 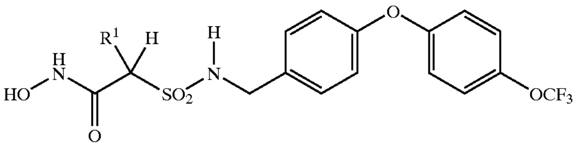 | |
|---|---|
| | 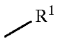 |
| 43 | 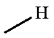 |
TABLE 197
| 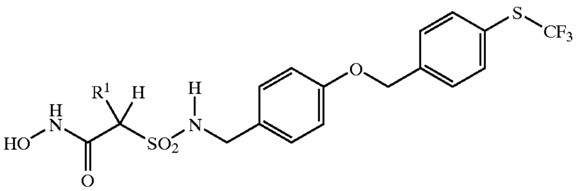 | |
|---|---|
| | 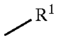 |
| 1 | $-CH_3$ |
| 2 | $-CH_2CH_3$ |
| 3 | $-CH(CH_3)_2$ |
| 4 | 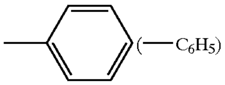 |
| 5 | 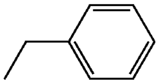 |
| 6 | 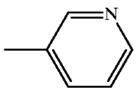 |
| 7 | 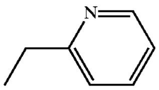 |
| 8 | $-CH_2-N(CH_3)_2$ |
| 9 | $-CH_2-N(CH_3)CH_2C_6H_5$ |
| 10 | 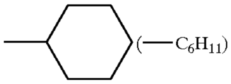 |
| 11 | 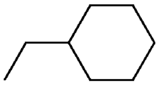 |
| 12 | 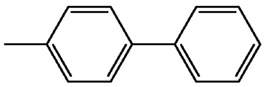 |
| 13 | 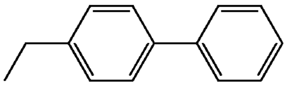 |
TABLE 197-continued
| 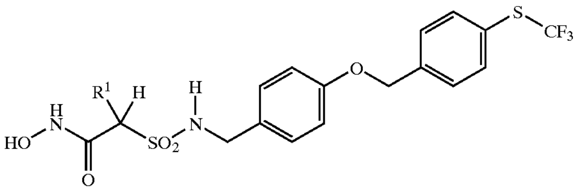 | |
|---|---|
| | 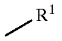 |
| 14 | $-CH_2CH{=}CHCH_3$ |
| 15 | 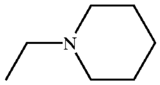 |
| 16 | 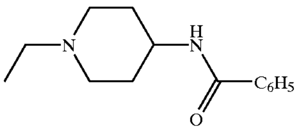 |
| 17 | 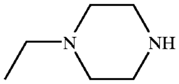 |
| 18 | 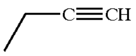 |
| 19 | 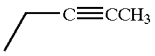 |
| 20 | 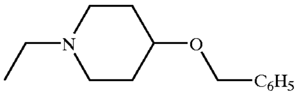 |
| 21 | 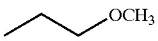 |
| 22 | 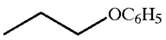 |
| 23 | 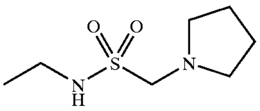 |
| 24 | 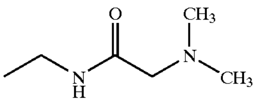 |
| 25 | 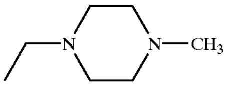 |
| 26 | 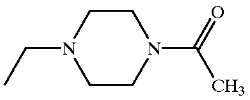 |
| 27 | 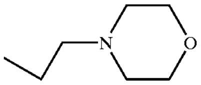 |

TABLE 197-continued
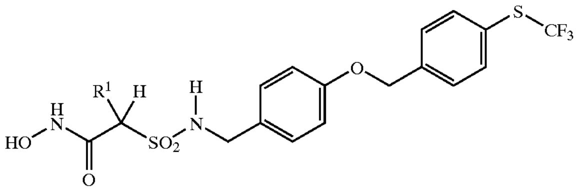
| | 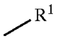 |
|---|---|
| 28 | 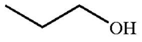 |
| 29 | 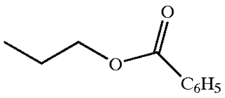 |
| 30 | 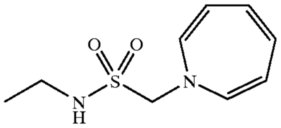 |
| 30 | 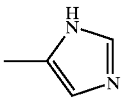 |
| 31 | 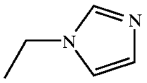 |
| 32 | 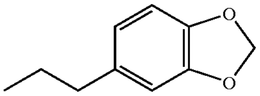 |
| 33 | 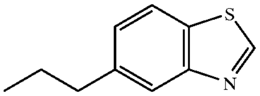 |
| 34 | 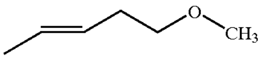 |
| 35 | 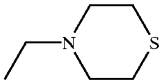 |
| 36 | 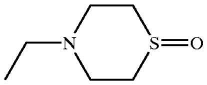 |
| 37 | 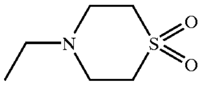 |
| 38 | 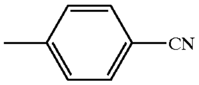 |
| 39 | 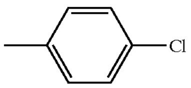 |
TABLE 197-continued
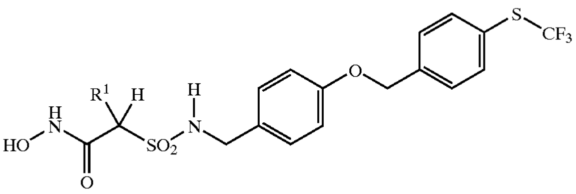
| | 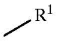 |
|---|---|
| 40 | 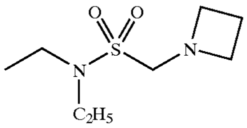 |
| 41 | 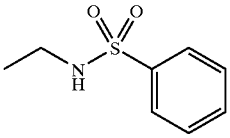 |
| 42 | 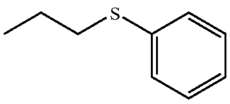 |
| 43 | 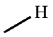 |
TABLE 198
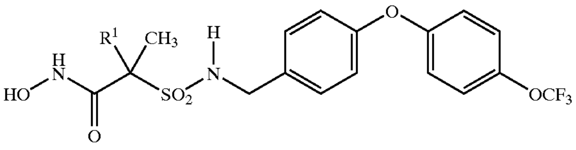
| | 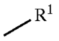 |
|---|---|
| 1 | $—CH_3$ |
| 2 | $—CH_2CH_3$ |
| 3 | $—CH(CH_3)_2$ |
| 4 | 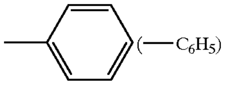 |
| 5 | 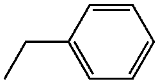 |
| 6 | 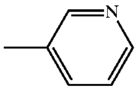 |
| 7 | 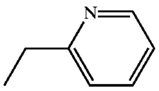 |
| 8 | $—CH_2—N(CH_3)_2$ |
| 9 | $—CH_2—N(CH_3)CH_2C_6H_5$ |

TABLE 198-continued
| 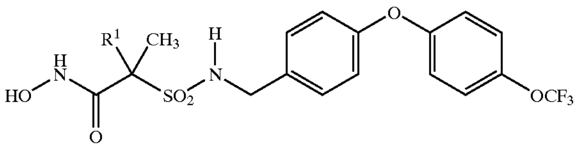 | 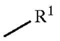 |
| --- | --- |
| 10 | 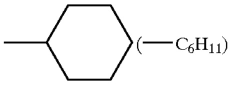 |
| 11 | 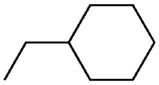 |
| 12 | 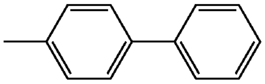 |
| 13 | 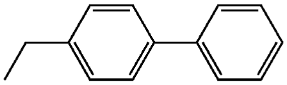 |
| 14 | $—CH_2CH{=}CHCH_3$ |
| 15 | 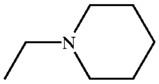 |
| 16 | 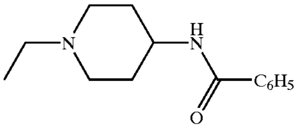 |
| 17 | 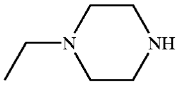 |
| 18 | 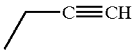 |
| 19 | 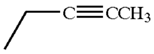 |
| 20 | 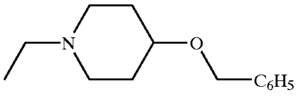 |
| 21 | 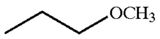 |
| 22 | 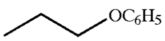 |
| 23 | 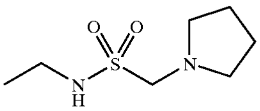 |
TABLE 198-continued
| 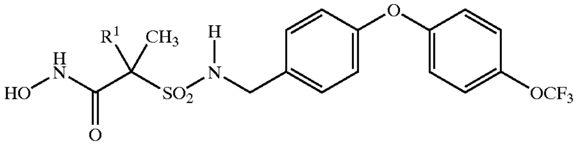 | 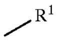 |
| --- | --- |
| 24 | 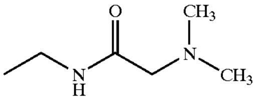 |
| 25 | 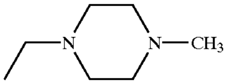 |
| 26 | 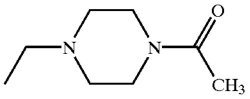 |
| 27 | 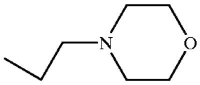 |
| 28 | 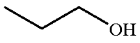 |
| 29 | 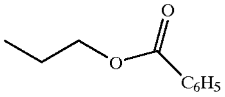 |
| 30 | 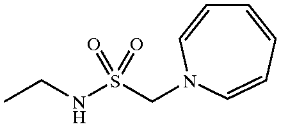 |
| 30 | 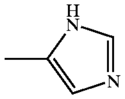 |
| 31 | 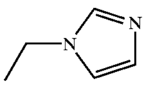 |
| 32 | 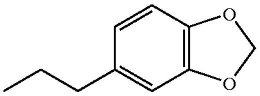 |
| 33 | 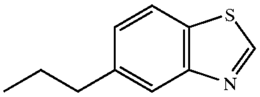 |
| 34 | 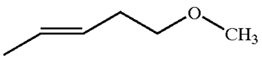 |
| 35 | 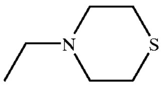 |

TABLE 198-continued
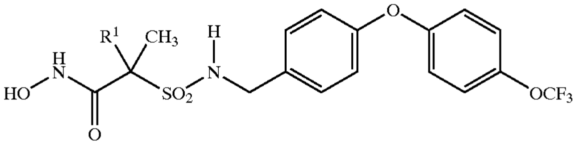
| | |
|---|---|
| 36 | 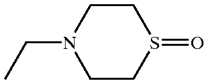 |
| 37 | 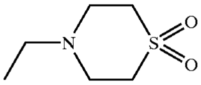 |
| 38 | 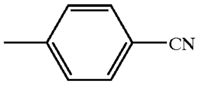 |
| 39 | 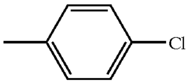 |
| 40 | 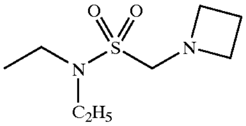 |
| 41 | 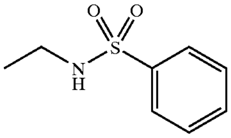 |
| 42 | 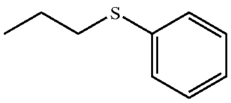 |
| 43 | 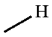 |
TABLE 199
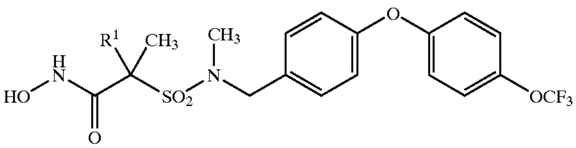
| | |
|---|---|
| 1 | $—CH_3$ |
| 2 | $—CH_2CH_3$ |
| 3 | $—CH(CH_3)_2$ |
| 4 | 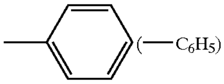 |
TABLE 199-continued
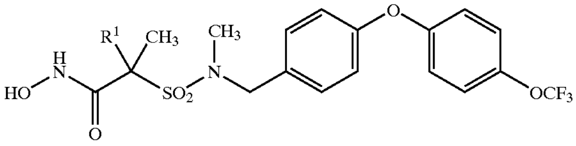
| | |
|---|---|
| 5 | 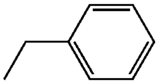 |
| 6 | 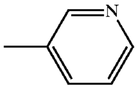 |
| 7 | 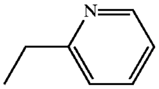 |
| 8 | $—CH_2—N(CH_3)_2$ |
| 9 | $—CH_2—N(CH_3)CH_2C_6H_5$ |
| 10 | 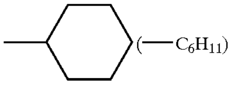 |
| 11 | 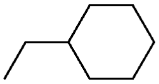 |
| 12 | 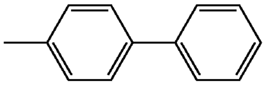 |
| 13 | 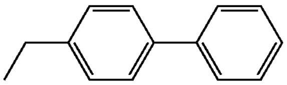 |
| 14 | $—CH_2CH{=}CHCH_3$ |
| 15 | 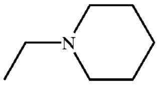 |
| 16 | 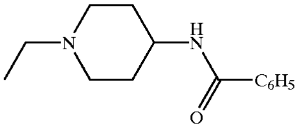 |
| 17 | 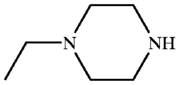 |
| 18 | 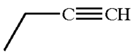 |
| 19 | 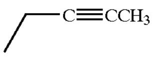 |

TABLE 199-continued
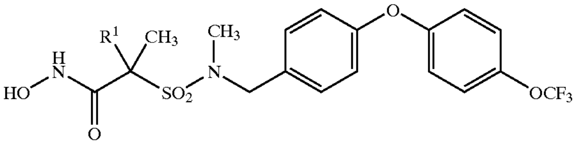
| | 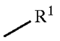 |
|---|---|
| 20 | 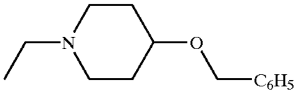 |
| 21 | 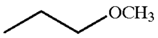 |
| 22 | 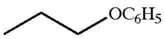 |
| 23 | 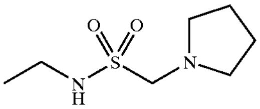 |
| 24 | 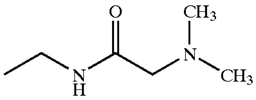 |
| 25 | 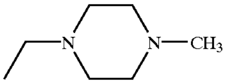 |
| 26 | 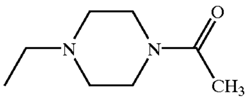 |
| 27 | 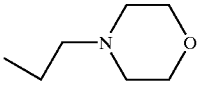 |
| 28 | 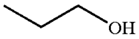 |
| 29 | 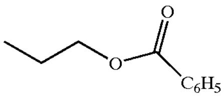 |
| 30 | 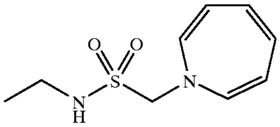 |
| 30 | 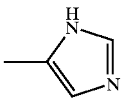 |
| 31 | 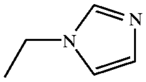 |
TABLE 199-continued
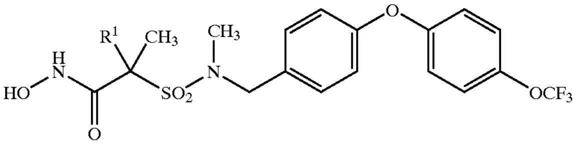
| | 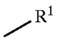 |
|---|---|
| 32 | 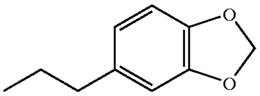 |
| 33 | 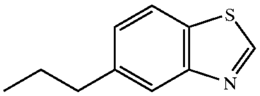 |
| 34 | 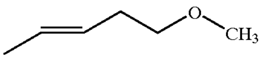 |
| 35 | 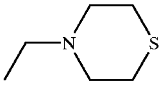 |
| 36 | 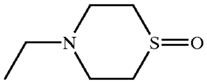 |
| 37 | 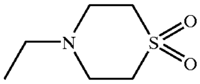 |
| 38 | 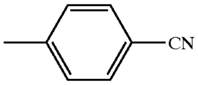 |
| 39 | 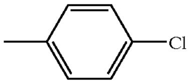 |
| 40 | 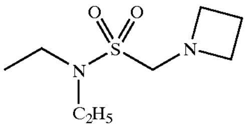 |
| 41 | 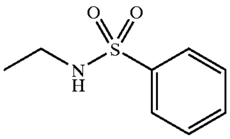 |
| 42 | 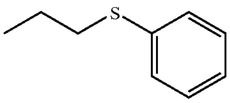 |
| 43 | 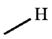 |

TABLE 200
| | $R^1$ |
|---|---|
| 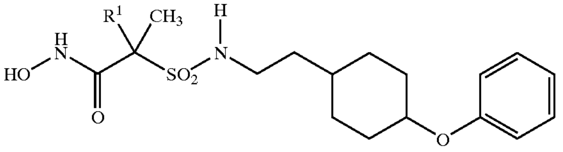 | 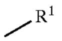 |
| 1 | $—CH_3$ |
| 2 | $—CH_2CH_3$ |
| 3 | $—CH(CH_3)_2$ |
| 4 | 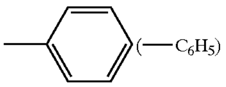 |
| 5 | 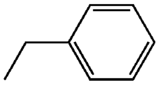 |
| 6 | 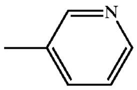 |
| 7 | 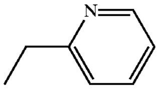 |
| 8 | $—CH_2—N(CH_3)_2$ |
| 9 | $—CH_2—N(CH_3)CH_2C_6H_5$ |
| 10 | 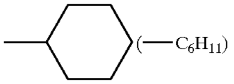 |
| 11 | 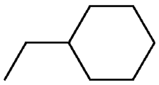 |
| 12 | 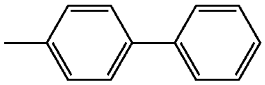 |
| 13 | 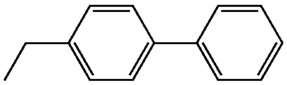 |
| 14 | $—CH_2CH{=}CHCH_3$ |
| 15 | 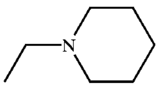 |
| 16 | 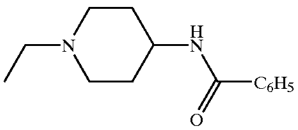 |
| 17 | 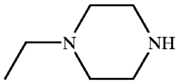 |
TABLE 200-continued
| | $R^1$ |
|---|---|
| 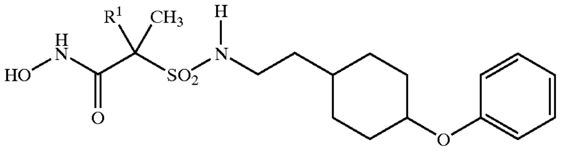 | 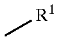 |
| 18 | 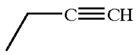 |
| 19 | 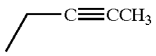 |
| 20 | 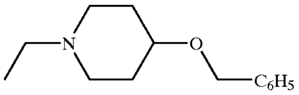 |
| 21 | 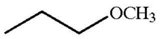 |
| 22 | 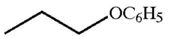 |
| 23 | 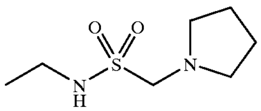 |
| 24 | 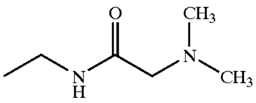 |
| 25 | 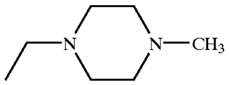 |
| 26 | 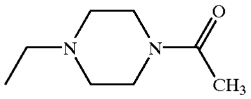 |
| 27 | 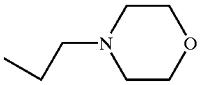 |
| 28 | 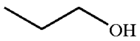 |
| 29 | 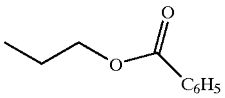 |
| 30 | 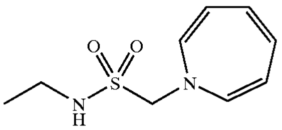 |
| 30 | 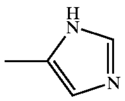 |

TABLE 200-continued
| 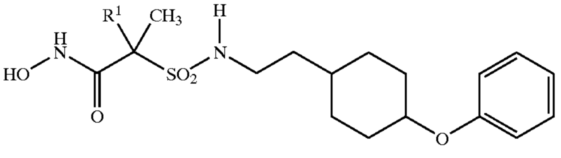 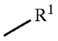 | |
|---|---|
| 31 | 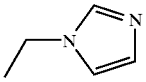 |
| 32 | 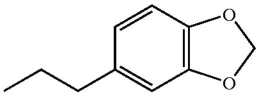 |
| 33 | 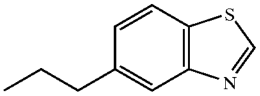 |
| 34 | 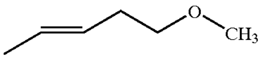 |
| 35 | 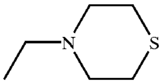 |
| 36 | 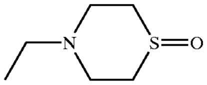 |
| 37 | 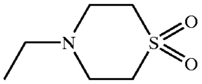 |
| 38 | 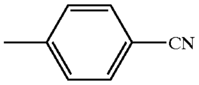 |
| 39 | 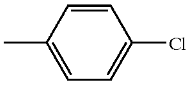 |
| 40 | 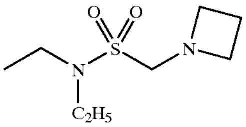 |
| 41 | 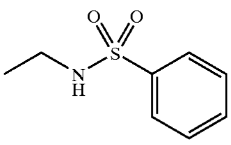 |
| 42 | 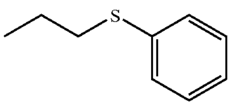 |
TABLE 200-continued
| 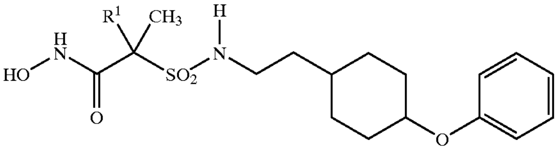 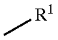 | |
|---|---|
| 43 | 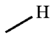 |
TABLE 201
| 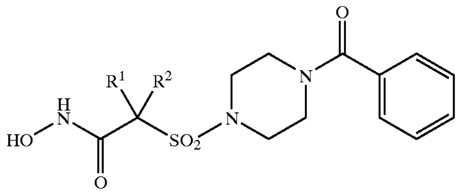 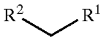 | |
|---|---|
| 1 | 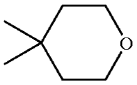 |
| 2 | 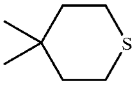 |
| 3 | 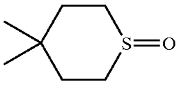 |
| 4 | 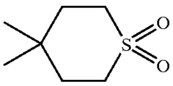 |
| 5 | 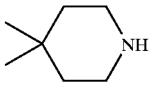 |
| 6 | 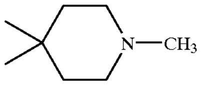 |
| 7 | 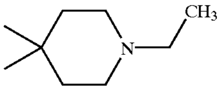 |
| 8 | 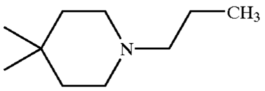 |
| 9 | 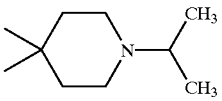 |

TABLE 201-continued
| | |
|---|---|
| 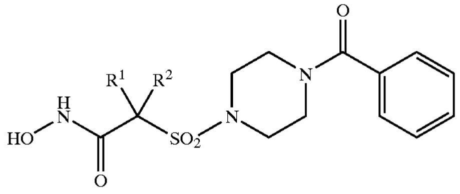 | |
| 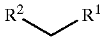 | |
| 10 | 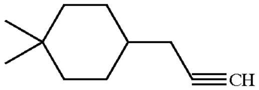 |
| 11 | 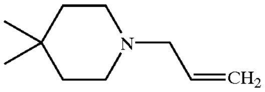 |
| 12 | 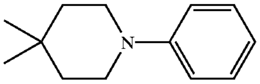 |
| 13 | 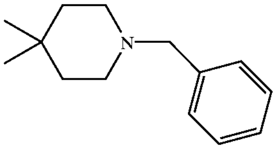 |
| 14 | 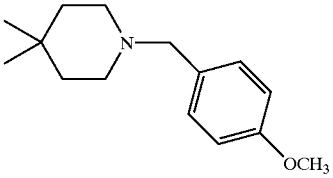 |
| 15 | 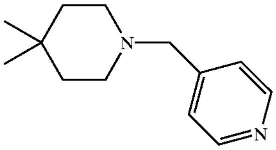 |
| 16 | 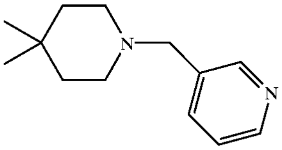 |
| 17 | 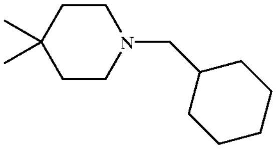 |
| 18 | 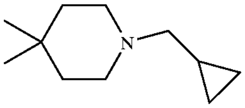 |
TABLE 201-continued
| | |
|---|---|
| 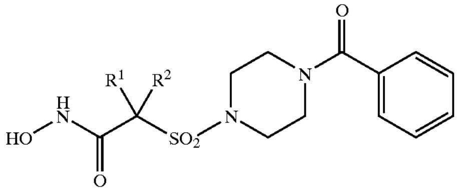 | |
| 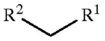 | |
| 19 | 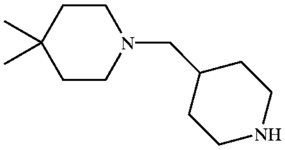 |
| 20 | 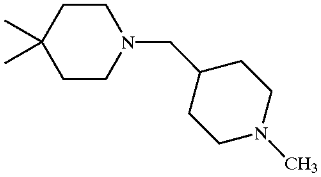 |
| 21 | 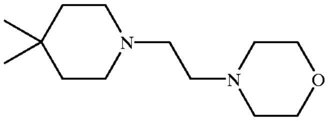 |
| 22 | 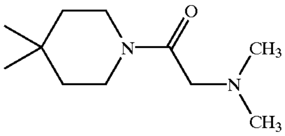 |
| 23 | 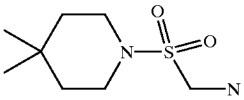 |
| 24 | 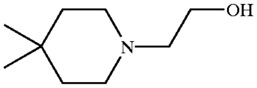 |
| 25 | 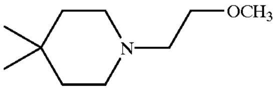 |
| 26 | 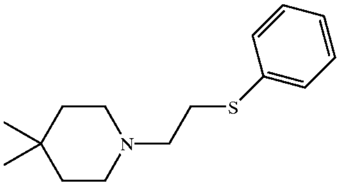 |
| 27 | 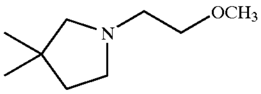 |

TABLE 201-continued
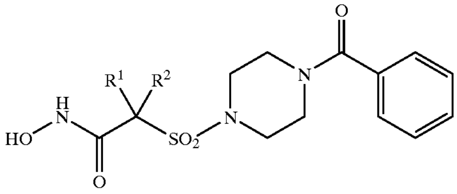
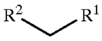
| | |
|---|---|
| 28 | 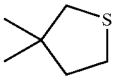 |
| 29 | 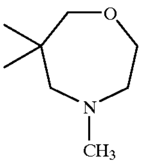 |
| 30 | 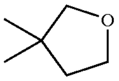 |
| 31 | 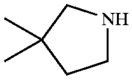 |
| 32 | 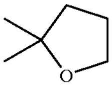 |
TABLE 202
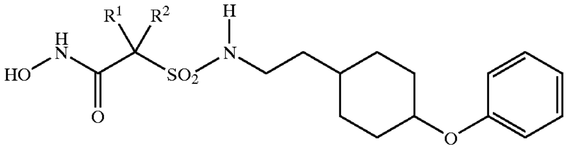
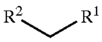
| | |
|---|---|
| 1 | 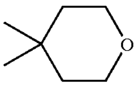 |
| 2 | 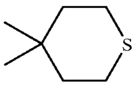 |
| 3 | 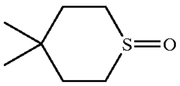 |
| 4 | 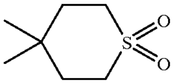 |
TABLE 202-continued
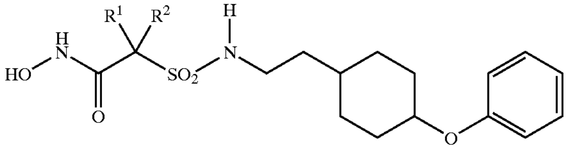
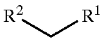
| | |
|---|---|
| 5 | 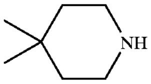 |
| 6 | 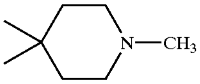 |
| 7 | 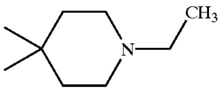 |
| 8 | 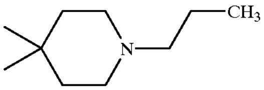 |
| 9 | 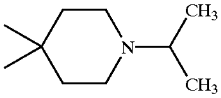 |
| 10 | 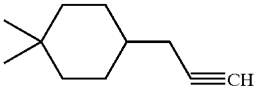 |
| 11 | 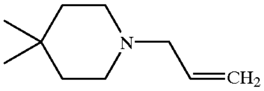 |
| 12 | 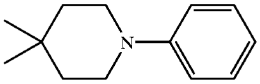 |
| 13 | 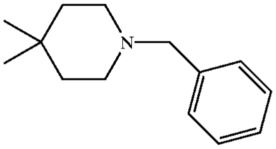 |
| 14 | 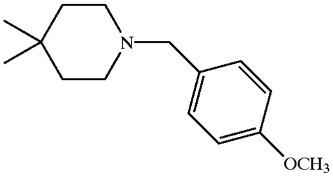 |
| 15 | 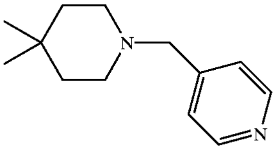 |

TABLE 202-continued
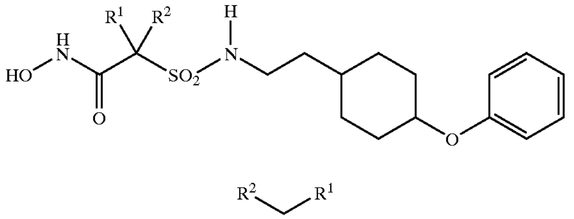
| | |
|---|---|
| 16 | 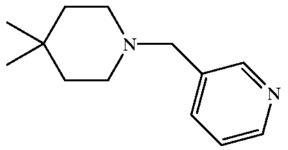 |
| 17 | 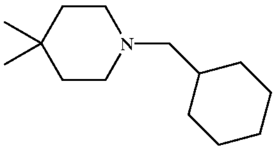 |
| 18 | 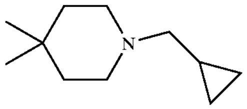 |
| 19 | 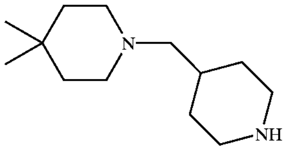 |
| 20 | 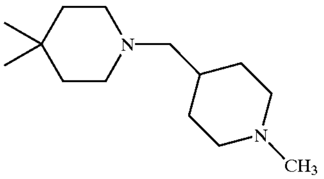 |
| 21 | 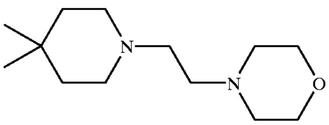 |
| 22 | 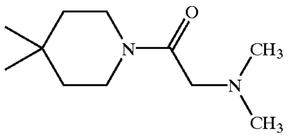 |
| 23 | 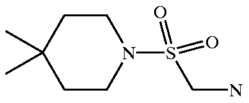 |
| 24 | 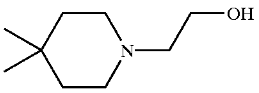 |
TABLE 202-continued
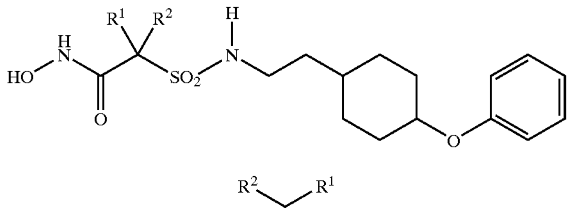
| | |
|---|---|
| 25 | 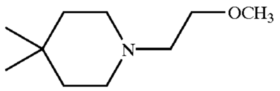 |
| 26 | 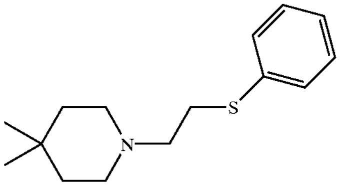 |
| 27 | 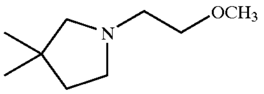 |
| 28 | 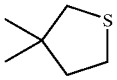 |
| 29 | 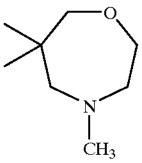 |
| 30 | 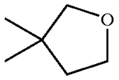 |
| 31 | 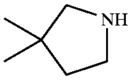 |
| 32 | 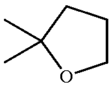 |
TABLE 203
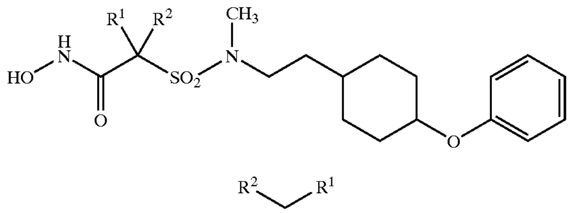
| | |
|---|---|
| 1 | 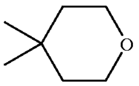 |

TABLE 203-continued
| | |
|---|---|
| | 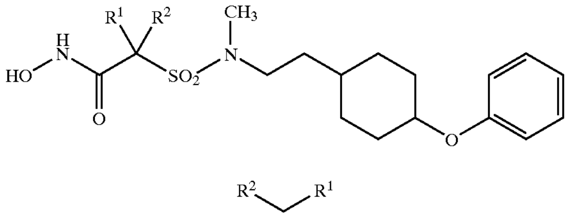 |
| 2 | 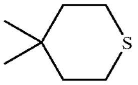 |
| 3 | 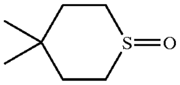 |
| 4 | 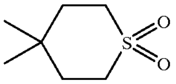 |
| 5 | 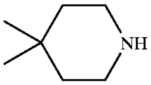 |
| 6 | 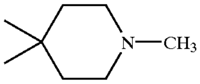 |
| 7 | 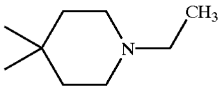 |
| 8 | 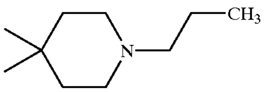 |
| 9 | 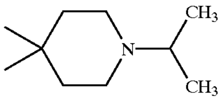 |
| 10 | 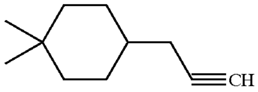 |
| 11 | 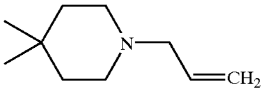 |
| 12 | 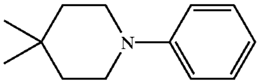 |
| 13 | 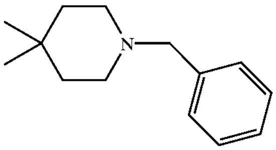 |
TABLE 203-continued
| | |
|---|---|
| | 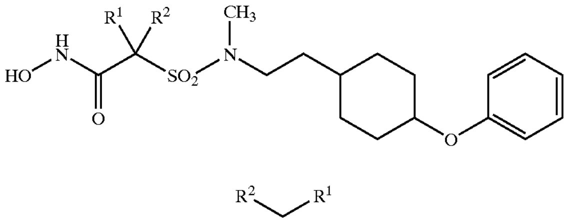 |
| 14 | 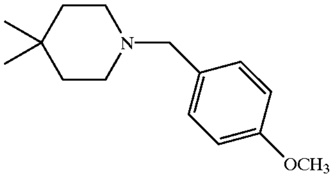 |
| 15 | 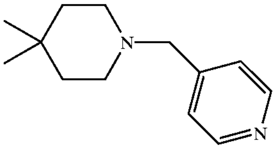 |
| 16 | 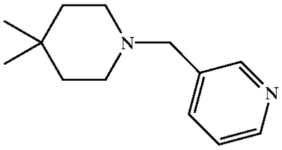 |
| 17 | 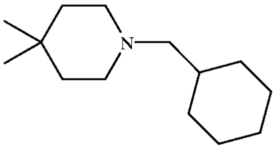 |
| 18 | 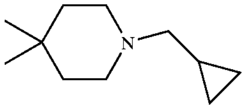 |
| 19 | 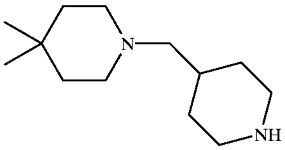 |
| 20 | 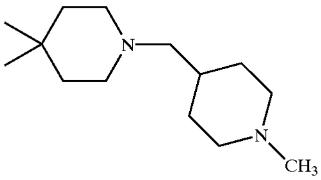 |
| 21 | 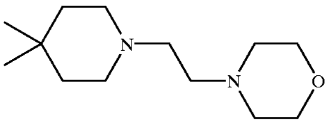 |

TABLE 203-continued
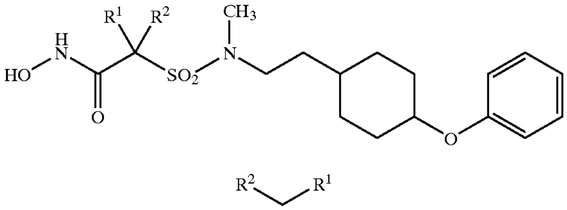
| | |
|---|---|
| 22 | 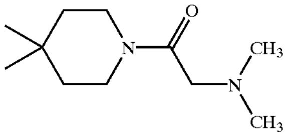 |
| 23 | 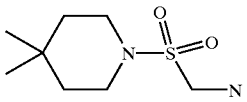 |
| 24 | 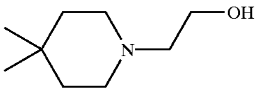 |
| 25 | 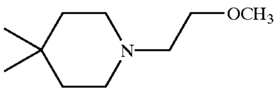 |
| 26 | 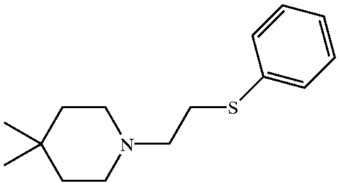 |
| 27 | 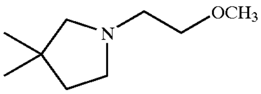 |
| 28 | 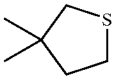 |
| 29 | 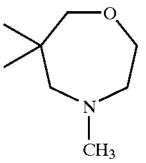 |
| 30 | 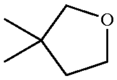 |
| 31 | 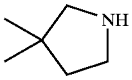 |
| 32 | 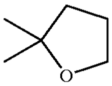 |
TABLE 204
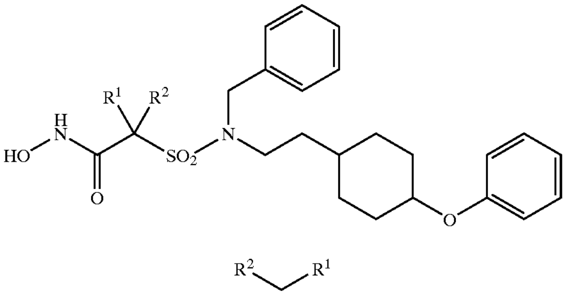
| | |
|---|---|
| 1 | 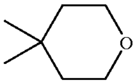 |
| 2 | 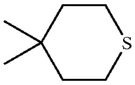 |
| 3 | 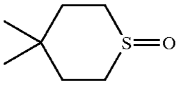 |
| 4 | 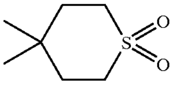 |
| 5 | 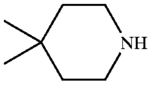 |
| 6 | 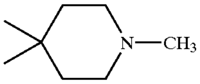 |
| 7 | 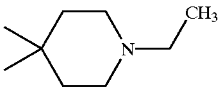 |
| 8 | 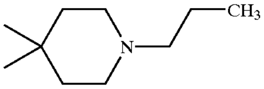 |
| 9 | 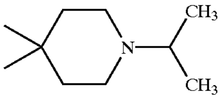 |
| 10 | 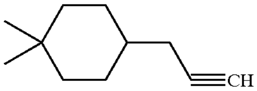 |
| 11 | 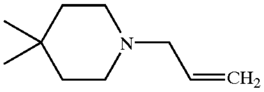 |
| 12 | 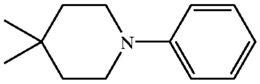 |

TABLE 204-continued
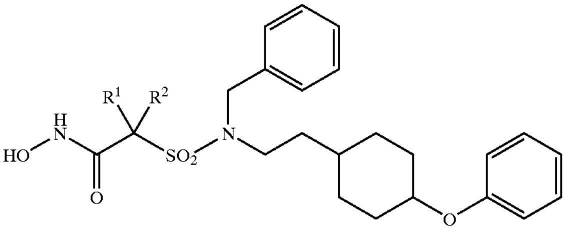
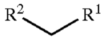
| | |
|---|---|
| 13 | 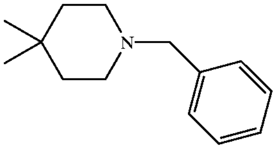 |
| 14 | 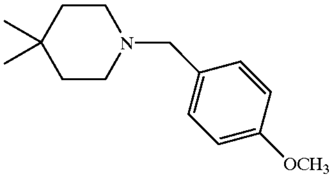 |
| 15 | 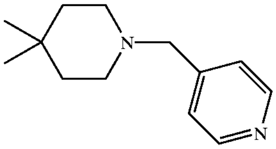 |
| 16 | 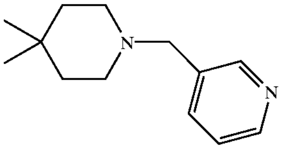 |
| 17 | 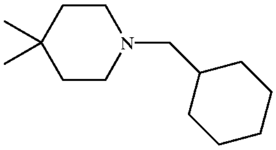 |
| 18 | 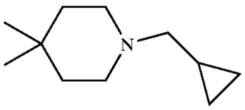 |
| 19 | 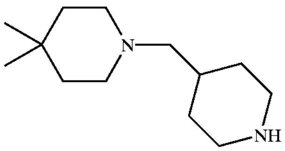 |
| 20 | 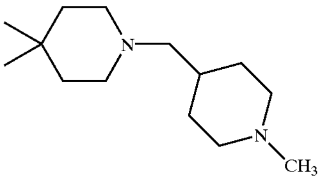 |
TABLE 204-continued
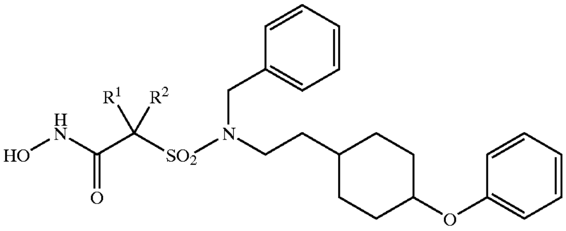
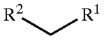
| | |
|---|---|
| 21 | 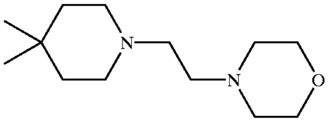 |
| 22 | 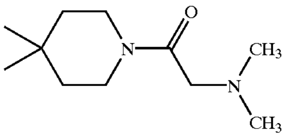 |
| 23 | 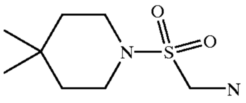 |
| 24 | 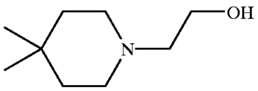 |
| 25 | 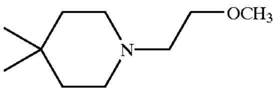 |
| 26 | 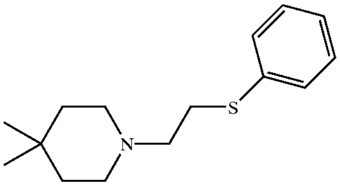 |
| 27 | 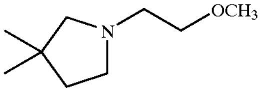 |
| 28 | 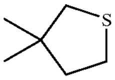 |
| 29 | 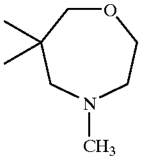 |
| 30 | 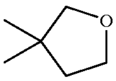 |

TABLE 204-continued
| | |
|---|---|
| | 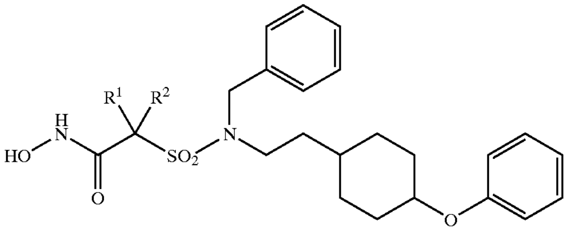 |
| | 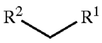 |
| 31 | 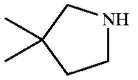 |
| 32 | 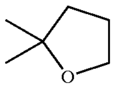 |
TABLE 205
| | |
|---|---|
| | 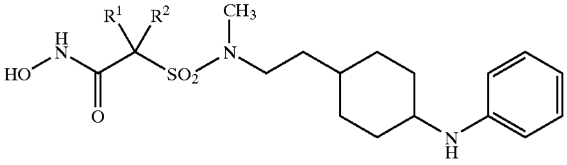 |
| | 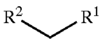 |
| 1 | 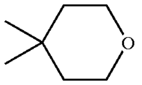 |
| 2 | 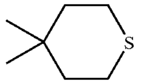 |
| 3 | 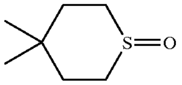 |
| 4 | 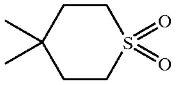 |
| 5 | 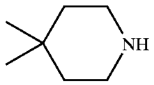 |
| 6 | 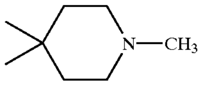 |
| 7 | 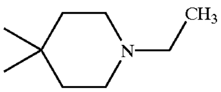 |
TABLE 205-continued
| | |
|---|---|
| | 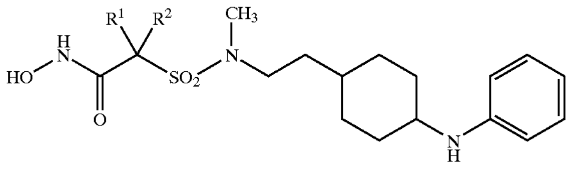 |
| | 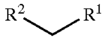 |
| 8 | 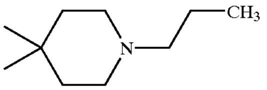 |
| 9 | 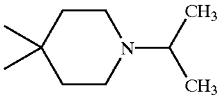 |
| 10 | 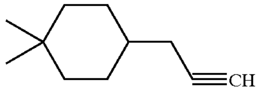 |
| 11 | 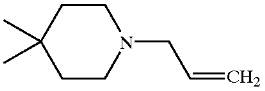 |
| 12 | 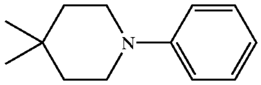 |
| 13 | 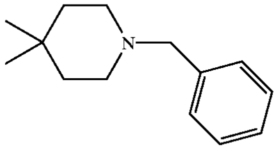 |
| 14 | 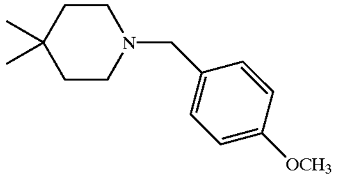 |
| 15 | 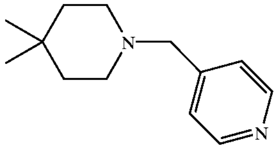 |
| 16 | 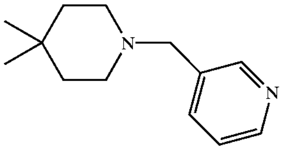 |
| 17 | 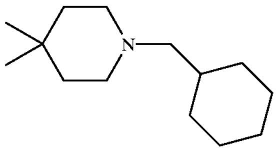 |

TABLE 205-continued
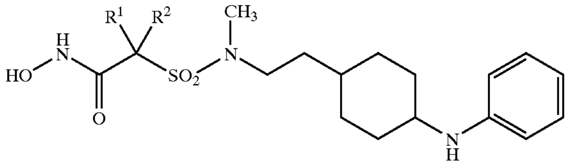
| | 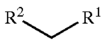 |
|---|---|
| 18 | 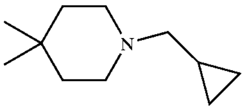 |
| 19 | 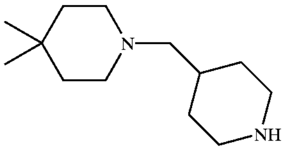 |
| 20 | 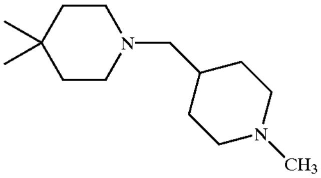 |
| 21 | 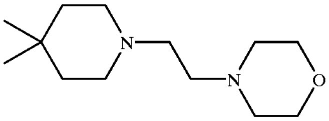 |
| 22 | 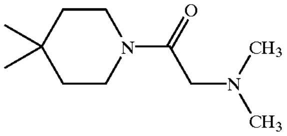 |
| 23 | 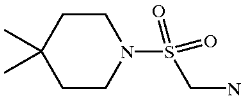 |
| 24 | 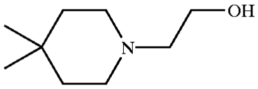 |
| 25 | 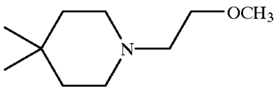 |
| 26 | 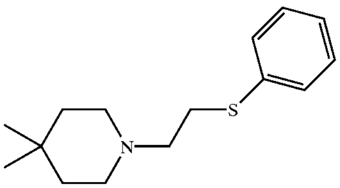 |
TABLE 205-continued
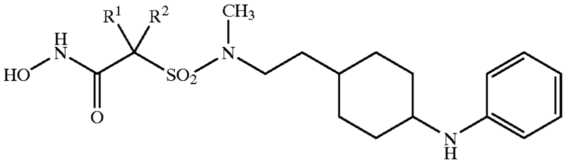
| | 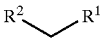 |
|---|---|
| 27 | 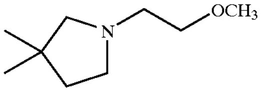 |
| 28 | 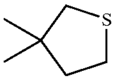 |
| 29 | 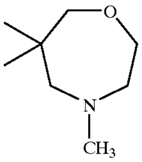 |
| 30 | 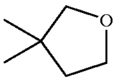 |
| 31 | 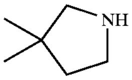 |
| 32 | 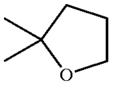 |
TABLE 206
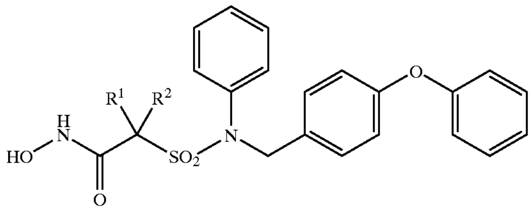
| | 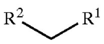 |
|---|---|
| 1 | 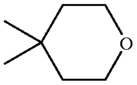 |
| 2 | 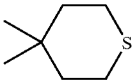 |
| 3 | 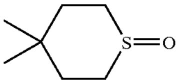 |

TABLE 206-continued
| | 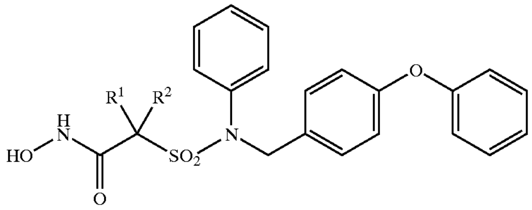 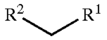 |
|---|---|
| 4 | 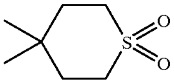 |
| 5 | 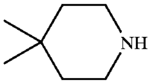 |
| 6 | 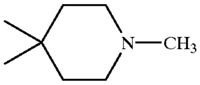 |
| 7 | 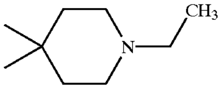 |
| 8 | 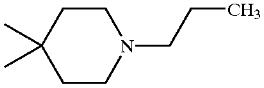 |
| 9 | 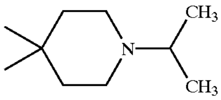 |
| 10 | 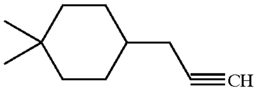 |
| 11 | 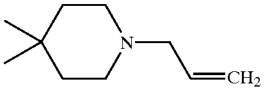 |
| 12 | 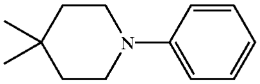 |
| 13 | 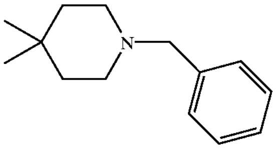 |
| 14 | 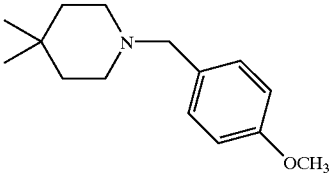 |
TABLE 206-continued
| | 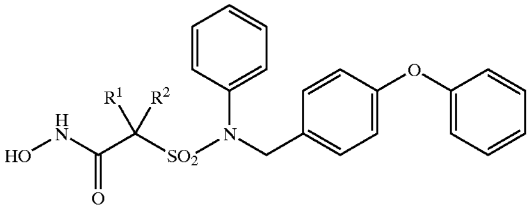 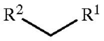 |
|---|---|
| 15 | 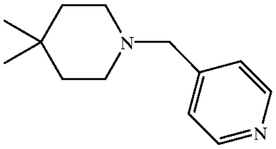 |
| 16 | 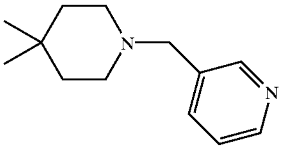 |
| 17 | 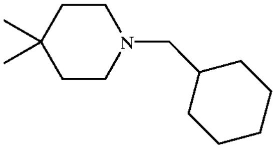 |
| 18 | 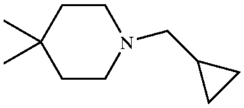 |
| 19 | 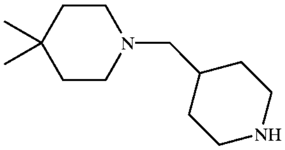 |
| 20 | 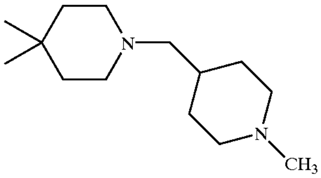 |
| 21 | 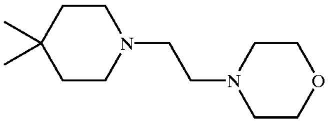 |
| 22 | 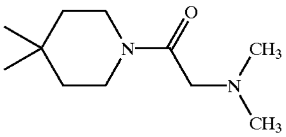 |

TABLE 206-continued
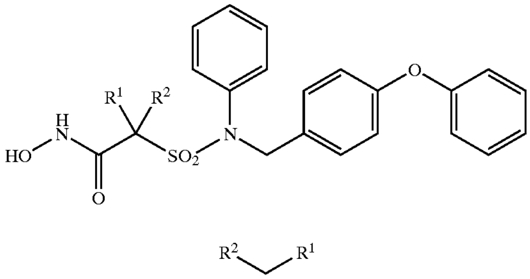
| | |
|---|---|
| 23 | 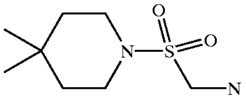 |
| 24 | 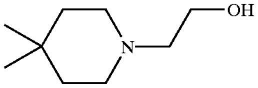 |
| 25 | 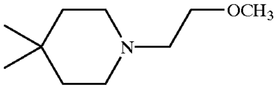 |
| 26 | 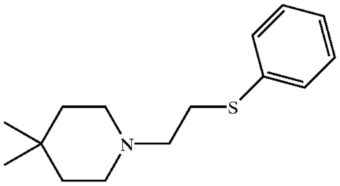 |
| 27 | 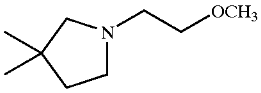 |
| 28 | 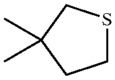 |
| 29 | 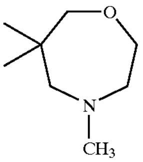 |
| 30 | 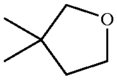 |
| 31 | 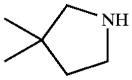 |
| 32 | 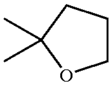 |
TABLE 207
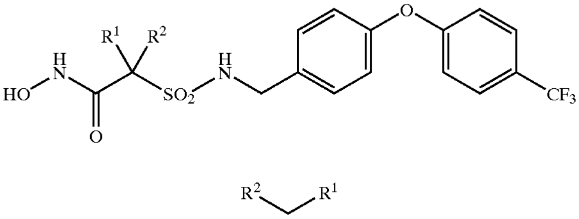
| | |
|---|---|
| 1 | 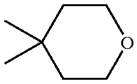 |
| 2 | 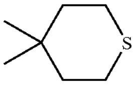 |
| 3 | 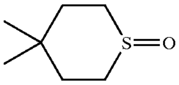 |
| 4 | 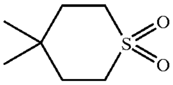 |
| 5 | 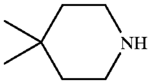 |
| 6 | 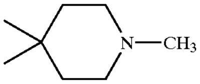 |
| 7 | 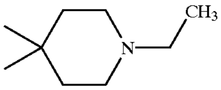 |
| 8 | 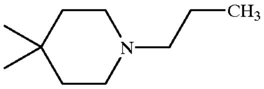 |
| 9 | 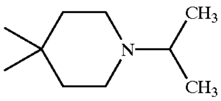 |
| 10 | 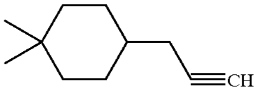 |
| 11 | 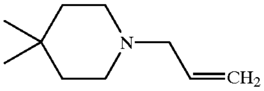 |
| 12 | 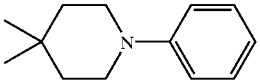 |

TABLE 207-continued
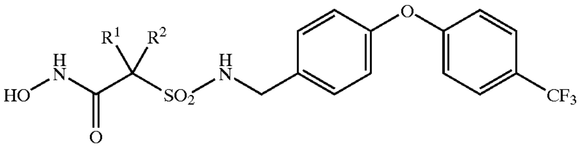
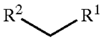
| | |
|---|---|
| 13 | 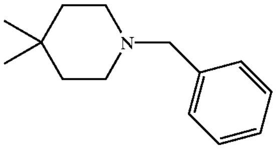 |
| 14 | 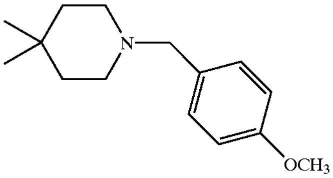 |
| 15 | 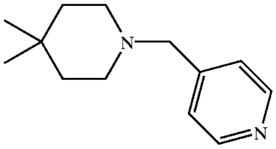 |
| 16 | 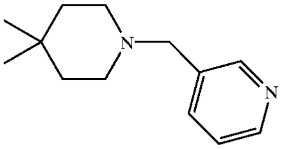 |
| 17 | 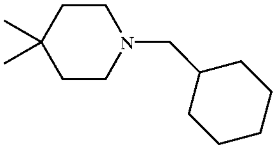 |
| 18 | 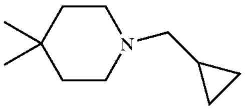 |
| 19 | 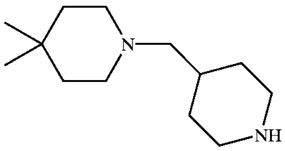 |
| 20 | 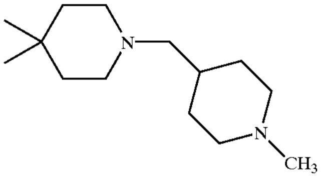 |
TABLE 207-continued
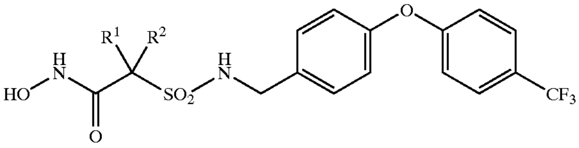
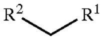
| | |
|---|---|
| 21 | 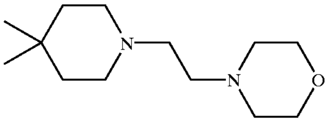 |
| 22 | 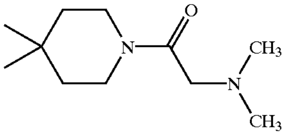 |
| 23 | 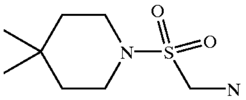 |
| 24 | 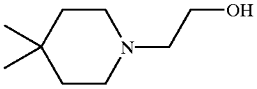 |
| 25 | 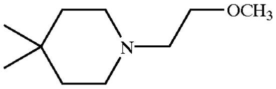 |
| 26 | 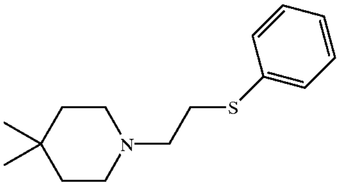 |
| 27 | 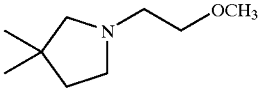 |
| 28 | 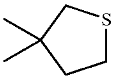 |
| 29 | 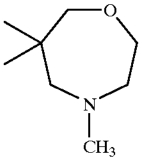 |
| 30 | 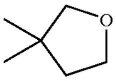 |
| 31 | 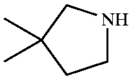 |

TABLE 207-continued
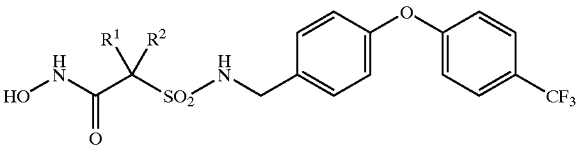
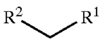
| | |
|---|---|
| 32 | 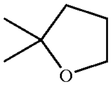 |
TABLE 208
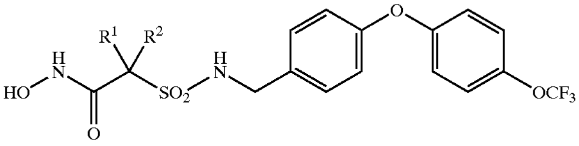
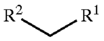
| | |
|---|---|
| 1 | 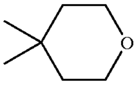 |
| 2 | 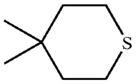 |
| 3 | 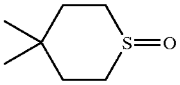 |
| 4 | 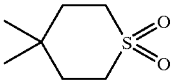 |
| 5 | 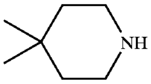 |
| 6 | 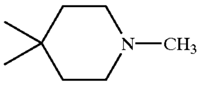 |
| 7 | 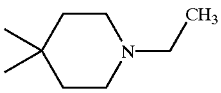 |
| 8 | 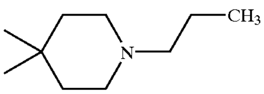 |
| 9 | 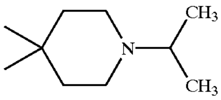 |
TABLE 208-continued
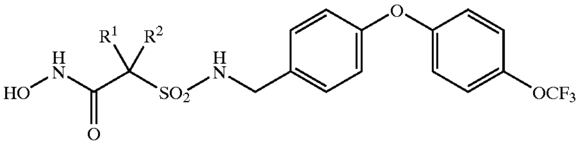
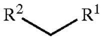
| | |
|---|---|
| 10 | 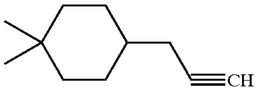 |
| 11 | 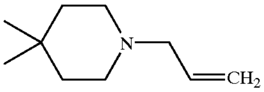 |
| 12 | 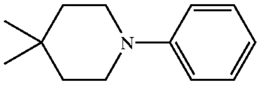 |
| 13 | 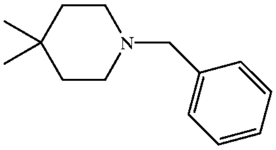 |
| 14 | 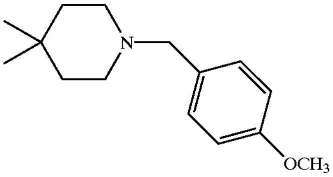 |
| 15 | 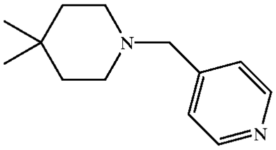 |
| 16 | 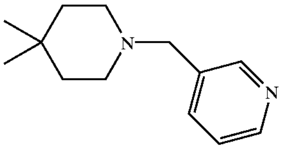 |
| 17 | 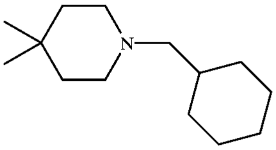 |
| 18 | 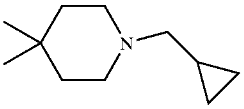 |

TABLE 208-continued
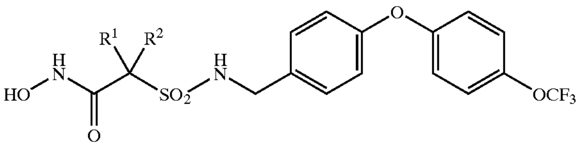
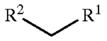
| | |
|---|---|
| 19 | 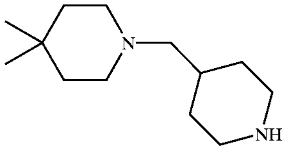 |
| 20 | 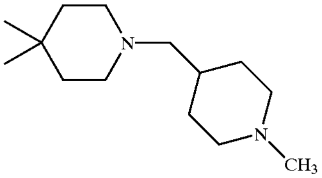 |
| 21 | 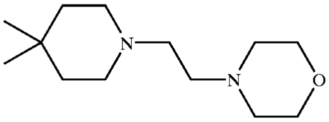 |
| 22 | 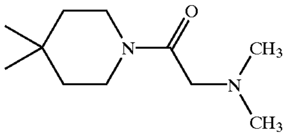 |
| 23 | 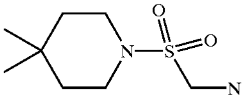 |
| 24 | 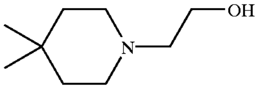 |
| 25 | 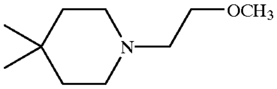 |
| 26 | 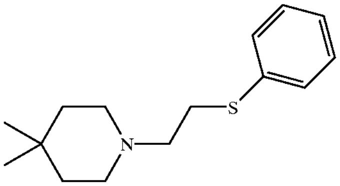 |
| 27 | 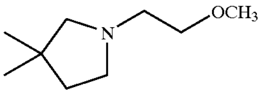 |
| 28 | 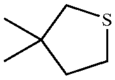 |
TABLE 208-continued
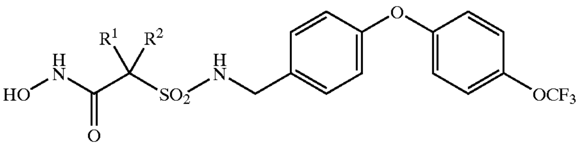
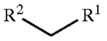
| | |
|---|---|
| 29 | 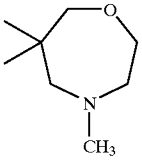 |
| 30 | 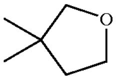 |
| 31 | 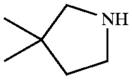 |
| 32 | 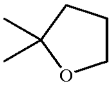 |
TABLE 209
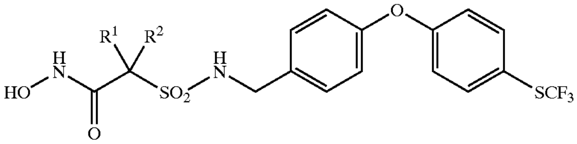
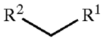
| | |
|---|---|
| 1 | 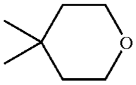 |
| 2 | 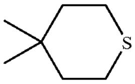 |
| 3 | 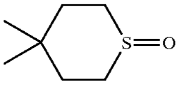 |
| 4 | 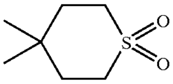 |
| 5 | 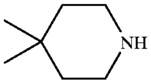 |
| 6 | 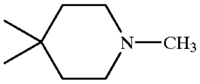 |

TABLE 209-continued
| | |
|---|---|
| 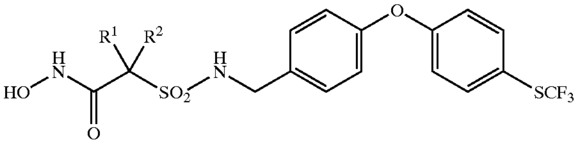 | |
| 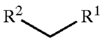 | |
| 7 | 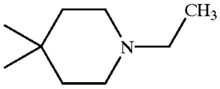 |
| 8 | 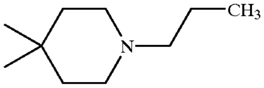 |
| 9 | 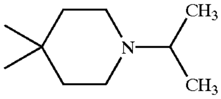 |
| 10 | 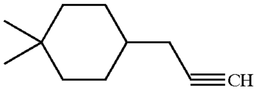 |
| 11 | 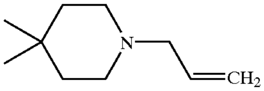 |
| 12 | 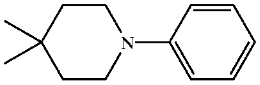 |
| 13 | 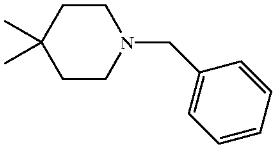 |
| 14 | 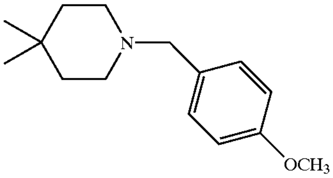 |
| 15 | 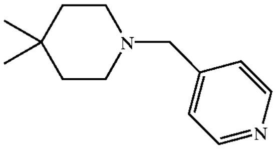 |
| 16 | 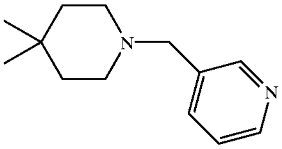 |
TABLE 209-continued
| | |
|---|---|
| 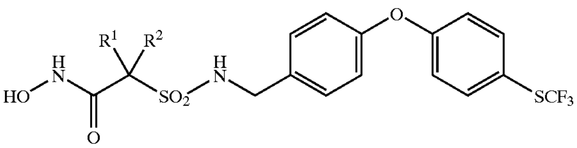 | |
| 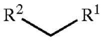 | |
| 17 | 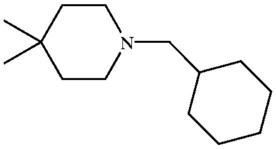 |
| 18 | 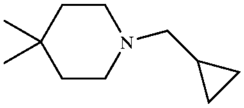 |
| 19 | 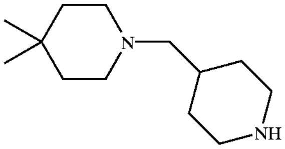 |
| 20 | 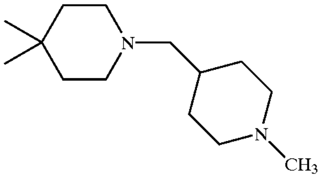 |
| 21 | 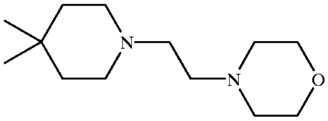 |
| 22 | 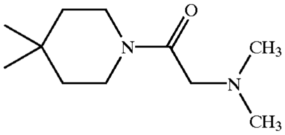 |
| 23 | 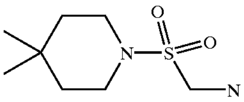 |
| 24 | 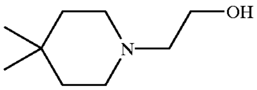 |
| 25 | 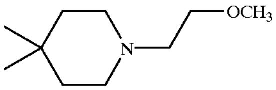 |

TABLE 209-continued
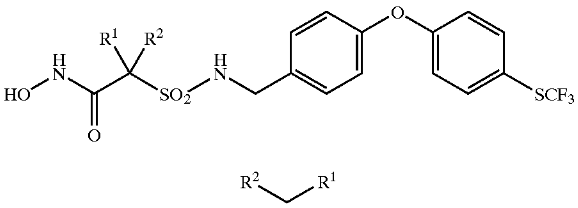
| | |
|---|---|
| 26 | 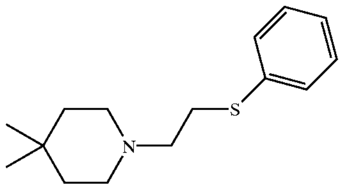 |
| 27 | 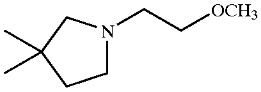 |
| 28 | 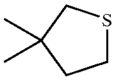 |
| 29 | 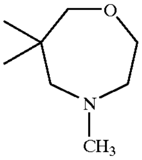 |
| 30 | 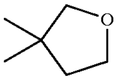 |
| 31 | 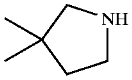 |
| 32 | 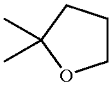 |
TABLE 210
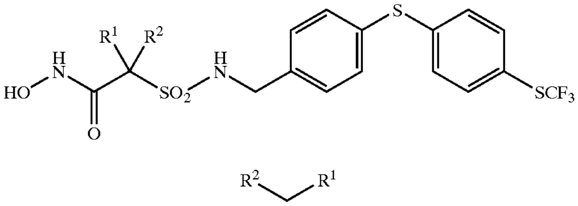
| | |
|---|---|
| 1 | 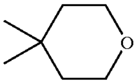 |
| 2 | 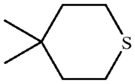 |
TABLE 210-continued
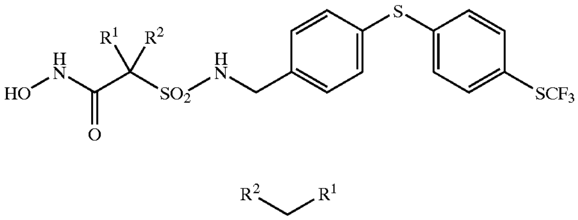
| | |
|---|---|
| 3 | 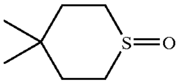 |
| 4 | 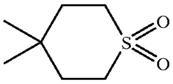 |
| 5 | 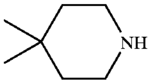 |
| 6 | 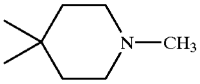 |
| 7 | 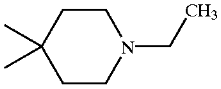 |
| 8 | 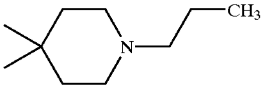 |
| 9 | 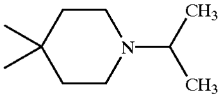 |
| 10 | 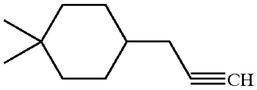 |
| 11 | 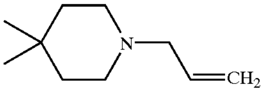 |
| 12 | 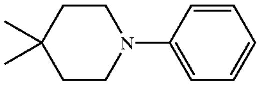 |
| 13 | 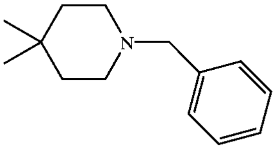 |

TABLE 210-continued
| 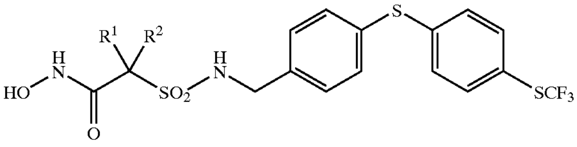 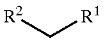 | |
|---|---|
| 14 | 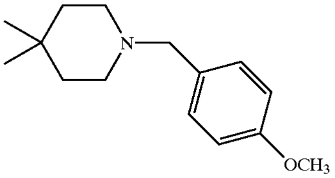 |
| 15 | 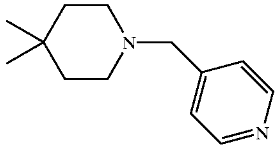 |
| 16 | 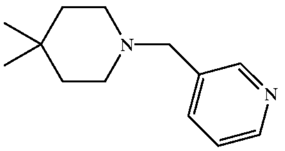 |
| 17 | 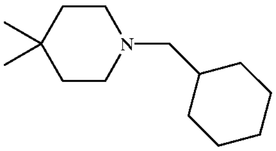 |
| 18 | 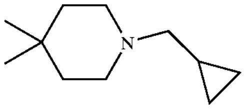 |
| 19 | 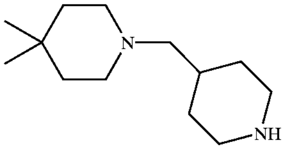 |
| 20 | 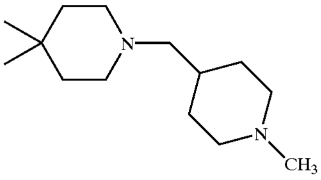 |
| 21 | 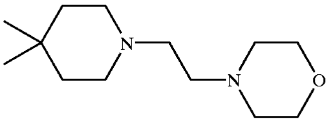 |
TABLE 210-continued
| 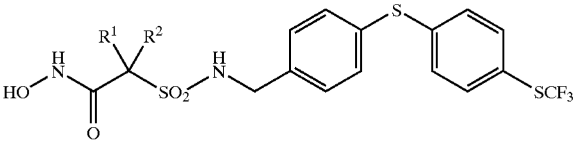 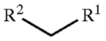 | |
|---|---|
| 22 | 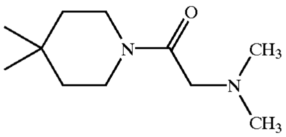 |
| 23 | 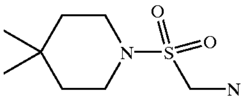 |
| 24 | 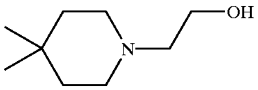 |
| 25 | 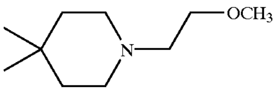 |
| 26 | 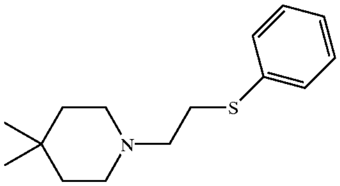 |
| 27 | 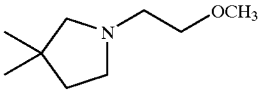 |
| 28 | 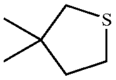 |
| 29 | 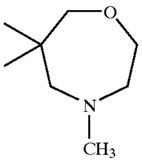 |
| 30 | 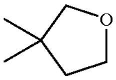 |
| 31 | 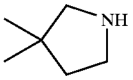 |
| 32 | 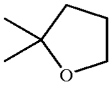 |

TABLE 211
| | |
|---|---|
| | 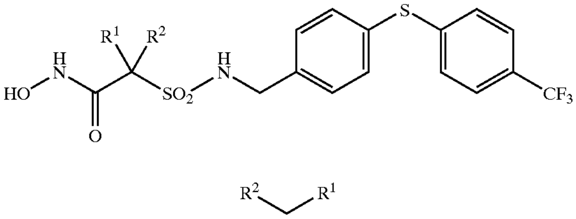 |
| 1 | 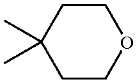 |
| 2 | 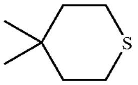 |
| 3 | 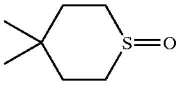 |
| 4 | 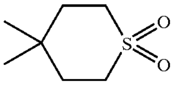 |
| 5 | 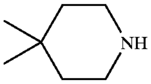 |
| 6 | 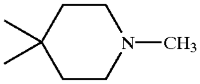 |
| 7 | 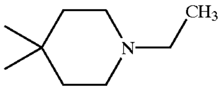 |
| 8 | 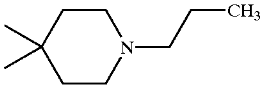 |
| 9 | 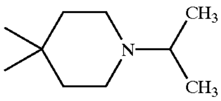 |
| 10 | 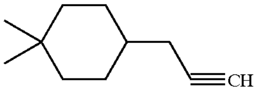 |
| 11 | 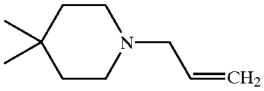 |
| 12 | 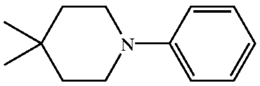 |
TABLE 211-continued
| | |
|---|---|
| | 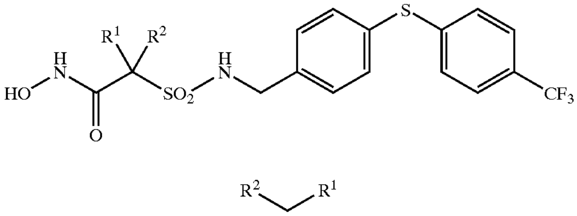 |
| 13 | 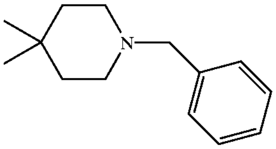 |
| 14 | 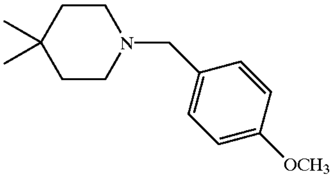 |
| 15 | 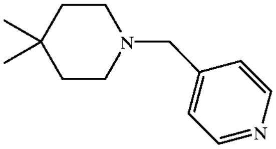 |
| 16 | 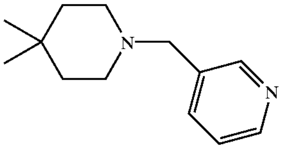 |
| 17 | 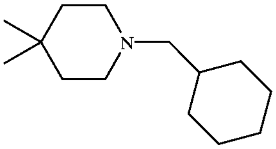 |
| 18 | 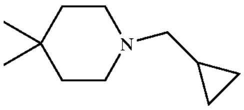 |
| 19 | 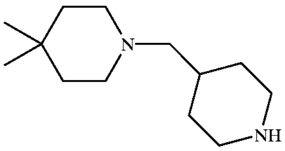 |
| 20 | 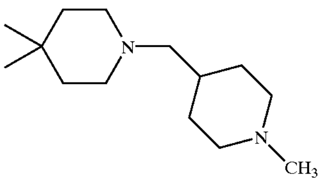 |

TABLE 211-continued
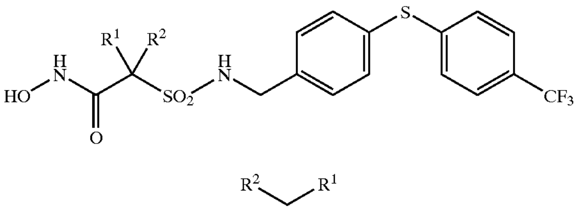
| | |
|---|---|
| 21 | 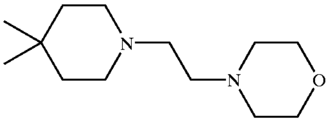 |
| 22 | 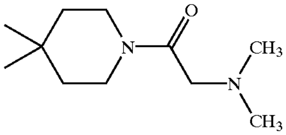 |
| 23 | 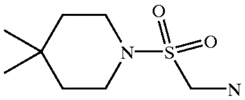 |
| 24 | 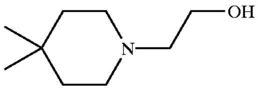 |
| 25 | 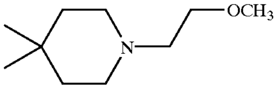 |
| 26 | 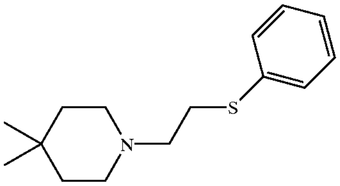 |
| 27 | 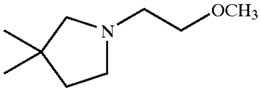 |
| 28 | 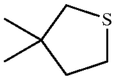 |
| 29 | 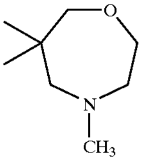 |
| 30 | 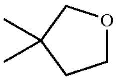 |
| 31 | 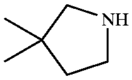 |
TABLE 211-continued
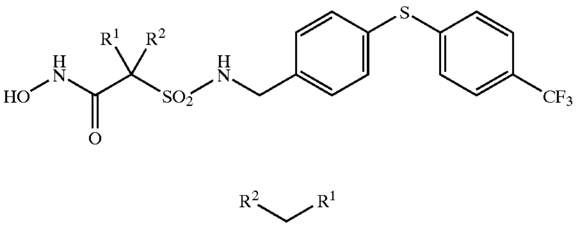
| | |
|---|---|
| 32 | 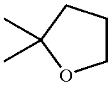 |
TABLE 212
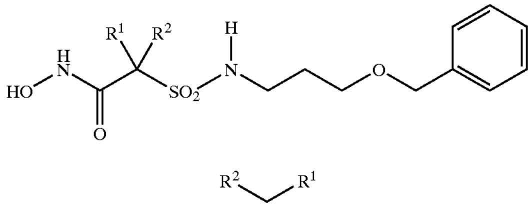
| | |
|---|---|
| 1 | 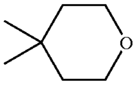 |
| 2 | 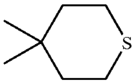 |
| 3 | 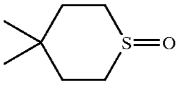 |
| 4 | 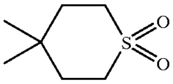 |
| 5 | 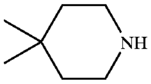 |
| 6 | 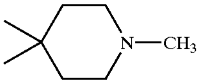 |
| 7 | 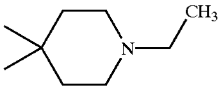 |
| 8 | 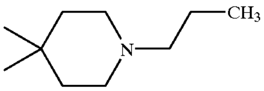 |
| 9 | 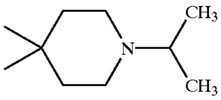 |

TABLE 212-continued
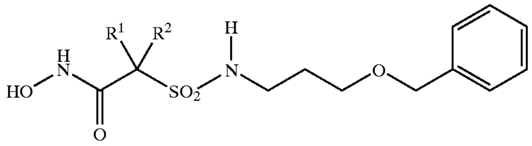
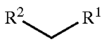
| | |
|---|---|
| 10 | 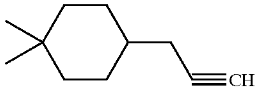 |
| 11 | 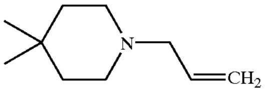 |
| 12 | 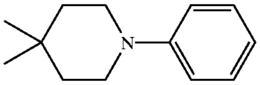 |
| 13 | 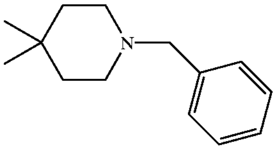 |
| 14 | 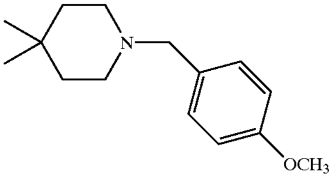 |
| 15 | 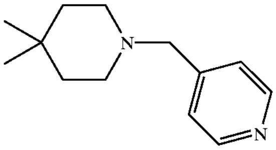 |
| 16 | 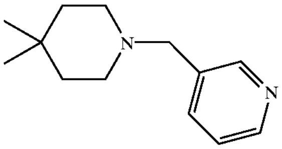 |
| 17 | 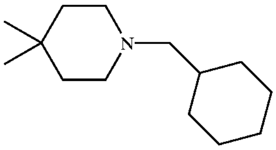 |
| 18 | 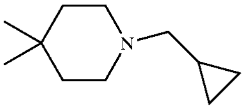 |
TABLE 212-continued
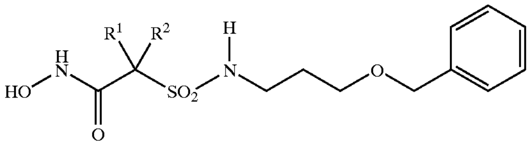
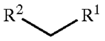
| | |
|---|---|
| 19 | 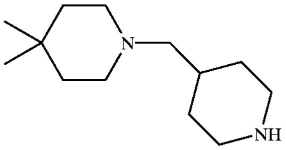 |
| 20 | 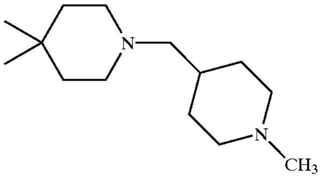 |
| 21 | 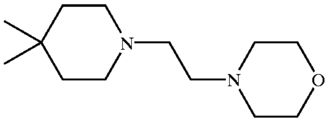 |
| 22 | 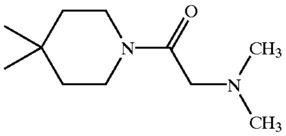 |
| 23 | 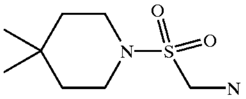 |
| 24 | 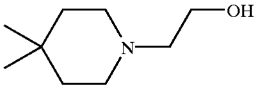 |
| 25 | 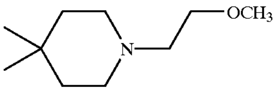 |
| 26 | 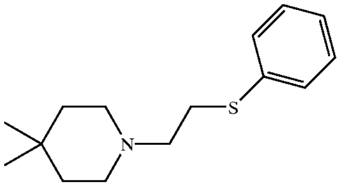 |
| 27 | 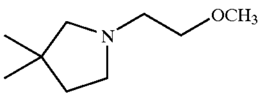 |
| 28 | 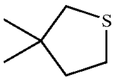 |

TABLE 212-continued
| | |
|---|---|
| 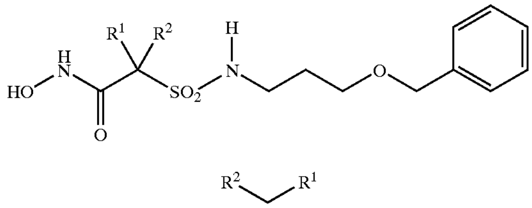 | |
| 29 | 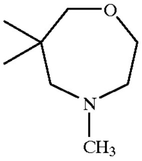 |
| 30 | 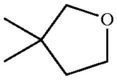 |
| 31 | 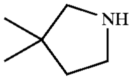 |
| 32 | 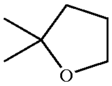 |
TABLE 213
| | |
|---|---|
| 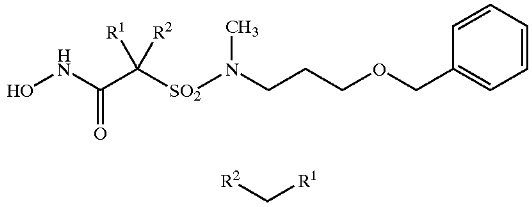 | |
| 1 | 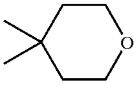 |
| 2 | 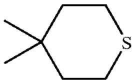 |
| 3 | 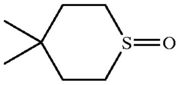 |
| 4 | 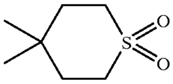 |
| 5 | 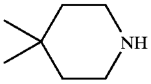 |
| 6 | 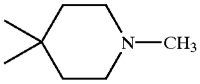 |
TABLE 213-continued
| | |
|---|---|
| 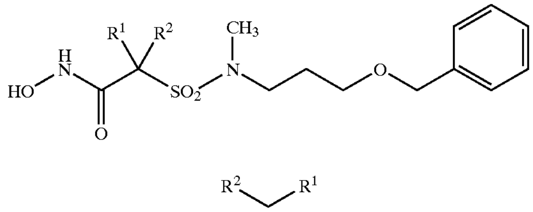 | |
| 7 | 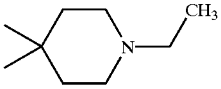 |
| 8 | 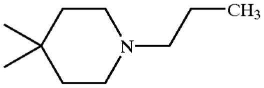 |
| 9 | 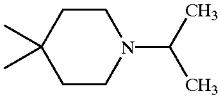 |
| 10 | 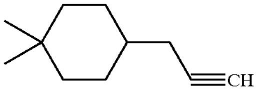 |
| 11 | 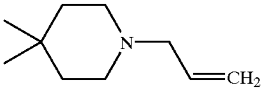 |
| 12 | 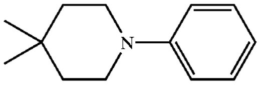 |
| 13 | 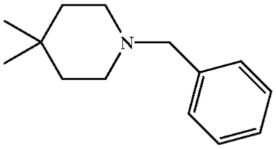 |
| 14 | 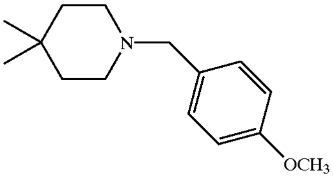 |
| 15 | 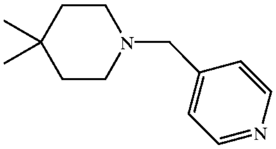 |
| 16 | 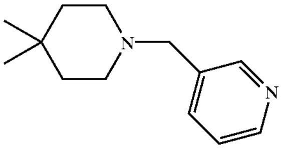 |

TABLE 213-continued
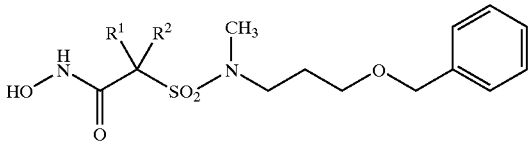
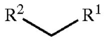
| | |
|---|---|
| 17 | 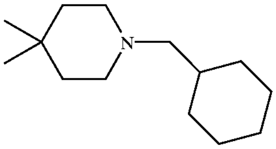 |
| 18 | 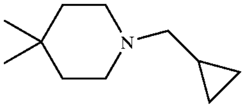 |
| 19 | 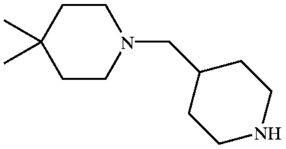 |
| 20 | 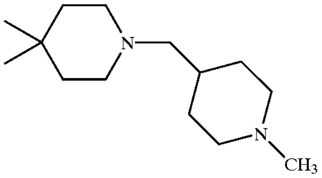 |
| 21 | 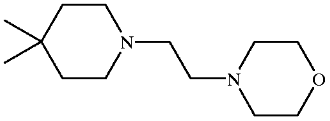 |
| 22 | 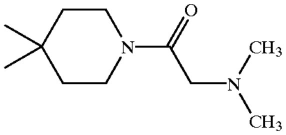 |
| 23 | 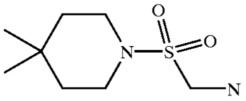 |
| 24 | 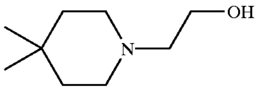 |
| 25 | 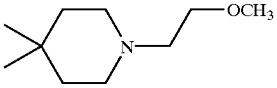 |
TABLE 213-continued
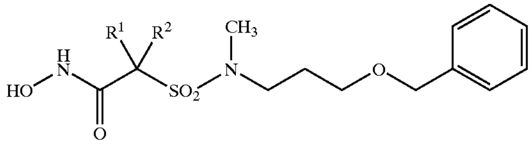
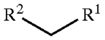
| | |
|---|---|
| 26 | 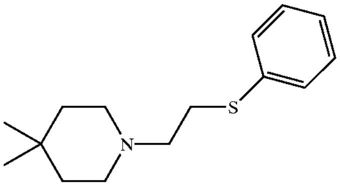 |
| 27 | 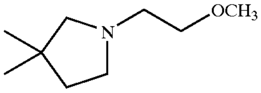 |
| 28 | 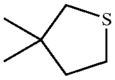 |
| 29 | 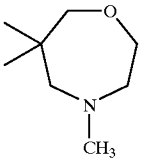 |
| 30 | 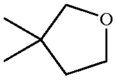 |
| 31 | 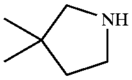 |
| 32 | 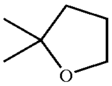 |
TABLE 214
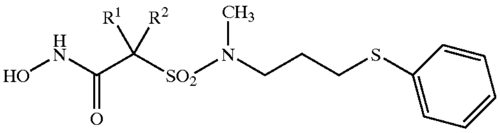
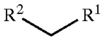
| | |
|---|---|
| 1 | 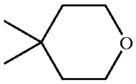 |
| 2 | 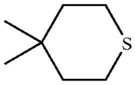 |

TABLE 214-continued
| | 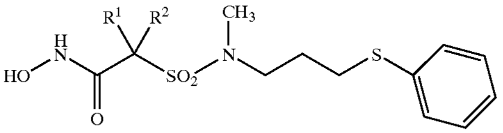 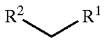 |
|---|---|
| 3 | 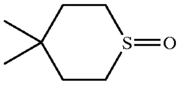 |
| 4 | 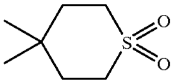 |
| 5 | 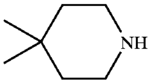 |
| 6 | 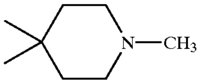 |
| 7 | 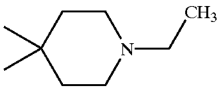 |
| 8 | 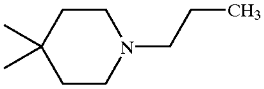 |
| 9 | 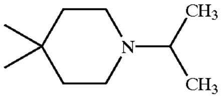 |
| 10 | 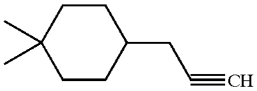 |
| 11 | 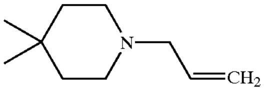 |
| 12 | 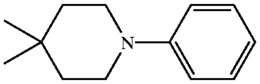 |
| 13 | 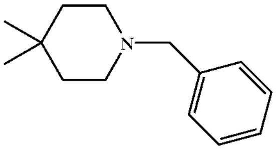 |
| 14 | 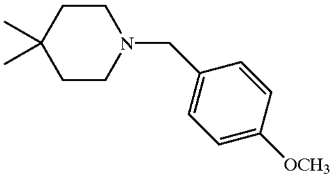 |
TABLE 214-continued
| | 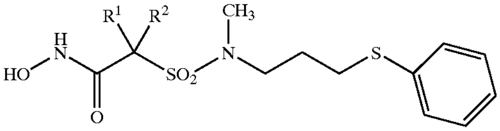 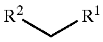 |
|---|---|
| 15 | 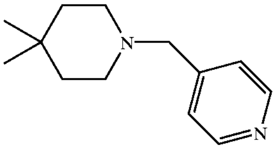 |
| 16 | 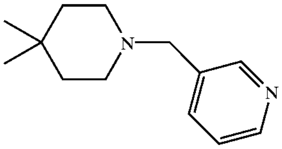 |
| 17 | 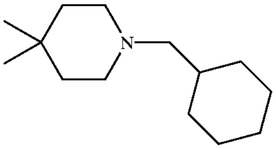 |
| 18 | 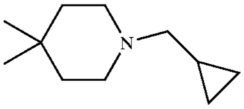 |
| 19 | 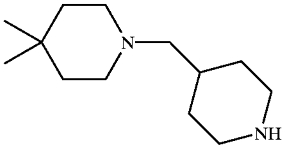 |
| 20 | 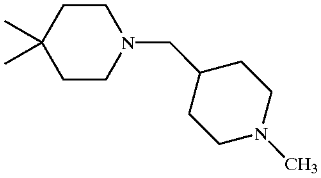 |
| 21 | 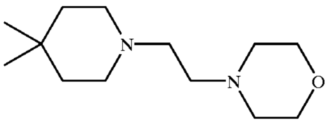 |
| 22 | 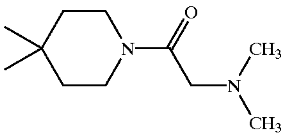 |
| 23 | 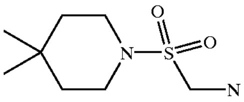 |

TABLE 214-continued
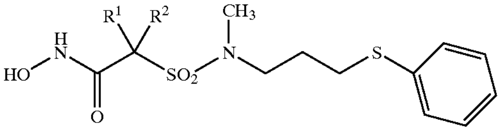
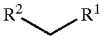
| | |
|---|---|
| 24 | 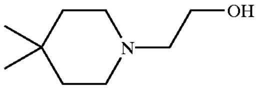 |
| 25 | 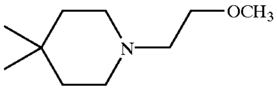 |
| 26 | 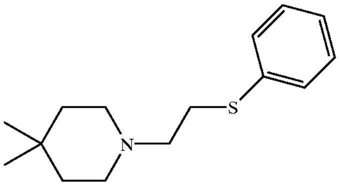 |
| 27 | 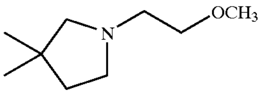 |
| 28 | 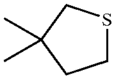 |
| 29 | 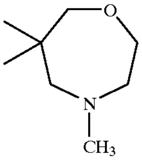 |
| 30 | 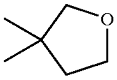 |
| 31 | 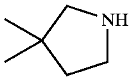 |
| 32 | 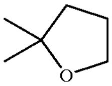 |
TABLE 215
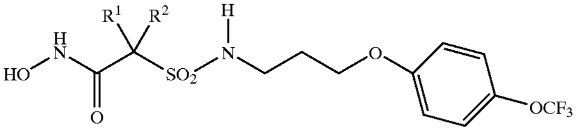
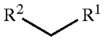
| | |
|---|---|
| 1 | 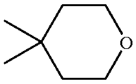 |
| 2 | 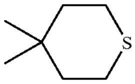 |
| 3 | 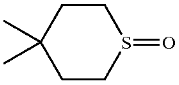 |
| 4 | 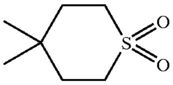 |
| 5 | 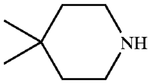 |
| 6 | 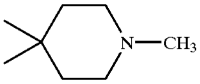 |
| 7 | 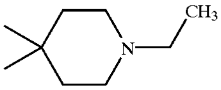 |
| 8 | 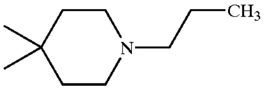 |
| 9 | 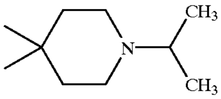 |
| 10 | 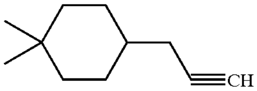 |
| 11 | 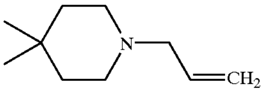 |
| 12 | 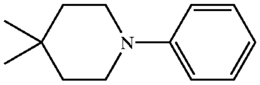 |

TABLE 215-continued
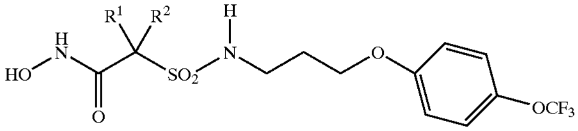
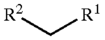
13 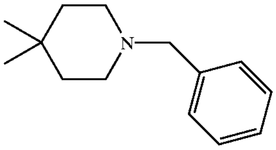
14 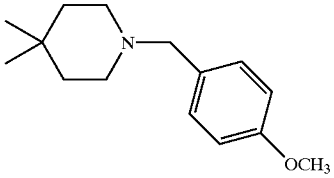
15 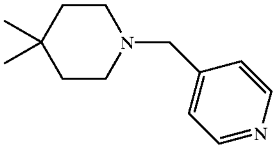
16 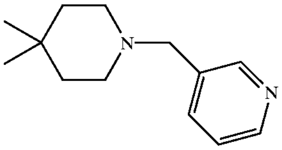
17 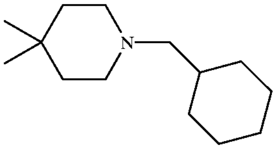
18 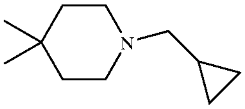
19 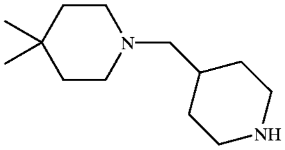
20 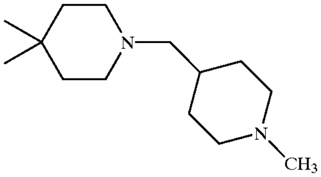
TABLE 215-continued
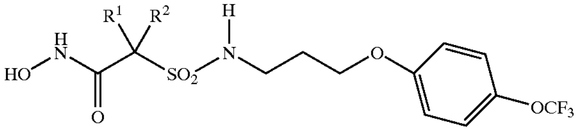
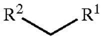
21 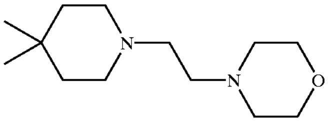
22 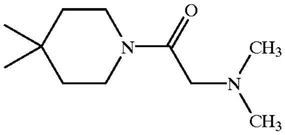
23 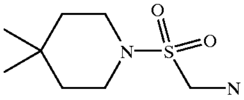
24 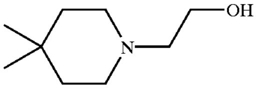
25 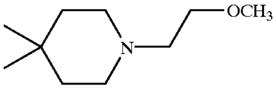
26 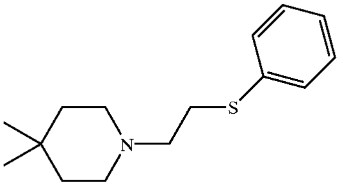
27 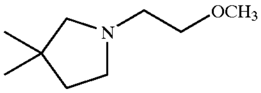
28 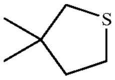
29 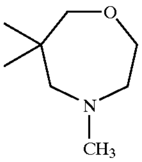
30 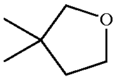
31 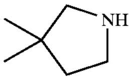

TABLE 215-continued
| 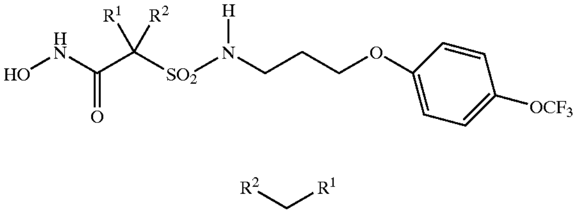 | |
|---|---|
| 32 | 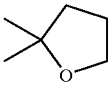 |
TABLE 216
| 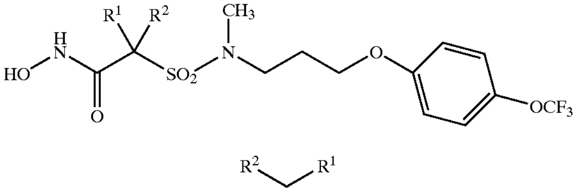 | |
|---|---|
| 1 | 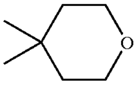 |
| 2 | 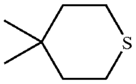 |
| 3 | 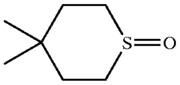 |
| 4 | 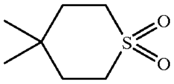 |
| 5 | 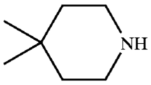 |
| 6 | 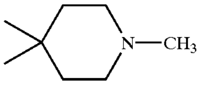 |
| 7 | 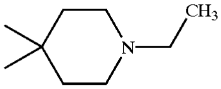 |
| 8 | 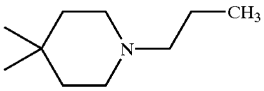 |
| 9 | 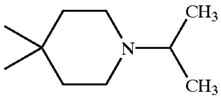 |
TABLE 216-continued
| 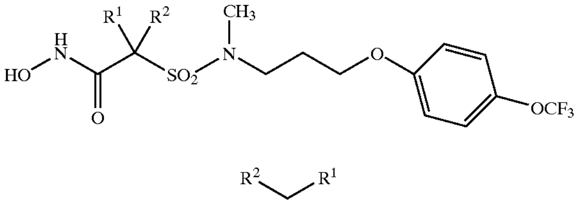 | |
|---|---|
| 10 | 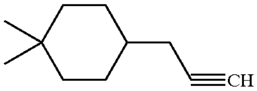 |
| 11 | 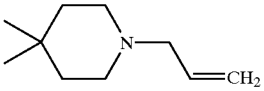 |
| 12 | 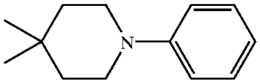 |
| 13 | 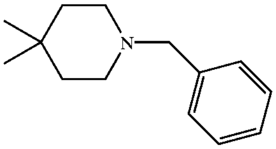 |
| 14 | 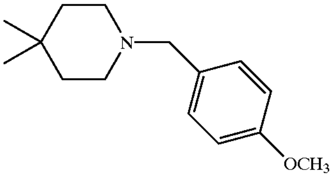 |
| 15 | 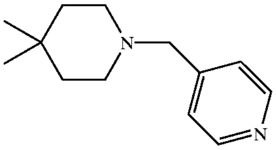 |
| 16 | 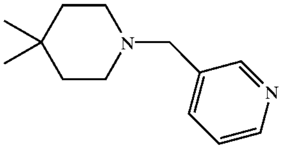 |
| 17 | 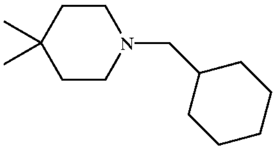 |
| 18 | 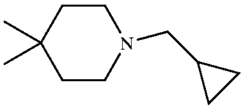 |

TABLE 216-continued
| | |
|---|---|
| | 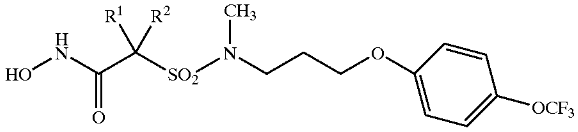 |
| | 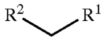 |
| 19 | 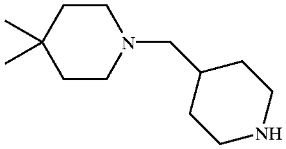 |
| 20 | 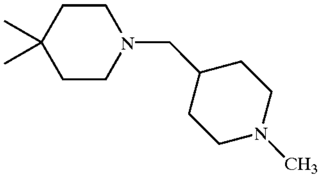 |
| 21 | 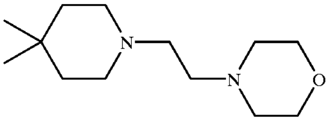 |
| 22 | 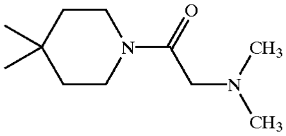 |
| 23 | 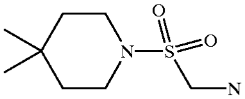 |
| 24 | 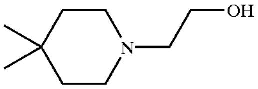 |
| 25 | 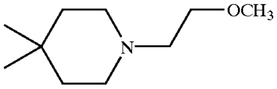 |
| 26 | 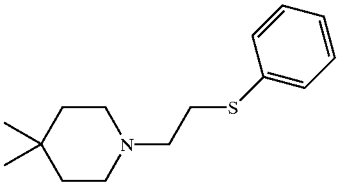 |
| 27 | 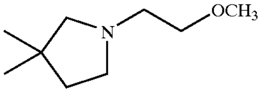 |
| 28 | 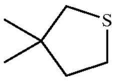 |
TABLE 216-continued
| | |
|---|---|
| | 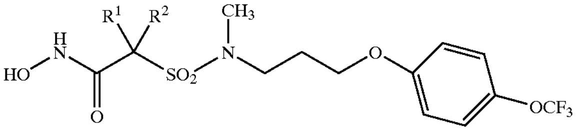 |
| | 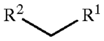 |
| 29 | 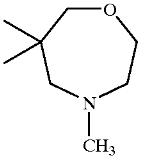 |
| 30 | 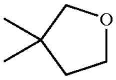 |
| 31 | 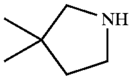 |
| 32 | 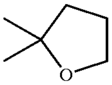 |
TABLE 217
| | |
|---|---|
| | 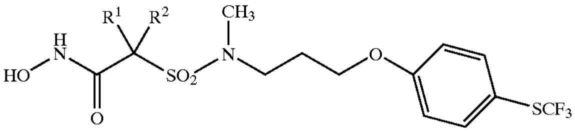 |
| | 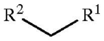 |
| 1 | 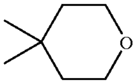 |
| 2 | 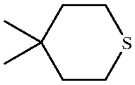 |
| 3 | 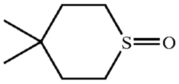 |
| 4 | 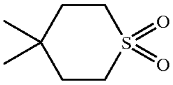 |
| 5 | 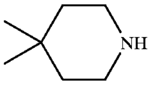 |
| 6 | 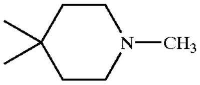 |

TABLE 217-continued
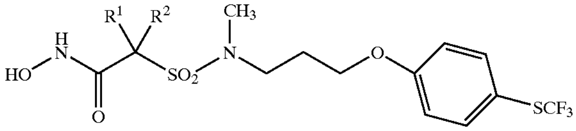
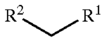
| | |
|---|---|
| 7 | 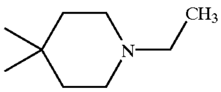 |
| 8 | 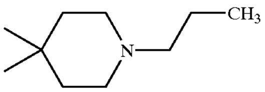 |
| 9 | 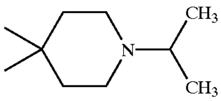 |
| 10 | 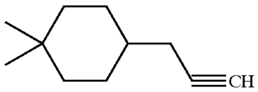 |
| 11 | 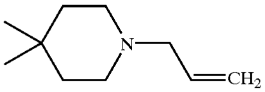 |
| 12 | 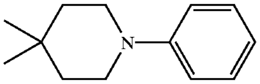 |
| 13 | 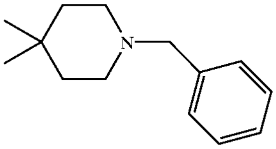 |
| 14 | 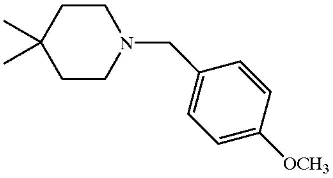 |
| 15 | 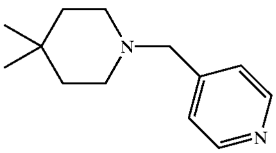 |
| 16 | 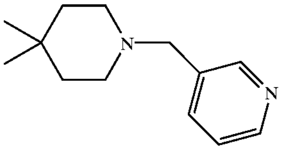 |
TABLE 217-continued
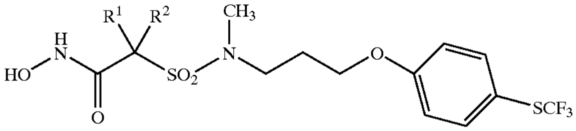
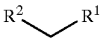
| | |
|---|---|
| 17 | 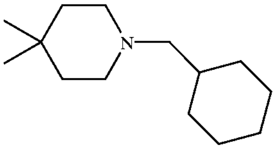 |
| 18 | 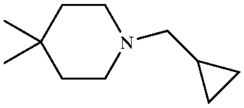 |
| 19 | 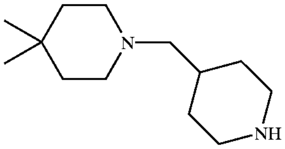 |
| 20 | 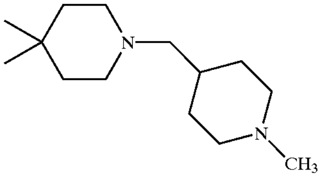 |
| 21 | 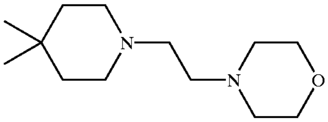 |
| 22 | 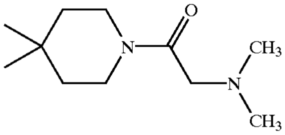 |
| 23 | 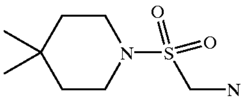 |
| 24 | 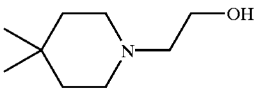 |
| 25 | 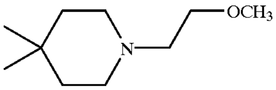 |

TABLE 217-continued
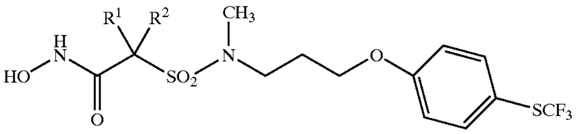
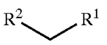
| | |
|---|---|
| 26 | 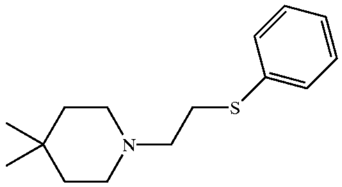 |
| 27 | 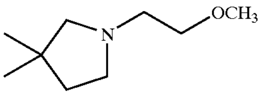 |
| 28 | 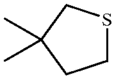 |
| 29 | 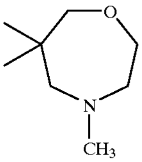 |
| 30 | 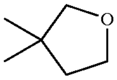 |
| 31 | 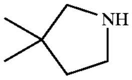 |
| 32 | 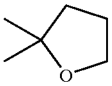 |
TABLE 218
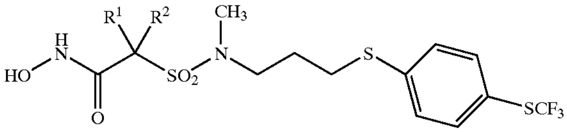
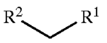
| | |
|---|---|
| 1 | 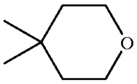 |
| 2 | 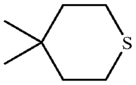 |
TABLE 218-continued
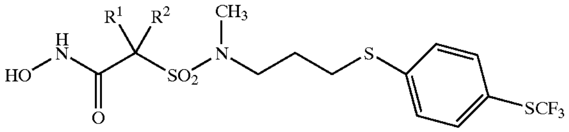
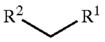
| | |
|---|---|
| 3 | 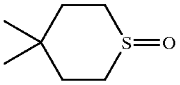 |
| 4 | 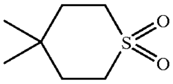 |
| 5 | 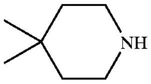 |
| 6 | 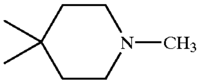 |
| 7 | 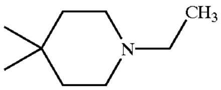 |
| 8 | 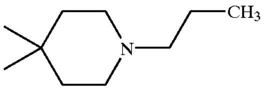 |
| 9 | 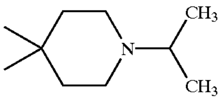 |
| 10 | 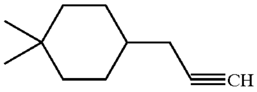 |
| 11 | 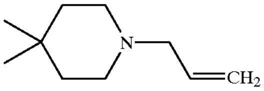 |
| 12 | 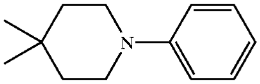 |
| 13 | 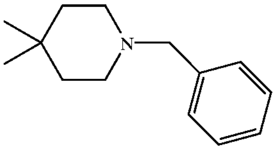 |
| 14 | 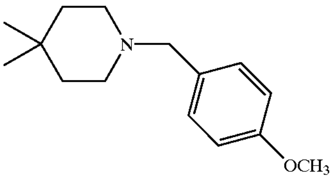 |

TABLE 218-continued
| 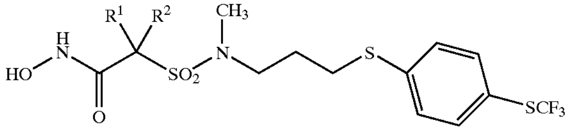 | 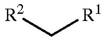 |
| --- | --- |
| 15 | 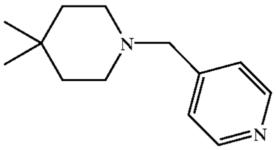 |
| 16 | 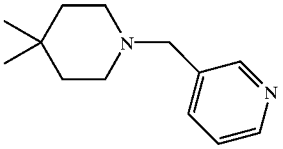 |
| 17 | 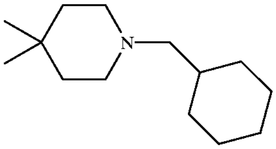 |
| 18 | 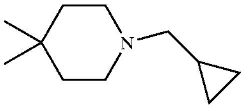 |
| 19 | 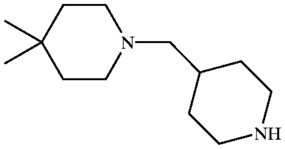 |
| 20 | 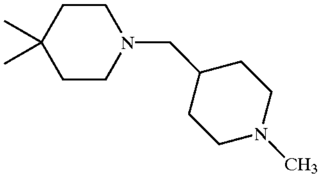 |
| 21 | 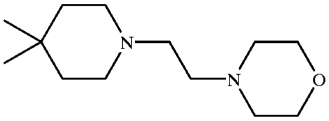 |
| 22 | 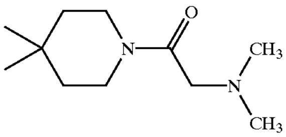 |
| 23 | 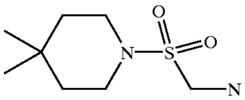 |
TABLE 218-continued
| 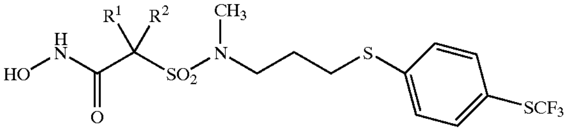 | 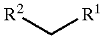 |
| --- | --- |
| 24 | 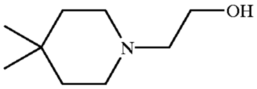 |
| 25 | 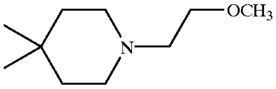 |
| 26 | 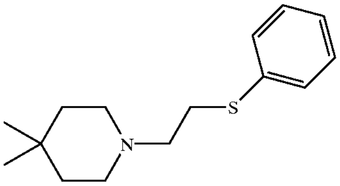 |
| 27 | 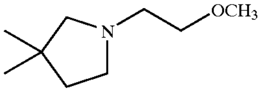 |
| 28 | 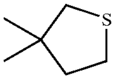 |
| 29 | 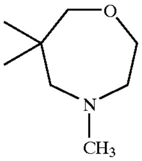 |
| 30 | 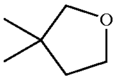 |
| 31 | 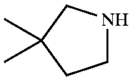 |
| 32 | 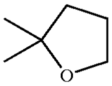 |

TABLE 219
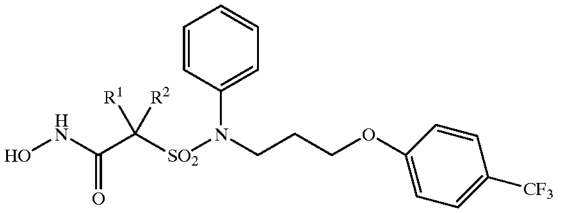
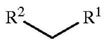
| | |
|---|---|
| 1 | 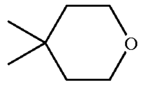 |
| 2 | 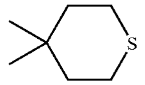 |
| 3 | 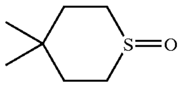 |
| 4 | 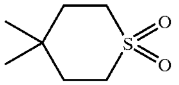 |
| 5 | 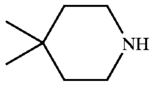 |
| 6 | 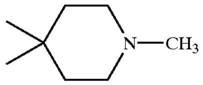 |
| 7 | 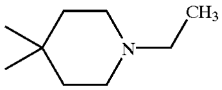 |
| 8 | 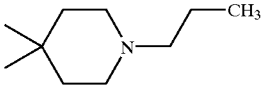 |
| 9 | 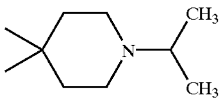 |
| 10 | 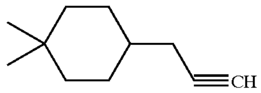 |
| 11 | 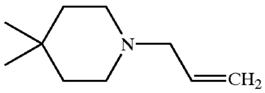 |
| 12 | 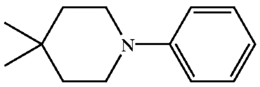 |
TABLE 219-continued
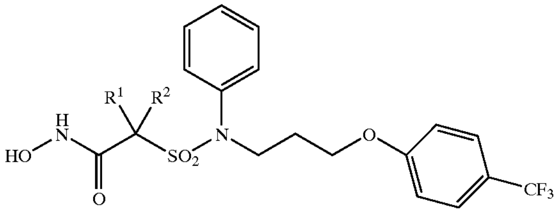
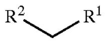
| | |
|---|---|
| 13 | 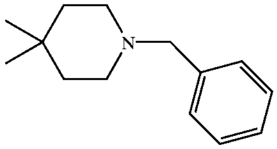 |
| 14 | 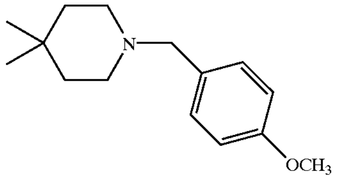 |
| 15 | 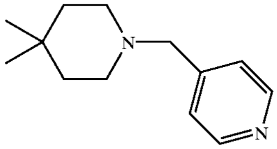 |
| 16 | 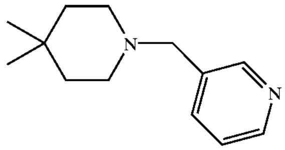 |
| 17 | 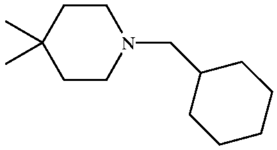 |
| 18 | 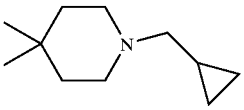 |
| 19 | 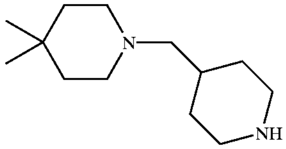 |
| 20 | 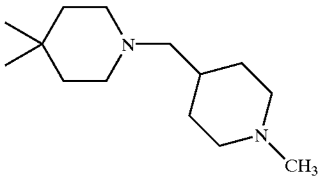 |

TABLE 219-continued
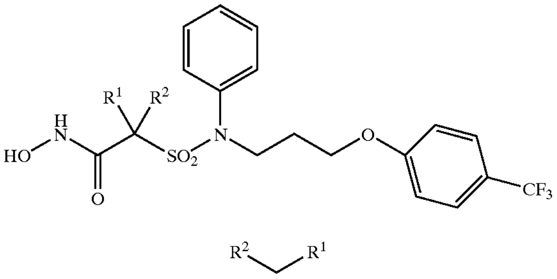
21 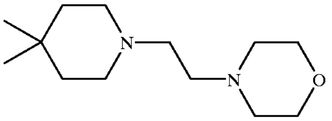
22 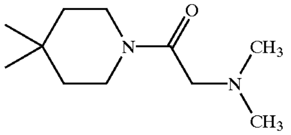
23 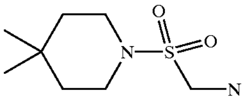
24 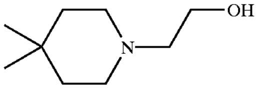
25 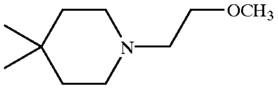
26 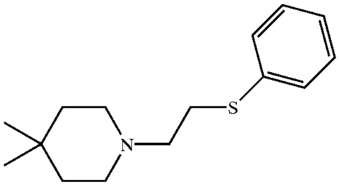
27 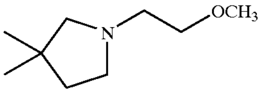
28 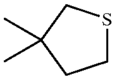
29 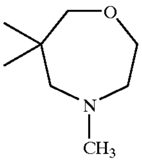
30 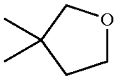
TABLE 219-continued
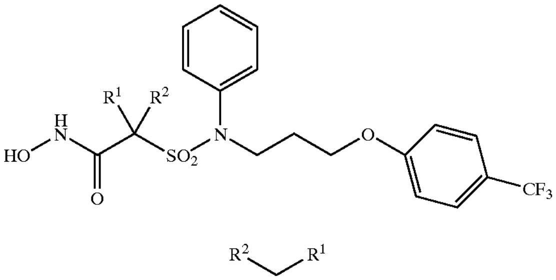
31 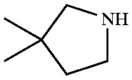
32 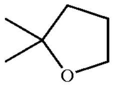
TABLE 220
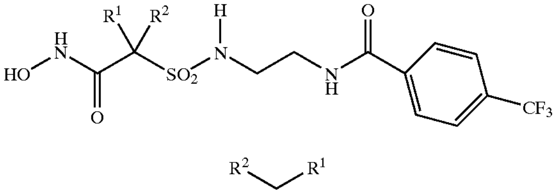
1 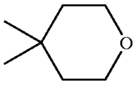
2 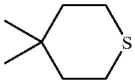
3 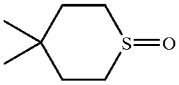
4 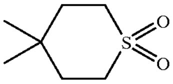
5 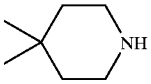
6 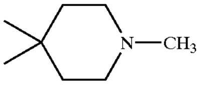
7 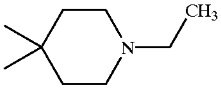
8 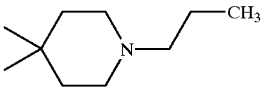

TABLE 220-continued
| | |
|---|---|
| | 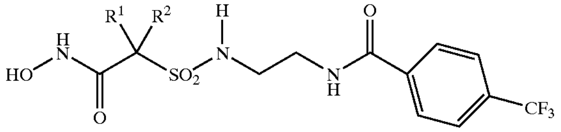 |
| | 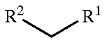 |
| 9 | 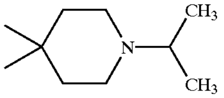 |
| 10 | 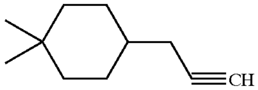 |
| 11 | 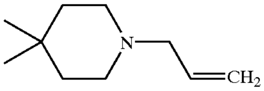 |
| 12 | 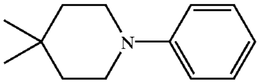 |
| 13 | 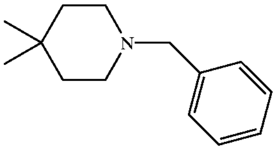 |
| 14 | 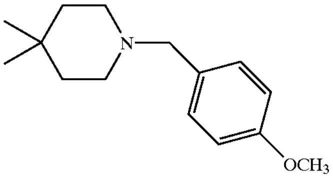 |
| 15 | 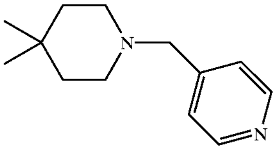 |
| 16 | 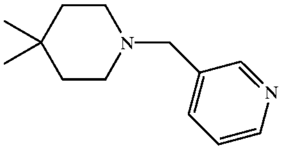 |
| 17 | 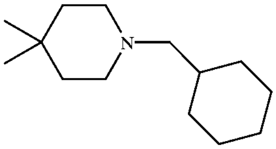 |
| 18 | 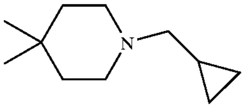 |
TABLE 220-continued
| | |
|---|---|
| | 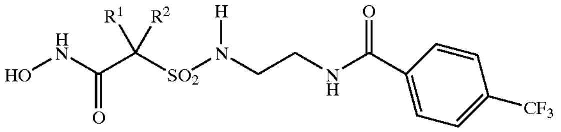 |
| | 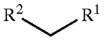 |
| 19 | 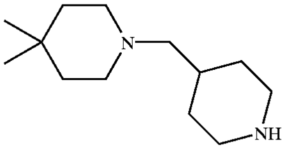 |
| 20 | 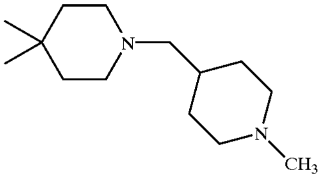 |
| 21 | 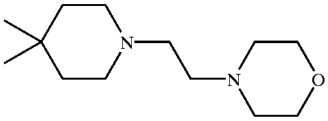 |
| 22 | 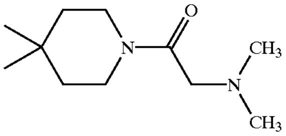 |
| 23 | 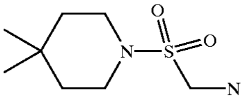 |
| 24 | 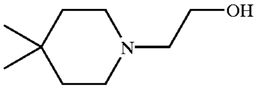 |
| 25 | 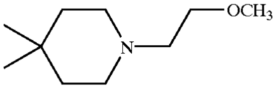 |
| 26 | 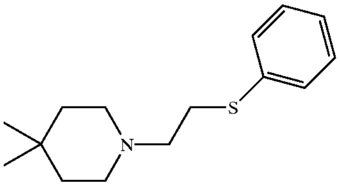 |
| 27 | 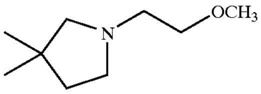 |
| 28 | 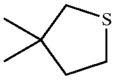 |

TABLE 220-continued
| | |
|---|---|
| | 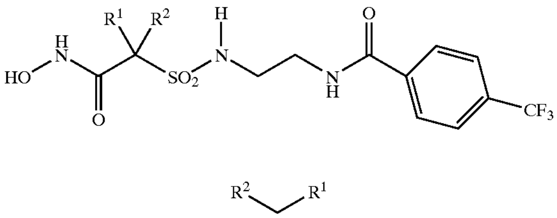 |
| 29 | 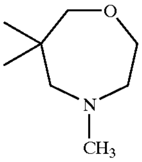 |
| 30 | 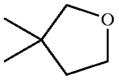 |
| 31 | 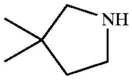 |
| 32 | 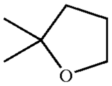 |
TABLE 221
| | |
|---|---|
| | 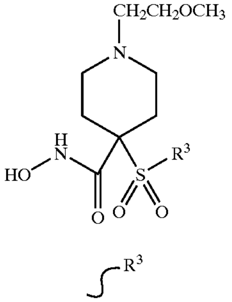 |
| 1 | 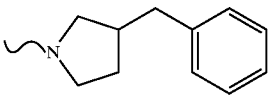 |
| 2 | 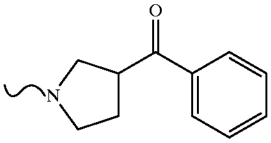 |
| 3 | 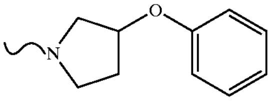 |
TABLE 221-continued
| | |
|---|---|
| | 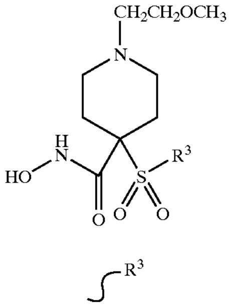 |
| 4 | 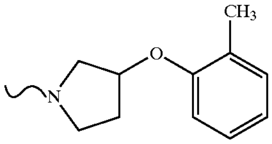 |
| 5 | 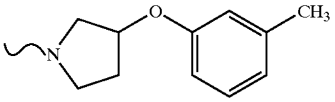 |
| 6 | 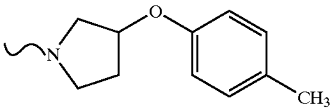 |
| 7 | 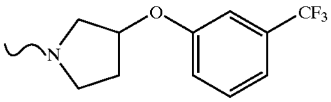 |
| 8 | 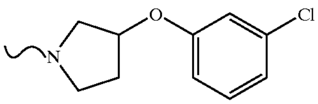 |
| 9 | 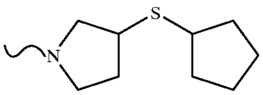 |
| 10 | 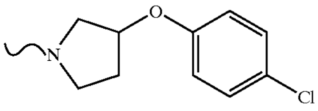 |
| 11 | 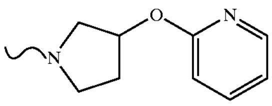 |
| 12 | 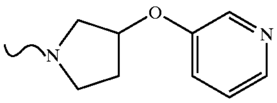 |
| 13 | 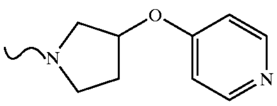 |

TABLE 221-continued
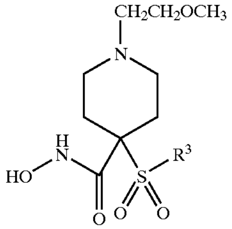
| | 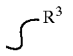 |
|---|---|
| 14 | 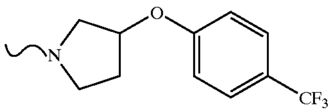 |
| 15 | 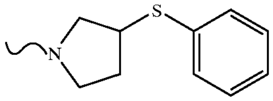 |
| 16 | 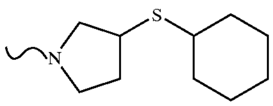 |
| 17 | 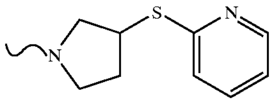 |
| 18 | 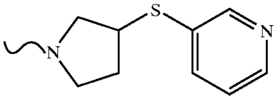 |
TABLE 221-continued
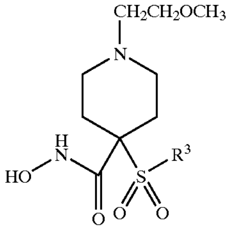
| | 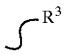 |
|---|---|
| 19 | 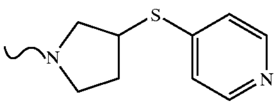 |
| 20 | 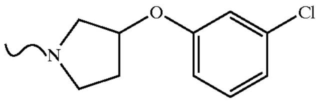 |
| 21 | 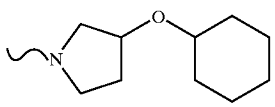 |
Preparation Process
Also according to the present invention, there are provided processes for preparing the compounds of the present invention. Synthesis schemes, generic Schemes 1–4 and specific Schemes A–D, illustrating such processes are illustrated below.
Scheme 1
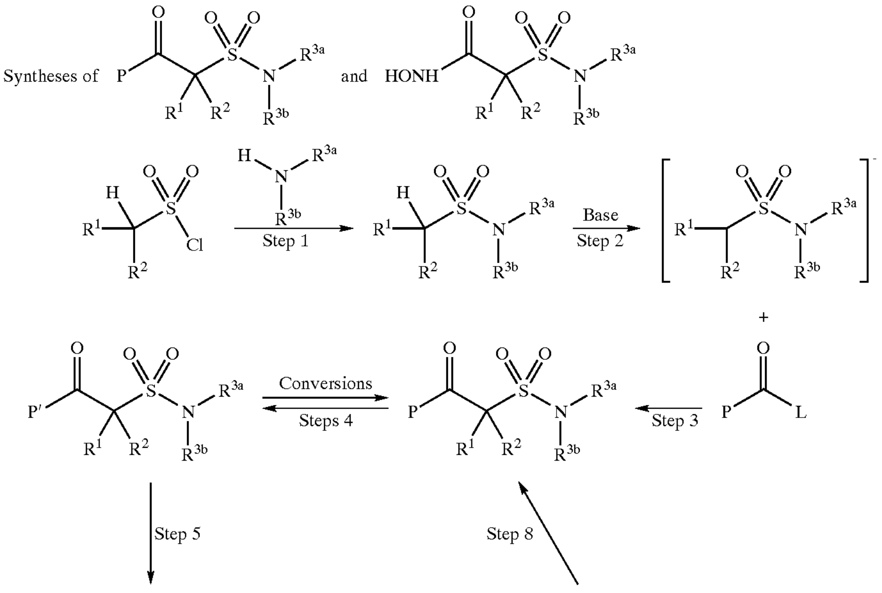

-continued
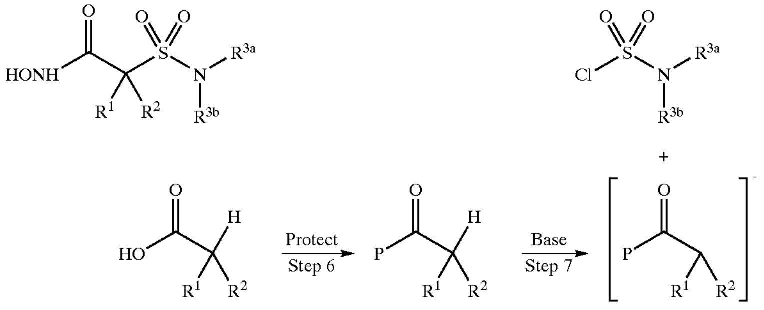
15
P is a protecting group
P' is a protecting group
L is a leaving group
R', $R^2$, $R^{3a}$, $R^{3b}$ are as defined herein
Scheme 2A and 2B
Syntheses of 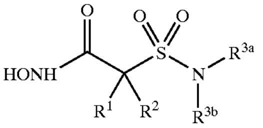 and 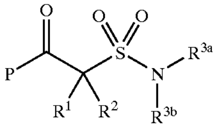
Scheme 2A
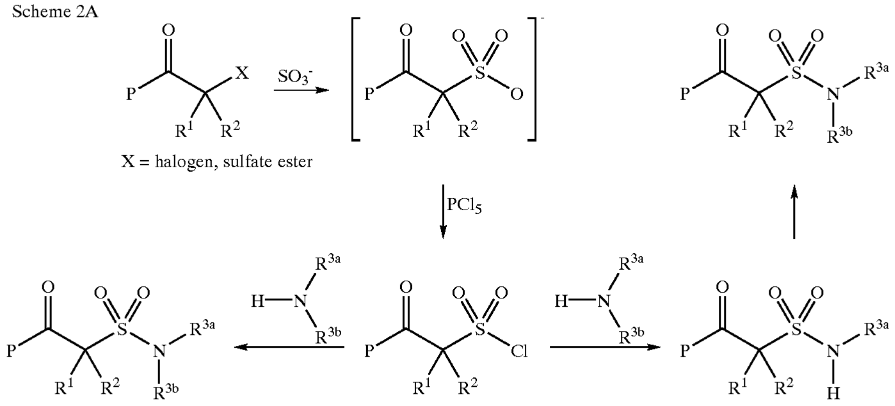
Scheme 2B
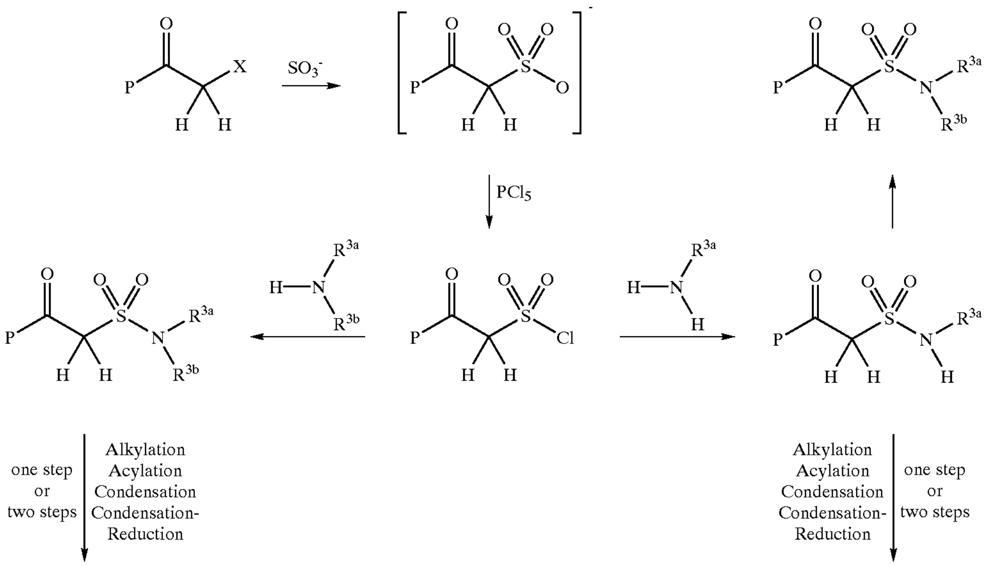

-continued
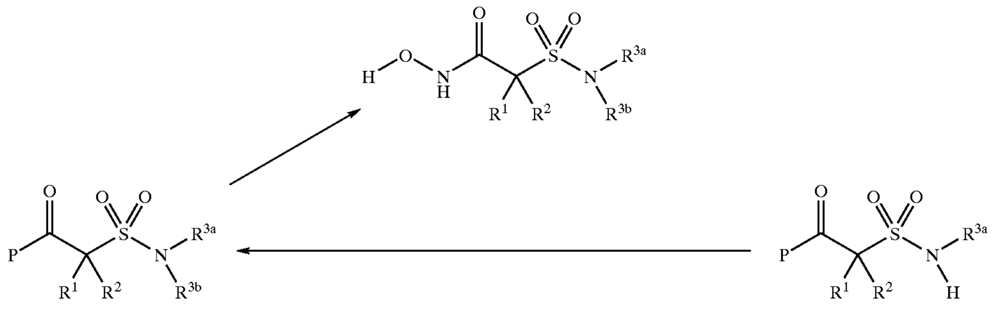
Scheme 3
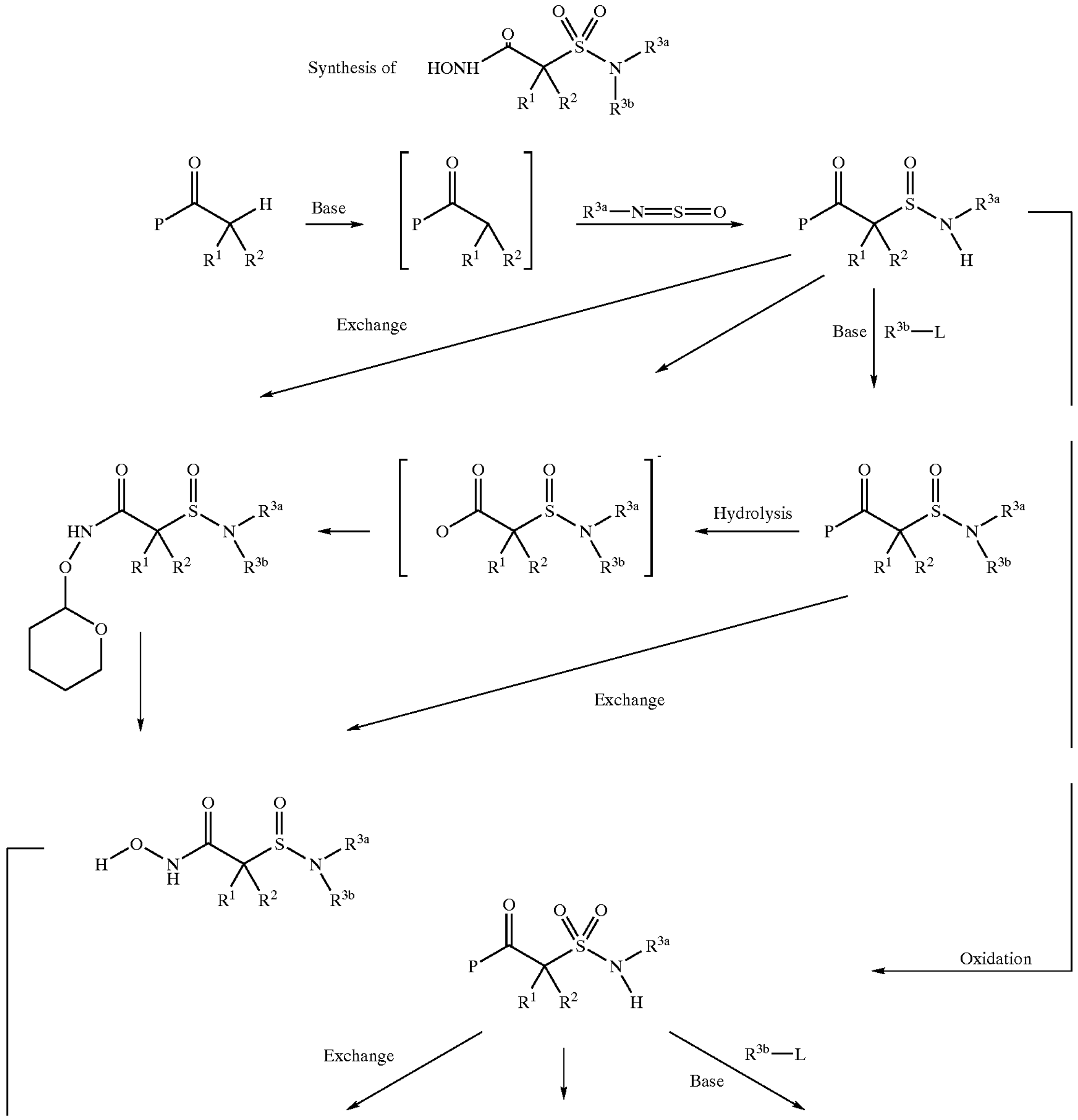

-continued
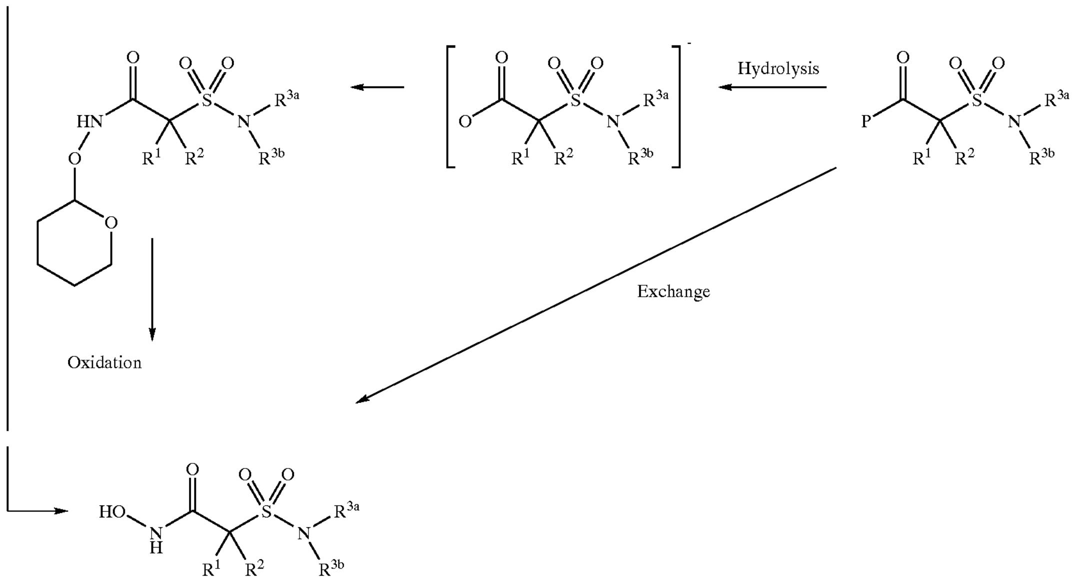
Schemes 4A and 4B
Syntheses of
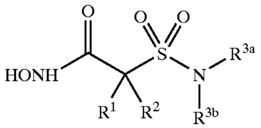
Scheme 4A
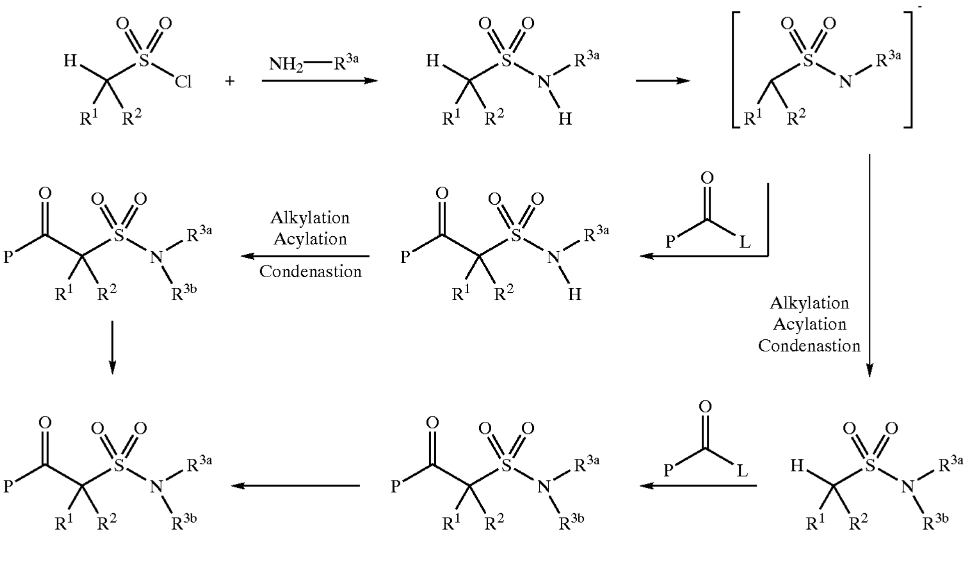
Scheme 4B
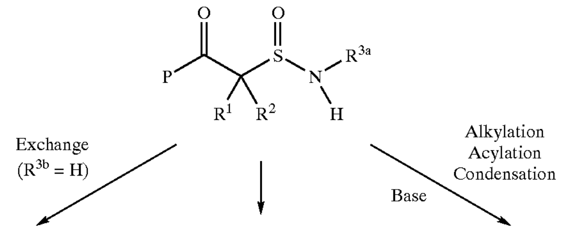

-continued
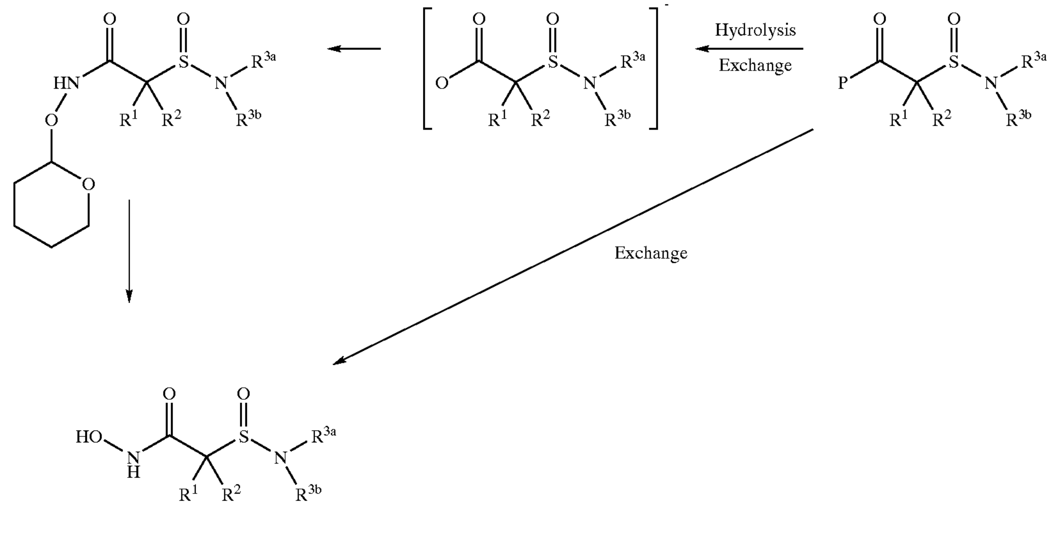
Scheme A
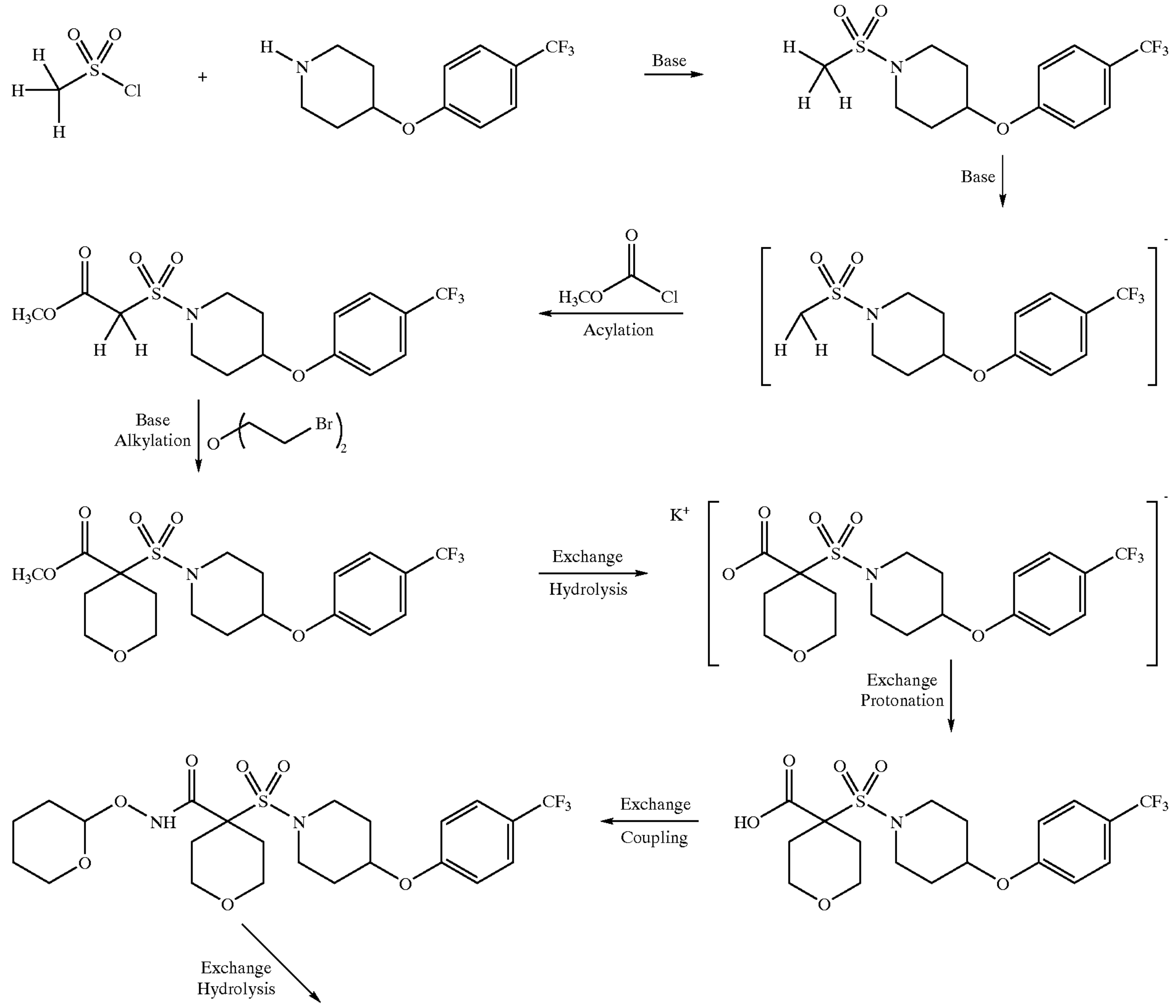

-continued
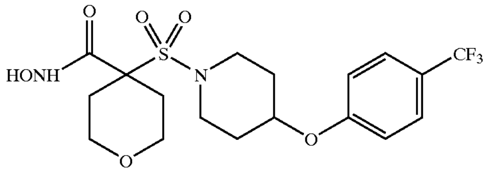
Scheme B
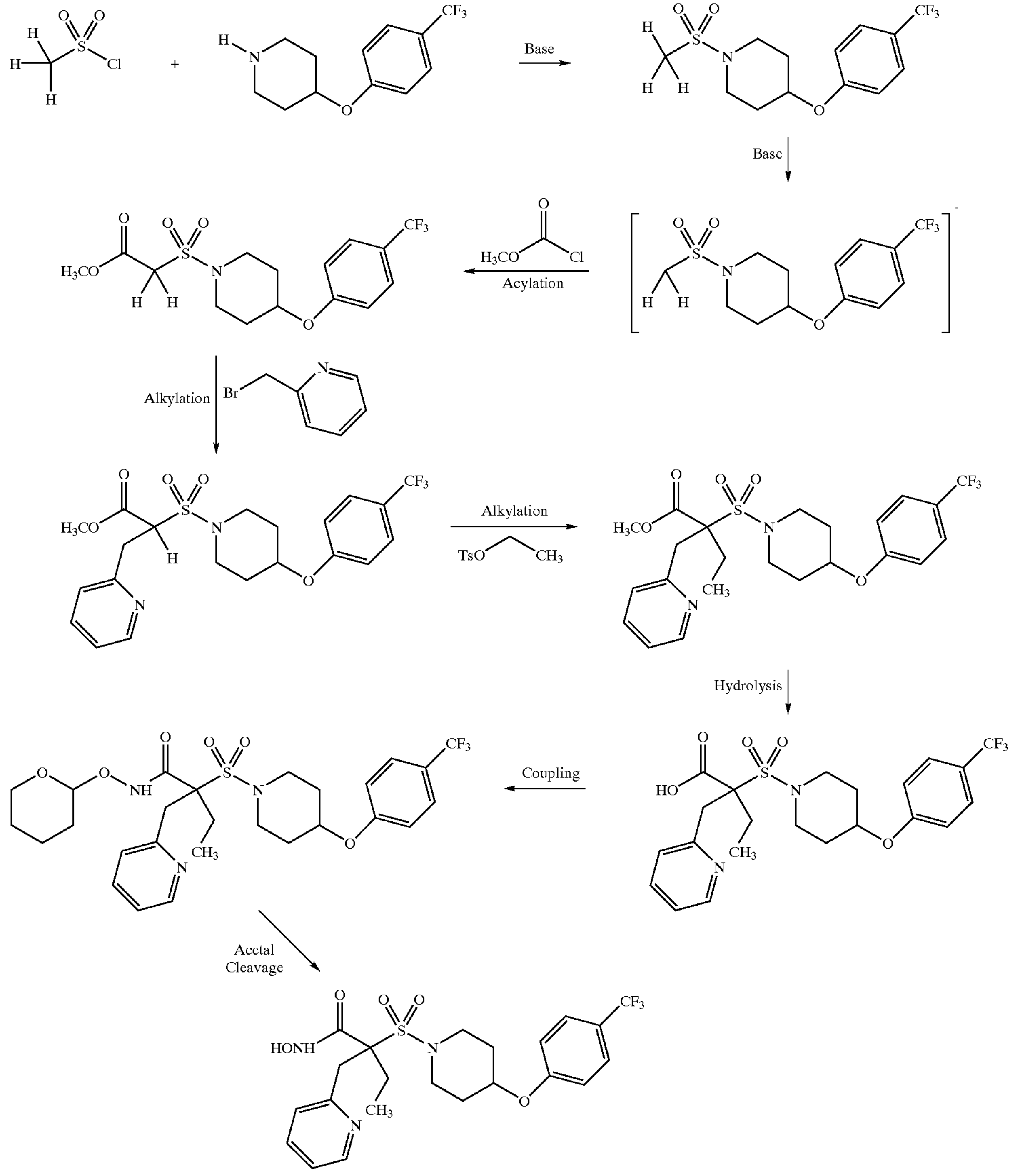

Scheme C
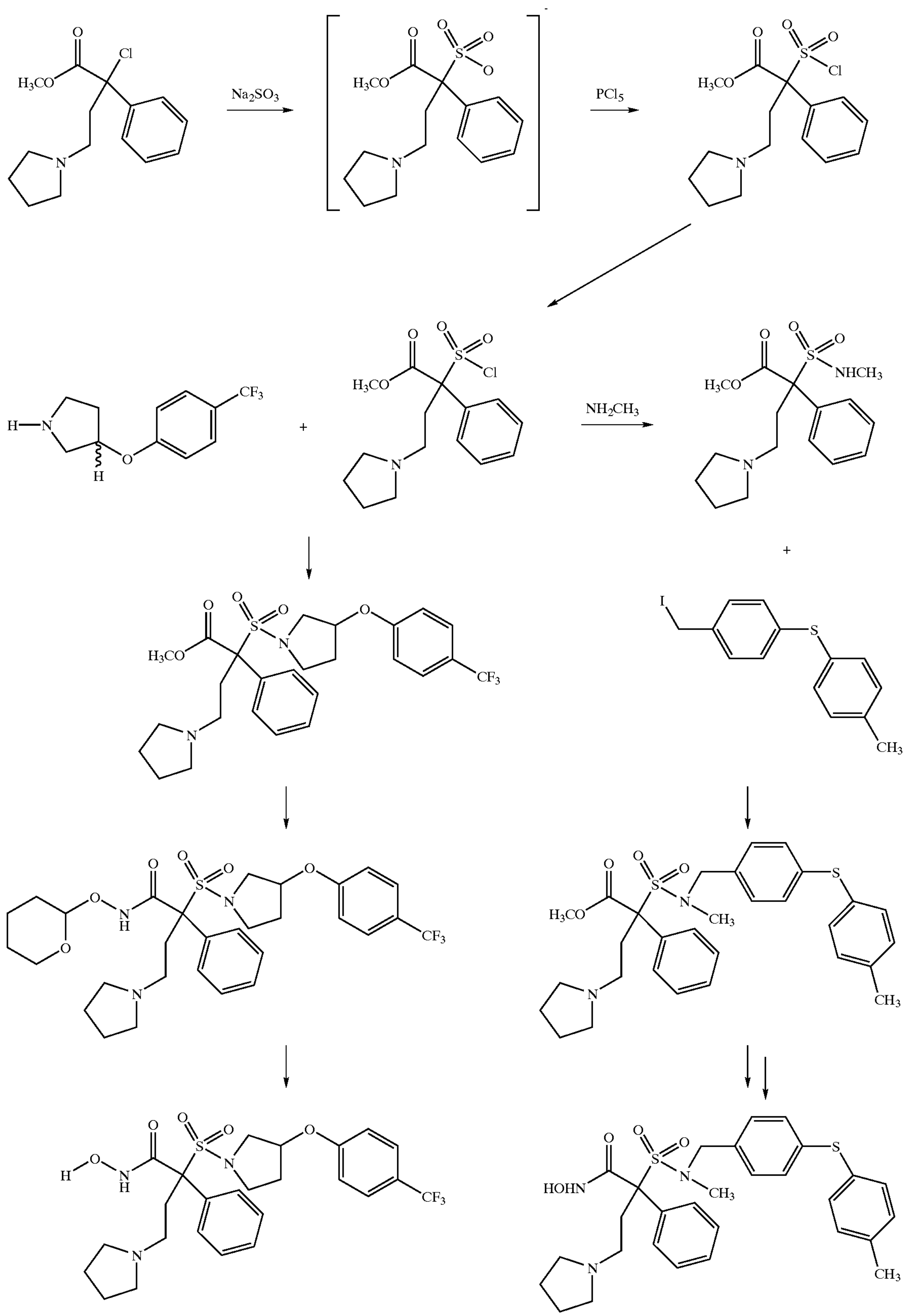

Scheme D
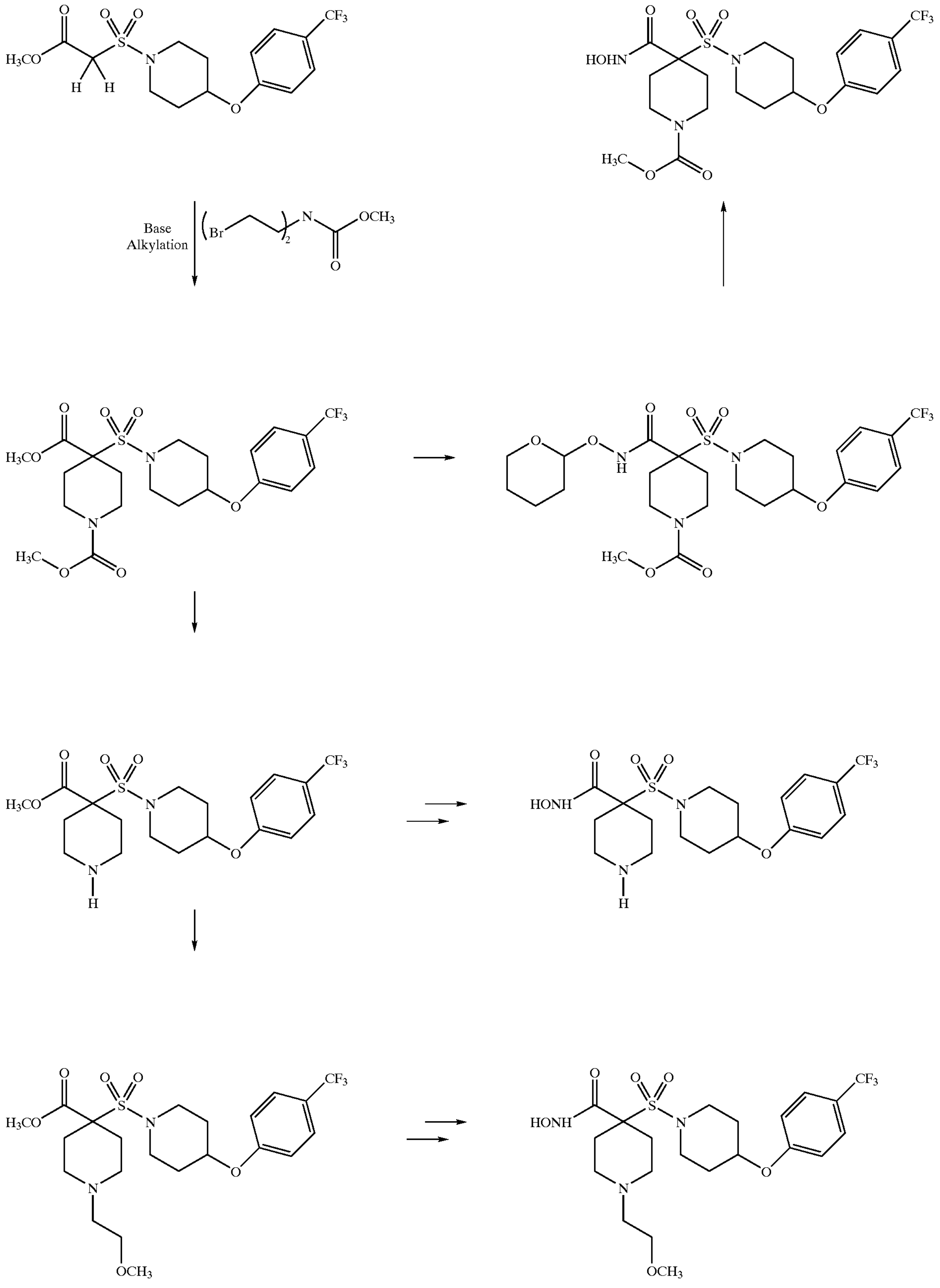

Scheme E-1
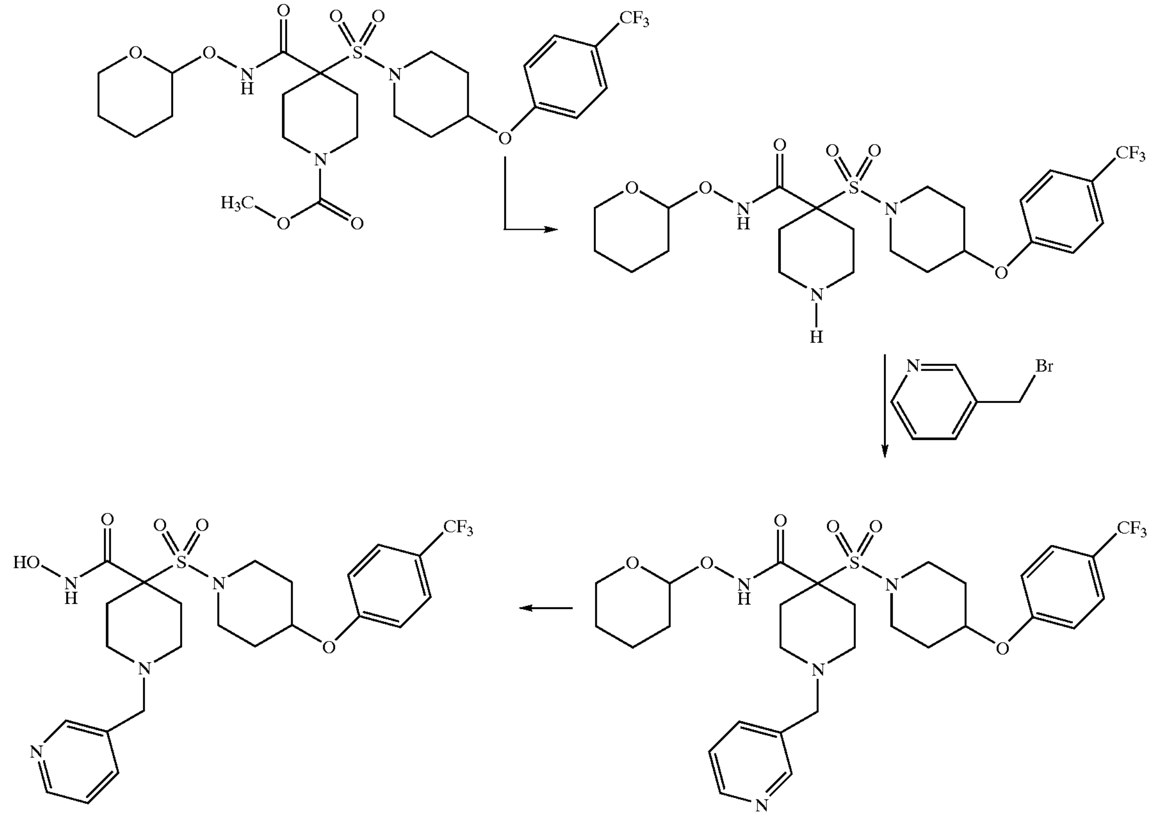
Scheme E-2
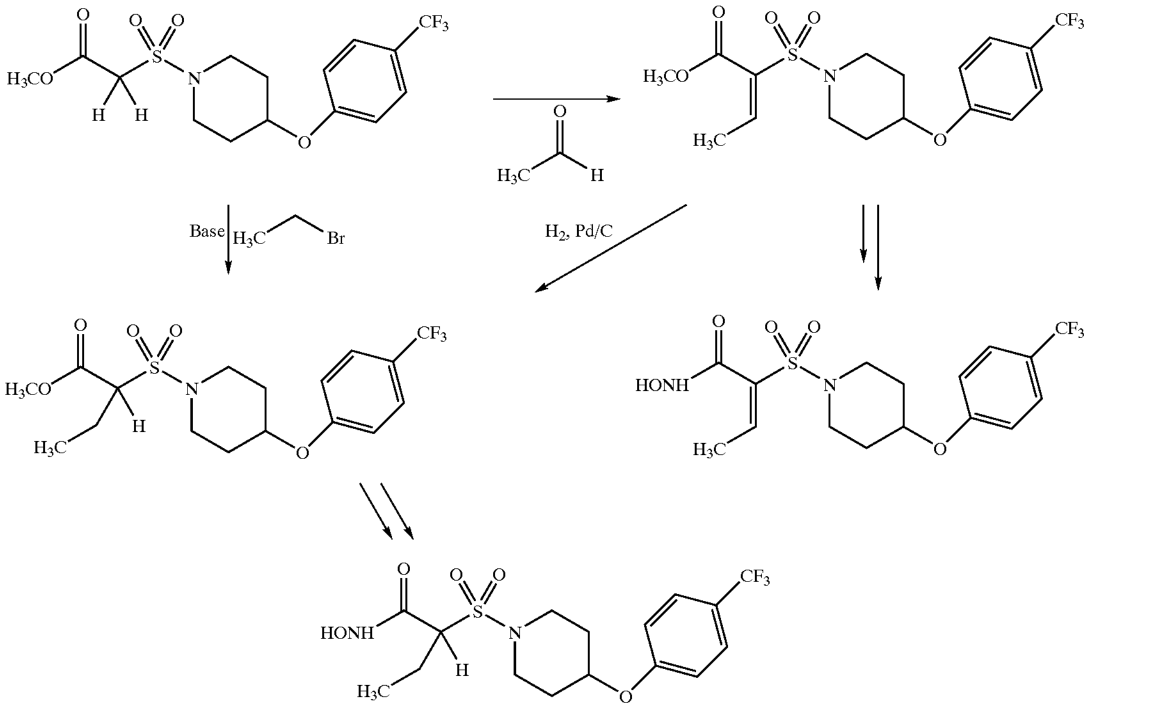

Scheme 5
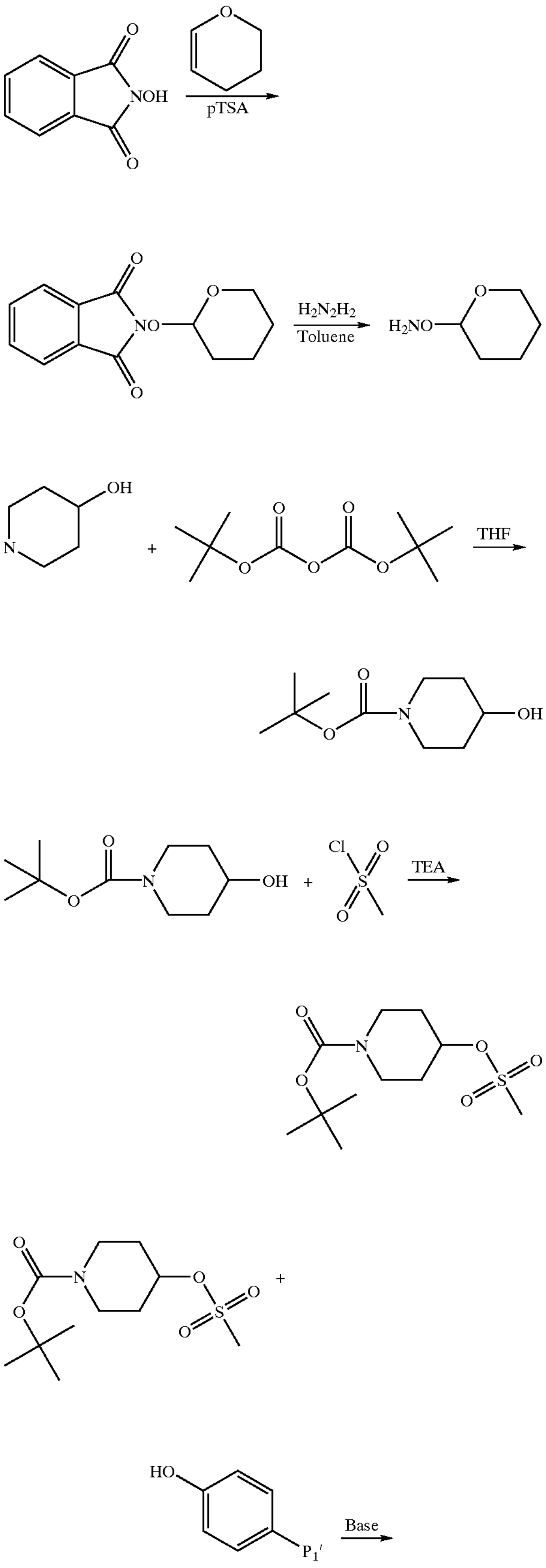
-continued
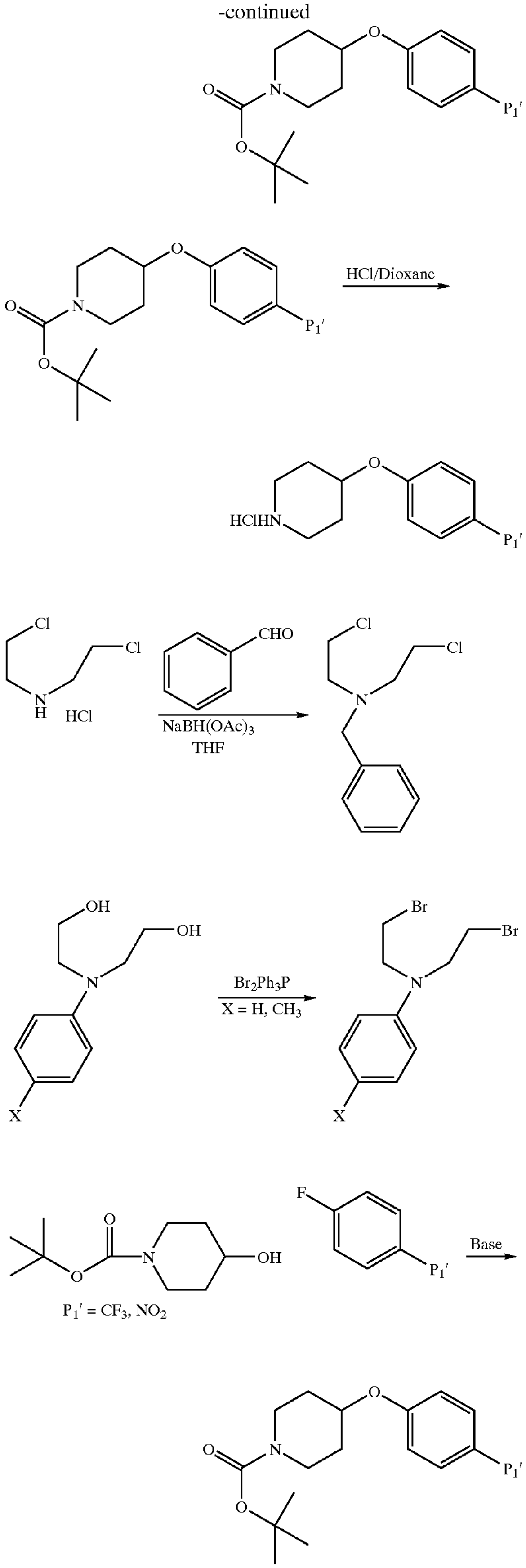

Scheme 6A
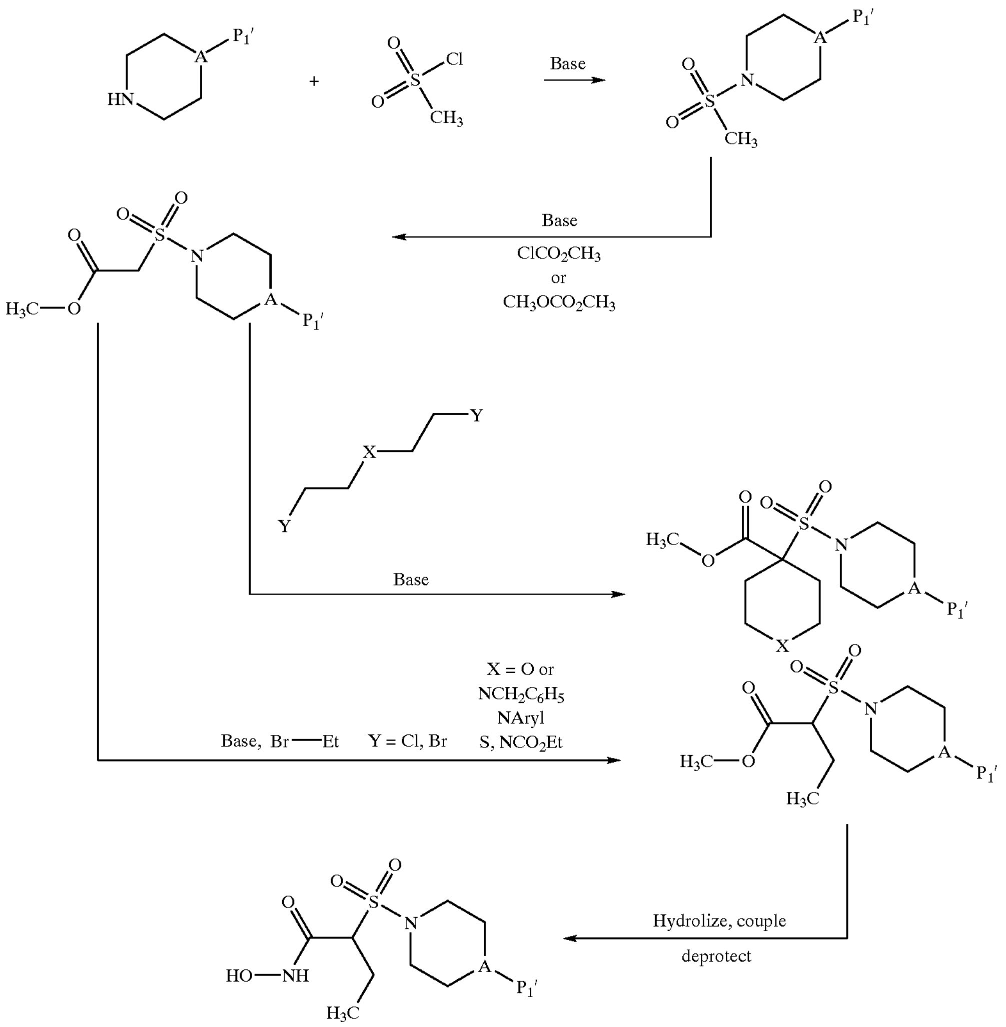
Scheme 6B
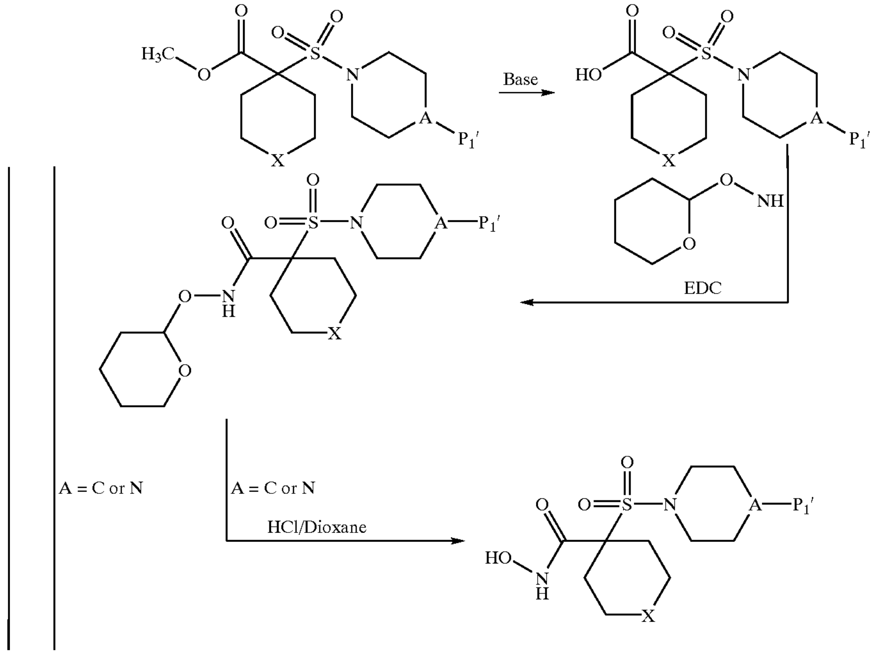

-continued
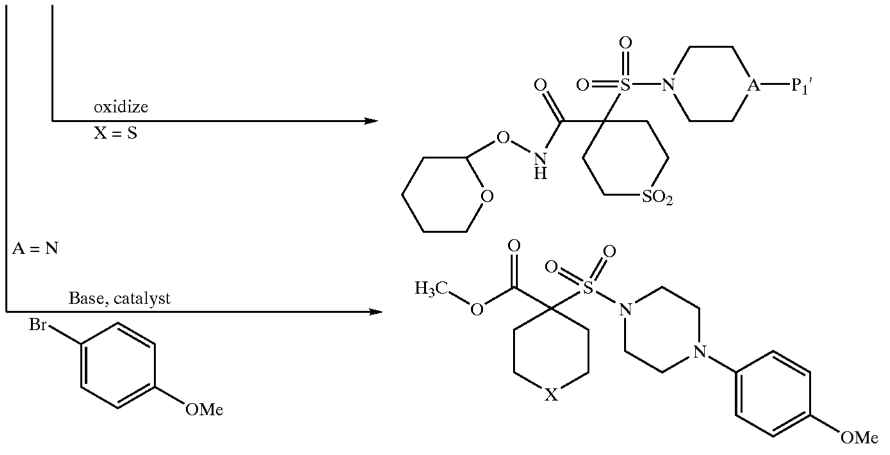
Scheme 7
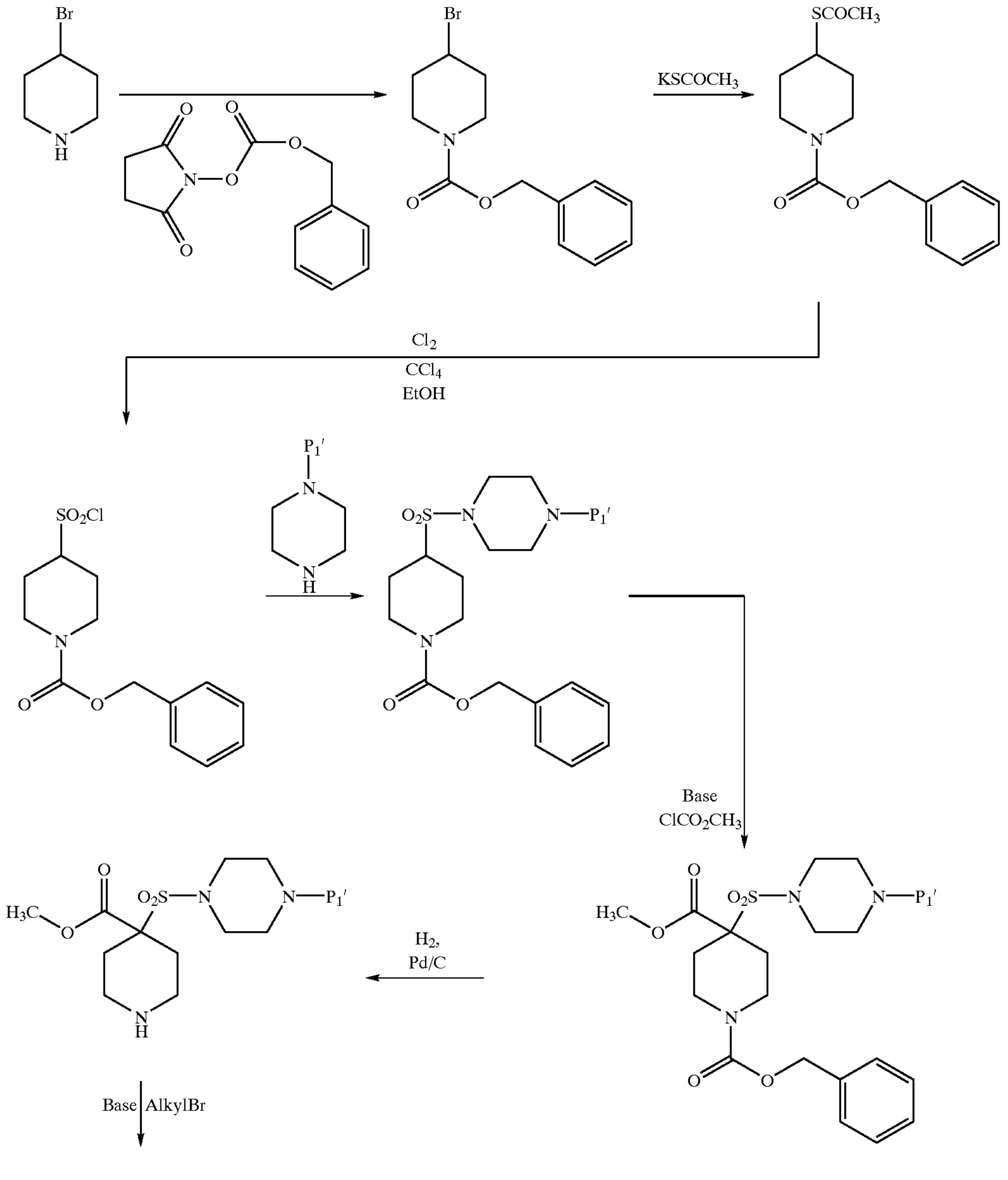

-continued

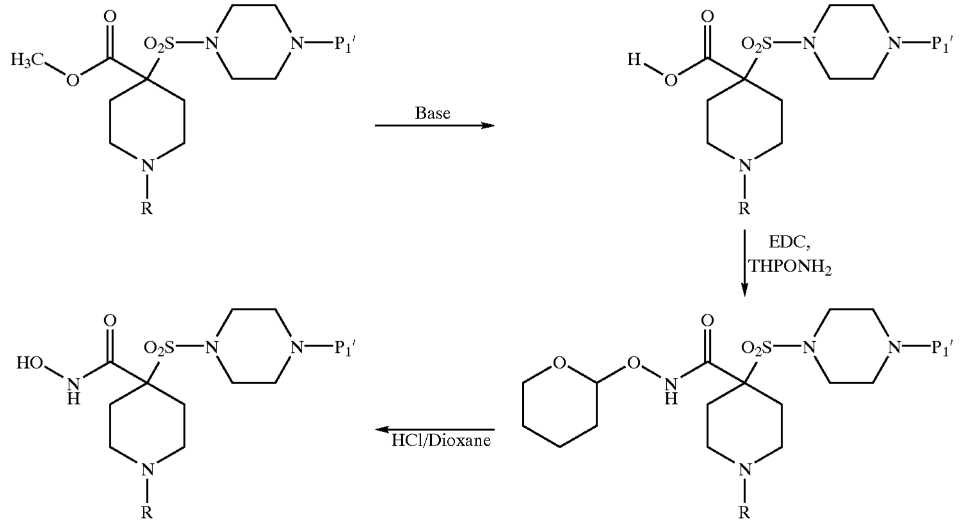

As utilized herein, the term "alkyl", alone or in combination, means a straight-chain or branched-chain alkyl radical containing 1 to about 18 carbon atoms, preferably 1 to about 12 carbon atoms, and more preferably 1 to about 8 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 18 carbon atoms preferably 2 to about 12 carbon atoms, and more preferably, 2 to about 8 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like.

The term "alkynyll", alone or in combination, means a straight-chain hydrocarbon radical having one or more triple bonds and containing 2 to about 18 carbon atoms, preferably 2 to about 12 carbon atoms, and more preferably, 2 to about 8 carbon atoms. Examples of alkynyl radicals include ethynyl, 2-propynyl, 3-propynyl, decynyl, 1-butynyl, 2-butynyl, 3-butynyl, and the like.

The term "carbonyl" or "oxo", alone or in combination, means a —C(═O)— group wherein the remaining two bonds (valences) can be independently substituted. The term carbonyl is also intended to encompass a hydrated carbonyl group —$C(OH)_2$—.

The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —$NH_2$ group whereas the term mono-substituted amino, alone or in combination, means a substituted amine —N(H) (substituent) group wherein one hydrogen atom is replaced with a substituent, and disubstituted amine means a —$N(substituent)_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or N,N-disubstituted depending on the degree of substitution of the amino nitrogen. Quaternary amine (ammonium)(IV°) means a nitrogen with four substituents [—$N^+(substituent)_4$] that is positively charged and accompanied by a counter ion, whereas N-oxide means one substituent is oxygen and the group is represented as [—$N^+(substituent)_3$—$O^-$]; i.e., the charges are internally compensated.

The term "cyano", alone or in combination, means a —C-triple bond-N (—C≡N, nitrile) group. The term "azido", alone or in combination, means a —N-triple bond-N (—N≡N) group. The term "hydroxyl", alone or in combination, means a —OH group. The term "nitro", alone or in combination, means a —$NO_2$ group. The term "azo", alone or in combination, means a —N═N— group wherein the bonds at the terminal positions can be independently substituted.

The term "hydrazino", alone or in combination, means a —NH—NH— group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —$SO_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —$SO_2$— group wherein the depicted remaining two bonds (valences) can be independently substituted. The term "sulfenamide", alone or in combination, means a —SON═ group wherein the remaining three depicted bonds (valences) can be independently substituted. The term "sulfide", alone or in combination, means a —S— group wherein the remaining two bonds (valences) can be independently substituted.

The term "alkoxyl", alone or in combination, means an alkyl ether radical or redicals with one, two or three oxygen atoms wherein the term alkyl is as defined above. Examples of suitable alkyl ether radicals include methoxy, ethoxy, n-propoxy, isopropoxy, n-butoxy, iso-butoxy, sec-butoxy, tert-butoxy, methoxyethoxypropyl ($CH_3OCH_2CH_2$-$OCH_2CH_2CH_2$—), 1,1-dimethoxyethane. 1,2-dimethoxyethane and the like. The term "alkyloxy" is used to mean a substituted alkoxy group.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

A heterocyclic (heterocyclo) group or the like alone or in combination is a saturated, unsaturated or partially unsaturated (non-aromatic) monocyclic, bicyclic or tricyclic heterocycle that contains one or more hetero atoms, typically one to three hetero atoms selected from nitrogen, oxygen and sulfur. A heterocyclic group can contain 4 to about 14 atoms in the one to three rings that also contain at least one nitrogen, oxygen or sulfur atom in addition to the carbon atoms. Preferably, a single ring is present and that ring contains 5 to 7 atoms and one hetero atom. Sulfur atoms, independently, may optionally be oxidized to, for example, —SO— or —$SO_2$-groups. Such a moiety can be optionally substituted on one or more ring carbon atoms by halogen, alkyl, alkoxy, oxo, and the like or as stated herein, and/or on a secondary nitrogen atom (i.e., —NH—) of the ring by alkyl, aralkoxycarbonyl, alkanoyl, aryl or arylalkyl or other groups listed herein or on a tertiary nitrogen atom (i.e., =N—) by oxido and that is attached via a carbon atom. The tertiary nitrogen atom with three substituents can also attached to form a N-oxide [=N(O)—] group. A "heterocycloalkyl" group is an alkyl group substituted with a heterocyclo group.

The term "aryl", alone or in combination, means a 5- or 6-membered carbocyclic aromatic ring-containing moiety or a fused ring system containing two or three rings that have all carbon atoms in the ring; i.e., a carbocyclic aryl radical. Exemplary carbocyclic aryl radicals include phenyl, indenyl and naphthyl radicals.

The term "biaryl", alone or in combination means an aryl ring as define herein connected directly by a single bond to further aryl rings. Exemplary biaryl radicals include phenylphenyl (biphenyl), 2-phenylnapthlenyl and phenylindenyl and 1-phenyl-anthracenyl radicals.

The term "heteroaryl" alone or in combination means a 5- or 6-membered aromatic ring-containing moiety or a fused ring system (radical) containing two or three rings that have carbon atoms and also one or more heteroatoms in the ring(s) such was sulfur, oxygen and nitrogen. Sulfur atoms, independently, may optionally be oxidized to, for example, —SO— or —$SO_2$-groups. Nitrogen atoms, independently, may be optionally oxidzed to, for example, N-oxide groups or quaternized. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyridyl-N-oxide, pyrazinyl, pyrimidinyl, furyl, tetrahydrofuryl, thienyl, thienyl-S-oxide, triazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

The term "heterocyclocarbonyl", alone or in combination, means a heterocyclogroup attached to a —(C=O)-group.

The term "heterocyclooxycarbony ", alone or in combination, means a heterocyclogroup attached to a —O(C=O)-group.

The term "heterocycloalkoxycarbony", alone or in combination, means a heterocyclogroup attached to a -alkylO(C=O)-group.

The term "heterocycloalkyl", alone or in combination, means a heterocyclogroup attached to an alkyl group.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula aralkyl-O—C(O)— in which the term "aralkyl" has the significance given above. An example of an aralkoxycarbonyl radical is benzyloxycarbonyl.

The term "aryloxy" means a radical of the formula aryl-O— in which the term aryl has the significance given above. The phenoxy radical is an exemplary aryloxy radical.

The terms "heteroaralkyl" and "heteroaryloxy" mean radicals structurally similar to aralkyl and aryloxy that are formed from heteroaryl radicals. Exemplary radicals include 4-picolinyl and 2-pyrimidinoxy, respectively.

The terms "alkanoyl" or "alkylcarbonyl", alone or in combination, means an acyl radical derived from an alkanecarboxylic acid, examples of which include formyl, acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benzfused monocyclic cycloalkanecarboxylic acid that is optionally substituted by, for example, alkanoylamino, such as 1,2,3,4-tetrahydro-2-naphthoyl, 2-acetamido-1,2,3,4-tetrahydro-2-naphthoyl.

The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above.

The term "heterocycloalkanoyl" is an acyl radical of the formula heterocyclo-substituted alkane carboxylic acid wherein heterocyclo has the significance given above. The term "heterocycloalkoxycarbonyl" means an acylradical of the formula heterocyclo-substituted alkane-O—CO— wherein heterocyclo has the significance given above.

The term "heteroaryloxycarbonyl" means an acyl radical represented by the formula heteroaryl-O—CO— wherein heteroaryl has the significance given above.

The term "aminocarbonyl" (carboxamide) alone or in combination, means an amino-substituted carbonyl (carbamoyl) group derived from an amine reacted with a carboxylic acid wherein the amino (amido nitrogen) group is unsubstituted (—$NH_2$) or a substituted primary or secondary amino group containing one or two substituents selected from the group consisting of hydrogen, alkyl, aryl, aralkyl, cycloalkyl, cycloalkylalkyl radicals and the like, as recited. A hydroxamate is a N-hydroxycarboxamide.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term "perfluoroalkyl" means an alkyl group wherein each hydrogen has been replaced by a fluorine atom. Examples of such perfluoroalkyl groups, in addition to trifluoromethyl above, are perfluorobutyl, perfluoroisopropyl, perfluorododecyl and perfluorodecyl.

The term "perfluoroalkoxy" alone or in combination, means a perfluoroalkyl ether radical wherein the term perfluoroalkyl is as defined above. Examples of such perfluoroalkoxy groups, in addition to trifluoromethoxy ($F_3C$—O—), are perfluorobutoxy, perfluoroisopropoxy, perfluorododecoxy and The term "perfluoroalkylthio" alone or in combination, means a perfluoroalkyl thioether radical wherein the term perfluoroalkyl is as defined above. Examples of such perfluoroalkylthio groups, in addition to trifluoromethylthio ($F_3C$—S—), are perfluorobutylthio, perfluoroisopropylthio, perfluorododecylthio and perfluorodecylthio.

The term "aromatic ring" in combinations such as substituted-aromatic ring sulfone or substituted-aromatic ring sulfoxide means aryl or heteroaryl as defined before.

Compounds contemplated herein can possess one or more asymmetric carbon atoms and are thus capable of existing in the form of optical isomers, enantiomers, diastereoisomers, as well as in the form of racemic or nonracemic mixtures. A compound can also exist in other isomeric forms such as ortho, meta and para isomers, cis and trans isomers, syn and anti isomers, E and Z isomers, tautomeric isomers, alpha and beta isomers, axial and equatorial isomers and isomers due to hindered rotation. An isomer can exist in equilibrium with another isomer in a mammal or a test system. Such isomeric equiliberia can also occur during synthesis, storage, formulation, as formulated pharmaceuticals, as liquids, solutions, solids, polymorphs and the like. Such a compound can also exist as an isomeric equilibrium system with a solvent or water, for example, as a hydrated ketone or aldehyde, hemiketal, hemiacetal, ketal, acetal or other class or type of solvate as is well known in the art. All isomers are included as compounds of this invention.

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, are applicable to the preparation of the corresponding compounds that are contemplated.

"M" utilized in the reaction schemes that follow represents a leaving group such as halogen, phosphate ester or sulfate ester.

It is understood that the definition of the compounds of the various formulas herein that contain asymmetric carbons, encompass all possible stereoisomers and mixtures thereof that posses the activity discussed herein. In particular, it encompasses racemic modifications and any optical isomers which possesses the indicated activity. Optical isomers can be obtained in pure form by standard separation techniques.

Treatment Process

A process for treating a host mammal having a condition associated with pathological matrix metalloprotease activity is also contemplated. That process comprises administering a compound described hereinbefore in an MMP enzyme-inhibiting effective amount to a mammalian host having such a condition. The use of administration repeated a plurality of times is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-$\alpha$ convertase or a member of the adamalysin family of enzymes such as ADAM 10. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinas activity, a contemplated MMP inhibitor compound can be used, where appropriate, in the form of a pharmaceutically acceptable amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentane-propionate, dodecylsulfate, ethanesulfonate, formate. glutamate, glucoheptanoate, gluconate, glucurantae, glycerophosphate, hemisulfate, heptanoate, hexanoate, fumarate, hydrochloride, hydrobromide, hydroiodide, 2-hydroxyethanesulfonate, isocitrate, lactate, malate, maleate, methanesulfonate, nicotinate, 2-naphthalenesulfonate, oxalate, oxalacetate, palmoate, pectinate, persulfate, 3-phenylpropionate, phosphate, monohydrogen phosphate, dihydrogen phosphate, picrate, pivalate, propionate, pyruvate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form pharmaceutically acceptable salts. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines an& quaternary ammonium cations, including in part, trimethylamine, diethylamine, N,N'-dibenzyl-ethylenediamine, chloroprocaine, choline, diethanolamine, ethylenediamine, meglumine (N-methylglucamine) and procaine.

The term "pharmaceutically acceptable" is used adjectivally herein to mean that the modified noun is appropriate for use in a pharmaceutical product.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight daily, preferably about 0.001 to about 30 mg/kg body weight daily and more usually about 0.01 to about 10 mg. Dosage unit compositions can contain such amounts or submultiples thereof to make up the daily dose.

A suitable dose can be administered, in multiple sub-doses per day. Multiple doses per day can also increase the total daily dose, should such dosing be desired by the person prescribing the drug. Such composition can be administered 1 to 6 times a day, more usually 1 to 4 times a day.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, which is preferred, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H.A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

Abbreviations are often used for reagents and solvents in the specific examples that follow. Those abbreviations and their meanings are as follows:

BOC=t-butoxycarbonyl

DEAD=diethyl azodicarboxylate

DMF dimethylformamide

DMPU=1,3-dimethyl-3,4,5,6-tetrahydro-2(1H)-pyrimidinone

EtOAc=ethyl acetate

EDC=1-ethyl-3-[3-(dimethylamino)-propyl]carbodiimide hydrochloride $Et_2O$=diethyl ether HOBT=1-hydroxybenzotriazole MeOH=methanol $MeCl_2$=methylene chloride MsCl=methanesulfonyl chloride NMM=N-methyl morpholine THF=tetrahydrofruan TsCl toluenesulfonyl chloride THP-O-hydroxylamine=O-tetrahydropyran-hydroxylamine and O-tetrahydro-2H-pyran-2-yl-hydroxylamine

EXAMPLE 1

Preparation of

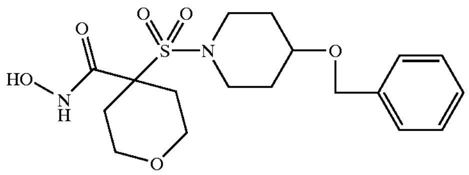

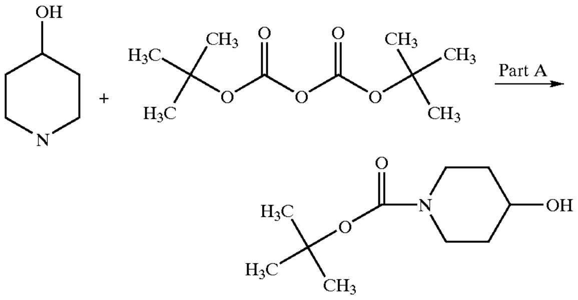

Part A: To a slurry of 4-hydroxypiperadine (46.3 g, 458 mmol) in tetrahydrofuran (400 mL) was added triethylamine (67 mL, 481 mmol), followed by slow addition of a solution of di-tert-butyl-dicarbonate (100 g, 458 mmol) in tetrahyrd-ofuran (200 mL). The temperature was monitored and maintained below 32° C. The mixture was stirred for 4 hours before working up. Work up comprised stripping the tetrahydrofuran by rotary evaporation and taking the residue up in ethyl acetate (300 mL). The organic was then washed with 5% $KHSO_4$ (3x–150 mL), saturated $NaHCO_3$ (3x–150 mL), and brine (2x–150 mL). The organic portion was then dried over anhydrous $MgSO_4$—, filtered, and concentrated to afford a crude yellow oil. The oil was crystallized from hexanes providing the N-BOC-4-hydroxypiperidine product as a tan solid (86 g, 93% yield). $^1$H NMR showed the desired compound.

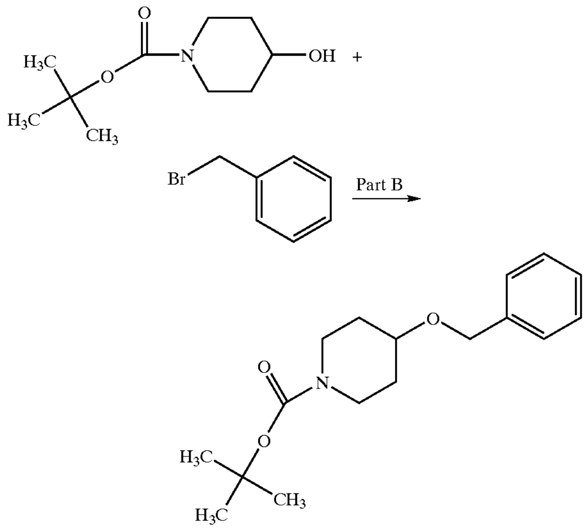

Part B: To a slurry of NaH (60% oil dispersion, 2.4 g, 60 mmol) in N,N-dimethylformamide (DMF; 70 mL) cooled to zero degrees C. under $N_2$ was slowly added a solution of the N-BOC-4-hydroxypiperidine product from Part A (10 g, 50 mmol) in DMF (20 mL). The temperature was monitored and maintained at <50° C. The mixture was stirred 15 minutes before slowly adding a solution of benzyl bromide (9 mL, 60 mmol) in DMF (10 mL), keeping temperature at <10° C. The reaction was allowed to come to room temperature and was stirred 12 hours. To quench, the reaction was cooled to zero degrees C. and $H_2O$ (50 mL) was added. Work up comprised stripping the solvents by rotary evaporation and dissolving the residue in ethyl acetate (150 mL) and $H_2O$ (100 mL). The layers were separated and the aqueous was extracted via ethyl acetate (2x–150 mL). The organic portions were washed with saturated $NaHCO_3$ (2x–100 mL), $H_2O$ (1x–150 mL), and brine (1x–150 mL), then dried over $Na_2SO_4$, filtered, and concentrated to afford a crude oil (18 g, $100^+$% crude yield). $^1$H NMR showed the desired compound along with the benzyl bromide starting material.

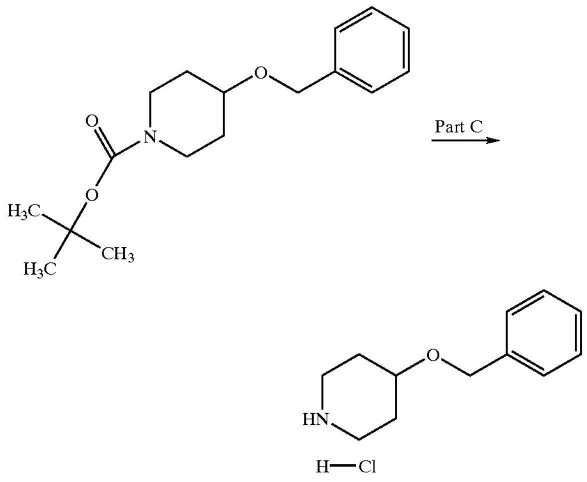

Part C: To a solution of the crude product of Part B in 1,4-dioxane (10 mL) was added 4N HCl in dioxane (50 mL, 200 mmol). The mixture stirred at room temperature until starting material was gone by LC (~1 h). The solvents were then stripped and the residue was slurried in diethyl ether and filtered. The solid was washed with diethyl ether (2×–50 mL) and dried in vacuo to afford a white solid (11.5 g, 100% yield). $^1$H NMR showed the desired compound as the HCl salt.

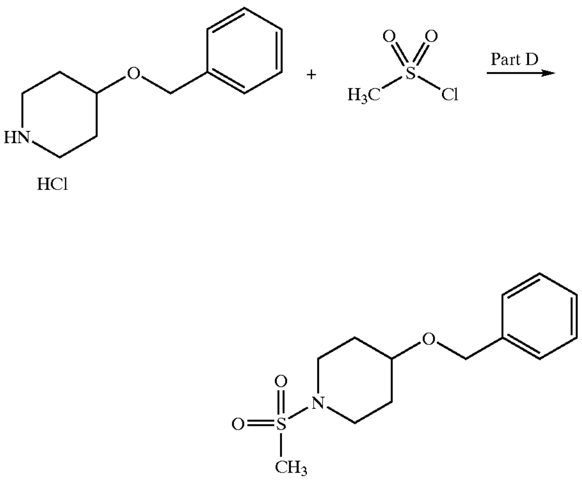

Part D: The HCl salt of Part C (log, 44 mmol) and triethylamine (15.3 mL, 110 mmol) were slurried in $CH_2Cl_2$ (170 mL) and cooled to zero degrees C. A solution of methane sulfonyl chloride (5.1 mL, 66 mmol) in $CH_2Cl_2$ (50 mL) was slowly added, maintaining the temperature below 10° C. with an ice bath. After the addition, the ice bath was removed and the reaction stirred for 1 hour as it came to room temperature. After the disappearance of the starting material, the solvent was stripped and the residue was dissolved in ethyl acetate (100 mL) and $H_2O$ (30 mL). Once separated, the organic layer was washed with 5% $KHSO_4$ (3×–50 mL) and brine (1×–50 mL). The organic layer was then dried over $Na_2SO_4$, filtered, and concentrated to afford an oily solid that was recrystallized from diethylether and hexanes, affording an off-white solid (12.3 g, 95% yield), SC 79767. $^1$H NMR showed the desired compound. HPLC showed 100% at $t_r$=12.1 minutes.

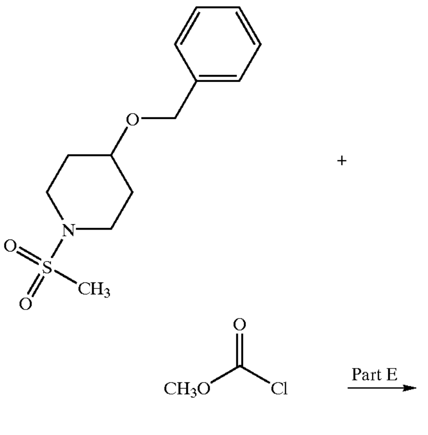

-continued

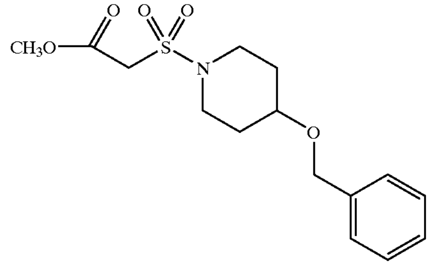

Part E: Oven-dried glassware was charged with the product of Part D (5.0 g, 16.9 mmol) and tetrahydrofuran (34 mL) and the composition was cooled to –75° C. Lithium bis(trimethylsilyl)amide (1.0 M in tetrahydrofuran, 34 mL, 34 mmol was slowly added, keeping temperature <–60° C. Reaction was stirred for 30 minutes after the addition, and was then charged with a solution of methyl chloroformate (1.3 mmol, 16.9 mmol) in tetrahydrofuran (17 mL), again keeping the temperature <–60° C. After stirring for 1 hour at –75° C., the reaction was quenched with saturated $NH_4Cl$, keeping temperature <–20° C. The aqueous portion froze into a solid chunk of ice. After warming to 5° C., the mixture was extracted with ethyl acetate (3×–200 mL). The resulting organic portions were washed with saturated $NH_4Cl$ (2×–100 mL) and brine (1×–100 mL), then dried over $Na_2SO_4$ and concentrated to afford the depicted product as a tan oil (5.0 g, 91% crude yield). $^1$H NMR showed the desired compound with some starting material present. HPLC showed 90% at $t_r$=13.9 minutes, 10% at 12.1 minutes.

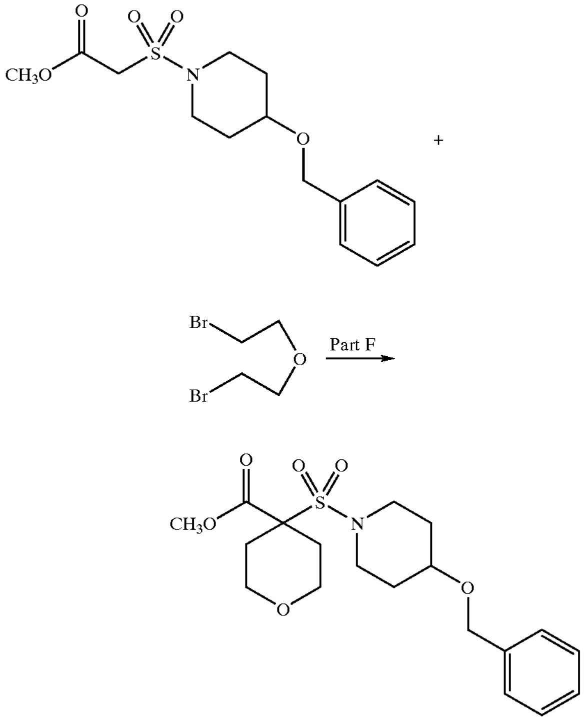

Part F: To a solution of the product of Part E (4.5 g, 13.7 mmol) and dibromodiethylether (1.9 mL, 15.1 mmol) in DMF (28 mL) was added 18-Crown-6 (500 mg, cat.) followed by potassium carbonate (3.8 g, 27.4 mmol). The mixture was heated at 60° C. for 4 hours after which more potassium carbonate (1.9 g, 13.7 mmol) was added, and the reaction continued at 60° C. for 14 hours. Liquid chromatography showed <10% starting material remained. The reaction was worked up by pouring into stirring 10% HClaq (200 mL). A gummy solid resulted that was extracted with ethyl acetate (3x–300 mL). The resulting organic portions were washed with brine (2x–200 mL), dried over $Na_2SO_4$, and concentrated to afford a dark brown oil. The product was crystallized from diethylether and hexanes. The product was dried to afford the pyran methyl ester as an orange solid (3.7 g, 69% yield). $^1$H NMR showed the desired compound. HPLC showed 96% at $t_r$=25.2 minutes.

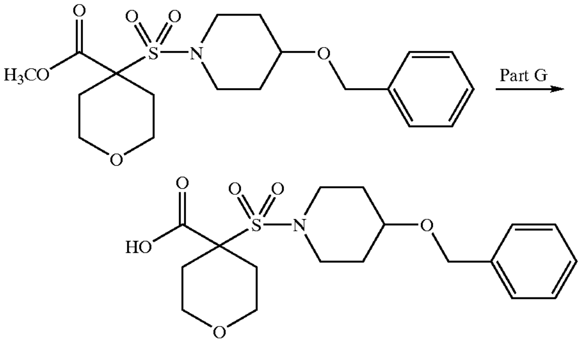

Part G: To a solution of the product of Part F (3.5 g, 8.8 mmol) in tetrahydrofuran (20 mL) was added potassium trimethylsilonate (2.7 g, 21.1 mmol). The reaction stirred overnight (about eighteen hours) at room temperature. Liquid chromatography showed that <3% starting material remained. Work up comprised stripping the tetrahydrofuran- and taking the residue up in $H_2O$ (100 mL). The solution was washed with diethylether (50 mL). The aqueous portion was then cooled to zero degrees C. and 10% $HCl_{aq}$ was slowly added until about pH 3. The acidic mixture was then extracted with ethyl acetate (3x–150 mL). The organic portions were washed with brine (1x–100 mL), dried over $Na_2SO_4$, and concentrated to afford a wet solid. The solid was dried in vacuo with phosphorous pentoxide yielding an orange solid (2.4 g, 72% yield). $^1$H NMR showed the desired carboxylic acid compound. HPLC showed 97% at $t_r$=21.3 minutes.

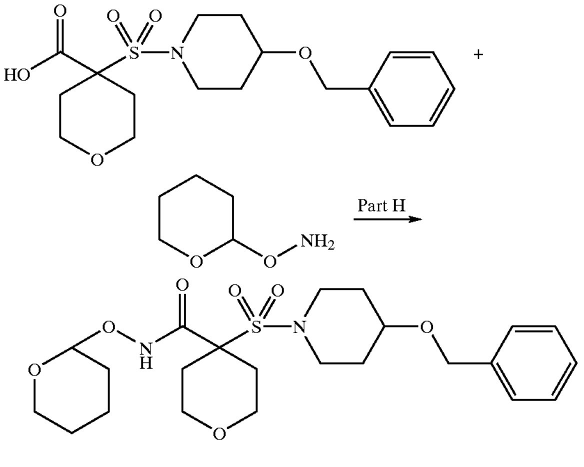

Part H: To a solution of the Part G acid product (2.4 g, 6.2 mmol) in dimethylacetamide (10 mL) was added N-methylmorpholine (2.0 mL, 18.6 mmol) followed by N-hydroxybenzotriazole hydrate (1.0 g, 7.4 mmol), O-(tetrahydro-2H-pyran-2-yl)hydroxylamine (1.1 g, 9.4 mmol), and 1-(3-dimethylaminopropyl)-3-ethylcarbodiimide hydrochloride (1.8 g, 9.4 mmol). The mixture stirred overnight (about eighteen hours) and was then stripped of solvent. The residue was dissolved in ethyl acetate (250 mL) and washed with 5% $NaHSO_4$ (1x–150 mL), saturated potassium carbonate (1x–150 mL), and brine (1x–150 mL). The organic portions were then dried over $Na_2SO_4$ and concentrated to afford a viscous oil (3.2 g, 100+% crude yield). $^1$H NMR showed the desired compound. HPLC showed 95% at $t_r$=23.5 minutes.

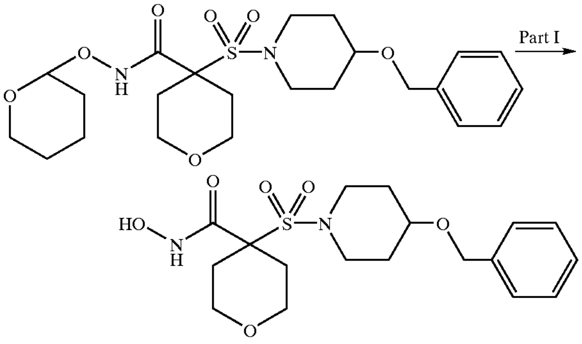

Part I: The crude oil product of Part H (3.0 g, 6.2 mmol) was dissolved in acetonitrile (10 mL) and stirred with 10% $HCl_{aq}$ (15 mL) for 2 hours at which time liquid chromatography showed no more starting material present. The acetonitrile was removed using an $N_2$ stream, affording a solid that was collected, washed with $H_2O$ (1x–20 mL), and dried in vacuo to afford the product as a tan solid (1.6 g, 64% yield). $^1$H NMR showed the desired compound. HPLC showed 99% at $t_r$=18.8 minutes. Mass spectroscopy showed $M^{+H}_{found}$=399 ($M^{+H}_{calc}$=399).

EXAMPLE 2

Preparation of Tetrahydro-N-hydroxy-4-[[4-[4-(trifluoromethyl)phenoxy]-1-piperidinyl]sulfonyl]-2H-pyran-4-caxboxamide

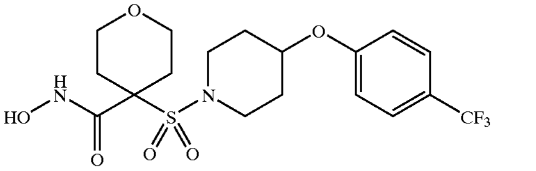

Part A: In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo to give the BOC piperidine as a white solid (37.7 g, 94%).

Part B: Preparation of 1,1-Dimethylethyl 4-[4-(Trifluoromethyl)phenoxy]-1-piperidinecarboxylate To a solution of the BOC piperidine from Part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours, cesium carbonate (3.26g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from Part B (5.95 g, 17.2 mmol) in 1,4-dioxane (10 mL) was added 4N HCl dioxane solution (17 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from Part C (4.6 g, 16.9 mmol) and triethylamine (5.9 mL, 42.4 mmol) in methylene chloride (45 mL) at zero degrees Celsius was added a solution of methanesulfonyl chloride (1.97 mL, 25.4 mmol) in methylene chloride (10 mL). After one hour at ambient temperature, the solvent was removed in vacuo. The residue was taken up in ethyl acetate, washed with water two times, brine, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl) phenoxy]-1-piperidinyl]sulfonyl]acetate In dry equipment under nitrogen, the sulfonamide from Part D (4.2 g, 13 mmol) was dissolved in dry tetrahydrofuran (26 mL), chilled to minus seventy-five degrees Celsius, and a 1M solution of lithium bis(trimethylsilyl)amide (26 mL) was added while maintaining the temperature below minus sixty-five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, brine, dried over $Na_2SO_4$, filtered, and concentrated in vacuo to give the methylene sulfonamide as a yellow oil (4.95 g, 100%).

Part F: Preparation of Methyl Tetrahydro-4-[[4-[4-(Trifluoromethyl)phenoxy]-1-piperidinyl]sulfonyl)-2H-pyran-4-carboxylate To a solution of the methylene sulfonamide from Part E (6.15 g, 16 mmol) in dimethylformamide (32 mL) was added potassium carbonate (7.8 g, 56.6 mmol), bis-(2-bromoethyl)ether (2.1 mL, 16 mmol) and 18-Crown-6 (500 mg). The slurry was stirred at sixty degrees Celsius. After sixteen hours, potassium carbonate (2.0 g, 14 mmol) and bis-(2-bromoethyl)ether (0.2 mL, 1.6 mmol) were added and the reaction stirred at sixty degrees Celsius. After a total of twenty two hours, the reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the THP-substituted sulfonamide as a white solid (4.75 g, 65%).

Part G: Preparation of Tetrahydro-4-[[4-[4-(trifluoromethyl) phenoxy]-1-piperidinyl]sulfonyl]-2H-pyran-4-carboxylic Acid In dry equipment under nitrogen, the THP-substituted sulfonamide from Part F (0.9 g, 2 mmol) was dissolved in dry tetrahydrofuran (4.0 mL) and potassium trimethylsilonate (0.38 g, 3.0 mmol) was added at ambient temperature. After twenty four hours water (100 mL) was added and the solution concentrated in vacuo. The residue was taken up in water and extracted with ethyl acetate to remove unreacted starting material. The aqueous solution was treated with 6 N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a white solid (635 mg, 73%).

Part H: Preparation of Tetrahydro-N-[(tetrahydro-2H-pyran-2-yl)-oxy)-4-[[4-[4-(trifluoromethyl)phenoxy]-1-piperidinyl]sulfonyl]-2H-pyran-4-carboxamide In dry equipment under nitrogen, the carboxylic acid from Part G (3.0 g, 6.86 mmol) was dissolved in dry dimethylformamide (17 mL) and the remaining reagents were added to the solution in the following order: N-hydroxybenzotriazole hydrate (1.11 g, 8.24 mmol), N-methylmorpholine (2.26 mL, 20.6 mmol), O-(tetrahydro-2H-pyran-2-yl) hydroxylamine (2.49 g, 21.3 mmol), and 1-(3-dimethylaminopropyl)-3-ethylcarbodiimide hydrochloride (1.84 g, 9.6 mmol). After two hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the THP hydroxamate as a white foam (2.3 g, 63%). HRMS (ES+) $M+H^+$ calculated for $C_{23}H_{31}N_2O_7$ $S_1F_3$: 537.1882, found 537.1856.

Part I: Preparation of Tetrahydro-N-hydroxy-4-[[4-[4-(trifluoromethyl)phenoxy]-1-piperidinyl]sulfonyl]-2H-pyran-4-carboxamide To a solution of the THP hydroxamate from Part H (1.55 g, 2.89 mmol) in 1,4-dioxane (7 mL) was added 4 N HCl dioxane solution (7 mL) and methanol (7 mL). After one hour at ambient temperature the reaction was diluted with ethyl acetate and washed with water, dried over $Na_2SO_4$, filtered, and concentrated in vacuo. The product was recrystallized (acetone/hexanes) to give the depicted compound as a white solid (1.23 g, 95%). HRMS (ES+) $M+H^+$ calculated for $C_{18}H_23N_2O_6$ $S_1F_3$: 453.1307, found 453.1319.

EXAMPLE 3

Preparation of Tetrahydro-N-hydroxy-4-[[4-[[4-[(trifluoromethyl)thio]phenyl]-thiol-1-piperidinyl] sulfonyl)-2H-pyran-4-carboxamide

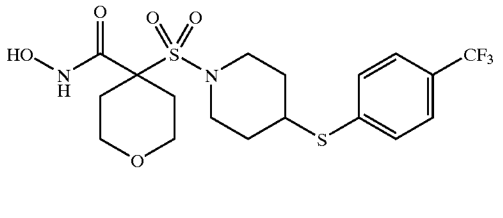

Part 1: Preparation of

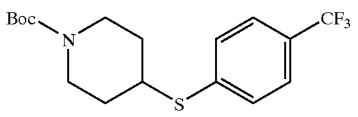

To a slurry of $Cs_2CO_3$ (Aldrich, 20 g, 50 mmol) and 4-(methylsulfonyl)hydroxy-1-piperidinecarboxylic acid, 1,1-dimethylethyl ester of Example 14, part B (5 g, 25 mmol) in acetone (70 mL) at 25° C. under $N_2$ was slowly added 4-trifluromethyl thiophenol (10 g, 50 mmol). The mixture was stirred 48 hours. After this time the acetone was removed by roto-evaporation and taking the residue up in ethyl acetate (150 mL) and $H_2O$ (100 mL) The layers were separated and the aqueous was extracted via ethyl acetate (2x–150 mL). The organics were washed with saturated $K_2CO_3$ (2x–100 mL), $H_2O$ (1x–150 mL), and brine (1x–150 mL), then dried over $Na_2SO_4$, filtered, and concentrated to afford the crude N-Boc piperidine as an oil. The oil was purified on silica gel to give 6 g of a clear oil. $^1H$ NMR and mass spectrum were consistent with the desired compound.

Part 2: Preparation of

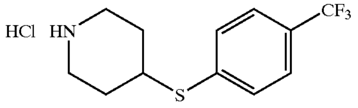

To a solution of the product (6 g) of Part 1 in 1,4-dioxane (10 mL) was added 4 N HCl in dioxane (50 mL, 200 mmol). The mixture stirred at room temperature until starting material was gone by LC (about one hour). The solvents were then removed and the residue was slurried in diethyl ether and filtered. The solid was washed with diethyl ether (2x–50 mL) and dried in vacuo to afford the piperidine HCl salt as a white solid (6 g). $^1H$ NMR and mass spectrum showed the desired compound as the HCl salt.

Part 3: Preparation of

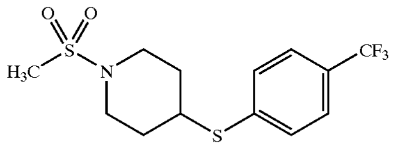

The HCl salt of Part 2 (6 g, 30 mmol) and triethylamine (Aldrich, 10 mL, 110 mmol) were slurried in $CH_2Cl_2$ (100 mL) and cooled to zero° C. A solution of methane sulfonyl chloride (Aldrich, 4 g, 45 mmol) in $CH_2Cl_2$ (20 mL) was slowly added, maintaining the temperature below 10° C. After the addition, the ice bath was removed and the reaction stirred 1 hour as it warmed to ambient temperature. After the disappearance of the starting material, the solvent was removed and the residue was taken up in ethyl acetate (100 mL) and $H_2O$ (30 mL). Once separated, the organic layer was washed with 5% $KHSO_4$ (3x–50 mL) and brine (1x–50 mL). The organic layer was then dried over $Na_2SO_4$, filtered, and concentrated to afford the piperidine as an oily solid that was recrystallized from diethyl ether, affording an off-white solid (3.5 g). $^1H$ NMR and mass spectrum showed the desired compound.

Part 4: Preparation of

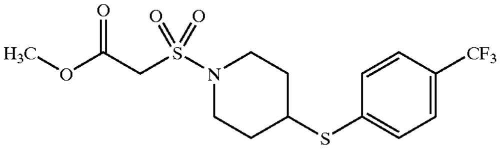

Oven-dried glassware was charged with the compound from Part 3 (3.0 g, 12 mmol), tetrahydrofuran (34 mL,) and cooled to −75° C. Lithium bis(trimethylsilyl)amide (Aldrich, 1.0 M in tetrahydrofuran, 35 mL, 33 mmol) was slowly added, keeping temperature lessthan −60° C. The reaction was stirred for 30 minutes after the addition and was then charged with a solution of methylchloroformate (Aldrich, 1.3 mmol, 16.9 mmol) in tetrahydrofuran (17 mL), again keeping the temperature at less than −60° C. After stirring for 1 hour at −75° C., the reaction was quenched with saturated $NH_4Cl$, keeping temperature at less than −20° C. The aqueous portion freezes into a solid chunk of ice. After warming to 50° C., the mixture was extracted via ethyl acetate (3x–200 mL). Organics were washed with saturated $NH_4Cl$ (2x–100 mL) and brine (1x–100 mL), then dried over $Na_2SO_4$ and concentrated to afford the methylene piperidine as a tan oil (5.0 g, 91% crude yield). $^1H$ NMR and mass spectrum indicated desired compound.

Part 5: Preparation of

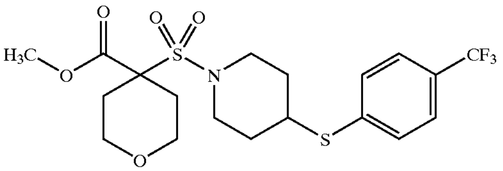

To a solution of compound from Part 4 (3 g, 11 mmol) and dibromo-diethylether (Lancaster, 1.8 mL, 15.1 mmol) in dimethylformamide (28 mL) was added 18-Crown-6 (Aldrich, 500 mg, cat.), followed by potassium carbonate (Aldrich, 3.8 g, 27.4 mmol). The mixture was heated at 60° C. for 16 hours. The product was isolated by pouring the reaction mixture into stirring 10% $HCl_{aq}$ (200 mL) and extraction with ethylacetate (3x–300 mL). Organics were washed with brine (2x–200 mL), dried over $Na_2SO_4$, and concentrated to afford the ester as an oil. The oil was crystallized from diethylether (1.6 g). $^1H$ NMR and mass spectrum showed the desired compound.

Part 6: Preparation of

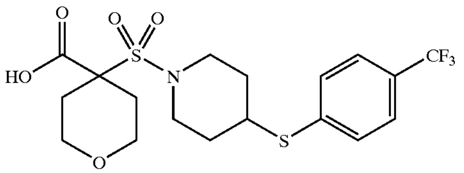

To a solution from Part 5 (2 g, 7 mmol) in tetrahydrofuran (20 mL) was added potassium trimethylsilonate (Aldrich, 2 g, 18 mmol). The reaction stirred overnight (about 18 hours) at room temperature. LC showed less than 3% starting material remained. Work up comprised removing the tetrahydrofuran and taking the residue up in $H_2O$ (100 mL). The solution was washed with diethylether (50 mL). The aqueous was then cooled to zero° C. and 10% $HCl_{aq}$ was slowly added until pH=3. The acidic mixture was then extracted with ethyl acetate (3x–150 mL). The organics were washed with brine (1x–100 mL), dried over $Na_2SO_4$, and concentrated to afford a wet solid. The solid was dried in vacuo with phosphorous pentoxide yielding the acid as an orange solid (2.4 g, 72% yield). $^1H$ NMR and mass spectrum showed the desired compound.

Part 7: Preparation of

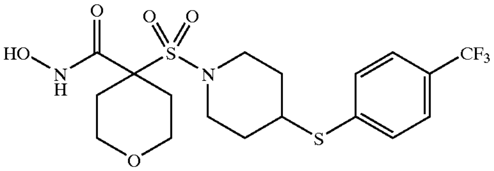

To a solution of the acid product in Part 6 (2.4 g, 6.2 mmol) in dimethylacetamide (10 mL) was added N-methylmorpholine (Aldrich, 2.0 mL, 18.6 mmol) followed by N-hydroxybenzotriazole hydrate (Aldrich, 1.0 g, 7.4 mmol), O-(tetrahydro-2H-pyran-2-yl) hydroxylamine (1.1 g, 9.4 mmol), and, lastly, 1-(3-dimethylaminopropyl)-3-ethylcarbodiimide hydrochloride (Sigma, 1.8 g, 9.4 mmol). The mixture stirred overnight (about 18 hours) and was then stripped of solvent. The residue was taken up in ethyl acetate (250 mL) and washed with 5% $NaHSO_4$ (1x–150 mL), saturated potassium carbonate (1x–150 mL), and brine (1x–150 mL). The organic layer was dried over $Na_2SO_4$ and concentrated to afford a viscous oil. $^1H$ NMR and MS showed the desired compound.

The viscous crude oil (3.0 g, 6.2 mmol) was dissolved in acetonitrile (10 mL) and stirred with 10% $HCl_{aq}$ (15 mL) for 2 hours, after which, liquid chromatography (LC) showed no more starting material. The acetonitrile was removed with $N_2$ stream over the surface of the solution affording a solid that was collected, washed with $H_2O$ (1x–20 mL), and dried in vacuo to afford the product as a tan solid (1.6 g, 64% yield). $^1H$ NMR showed the desired compound. Mass spectroscopy showed: $C_{18}H_{23}F_3N_2O_5S_3$ $M^{+H}_{found}$=500 ($M^{+H}_{calc}$=500).

EXAMPLE 4

Preparation of

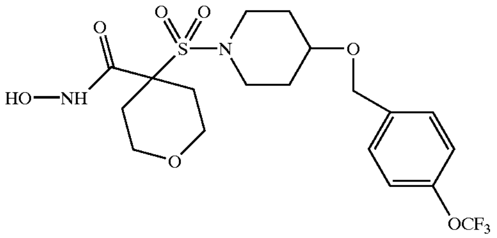

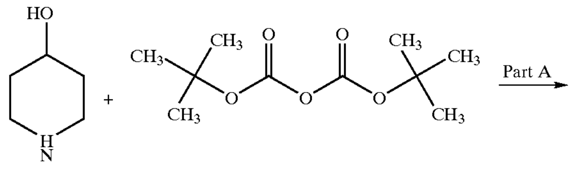

-continued

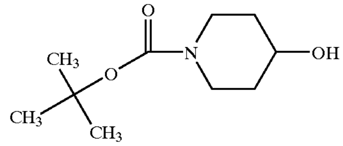

Part A: To a slurry of 4-hydroxypiperidine (46.3 g, 458 mmol) in tetrahydrofuran (400 mL) was added triethylamine (67 mL, 481 mmol), followed by slow addition of a solution of di-tert-butyl-dicarbonate (100 g, 458 mmol) in tetrahyrdofuran (200 mL). The temperature was monitored and maintained below 32° C. The mixture was stirred for 4 hours before working up. Work up consisted of removing the tetrahydrofuran in vacuo and taking the residue up in ethyl acetate (300 mL). The organic phase was then washed with 5% $KHSO_4$ (3x–150 mL), saturated $NaHCO_3$ (3x–150 mL), and brine (2x–150 mL). The organic phase was then dried over anhydrous $MgSO_4$, filtered, and concentrated to afford a crude yellow oil. The oil was crystallized from hexanes providing the N-BOC-4-hydroxypiperidine product as a tan solid (86 g, 93% yield). $^1H$ NMR showed the desired compound.

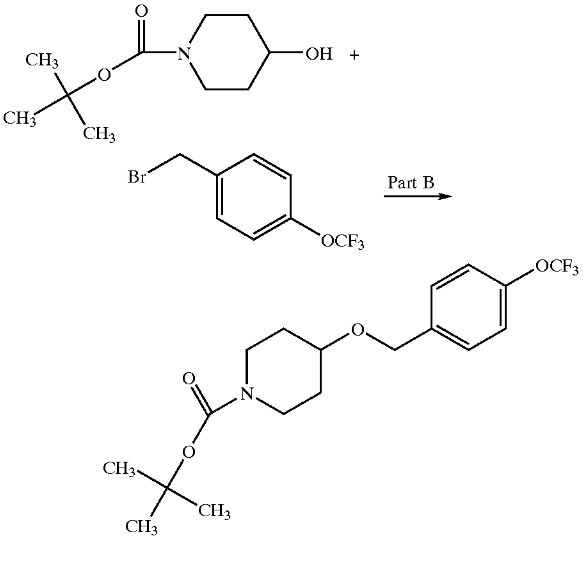

Part B: To a slurry of NaH (60% oil dispersion, 2.4 g, 60 mmol) in N,N-dimethylformamide (70 mL) cooled to zero degrees C. under $N_2$ was slowly added a solution of the N-BOC-4-hydroxypiperidine product from Part A (10 g, 50 mmol) in N,N-dimethylformamide (20 mL). The temperature was monitored and maintained at <5° C. The mixture was stirred 15 minutes before slowly adding a solution of benzyl bromide (9 mL, 60 mmol) in N,N-dimethylformamide (10 mL), keeping temperature <10° C. The reaction was permitted to come to room temperature and was stirred 12 hours. To quench, the reaction was cooled to zero degrees C. and $H_2O$ (50 mL) was added. Work up consisted of removing the solvents in vacuo and taking the residue up in ethyl acetate (150 mL) and $H_2O$ (100 mL). The layers were separated and the aqueous layer was extracted with ethyl acetate (2x–150 mL). The organic phase was washed with saturated $NaHCO_3$ (2x–100 mL), $H_2O$ (1x–150 mL), and brine (1x–150 mL), then dried over $Na_2SO_4$, filtered, and concentrated to afford a crude oil (18 g, $100^{+}$% crude yield). $^1H$ NMR showed the desired compound along with the benzyl bromide starting material.

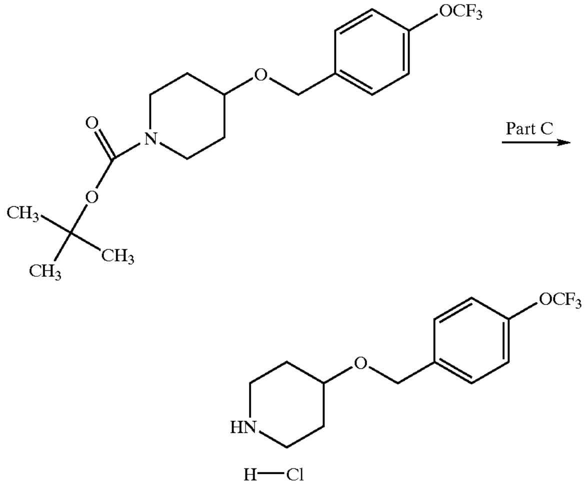

Part C: To a solution of the crude product of Part B in 1,4-dioxane (10 mL) was added 4 N HCl in dioxane (50 mL, 200 mmol). The mixture stirred at room temperature until starting material was gone by liquid chromatography (LC; about 1 hour). The solvents were then removed and the residue was slurried in diethyl ether and filtered. The solid was washed with diethyl ether (2x–50 mL) and dried in vacuo to afford a white solid (11.5 g, 100% yield). $^1$H NMR showed the desired compound as the HCl salt.

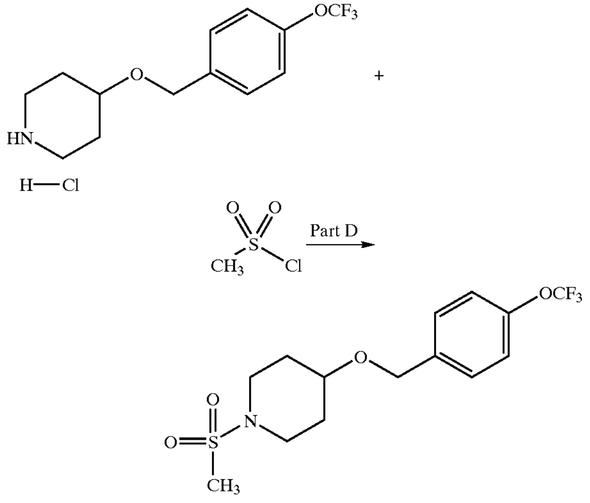

Part D: The HCl salt of Part C (10 g, 44 mmol) and triethylamine (15.3 mL, 110 mmol) were slurried in $CH_2Cl_2$ (170 mL) and cooled to zero degrees C. with an ice bath. A solution of methanesulfonyl chloride (5.1 mL, 66 mmol) in $CH_2Cl_2$ (50 mL) was slowly added, maintaining the temperature below 10° C. After the addition, the ice bath was removed and the reaction stirred 1 h as it came to room temperature. After the disappearance of the starting material, the solvent was removed and the residue was taken up in ethyl acetate (100 mL) and $H_2O$ (30 mL). Once separated, the organic layer was washed with 5% $KHSO_4$ (3x–50 mL) and brine (1x–50 mL). The organic layer was then dried over $Na_2SO_4$, filtered, and concentrated to afford an oily solid that was recrystallized from diethyl ether and hexanes, affording an off-white solid (12.3 g, 95% yield), the sulfonamide. $^1$H NMR showed the desired compound. HPLC showed 100% at $t_r$=12.1 minutes.

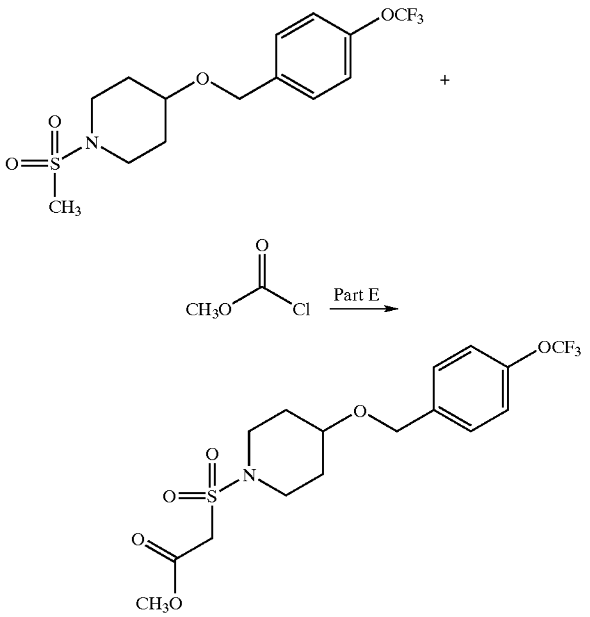

Part E: Oven-dried glassware was charged with the sulfonamide of Part D (5.0 g, 16.9 mmol) and tetrahydrofuran (34 mL) and cooled to −75° C. Lithium bis(trimethylsilyl) amide (1.0 M in tetrahydrofuran, 34 mL, 34 mmol) was slowly added, keeping temperature <−60° C. Reaction mixture was stirred for 30 minutes after the addition and was then charged with a solution of methyl chloroformate (1.3 mmol, 16.9 mmol) in tetrahydrofuran (17 mL) again keeping the temperature <−60° C. After stirring for 1 hour at −75° C., the reaction was quenched with saturated $NH_4Cl$, keeping temperature <−20° C. The aqueous portion froze into a solid chunk of ice. After warming to 5° C., the mixture was extracted via ethyl acetate (3x–200 mL). Organic layers were washed with saturated $NH_4Cl$ (2x–100 mL) and brine (1x–100 mL), then dried over $Na_2SO_4$ and concentrated to afford the methyl formate as a tan oil (5.0 g, 91% crude yield). $^1$H NMR showed the desired compound with some starting material present. HPLC showed 90% at $t_r$=13.9 minutes, 10% at 12.1 minutes.

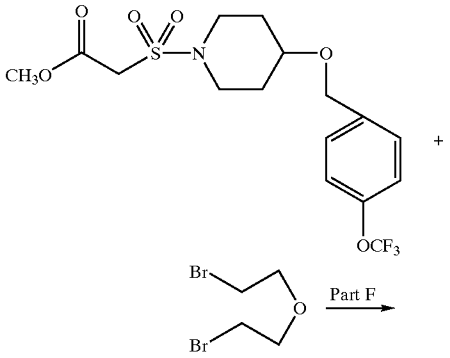

-continued

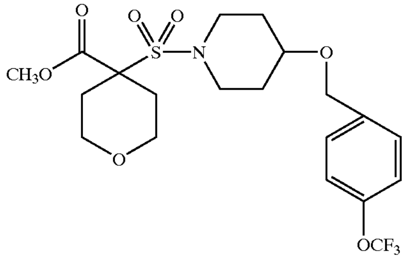

Part F: To a solution of the methyl formate of Part E (4.5 g, 13.7 mmol) and dibromo-diethylether (Lancaster, 1.9 mL, 15.1 mmol) in dimethylformamide (28 mL) was added 18-Crown-6 (500 mg, cat.), followed by potassium carbonate (3.8 g, 27.4 mmol). The mixture was heated at 60° C. for 4 hours, after which more potassium carbonate (1.9 g, 13.7 mmol) was added, and the reaction continued at 60° C. for 14 hours. LC showed <10% starting material remained. The reaction was worked up by pouring into stirring 10% $HCl_{aq}$ (200 mL). A gummy solid resulted that was extracted with ethyl acetate (3x–300 mL). Organic layers were washed with brine (2x–200 mL), dried over $Na_2SO_4$, and concentrated to afford a dark brown oil. Oil was crystallized from diethyl ether and hexanes. The solid was dried to afford the pyran methyl ester as an orange solid (3.7 g, 69% yield). $^1H$ NMR showed the desired compound. HPLC showed 96% at $t_r$=25.2 minutes.

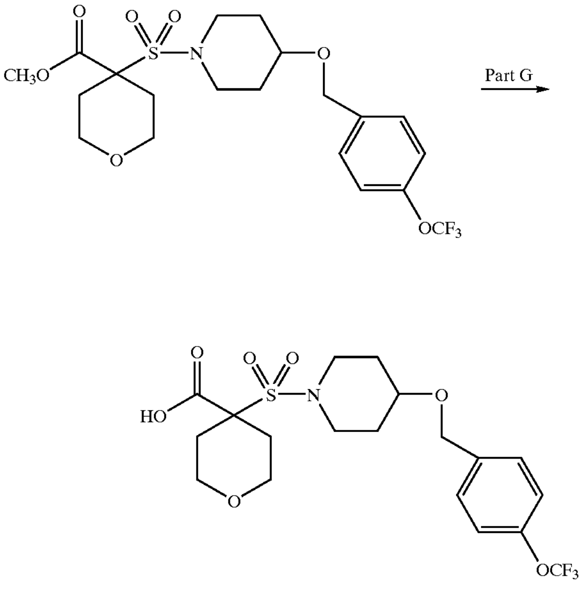

Part G: To a solution of the pyran methyl ester of Part F (3.5 g, 8.8 mmol) in tetrahydrofuran (20 mL) was added potassium trimethylsilonate (2.7 g, 21.1 mmol). The reaction stirred overnight (about eighteen hours) at room temperature. LC showed <3% starting material remained. Work up consisted of removing the tetrahydrofuran and taking the residue up in $H_2O$ (100 mL). The solution was washed with diethyl ether (50 mL). The aqueous phase was then cooled to zero degrees C. and 10% $HCl_{aq}$ was slowly added until pH value of about 3. The acidic mixture was then extracted with ethyl acetate (3x–150 mL). The organic layers were washed with brine (1x–100 mL), dried over $Na_2SO_4$, and concentrated to afford a wet solid. The solid was dried in vacuo with phosphorous pentoxide yielding the carboxylic acid as an orange solid (2.4 g, 72% yield). $^1H$ NW showed the desired compound. HPLC showed 97% at $t_r$=21.3 minutes.

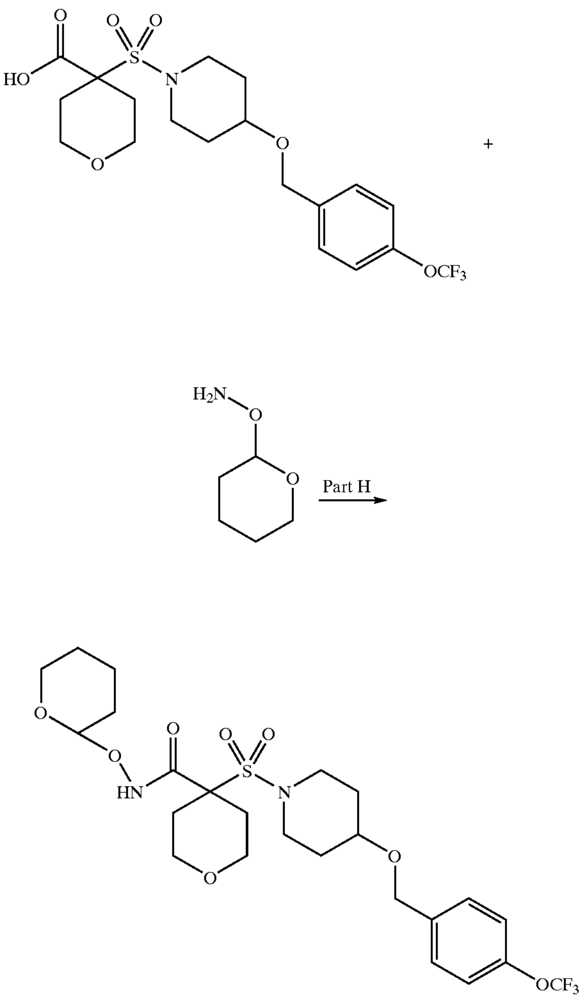

Part H: To a solution of the Part G carboxylic acid product (2.4 g, 6.2 mmol) in dimethylacetamide (10 mL) was added N-methylmorpholine (2.0 mL, 18.6 mmol), followed by N-hydroxybenzotriazole hydrate (1.0 g, 7.4 mmol), O-(tetrahydro-2H-pyran-2-yl) hydroxylamine (1.1 g, 9.4 mmol), and 1-(3-dimethylaminopropyl)-3-ethylcarbodiimide hydrochloride (1.8 g, 9.4 mmol). The mixture was stirred overnight (about eighteen hours) and then solvent was removed. The residue was taken up in ethyl acetate (250 mL) and washed with 5% $NaHSO_4$ (1x–150 mL), saturated potassium carbonate (1x–150 mL), and brine (1x–150 mL). The organic phase was then dried over $Na_2SO_4$ and concentrated to afford a viscous oil (3.2 g, 100+% crude yield). $^1H$ NMR showed the desired compound. HPLC showed 95% at $t_r$=23.5 minutes.

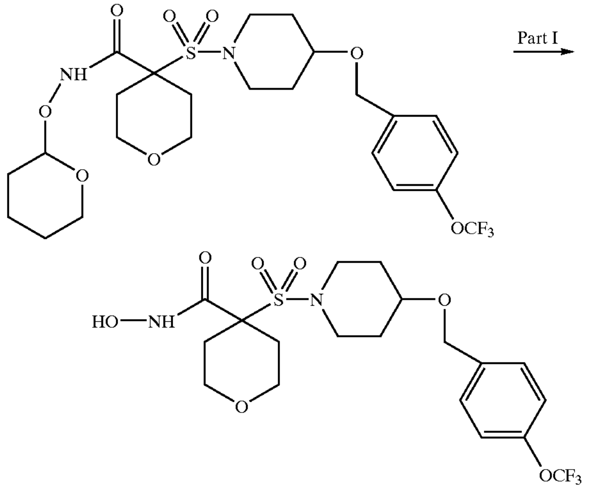

Part I: The viscous oil product of Part H (3.0 g, 6.2 mmol) was dissolved in acetonitrile (10 mL) and stirred with 10% $HCl_{aq}$ (15 mL) for 2 hours. After which time, LC showed no more starting material. The acetonitrile was removed via $N_2$ stream affording a solid that was collected, washed with $H_2O$ (1x–20 mL), and dried in vacuo to afford the depicted hydroxamate as a tan solid (1.6 g, 64% yield). $^1H$ NMR showed the desired compound. HPLC showed 99% at $t_r$=18.8 minutes. Mass spectroscopy showed $M^{+H}{}_{found}$=399 ($M^+{}_H$calc=399).

EXAMPLE 5

Preparation of 4-[[4-(4-bromophenyl)-4-hydroxy-1-piperidinyl]sulfonyl]-tetrahydro-N-hydroxy-2H-pyran-4-carboxamide

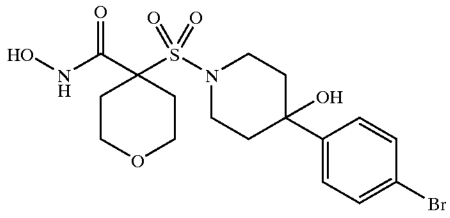

Part 1: Preparation of

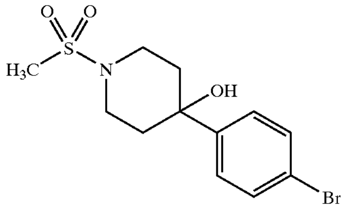

4-(4-Bromophenyl)-4-hydroxypiperidine (Aldrich, 3 g, 1.3 mmol) and N-methylmorpholine (Aldrich, 1.5 g, 2.6 mmol) were slurried in $CH_2Cl_2$ (50 mL) and cooled to zero° C. A solution of methane sulfonyl chloride (Aldrich, 2 g, 2.1 mmol) in $CH_2Cl_2$ (20 mL) was slowly added, maintaining the temperature below 10° C. After the addition, the ice bath was removed and the reaction stirred 1 hour as it warmed to ambient temperature. After the disappearance of the starting material, the solvent was removed under reduced pressure Water (100 mL) was added and 10% aqueous hydrochloride acid and the product filtered to result in the methylsulonamide as an off-white solid (3.5 g). $^1H$ NMR and mass spectroscopy showed the desired compound.

Part 2: Preparation of

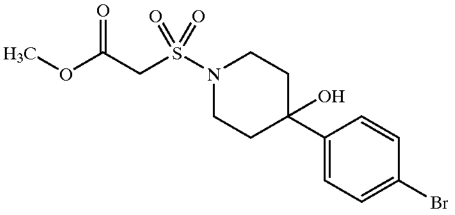

Oven-dried glassware was charged with the compound from Part 1 (5.0 g, 15 mmol) and tetrahydrofuran (30 mL,) and cooled to −75° C. Lithium bis(trimethylsilyl)amide (Aldrich, 1.0 M in tetrahydrofuran, 50 mL, 33 mmol) was slowly added, keeping temperature less than −60° C. Reaction stirred for 30 minutes after the addition and was then charged with a solution of methyl chloroformate (Aldrich, 1.3 mmol, 16.9 mmol) in tetrahydrofuran (17 mL) again keeping the temperature at less −60° C. After stirring for 1 hour at −75° C., the reaction was quenched with saturated $NH_4Cl$, keeping temperature less than −20° C. The aqueous does freeze into a solid chunk of ice. After warming to 50° C., the mixture was extracted via ethyl acetate (3x–200 mL). Organics were washed with saturated $NH_4Cl$ (2x–100 mL) and brine (1x–100 mL), then dried over $Na_2SO_4$ and concentrated to afford the methylene sulfonamide as an amber oil (6.0 g, 91% crude yield). $^1H$ NMR and mass spectroscopy indicated desired compound.

Part 3: Preparation of

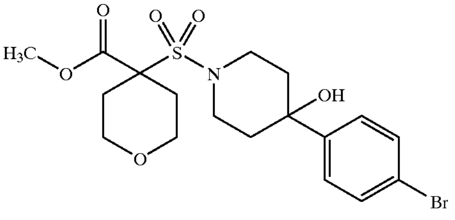

To a solution of compound from Part 2 (5 g, 13 mmol) and dibromo-diethylether (Lancaster, 1.8 mL, 15.1 mmol) in dimethylformamide (28 mL) was added 18-Crown-6 (Aldrich, 500 mg, cat.) followed by potassium carbonate (Aldrich, 3.8 g, 27.4 mmol). The mixture was heated at 60° C. for 16 hours. The product was isolated by pouring into stirring 10% $HCl_{aq}$ (200 mL) and extracted with ethyl acetate (3x–300 mL). Organics were washed with brine (2x–200 mL), dried over $Na_2SO_4$, and concentrated to afford the ester as an oil. The crystallized to result in 3 grams of a tan solid. $^1H$ NMR and mass spectroscopy showed the desired compound.

Part 4: Preparation of

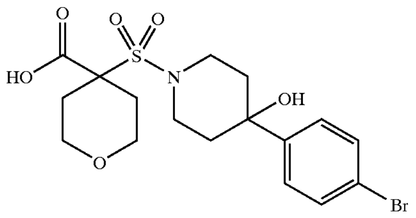

To a solution from Part 3 (3 g, 7 mmol) in tetrahydrofuran (20 mL) was added potassium trimethylsilonate (Aldrich, 3 g, 23 mmol). The reaction stirred overnight (about 18 hours) at room temperature. Liquid chromatography (LC) showed less than 3% starting material remained. Work up comprised removing the tetrahydrofuran and taking the residue up in $H_2O$ (100 mL). The solution was washed with diethylether (50 mL). The aqueous was then cooled to 0° C. and 10% $HCl_{aq}$ was slowly added until pH=3. The acidic mixture was then extracted via ethyl acetate (3×–150 mL). The organics were washed with brine (1×–100 mL), dried over $Na_2SO_4$, and concentrated to afford a wet solid. The solid was dried in vacuo with phosphorous pentoxide yielding the acid as an orange solid (3 g, 72% yield). $^1H$ NMR and mass spectroscopy showed the desired compound.

Part 5: Preparation of

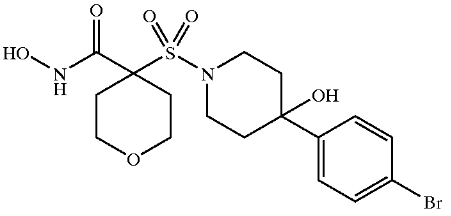

To a solution of the acid product in Part 4 (3.5 g, 8 mmol) in dimethylacetamide (10 mL) was added N-methylmorpholine (Aldrich, 2.0 mL, 18.6 mmol) followed by N-hydroxybenzotriazole hydrate (Aldrich, 1.0 g, 12 mmol), O-(tetrahydro-2H-pyran-2-yl) hydroxylamine (1.1 g, 12 mmol), and 1-(3-dimethylaminopropyl)-3-ethylcarbodiimide hydrochloride (Sigma, 2.3 g, 12 mmol). The mixture was stirred overnight (about 18 hours) and was then stripped of solvent. The residue was taken up in ethyl acetate (250 mL) and washed with 5% $NaHSO_4$ (1×–150 mL), saturated potassium carbonate (1×–150 mL), and brine (1×–150 mL). The organic layer was then dried over $Na_2SO_4$ and concentrated to afford a viscous oil. $^1H$ NMR and mass spectroscopy showed the desired compound.

The viscous crude oil (4.0 g, 6.2 mmol) was dissolved in acetonitrile (10 mL) and stirred with 10% $HCl_{aq}$ (15 mL) for 2 hours, after which, LC showed no more starting material. The acetonitrile was removed with $N_2$ stream over the surface of the solution affording a solid that was collected, washed with $H_2O$ (1×–20 mL), and dried in vacuo to afford the product as a tan solid (2 g). $^1H$ NMR showed the desired compound. Mass spectroscopy showed: $C_{17}H_{23}F_3N_2O_6SBr$ $M^{+H}_{found}$=463 ($M^{+H}_{calc}$=463).

EXAMPLE 6

Preparation of Ethyl 4-[(hydroxyamino)-carbonyl]-4-[(4-[4-(trifluoromethyl)-phenoxy)-1-piperidinyl] sulfonyl]-1-piperidinecarboxylate

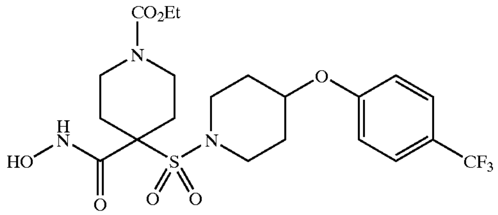

Part A: Preparation of 1,1-Dimethylethyl 4-hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) were added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from part B (5.95 g, 17.2 mmol) in 1,4-dioxane (10 mL) was added 4N HCl dioxane solution (17 mL). After one hour at ambient temperature, the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl) phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added while maintaining the temperature below minus sixty five degrees.

After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of 1-Ethyl 4-Methyl 4-(f4-[4-(Trifluoromethyl)phenoxy]-1-piperidinyl]-sulfonyl]-1,4-piperidinecarboxylate To a solution of the methylene sulfonamide from part E (6.15 g, 16 mmol) in dimethylformamide (32 mL) were added potassium carbonate (7.8 g, 56.6 mmol), bis-(2-bromoethyl)amine ethyl carbamate (3.0 g, 10.75 mmol; prepared by method found in *Synth. Commun.*; 11;1;1981;p.17–24] and 18-Crown-6 (500 mg). The slurry was stirred at sixty degrees Celsius. After sixteen hours, potassium carbonate (2.0 g, 14 mmol) was added and the reaction stirred at sixty degrees Celsius. After a total of twenty four hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a clear colorless oil (1.2 g, 31%).

Part G: Preparation of 1-Ethyl Hydrogen 4-[[4-[4-(Trifluoromethyl)phenoxy]-1-piperidinyl]-sulfonyl]-1,4-piperidinecarboxylate In dry equipment under nitrogen, the piperidine sulfonamide from part F (1.0 g, 1.9 mmol) was dissolved in dry tetrahydrofuran (7.0 mL) and potassium trimethylsilonate (0.38 g, 3.0 mmol) was added at ambient temperature. After eighteen hours, water (100 mL) was added and the solution concentrated in vacuo. The residue was taken up in water and extracted with ethyl acetate. The combined ethyl acetate extracts were concentrated in vacuo. The residue was wetted with water and 1 N HCl solution (1.5 mL) was added, the slurry was extracted with ethyl acetate and the combined extracts washed with saturated sodium chloride solution, dried over $Na_2SO_4$, filtered, and concentrated in vacuo to give the carboxylic acid as a white foam (860 mg, 89%).

Part H: Preparation of Ethyl 4-[[[(Tetrahydro-2H-pyran-2-yl)oxy]amino]carbonyl]-4-[[4-[4-(trifluoromethyl) phenoxy]-1-piperidinyl]-sulfonyl]-1-piperidinecarboxylate In dry equipment under nitrogen, the carboxylic acid from part G (0.82 g, 1.6 mmol) was dissolved in dry dimethylformamide (4 mL) and the remaining reagents were added to the solution in the following order: N-hydroxybenzotriazole hydrate (0.26 g, 1.9 mmol), N-methylmorpholine (0.53 mL, 4.84 mmol), O-(tetrahydro-2H-pyran-2-yl)hydroxylamine (0.585 g, 5.0 mmol), and 1-(3-dimethylaminopropyl)-3-ethylcarbodiimide hydrochloride (0.43 g, 2.26 mmol). After two hours at ambient temperature, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (0.72 g, 73%).

Part I: Preparation of Ethyl 4-[(Hydroxyamino)-carbonyl]-4-[[4-[4-(trifluoromethyl)-phenoxy]-1-piperidinyl] sulfonyl]-1-piperidinecarboxylate To a solution of the THP hydroxamate from part H (0.69 g, 1.1 mmol) in 1,4-dioxane (3 mL) were added 4 N HCl dioxane solution (3 mL) and methanol (3 mL). After two hours at ambient temperature, the reaction was diluted with ethyl acetate and washed with water, dried over $Na_2SO_4$, filtered, and concentrated in vacuo. The product was recrystallized (acetone/hexanes) to give the title compound as a white solid (420 mg, 73%). HRMS (ES+) $M+NH_4^+$ calculated for $C_{21}H_{28}N_3O_7S_1F_3$: 541.1944, found 541.1904.

EXAMPLE 7

Preparation of 4-[(3,5-Dimethyl-1-piperidinyl) sulfonyl]tetrahydro-N-hydroxy-2H-pyran-4-carboxamide

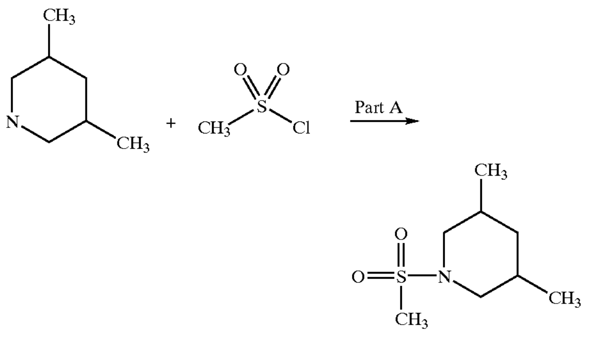

Part A: 3,5-Dimethylpiperadine (70% cis/30% trans, 7.0 mL, 53 mmol) and triethylamine (11.2 mL, 80 mmol) were slurried in $CH_2Cl_2$ (75 mL) and cooled to zero degrees C. A solution of methanesulfonyl chloride (6.2 mL, 80 mmol) in $CH_2Cl_2$ (25 mL) was slowly added, maintaining the temperature <10° C. with an ice bath. After the addition, the ice bath was removed and the reaction stirred 1 hour as it came to room temperature. After the disappearance of the starting material, the solvent was removed and the residue was taken up in ethyl acetate (200 mL) and $H_2O$ (50 mL). Once separated, the organic layer was washed with 5% $KHSO_4$ (3x–50 mL) and brine (1x–50 mL). The organic layer was then dried over $Na_2SO_4$, filtered, and concentrated to afford the methyl sulfonamide an off white solid (10.0 g, 99% yield. $^1H$ NMR showed the desired compound.

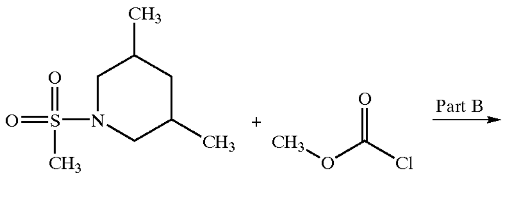

-continued

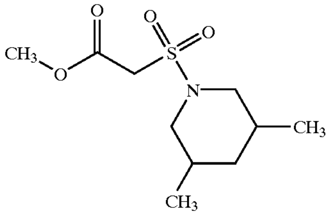

Part B: Oven-dried glassware was charged with the methyl sulfonamide product of Part A (10.0 g, 52.3 mmol) and tetrahydrofuran (160 mL), and cooled to −75° C. Lithium bis(trimethylsilyl)amide (1.0 M in tetrahydrofuran, 157 mL, 157 mmol) was slowly added, keeping temperature <−60° C. Reaction was stirred for 30 minutes after the addition and was then charged with a solution of methyl chloroformate (4.0 mL, 52.3 mmol) in tetrahydrofuran (80 mL), again keeping the temperature at <−60° C. After stirring for 1 hour at −75° C., the reaction was quenched with saturated $NH_4Cl$, keeping temperature <−20° C. The aqueous portion froze into a solid chunk of ice. After warming to 5° C., the mixture was extracted with ethyl acetate (3x–200 mL). Organic phases were washed with saturated $NH_4Cl$ (2x–100 mL) and brine (1x–100 mL), then dried over $Na_2SO_4$ and concentrated to afford the methyl ester as a brown oil (10.7 g, 82% crude yield). $^1$H-NMR showed the desired compound.

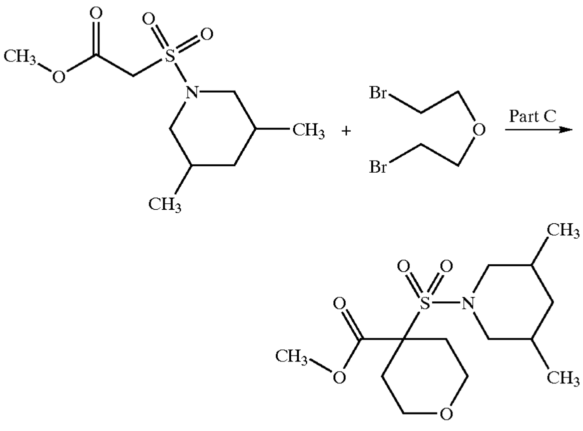

Part C: To a solution of the methyl ester product from Part B (5.0 g, 20 mmol) and dibromo-diethylether (3.0 mL, 24.1 mmol) in dimethylformamide (40 mL) was added 18-Crown-6 (500 mg, cat.) followed by potassium carbonate (8.3 g, 60.0 mmol). The mixture was heated at 60° C. for 4 hours, after which time more potassium carbonate (1.9 g, 13.7 mmol) was added, and the reaction continued at 60° C. for 14 hours. LC showed <5% starting material remained. The reaction was worked up by pouring into stirring 10% $HCl_{aq}$ (200 mL). A gummy solid resulted that was extracted with ethyl acetate (3x–300 mL). Organic layers were washed with brine (2x–200 mL), dried over $Na_2SO_4$, and concentrated to afford the as an orange solid (3.6 g, 56% yield). $^1$H-NMR showed the desired compound.

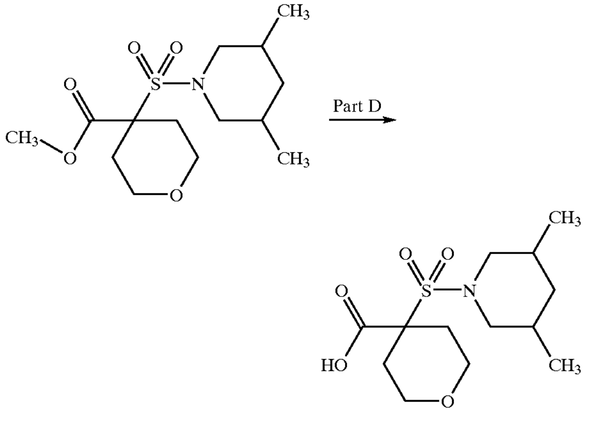

Part D: Potassium trimethylsilanolate (4.3 g, 34 mmol) was added to a solution of the pyran methyl ester product from Part C (3.6 g, 11.3 mmol) in tetrahydrofuran (30 mL). The reaction stirred overnight (about eighteen hours) at room temperature. Work up consisted of removing the tetrahydrofuran and taking the residue up in $H_2O$ (100 mL). The solution was washed with diethyl ether (50 mL). The aqueous portion was then cooled to zero degrees C. and 10% HCl was slowly added until about a pH value of 3. The acidic mixture was then extracted with ethyl acetate (3x–150 mL). The organic layers were washed with brine (1x–100 mL), dried over $Na_2SO_4$, and concentrated to afford the carboxylic acid as a yellow solid (2.5 g, 72% yield). $^1$H-NMR showed the desired compound.

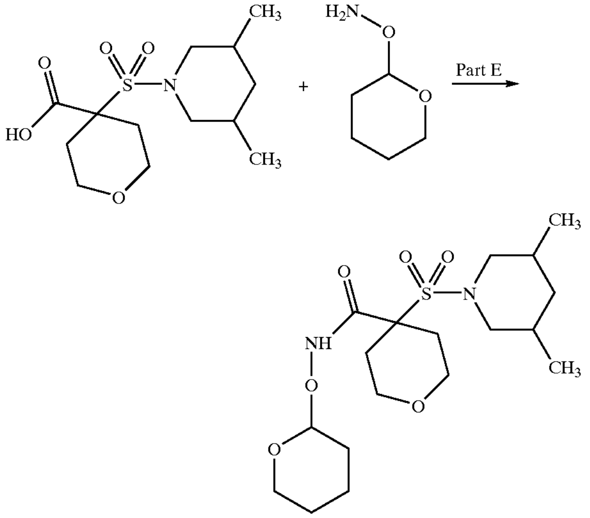

Part E: To a solution of the carboxylic acid product of Part D (2.2 g, 7.2 mmol) in dimethylacetamide (15 mL) was added N-methylmorpholine (2.4 mL, 22.0 mmol) followed by N-hydroxybenzotriazole hydrate (1.2 g, 8.6 mmol), O-(tetrahydro-2H-pyran-2-yl)hydroxylamine (1.3 g, 10.8 mmol), and 1-(3-dimethylaminopropyl)-3-ethylcarbodiimide hydrochloride (2.1 g, 10.8 mmol). The mixture was stirred overnight (about eighteen hours) and was then the solvent was removed. The residue was taken up in ethyl acetate (250 mL) and washed with 5% $NaHSO_4$ (1x–150 mL), saturated potassium carbonate (1x–150 mL), and brine (1x–150 mL). The organic layer was then dried over $Na_2SO_4$ and concentrated to afford the THP-protected hydroxamate as a brown oil (2.7 g, 93% yield). $^1$H-NMR showed the desired compound.

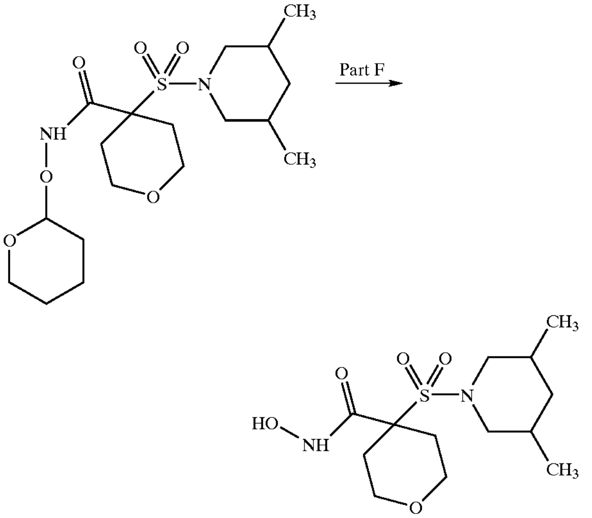

Part F: The crude the THP-protected hydroxamate oil product of Part E (2.7 g, 6.7 mmol) was dissolved in acetonitrile (15 mL) and stirred with 10% HCl (15 mL) for 3 hours, after which time LC showed no more starting material. The solution was reduced to one-half volume, and then acetonitrile (10 mL) and trifluoroacetic acid (1 mL) were added. The solution was filtered and purified by preparatory reverse phase LC (acetonitrile/water) affording title product as a tan solid (1.7 g, 79% yield). $^1$H-NMR showed the desired compound. HPLC showed product as a mixture of 70% cis and 30% trans. Mass spectroscopy showed $M^{+H}_{found}$=321 ($M^{+H}_{calc}$=321).

EXAMPLE 8

Preparation of Tetrahydro-N-hydroxy-4-[[4-(phenylmethyl)-1-piperidinyl]-sulfonyl]-2H-pyran-4-carboxamide

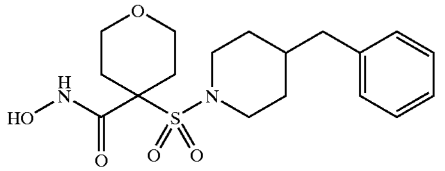

Part A: To a solution of 4-benzylpiperidine (10.55 mL, 60 mmol) and triethylamine (12.5 mL, 90 mmol) in methylene chloride (250 mL) at zero degrees Celsius was added a solution of methanesulfonyl chloride (7 mL, 60 mmol) in methylene chloride (50 mL). After one hour at ambient temperature, the solvent was removed in vacuo. The residue was taken up in ethyl acetate, washed with water two times, brine, dried over $Na_2SO_4$, filtered, and concentrated in vacuo. The product was recrystallized (ethyl acetate/hexanes) to give the sulfonamide as a beige solid (14.2 g, 94%). HRMS (ES+) M+H$^+$ calculated for $C_{13}H_{19}N_1O_2S_1$: 254.1215, found 254.1211.

Part B: Preparation of Methyl [[4-(Phenylmethyl)-1-piperidinyl]sulfonyl]acetate

In dry equipment under nitrogen, the sulfonamide from Part A (2.53 g, 10 mmol) was dissolved in dry tetrahydrofuran (20 mL), chilled to minus seventy-five degrees Celsius, and a 1M solution of lithium bis(trimethylsilyl) amide (20 mL) was added while maintaining the temperature below minus sixty-five degrees. After thirty minutes at minus seventy-five degrees Celsius, a solution of methyl chloroformate (0.77mL, 10 mmol) in dry tetrahydrofuran (10 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, brine, dried over $Na_2SO_4$, filtered, and concentrated in vacuo to give the methylene sulfonamide as a yellow oil (3.05 g, 100%).

Part C: Preparation of Methyl Tetrahydro-4-[[4-(phenylmethyl)-1-piperidinyl]sulfonyl]-2H-pyran-4-carboxylate To a solution of the methylene sulfonamide from Part B (4.1 g, 13.2 mmol) in dimethylformamide (26 mL) was added potassium carbonate (7.8 g, 56.6 mmol), bis-(2-bromoethyl)ether (1.73 mL, 13.2 mmol) and 18-Crown-6 (500 mg). The slurry was stirred at sixty degrees Celsius. After sixteen hours, potassium carbonate (2.0 g, 14 mmol) and bis-(2-bromoethyl)ether (0.2 mL, 1.6 mmol) were added and the reaction stirred at sixty degrees Celsius After a total of twenty-eight hours, the reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the THP-substituted sulfonamide as a white solid (2.85 g, 57%).

Part D: Preparation of Tetrahydro-4-[[4-(phenylmethyl)-1-piperidinyl]sulfonyl]-2H-pyran-4-carboxylic Acid In dry equipment under nitrogen, the THP-substituted sulfonamide from Part C (2.8 g, 7.3 mmol) was dissolved in dry tetrahydrofuran 25 mL) and potassium trimethylsilonate (1.4 g, 11.0 mmol) was added at ambient temperature. After sixteen hours, water (100 mL) was added and the solution concentrated in vacuo. The residue was taken up in water and extracted with ethyl acetate to remove unreacted starting material. The aqueous solution was treated with 6 N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a white solid (1.96 g, 73%).

Part E: Preparation of Tetrahydro-4-[[4-(phenylmethyl)-1-piperidinyl]sulfonyl]-N-[(tetrahydro-2H-pyran-4-carboxamide In dry equipment under nitrogen, the carboxylic acid from Part D (1.9 g, 5.18 mmol) was dissolved in dry dimethylformamide (13 mL) and the remaining reagents were added to the solution in the following order: N-hydroxybenzotriazole hydrate (0.84 g, 6.2 mmol), N-methylmorpholine (1.71 mL, 15.5 mmol), O-(tetrahydro-2H-pyran-2-yl) hydroxylamine (1.88 g, 16.0 mmol), and 1-(3-dimethylaminopropyl)-3-ethylcarbodiimide hydrochloride (1.39 g, 7.25 mmol). After two hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the TPH hydroxamate as a white foam (2.22 g, 93%).

Part F: Preparation of Tetrahydro-N-hydroxy-4-[[4-(phenylmethyl)-1-piperidinyl]sulfonyl]-2H-pyran-4-carboxamide To a solution of the THP hydroxamate from Part E (2.15 g, 4.6 mmol) in 1,4-dioxane (12 mL) was added 4 N HCl dioxane solution (12 mL) and methanol (12 mL). After thirty minutes at ambient temperature, the reaction was diluted with ethyl acetate and washed with water, dried over $Na_2SO_4$, filtered, and concentrated in vacuo. The product was recrystallized (acetone/hexanes) to give the depicted compound as a white solid (1.45 g, 82%). HRMS (ES+) $M+H^+$ calculated for $C_{18}H_{26}N_2O_5S_1$: 383.1641, found 383.1640.

EXAMPLE 9

Preparation of N-Hydroxy-2-[[4-[4-(trifluoromethyl)phenoxy]-1-piperidinyl]-sulfonyl]butanamide

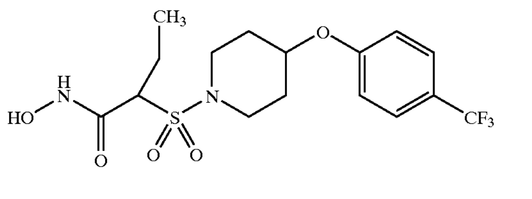

Part A: Preparation of 1,1-Dimethylethyl 4-hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from Part A (6.03 g, 30 mmol) in dimethylformamide (60 mL) were added cesium carbonate (9.77 g, 30 mmol) and 4-fluorobenzotrifluoride (3.8 mL, 30 mmol). The resulting slurry was stirred at ninety degrees Celsius. After nineteen hours, cesium carbonate (3.26 g, 10 mmol) and 4-fluorobenzotrifluoride (0.95 mL, 10 mmol) were added and the reaction continued at ninety degrees Celsius. After a total of forty-six hours, the reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy]piperidine

To a slurry of the substituted BOC piperidine from Part B (5.95 g, 17.2 mmol) in 1,4-dioxane (10 mL) was added 4 N HCl dioxane solution (17 mL). After one hour at ambient temperature, the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from Part C (4.6 g, 16.9 mmol) and triethylamine (5.9 mL, 42.4 mmol) in methylene chloride (45 mL) at zero degrees Celsius was added a solution of methanesulfonyl chloride (1.97 mL, 25.4 mmol) in methylene chloride (10 mL). After one hour at ambient temperature, the solvent was removed in vacuo. The residue was taken up in ethyl acetate, washed with water two times, brine, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl)phenoxy]-1-piperidinyl]-sulfonyl]acetate In dry equipment under nitrogen, the sulfonamide from Part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added while maintaining the temperature below minus sixty-five degrees. After thirty minutes at minus seventy-five degrees Celsius, a solution of methyl chloroformate (1.0 mL, 13 mmol) in dry tetrahydrofuran (13 mL) was added while maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, brine, dried over $Na_2SO_4$, filtered, and concentrated in vacuo to give the methylene sulfonamide as a yellow oil (4.95 g, 100%).

Part F: Preparation of Methyl 2-[[4-[4-(trifluoromethyl)phenoxy]-1-piperidinyl]-sulfonyl]butanoate To a solution of the methylene sulfonamide from Part E (6.15 g, 16 mmol) in dimethylformamide (32 mL) were added potassium carbonate (7.8 g, 56.6 mmol), bis-(2-bromoethyl)amine ethyl carbamate (3.0 g, 10.75 mmol; partially purified) and 18-Crown-6 (500 mg). The resulting slurry was stirred at sixty degrees Celsius. After sixteen hours, potassium carbonate (2.0 g, 14 mmol) was added and the reaction stirred at sixty degrees Celsius. After a total of twenty four hours, the reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the ethyl sulfonamide as a light yellow oil (0.3 g, 10%).

Part G: Preparation of 2-[[4-[4-(Trifluorometyl)-phenoxy]-1-piperidinyl]sulfonyl]butanoic Acid In dry equipment under nitrogen, the ethyl sulfonamide from Part F (0.82 g, 12.0 mmol) was dissolved in dry tetrahydrofuran (5.0 mL) and potassium trimethylsilonate (0.51 g, 4.0 mmol) was added at ambient temperature. After eighteen hours water (100 mL) was added and the solution concentrated in vacuo. The residue was taken up in water and extracted with ethyl acetate. The combined extracts were concentrated in vacuo. The residue was wetted with water and 1N HCl solution (3.0 mL) was added, the resulting slurry was extracted with ethyl acetate and the combined extracts washed with brine, dried over $Na_2SO_4$, filtered, and concentrated in vacuo to give the carboxylic acid as an off-white solid (669 mg, 85%).

Part H: Preparation of N-[(Tetrahydro-2H-pyran-2-yl)oxy]-2-[[4-[4-(trifluoromethyl)phenoxy]-1-piperidinyl]sulfonyl]butanamide In dry equipment under nitrogen, the carboxylic acid from Part G (0.627 g, 1.59 mmol) was dissolved in dry dimethylformamide (4 mL) and the remaining reagents were added to the solution in the following order: N-hydroxybenzotriazole hydrate (0.26 g, 1.9 mmol), N-methylmorpholine (0.53 mL, 4.84 mmol), O-(tetrahydro-2H-pyran-2-yl)

hydroxylamine (0.585 g, 5.0 mmol), and 1-(3-dimethylaminopropyl)-3-ethylcarbodiimide hydrochloride (0.43 g, 2.26 mmol). After fourteen hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the THP hydroxamate as a white solid (0.666 g, 8S%).

Part I: Preparation of N-Hydroxy-2-[[4-[4-(trifluoromethyl) phenoxy]-1-piperidinyl]-sulfonyl]butanamide To a solution of the THP hydroxamate from Part H (0.61 g, 1.23 mmol) in 1,4-dioxane (3 mL) were added 4 N HCl dioxane solution (3 mL) and methanol (3 mL). After two hours at ambient temperature, the reaction was diluted with ethyl acetate and washed with water, dried over $Na_2SO_4$, filtered, and concentrated in vacuo. The product was recrystallized (acetone/hexanes) to give the depicted compound as a white solid (490 mg, 97%). HRMS (ES+) $M+NH_4^+$ calculated for $C_{16}H_{21}N_2O_5$ $S_1F_3$: 428.1467, found 428.1451.

EXAMPLE 10

Preparation of Tetrahydro-N-hydroxy-4-[[4-[4-(trifluoromethoxy)phenyl]-1-piperazinyl]sulfonyl]-2H-pyran-4-carboxamide, Monohydrochloride

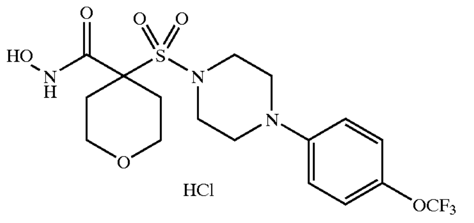

Part A: To a solution of tert-butyl-piperazine (25.0 g, 134 mmol) in dichloromethane (200 mL), cooled to zero degrees Celsius, was added triethylamine (28.3 mL, 201 mmol) followed by methanesulfonyl chloride (15.5 mL, 201 mmol). Once the addition was complete the cooling bath was removed and the reaction mixture was stirred at ambient temperature. After 1 hour the reaction mixture was concentrated in vacuo. The residue was partitioned between $H_2O$ and ethyl acetate and the aqueous was further extracted with ethyl acetate. The combined organic layers were washed with saturated NaCl and dried over $Na_2SO_4$. Concentration in vacuo provided the sulfonamide as an off-white solid (36.4 g, >100%).

Part B: To a solution of the sulfonamide of part A (35.0 g, 132 mmol) in tetrahydrofuran (200 mL) was slowly added a solution of lithium bis(trimethylsilyl)amide (66.5 g, 397 mmol) in tetrahydrofuran (300 mL) at such a rate that the temperature never exceeded minus sixty degrees Celsius. After stirring at minus seventy-eight degrees Celsius for 1.5 hours a solution of dimethyl carbonate (10.2 mL, 132 mmol) in tetrahydrofuran (100 mL) was slowly added at such a rate that the temperature of the reaction never exceeded minus sixty degrees Celsius. After stirring for 1 hour at minus seventy-eight degrees Celsius the reaction was quenched by the addition of saturated $NH_4Cl$. The reaction mixture was diluted with $H_2O$ and extracted with ethyl acetate. The combined organic layers were washed with 5% HCl, saturated $NH_4Cl$, saturated NaCl and dried over $Na_2SO_4$. Concentration in vacuo provided the sulfonamide ester as an orange oil (34.1 g, 80%).

Part C: To a solution of the sulfonamide ester of part B (15.00 g, 46.53 mmol) in N,N-dimethylformamide (200 mL) was added $K_2CO_3$ (19.29 g, 139.59 mmol), 18-crown-6 (4.65 g) and bis(2-bromoethyl)ether (10.79 g, 46.53 mmol). The resulting mixture was heated to sixty degrees Celsius for 22 hours and then additional $K_2CO_3$ (19.3 g, 139.6 mmol) and bis(2-bromoethyl)ether (5.8 mL, 23.2 mmol) was added and stirring was continued at sixty degrees Celsius for 22 hours. The reaction mixture was then concentrated in vacuo. The residue was dissolved in acetonitrile and filtered through a pad of Celite®. The filtrate was concentrated in vacuo and the residue was partitioned between $H_2O$ and ethyl acetate. The organic layers were washed with saturated $NaHCO_3$, saturated NaCl and dried over $Na_2SO_4$. Chromatography (on silica, ethyl acetate/hexanes) provided the cyclized ester as a pale yellow solid (7.23 g, 40%).

Part D: The cyclized ester of part C (7.23 g, 18.42 mmol) was treated with a solution of 4N HCl in dioxane (46 mL). After stirring at ambient temperature for 1 hour the reaction mixture was concentrated in vacuo to provide the piperazine sulfonamide as a tan solid (5.83 g, 96%).

Part E: To a suspension of the piperazine sulfonamide of part D (2.15 g, 6.53 mmol) in toluene (15 mL), precooled to zero degrees Celsius, was added sodium tert-butoxide (1.43 g, 14.93 mmol). Once the addition was complete the cooling bath was removed and the reaction mixture was allowed to warm to ambient temperature at which time 4-(trifluoromethoxy)bromobenzene (1.50 g, 6.22 mmol), BINAP (0.116 g, 0.187 mmol) and tris(dibenzyldeneacetone)dipallidium (0) (0.057 g, 0.062 mmol) were added. The resulting mixture was stirred at eighty degrees Celsius for 12 hours and then concentrated in vacuo. The residue was heated in boiling methanol, decanted from the salts and concentrated in vacuo. The residue was dissolved in $H_2O$ and acidified (pH-2) with 1N HCl. The aqueous layer was then extracted with ethyl acetate. The combined organic layers were dried over $Na_2SO_4$ to give the acid as a yellow solid (1.06 g, 39%).

Part F: To a solution of the acid of part E (1.06 g, 2.42 mmol) in N,N-dimethylformamide (5.0 mL) was added 1-hydroxybenzotriazole (0.392 g, 2.90 mmol), N-methylmorpholine (0.790 mL, 7.26 mmol), O-(tetrahydropuranyl) hydroxylamine (0.425 g, 3.63 mmol) and 1-3-[(dimethylamino)propyl]-3-ethylcarbodiimide hydrochloride (0.650 g, 3.39 mmol). After stirring at ambient temperature for 7 hours the reaction was diluted with $H_2O$ and extracted with ethyl acetate. The combined organic layers were washed with saturated $NaHCO_3$, saturated NaCl and dried over $Na_2SO_4$. Chromatography (on silica, ethyl acetate with 5% methanol/hexanes) provided the protected hydroxamate as a white solid (1.02 g, 78%).

Part G: The protected hydroxamate of part F (1.02 g, 1.90 mmol) was treated with a solution of 2N HCl in diethyl ether (9.5 mL) and methanol (0.77 mL, 18.97 mmol). The reaction mixture became gelatinous and a solution of 4 N HCl in dioxane (4.0 mL) was added. After stirring at ambient temperature for 2 hours the solids were collected by filtration, washing with diethyl ether, to give the title compound as a white solid (0.869 g, 93%). MS $MH^+$ calculated for $C_{17}H_{23}O_6N_3S_1F_3$: 454, found 454.

EXAMPLE 11

Preparation of N-Hydroxy-2-[[4-[4-(trifluoromethyl) phenoxy]-1-piperidinyl]-sulfonyl]acetamide

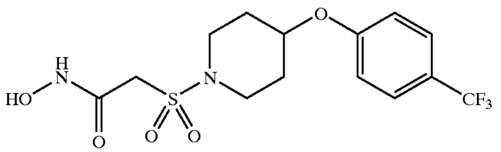

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) were added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

A solution of 4 N HCl dioxane solution (17 mL) was added to a slurry of the substituted BOC piperidine from part B (5.95 g, 17.2 mmol) in 1,4-dioxane (10 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine A solution of methane sulfonyl chloride (1.97 mL, 25.4 mmol) in dichloromethane (10 mL) was added to a solution of the hydrochloride salt from part C (4.6 g, 16.9 mmol) and triethylamine (5.9 mL, 42.4 mmol) in dichloromethane (45 mL) at zero degrees Celsius. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl)-phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added while maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of [[4-[4-(Trifluoromethyl)-phenoxy]-1-piperidinyl]sulfonyl]acetic Acid In dry equipment under nitrogen, the methylene sulfonamide from part E (1.52 g, 4.0 mmol) was dissolved in dry tetrahydrofuran(10 mL) and potassium trimethylsilonate (1.03 g, 8.0 mmol) was added at ambient temperature. After fifteen hours, water (50 mL) was added, and at 5 degrees Celsius 6 N HCl was added until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a white solid (1.25 g, 85%).

Part G: Preparation of N-[(Tetrahydro-2H-pyran-2-yl)oxy]-2-[[4-[4-(trifluoromethyl)phenoxy]-1-piperidinyl]sulfonyl] acetamide In dry equipment under nitrogen, the carboxylic acid from part F (1.2 g, 3.3 mmol) was dissolved in dry dimethylformamide (8 mL) and the remaining reagents were added to the solution in the following order: N-hydroxybenzotriazole hydrate (0.53 g, 3.9 mmol), N-methylmorpholine (1.08 mL, 9.8 mmol), O-(tetrahydro-2H-pyran-2-yl)hydroxylamine (1.19 g, 10.1 mmol), and 1-(3-dimethylaminopropyl)-3-ethylcarbodiimide hydrochloride (0.88 g, 4.6 mmol). After two hours at ambient temperature, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white solid (1.16 g,. 76%).

Part H: Preparation of N-Hydroxy-2-[[4-[4-(Trifluoromethyl)phenoxy]-1-piperidinyl]-sulfonyl] acetamide To a solution of the THP hydroxamate from part G (1.11 g, 2.4 mmol) in 1,4-dioxane (6 mL) were added 4 N HCl dioxane solution (6 mL) and methanol (6 mL). After ninety minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (0.60 g, 67%). HRMS (ES+) $M+H^+$ calculated for $C_{14}H_{17}F_3N_2O_5S_1$: 383.0889, found 383.0885.

EXAMPLE 12

Preparation of N-Hydroxy-1-(2-methoxyethyl)-4-[[4-[4-(trifluoromethyl)-phenoxy]-1-piperidinyl) sulfonyl]-4-piperidinecarboxamide, Monohydrochloride

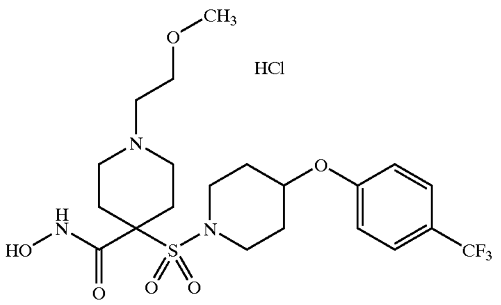

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(Trifluoromethyl)phenoxy]-1-piperidinecarboxylate To a solution of the BOC piperidine from part A (6.03 g, 30 mmol) in dimethylformamide (60 mL) were added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from part B (5.95 g, 17.2 mmol) in 1,4-dioxane (10 mL) was added 4 N HCl dioxane solution (17 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(trifluoromethyl) phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Methyl 1-(Phenylmethyl)-4-[[4-[4-(trifluoromethyl)phenoxy]-1-piperidinyl]-sulfonyl]-4-piperidinecarboxylate To a solution of the methylene sulfonamide from part E (1.14 g, 3 mmol) in dimethylformamide (6 mL) were added potassium carbonate (1.24 g, 9 mmol), bis-(2-chloroethyl) benzyl amine (0.7 g, 3 mmol; and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a white solid (950 mg, 59%).

Part G: Preparation of Methyl 1-(2-Methoxyethyl)-4-[[4-[4-(trifluoromethyl)phenoxy]-1-piperidinyl]sulfonyl]-4-piperidinecarboxylate To a slurry of the piperidine sulfonamide from part F (420 mg, 0.8 mmol) in methanol (15 mL) was added ammonium formate (147 mg, 2.3 mmol). The system was purged with nitrogen for 10 minutes. The nitrogen stream was removed and palladium on carbon (80 mg of 10 weight % on activated carbon, 50% water) was added. The reaction was refluxed for forty five minutes, cooled, filtered through Celite under nitrogen, and concentrated in vacuo. The residue was dissolved in dry dimethylformamide (5 mL) and potassium carbonate (150 mg, 1.07 mmol) and 2-bromoethyl methyl ether (100 uL, 1.07 mmol) were added. The reaction was stirred at thirty five degrees Celsius for thirty hours and then concentrated in vacuo. The residue was taken up in ethyl acetate and filtered through Celite. The filtrate washed with water two times, saturated sodium chloride solution, dried over $Na_2SO_4$, filtered, and concentrated in vacuo. The product was recrystallized (methanol) to give the N-methoxyethyl piperidine sulfonamide as an off-white solid (190 mg, 53%).

Part H: Preparation of 1-(2-Methoxyethyl)-4-[[4-[4-(trifluoromethyl)phenoxy)-1-piperidinyl]-sulfonyl]-4-piperidinecarboxylic Acid In dry equipment under nitrogen, the N-methoxyethyl piperidine sulfonamide from part G (1.51 g, 2.97 mmol) was dissolved in dry tetrahydrofuran (30 mL) and potassium trimethylsilonate (1.27 g, 8.91 mmol) was added at ambient temperature. After five hours, water (10 mL) was added and at 5 degrees Celsius, 6 N HCl was added until pH=1. The slurry was filtered, washed with water and dried in vacuo to give the carboxylic acid as a white solid (1.47 g, 100%).

Part I: Preparation of 1-(2-Methoxyethyl)-N-[(tetrahydro-2H-pyran-2-yl)oxy]-4-[[4-[4-(trifluoromethyl)phenoxy]-1-piperidinyl]-sulfonyl]-4-piperidinecarboxamide In dry equipment under nitrogen, the carboxylic acid from part H (1.4 g, 2.83 mmol) was dissolved in dry dimethylformamide (12 mL) and the remaining reagents were added to the solution in the following order: N-hydroxybenzotriazole hydrate (0.46 g, 3.4 mmol), N-methylmorpholine (0.93 mL, 8.5 mmol), O-(tetrahydro-2H-pyran-2-yl) hydroxylamine (1.03 g, 8.8 mmol), and 1-(3-dimethylaminopropyl)-3-ethylcarbodiimide hydrochloride (0.76 g, 4.0 mmol). The reaction was stirred at forty five degrees Celsius. After forty eight hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white solid (800 mg, 48%).

Part J: Preparation of N-Hydroxy-1-(2-methoxyethyl)-4-[[4-[4-(trifluoromethyl)phenoxy]-1-piperidinyl]sulfonyl)-4-piperidinecarboxamide, Monohydrochloride To a solution of the THP hydroxamate from part I (760 mg, 1.28 mmol) in 1,4-dioxane (3 mL) was added 4N HCl dioxane solution (3.2 mL) and methanol (3.5 mL). After thirty minutes at ambient temperature the reaction was poured into 100 mL acetonitrile. The slurry was filtered under nitrogen, washed with acetonitrile and dried in vacuo to give the title compound as an off white solid (0.62 g, 89%). HRMS (ES+) $M+H^+$ calculated for $C_{21}H_{30}F_3N_3O_6S_1$: 510.1886, found 510.1862.

EXAMPLE 13

Preparation of Tetrahydro-N-hydroxy-4-[[4-(4-nitrophenoxy)-1-piperidinyl]sulfonyl]-2H-pyran-4-carboxamide

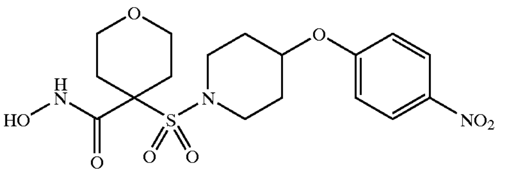

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-(4-nitrophenoxy)-1-piperidinyl Carboxylate To a solution of the BOC piperidine from part A (10.05 g, 0.05 mol) in dimethylformamide (100 mL) were added cesium carbonate (16.3 g, 0.05 mol) and 4-fluoronitrobenzene (5.3 mL, 0.05 mol). The slurry was stirred at eighty five degrees Celsius. After eight hours cesium carbonate (1.6 g, 5 mmol) was added and the reaction continued at ninety degrees Celsius. After a total of twenty four hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as an yellow solid (13.6 g, 84%).

Part C: Preparation of 4-(4-Nitrophenoxy)piperidine, Monohydrochloride

To a slurry of the substituted BOC piperidine from part B (6.44 g, 20 mmol) in 1,4-dioxane (5 mL) was added 4 N HCl dioxane solution (20 mL). After two hour at ambient temperature the reaction was concentrated in vacuo. The residue was slurried in diethyl ether and vacuum filtration of the resulting precipitate provided the hydrochloride salt as a light yellow solid (5.2 g, 100%).

Part D: Preparation of 1-(Methylsulfonyl)-4-(4-nitrophenoxy)piperidine

To a solution of the hydrochloride salt from part C (5.17 g, 20 mmol) and triethylamine (7.0 mL, 50 mmol) in dichloromethane (80 mL) at zero degrees Celsius was added a solution of methane sulfonyl chloride (2.32 mL, 30 mmol) in dichloromethane (20 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The product was recrystallized (ethyl acetate/hexanes) to give the sulfonamide as an yellow solid (4.57 g, 76%).

Part E: Preparation of Methyl [[4-(4-Nitrophenoxy)-1-piperidinyl]sulfonyl]acetate In dry equipment under nitrogen, the sulfonamide from part D (4.48 g, 14.9 mmol) was dissolved in dry tetrahydrofuran (30 mL), chilled to minus seventy-five degrees Celsius, and a 1 M solution of lithium bis(trimethylsilyl) amide (30 mL) was added maintaining the temperature below minus sixty five degrees. After thirty minutes at minus seventy-five degrees Celsius, a solution of methyl chloroformate (1.15mL, 14.9 mmol) in dry tetrahydrofuran (15 mL) was added while maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo. Chromatography (on silica, ethyl acetate/hexanes) provided the methylene sulfonamide as a white solid (3.9 g, 73%).

Part F: Preparation of Methyl Tetrahydro-4-[[4-(4-nitrophenoxy)-1-piperidinyl]sulfonyl]-2H-pyran-4-carboxylate To a solution of the methylene sulfonamide from part E (3.73 g, 10.4 mmol) in dimethylformamide (20 mL) was added potassium carbonate (5.75 g, 41.6 mmol), bis-(2-bromoethyl)ether (1.36 mL, 10.4 mmol) and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. The product was recrystallized (ethyl acetate) to give the tetrahydropyran sulfonamide as a white solid (2.1 g, 47%).

Part G: Preparation of Tetrahydro-4-[[4-(4-nitrophenoxy)-1-piperidinyl)sulfonyl]-2H-pyran-4-carboxylic Acid In dry equipment under nitrogen, the tetrahydropyran sulfonamide from part F (2.04 g, 4.77 mmol) was dissolved in dry tetrahydrofuran (12 mL) and potassium trimethylsilonate (2.04 g, 14.3 mmol) was added at ambient temperature. After five hours water (50 mL) was added and the tetrahydrofuran was stripped off in vacuo. The residue was washed with ethyl acetate, the layers were separated, the aqueous was chilled to 5 degrees Celsius and 6 N HCl was added until pH=1. The slurry was filtered, washed with water and dried in vacuo to give the carboxylic acid as a white solid (1.66 g, 84%).

Part H: Preparation of Tetrahydro-4-[[4-(4-nitrophenoxy)-1-piperidinyl]sulfonyl]-N-[(tetrahydro-2H-pyran-2-yl)oxy]-2H-pyran-4-carboxamide In dry equipment under nitrogen, the carboxylic acid from part G (1.63 g, 3.9 mmol) was dissolved in dry dimethylformamide (10 mL) and the remaining reagents were added to the solution in the following order: N-hydroxybenzotriazole hydrate (0.640 g, 4.7 mmol), N-methylmorpholine (1.3 mL, 11.8 mmol), O-(tetrahydro-2H-pyran-2-yl)hydroxylamine (1.43 g, 12.2 mmol), and 1-(3-dimethylaminopropyl)-3-ethylcarbodiimide hydrochloride (1.1 g, 5.5 mmol). The reaction was stirred at forty five degrees Celsius. After forty eight hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/methanol/hexanes) provided the THP hydroxamate as a white solid (1.89 g, 95%).

Part I: Preparation of Tetrahydro-N-hydroxy-4-[[4-(4-nitrophenoxy)-1-piperidinyl]sulfonyl]-2H-pyran-4-carboxamide To a solution of the THP hydroxamate from part H (1.85 g, 3.6 mmol) in 1,4-dioxane (9 mL) were added 4 N HCl dioxane solution (9 mL) and methanol (1 mL). After fifteen minutes at ambient temperature the product precipitated from the reaction. The reaction was diluted with diethyl ether, the solids filtered under nitrogen and dried in vacuo to give the title compound as a white solid (1.4 g, 93%). HRMS (ES+) $M+H^+$ calculated for $C_{17}H_{23}N_3O_8S_1$: 430.1284, found 430.1314.

EXAMPLE 14

Preparation of N-Hydroxy-1-(phenyl-methyl)-4-[[4-[4-(trifluoromethoxy)-phenoxy]-1-piperidinyl] sulfonyl3-4-piperidinecarboxamide, Monohydrochloride

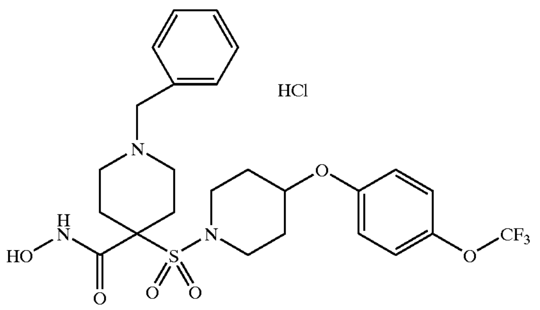

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(Methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-dimethylethyl Ester In dry equipment under nitrogen, 4-trifluoromethoxyphenol (10.15 g, 57 mmol) was dissolved in dry dimethylformamide (125 mL) and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol), and at zero degrees Celsius a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(trifluoromethoxy) phenoxy]-1-piperidinyl]-sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl)

amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Methyl 1-(Phenylmethyl)-4-[[4-[4-(trifluoromethoxy)phenoxy]-1-piperidinyl]sulfonyl]-4-piperidinecarboxylate To a solution of the methylene sulfonamide from part F (20.46 g, 51.5 mmol) in dimethylformamide (90 mL) was added potassium carbonate (21.3 g, 154.7 mmol), bis-(2-chloroethyl)benzyl amine (12.0 g, 51.5 mmol; and 18-Crown-6 (700 mg). The slurry was stirred at sixty degrees Celsius. After twenty four hours the reaction was concentrated in vacuo. The residue was taken up in ethyl acetate, washed with water three times, saturated sodium chloride solution, dried over $Na_2SO_4$, filtered, and concentrated in vacuo. The residue was recrystallized (methanol) to give the N-benzyl piperidine sulfonamide as a white solid (15 g, 52%).

Part H: Preparation of 1-(Phenylmethyl)-4-f[4-[4-(trifluoromethoxy)phenoxy]-1-piperidinyl]-sulfonyl]-4-piperidinecarboxylic Acid In dry equipment under nitrogen, the N-benzyl piperidine sulfonamide from part G (1.5 g, 2.7 mmol) was dissolved in dry tetrahydrofuran (30 mL) and potassium trimethylsilonate (1.15 g, 8.1 mmol) was added at ambient temperature. After twenty four hours, water (10 mL) was added and at 5 degrees Celsius, 6 N HCl was added until pH=7. The slurry was filtered, washed with water and dried in vacuo to give the carboxylic acid as a white solid (1.24 g, 85%).

Part I: Preparation of 1-(Phenylmethyl)-N-[(tetrahydro-2H-pyran-2-yl)oxy-4-[[4-[4-(trifluoromethoxy)phenoxy]-1-piperidinyl]-sulfonyl]-4-piperidinecarboxylate In dry equipment under nitrogen, the carboxylic acid from part H (1.2 g, 2.2 mmol) was dissolved in dry dimethylformamide (6 mL) and the remaining reagents were added to the solution in the following order: N-hydroxybenzotriazole hydrate (0.36 g, 2.66 mmol), N-methylmorpholine (0.73 mL, 6.64 mmol), O-(tetrahydro-2H-pyran-2-yl) hydroxylamine (0.83 g, 6.86 mmol), and 1-(3-dimethylaminopropyl)-3-ethylcarbodiimide hydrochloride (0.59 g, 3.1 mmol) The reaction was stirred at forty five degrees Celsius. After two hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white solid (1.24 mg, 88%).

Part J: Preparation of N-Hydroxy-1-(Phenylmethyl)-4-[(4-[4-(trifluoromethoxy)phenoxy]-1-piperidinyl]sulfonyl]-4-piperidinecarboxamide, Monohydrochloride To a solution of the THP hydroxamate from part I (1.18 g, 1.84 mmol) in 1,4-dioxanes (5 mL) was added 4 N HCl dioxane solution (5 mL) and methanol (1 mL). After thirty minutes, the reaction was diluted with diethyl ether, the solids filtered under nitrogen and dried in vacuo to give the title compound as a white solid (0.96 g, 88%). HRMS (ES+) $M+H^+$ calculated for $C_{25}H_{30}F_3N_3O_6S_1$: 558.1886, found 558.1961.

EXAMPLE 15

Preparation of N-Hydroxy-1-(2-methoxyethyl)-4-[[4-[4-(trifluoromethoxy)phenoxy]-1-piperidinyl] sulfonyl]-4-piperidinecarboxamide, Monohydrochloride

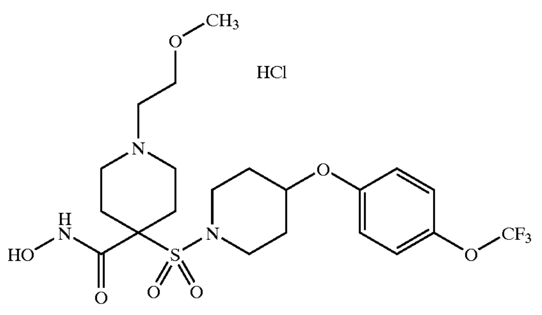

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(Methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-dimethylethyl Ester In dry equipment under nitrogen, 4-trifluoromethoxyphenol (10.15 g, 57 mmol) was dissolved in dry dimethylformamide (125 mL), and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxane (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol), and at zero degrees Celsius, a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(Trifluoromethoxy) phenoxy]-1-piperidinyl]sulfonyl-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Methyl 1-(Phenylmethyl)-4-[[4-[4-(trifluoromethoxy)phenoxy]-1-piperidinyl]sulfonyl]-4-piperidinecarboxylate To a solution of the methylene sulfonamide from part P (20.46 g, 51.5 mmol) in dimethylformamide (90 mL) was added potassium carbonate (21.3 g, 154.7 mmol), bis-(2-chloroethyl)benzyl amine (12.0 g, 51.5 mmol; and 18-Crown-6 (700 mg). The slurry was stirred at sixty degrees Celsius. After twenty four hours the reaction was concentrated in vacuo. The residue was taken up in ethyl acetate, washed with water three times, saturated sodium chloride solution, dried over $Na_2SO_4$, filtered, and concentrated in vacuo. The residue was recrystallized (methanol) to give the N-benzyl piperidine sulfonamide as a white solid (15 g, 52%).

Part H: Preparation of 4-[[4-[4-(Trifluoromethoxy)-phenoxy]-1-piperidinyl]sulfonyl]-4-piperidinecarboxylic Acid, Methyl Ester To a slurry of the N-benzyl piperidine sulfonamide from part G (4.17 g, 7.5 mmol) in methanol (50 mL) was added ammonium formate (1.46 g, 22.5 mmol). The system was purged with nitrogen for 10 minutes. The nitrogen stream was removed and palladium on carbon (1.5 g of 10 weight % on activated carbon, 50% water) was added. The reaction was refluxed for thirty minutes, cooled, filtered through Celite under nitrogen, and concentrated in vacuo to give the unsubstituted piperidine sulfonamide as a beige solid (3.15 g, 90%).

Part I: Preparation of Methyl 1-(2-Methoxyethyl)-4-[[4-[4-(trifluoromethoxy)phenoxy]-1-piperidinyl]sulfonyl]-4-piperidinecarboxylate The unsubstituted piperidine sulfonamide from part H (3.0 g, 6.45 mmol) was dissolved in dry dimethylformamide (15 mL) and potassium carbonate (1.3 g, 9.7 mmol) and 2-bromoethyl methyl ether (908 uL, 9.7 mmol) were added. The reaction was stirred at thirty five degrees Celsius for sixteen hours and then concentrated in vacuo. The residue was taken up in ethyl acetate and filtered through Celite. The filtrate washed with water two times, saturated sodium chloride solution, dried over $Na_2SO_4$, filtered, and concentrated in vacuo. Chromatography (on silica, ethyl acetate/hexanes) provided the N-methoxyethyl piperidine sulfonamide as a white solid (1.65 g, 50%).

Part J: Preparation of 1-(2-Methoxyethyl)-4-[[4-[4-(trifluoromethoxy)phenoxy]-1-piperidinyl)-sulfonyl]-4-piperidinecarboxylic Acid In dry equipment under nitrogen, the N-methoxyethyl piperidine sulfonamide from part I (1.6 g, 3.0 mmol) was dissolved in dry tetrahydrofuran (25 mL) and potassium trimethylsilonate (1.3 g, 9.13 mmol) was added at ambient temperature. After twenty four hours, water (10 mL) was added and at 5 degrees Celsius, 6 N HCl was added until pH=7. The slurry was filtered, washed with water and dried in vacuo to give the carboxylic acid as an off-white solid (1.39 g, 90%).

Part K: Preparation of 1-(2-Methoxyethyl)-N-[(tetrahydro-2H-pyran-2-yl)oxy]-4-[[4-[4-(trifluoromethoxy)phenoxy]-1-piperidinyl]-sulfonyl]-4-piperidinecarboxylate In dry equipment under nitrogen, the carboxylic acid from part J (1.36 g, 2.67 mmol) was dissolved in dry dimethylformamide (9 mL) and the remaining reagents were added to the solution in the following order: N-hydroxybenzotriazole hydrate (0.43 g, 3.2 mmol), N-methylmorpholine (0.88 mL, 8.0 mmol), O-(tetrahydro-2H-pyran-2-yl)hydroxylamine (0.97 g, 8.0 mmol), and 1-(3-dimethylaminopropyl)-3-ethylcarbodiimide hydrochloride (0.72 g, 3.7 mmol). The reaction was stirred at forty degrees Celsius. After twenty hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white solid (1.42 g, 90%).

Part L: Preparation of N-Hydroxy-1-(2-methoxyethyl)-4-[[4-[4-(trifluoromethoxy)phenoxy]-1-piperidinyl]sulfonyl]-4-piperidinecarboxamide, Monohydrochloride To a solution of the THP hydroxamate from part K (1.3 g, 2.13 mmol) in 1,4-dioxanes (2 mL) was added 4 N HCl dioxane solution (5.3 mL) and methanol (0.5 mL). After ten minutes, the reaction was diluted with diethyl ether, the solids filtered under nitrogen and dried in vacuo to give the title compound as a white solid (1.15 g, 96%). HRMS (ES+) $M+H^+$ calculated for $C_{21}H_{30}F_3N_3O_7S_1$: 526.1835, found 526.1805.

EXAMPLE 16

Preparation of N-Hydroxy-2-[[4-[4-(Trifluoromethoxy)phenoxy]-1-piperidinyl]sulfonyl] acetamide

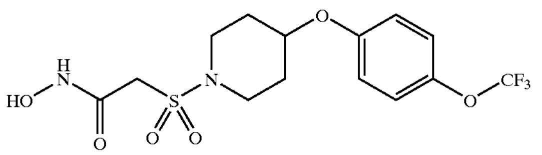

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(Methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-Dimethylethyl Ester In dry equipment under nitrogen, 4-trifluoromethoxy-phenol (10.15 g, 57 mmol) was dissolved in dry dimethyl-formamide (125 mL) and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from, part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol) and at zero degrees Celsius a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(Trifluoromethoxy) phenoxy)-1-piperidinyl]sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of [[4-[4-(Trifluoromethoxy)-phenoxy]-1-piperidinyl]sulfonyl]acetic Acid In dry equipment under nitrogen, the methylene sulfonamide from part F (1.59 g, 4.0 mmol) was dissolved in dry tetrahydrofuran (10 mL) and potassium trimethylsilonate (1.2 g, 8.5 mmol) was added at ambient temperature. After fifteen hours water (50 mL) was added and at 5 degrees Celsius 6N HCl was added until pH=1. The slurry was extracted with ethyl acetate and the combined extracts washed with water, dried over $Na_2SO_4$, filtered, and concentrated in vacuo. The product was recrystallized (hexanes/ethyl acetate) to give the carboxylic acid as a white solid (1.15 g, 75%).

Part H: Preparation of N-[(Tetrahydro-2H-pyran-2-yl)oxy]-2-[[4-[4-(trifluoromethoxy)phenoxy]-1-piperidinyl] sulfonyl]acetamide In dry equipment under nitrogen, the carboxylic acid from part G (1.0 g, 2.6 mmol) was dissolved in dry dimethylformamide (7 mL) and the remaining reagents were added to the solution in the following order: N-hydroxybenzotriazole hydrate (0.42 g, 3.1 mmol), N-methylmorpholine (0.86 mL, 7.8 mmol), O-(tetrahydro-2H-pyran-2-yl)hydroxylamine (0.9 g, 7.8 mmol), and 1-(3-dimethylaminopropyl)-3-ethylcarbodiimide hydrochloride (0.7 g, 3.7 mmol). After three hours at ambient temperature, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. The product was recrystallized (hexanes/ethyl acetate) to give the THP hydroxamate as a white solid (0.9 g, 71%).

Part I: Preparation of N-Hydroxy-2-[[4-[4-(trifluoromethoxy)phenoxy]-1-piperidinyl]-sulfonyl] acetamide To a solution of the THP hydroxamate from part H (0.84 g, 2.4 mmol) in 1,4-dioxane (4.5 mL) was added 4N HCl dioxane solution (4.5 mL) and methanol (64.5 mL). After thirty minutes at ambient temperature the reaction was diluted with ethyl acetate and washed with water, dried over $Na_2SO_4$, filtered, and concentrated in vacuo. The product was recrystallized (ethyl acetate/hexanes) to give the title compound as a white solid (0.35 g, 51%). HRMS (ES+) $M+H^+$ calculated for $C_{14}H_{17}F_3N_2O_6S_1$: 416.1103, found 416.1117.

EXAMPLE 17

Preparation of Tetrahydro-N-hydroxy-4-[[4-[4-(trifluoromethoxy)phenoxy]-1-piperidinyl]sulfonyl]-2H-pyran-4-carboxamide

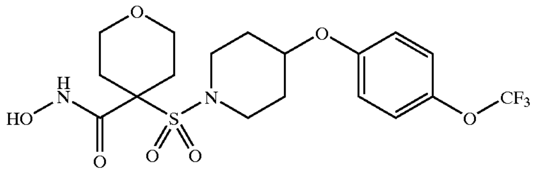

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(Methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-Dimethylethyl Ester In dry equipment under nitrogen, 4-trifluoromethoxy-phenol (10.15 g, 57 mmol) was dissolved in dry dimethyl-formamide (125 mL) and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol) and at zero degrees Celsius a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(Trifluoromethoxy) phenoxy]-1-piperidinyl]sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Methyl Tetrahydro-4-[[4-[4-(trifluoromethoxy)phenoxy]-1-piperidinyl]-sulfonyl]-2H-pyran-4-carboxylate To a solution of the methylene sulfonamide from part F (5.17 g, 13 mmol) in dimethylformamide (26 mL) was added potassium carbonate (7.2 g, 52.1 mmol), bis-(2-bromoethyl)ether (1.7 mL, 13 mmol) and 18-Crown-6 (500 mg). The slurry was stirred at sixty degrees Celsius. After sixteen hours potassium carbonate (2.0 g, 14 mmol) and bis-(2-bromoethyl)ether (0.2 mL, 1.6 mmol) were added and the reaction stirred at sixty degrees Celsius. After a total of forty hours, the reaction was concentrated in vacuo. The residue was taken up in ethyl acetate, washed with water three times, saturated sodium chloride solution, dried over $Na_2SO_4$, filtered, and concentrated in vacuo. The product was recrystallized (ethyl acetate/hexanes) to give the THP substituted sulfonamide as a white solid (1.85 g, 30%).

Part H: Preparation of Tetrahydro-4-[[4-[4-(trifluoromethoxy)phenoxy]-1-piperidinyl]-sulfonyl]-2H-pyran-4-carboxylic Acid In dry equipment under nitrogen, the THP substituted sulfonamide from part G (1.9 g, 40.7 mmol) was dissolved in dry tetrahydrofuran (80.0 mL) and potassium trimethylsilonate (17.4 g, 122.0 mmol) was added at thirty five degrees Celsius. After two hours water (100 mL) was added and the solution concentrated in vacuo. The residue was taken up in water and extracted with ethyl acetate to remove unreacted starting material. The aqueous solution was treated with 6N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a white solid (18.5 g, 100%)

Part I: Preparation of Tetrahydro-N-[(tetrahydro-2H-pyran-2-yl)oxy)-4-[[4-[4-(trifluoromethoxy)-phenoxy]-1-piperidinyl]sulfonyl]-2H-pyran-4-carboxamide In dry equipment under nitrogen, the carboxylic acid from part H (1.63 g, 3.6 mmol) was dissolved in dry dimethylformamide (7.5 mL) and the remaining reagents were added to the solution in the following order: N-hydroxybenzotriazole hydrate (0.97 g, 7.2 mmol), N-methylmorpholine (1.2 mL, 10.8 mmol), O-(tetrahydro-2H-pyran-2-yl)hydroxylamine (1.38 g, 7.2 mmol), and 1-(3-dimethylaminopropyl)-3-ethylcarbodiimide hydrochloride (1.38 g, 7.2 mmol). After one hour at forty five degrees Celsius, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (1.1 g, 55%).

Part J: Preparation of Tetrahydro-N-hydroxy-4-[[4-[4-(trifluoromethoxy)phenoxy]-1-piperidinyl]-sulfonyl]-2H-pyran-4-carboxamide To a solution of the THP hydroxamate from part I (1.0 g, 1.8 mmol) in 1,4-dioxane (5 mL) was added 4N HCl dioxane solution (5 mL) and methanol (5 mL). After thirty minutes at ambient temperature the reaction was diluted with ethyl acetate and washed with water, dried over $Na_2SO_4$, filtered, and concentrated in vacuo. The product was recrystallized (acetone/hexanes) to give the title compound as a white solid (0.58 g, 68%). HRMS (ES+) $M+H^+$ calculated for $C_{18}H_{23}N_2O_7S_1F_3$: 469.1256, found 469.1287.

EXAMPLE 18

Preparation of N-Hydroxy-1-(phenylmethyl)-4-[[4-[4-(trifluoromethyl)phenoxy)-1-piperidinyl]-sulfonyl]-4-piperidinecarboxamide Monohydrochloride

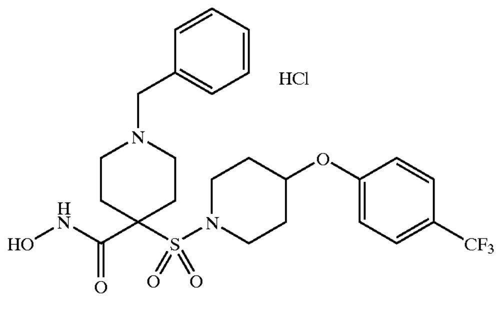

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(Trifluoromethyl)phenoxy]-1-piperidinecarboxylate To a solution of the BOC piperidine from part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy]piperidine

To a slurry of the substituted BOC piperidine from part B (5.95 q, 17.2 mmol) in 1,4-dioxane (10 mL) was added 4N HCl dioxane solution (17 mL). After one hour at ambient temperature, the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(trifluoromethyl)phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees.

After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Methyl 1-(phenylmethyl)-4-([4-[4-(trifluoromethyl)phenoxy]-1-piperidinyl]-sulfonyl]-4-piperidinecarboxylate To a solution of the methylene sulfonamide from part E (1.14 g, 3 mmol) in dimethylformamide (6 mL) were added potassium carbonate (1.24 g, 9 mmol), bis-(2-chloroethyl) benzyl amine (0.7 g, 3 mmol, and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a white solid (950 mg, 59%).

Part G: Preparation of 1-(Phenylmethyl)-4-[[4-[4-(trifluoromethyl)phenoxy]-1-piperidinyl]-sulfonyl]-4-piperidinecarboxylic Acid In dry equipment under nitrogen, the piperidine sulfonamide from part F (7.2 g, 13.3 mmol) was dissolved in dry tetrahydrofuran (26 mL) and potassium trimethylsilonate (5.7 g, 40 mmol) was added and stirred at forty degrees Celsius. After twenty four hours water (50 mL) was added and at 5 degrees Celsius, 6N HCl was added until pH=1. The slurry was filtered, washed with water and dried in vacuo to give the carboxylic acid as a white solid (6.5 g, 93%).

Part H: Preparation of 1-(Phenylmethyl)-N-[(tetrahydro-2H-pyran-2-yl)oxy]-4-[[4-[4-(trifluoromethyl)phenoxy]-1-piperidinyl]-sulfonyl]-4-piperidinecarboxamide In dry equipment under nitrogen, the carboxylic acid from part G (6.46 g, 12.2 mmol) was dissolved in dry dimethylformamide (25 mL) and the remaining reagents were added to the solution in the following order: N-hydroxybenzotriazole hydrate (2.0 g, 14.7 mmol), N-methylmorpholine (4.0 mL, 36.8 mmol), O-(tetrahydro-2H-pyran-2-yl)hydroxylamine (4.3 g, 36.8 mmol), and 1-(3-dimethylaminopropyl)-3-ethylcarbodiimide hydrochloride (3.3 g, 17.2 mmol). The reaction was stirred at forty five degrees Celsius. After three hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white solid (6.1 g, 80%).

Part I: Preparation of N-Hydroxy-1-(phenylmethyl)-4-[[4-[4-(trifluoromethyl)phenoxy]-1-piperidinyl]sulfonyl]-4-piperidinecarboxamide Monohydrochloride To a solution of the THP hydroxamate from part H (6.0 g, 9.6 mmol) in 1,4-dioxane (2.4 mL) was added 4 N HCl dioxane solution (2.4 mL) and methanol (2.4 mL). After thirty minutes at ambient temperature the reaction was poured into diethyl ether (100 mL). The slurry was filtered under nitrogen, washed with diethyl ether, and dried in vacuo to give the title compound as an off white solid (5.4 g, 97%). HRMS (ES+) $M+H^+$ calculated for $C_{25}H_{30}F_3N_3O_5S_1$: 542.1937, found 542.1938.

EXAMPLE 19

Preparation of N-Hydroxy-1-(2-pyridinylmethyl)-4-[[4-(4-(trifluoromethoxy)phenoxy]-1-piperidinyl] sulfonyl]-4-piperidinecarboxamide, Monohydrochloride

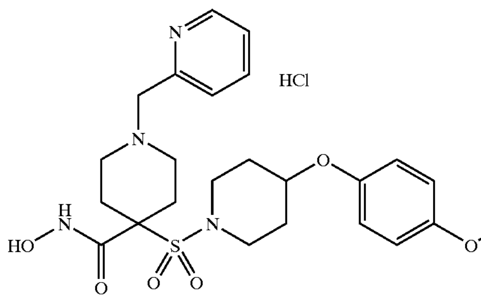

Part A: Preparation of 1,1-Fimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(Methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol) Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-Dimethylethyl Ester In dry equipment under nitrogen, 4-trifluoromethoxyphenol (10.15 g, 57 mmol) was dissolved in dry dimethylformamide (125 mL) and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol) and at zero degrees Celsius a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(trifluoromethoxy) phenoxy]-1-piperidinyl]-sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Methyl 1-(Phenylmethyl)-4-[[4-[4-(trifluoromethoxy)phenoxy]-1-piperidinyl]sulfonyl]-4-piperidinecarboxylate To a solution of the methylene sulfonamide from part F (20.46 g, 51.5 mmol) in dimethylformamide (90 mL) was added potassium carbonate (21.3 g, 154.7 mmol), bis-(2-chloroethyl)benzyl amine (12.0 g, 51.5 mmol; and 18-Crown-6 (700 mg). The slurry was stirred at sixty degrees Celsius. After twenty four hours the reaction was concentrated in vacuo. The residue was taken up in ethyl acetate, washed with water three times, saturated sodium chloride solution, dried over $Na_2SO_4$, filtered, and concentrated in vacuo. The residue was recrystallized (methanol) to give the N-benzyl piperidine sulfonamide as a white solid (15 g, 52%).

Part H: Preparation of 4-[[4-[4-(Trifluoromethoxy)-phenoxy]-1-piperidinyl]sulfonyl]-4-piperidinecarboxylic Acid, Methyl Ester To a slurry of the N-benzyl piperidine sulfonamide from part G (4.17 g, 7.5 mmol) in methanol (50 mL) was added ammonium formate (1.46 g, 22.5 mmol). The system was purged with nitrogen for 10 minutes. The nitrogen stream was removed and palladium on carbon (1.5 g of 10 weight % on activated carbon, 50% water) was added. The reaction was refluxed for thirty minutes, cooled, filtered through Celite under nitrogen, and concentrated in vacuo to give the unsubstituted piperidine sulfonamide as a beige solid (3.15 g, 90%).

Part I: Preparation of Methyl 1-(2-Pyridinylmethyl)-4-[[4-[4-(trifluoromethoxy)phenoxy]-1-piperidinyl]sulfonyl]-4-piperidinecarboxylate The unsubstituted piperidine sulfonamide from part H (7.9 g, 16.95 mmol) was dissolved in dry dimethylformamide (35 mL) and potassium carbonate (7.05 g, 51.1 mmol) and 2-picolyl chloride hydrochloride (4.21 g, 25.67 mmol) were added. The reaction was stirred at thirty five degrees Celsius for sixteen hours and then concentrated in vacuo. The residue was taken up in ethyl acetate and filtered through Celite. The filtrate washed with water two times, saturated sodium chloride solution, dried over $Na_2SO_4$, filtered, and concentrated in vacuo. Chromatography (on silica, ethyl acetate/hexanes) provided the N-picolyl piperidine sulfonamide as a white solid (6.8 g, 72%).

Part J: Preparation of 1-(2-Pyridinylmethyl)-N-[(tetrahydro-2H-pyran-2-yl)oxy]-4-[[4-[4-(trifluoromethoxy)phenoxy]-1-piperidinyl]-sulfonyl]-4-piperidinecarboxamide In dry equipment under nitrogen, the N-picolyl piperidine sulfonamide from part I (8.5 g, 15.3mmol) was dissolved in dry tetrahydrofuran (30 mL) and potassium trimethylsilonate (6.52 g, 45.8 mmol) was added at ambient temperature. After eighteen hours water (50 mL) was added and at 5 degrees Celsius, 6 N HCl was added until pH=7. The slurry was filtered, washed with water and dried in vacuo to give the carboxylic acid as a off-white solid (6.9 g, 84%). In dry equipment under nitrogen, the carboxylic acid (6.8 g, 12.5 mmol) was dissolved in dry dimethylformamide (25 mL) and the remaining reagents were added to the solution in the following order: N-hydroxybenzotriazole hydrate (2.03 g, 15.0 mmol), N-methylmorpholine (4.1 mL, 37.6 mmol), O-(tetrahydro-2H-pyran-2-yl)hydroxylamine (4.4 g, 37.6 mmol), and 1-(3-dimethylaminopropyl)-3-ethylcarbodiimide hydrochloride (3.36 g, 17.5 mmol). The reaction was stirred at forty degrees Celsius. After twelve hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a light yellow foam (7.55 g, 94%).

Part K: Preparation of N-Hydroxy-1-(2-pyridinylmethyl)-4-[[4-[4-(trifluoromethoxy)-phenoxy]-1-piperidinyl] sulfonyl]-4-piperidinecarboxamide, Monohydrochloride To a solution of the THP hydroxamate from part J (7.4 g, 11.5 mmol) in 1,4-dioxane (2 mL) was added 4N HCl dioxane solution (29 mL, 115.2 mmol) and methanol (2.9 mL). After fifteen minutes, the reaction was diluted with diethyl ether, the solids filtered under nitrogen and dried in vacuo to give the title compound as a white solid (1.15 g, 96%). HRMS (ES+) $M+H^+$ calculated for $C_{24}H_{29}P_3N_4O_6S_1$: 559.1838, found 559.1864.

EXAMPLE 20

Preparation of N-Hydroxy-1-(2-pyrimidinyl)-4-[[4-[4-(trifluoromethyl)-phenoxy]-1-piperidinyl]sulfonyl]-4-piperidinecarboxamide, Monohydrochloride

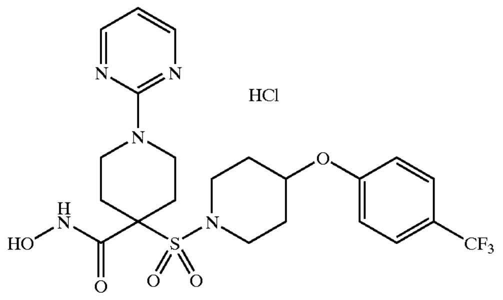

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy]piperidine

To a slurry of the substituted BOC piperidine from part B (5.95 g, 17.2 mmol) in 1,4-dioxane (10 mL) was added 4N HCl dioxane solution (17 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(trifluoromethyl)phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Methyl 1-(Phenylmethyl)-4-[[(4-[4-(trifluoromethyl)phenoxy]-1-piperidinyl]-sulfonyl]-4-piperidinecarboxylate To a solution of the methylene sulfonamide from part E (1.14 g, 3 mmol) in dimethylformamide (6 mL) was added potassium carbonate (1.24 g, 9 mmol), bis-(2-chloroethyl) benzyl amine (0.7 g, 3 mmol; and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a white solid (950 mg, 59%).

Part G: Preparation of Methyl 1-(2-Pyrimidinyl)-4-[[4-[4-(trifluoromethyl)phenoxy]-1-piperidinyl]sulfonyl]-4-piperidinecarboxylate To a slurry of the piperidine sulfonamide from part F (6.3 g, 12.0 mmol) in methanol (25 mL) was added ammonium formate (2.2 g, 34.5 mmol). The system was purged with nitrogen for 10 minutes. The nitrogen stream was removed and palladium on carbon (1.2 g of 10 weight % on activated carbon, 50% water) was added. The reaction was refluxed for forty five minutes, cooled, filtered through Celite under nitrogen, and concentrated in vacuo. The residue (6.21 g, 13.8 mmol) was dissolved in dry dimethylformamide (28 mL) and potassium carbonate (5.7 g, 41.4 mmol) and 2-chloropyrimidine (3.16 g, 27.6 mmol) were added. The reaction was stirred at eighty five degrees Celsius for one hour and then concentrated in vacuo. The residue was taken up in ethyl acetate and filtered through Celite. The filtrate washed with water two times, saturated sodium chloride solution, dried over $Na_2SO_4$, filtered, and concentrated in vacuo. The product was recrystallized (methanol) to give the N-pyrimidinyl piperidine sulfonamide as a white solid (4.94 g, 68%).

Part H: Preparation of 1-(2-Pyrimidinyl)-4-[[4-[4-(trifluoromethyl)phenoxy]-1-piperidinyl]-sulfonyl]-4-piperidinecarboxylic Acid In dry equipment under nitrogen, the N-pyrimidinyl piperidine sulfonamide from part G (4.9 g, 9.28 mmol) was dissolved in dry tetrahydrofuran (35 mL) and potassium trimethylsilonate (3.97 g, 27.8 mmol) was added at thirty five degrees Celsius. After sixteen hours water (50 mL) was added and at 5 degrees Celsius, 6 N HCl was added until pH=2. The aqueous slurry was extracted with ethyl acetate. The ethyl acetate solution was washed with water, saturated sodium chloride solution, dried over $Na_2SO_4$, filtered, and concentrated in vacuo. The solids were slurried in acetonitrile, filtered under nitrogen, washed with hexanes and dried in vacuo to give the carboxylic acid as a white solid (4.7 g, 98%).

Part I: Preparation of 1-(2-Pyrimidinyl)-N-[(tetrahydro-2H-pyran-2-yl)oxy]-4-[[4-[4-(trifluoromethyl)phenoxy]-1-piperidinyl]-sulfonyl]-4-pioeridinecarboxamide In dry equipment under nitrogen, the carboxylic acid from part H (4.6 g, 8.95 mmol) was dissolved in dry dimethylformamide (18 mL) and the remaining reagents were added to the solution in the following order: N-hydroxybenzotriazole hydrate (1.45 g, 10.7mmol), N-methylmorpholine (2.95 mL, 26.8 mmol), O-(tetrahydro-2H-pyran-2-yl)hydroxylamine (3.14 g, 26.8 mmol), and 1-(3-dimethylaminopropyl)-3-ethylcarbodiimide hydrochloride (2.4 g, 12.5 mmol). The reaction was stirred at thirty degrees Celsius. After sixteen hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. The product was recrystallized (methanol) to give the THP hydroxamate as a white solid (5.0 g, 91%).

Part J: Preparation of N-Hydroxy-1-(2-pyrimidinyl)-4-[[4-[4-(trifluoromethyl)phenoxy]-1-piperidinyl]sulfonyl]-4-piperidinecarboxamide, Monohydrochloride To a solution of the THP hydroxamate from part I (4.97 g, 8.1 mmol) in 1,4-dioxane (3 mL) was added 4N HCl dioxane solution (20 mL, 81.1 mmol) and methanol (2 mL). After thirty minutes at ambient temperature the reaction was poured into 100 mL acetonitrile. The slurry was filtered under nitrogen, washed with acetonitrile and dried in vacuo to give the title compound as a white solid (3.3 g, 72%). HRMS (ES+) M+H$^+$ calculated for $C_{22}H_{26}F_3N_5O_5S_1$: 530.1685, found 530.1696.

EXAMPLE 21

Preparation of N-Hydroxy-4-[[4-[4-(trifluoromethyl) phenoxy]-1-piperidinyl sulfonyl]-1-[4-(trifluoromethyl)-2-pyrimidinyl]-4-piperidinecarboxamide, Monohydrochloride

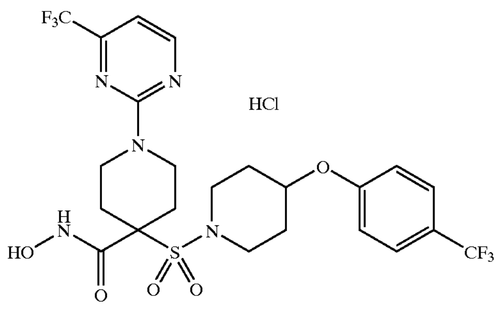

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from part B (5.95 g, 17.2 mmol) in 1,4-dioxane (10 mL) was added 4 N HCl dioxane solution (17 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl) phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Methyl 1-(Phenylmethyl)-4-[[4-[4-(trifluoromethyl)phenoxy]-1-piperidinyl]-sulfonyl]-4-piperidinecarboxylate To a solution of the methylene sulfonamide from part E (1.14 g, 3 mmol) in dimethylformamide (6 mL) was added potassium carbonate (1.24 g, 9 mmol), bis-(2-chloroethyl)

benzyl amine (0.7 g, 3 mmol; and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a white solid (950 mg, 59%).

Part G: Preparation of Methyl 4-[[4-[4-(Trifluoromethyl) phenoxy]-1-piperidinyl]-sulfonyl]-1-[4-(trifluoromethyl)-2-pyrimidinyl]-4-piperidinecarboxylate To a slurry of the piperidine sulfonamide from part F (6.3 g, 12.0 mmol) in methanol (25 mL) was added ammonium formate (2.2 g, 34.5 mmol). The system was purged with nitrogen for 10 minutes. The nitrogen stream was removed and palladium on carbon (1.2 g of 10 weight % on activated carbon, 50% water) was added. The reaction was refluxed for forty five minutes, cooled, filtered through Celite under nitrogen, and concentrated in vacuo. The residue (4.5 g, 10 mmol) was dissolved in dry dimethylformamide (20 mL) and potassium carbonate (4.14 g, 30 mmol) and 2-chloro-4-trifluoromethylpyrimidine (2.4 mL, 20 mmol) were added. The reaction was stirred at seventy degrees Celsius for three hour and then concentrated in vacuo. The residue was taken up in ethyl acetate and filtered through Celite. The filtrate washed with water two times, saturated sodium chloride solution, dried over $Na_2SO_4$, filtered, and concentrated in vacuo. The product was recrystallized (methanol) to give the N-pyrimidinyl piperidine sulfonamide as a white solid (4.51 g, 76%).

Part H: Preparation of 4-[[4-[4-(Trifluoromethyl)-phenoxy]-1-piperidinyl]sulfonyl]-1-[4-(trifluoromethyl)-2-pyrimidinyl]-4-piperidinecarboxylate In dry equipment under nitrogen, the N-pyrimidinyl piperidine sulfonamide from part G (4.9 g, 9.28 mmol) was dissolved in dry tetrahydrofuran (35 mL) and potassium trimethylsilonate (3.2 g, 22.45 mmol) was added at forty five degrees Celsius. After four hours water (100 mL) was added and at 5 degrees Celsius, 6 N HCl was added until pH=2. The slurry was filtered under nitrogen, the solids washed with hexanes and dried in vacuo to give the carboxylic acid as a white solid (4.13 g, 95%).

Part I: Preparation of N-((Tetrahydro-2H-pyran-2-yl)oxy)-4-[[4-[4-(trifluoromethyl)phenoxy]-1-piperidinyl]sulfonyl]-1-[4-(trifluoromethyl)-2-pyrimidinyl]-4-piperidinecarboxamide In dry equipment under nitrogen, the carboxylic acid from part H (4.0 g, 6.87 mmol) was dissolved in dry dimethylformamide (20 mL) and the remaining reagents were added to the solution in the following order: N-hydroxybenzotriazole hydrate (1.1 g, 8.25 mmol), N-methylmorpholine (2.2 mL, 20.6 mmol), O-(tetrahydro-2H-pyran-2-yl) hydroxylamine (2.4 g, 20.6 mmol), and 1-(3-dimethylaminopropyl)-3-ethylcarbodiimide hydrochloride (1.84 g, 9.62 mmol) The reaction was stirred at forty five degrees Celsius. After sixteen hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo. The product was recrystallized (methanol) to give the THP hydroxamate as a white solid (4.06 g, 87%).

Part J: Preparation of N-Hydroxy-4-[[4-[4-(trifluoromethyl) phenoxy]-1-piperidinyl]-sulfonyl]-1-[4-(trifluoromethyl)-2-pyrimidinyl]-4-piperidinecarboxamide, Monohydrochloride To a solution of the THP hydroxamate from part I (5.0 g, 5.87 mmol) in 1,4-dioxane (3 mL) was added 4N HCl dioxane solution (14.7 mL, 58.7 mmol) and methanol (1.5 mL). After thirty minutes at ambient temperature the reaction was poured into 100 mL acetonitrile. The slurry was filtered under nitrogen, washed with acetonitrile and dried in vacuo to give the title compound as a white solid (2.95 g, 80%). HRMS (ES+) $M+H^+$ calculated for $C_{23}H_{25}F_6N_5O_5S_1$: 598.1559, found 598.1531.

EXAMPLE 22

Preparation of 1-(5-Ethyl-2-pyrimidinyl)-N-hydroxy-4-[[4-[4-(trifluoromethyl)-phenoxy]-1-piperidinyl]sulfonyl]-4-piperidinecarboxamide, Monohydrochloride

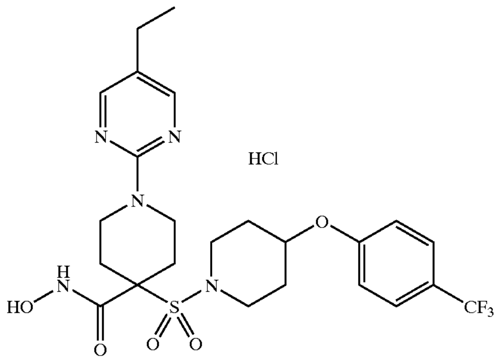

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from part B (5.95 g, 17.2 mmol) in 1,4-dioxane (10 mL) was added 4N HCl dioxane solution (17 mL)). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(trifluoromethyl)phenoxy]-1-piperidinyl]-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Methyl 1-(Phenylmethyl)-4-[[4-[4-(trifluoromethyl)phenoxy]-1-piperidinyl]-sulfonyl]-4-piperidinecarboxylate To a solution of the methylene sulfonamide from part E (1.14 g, 3 mmol) in dimethylformamide (6 mL) was added potassium carbonate (1.24 g, 9 mmol), bis-(2-chloroethyl) benzyl amine (0.7 g, 3 mmol and 18-Crown-6 (500 mg). The slurry was stirred at sixty degrees Celsius. After sixteen hours the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the piperidine sulfonamide as a white solid (950 mg, 59%).

Part G: Preparation of Methyl 1-(5-Ethyl-2-pyrimidinyl)-4-[[4-[4-(trifluoromethyl)-phenoxy]-1-piperidinyl)sulfonyl]-4-piperidinecarboxylate To a slurry of the piperidine sulfonamide from part F (6.3 g, 12.0 mmol) in methanol (25 mL) was added ammonium formate (2.2 g, 34.5 mmol). The system was purged with nitrogen for 10 minutes. The nitrogen stream was removed and palladium on carbon (1.2 g of 10 weight % on activated carbon, 50% water) was added. The reaction was refluxed for forty five minutes, cooled, filtered through Celite under nitrogen, and concentrated in vacuo. The residue (4.5 g, 10 mmol) was dissolved in dry dimethylformamide (20 mL) and potassium carbonate (3.45 g, 325mmol) and 2-chloro-5-ethylpyrimidine (1.82 mL, 15 mmol) were added. The reaction was stirred at eighty degrees Celsius for four hour and then concentrated in vacuo. The residue was taken up in ethyl acetate and filtered through Celite. The filtrate washed with water two times, saturated sodium chloride solution, dried over $Na_2SO_4$, filtered, and concentrated in vacuo. The product was recrystallized (methanol) to give the N-pyrimidinyl piperidine sulfonamide as a white solid (3.33 g, 60%).

Part H: Preparation of 1-(5-Ethyl-2-pyrimidinyl)-4-[[4-[4-(trifluoromethyl)phenoxy]-1-piperidinyl]sulfonyl]-4-piperidinecarboxylic Acid In dry equipment under nitrogen, the N-pyrimidinyl piperidine sulfonamide from part G (3.3 g, 5.94 mmol) was dissolved in dry tetrahydrofuran (12 mL) and potassium trimethylsilonate (2.54 g, 17.8 mmol) was added at forty five degrees Celsius. After two hours water (100 mL) was added and at 5 degrees Celsius, 6N HCl was added until pH=2. The slurry was filtered under nitrogen, the solids washed with hexanes and dried in vacuo to give the carboxylic acid as a white solid (3.11 g, 97%).

Part I: Preparation of 1-(5-Ethyl-2-pyrimidinyl)-N-[(tetrahydro-2H-pyran-2-yl)oxy]-4-[[4-[4-(trifluoromethyl)phenoxy]-1-piperidinyl]-sulfonyl]-4-piperidinecarboxamide In dry equipment under nitrogen, the carboxylic acid from part H (3.0 g, 5.5mmol) was dissolved in dry dimethylformamide (15 mL) and the remaining reagents were added to the solution in the following order: N-hydroxybenzotriazole hydrate (0.9 g, 6.64 mmol), N-methylmorpholine (1.8 mL, 16.6 mmol), O-(tetrahydro-2H-pyran-2-yl)hydroxylamine (1.9 g, 16.6 mmol), and 1-(3-dimethylaminopropyl)-3-ethylcarbodiimide hydrochloride (1.49 g, 7.75 mmol). The reaction was stirred at forty five degrees Celsius. After three hours, the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. The product was recrystallized (methanol) to give the THP hydroxamate as a white solid (3.34 g, 96%).

Part J: Preparation of 1-(5-Ethyl-2-pyrimidinyl)-N-hydroxy-4-[[4-[4-(trifluoromethyl)phenoxy]-1-piperidinyl]sulfonyl]-4-piperidinecarboxamide, Monohydrochloride To a solution of the THP hydroxamate from part I (3.3 g, 5.15 mmol) in 1,4-dioxane (3 mL) was added 4 N HCl dioxane solution (13 mL, 51.5 mmol) and methanol (1.3 mL). After thirty minutes at ambient temperature the reaction was poured into 100 mL acetonitrile. The slurry was filtered under nitrogen, washed with acetonitrile and dried in vacuo to give the title compound as a white solid (2.59 g, 85%). HRMS (ES+) $M+H^+$ calculated for $C_{24}H_{30}F_3N_5O_5S_1$: 5581998, found 558.198.

EXAMPLE 23

Preparation of Tetrahydro-N-hydroxy-4-[[4-[4-(trifluoromethoxy)phenoxy]-1-piperidinyl)sulfonyl]-2H-thiopyran-4-carboxamide

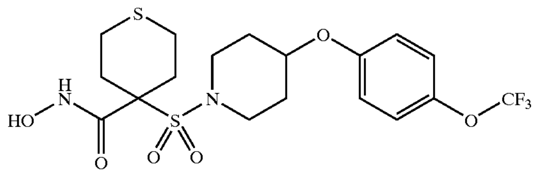

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation o w 4-(Methylsulfonyl)hydroxy-L piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy)-1-piperidinecarboxylic Acid, 1,1-Dimethylethyl Ester In dry equipment under nitrogen, 4-trifluoromethoxy-phenol (10.15 g, 57 mmol) was dissolved in dry dimethyl-formamide (125 mL) and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%)

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with 5 N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) with triethylamine (12.3 mL, 88.1 mmol) and at zero degrees Celsius a solution of methane sulfonyl chloride (5.1 mL, 66.1 mmol) in dichloromethane (20 mL) was added. After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(trifluoromethoxy) phenoxy]-1-piperidinyl]-sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Tetrahydro-4-[[4-[4-(trifluoromethoxy)phenoxy]-1-piperidinyl]-sulfonyl]-2H-thiopyran-4-carboxylic Acid To a solution of the methylene sulfonamide from part F (6.0 g, 15 mmol) in dimethylformamide (30 mL) were added potassium carbonate (6.2 g, 45 mmol), bis-(2-bromoethyl) sulfide (3.72 g, 15 mmol; J.Chem.Soc., 1948;37) and 18-Crown-6 (500 mg). The slurry was stirred at Forty degrees Celsius. After twenty hours the reaction was concentrated in vacuo. The residue was taken up in ethyl acetate, washed with water three times, saturated sodium chloride solution, dried over $Na_2SO_4$, filtered, and concentrated in vacuo to give impure tetrahydrothiopyran substituted sulfonamide (4.68 g, 65%). In dry equipment under nitrogen, the tetrahydrothiopyran substituted sulfonamide (4.6 g, 9.52 mmol) was dissolved in dry tetrahydrofuran (20 mL) and potassium trimethylsilonate (4.07 g, 28.6 mmol) was added at fifty degrees Celsius. After four hours water (100 mL) was added and the solution concentrated in vacuo. The residue was taken up in water and extracted with ethyl acetate to remove impurities. The aqueous solution was treated with 6N HCl until pH=1. The slurry was extracted with ethyl acetate and the combined extracts washed with water, dried over $Na_2SO_4$, filtered, and concentrated in vacuo. The residue was recrystallized (acetone/hexanes) to give the carboxylic acid as a white solid (2.62 g, 59%).

Part H: Preparation of Tetrahydro-N-[(tetrahydro-2H-pyran-2-yl)oxy]-4-[[4-[4-(trifluoromethoxy)-phenoxy]-1-piperidinyl]sulfonyl]-2H-thiopyran-4-carboxamide In dry equipment under nitrogen, the carboxylic acid from part G (2.6 g, 5.54 mmol) was dissolved in dry dimethylformamide (11 mL) and the remaining reagents were added to the solution in the following order: N-hydroxybenzotriazole hydrate (0.9 g, 6.65 mmol), N-methylmorpholine (1.83 mL, 16.6 mmol), O-(tetrahydro-2H-pyran-2-yl)hydroxylamine (1.95 g, 16.6 mmol), and 1-(3-dimethylaminopropyl)-3-ethylcarbodiimide hydrochloride (1.49 g, 7.72 mmol). After two hour at thirty five degrees Celsius, the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (2.69 g, 85%).

Part I: Preparation of Tetrahydro-N-hydroxy-4-[[4-[4-(trifluoromethoxy)phenoxy]-1-piperidinyl]-sulfonyl]-2H-thiopyran-4-carboxamide To a solution of the THP hydroxamate from part H (0.99 g, 1.75 mmol) in 1,4-dioxane (3.5 mL) was added 4N HCl dioxane solution (0.9 mL, 3.5 mmol) and methanol (0.14 mL). After thirty minutes at ambient temperature the reaction was diluted with ethyl acetate and washed with water, dried over $Na_2SO_4$, filtered, and concentrated in vacuo. The product was slurried in diethyl ether, filtered under nitrogen and dried to give the title compound as a white solid (0.65 g, 77%). HRMS (ES+) $M+H^+$ calculated for $C_{18}H_{23}N_2O_6S_2F_3$: 485.1028, found 485.1034.

EXAMPLE 24

Preparation of Tetrahydro-N-hydroxy-4-[[4-[4-(trifluoromethoxy)phenoxy]-1-piperidinyl]sulfonyl]-2H-thiopyran-4-carboxamide, 1,1-dioxide

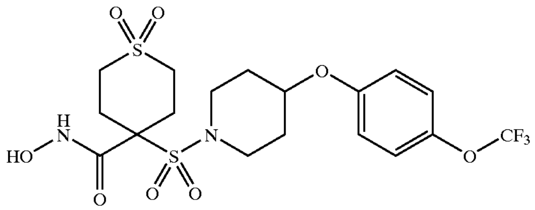

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 4-(methylsulfonyl)hydroxy-1-piperidinecarboxylic Acid, 1,1-Dimethylethyl Ester To a solution of the BOC piperidine of part A (5.00 g, 24.84 mmol) in dichloromethane (50 mL) at zero degrees Celsius, was added triethylamine (3.81 mL, 27.32 mmol) followed by methane sulfonyl chloride (2.02 mL, 26.08 mmol). Once the addition was complete the cooling bath was removed. After stirring for two hours, the reaction mixture was concentrated in vacuo. The residue was taken up in ethyl acetate, washed with water two times, saturated sodium chloride solution, dried over $Na_2SO_4$, filtered, and concentrated in vacuo to provide the mesylate as an off-white solid (7.34 g, >100%).

Part C: Preparation of 4-[4-(Trifluoromethoxy)-phenoxy]-1-piperidinecarboxylic Acid, 1,1-Dimethylethyl Ester In dry equipment under nitrogen, 4-trifluoromethoxy-phenol (10.15 g, 57 mmol) was dissolved in dry dimethyl-formamide (125 mL), and at minus five degrees Celsius sodium hydride (2.74 g, 68.4 mmol of the 60% oil dispersion) was added and the ice bath was removed. After one hour at ambient temperature, the mesylate from part B (15.9 g, 57 mmol) was added and the reaction stirred at eighty degrees Celsius. After stirring at ambient temperature for four hours, the reaction was concentrated in vacuo. The residue was taken up in diethyl ether, washed with water, saturated sodium chloride solution, dried over $Na_2SO_4$, filtered, and concentrated in vacuo to provide the substituted BOC-piperidine as a beige solid (20.6 g, 100%).

Part D: Preparation of 4-[4-(Trifluoromethoxy)-phenoxy] piperidine

At fifteen degrees Celsius, 4 N HCl in dioxanes (125 mL) was slowly added to the substituted BOC-piperidine from part C (20.6 g, 57 mmol) and stirred for ninety minutes. The reaction was concentrated in vacuo. The residue was dissolved in water (150 mL) and washed two times with ethyl acetate. The aqueous solution was cooled to five degrees Celsius and the pH adjusted to eleven with S N sodium hydroxide solution and extracted with ethyl acetate. The ethyl acetate was dried over $Na_2SO_4$, filtered, and concentrated in vacuo to provide the substituted piperidine as a beige solid (11.9 g, 80%).

Part E: Preparation of 1-(Methylsulfonyl)-4-[4-(trifluoromethoxy)phenoxy]piperidine The substituted piperidine from part D (11.5 g, 44.1 mmol) was dissolved in dichloromethane (125 mL) 30 with triethylamine (12.3 mL, 88.1 mmol) and at zero degrees Celsius a solution of methane sulfonyl chloride (5.1 mL, 66.1 mmol) in dichloromethane (20 mL) was added. After one hour. at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was recrystallized (ethyl acetate/hexanes) to give the sulfonamide as an off-white solid (10.77 g, 72%).

Part F: Preparation of Methyl [[4-[4-(trifluoromethoxy) phenoxy]-1-piperidinyl]-sulfonyl]-4-piperidinecarboxylate In dry equipment under nitrogen, the sulfonamide from part E (10.77 g, 31.8 mmol) was dissolved in dry tetrahydrofuran (64 mL), chilled to minus seventy-five degrees Celsius, and a 1 M solution of lithium bis(trimethylsilyl) amide (80 mL) was added maintaining the temperature below minus sixty five degrees. After thirty minutes at minus seventy-five degrees Celsius, a solution of methyl chloroformate (2.45 mL, 31.8 mmol) in dry tetrahydrofuran (32 mL) was added maintaining the temperature below minus sixty degrees. After thirty minutes at minus seventy-five degrees Celsius, the reaction was quenched with saturated ammonium chloride solution (125 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (12.69 g, 100%).

Part G: Preparation of Tetrahydro-4-[[4-[4-(trifluoromethoxy)phenoxy]-1-piperidinyl]-sulfonyl)-2H-thiopyran-4-carboxylic Acid To a solution of the methylene sulfonamide from part F (6.0 g, 15 mmol) in dimethylformamide (30 mL) was added potassium carbonate (6.2 g, 45 mmol), bis-(2-bromoethyl) sulfide (3.72 g, 15 mmol; *J.Chem.Soc.*;1948;37) and 18-Crown-6 (500 mg). The slurry was stirred at forty degrees Celsius. After twenty hours the reaction was concentrated in vacuo. The residue was taken up in ethyl acetate, washed with water three times, saturated sodium chloride solution, dried over $Na_2SO_4$, filtered, and concentrated in vacuo to give impure tetrahydrothiopyran substituted sulfonamide (4.68 g, 65%). In dry equipment under nitrogen, the tetrahydrothiopyran substituted sulfonamide (4.6 g, 9.52 mmol) was dissolved in dry tetrahydrofuran (20 mL) and potassium trimethylsilonate (4.07 g, 28.6 mmol) was added at fifty degrees Celsius. After four hours, water (100 mL) was added and the solution concentrated in vacuo. The residue was taken up in water and extracted with ethyl acetate to remove impurities. The aqueous solution was treated with 6N HCl until pH=1. The slurry was extracted with ethyl acetate and the combined extracts washed with water, dried over $Na_2SO_4$, filtered, and concentrated in vacuo. The residue was recrystallized (acetone/hexanes) to give the carboxylic acid as a white solid (2.62 g, 59%).

Part H: Preparation of Tetrahydro-N-[(tetrahydro-2H-pyran-2-yl)oxy)-4-[[4-[4-(trifluoromethoxy)-phenoxy]-1-piperidinyl]sulfonyl]-2H-thiopyran-4-carboxamide In dry equipment under nitrogen, the carboxylic acid from part G (2.6 g, 5.54 mmol) was dissolved in dry dimethyl-formamide (11 mL) and the remaining reagents were added to the solution in the following order: N-hydroxybenzotriazole hydrate (0.9 g, 6.65 mmol), N-methylmorpholine (1.83 mL, 16.6 mmol), O-(tetrahydro-2H-pyran-2-yl) hydroxylamine (1.95 g, 16.6 mmol), and 1-(3-dimethylaminopropyl)-3-ethylcarbodiimide hydrochloride (1.49 g, 7.72 mmol). After two hour at thirty five degrees Celsius, the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (2.69 g, 85%).

Part I: Preparation of Tetrahydro-N-[(tetrahydro-2H-pyran-2-yl)oxy]-4-[[4-[4-(trifluoromethoxy)-phenoxy]-1-piperidinyl]sulfonyl]-2H-thiopyran-4-carboxamide, 1,1-Dioxide The THP hydroxamate from part H (1.0 g, 1.76 mmol) was dissolved in dichloromethane (10 mL) and 3-chloroperoxybenzoic acid (1.33 g, 4.4 mmol, 57–86%) was added at twenty five degrees Celsius. After two hours, a solution of saturated $NaHCO_3$ with 5% sodium thiosulfate (10 mL) was added and the mixture was stirred for ten minutes. The layers were separated and washed with saturated $NaHCO_3$, saturated sodium chloride solution, dried over $Na_2SO_4$, filtered, and concentrated in vacuo. Chromatography (on silica, ethyl acetate/hexanes) provided the sulfone THP hydroxamate as a white solid (0.907 g, 92%).

Part J: Preparation of Tetrahydro-N-hydroxy-4-[[4-[4-(trifluoromethoxy)phenoxy]-1-piperidinyl]-sulfonyl]-2H-thiopyran-4-carboxamide, 1,1-Dioxide To a solution of the sulfone THP hydroxamate from part I (0.9 g, 1.5 mmol) in 1,4-dioxane (3 mL) was added 4N HCl dioxane solution (1.9 mL, 7.5 mmol) and methanol (0.5 mL). After ten minutes at ambient temperature the reaction was diluted with ethyl acetate and washed with water, dried over $Na_2SO_4$, filtered, and concentrated in vacuo. The product was slurried in diethyl ether, filtered under nitrogen and dried to give the title compound as a white solid (0.70 g, 90%). HRMS (ES+) $M+NH_4^+$ calculated for $C_{18}H_{23}N_2O_8S_2F_3$: 534.1192, found 534.1231.

EXAMPLE 25

Preparation of Tetrahydro-N-hydroxy-4-[[4-[4-(trifluoromethyl)phenoxy]-1-piperidinyl]sulfonyl]-2H-thiopyran-4-carboxamide

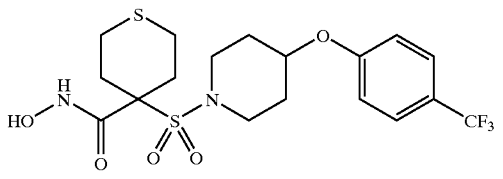

Part A: Preparation of 1,1-Dimethylethyl 4-Hydroxy-1-piperidinecarboxylate

In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below thirty degrees Celsius. After stirring at ambient temperature for four hours, the reaction was concentrated in vacuo. The residue was taken up in ethyl acetate, washed with water, 5% $KHSO_4$, saturated $NaHCO_3$, saturated sodium chloride solution, dried over $Na_2SO_4$, filtered, and concentrated in vacuo to give the BOC piperidine as a white solid (37.7 g, 94%).

Part B: Preparation of 1,1-Dimethylethyl 4-[4-(trifluoromethyl)phenoxy]-1-piperidinecarboxylate To a solution of the BOC piperidine from part A (6.03 g, 30 mmol) in dimethylformamide (60 mL) was added cesium carbonate (9.77 g, 30 mmol) and 4-fluorobenzotrifluoride (3.8 mL, 30 mmol). The slurry was stirred at ninety degrees Celsius. After nineteen hours cesium carbonate (3.26 g, 10 mmol) and 4-fluorobenzotrifluoride (0.95 ml mL, 10 mmol) were added and the reaction continued at ninety degrees Celsius. After a total of forty six hours, the reaction was concentrated in vacuo. The residue was taken up in ethyl acetate, washed with water three times, saturated sodium chloride solution, dried over $Na_2SO_4$, filtered, and concentrated in vacuo. Chromatography (on silica, ethyl acetate/hexanes) provided the substituted BOC piperidine as a white solid (6.0 g, 58%).

Part C: Preparation of 4-[4-(Trifluoromethyl)-phenoxy] piperidine

To a slurry of the substituted BOC piperidine from partl B (5.95 g, 17.2 mmol) in 1,4-dioxane (10 mL) was added 4 N HCl dioxane solution (17 mL). After one hour at ambient temperature the reaction was concentrated in vacuo. The residue was slurried in diethyl ether and vacuum filtration of the resulting precipitate provided the hydrochloride salt as a white solid (4.6 g, 100%).

Part D: Preparation of 1-(Methylsulfonyl)-4-[4-(trifluoromethyl)phenoxy]piperidine To a solution of the hydrochloride salt from part C (4.6 g, 16.9 mmol) and triethylamine (5.9 mL, 42.4 mmol) in dichloromethane (45 mL) at zero degrees Celsius was added a solution of methane sulfonyl chloride (1.97 mL, 25.4 mmol) in dichloromethane (10 mL). After one hour at ambient temperature, the solvent was stripped in vacuo. The residue was taken up in ethyl acetate, washed with water two times, saturated sodium chloride solution, dried over $Na_2SO_4$, filtered, and concentrated in vacuo. The residue was slurried in diethyl ether and vacuum filtration of the resulting precipitate provided the sulfonamide as an off-white solid (5.25 g, 96%).

Part E: Preparation of Methyl [[4-[4-(Trifluoromethyl) phenoxy]-1-piperidinyl-sulfonyl]acetate In dry equipment under nitrogen, the sulfonamide from part D (4.2 g, 13 mmol) was dissolved in dry tetrahydrofuran (26 mL), chilled to minus seventy-five degrees Celsius, and a 1 M solution of lithium bis(trimethylsilyl)amide (26 mL) was added maintaining the temperature below minus sixty five degrees. After thirty minutes at minus seventy-five degrees Celsius, a solution of methyl chloroformate (1.0 mL, 13 mmol) in dry tetrahydrofuran (13 mL) was added maintaining the temperature below minus sixty degrees. After thirty minutes at minus seventy-five degrees Celsius, the reaction was quenched with saturated ammonium chloride solution (100 mL) and extracted with ethyl acetate. The combined extracts were washed with saturated ammonium chloride solution, saturated sodium chloride solution, dried over $Na_2SO_4$, filtered, and concentrated in vacuo to give the methylene sulfonamide as an yellow oil (4.95 g, 100%).

Part F: Preparation of Tetrahydro-4-[[4-[4-(trifluoromethyl) phenoxy]-1-piperidinyl)-sulfonyl]-2H-thiopyran-4-carboxylic Acid To a solution of the methylene sulfonamide from part E (5.7 g, 15 mmol) in dimethylformamide (30 mL) was added potassium carbonate (6.2 g, 45 mmol), bis-(2-bromoethyl) sulfide (3.72 g, 15 mmol; J. Chem. Soc.; 1948; 37) and 18-Crown-6 (500 mg). The slurry was stirred at forty degrees Celsius. After sixty hours the reaction was concentrated in vacuo. The residue was taken up in ethyl acetate, washed with water three times, saturated sodium chloride solution, dried over $Na_2SO_4$, filtered, and concentrated in vacuo to give impure tetrahydrothiopyran substituted sulfonamide (3.7 g, 53%). In dry equipment under nitrogen, the tetrahydrothiopyran substituted sulfonamide (3.68 g, 7.88 mmol) was dissolved in dry tetrahydrofuran (15 mL) and potassium trimethylsilonate (3.37 g, 23.6 mmol) was added at fifty degrees Celsius. After ninety minutes water (100 mL) was added and the solution concentrated in vacuo. The residue was taken up in water and extracted with ethyl acetate to remove impurities. The aqueous solution was treated with 6 N HCl until pH=1. The slurry was extracted with ethyl acetate and the combined extracts washed with water, dried over $Na_2SO_4$, filtered, and concentrated in vacuo to give the carboxylic acid as a white foam (1.66 g, 46%).

Part G: Preparation of Tetrahydro-N-[(tetrahydro-2H-pyran-2-yl)oxy]-4-[[4-[4-(trifluoromethyl)-phenoxy]-1-piperidinyl]sulfonyl]-2H-thiopyran-4-carboxamide In dry equipment under nitrogen, the carboxylic acid from part F (1.5 g, 3.31 mmol) was dissolved in dry dimethylformamide (7 mL) and the remaining reagents were added to the solution in the following order: N-hydroxybenzotriazole hydrate (0.54 g, 3.97 mmol), N-methylmorpholine (1.1 mL, 9.93 mmol), O-(tetrahydro-2H-pyran-2-yl)hydroxylamine (1.16 g, 9.93 mmol), and 1-(3-dimethylaminopropyl)-3-ethylcarbodiimide hydrochloride (0.89 g, 4.64 mmol). After ninety minutes at thirty five degrees Celsius, the reaction was concentrated in vacuo. The residue was taken up in ethyl acetate, washed with water, saturated $NaHCO_3$, saturated sodium chloride solution, dried over $Na_2SO_4$, filtered, and concentrated in vacuo. Chromatography (on silica, ethyl acetate/hexanes) provided the THP hydroxamate as a white foam (0.85 g, 47%).

Part H: Preparation of Tetrahydro-N-hydroxy-4-[[4-[4-(trifluoromethyl)phenoxy]-1-piperidinyl]-sulfonyl]-2H-thiopyran-4-carboxamide To a solution of the THP hydroxamate from part G (0.7 g, 1.27 mmol) in 1,4-dioxane (2.5 mL) was added 4 N HCl dioxane solution (1.6 mL, 6.34 mmol) and methanol (0.4 mL). After ten minutes at ambient temperature the reaction was diluted with ethyl acetate and washed with water, dried over $Na_2SO_4$, filtered, and concentrated in vacuo. Dichloromethane (20 mL) was added and the solution was stripped. The product was slurried in diethyl ether, filtered under nitrogen and dried to give the title compound as a white solid (0.56 g, 94%). HRMS (ES+) $M+H^+$ calculated for $C_{18}H_{23}N_2O_5S_2F_3$: 469.1079, found 469.1061.

EXAMPLE 26

Preparation of N-Hydroxy-4 [[1'-(n-pentyl)[4,4'-bipiperidin]-1-yl]-sulfonyl]-tetrahydro-2H-pyran-4-carboxamide

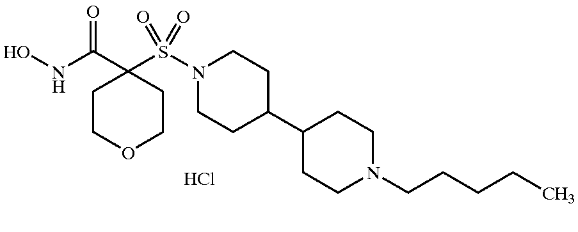

Part 1: Preparation of

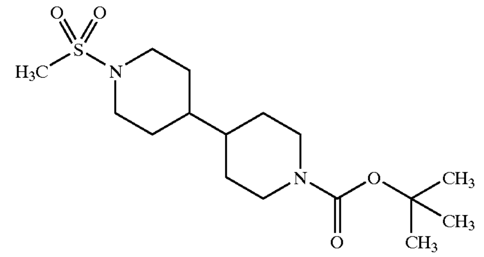

To a solution of the N-(t-butoxycarbonyl)-4,4'-bipiperdine (prepared using Preparation 22 in patent application WO 94/14776) (32.3 g, 120.0 mmol) and triethylamine (30.1 mL, 216.0 mmol) in dichloromethane (330 mL) at zero degrees Celsius was added a solution of methane sulfonyl chloride (16.2 mL, 209.0 mmol) in dichloromethane (100 mL). After 2.5 hours at ambient temperature, the solvent was removed in vacuo. The residue was partitioned between ethyl acetate (1 L) and water (0.5 L). The aqueous layer was extracted twice with ethyl acetate (300 mL), then the combined organic layers were washed with brine, dried over $Na_2SO_4$, filtered, and concentrated in vacuo. The residue was triturated with diethyl ether to give the methyl sulfonamide N'-t-butoxycarbamate as a white solid (33.31 g, 80%). $^1H$ NMR and mass spectrum were consistent with the desired compound.

Part 2: Preparation of

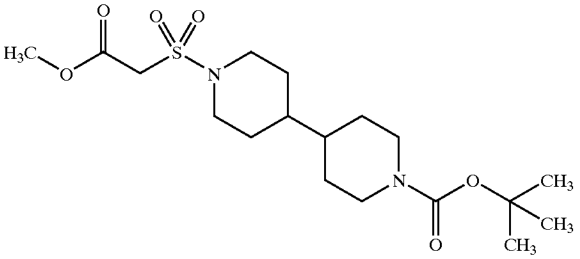

In dry equipment under nitrogen, the methyl sulfonamide N'-t-butoxycarbamate from part 1 (28.0 g, 81.0 mmol) was dissolved in dry tetrahydrofuran (160 mL) and cooled to minus seventy-five degrees Celsius. The resulting solution was then treated with a 1 M solution of lithium bis (trimethylsilyl)amide (210 mL, 210.0 mmol) at a rate such that the temperature remained below minus sixty five degrees. After addition was complete, the reaction mixture was allowed to warm to zero degrees Celsius. After 1 hour, the solution was cooled to minus seventy-five degrees Celsius and treated with a solution of methyl chloroformate (8.2 mL, 97.0 mmol) in dry tetrahydrofuran (50 mL), while maintaining the temperature below minus seventy degrees. After 1 hour at minus seventy-five degrees Celsius, the reaction was quenched with saturated ammonium chloride aqueous solution (60 mL), warmed to ambient temperature and concentrated in vacuo. The resulting residue was partitioned between ethyl acetate (500 mL) and 5% aqueous $HSO_4$ (500 mL). The aqueous layer was extracted with ethyl acetate (250 mL), then the combined organic layers were washed with water (250 mL), twice with brine (2×50 mL), dried over $Na_2SO_4$, filtered, and concentrated in vacuo to give the methylene sulfonamide Nu-t-butoxycarbamate as a yellow solid (32.6 g, 99.9%). $^1H$ NMR and mass spectrum were consistent with the desired compound.

Part 3: Preparation of

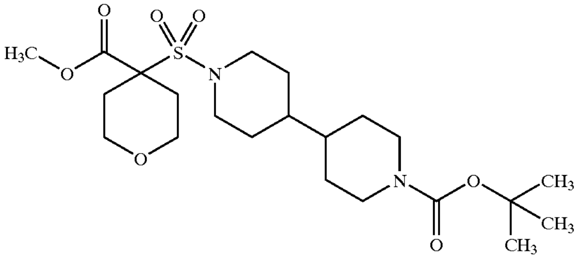

To a solution of the methylene sulfonamide N'-t-butoxycarbamate from part 2 (15.0 g, 37.0 mmol) in dimethylformamide (75 mL) was added bis-(2-bromoethyl)ether (10.3 g, 44 mmol), 18-Crown-6 (400 mg), followed by potassium carbonate (15.4 g, 111.0 mmol). The heterogeous mixture was stirred at sixty degrees Celsius. After 48 hours, the reaction was concentrated in vacuo, and the resulting oil was partitioned between ethyl acetate (300 mL) and water (200 mL). The organic layer was washed with 5% aqueous $KHSO_4$ (50 mL) twice with water (2x50 mL), brine (50 mL), dried over $Na_2SO_4$, filtered, and concentrated in vacuo to give the pyran sulfonamide N'-t-butoxycarbamate as a white solid. (18 g, 97%). $^1$H NMR and mass spectrum were consistent with the desired compound.

Part 4: Preparation of

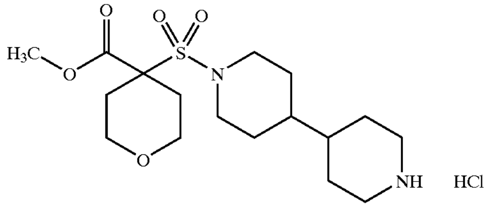

The pyran sulfonamide N'-t-butoxycarbamate (17 g, 36 mmol) from part 3 was dissolved in 4 N HCl 1,4-dioxane solution (90 mL). After 2 hours at ambient temperature the clear yellow solution began to form a precipitate. After 4 hours, the reaction was diluted with diethyl ether and vacuum filtration of the resulting white suspension provided the pyran sulfonamide hydrochloride salt as a white solid (13.4 g, 91%). $^1$H NMR and mass spectrum were consistent with the desired compound.

Part 5: Preparation of

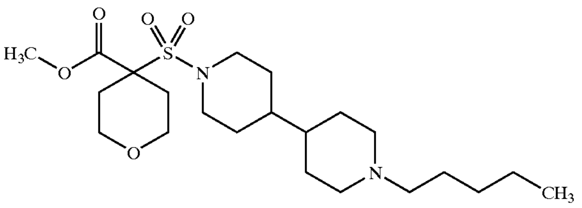

A suspension of the pyran sulfonamide hydrochloride salt from part 4 (3.5 g, 8.5 mmol) in tetrahydrofuran (26 mL) was treated with sodium acetate (0.7 g, 8.9 mmol), valeraldehyde (0.9 mL, 8.5 mmol), followed by sodium triacetoxyborohydride (2.2 g, 10.0 mmol). After 96 hours at ambient temperature, the reaction mixture was concentrated in vacuo. The resulting residue was partitioned between ethyl acetate (100 mL) and water (70 mL) and treated with saturated sodium carbonate aqueous solution until pH=8. The aqueous layer was extracted with ethyl acetate (25 mL) and the combined organic layers were washed with water (20 mL), brine (30 mL), dried over $Na_2SO_4$, filtered, and concentrated in vacuo to give the pyran sulfonamide N'-n-pentyl amine as a light yellow solid (3.7 g, 97%). $^1$H NMR and mass spectrum were consistent with the desired compound.

Part 6: Preparation of

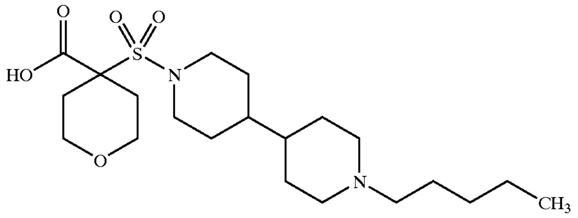

In dry equipment under nitrogen, the pyran sulfonamide N'-n-pentyl amine from part 5 (3.2 g, 7.2 mmol) was dissolved in dry tetrahydrofuran (36 mL) and potassium trimethylsilanolate (3.1 g, 22.0 mmol) was added at ambient temperature. After 21 hours, the reaction was concentrated in vacuo, and the resulting residue was dissolved in water (20 mL) and treated with 2N HCl until pH=7. The white suspension was vacuum filtered, washed with water and dried in vacuo to give the carboxylic acid as a white solid (2.36 g, 76%). $^1$H NMR and mass spectrum were consistent with the desired compound.

Part 7: Preparation of

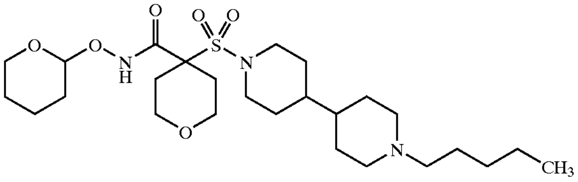

In dry equipment under nitrogen, the carboxylic acid from part 6 (2.2 g, 5.1 mmol) was dissolved in dry dimethylformamide (17 mL) and treated with 1-(3-dimethylamino-propyl)-3-ethylcarbodiimide hydrochloride (1.5 g, 7.63 mmol) and N-hydroxybenzo-triazole hydrate (1.03 g, 7.63 mmol). The resulting suspension became a clear amber solution after stirring at fifty degrees Celsius for 1.5 hours. The reaction was then treated with O-(tetrahydro-2H-pyran-2-yl)hydroxylamine (0.9 g, 7.63 mmol), followed by N-methylmorpholine (1.7 mL, 15 mmol) three minutes later. The reaction was stirred at fifty degrees Celsius. After 64 hours, the reaction was treated again with 1-(3-dimethylamino-propyl)-3-ethylcarbodiimide hydrochloride (0.49 g, 2.6 mmol), N-hydroxybenzo-triazole hydrate (0.34 g, 2.6 mmol), O-(tetrahydro-2H-pyran-2-yl)hydroxylamine (0.30 g, 2.6 mmol), followed by N-methylmorpholine (0.28 mL, 2.6 mmol). After 98 hours, the reaction was concentrated in vacuo. The resulting residue was partitioned between ethyl acetate (100 mL) and water (40 mL). The organic layer was washed three times with saturated sodium bicarbonate aqueous solution (3x25 mL), twice with brine (2x25 mL), dried over $Na_2SO_4$, filtered, and concentrated in vacuo. The resulting oil was recrystallized in methanol (4 mL) to give the THP hydroxamate as a white solid (1.28 g, 48%). $^1$H NMR and mass spectrum were consistent with the desired compound.

Part 8: Preparation of

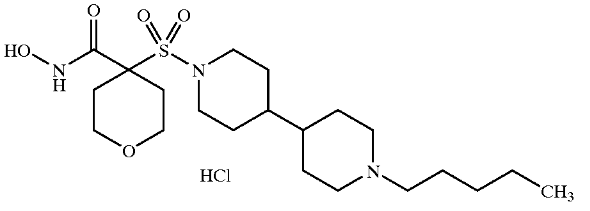

The THP hydroxamate from part 7 (1.1 g, 2.08 mmol) was suspended in methanol (0.5 mL) and the treated with 4 N HCl in 1,4-dioxane solution (5.2 mL, 21 mmol). After 2 hours at ambient temperature, the reaction was concentrated to half the reaction volume and then diluted with diethyl ether (200 mL). The white suspension was filtered under nitrogen and dried in vacuo to give the title compound as a white solid (0.94 g, 94%). MS(ES+) m/z calculated for $C_{21}H_{39}N_3O_5S$: 445, found (M+1) 446.

EXAMPLE 27

Preparation of N-Hydroxy-4[[1'-(4-methoxybenzoyl) [4,4'-bipiperidin]-1-yl]sulfonyl]-tetrahydro-2H-pyran-4-carboxamide

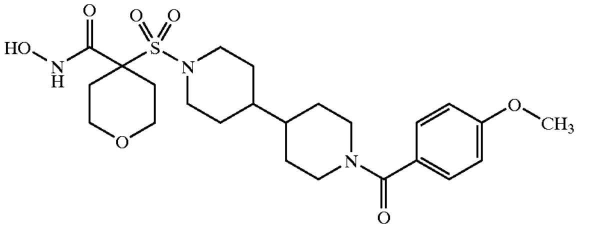

Part 9: Preparation of

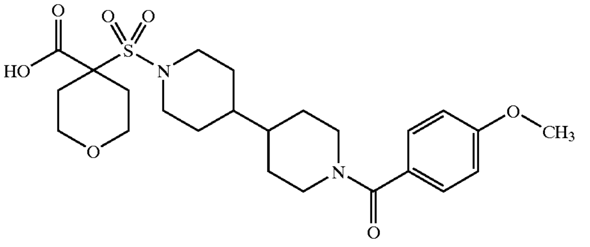

A suspension of the pyran sulfonamide hydrochloride salt from part 4 of Example 26 (3.0 g, 7.3 mmol), in dichloromethane (15 mL) and triethylamine (1.12 mL, 8.0 mmol) was cooled to zero degrees Celsius and treated with 4-(dimethylamino)pyridine (0.19) followed by p-anisoyl chloride (1.37 9 g, 8.0 mmol). The cooling bath was removed and the reaction was stirred at ambient temperature for 22 hours. The reaction was again treated with triethylamine (0.51 mL, 3.65 mmol) p-anisoyl chloride (0.62 g, 3.65 mmol). After stirring for 8 days, the reaction was diluted with dichloromethane (75 mL) and partitioned with water (50 mL). The aqueous layer was extracted twice with dichloromethane (2x25 mL). The combined organic layers were washed twice with 5% aqueous $KHSO_4$ (2x30 mL), water (20 mL), saturated sodium bicarbonate aqueous solution (25 mL), brine (10 mL), dried over $Na_2SO_4$, filtered, and concentrated in vacuo to give the amide methyl ester as a white solid. (3.7 g, crude).

The amide methyl ester was suspended in dry tetrahydrofuran (42 mL) and treated with potassium trimethylsilanolate (2.73 g, 21.0 mmol) and stirred at forty degrees Celsius. After 4.5 days, the reaction was diluted with water (50 mL) and treated with 2 N HCl until pH=1. The resulting white, yellow suspension was vacuum filtered, washed with water and dried in vacuo to give the carboxylic acid as a light yellow solid solid (2.55 g, 82% over 2 steps). $^1H$ NMR and mass spectrum were consistent with the desired compound.

Part 10: Preparation of

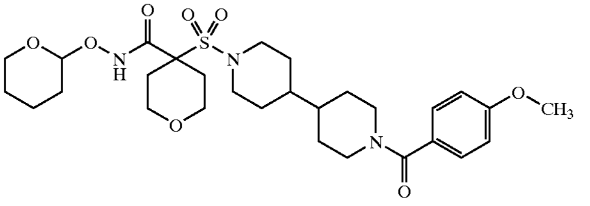

In dry equipment under nitrogen, the carboxylic acid from part 9 (2.2 g, 4.6 mmol) was dissolved in dry dimethylformamide (15 mL) and treated with 1-(3-dimethylaminopropyl)-3-ethylcarbodiimide hydrochloride (1.3 g, 6.7 mmol) and N-hydroxybenzo-triazole hydrate (0.9 g, 6.7 mmol). The resulting suspension became a clear amber solution after stirring at fifty degrees Celsius for 50 minutes. The reaction was then treated with O-(tetrahydro-2H-pyran-2-yl)hydroxylamine (0.8 g, 6.7 mmol), followed by N-methylmorpholine (1.47 mL, 13 mmol) three minutes later. The reaction was stirred at fifty degrees Celsius. After 25 hours, the reaction was concentrated in vacuo. The resulting residue was partitioned between ethyl acetate (100 mL) and water (50 mL). The aqueous layer was extracted with ethyl acetate (25 mL), and the combined organic layers were washed twice with saturated sodium bicarbonate aqueous solution (2x25 mL), brine (25 mL), dried over $Na_2SO_4$, filtered, and concentrated in vacuo. The resulting yellow oil was recrystallized in methanol (4 mL) to give the THP hydroxamate as a white solid (1.81 g, 69%). $^1H$ NMR and mass spectrum were consistent with the desired compound.

Part 11: Preparation of

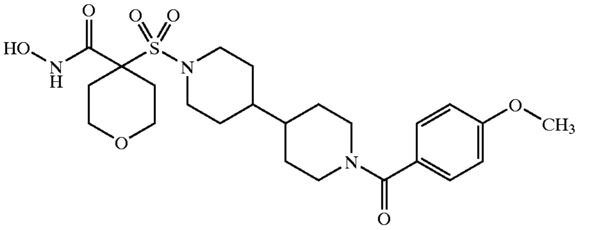

The THP hydroxamate from part 10 (1.44 g, 2.43 mmol) was dissolved in acetonitrile (25 mL), diluted with water (15 mL), and then treated with aqueous 2N HCl (2.5 mL, 4.85 mmol). After 2 hours at ambient temperature, the acetonitrile and excess hydrochloric acid were removed with a stream of nitrogen. The resulting white suspension was filtered under nitrogen, washed with water and dried in vacuo to give the title compound as a white solid (0.67 g, 56%). MS(ES+) m/z calculated for $C_{24}H_{35}N_3O_7S$: 509, found (M+1) 510.

EXAMPLE 28

Preparation of N-Hydroxy-4-[[4-[4-(trifluoromethyl) phenoxy]-1-piperidinyl)-sulfonyl]-4-piperidinecarboxamide, Monohydrochloride

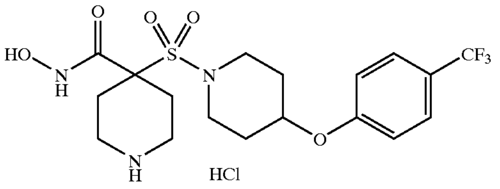

Part 12: Preparation of

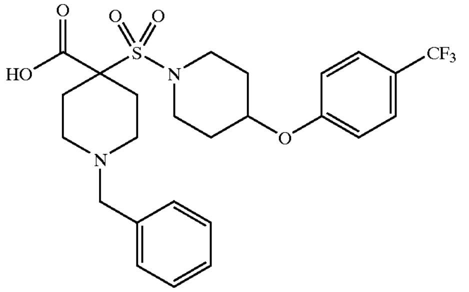

In dry equipment under nitrogen, the compound of Example 20, part F (16.51 g, 30.5 mmol) was dissolved in dry tetrahydrofuran (61 mL) and potassium trimethylsilanolate (11.8 g, 91.6 mmol) was added at ambient temperature. After 21 hours, the reaction was concentrated in vacuo, and the resulting residue was dissolved in water (100 mL) and treated with 2N HCl until pH=7. The white suspension was vacuum filtered, washed with water and dried in vacuo to give the carboxylic acid as a white solid (15.45 g, 96%). $^1$H NMR and mass spectrum were consistent with the desired compound.

Part 13: Preparation of

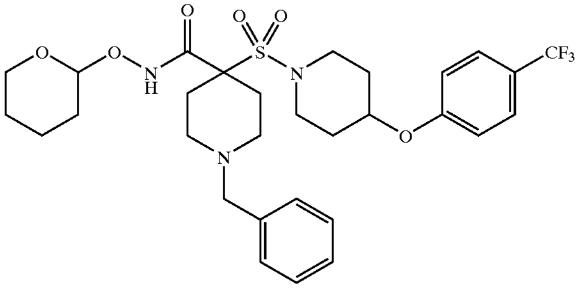

In dry equipment under nitrogen, the carboxylic acid from part 12 (15.45 g, 29.3 mmol) was dissolved in dry dimethylformamide (147 mL) and treated with 1-(3-dimethylamino-propyl)-3-ethylcarbodiimide hydrochloride (8.44 g, 44 mmol) and N-hydroxybenzo-triazole hydrate (5.95 g, 44 mmol). After 1 hour and 20 minutes at ambient temperature, the suspension was treated with O-(tetrahydro-2H-pyran-2-yl)hydroxylamine (5.15 g, 44 mmol), followed by N-methylmorpholine (9.7 mL, 88 mmol) three minutes later. After stirring for 16 hours at ambient temperature, the reaction was heated to fifty degrees Celsius for 3 hours, and then treated with 1-(3-dimethylamino-propyl)-3-ethylcarbodiimide hydrochloride (1.41 g, 7.4 mmol), N-hydroxybenzo-triazole hydrate (0.99 g, 7.3 mmol), O-(tetrahydro-2H-pyran-2-yl)hydroxylamine (0.86 g, 7.3 mmol), and N-methylmorpholine (1.61 mL, 14.6 mmol). After 20 hours, the reaction was concentrated in vacuo, and the resulting residue was partitioned between ethyl acetate (400 mL) and water (400 mL). The aqueous layer was extracted with ethyl acetate (200 mL), and the combined organic layers were washed with saturated sodium bicarbonate aqueous solution (100 mL), water (100 mL), brine (100 mL), dried over $Na_2SO_4$, filtered, and concentrated in vacuo to give the THP hydroxamate piperidine N-benzyl as a brown oil (18.4 g, 100%). $^1$H NMR and mass spectrum were consistent with the desired compound.

Part 14: Preparation of

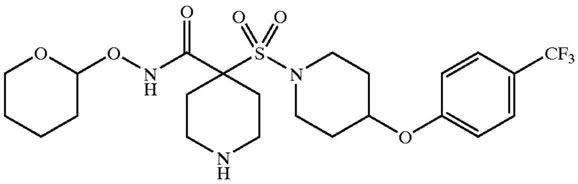

The THP hydroxymate piperidine N-benzyl from part 13 (1.0 g, 1.6 mmol) was dissolved in methanol (4.5 mL) and then treated with ammonium formate (302 mg, 4.8 mmol) followed by palladium on carbon (Degussa catalyst, 400 mg of 10 weight % on activated carbon, 50% water). The black heterogeneous mixture was stirred at ambient temperature for 30 minutes, diluted with methanol (4.5 mL), and then stirred for another 3 hours. The reaction was then filtered through a methanol washed pad of Celite under nitrogen, and the filtrate was concentrated in vacuo to give the THP hydroxamate piperidine as a white glassy foam (0.73 g, 85%). $^1$H NMR and mass spectrum were consistent with the desired compound.

Part 15: Preparation of

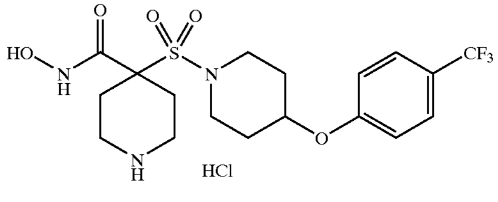

The THP hydroxamate piperidine from part 14 (0.34 g, 0.64 mmol) was treated with methanol (0.2 mL) followed by 4 N HCl in 1,4-dioxane solution (2 mL, 8 mmol), which formed a white precipitate. After 1 hour at ambient temperature, the reaction diluted with diethyl ether (5 mL), and the white suspension was filtered under nitrogen, washed with diethyl ether and dried in vacuo to give the title compound as a white solid (0.18 g, 58%). MS(FABMS) m/z calculated for $C_{18}H_{24}N_3O_5SF_3$: 451, found (M+1) 452.

EXAMPLE 29

Preparation of bis(2-Chloroethyl)-benzylamine (Part 16)

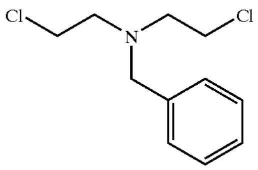

A suspension of bis(2-chloroethyl)amine hydrochloride (Aldrich, 500 g, 2.8 mol), sodium acetate (229.8 g, 2.8 mol), and benzaldehyde (270.5 mL, 2.66 mol), in tetrahydrofuran (2.5 L), was cooled to ten degrees Celsius, and treated with sodium triacetoxyborohydride (712.4 g, 3.36 mol) at a rate such that the temperature did not exceed eighteen degrees Celsius. After stirring the white suspension at ambient temperature for 25 hours, the reaction was quenched with the addition of ethyl acetate (4 L) followed by 2.5 M sodium hydroxide (3.5 L), which made the mixture pH=9. The mixture was partitioned with the addition of water (3 L). The aqueous layer was extracted with ethyl acetate (1.5 L). The combined organic layers were washed twice with brine (2×1 L), dried over $MgSO_4$, filtered, and concentrated in vacuo. The crude yellow oil was purified on silica gel (hexanes) to give a clear, colorless oil (482.6 g, 78%). $^1H$ NMR and mass spectrum were consistent with the desired compound.

EXAMPLE 30

Preparation of 1-(2-Furanylmethyl)-N-hydroxy-4-[[4-[4-(trifluoromethyl)-phenoxy]-1-piperidinyl]sulfonyl]-4-piperidinecarboxamide

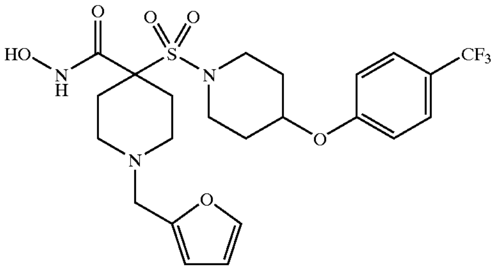

Part 17: Preparation of

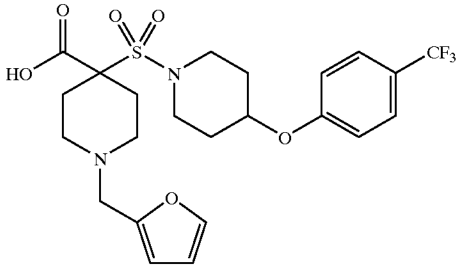

To a solution of the piperidine methyl ester from Part 1 of Example 42 (3.91 g, 8.7 mmol) and 2-furaldehyde (0.79 mL, 9.6 mmol) in dichloroethane (58 mL) was added glacial acetic acid (0.5 mL, 8.7 mmol) followed by sodium triacetoxyborohydride (2.4 g, 11.3 mmol). After 64 hours, the reaction was concentrated in vacuo and partitioned between ethyl acetate (75 mL) and water (75 mL). The aqueous layer was made basic (pH=8) with saturated sodium bicarbonate aqueous solution, then extracted three times with ethyl acetate (3×50 mL). The combined organic layers were washed with water (25 mL), twice with brine (2×25 mL), dried with $MgSO_4$, filtered, and concentrated in vacuo. Recrystallization of the crude oil in methanol yielded a brown, tan solid, which was suspended in tetrahydrofuran (17.4 mL) and treated with potassium trimethylsilanolate (3.34 g, 26.0 mmol). After 20 hours at ambient temperature, the reaction was diluted with tetrahydrofuran (10 mL) and charged again with potassium trimethylsilanolate (2.22 g, 17.3 mmol). After 7 hours, the reaction was concentrated in vacuo, and the resulting residue was dissolved in water (100 mL) and treated with 2 N HCl until pH=7. The white suspension was vacuum filtered, washed with water and dried in vacuo to give the carboxylic acid as a white solid (4.4 g, 97%). $^1H$ NMR and mass spectrum were consistent with the desired compound.

Part 18: Preparation of

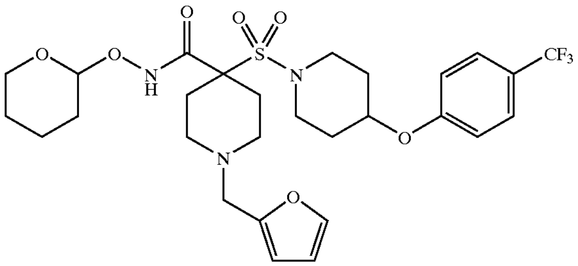

In dry equipment under nitrogen, the carboxylic acid from part 17 (3.93 g, 7.61 mmol) was dissolved in dry dimethylformamide (38 mL) and treated with 1-(3-dimethylaminopropyl)-3-ethylcarbodiimide hydrochloride (2.2 g, 11.4 mmol), N-hydroxybenzo-triazole hydrate (1.54 g, 11.4 mmol), O-(tetrahydro-2H-pyran-2-yl)hydroxylamine (1.34 g, 11.4 mmol), followed by N-methylmorpholine (2.51 mL, 22.8 mmol). After 17 hours at ambient temperature, the reaction was concentrated in vacuo, and the resulting residue was partitioned between ethyl acetate (175 mL) and water (175 mL). The aqueous layer was extracted with ethyl acetate (100 mL), and the combined organic layers were washed with saturated sodium bicarbonate aqueous solution (100 mL), water (100 mL), brine (100 mL), dried over $Na_2SO_4$, filtered, and concentrated in vacuo. The resulting yellow oil was recrystallized in methanol (6 mL) to give the THP-hydroxamate as a white solid (2.48 g, 53%). $^1H$ NMR and mass spectrum were consistent with the desired compound.

Part 19: Preparation of

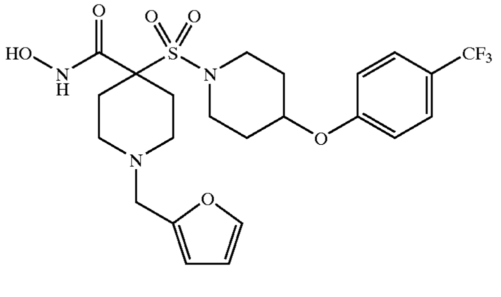

The THP-hydroxamate from part 18 (2.41 g, 3.91 mmol) was dissolved in methanol (1.0 mL) and 1,4-dioxane (15 mL), then treated with 4 N HCl in 1,4-dioxane solution (10 mL, 39 mmol), which formed a tan precipitate. After 1 hour at ambient temperature, the reaction was diluted with acetonitrile (3 mL), and the suspension was filtered under nitrogen, washed with acetonitrile and dried in vacuo to give the title compound as a white solid (1.68 g, 81%). MS(EI) m/z calculated for $C_{23}H_{28}N_3O_6SF_3$: 531, found (M+1) 532.

EXAMPLE 31

Preparation of 4-[[4-[4-[4-(trifluoromethyl)phenoxy]phenoxy]-1-piperidinyl]sulfonyl]tetrahydro-N-hydroxy-2H-pyran-4-carboxamide

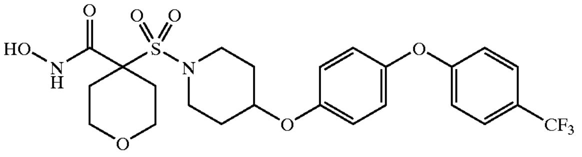

Part 20: Preparation of

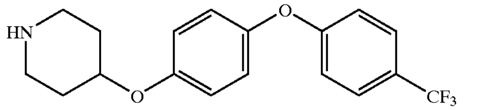

In dry equipment under nitrogen, 4-[4-(trifluoromethyl)phenoxy]phenol (Aldrich, 6.0 g, 23.6 mmol) was added to a dimethylformamide (53 mL) suspension of sodium hydride (60% dispersion in mineral oil, 0.95 g, 23.6 mmol), which was pre-washed in hexanes, while at zero degrees Celsius. After addition, the cold bath was removed and the reaction was warmed to ambient temperature. After 30 minutes, the reaction was cooled to zero degrees Celsius, charged with 4-(methylsulfonyl)hydroxy-1-piperidinecarboxylic acid, 1,1-dimethylethyl ester (Example 23, part B) (5.5 g, 19.7 mmol), then heated to eighty degrees Celsius. After 17 hours, the reaction was again treated with sodium hydride (60% dispersion in mineral oil, 0.95 g, 23.6 mmol), and then 10 minutes later with 4-(methylsulfonyl)hydroxy-1-piperidinecarboxylic acid, 1,1-dimethylethyl ester (5.5 g, 19.7 mmol). After 47 hours, the reaction was cooled to ambient temperature, quenched with water (10 mL), concentrated in vacuo, and partitioned between diethyl ether (100 L) and water (100 mL). The aqueous layer was extracted twice with diethyl ether (2×25 mL) and then with ethyl acetate (50 mL). The combined organic layers were washed with water (25 mL), twice with brine (2×25 mL), dried over $Na_2SO_4$, filtered, concentrated and dried in vacuo to give a brown oil.

The crude oil was treated with 4N HCl in 1,4-dioxane solution (47 mL, 188 mmol) at ambient temperature. After 2 hours, the reaction was concentrated in vacuo, and partitioned between ethyl acetate (100 mL) and water (50 mL). The aqueous layer was made pH=8 with the addition of saturated sodium bicarbonate aqueous solution, then extracted twice with ethyl acetate (2×25 mL). The combined organic layers were washed with saturated sodium bicarbonate aqueous solution (50 mL), water (50 mL) brine (25 mL), dried over $Na_2SO_4$, filtered, concentrated and dried in vacuo to give a brown oil. The crude product was purified on silica gel (hexanes/ethyl acetate) to give the amine as a yellow, orange solid (5.5 g, 69% over 2 steps). $^1H$ NMR and mass spectrum were consistent with the desired compound.

Part 21: Preparation of

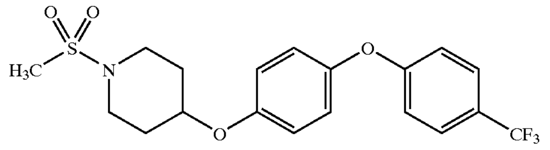

To a solution of the amine from part 20 (4.5 g, 13.3 mmol) and triethylamine (3.72 mL, 26.7 mmol) in dichloromethane (12 mL) at zero degrees Celsius was added a solution of methane sulfonyl chloride (1.55 mL, 20.0 mmol) in dichloromethane (15 mL). After 2.5 hours at ambient temperature, the solvent was removed in vacuo. The residue was partitioned between ethyl acetate (100 mL), water (100 mL), and 10% aqueous hydrochloric acid until pH=4. The organic layer was washed with saturated sodium bicarbonate aqueous solution (50 mL), brine (25 mL), dried over $Na_2SO_4$, filtered, and concentrated in vacuo to give the methyl sulfonamide as a white, yellow solid (5.6 g, 100%). $^1H$ NMR and mass spectrum were consistent with the desired compound.

Part 22: Preparation of

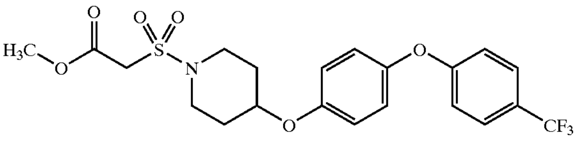

In dry equipment under nitrogen, the methyl sulfonamide from part 21 (5.62 g, 13.5 mmol) was dissolved in dry tetrahydrofuran (27 mL) and cooled to minus seventy-five degrees Celsius. The resulting solution was then treated with a 1M solution of lithium bis(trimethylsilyl)amide (40.6 mL, 41.0 mmol) at a rate such that the temperature remained below minus sixty five degrees. After 30 minutes, the reaction was treated with a solution of methyl chloroformate (1.05 mL, 13.5 mmol) in dry tetrahydrofuran (13 mL), while maintaining the temperature below minus seventy degrees. After 3 hours at minus sixty degrees Celsius, the reaction was quenched with saturated ammonium chloride aqueous solution (100 mL), warmed to ambient temperature and concentrated in vacuo. The resulting residue was partitioned between ethyl acetate (150 mL) and water (100 mL)

The organic layer was washed with water (50 mL), brine (50 mL), dried over $Na_2SO_4$, filtered, and concentrated in vacuo to give the methylene sulfonamide as a yellow oil (6.32 g, 98.6%). $^1H$ NMR and mass spectrum were consistent with the desired compound.

Part 23: Preparation of

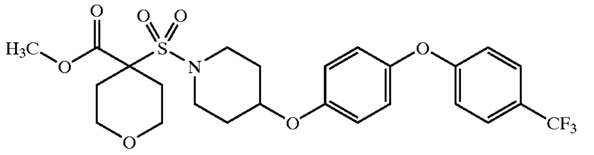

To a solution of the methylene sulfonamide from part 22 (2.56 g, 5.41 mmol) in dimethylformamide (14 mL) was added bis-(2-bromoethyl)ether (1.38 g, 5.95 mmol), 18-Crown-6 (250 mg), followed by potassium carbonate (2.24, 16.2 mmol). After the heterogeneous mixture was stirred at sixty degrees Celsius for 22 hours, more potassium carbonate (0.75 g, 5.4 mmol) was added to the reaction. After another 17 hours, the reaction was charged with more potassium carbonate (0.75 g, 5.4 mmol). The reaction was concentrated in vacuo after 30 hours, and the resulting oil was partitioned between ethyl acetate (150 mL) and water (150 mL). The aqueous layer was extracted twice with ethyl acetate (2×50 mL), then the combined organic layers were washed with water (50 mL), brine (25 mL), dried over $Na_2SO_4$, filtered, and concentrated in vacuo to give the pyran methyl ester as a white solid. (2.84 g, 97%). $^1$H NMR and mass spectrum were consistent with the desired compound.

Part: 24: Preparation of

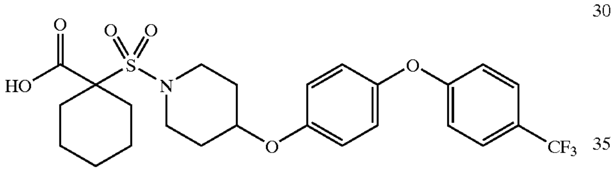

In dry equipment under nitrogen, the pyran methyl ester from part 23 (2.55 g, 4.69 mmol) was suspended in dry tetrahydrofuran (10 mL) and potassium trimethylsilanolate (1.81 g, 14.1 mmol) was added at ambient temperature. After 28 hours, the reaction was charged with more potassium trimethylsilanolate (0.3 g, 2.3 mmol). After 21 hours, the reaction was again charged with more potassium trimethylsilanolate (0.3 g, 2.3 mmol). After 3 hours, the reaction was concentrated in vacuo, and the resulting residue was partitioned between ethyl acetate (50 mL) and water (50 mL) The aqueous layer was extracted twice with ethyl acetate (2×25 mL), then the combined organic layers were washed with brine (30 mL), dried over $Na_2SO_4$, filtered, concentrated and dried in vacuo to give the carboxylic acid as a tan solid (1.71 g, 69%). $^1$H NMR and mass spectrum were consistent with the desired compound.

Part 25: Preparation of

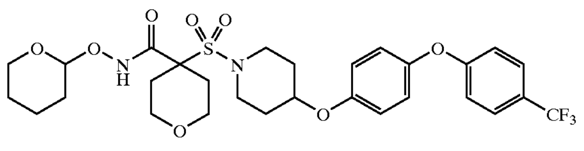

In dry equipment under nitrogen, the carboxylic acid from part 24 (1.44 g, 2.72 mmol) was dissolved in dry dimethylformamide (14 mL) and treated with 1-(3-dimethylamino-propyl)-3-ethylcarbodiimide hydrochloride (0.78 g, 4.1 mmol), N-hydroxybenzo-triazole hydrate (0.55 g, 4.1 mmol), O-(tetrahydro-2H-pyran-2-yl)hydroxylamine (0.48 g, 4.1 mmol), followed by N-methylmorpholine (0.90 mL, 8.16 mmol). After 26 hours at ambient temperature, the reaction was concentrated in vacuo, and the resulting residue was partitioned between ethyl acetate (50 mL) and water (50 mL). The aqueous layer was extracted with ethyl acetate (20 mL), and the combined organic layers were washed with 5% $KHSO_4$ aqueous solution (30 mL), brine (30 mL), dried over $Na_2SO_4$, filtered, and concentrated in vacuo. The resulting yellow oil was purified on silica gel (1:1, hexanes:ethyl acetate) to give the THP hydroxamate as a yellow oil (0.96 g, 56%). $^1$H NMR and mass spectrum were consistent with the desired compound.

Part 26: Preparation of

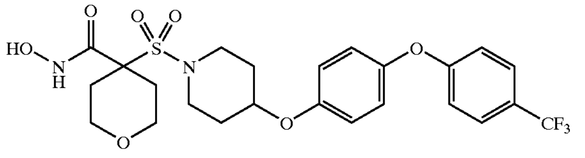

The THP hydroxamate from part 25 (0.82 g, 1.3 mmol) was dissolved in acetonitrile (10 mL) and then treated with aqueous 10% aqueous hydrochloric acid solution (10 mL, 12 mmol). After 25 hours at ambient temperature, the acetonitrile and excess hydrochloric acid were removed with a stream of nitrogen. The resulting white suspension was filtered under nitrogen, washed with water and dried in vacuo to give the title compound as a white solid (0.39 g, 55%). HRMS m/z calculated for $C_{24}H_{35}N_3O_7S$: 545.1569, observed 545.1586.

EXAMPLE 32

Preparation of Tetrahydro-N-hydroxy-4-[[4-(4-pentylphenyl)-1-piperazinyl]-sulfonyl]-2H-pyran-4-carboxamide, Monohydrochloride

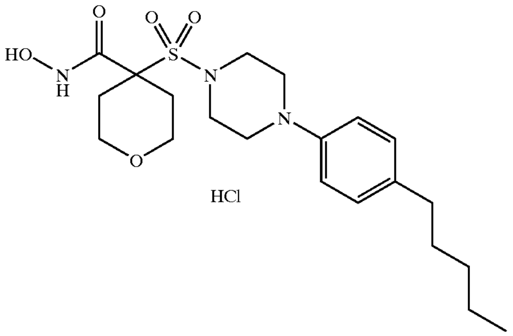

Part A: To a solution of tert-butyl-piperazine (5.00 g, 26.84 mmol) in toluene (50 mL) was added sodium tert-butoxide (3.01 g, 31.32 mmol). After stirring at ambient temperature for 5 minutes, 1-bromo-4-n-pentylbenzene (5.08 g, 22.37 mmol), 2,2'-bis(diphenylphosphino)-1,1'-binaphthyl (BINAP) (0.418 g, 0.671 mmol) and tris (dibenzyldeneacetone)-dipallidium (0) (0.205 g, 0.224 mmol) were added to the reaction mixture. The resulting mixture was heated to eighty degrees Celsius for 22 hours. After cooling to ambient temperature the reaction mixture was filtered through a pad of Celite®, washing with tetrahydrofuran and methanol. The filtrate was concentrated in vacuo to give the aryl Boc-piperazine as an orange oily solid (9.60 g, >100%).

Part B: The aryl Boc-piperazine of part A (9.60 g, ~22.37 mmol) was treated with a solution of 4N HCl in dioxane (56 mL). The resulting mixture was stirred at ambient temperature for 2 hours then the reaction was concentrated in vacuo. Diethyl ether (50 mL) was added and the precipitate was collected by filtration to give the aryl piperazine as a tan solid (8.49 g, 100%').

Part C: To a solution of the aryl piperazine of part B (4.00 g, 13.10 mmol) in dichloromethane (50 mL), cooled to zero degrees Celsius, was added triethylamine (5.48 mL, 39.30 mmol) followed by methanesulfonyl chloride (1.22 mL, 15.72 mmol). Once the addition was complete the cooling bath was removed and the resulting mixture was stirred for 2 hours. The reaction mixture was then concentrated in vacuo and the residue was partitioned between $H_2O$ and ethyl acetate. An emulsion formed and the solids were collected by filtration. The solids were triturated with ethyl acetate to give the methyl sulfonamide as a tan solid (3.99 g, 98%).

Part D: To a suspension of the methyl sulfonamide of part C (3.35 g, 10.79 mmol) in tetrahydrofuran (50 mL), cooled to minus seventy-eight degrees Celsius, was added lithium bis(trimethylsilyl)amide (24.00 mL, 1.0 M in tetrahydrofuran, 24.00 mmol) at such a rate that the temperature of the reaction mixture never exceeded minus seventy degrees Celsius. Once the addition was complete, the cooling bath was removed. After 30 minutes, the cooling bath was replaced and a solution of dimethyl carbonate (1.09 mL, 12.95 mmol) in tetrahydrofuran (5.0 mL) was added. After 30 minutes additional lithium bis(trimethylsilyl)amide (5.40 mL, 1.0 M in tetrahydrofuran, 5.40 mmol) was added followed by additional dimethyl carbonate (0.273 mL, 3.24 mmol). After stirring at minus seventy-eight degrees Celsius for 1 hour the reaction was quenched by the addition saturated $NH_4Cl$ and concentrated in vacuo. The residue was diluted with $H_2O$ and extracted with ethyl acetate. The combined organic layers were washed with 5% $KHSO_4$, saturated NaCl and dried over $Na_2SO_4$. Chromatography (on silica, ethyl acetate/hexanes) provided the sulfonamide ester as a tan solid (1.20 g, 30%).

Part E: To a solution of the sulfonamide ester of part D (1.20 g, 3.26 mmol) in N,N-dimethylformamide (10 mL) was added $K_2CO_3$ (1.35 g, 9.78 mmol) and dibromoethyl ether (0.430 mL, 3.42 mmol) and the resulting mixture was heated to forty degrees Celsius. After 21 hours additional $K_2CO_3$ (0.450 g, 3.26 mmol) and dibromoethyl ether (0.102 mL, 0.815 mmol) were added and the resulting mixture was heated to forty degrees Celsius for 4 hours. After cooling to ambient temperature the reaction was diluted with $H_2O$ and extracted with ethyl acetate. The combined organic layers were washed with saturated NaCl and dried over $Na_2SO_4$. Chromatography (on silica, ethyl acetae/hexanes) provided the ester as a pale yellow solid (1.23 g, 86%).

Part F: To a solution of the ester of part E (1.23 g, 2.80 mmol) in tetrahydrofuran (10 mL) was added potassium trimethylsilanolate (0.718 g, 5.60 mmol). The resulting mixture was stirred at ambient temperature overnight (about 18 hours) and then diluted with $H_2O$ and acidified (pH-7.0) with 1 N HCl. The precipitate was collected by filtration. The solids were suspended in acetonitrile and then concentrated in vacuo to give the acid as an off-white solid (0.910 g, 76%).

Part G: To a suspension of the acid of part F (0.910 g, 2.14 mmol) in N,N-dimethylformamide (10 mL) was added 1-hydroxybenzotriazole (0.347 g, 2.57 mmol), N-methylmorpholine (0.701 mL, 6.42 mmol), O-(tetrahydropuranyl) hydroxylamine (0.752 g, 6.42 mmol) and 1-3-[(dimethylamino)propyl]-3-ethylcarbodiimide hydrochloride (0.574 g, 3.00 mmol). The resulting mixture was stirred at ambient temperature for 22 hours. Then the reaction mixture was diluted with $H_2O$ and extracted with ethyl acetate. The combined organic layers were washed with $H_2O$, saturated $NaHCO_3$, saturated NaCl and dried over $Na_2SO_4$. Chromatography (on silica, ethyl acetate/hexanes) provided the protected hydroxamate as a clear oil (1.11 g, 99%).

Part H: The protected hydroxamate of part G (1.10 g, 2.10 mmol) was treated with a solution of 4N HCl in dixoane (5.25 mL) and methanol (0.851 mL, 21.00 mmol) and the resulting mixture was stirred at ambient temperature for 2 hours. Diethyl ether (20 mL) was added and the precipitate was collected by filtration to provide the title compound as an off-white solid (0.972 g, 97%). MS $MH^+$ calculated for $C_{21}H_{34}O_5N_3S$: 440, found 440.

EXAMPLE 33

Preparation of Tetrahydro-N-hydroxy-4-[(4-phenyl-1-piperazinyl)sulfonyl]-2H-pyran-4-carboxamide

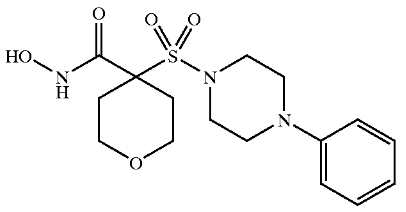

Part A: To a solution of bis(2-bromoethyl)ether (1.55 g, 6.70 mmol) in acetone (30 mL) was added $K_2CO_3$ (9.26 g, 67.00 mmol), 18-crown-6 (500 mg) and the sulfonamide ester of part B for SC-81434A (2.00 g, 6.70 mmol). The reaction mixture was heated at reflux for 15 hours then filtered through a pad of Celite® and the filtrate was concentrated in vacuo. The residue was dissolved in N,N-dimethylformamide (30 mL) and treated with $K_2CO_3$ (9.26 g, 67.00 mmol), 18-crown-6 (500 mg) and bis(2-bromoethyl)ether (1.55 g, 6.70 mmol) and the resulting mixture was heated at sixty degrees Celsius for 6 hours. The reaction mixture was concentrated in vacuo and the residue was partitioned between $H_2O$ and chloroform. The aqueous layer was further extracted with chloroform. The combined organic layers were washed with $H_2O$ and dried over $Na_2SO_4$. Chromatography (on silica, ethyl acetate with 5% acetonitrile/hexanes) provided the cyclized ester as a pale yellow oil (1.34 g, 54%).

Part B: To a solution of the cyclized ester of part A (1.34 g, 3.64 mmol) in tetrahydrofuran (15 mL) was added potassium trimethylsilanolate (1.40 g, 10.92 mmol). The resulting mixture was stirred at ambient temperature for 24 hours and then the tetrahydrofuran was removed by blowing $N_2$ over the reaction mixture. The residue was dissolved in $H_2O$, washed with diethyl ether, then acidified (pH-3.0) with 1N HCl and extracted with ethyl acetate. The combined organic layers were washed with saturated NaCl and dried over $Na_2SO_4$. Concentration in vacuo provided the acid as an off-white solid (1.20 g, 79%).

Part C: To a solution of the acid of part B (1.00 g, 2.82 mmol) in N,N-dimethylformamide (6.0 mL) was added 1-hydroxybenzotriazole (0.457 g, 3.38 mmol), N-methylmorpholine (0.924 mL, 8.46 mmol), O-(tetrahydropuranyl) hydroxylamine (0.469 g, 4.23 mmol) and 1-3-[(dimethylamino)propyl]-3-ethylcarbodiimide hydrochloride (0.757 g, 3.95 mmol).

The resulting mixture was stirred at ambient temperature for 23 hours and then concentrated in vacuo. The residue was partitioned between ethyl acetate and $H_2O$. The aqueous layer was further extracted with ethyl acetate. The organic layers were washed with saturated $NaHCO_3$, saturated NaCl and dried over $Na_2SO_4$. The resulting solids were washed with diethyl ether to provide the protected hydroxamate as an off-white solid. (1.08 g, 84%).

Part D: To a solution of the protected hydroxamate of part C (1.08 g, 2.38 mmol) in acetonitrile (8.0 ML) and $H_2O$ (4.0 mL) was added 10% HCl (2.0 mL). After stirring at ambient temperature for 20 hours the acetonitrile was removed by blowing $N_2$ over the reaction mixture. The aqueous reaction mixture was diluted with $H_2O$ and extracted with ethyl acetate. The combined organic layers were washed with saturated NaCl and dried over $Na_2SO_4$. After concentration in vacuo, the solids were washed with diethyl ether to give the title compound as a pale pink solid (0.503 g, 57%). MS $MH^+$ calculated for $C_{16}H_{24}O_5N_3S_1$: 370, found 370.

EXAMPLE 34

Preparation of N-Hydroxy-1-(2-methoxyethyl)-4-[[4-[[4-(trifluoromethyl)benzoyl]amino]-1-piperidinyl]sulfonyl]-4-piperidinecarboxamide, Monohydrochloride

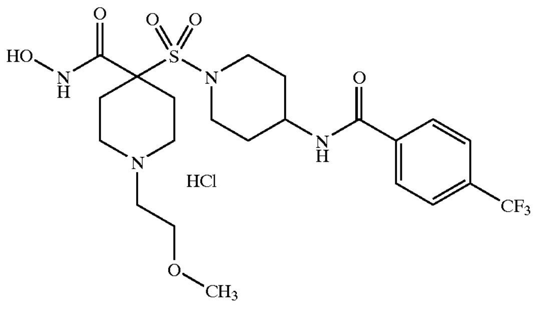

Part A: To a solution of 4-amino-1-benzylpiperidine (10.0 g, 45.82 mmol) in tetrahydrofuran (100 mL) was added di-tert-butyl dicarbonate (30.0 g, 137.46 mmol) and a catalytic amount of N,N-dimethylaminopyridine. The resulting mixture was heated at reflux for 5 hours. After cooling to ambient temperature the reaction mixture was concentrated in vacuo. The solids were washed with hexanes to provide the carbamate as a white crystalline solid (13.7 g, >100%).

Part B: To a solution of the carbamate of part A (10.0 g, 34.43 mmol) in methanol (200 mL) was added ammonium formate (6.51 g, 103.29 mmol) and 4% Pd/C. The resulting mixture was heated at reflux for 1.5 hours. After cooling to ambient temperature the reaction mixture was filtered through a pad of Celite®, washing with methanol. The filtrate was concentrated in vacuo to provide the piperidine as an off-white solid (6.90 g, 100%).

Part C: To a solution of the piperidine of part B (6.90 g, 34.43 mmol) in dichloromethane (100 mL), cooled to zero degrees Celsius, was added triethylamine (5.28 mL, 37.87 mmol) followed by methanesulfonyl chloride (2.79 mL, 36.12 mmol). Once the addition was complete the cooling bath was removed and the resulting mixture was stirred for 15 hours. After concentration in vacuo the residue was partitioned between $H_2O$ and ethyl acetate. The combined organic layers were washed with saturated NaCl and dried over $Na_2SO_4$. The resulting solids were washed with hexanes to give the sulfonamide as an off-white solid (9.12 g, 95%).

Part D: To a solution of lithium bis(trimethylsilyl)amide (50.0 mL, 1.0M in tetrahydrofuran, 50.00 mmol), cooled to minus seventy-eight degrees Celsius, was added a suspension of the sulfonamide of part C (4.49 g, 16.13 mmol) in tetrahydrofuran (40 mL). Once the addition was complete, the cooling bath was removed and replaced after 0.5 hours. To the resulting mixture was quickly added methyl chloroformate (1.37 mL, 17.74 mmol). After 0.5 hours, the reaction mixture was quenched by the addition of saturated $NH_4C_1$ and then the tetrahydrofuran was concentrated in vacuo. The reaction mixture was diluted with $H_2O$ and extracted with ethyl acetate. The combined organic layers were washed with saturated NaCl and dried over $Na_2SO_4$. Concentration in vacuo provided the sulfonamide ester as an off-white solid (5.29 g, 97%).

Part E: The sulfonamide ester of part D (5.27 g, 5.67 mmol) was treated with a solution of 4 N HCl in dioxane (40 mL). After stirring at ambient temperature for 1 hour the reaction mixture was concentrated in vacuo. The resulting solids were washed with hexanes to provided the amine as a tan solid (4.19 g, 98%).

Part F: To a solution of the amine of part E (1.50 g, 5.50 mmol) in dichloromethane (10 mL), cooled to zero degrees Celsius, was added triethylamine (1.61 mL, 11.55 mmol) followed by 4-(trifluoromethyl)benzoyl chloride (0.858 mL, 5.78 mmol). Once the addition was complete the cooling bath was removed and after stirring at ambient temperature for 3.5 hours the reaction mixture was concentrated in vacuo. The solids were washed with $H_2O$ and diethyl ether to provide the amide as a tan solid (1.79 g, 80%).

Part G: To a solution of the amide of part F (1.52 g, 3.72 mmol) in N,N-dimethylformamide (10.0 mL) was added $K_2CO_3$ (1.54 g, 11.16 mmol), 18-crown-6 (0.50 g) and bis(2-chloroethyl)benzyl amine (0.864 g, 3.72 mmol). The resulting mixture was heated to sixty degrees Celsius of 22 hours, at which time additional $K_2CO_3$ (0.514 g, 3.72 mmol) and bis(2-chloroethyl)benzyl amine (0.216 g, 0.93 mmol) were added. The resulting mixture was heated to sixty degrees Celsius for 14.5 hours at which time additional $K_2CO_3$ (0.514 g, 3.72 mmol) was added. The resulting mixture was heated to sixty degrees Celsius of 14 hours, at which time additional $K_2CO_3$ (0.514 g, 3.72 mmol) and bis(2-chloroethyl)benzyl amine (0.216 g, 0.93 mmol Prepared by Darren Kassib) were added. The resulting mixture was heated to sixty degrees Celsius for 24 hours. After cooling to ambient temperature the reaction mixture was diluted with $H_2O$ and extracted with chloroform. The combined organic layers were washed with saturated NaCl and dried over $Na_2SO_4$. Chromatography (on silica, ethyl acetate with 5% methanol/hexanes) followed by trituration with diethyl ether provided the cyclized ester as an off-white solid (0.950 g, 45%).

Part H: To a solution of the cyclized ester of part G (0.950 g, 1.67 mmol) in methanol (10 mL) was added ammonium formate (0.317 g, 5.02 mmol) and 10% Pd/C (0.320 g). The resulting mixture was heated at reflux for 1.5 hours. After cooling to ambient temperature, the reaction mixture was filtered through a pad of Celite 0, washing with methanol. The filtrate was concentrated in vacuo to provide the amine as a gray solid (0.760 g, 95%).

Part I: To a solution of the amine of part H (0.760 g, 1.59 mmol) in N,N-dimethylformamide (5.0 mL) was added $K_2CO_3$ (0.330 g, 2.39 mmol) and 2-bromoethyl methyl ether (0.225 mL, 2.39 mmol). The resulting mixture was stirred at ambient temperature over the weekend then additional $K_2CO_3$ (0.055 g, 0.398 mmol) and 2-bromoethyl methyl ether (0.037 mL, 0.398 mmol) was added. After stirring at ambient temperature for 24 hours the reaction mixture was diluted with $H_2O$ and extracted with ethyl acetate. The combined organic layers were washed with saturated NaCl and dried over $Na_2SO_4$. Chromatography (on silica, ethyl acetate with 5% methanol/hexanes) provided the alkylated amine as a white solid (0.550 g, 65%).

Part J: To a solution of the alkylated amine of part I (0.540 g, 1.01 mmol) in tetrahydrofuran (5.0 mL) was added potassium trimethylsilanolate (0.388 g, 3.02 mmol). The resulting mixture was stirred at ambient temperature for 18 hours then the tetrahydrofuran was removed by blowing $N_2$ over the reaction mixture. The reaction mixture was diluted with $H_2O$ and neutralized (pH=7) with 1N HCl. The resulting aqueous reaction mixture was concentrated in vacuo to provide the crude acid as a pink solid (0.610 g, >100%).

Part K: To a solution of the crude acid of part J (0.610 g, ~1.01 mmol) in N,N-dimethylformamide (5.0 mL) was added 1-hydroxybenzotriazole (0.164 g, 1.21 mmol), N-methylmorpholine (0.331 mL, 3.03 mmol), O-(tetrahydropuranyl) hydroxylamine (0.177 g, 1.52 mmol) and 1-3-[(dimethylamino)propyl]-3-ethylcarbodiimide hydrochloride (0.271 g, 1.41mmol). After stirring at ambient temperature for 0.5 hours, additional N,N-dimethylformamide (5.0 mL) was added. After stirring at ambient temperature overnight (about 18 hours) the reaction mixture was heated to forty-five degrees Celsius for 24 hours. The reaction mixture was then diluted with $H_2O$ and extracted with ethyl acetate. The combined organic layers were washed with saturated $NaHCO_3$, saturated NaCl and dried over $Na_2SO_4$. The resulting solids were washed with diethyl ether to give the protected hydroxamate as an off-white solid (0.300 g, 49%).

Part L: To a solution of the protected hydroxamate of part K (0.300 g, 0.483 mmol) in dioxane (3.0 mL) and methanol (1.0 mL) was added a solution of 4N HCl in dioxane (1.2 mL). After stirring at ambient temperature for 1.5 hours the solvent was removed by blowing $N_2$ over the reaction mixture. The resulting solids were washed with diethyl ether to give the title compound as a pink solid (0.193 g, 70%). MS $MH^+$ calculated for $C_{22}H_{32}O_6N_4S_1F_3$: 537, found 537.

EXAMPLE 35

Preparation of N-Hydroxy-1-phenyl-4-[[4-[4-(trifluoromethoxy)phenoxy]1-piperidinyl]sulfonyl]-4-piperidinecarboxamide, Monohydrochloride

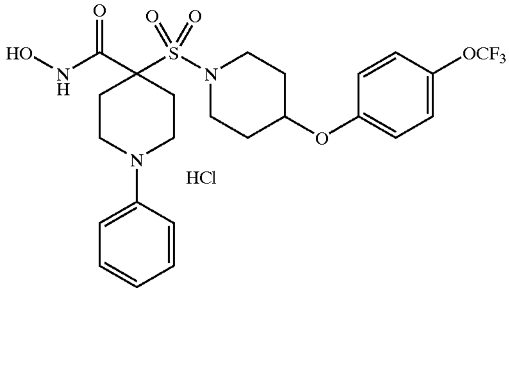

Part A: To a solution of commercially available 4-hydroxypiperidine (46.3 g, 458 mmol) in tetrahydrofuran (300 mL) was slowly added triethylamine (67.0 mL, 481 mmol) followed by a solution of di-tert-butyl dicarbonate (100 g, 458 mmol) in tetrahydrofuran (200 mL). After stirring at ambient temperature for 17 hours the reaction mixture was concentrated in vacuo. The residue was dissolved in ethyl acetate (500 mL) and washed with 5% $KHSO_4$, saturated $NaHCO_3$, saturated NaCl and dried over $Na_2SO_4$. Crystallization with hexanes provided the carbamate as an off-white solid (87.8 g, 95%).

Part B: To a solution of the carbamate of part A (5.00 g, 24.84 mmol) in dichloromethane (50 mL), precooled in an ice-bath, was added triethylamine (3.81 mL, 27.32 mmol) followed by methanesulfonyl chloride (2.02 mL, 26.08 mmol). Once the addition was complete, the cooling bath was removed. After stirring for 2 hours, the reaction mixture was concentrated in vacuo. The residue was partitioned between ethyl acetate and $H_2O$. The aqueous layer was further extracted with ethyl acetate. The combined organic layers were washed with saturated NaCl and dried over $Na_2SO_4$. Concentration in vacuo provided the mesylate as an off-white solid (7.34 g, >100%).

Part C: To a solution of 4-(trifluoromethoxy)-phenol (2.00 g, 11.23 mmol) in N,N-dimethylformamide (25 mL), cooled to zero degrees Celsius, was added sodium hydride (0.449 g, 60% oil dispersion, 11.23 mmol). Once the addition was complete the cooling bath was removed and then replaced after 0.5 hours. To the resulting mixture was added the mesylate of part B (2.61 g, 9.36 mmol). The reaction mixture was then heated to forty degrees Celsius. After stirring at forty degrees Celsius for 15 hours the temperature of the reaction was increased to eighty degrees Celsius. After 8 hours at eighty degrees Celsius the reaction mixture was cooled in an ice-bath and additional sodium hydride (0.225 g, 60% oil dispersion, 5.62 mmol) was added. After 30 minutes additional mesylate of part B (1.31 g, 4.68 mmol) was added and the resulting mixture was heated to eighty degrees Celsius. After 15 hours at eighty degrees Celsius the reaction was cooled to ambient temperature and concentrated in vacuo. The residue was partitioned between $H_2O$ and diethyl ether. The organic layer was washed with saturated NaCl and dried over $Na_2SO_4$. After concentration in vacuo the residue was treated with a solution of 4 N HCl in dioxane (30 mL). After stirring at ambient temperature for 2 hours, the reaction mixture was concentrated in vacuo. Water was added and the reaction was extracted with ethyl acetate. The aqueous layer was then made alkaline (pH-10) with 2.5 N NaOH and extracted with ethyl acetate. The combined organic layers were washed with saturated NaCl and dried over $Na_2SO_4$. Concentration in vacuo provided the amine as an off-white solid (1.67 g, 68%).

Part D: To a solution of the amine of part C (11.5 g, 44.1 mmol) in dichloromethane (125 mL), precooled in an ice-bath, was added triethylamine (12.3 mL, 88.1 mmol) followed by a solution of methanesulfonyl chloride (5.1 mL, 66.1 mmol) in dichloromethane (20 mL). Once the addition was complete, the cooling bath was removed. After 1 hour at ambient temperature, the reaction mixture was concentrated in vacuo. The residue was partitioned between $H_2O$ and ethyl acetate. The organic layer was washed with saturated NaCl and dried over $Na_2SO_4$. Recrystallization from ethyl acetate/hexanes provided the sulfonamide as an off-white solid (10.77 g, 72%).

Part E: To a solution of the sulfonamide of part D (10.77 g, 31.8 mmol) in tetrahydrofuran (64 mL), cooled to minus seventy-five degrees Celsius, was added lithium bis (trimethylsilyl)amide (80 mL, 1M in tetrahydrofuran, 80.0 mmol), at such a rate that the temperature of the reaction never exceeded minus sixty five degrees Celsius. After stirring at minus seventy-five degrees Celsius for 30 minutes, a solution of methyl chloroformate (2.45 mL, 31.8 mmol) in tetrahydrofuran (32 mL) was slowly added at such a rate that the temperature of the reaction never exceeded minus sixty five degrees Celsius. After stirring at minus seventy-five degrees Celsius for 30 minutes the reaction was quenched by the addition of saturated $NH_4Cl$ and extracted with ethyl acetate. The combined organic layers were washed with saturated NaCl and dried over $Na_2SO_4$. Concentration in vacuo gave the sulfonamide ester as a yellow oil (12.6 g, 100%).

Part F: To a suspension of dibromotriphenyl-phosphorane (50.0 g, 118.45 mmol) in dichloromethane (200 mL), cooled to zero degrees Celsius, was added N-phenyldiethanol amine (10.0 g, 55.18 mmol). Once the addition was complete, the cooling bath was removed. After stirring at ambient temperature for 17.5 hours, the reaction mixture was concentrated in vacuo. The residue was then treated with warm ethyl acetate and the resulting precipitate was removed and the filtrate was concentrated in vacuo. Chromatography (on silica, hexanes/dichloromethane) provided the dibromoamine as a light yellow oil (5.85 g, 35%).

Part G: To a solution of the dibromoamine of part F(5.60 g, 18.24 mmol) in N,N-dimethylformamide were added $K_2CO_3$ (6.87 g, 49.74 mmol), the sulfonamide ester of part E (6.59 g, 16.58 mmol) and 18-crown-6 (1.66 g). The resulting mixture was heated to eighty degrees Celsius for 14.5 hours at which time additional $K_2CO_3$ (3.44 g, 24.89 mmol) was added. After stirring at eighty degrees Celsius for 7.5 hours the reaction mixture was cooled to ambient temperature and then concentrated in vacuo. The residue was dissolved in ethyl acetate, filtered through a pad of Celite® and the filtrate was concentrated in vacuo. Chromatography (on silica, ethyl acetate/hexanes) gave a yellow solid that after washing with hot methanol provided the cyclized ester as an off-white solid (3.15 g, 35%).

Part H: To a solution of the cyclized ester of part G (3.15 g, 5.81 mmol) in tetrahydrofuran (25 mL) was added potassium trimethylsilanolate (2.24 g, 17.43 mmol). The resulting mixture was stirred at ambient temperature for 24 hours and then $H_2O$ was added. After neutralization (pH-7) with 1 N HCl, the tetrahydrofuran was removed by concentration in vacuo. After readjusting the pH of the aqueous reaction mixture (pH=7) the precipitate was collected by filtration of give the acid as an off-white solid (2.97 g, 97%).

Part I: To a solution of the acid of part H (2.97 g, 5.62 mmol) in N,N-dimethylformamide (20 mL) were added 1-hydroxybenzotriazole (0.911 g, 6.74 mmol), N-methylmorpholine (1.85 mL, 16.86 mmol), O-(tetrahydropuranyl) hydroxylamine (1.98 g, 16.86 mmol) and 1-3-[(dimethylamino)propyl]-3-ethylcarbodiimide hydrochloride (1.51 g, 7.87 mmol). After stirring at ambient temperature for 18 hours the reaction mixture was concentrated in vacuo. water was added and the aqueous reaction mixture was extracted with ethyl acetate. The combined organic layers were washed with saturated $NaHCO_3$, saturated NaCl and dried over $Na_2SO_4$. The resulting solids were washed with hot methanol to give the protected hydroxamate as a white solid (3.09 g, 88%).

Part J: The protected hydroxamate of part I (3.09 g, 4.92 mmol) was treated with a solution of 4 N HCl in dioxane (12.0 mL) and methanol (1.99 mL, 49.23 mmol). After stirring at ambient temperature for several minutes additional dioxane (10 mL) was added. After stirring at ambient temperature for 1.5 ours diethyl ether was added and the precipitate was collected by filtration to give the title compound as an off-white solid (2.67 g, 94%). MS $MH^+$ calculated for $C_{24}H_{29}O_6N_3S_1F_3$: 544, found 544.

EXAMPLE 36

Preparation of N-Hydroxy-1-phenyl-4-[[4-[4-(trifluoromethyl)phenoxy]-1-piperidinyl]sulfonyl]-4-piperidinecarboxamide, Monohydrochloride

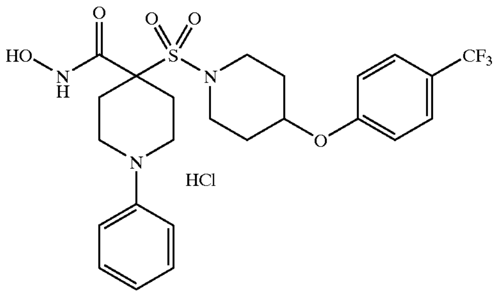

Part A: To a solution of the carbamate of part A for Example 35 (6.03 g, 30.0 mmol) in N,N-dimethylformamide (60 mL), were added $Cs_2CO_3$ (9.77 g, 30.0 mmol) and 4-fluorobenzotrifluoride (3.8 mL, 30.0 mmol). After stirring at ninety degrees Celsius for 19 hours, additional $Cs_2CO_3$ (3.26 g, 10.0 mmol) and 4-fluorobenzotrifluoride (0.95 mL, 10.0 mmol) were added. After stirring at ninety degrees Celsius for 46 hours, the reaction mixture was concentrated in vacuo. The residue was dissolved in ethyl acetate and the organic layer was washed with $H_2O$, saturated NaCl and dried over $Na_2SO_4$. Chromatography (on silica, ethyl acetate/hexanes) provided the Boc-amine as a white solid (6.0 g, 58%).

Part B: The Boc-amine of part A (4.10 g, 11.87 mmol) was treated with a solution of 4N HCl in dioxane (20.0 mL). After stirring at ambient temperature for 1.5 hours, the reaction mixture was concentrated in vacuo to provide the amine as a white solid (3.54 g, >100%).

Part C: To a solution of the amine of part B (3.34 g, 11.87 mmol) in dichloromethane (40 mL), cooled in an ice-bath, was added triethylamine (3.31 mL, 23.74 mmol) followed by methanesulfonyl chloride (1.38 mL, 17.81 mmol). Once the addition was complete the cooling bath was removed. After stirring at ambient temperature for 2 hours, the reaction mixture was concentrated in vacuo. The residue was partitioned between $H_2O$ and ethyl acetate. The organic layer was washed with 5% $KHSO_4$, saturated NaCl and dried over $Na_2SO_4$. Concentration in vacuo provided the sulfonamide as a pale yellow solid (4.25 g, >100%).

Part D: To a solution of the sulfonamide of part C (5.00 g, 15.46 mmol) in tetrahydrofuran (30 mL), cooled to minus forty degrees Celsius, was added lithium bis(trimetylsilyl) amide (31.0 mL, 1 M in tetrahydrofuran, 31.0 mmol) at such a rate that the temperature of the reaction never exceeded minus thirty five degrees Celsius. After stirring at minus forty degrees Celsius for 30 minutes, a solution of dimethyl carbonate (1.56 mL, 18.55 mmol) in tetrahydrofuran (10 mL) was added at such a rate that the temperature of the reaction never exceeded minus thirty five degrees Celsius. After stirring at minus forty degrees Celsius for 30 minutes, the reaction was quenched by the addition of saturated $NH_4Cl$. The resulting mixture was slowly permitted to warm to ambient temperature and then the tetrahydrofuran was removed in vacuo. The aqueous reaction mixture was diluted with $H_2O$ and extracted with ethyl acetate and diethyl ether. The combined organic layers were washed with 5% $KHSO_4$, saturated NaCl and dried over $Na_2SO_4$. Concentration in vacuo provided the sulfonamide ester as a thick yellow oil (5.75 g, 97%)

Part E: To a solution of the dibromoamine of part F of Example 35 (7.00 g, 22.80 mmol) in N,N-dimethylformamide (45 mL), was added $K_2CO_3$ (9.45 g, 68.40 mmol), the sulfonamide ester of part D (8.70 g, 22.80 mmol) and 18-crown-6 (2.28 g). The resulting mixture was heated to eighty degrees Celsius for 15 hours and then additional $K_2CO_3$ (4.73 g, 34.22 mmol) was added. The resulting mixture was then heated to eighty degrees Celsius for 6 hours. After cooling to ambient temperature, the reaction mixture was diluted with $H_2O$ and extracted with ethyl acetate. The combined organic layers were washed with saturated NaCl and dried over $Na_2SO_4$. Chromatography (on silica, ethyl acetate/hexanes) followed by washing of the resulting solids with boiling methanol provided the cyclized ester as an off-white solid (4.50 g, 37%).

Part F: To a solution of the cyclized ester of part E (4.50 g, 8.55 mmol) in tetrahydrofuran (40 mL) was added potassium trimethylsilanolate (3.29 g, 25.64 mmol). The resulting mixture was stirred at ambient temperature for 22 hours. The reaction mixture was diluted with $H_2O$ and neutralized (pH-7) with 1N HCl. The tetrahydrofuran was removed in vacuo and the precipitate was collected by filtration. The solids were suspended in acetonitrile and concentrated in vacuo to provide the acid as a white solid (4.05 g, 92%).

Part G: To a solution of the acid of part F (4.05 g, 7.90 mmol) in N,N-dimethylformamide were added 1-hydroxybenzotriazole (1.28 g, 9.48 mmol), N-methylmorpholine (2.59 mL, 23.70 mmol), O-(tetrahydropuranyl) hydroxylamine (2.78 g, 23.70 mmol) and 1-3-[(dimethylamino)propyl]-3-ethylcarbodiimide hydrochloride (2.12 g, 11.06 mmol). After stirring at ambient temperature for 16 hours the reaction mixture was diluted with $H_2O$ and extraced with ethyl acetate. The combined organic layers were washed with saturated $NaHCO_3$, saturated NaCl and dried over $Na_2SO_4$. The solids were washed with boiling methanol to provide the protected hydroxamate as a white solid (4.12 g, 85%).

Part H: The protected hydroxamate of part G (4.12 g, 6.74 mmol) was treated with a solution of 4N HCl in dioxane (12.0 mL) and methanol (1.99 mL, 49.23 mmol). After stirring at ambient temperature for several minutes, additional dioxane (10 mL) was added. After stirring at ambient temperature for 1.5 hours, diethyl ether was added and the precipitate was collected by filtration to give the title compound as an off-white solid (3.32 g, 87%). MS $MH^+$ calculated for $C_{24}H_{29}O_5N_3S_1F_3$: 528, found 528.

EXAMPLE 37

Preparation of 4-[[4-[4-(1,1-Dimethylethyl)phenyl]-1-piperazinyl]-sulfonyl]-N-hydroxy-1-(2-methoxyethyl)-4-piperidinecarboxamide, Monohydrochloride

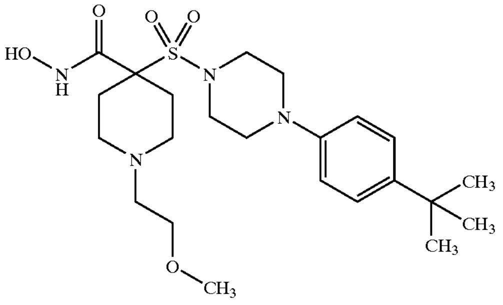

Part A: To a suspension of 4-bromopiperidine hydrobromide (30 g, 122.5 mmol) and N-5 (benzyloxycarbonyloxy) succinimide in tetrahydrofuran (250 mL) was added N-methylmorphoine (15 g, 148.3 mmol) followed by a catalytic amount of N,N-dimethylaminopyridine. After stirring at ambient temperature for 17 hours, the reaction mixture was concentrated in vacuo. The residue was partitioned between ethyl acetate and $H_2O$. The organic layer was washed with 10% HCl solution, saturated NaCl and dried over $Na_2SO_4$. Concentration in vacuo provided the carbamate as a clear oil (33.0 g, 90%).

Part B: To a solution of the carbamate of part A (30.4 g, 101.96 mmol) in N,N-dimethylformamide (200 mL) was added potassium thioacetate (12.75 g, 111.64 mmol) and the resulting mixture was stirred at ambient temperature After 23 hours, the reaction mixture was heated to sixty degrees Celsius. After heating at sixty degrees Celsius for 3 hour the reaction mixture was concentrated in vacuo. The residue was dissolved in ethyl acetate and filtered through a pad of Celite®. The filtrate was then concentrated in vacuo. The residue was redissolved in ethyl acetate and the organic layer was washed with saturated $NaHCO_3$, saturated NaCl and dried over $Na_2SO_4$. Chromatography (on silica, ethyl acetate/hexanes) provided the thioacetate as an orange oil (22.8 g, 76%).

Part C: Into a solution of the thioacetate of part B (22.8 g, 77.71 mmol) in carbon tetrachloride (240 mL) and ethanol (60 mL) was bubbled $Cl_2$. Once the exotherm was complete the bubbling of $Cl_2$ was discontinued. $N_2$ was bubbled through the reaction mixture for several minutes then the reaction was concentrated in vacuo to give the sulfonyl chloride as a brown oil (25.5 g, >100%).

Part D: To a solution of tert-butyl piperazine (5.24 g, 28.15 mmol) in toluene (50 mL) was added sodium tert-butoxide (3.16 g, 32.84 mmol). The resulting mixture was stirred at ambient temperature for several minutes and then 1-bromo-4-tert-butylbenzene (5.00 g, 23.46 mmol), BINAP (0.438 g, 0.704 mmol) and tris(dibenzyldeneacetone) dipallidium (0) (0.215 g, 0.235 mmol) were added. The resulting mixture was heated to eighty degrees Celsius for 16 hours. After cooling to ambient temperature, diethyl ether was added and the reaction mixture was filtered through a pad of Celite® and the filtrate was concentrated in vacuo. The residue was dissolved in diethyl ether and washed with $H_2O$, 5% $KHSO_4$, saturated NaCl and dried over $Na_2SO_4$. Concentration in vacuo provided the phenyl-piperazine as a brown solid (7.80 g, >100%).

Part E: The phenyl-piperazine of part D (7.80 g, 24.49 mmol) was treated with a solution of 4N HCl in dioxane (61 mL). The resulting reaction mixture was stirred at ambient temperature for 1 hour and then concentrated in vacuo. The solids were washed with diethyl ether to give the amine hydrochloride as a mustard colored solid (6.10 g, 98%).

Part F: To a suspension of the amine hydrochloride of part D (1.50 g, 5.89 mmol) and triethylamine (1.81 mL, 12.96 mmol) in dichloromethane (10 mL), cooled in an ice-bath, was added the sulfonyl chloride of part C (1.82 g, 5.73 mmol). Once the addition was complete the cooling bath was removed. After stirring at ambient temperature for 2 hours the reaction mixture was concentrated in vacuo. The residue was partitioned between $H_2O$ and ethyl acetate and the aqueous layer was further extracted with ethyl acetate. The combined organic layers were washed with 5% $KHSO_4$, saturated NaCl and dried over $Na_2SO_4$. The resulting solids were triturated with methanol to provide the sulfonamide as a light brown solid (1.41 g, 49%).

Part G: To a solution of the sulfonamide of part F (1.40 g, 2.80 mmol) in tetrahydrofuran (10 mL), at ambient temperature, was added lithium bis(trimethylsilyl)amide (6.20 mL, 1 M in tetrahydrofuran, 6.20 mmol). After stirring at ambient temperature for 1 hour, dimethyl carbonate (0.283 mL, 3.36 mmol) was added. The resulting mixture was stirred at ambient temperature for 3 hours and then additional lithium bis(trimethylsilyl)amide (3.10 mL, 1 M in tetrahydrofuran, 3.10 mmol) was added. After 2 hours at ambient temperature additional dimethyl carbonate (0.140 mL, 1.66 mmol) was added. After stirring at ambient temperature overnight (about 18 hours), the reaction was quenched by the addition of saturated $NH_4Cl$. The reaction was diluted with $H_2O$ and extracted with ethyl acetate. The combined organic layers were washed with 5% $KHSO_4$, saturated NaCl and dried over $Na_2SO_4$. The resulting solids were triturated with methanol to give the sulfonamide ester as a tan solid (1.29 g, 83%).

Part H: To a solution of the sulfonamide ester of part G (1.29 g, 2.31 mmol) in tetrahydrofuran (20 mL) and 10% Pd/C (0.300 g) was bubbled $H_2$. After bubbling $H_2$ through the reaction for 17 hours, the mixture was purged with $N_2$ and filtered through a pad of Celite®, washing with tetrahydrofuran. The filtrate was concentrated in vacuo to give the amine as a dark brown sticky solid (0.950 g, 97%).

Part I: To a solution of the amine of Part H (0.940 g, 2.22 mmol) in N,N-dimethylformamide (7.0 mL) was added $K_2CO_3$ (0.614 g, 4.44 mmol) and 2-bromoethyl methyl ether (0.313 mL, 3.33 mmol). The resulting mixture was stirred at ambient temperature for 3 days. The reaction mixture was concentrated in vacuo and the residue was dissolved in ethyl acetate and filtered through a pad of Celite®. Chromatography (on silica, ethyl acetate/hexanes) provided the alkylated amine as an off-white solid (0.595 g, 56%).

Part J: To a solution of the alkylated amine of part I (0.595 g, 1.24 mmol) in tetrahydrofuran (8.0 mL) was added potassium trimethylsilanolate (0.318 g, 2.48 mmol). After stirring at ambient temperature for 17 hours the tetrahydrofuran was removed by blowing $N_2$ over the reaction mixture. The residue was dissolved in $H_2O$ and the aqueous reaction mixture was neutralized (pH=7) with 1 N HCl. The precipitate was collected by filtration to provide the acid as an off-white solid (0.475 g, 82%).

Part K: To a solution of the acid part J (0.475 g, 1.02 mmol) in N,N-dimethylformamide (5.0 mL) was added 1-hydroxybenzotriazole (0.165 g, 1.22 mmol), N-methylmorpholine (0.334 mL, 3.06 mmol), O-(tetrahydropuranyl) hydroxylamine (0.359 g, 3.06 mmol) and 1-3-[(dimethylamino)propyl]-3-ethylcarbodiimide hydrochloride (0.274 g, 1.43 mmol). The resulting reaction mixture was stirred at ambient temperature for 17.5 hours and then heated to sixty degrees Celsius for 6 hours. To the reaction mixture was added triethylamine (0.427 mL, 3.06 mmol) and the resulting mixture was heated to sixty degrees Celsius for 21 hours. After cooling to ambient temperature, the reaction mixture was concentrated in vacuo. The residue was suspended in $H_2O$, acidified (pH=1) with 1 N HCl and then concentrated in vacuo. To a solution of the resulting solids in N,N-dimethylformamide (5.0 mL) were added 1-hydroxybenzotriazole (0.119 g, 0.881 mmol) and 1-3-[(dimethylamino)propyl]-3-ethylcarbodiimide hydrochloride (0.197 g, 1.03 mmol). After stirring at ambient temperature for 1 hour, N-methylmorpholine (0.400 mL, 3.67 mmol), O-(tetrahydropuranyl) hydroxylamine (0.258 g, 2.20 mmol) were added. After stirring at ambient temperature for 2 days the reaction mixture was diluted with $H_2O$, then neutralized (pH=7) and extracted with ethyl acetate. The combined organic layers were washed with saturated $NaHCO_3$, saturated NaCl and dried over $Na_2SO_4$. The crude protected hydroxamate was treated with a solution of 4 N HCl in dioxane (1.8 mL) and methanol (0.309 mL). After stirring at ambient temperature for 1.5 hours, diethyl ether was added and the precipitate was collected by filtration. The solids were washed with acetonitrile to give the title compound as a tan solid (0.188 g, 49%). MS $MH^+$ calculated for $C_{23}H_{39}O_5N_4S_1$: 483, found 483.

EXAMPLE 38

Preparation of 4-[[4-(4-(4-Butoxyphenyl)-1-piperazinyl]sulfonyl]-N-hydroxy-1-(2-methoxyethyl)-4-piperidinecarboxamide, Dihydrochloride

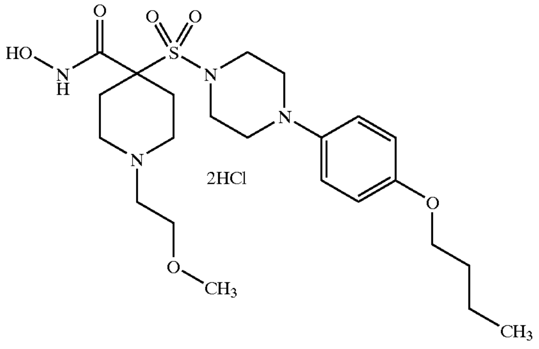

Part A: To a solution of n-butyloxybromobenzene (5.00 g, 21.82 mmol) in toluene (50 mL) was added tert-butyl piperazine (4.88 g, 26.18 mmol) and sodium tert-butoxide (2.94 g, 30.55 mmol). After stirring at ambient temperature for several minutes, BINAP (0.408 g, 0.655 mmol) and tris(dibenzyldeneacetone)-dipallidium (0) (0.200 g, 0.218 mmol) were added. The resulting mixture was heated to eighty degrees Celsius for 21 hours. After cooling to ambient temperature, the reaction mixture was filtered through a pad of Celite®, washing with diethyl ether and dichloromethane. Chromatography (on silica, ethyl acetate/hexanes) provided the phenyl-piperazine as a tan solid (5.56 g, 76%).

Part B: The phenyl-piperazine of part A (5.56 g, 16.62 mmol) was treated with a solution of 4 N HCl in dioxane (42 mL). The resulting mixture was stirred at ambient temperature for 1.5 hours and then concentrated in vacuo. The resulting solids were washed with diethyl ether to provide the amine hydrochloride as an off-white solid (4.60 g, >100%).

Part C: To a solution of the amine hydrochloride of part B (2.24 g, 8.26 mmol) and triethylamine (2.41 mL, 17.31 mmol) in dichloromethane, cooled to zero degreees Celsius, was slowly added a solution of the sulfonyl chloride of part C of Example 37 (2.50 g, 7.87 mmol) in dichloromethane (20 mL). Once the addition was complete, the cooling bath was removed. After stirring at ambient temperature for 4 hours, additional triethylamine (1.25 mL, 8.97 mmol) was added. The resulting mixture was stirred at ambient temperature for 2.5 hours and then concentrated in vacuo. The residue was partitioned between 5% $KHSO_4$ solution and ethyl acetate. The organic layer was washed with saturated NaCl and dried over $Na_2SO_4$. Chromatography (on silica, ethyl acetate/hexanes) provided the sulfonamide as an off-white solid (3.21 g, 75%).

Part D: To a solution of the sulfonamide (3.18 g, 6.17 mmol) in tetrahydrofuran (30 mL), cooled to zero degrees Celsius, was added lithium bis(trimethylsilyl)amide (13.6 mL, 1 M in tetrahydrofuran, 13.6 mmol). Once the addition was complete, the cooling bath was removed and replaced after 1 hour. To the resulting mixture was added dimethyl carbonate (0.624 mL, 7.40 mmol). Once the addition was complete the cooling bath was removed. After stirring at ambient temperature overnight (about 18 hours), additional dimethyl carbonate (0.260 mL, 3.09 mmol) was added. After stirring at ambient temperature for 2 hours, additional lithium bis(trimethylsilyl)amide (3.09 mL, 1 M in tetrahydrofuran, 3.09 mmol) was added. After stirring at ambient temperature for 2 hours, the reaction mixture was cooled to zero degrees Celsius, and quenched by the addition of saturated $NH_4Cl$. The tetrahydrofuran was concentrated in vacuo and the aqueous reaction mixture was diluted with $H_2O$ and extracted with diethyl ether. The combined organic layers were washed with 5% $KHSO_4$, saturated NaCl and dried over $Na_2SO_4$. Chromatography (on silica, ethyl acetate/hexanes) provided the sulfonamide ester as a pale yellow gum (1.76 g, 50%).

Part E: To a suspension of the sulfonamide ester of part D (1.76 g, 3.07 mmol) and 10% Pd/C (0.307 g) in tetrahydrofuran (25 mL) was bubbled $H_2$. After bubbling $H_2$ through the reaction mixture for 23 hours the mixture was purged with $N_2$ and filtered through a pad of Celite®, washing with methanol. The filtrate was concentrated in vacuo to give the amine as a pale yellow gum (1.19 g, 88%).

Part F: To a solution of the amine of part E (1.19 g, 2.71 mmol) in N,N-dimethylformamide (10 mL) were added $K_2CO_3$ (0.749 g, 5.42 mmol) and 2-bromoethyl methyl ether (0.382 mmol, 4.07 mmol). The resulting mixture was stirred at ambient temperature for 21 hours. The reaction mixture was concentrated in vacuo and the residue was dissolved in ethyl acetate and filtered through a pad of Celite®. Chromatography (on silica, ethyl acetate with 5% methanol/hexanes) provided the alkylated amine as a tan solid (0.770 g, 57%).

Part G: To a solution of the alkylated amine of part F (0.770 g, 1.55 mmol) in tetrahydrofuran (5.0 mL) was added potassium trimethylsilanolate (0.398 g, 3.10 mmol). After stirring at ambient temperature for 3 hours additional tetrahydrofuran (5.0 mL) was added. The resulting reaction mixture was stirred at ambient temperature for 24 hours and then the tetrahydrofuran was removed by blowing $N_2$ over the reaction mixture. To the residue was added acetonitrile (20 mL) and 1 N HCl (5 mL). The resulting mixture was stirred at ambient temperature for several minutes and then concentrated in vacuo to provide the crude acid as a tan solid (0.806 g, >100%).

Part H: To a suspension of the crude acid of part G (0.806 g, ~1.55 mmol) in N,N-dimethylformamide (7.0 mL) were added 1-hydroxybenzotriazole (0.251 g, 1.86 mmol) and 1-3-[(dimethylamino)propyl]-3-ethylcarbodiimide hydrochloride (0.416 g, 2.17 mmol). After stirring at ambient temperature for 1.5 hours, N-methylmorpholine (0.847 mL, 7.75 mmol) and O-(tetrahydropuranyl) hydroxylamine (0.545 g, 4.65mmol) were added. After stirring at ambient temperature overnight (about 18 hours) the reaction mixture was diluted with $H_2O$ and extracted with ethyl acetate. The combined organic layers were washed with saturated $NaHCO_3$, saturated NaCl and dried over $Na_2SO_4$. Chromatography (on silica, ethyl acetate with 5% methanol/hexanes) provided the protected hydroxamate as a yellow sticky oil (0.687 g, 76%).

Part I: The protected hydroxamate of part H (0.687 g, 1.18 mmol) was treated with a solution of 4 N HCl in dioxane (2.95 mL) and methanol (0.500 mL) The resulting mixture was stirred at ambient temperature for 1.5 hours and then diethyl ether was added. The precipitate was collected by filtration, washing with diethyl ether, to give the title compound as an off-white solid (0.530 g, 79%). MS $MH^+$ calculated for $C_{23}H_{39}N_4O_6S_1$: 499, found 499.

EXAMPLE 39

Preparation of N-Hydroxy-4-[[1'-(2-methoxyphenyl)[4,4'-bipiperidin]-1-yl]sulfonyl]-1-(phenylmethyl)-4-piperidinecarboxamide, Dihydrochloride

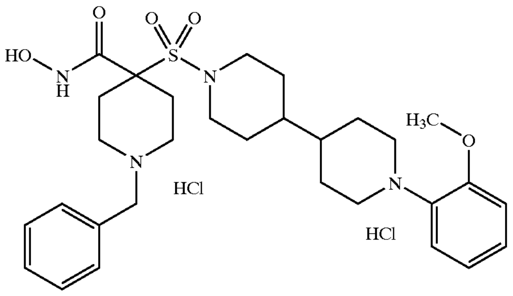

Part 1: Preparation of

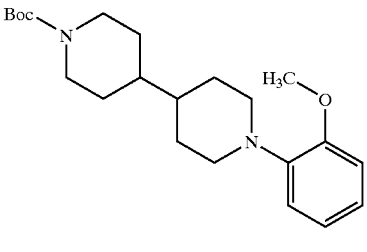

To N-(t-butoxycarbonyl)-4,4'-bipiperidine (prepared as described in WO94/14776; preparation 22; (3.5 g, 30 mmol) and sodium t-butoxxide (Aldrich, 1.8 mL, 110 mmol), 2-bromoanisole(Aldrich; 2 g, mmol), BINAP (Aldrich; 150 mg), palladium chloride(Aldrich, 50 mg) were slurried in toluene (22 mL) and heated to 80° C. After the disappearance of the starting material, the solvent wasremoved and the residue was taken up in ethyl acetate (100 mL) and $H_2O$ (30 mL). Once separated, the organic layer was washed with 5% $KHSO_4$ (3x–50 mL) and brine (1x–50 mL). The organic layer was then dried over $Na_2SO_4$, filtered, and concentrated to afford the N-aryl Boc bipiperidine as an oil (6.5 g). $^1H$ NMR and mass spectroscopy showed the desired compound.

Part 2: Preparation of

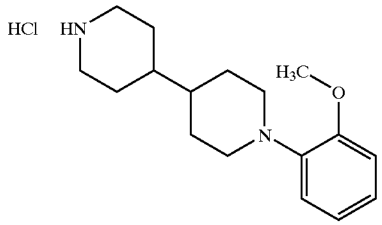

To a solution of the product (6 g) of Part 1 in 1,4-dioxane (10 mL) was added 4 N HCl in dioxane (50 mL, 200 mmol). The mixture was stirred at room temperature until starting material was gone by LC (about 1 hour). The solvents were then removed and the residue was slurried in diethyl ether and filtered. The solid was washed with diethyl ether (2x–50 mL) and dried in vacuo to afford the N-aryl bipiperidine as a white solid (6 g). $^1H$ NMR and mass spectroscopy showed the desired compound as the HCl salt.

Part 3: Preparation of

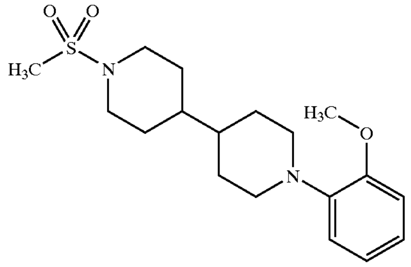

The HCl salt of Part 2 (5 g, 14 mmol) and triethylamine (Aldrich, 4.4 mL, 42 mmol) were slurried in $CH_2Cl_2$ (50 mL) and cooled to zero° C. A solution of methane sulfonyl chloride (Aldrich, 2 g, 50 mmol) in $CH_2Cl_2$ (20 mL) was slowly added, maintaining the temperature below 10° C. After the addition, the ice bath was removed and the reaction stirred 1 hour as it warmed to ambient temperature. After the disappearance of the starting material, the solvent was removed and the residue was taken up in ethyl acetate (100 mL) and $H_2O$ (30 mL). Once separated, the organic layer was washed with 5% $KHSO_4$ (3x–50 mL) and brine (1x–50 mL). The organic layer was then dried over $Na_2SO_4$, filtered, and concentrated to afford an oily solid that was recrystallized from diethyl ether, affording the N-aryl methylsulfonamide bipiperidine as an off-white solid (4 g). $^1H$ NMR and mass spectroscopy showed the desired compound.

Part 4: Preparation of

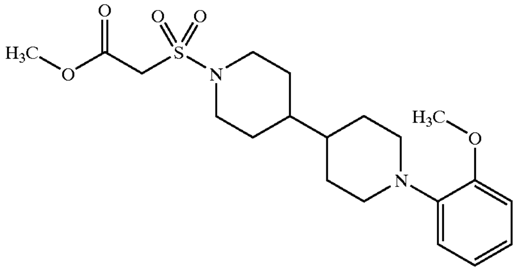

Oven-dried glassware was charged with the compound from Part 3 (3.5 g, 10 mmol) and tetrahydrofuran (20 mL,) and cooled to −75° C. Lithium bis(trimethylsilyl)amide (Aldrich, 1.0 M in tetrahydrofuran, 30 mL, 33 mmol) was slowly added, keeping temperature less than −60° C. The reaction was stirred for 30 minutes after the addition, and was then charged with a solution of methyl chloroformate (Aldrich, 1.1 mmol, 11 mmol) in tetrahydrofuran (1 mL) again keeping the temperature at less than −60° C. After stirring for 1 hour at −75° C., the reaction was quenched with saturated $NH_4Cl$, keeping temperature less than −20° C. The aqueous portion froze into a solid chunk of ice. After warming to 5° C., the mixture was extracted via ethyl acetate (3x–200 mL). Organics were washed with saturated $NH_4Cl$ (2x–100 mL) and brine (1x–100 mL), then dried over $Na_2SO_4$ and concentrated to afford the N-aryl bipiperidine methylene as a tan oil(4.0 g, 90% crude yield). $^1H$ NMR and mass spectroscopy indicated desired compound.

Part 5: Preparation of

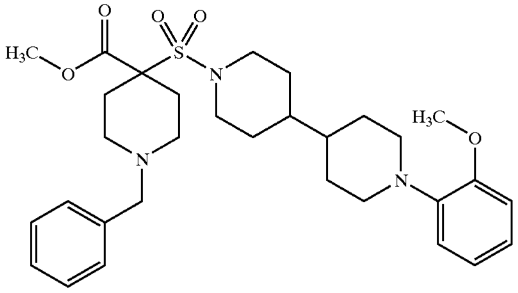

To a solution of compound from Part 4 (3 g, 11 mmol) and bis-(2-chloroethyl)benzyl amine (2.7 mL, 15.1 mmol) in dimethylformamide (30 mL) was added 18-Crown-6 (Aldrich, 500 mg, cat.), followed by potassium carbonate (Aldrich, 5 g, 27.4 mmol). The mixture was heated at 60° C. for 16 hours. The product was isolated by pouring into water(200 mL) and extraction with ethyl acetate (3x–300 mL) Organics were washed with brine (2x–200 mL), dried over $Na_2SO_4$, and concentrated to afford the amino ester an oil (3 g) that solidified on standing. $^1H$ NMR and mass spectroscopy showed the desired compound. Part 6: Preparation of

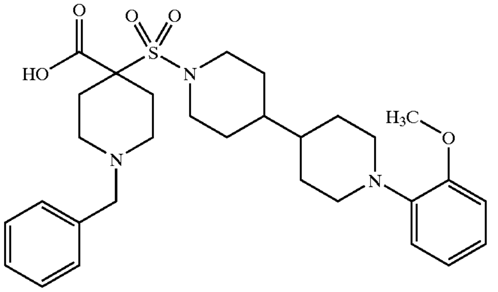

To a solution of the compound from Part 5 (2 g, 7 mmol) in tetrahydrofuran (20 mL) was added potassium trimethylsilonate (Aldrich, 2 g, 18 mmol). The reaction stirred overnight (about 18 hours) at room temperazture, at which time LC showed less than 3% starting material remained. Work up comprised removing the tetrahydrofuran and taking the residue up in $H_2O$ (100 mL). The solution was washed with diethylether (50 mL). The aqueous was then cooled to zero° C. and 10% $HCl_{aq}$ was slowly added until pH=3. The acidic mixture was then extracted with ethyl acetate (3x–150 mL) The organics were washed with brine (1x–100 mL), dried over $Na_2SO_4$, and concentrated to afford a wet solid. The solid was dried in vacuo with phosphorous pentoxide yielding the amino acid as an orange solid (2.4 g, 72% yield) $^1$H NMR and mass spectroscopy showed the desired compound.

Part 7: Preparation of

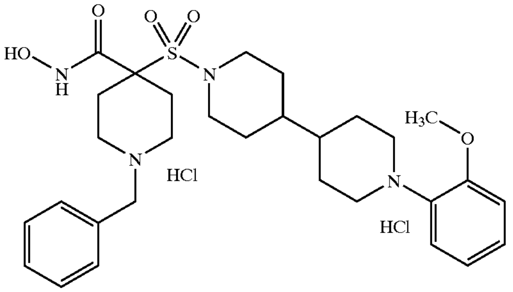

To a solution of the acid product in Part 6 (3 g, 5.2 mmol) in dimethylacetamide (20 mL) was added N-methylmorpholine (Aldrich, 3.0 mL, 15 mmol) followed by by N-hydroxybenzotriazole hydrate (Aldrich, 1.0 g, 5 mmol), O-(tetrahydro-2H-pyran-2-yl) hydroxylamine (1.1 g, 7.5 mmol) and 1-(3-dimethylaminopropyl)-3-ethylcarbodiimide hydrochloride (Sigma, 1.5 g, 9.4 mmol). The mixture was stirred overnight (about 18 hours) and was then stripped of solvent. The residue was taken up in ethyl acetate (250 mL) and washed with 5% $NaHSO_4$ (1x–150 mL), saturated potassium carbonate (1x–150 mL), and brine (1x–150 mL). The organic layer was then dried over $Na_2SO_4$ and concentrated to afford a viscous oil. $^1$H NMR and mass spectroscopy showed the desired compound.

The viscous crude oil (3.0 g, 6.2 mmol) was dissolved in acetonitrile (10 mL) and stirred with 10% $HCl_{aq}$ (15 mL) for 2 hours, after which LC showed no more starting material. The acetonitrile was removed with $N_2$ stream over the surface of the solution affording a solid that was collected, washed with $H_2O$ (1x–20 mL), and dried in vacuo to afford the product as a tan solid (950 mg, 60% yield). $^1$H NMR showed the desired compound. Mass spectroscopy showed: $C_{30}H_{42}N_4O_5S$-2HCl; $M^{+H}_{found}$=570 ($M^{+H}_{calc}$=570)

EXAMPLE 40

Preparation of 4-[[4-(4-Bromophenyl)-4-fluoro-1-piperidinyl]sulfonyl]-tetrahydro-N-hydroxy-2H-pyran-4-carboxamide

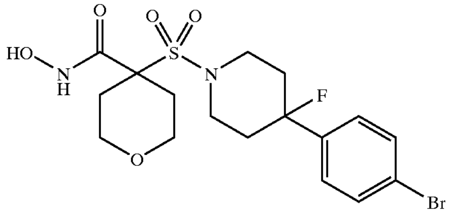

Part 1: Preparation of

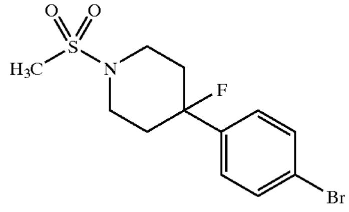

To 4(4-Bromophenyl)-4-hydroxypiperidine-N-methylsulfonamide (aldrich, 3 g, 9 mmol) dissolved in $CH_2Cl_2$ (75 mL) and cooled to −78° C. was added DAST (Aldrich, 1.9 g 12 mmol). After the addition, the dry ice bath/reaction was left to warmed to ambient temperature. After the disappearance of the starting material, aqueous ammonium chloride (100 mL) was added and the layers were separated. The organic layer was dried over sodium sulfate. The solvent was removed under reduced pressure to give the methylsulfonamide as a white solid (3 g). $^1$H NMR and mass spectroscopy showed the desired compound.

Part 2: Preparation of

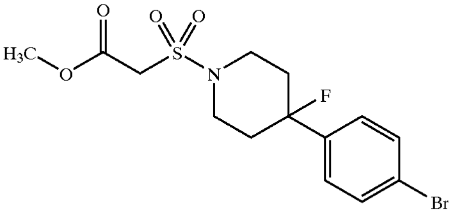

Oven-dried glassware was charged with the compound from Part 1 (4.0 g, 1.2 mmol) and tetrahydrofuran (25 mL,) and cooled to −75° C. Lithium bis(trimethylsilyl)amide (Aldrich, 1.0 M in tetrahydrofuran, 35 mL, 33 mmol) was slowly added, keeping temperature less than −60° C. The reaction was stirred for 30 minutes after the addition, and was then charged with a solution of methyl chloroformate (Aldrich, 1.3 mmol, 1.3 mmol) in tetrahydrofuran (17 mL), again keeping the temperature at less than −60° C. After stirring for 1 hour at −75° C., the reaction was quenched with saturated $NH_4Cl$, keeping temperature at less than −20° C. The aqueous portion freezes into a solid chunk of ice. After warming to 5° C., the mixture was extracted with ethyl acetate (3x–200 mL). Organics were washed with saturated $NH_4Cl$ (2x–100 mL) and brine (1x–100 mL), then dried over $Na_2SO_4$ and concentrated to afford the methylene sulfonamide as an amber oil (4.6 g, 90% crude yield). $^1$H NMR and mass spectroscopy indicated desired compound.

Part 3: Preparation of

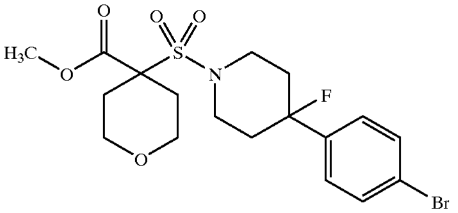

To a solution of compound from Part 2 (3.5 g, 1 mmol) and dibromo-diethylether (Lancaster, 3 g, 1.4 mmol) in dimethylformamide (28 mL) was added 18-Crown-6 (Aldrich, 500 mg, cat.) followed by potassium carbonate (Aldrich, 5 g, 3.6 mmol). The mixture was heated at 60° C. for 16 hours. The product was isolated by pouring into stirring 10% $HCl_{aq}$ (200 mL) and extracted with ethyl acetate (3×–300 mL). Organics were washed with brine (2×–200 mL), dried over $Na_2SO_4$, and concentrated to afford an oil. The crystallized to result in 4.8 grams of the ester as a tan solid. $^1$H NMR and mass spectroscopy showed the desired compound.

Part 4: Preparation of

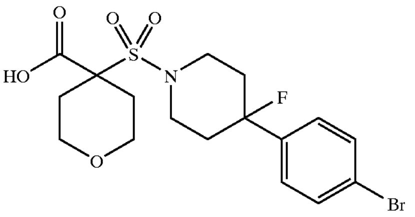

To a solution from Part 3 (2 g, 0.4 mmol) in tetrahydrofuran (20 mL) was added potassium trimethylsilonate (Aldrich, 2 g, 1.5 mmol). The reaction was stirred overnight (about 18 hours) at room temperature. LC showed less than 3% starting material remained. Work up comprised removing the tetrahydrofuran and taking the residue up in $H_2O$ (100 mL). The solution was washed with diethyl ether (50 mL). The aqueous was then cooled to zero° C. and 10% $HCl_{aq}$ was slowly added until pH=3. The product was filtered and washed with water to result in the acid as a white solid (1.5 g, 72% yield). $^1$H NMR and mass spectroscopy showed the desired compound.

Part 5: Preparation of

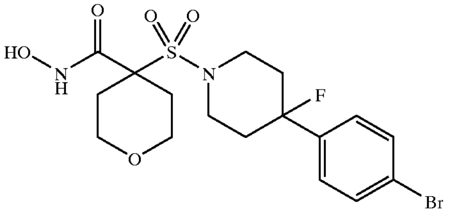

To a solution of the acid product in Part 4 (1 g, 0.2 mmol) in dimethylacetamide (10 mL) was added N-methylmorpholine (Aldrich, 2.0 mL, 2 mmol), followed by by N-hydroxybenzotriazole hydrate (Aldrich, 1.0 g, 0.7 mmol), O-(tetrahydro-2H-pyran-2-yl) hydroxylamine (1.1 g, 0.9 mmol), and 1-(3-dimethylaminopropyl)-3-ethylcarbodiimide hydrochloride (Sigma, 1.1 g, 0.6 mmol). The mixture was stirred overnight (about 18 hours) and was then stripped of solvent. The residue was taken up in ethyl acetate (250 mL) and washed with 5% $NaHSO_4$ (1×–150 mL), saturated potassium carbonate (1×–150 mL), and brine (1×–150 mL). The organic was then dried over $Na_2SO_4$ and concentrated to afford the protected hydroxamate as a viscous oil. $^1$H NMR and mass spectroscopy showed the desired compound.

The viscous crude oil from above was dissolved in acetonitrile (10 mL) and stirred with 10% $HCl_{aq}$ (15 mL) for 2 hours, after which LC showed no more starting material. The acetonitrile was removed with a $N_2$ stream over the surface of the solution affording a solid that was collected, washed with $H_2O$ (1×–20 mL), and dried in vacuo to afford the product as a tan solid (755 mg). $^1$H NMR showed the desired compound. Mass spectroscopy showed: $C_{17}H_{22}FN_2O_5SBrF$ $M^{+H}_{found}$=465 ($M^{+H}_{calc}$=465).

EXAMPLE 41

Preparation of 4-[[4-[4-(3,5-Dimethylphenoxy) phenoxy)-1-piperidinyl]-sulfonyl]tetrahydro-N-hydroxy-2H-pyran-4-carboxamide

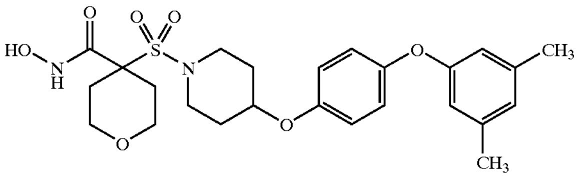

Part 1: Preparation of

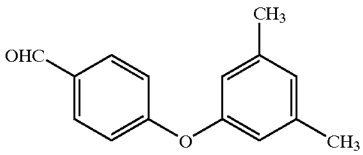

To a slurry of $Cs_2CO_3$ (Aldrich, 40 g, 12 mmol) and 3,5-dimethyl phenol (Aldrich, 5 g, 4 mmol) in dimethylformamide (60 mL) at 25° C. under $N_2$ was added 4-fluorobenzaldehyde (Aldrich, 5 g, 4 mmol). The mixture was stirred and heated to 90° C. for 16 hours. After this time, the solvent was removed by roto-evaporation and taking the residue up in ethyl acetate (150 mL) and $H_2O$ (100 mL). The layers were separated and the aqueous layer was extracted with ethyl acetate (2×–150 mL). The organics were washed with saturated $K_2CO_3$ (2×–100 mL), $H_2O$ (1×–150 mL), and brine (1×–150 mL), then dried over $Na_2SO_4$, filtered, and concentrated to afford a crude oil. The oil was purified on silica gel to give 8 g of the aldehyde as a clear oil. $^1$H NMR and mass spectroscopy was consistent with the des red compound.

Part 2: Preparation of

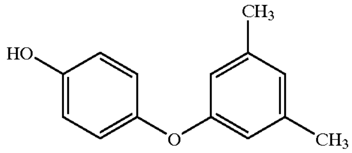

To a solution of aldehyde (8 g, 35 mmol) from part 1 in mehtylene chloride (100 mL) was added metachloroperoxybenzoic acid (8 g, 52 mmol). The reaction mixture was stirred at ambient temperature for 16 hours. After complete reaction, the solid meta-chlorobenzoic acid was removed by filtration. The solvent of the filtrate was removed under reduced pressure to give an oil. This oil was dissolved in methanol (100 mL) to which lithium hydroxide (2 g) was added. After 4 hours, the reaction was complete. The solvent was removed by rotory evaporation to give an oil, which was dissolved in ethyl acetate and washed with 10% aqueous hydrochloroic acid, separated and dried over sodium sulfate to result in 5.5 grams of the phenol as an oil. $^1H$ NMR and mass spectroscopy were consistent with the desired compound.

Part 3: Preparation of

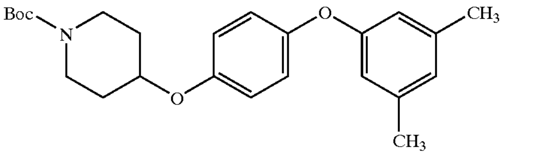

Sodium hydride (Aldrich, 2 g, 50 mmol) was added to a solution of 4-(methylsulfonyl)hydroxy-1-piperidinecarboxylic acid, 1,1-dimethylethyl ester of Example 14, B (10 g, 25 mmol) and the phenol from part 2 (5.5 g, 50 mmol) dissolved in dimethylformamide (60 mL) at 25° C. and under $N_2$. The mixture was stirred and heated to 80° C. for 16 hours. After this time, the solvent was removed by roto-evaporation, followed by taking the residue up in ethyl acetate (150 mL) and $H_2O$ (100 mL). The layers were separated and the aqueous was extracted via ethyl acetate (2×–150 mL). The organics were washed with saturated $K_2CO_3$ (2×–100 mL), $H_2O$ (1×–150 mL), and brine (1×–150 mL), then dried over $Na_2SO_4$, filtered, and concentrated to afford a crude oil. The oil was purified on silica gel to give log of the N-boc piperidine as a clear oil. $^1H$ NMR and mass spectroscopy was consistent with the desired compound.

Part 4: Preparation of

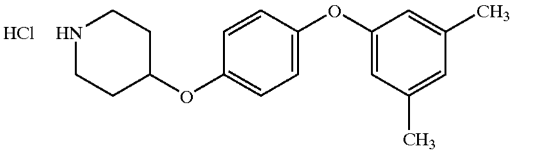

To a solution of the product (10 g) of Part 3 in 1,4-dioxane (10 mL) was added 4 N HCl in dioxane (50 mL, 200 mmol). The mixture was stirred at room temperature until starting material was gone by LC (about 1 hour). The solvents were then removed and the residue was slurried in diethyl ether and filtered. The solid was washed with diethyl ether (2×–50 mL) and dried in vacuo to afford a white solid (3 g). $^1H$ NMR and mass spectroscopy showed the desired compound as the HCl salt.

Part 5: Preparation of

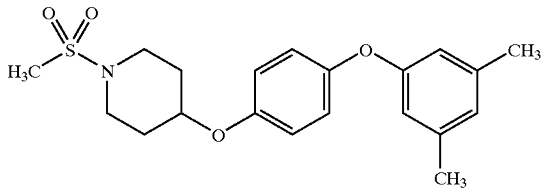

The HCl salt of Part 4 (3 g, 10 mmol) and triethylamine (Aldrich, 3 mL, 15 mmol) were slurried in $CH_2Cl_2$ (50 mL) and cooled to zero° C. A solution of methane sulfonyl chloride (Aldrich, 1.3 g, 13 mmol) in $CH_2Cl_2$ (20 mL) was slowly added, maintaining the temperature below 10° C. After the addition, the ice bath was removed and the reaction stirred 1 hour as it warmed to ambient temperature. After the disappearance of the starting material, the solvent was removed and the residue was taken up in ethyl acetate (100 mL) and $H_2O$ (30 mL). Once separated, the organic layer was washed with 5% $KHSO_4$ (3×–50 mL) and brine (1×–50 mL). The organic layer was then dried over $Na_2SO_4$, filtered, and concentrated to afford an oily solid that was recrystallized from diethyl ether, affording the methylsulfonamide as an off-white solid (1.2 g). $^1H$ NMR and mass spectroscopy showed the desired compound.

Part 6: Preparation of

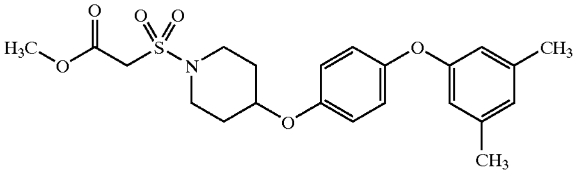

Oven-dried glassware was charged with the compound from Part 5 (1.2 g, 3.2 mmol) and tetrahydrofuran (25 mL), and cooled to −75° C. Lithium bis(trimethylsilyl)amide (Aldrich, 1.0 M in tetrahydrofuran, 9 mL, 6 mmol) was slowly added, keeping temperature less than −60° C. The reaction was stirred for 30 minutes after the addition, and was then charged with a solution of methyl chloroformate (Aldrich, 350 mg, 3.5 mmol) in tetrahydrofuran (1 mL) again keeping the temperature at less than −60° C. After stirring for 1 hour at −75° C., the reaction was quenched with saturated $NH_4Cl$, keeping temperature at less than −20° C. The aqueous phase froze into a solid chunk of ice. After warming to 5° C., the mixture was extracted with ethyl acetate (3×–200 mL). Organics were washed with saturated $NH_4Cl$ (2×–100 mL) and brine (1×–100 mL), then dried over $Na_2SO_4$ and concentrated to afford the methylene sulfonamide as a tan oil (2.0 g, 90% crude yield). $^1H$ NMR and mass spectroscopy indicated desired compound.

Part 7: Preparation of

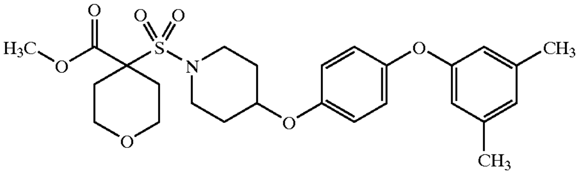

To a solution of compound from Part 6 (2 g, 11 mmol) and dibromo-diethylether (Lancaster, 1.8 mL, 15.1 mmol) in dimethylformamide (28 mL) was added 18-Crown-6 (Aldrich, 500 mg, cat.) followed by potassium carbonate (Aldrich, 3.8 g, 27.4 mmol.). The mixture was heated at 60° C. for 16 hours. The product was isolated by pouring the reaction mixture into stirring 10% $HCl_{aq}$ (200 mL), followed by extraction with ethyl acetate (3x–300 mL). Organics were washed with brine (2x–200 mL), dried over $Na_2SO_4$, and concentrated to afford the ester as an oil. The oil was crystallized from diethyl ether (2 g). $^1H$ NMR and mass spectroscopy showed the desired compound.

Part 8: Preparation of

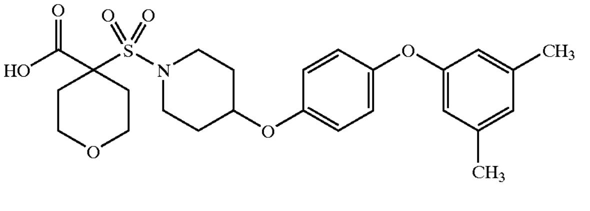

To a solution from Part 7 (2 g, 7 mmol) in tetrahydrofuran (20 mL) was added potassium trimethylsilonate (Aldrich, 2 g, 18 mmol). The reaction was stirred overnight (about 18 hours) at room temperature. LC showed less than 3% starting material remained. Work up comprised remmoving the tetrahydrofuran and taking the residue up in $H_2O$ (100 mL). The solution was washed with diethyl ether (50 mL). The aqueous layer was then cooled to zero° C. and 10% $HCl_{aq}$ was slowly added until pH=3. The acidic mixture was then extracted via ethyl acetate (3x–150 mL). The organics were washed with brine (1x–100 mL), dried over $Na_2SO_4$, and concentrated to afford a wet solid. The solid was dried in vacuo with phosphorous pentoxide yielding the acid as an orange solid (2 g, 92% yield). $^1H$ NMR and mass spectroscopy showed the desired compound.

Part 9: Preparation of

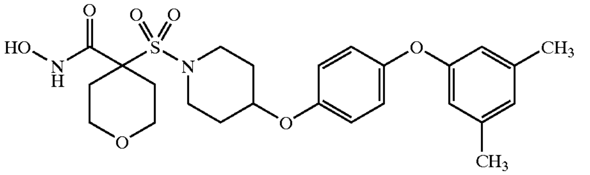

To a solution of the acid product in Part 8 (2 g, 6.2 mmol) in dimethylacetamide (10 mL) was added N-methylmorpholine (Aldrich, 2.0 mL, 18.6 mmol), followed by N-hydroxybenzotriazole hydrate (Aldrich, 1.0 g, 7.4 mmol), O-(tetrahydro-2H-pyran-2-yl) hydroxylamine (1.1 g, 9.4 mmol), and 1-(3-dimethylaminopropyl)-3-ethylcarbodiimide hydrochloride (Sigma, 1.8 g, 9.4 mmol). The mixture stirred overnight (about 18 hours), and was then stripped of solvent. The residue was taken up in ethyl acetate (250 mL) and washed with 5% $NaHSO_4$ (1x–150 mL), saturated potassium carbonate (1x–150 mL), and brine (1x–150 mL). The organic layer was then dried over $Na_2SO_4$ and concentrated to afford a viscous oil. $^1H$ NMR and MS showed the desired compound.

The viscous crude oil (3.0 g, 6.2 mmol) was dissolved in acetonitrile (10 mL) and stirred with 10% $HCl_{aq}$ (15 mL) for 2 hours, after which, LC showed no more starting material. The acetonitrile was removed with a $N_2$ stream over the surface of the solution affording a solid that was collected, washed with $H_2O$ (1x–20 mL), and dried in vacuo to afford the product as a tan solid (230 mg, 64% yield). $^1H$ NMR showed the desired compound. Mass spectroscopy showed: $C_{25}H_{32}F_3N_2O_7S$ $M^{+H}_{found}$=504 ($M^{+H}_{calc}$=504).

EXAMPLE 42

Preparation of 1-Cyclopropyl-N-hydroxy-4-[[4-[4-(trifluoromethyl)phenoxy]-1-piperidinyl]sulfonyl]-4-piperidinecarboxamide, Monohydrochloride

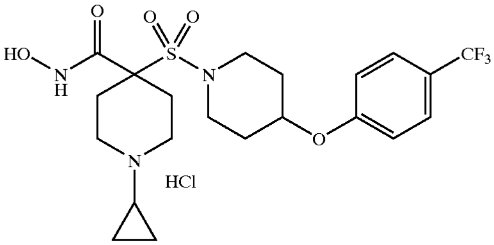

Part 1: Preparation of

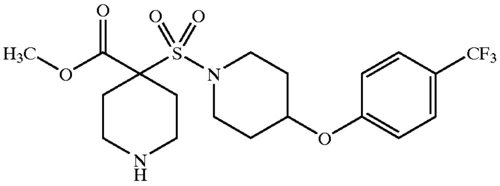

To a methanol (160 mL) solution of methyl 1-(phenylmethyl)-4-[[4-[4-(trifluoromethyl)phenoxy]-1-piperidinyl]sulfonyl]-4-piperidinecarboxylate of Example 12, Part F (40 g), and ammonium formate (15 g) was added 10%Pd on carbon (16 g, Degussa type catalyst). The black mixture was refluxed for 30–45 minutes. After complete reaction, the mixture was cooled and filtered through a Celite® pad. The solvent was removed under reduced pressure to give the piperidine methyl ester as an oil that solidified on standing (34 g). $^1H$ NMR and mass spectroscopy were consistent with the desired structure.

Part 2: Preparation of

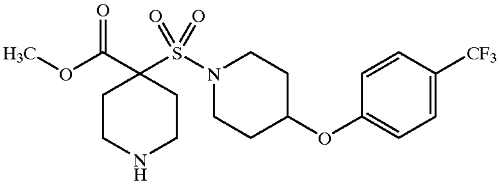

To a solution of compound from Part 1 (5 g, 1 mmol) in methanol (35 mL) were added [(1-ethoxycyclopropyl)oxy]-trimethylsilane (Aldrich, 7 g, 4 mmol), acetic acid (6 g, 10 mmol), sodium cyanoborohydride (1.8 g, 3 mmol) and molecular sieves (2.5 g). The reaction mixture was stirred and heated for 8 hours The progress of the reaction was monitored by RPHPLC. Work up comprised filtering the reaction mixture through a pad of Celite®, concentrating the methanol and partitioning the residue between in $H_2O$ (50 mL) and ethyl acetate (500 mL). The organics were washed with brine (1x–100 mL), dried over $Na_2SO_4$, and concentrated to afford the amino methyl ester as a semi-solid (3 g). $^1H$ NMR and mass spectroscopy were consistent with the desired structure.

Part 3: Preparation of

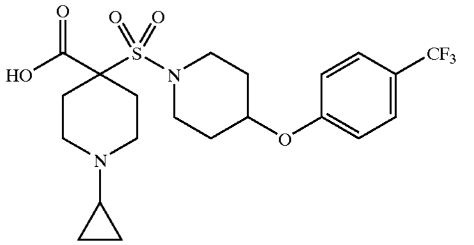

To a solution from Part 2 (3 g, 5 mmol) in tetrahydrofuran (20 mL) was added potassium trimethylsilonate (Aldrich, 1.5 g, 10 mmol). The reaction was complete overnight (about 18 hours) at room temperature. A nitrogen stream was blown over the surface of the solution to concentrate the mixture. Then water was added (20 mL) followed by aqueous 10% HCl until pH=7. The zwitterion was filtered washed with water (10 mL) and dried in vacuo with over phosphorous pentoxide yielding a solid (3 g). $^1$H NMR and mass spectroscopy were consistent with the desired structure.

Part 4: Preparation of

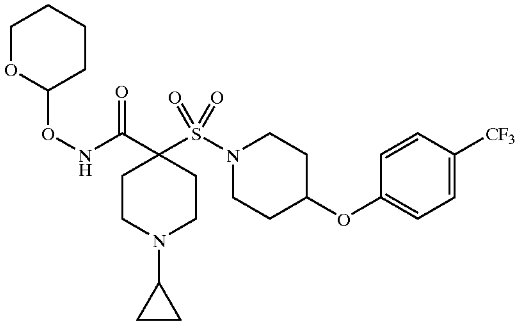

To a solution of the zwitterion product in Part 3 (3 g, 5 mmol) in dimethylacetamide (20 mL) were added 1-(3-dimethylaminopropyl)-3-ethylcarbodiimide hydrochloride (Sigma, 1.8 g, 9.4 mmol) and N-hydroxybenzotriazole hydrate (Aldrich, 1.0 g, 7.4 mmol), followed by heating to 50° C. for 15 minutes. N-Methylmorpholine (Aldrich, 2.0 mL, 18.6 mmol) was the added, followed by, O-(tetrahydro-2H-pyran-2-yl) hydroxylamine (1.1 g, 9.4 mmol). The mixture was stirred and heated for 1 hour then left to stir at room temperature overnight (about 18 hours). After complete reaction, the reaction mixture was concentrated under reduced pressure. The residue was taken up in ethyl acetate (250 mL) and washed with saturated potassium carbonate (1×–150 mL), and brine (1×–150 mL). The organic layer was dried over $Na_2SO_4$ and concentrated to afford a viscous oil. The oil was purified on $SiO_2$ using ethyl acetate in hexane to give 1.8 g of the THP-protected hydroxamate as a clear oil the solidified on standing. $^1$H NMR and mass spectroscopy were consistent with the desired structure.

Part 5: Preparation of

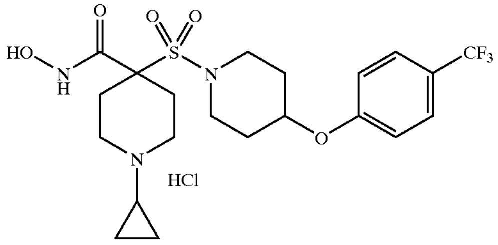

The solid from Part 4 (1.8 g) was slurried in methanol (600 mg) diethyl ether (10 mL). To this:was added 4 N HCl in dioxane (10 mL) and stirred for 2 hours, after which, RPHPLC showed complete reaction. The dioxane was concentrated by half, diethyl ether was added (100 mL) and the white solid (1.6 g, 64% yield) filtered and dried under vacuum. H NMR showed the desired compound. Mass spectroscopy showed: $C_{21}H_{28}F_3N_3O_5S$-HCl $M^{+H}_{found}$=527 ($M^{+H}_{calc}$=527).

EXAMPLE 43

Preparation of N-Hydroxy-1-(iminophenylmethyl)-4-[[4-[4-(trifluoromethyl)phenoxy]-1-piperidinyl]sulfonyl]-4-piperidinecarboxamide, Monohydrochloride

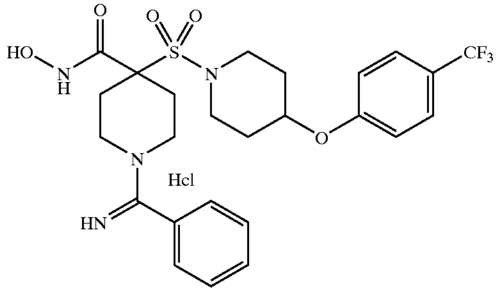

Part 1: Preparation of

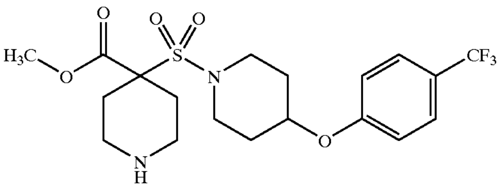

To a methanol (160 mL) solution of methyl 1-(phenylmethyl)-4-[[4-[4-(trifluoromethyl)phenoxy]-1-piperidinyl]sulfonyl]-4-piperidinecarboxylate of Example 12, Part F (40 g), and ammonium formate (15 g) was added 10%Pd on carbon (16 g, Degussa type catalyst). The black mixture was refluxed for 30–45 minuets. After complete reaction the mixture is cooled and filtered through a Celite® pad. The solvent wass removed under reduced pressure to give 34 g of the amino ester as an oil that solidified on standing. $^1$H NMR and mass spectroscopy were consistent with the desired structure.

Part 2: Preparation of

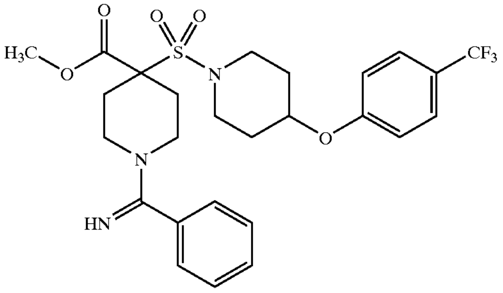

To a solution of compound from Part 1 (5 g, 1.0 mmol) in acetonitrile (50 mL) was added methyl benzimidate HCl (Aldrich, 2.5 g, 1.3 mmol) followed DMAP (100 mg). The reaction mixture was stirred and heated to 60 degrees Celcius for 8 hours. The progress of the reaction was monitored by RPHPLC. Work up comprised removing the solvent under reduced pressure. The resulting solid was triturated with water and filtered to give 7 grams of the amidino ester. $^{1}H$ NMR and mass spectroscopy were consistent with the desired structure.

Part 3: Preparation of

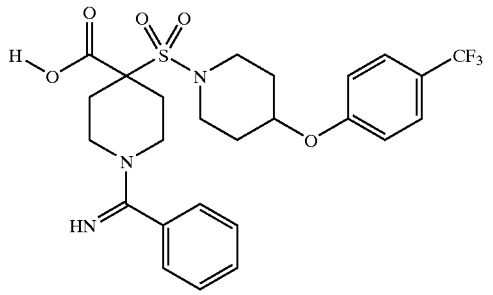

To a solution of the compound from Part 2 (5 g, 1 mmol) in tetrahydrofuran (45 mL) was added potassium trimethylsilonate (Aldrich, 2.5 g, 3 mmol). The reaction was complete overnight (about 18 hours) at room temperature. A nitrogen stream was blown over the surface of the solution to concentrate the mixture. Then water was added (20 mL) followed by aqueous 10% HCl until pH=7. The zwitterion was filtered washed with water (10 mL) and dried in vacuo with over phosphorous pentoxide yielding the amidino acid as a solid (3 g). $^{1}H$ NMR and mass spectroscopy were consistent with the desired structure.

Part 4: Preparation of

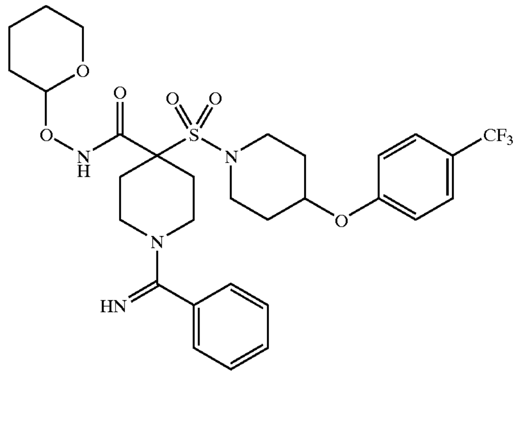

To a solution of the zwitterion product in Part 3 (2.7 g, 5 mmol) in dimethylacetamide (20 mL) were added 1-(3-dimethylaminopropyl)-3-ethylcarbodiimide hydrochloride (Sigma, 2.5 g, 9.4 mmol), N-hydroxybenzotriazole hydrate (Aldrich, 1.9 g, 7.4 mmol) and heated to 50° C. for 15 minutes. Thereafter, N-methylmorpholine (Aldrich, 4.0 mL, 18.6 mmol) was added, followed by O-(tetrahydro-2H-pyran-2-yl) hydroxylamine (2 g, 9.4 mmol). The mixture was stirred and heated for 1 hour, then left to stir at room temperature overnight (about 18 hours). After complete reaction, the reaction mixture was concentrated under reduced pressure. The residue was taken up in ethyl acetate (250 mL) and washed with saturated potassium carbonate (1×–150 mL), and brine (1×–150 mL). The organic layer was then dried over $Na_2SO_4$ and concentrated to afford the THP-protected amidino hydroxamate as a pink solid (1.7 g). $^{1}H$ NMR and mass spectroscopy were consistent with the desired structure.

Part 5: Preparation of

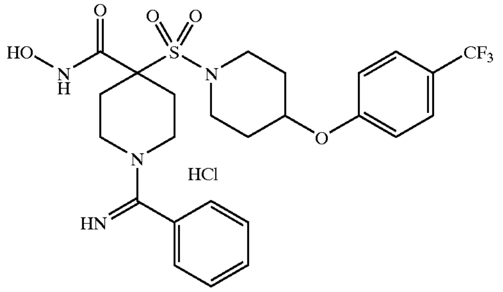

The solid from Part 4 (2.5 g) was slurried in methanol (800 mg) diethyl ether (30 mL). To this was added 4 N HCl in dioxane (10 mL) and the reaction mixture was stirred for 2 hours, after which RPHPLC showed complete reaction. The dioxane was concentrated by half, diethyl ether was added (100 mL) and the white solid (1 g, 70% yield) filtered and dried under vacuum. $^{1}H$ NMR showed the desired compound. Mass spectroscopy showed: $C_{25}H_{29}F_3N_4O_5S$—HClM$^{+H}_{found}$=591 (M$^{+H}_{calc}$=591).

EXAMPLE 44

Preparation of N-Hydroxy-1-[(4-hydroxyphenyl) iminomethyl)-4-[[4-[4-(trifluoromethyl)phenoxy]-1-piperidinyl]sulfonyl]-4-piperidinecarboxamide, Monohydrochloride

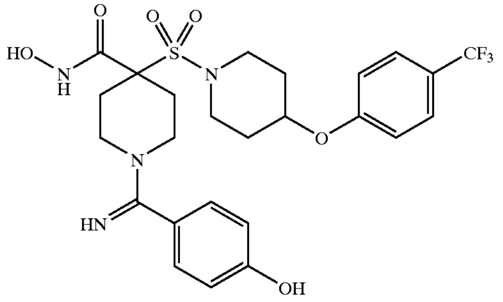

Part 1: Preparation of

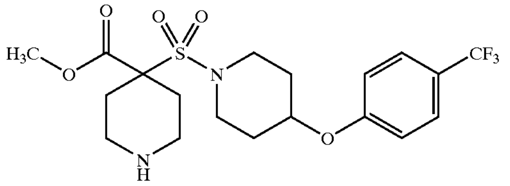

To a methanol (160 mL) solution of methyl 1-(phenylmethyl)-4-[[4-[4-(trifluoromethyl)phenoxy]-1-piperidinyl]sulfonyl]-4-piperidinecarboxylate of Example 12, Part F (40 g), and ammonium formate (15 g) was added 10%Pd on carbon (16 g, Degussa type catalyst). The black mixture was refluxed for 30–45 minuets. After complete reaction, the mixture is cooled and filtered through a Celite® pad. The solvent was removed under reduced pressure to give 34 g of the amino ester as an oil that solidified on standing. $^{1}H$ NMR and mass spectroscopy were consistent with the desired structure.

Part 2: Preparation of

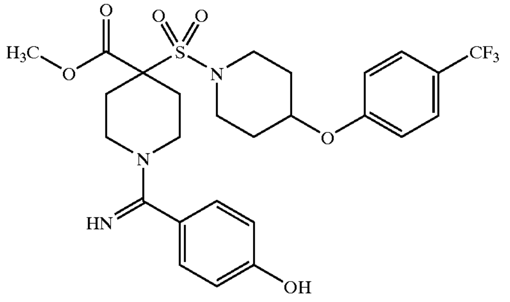

To a solution of compound from Part 1 (6 g, 1.2 mmol) in Dimethylformamide (20 mL) was added ethyl 4-hydroxybenzimidate HCl (Aldrich, 3 g, 1.4 mmol) followed by DMAP (150 mg). The reaction mixture was stirred and heated to 50 degrees Celcius for 8 hours. The progress of the reaction was monitored by RPHPLC. Work up comprised removing the solvent under reduced pressure. The resulting solid was triturated with water (50 mL) and filtered to give 5 grams of the amidino ester product. $^{1}H$ NMR and mass spectroscopy were consistent with the desired structure.

Part 3: Preparation of

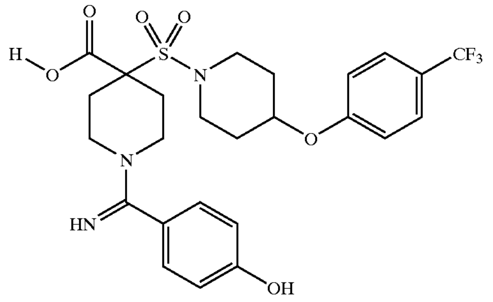

To a solution from Part 2 (3 g, 5 mmol) in tetrahydrofuran (20 mL) was added potassium trimethylsilonate (Aldrich, 1.5 g, 10 mmol). The reaction was complete overnight (about 18 hours) at room temperature. A nitrogen stream was blown over the surface of the solution to concentrate the mixture. Then water was added (20 mL) followed by aqueous 10% HCl until pH=7. The zwitterion was filtered, washed with water (10 mL) and dried in vacuo with over phosphorous pentoxide yielding the amidino acid as a solid (2.4 g). $^{1}H$ NMR and mass spectroscopy were consistent with the desired structure.

Part 4: Preparation of

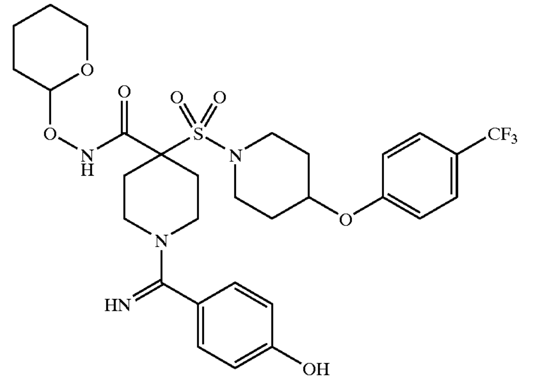

To a solution of the zwitterion product in Part 3 (1.1 g, 5 mmol) in dimethylacetamide (20 mL) were added 1-(3-dimethylaminopropyl)-3-ethylcarbodiimide hydrochloride (Sigma, 1.8 g, 9.4 mmol) and N-hydroxybenzotriazole hydrate (Aldrich, 1.0 g, 7.4 mmol), and the mixture was heated to 50° C. for 15 minutes. N-methylmorpholine (Aldrich, 2.0 mL, 18.6 mmol) was then added, followed by O-(tetrahydro-2H-pyran-2-yl) hydroxylamine (1.1 g, 9.4 mmol). The mixture was stirred and heated for 1 hour, then left to stir at room temperature overnight (about 18 hours). After complete reaction, the reaction mixture was concentrated under reduced pressure. The residue was taken up in ethyl acetate (250 mL) and washed with saturated potassium carbonate (1×–150 mL), and brine (1×–150 mL). The organic layer was then dried over $Na_2SO_4$ and concentrated to afford the THP-protected hydroxamate as a viscous oil. The oil solidified (700 mg) on standing. $^{1}H$ NMR and mass spectroscopy were consistent with the desired structure.

Part 5: Preparation of

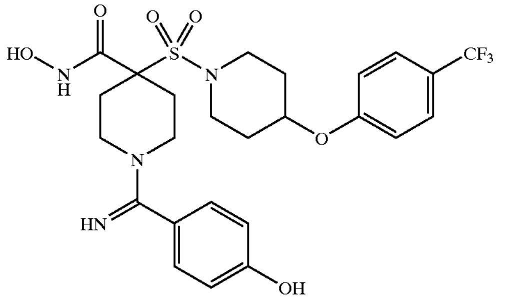

The solid from Part 4 (700 mg) was slurried in methanol (800 mg) and diethyl ether (30 mL). To this was added 4 N HCl in dioxane (10 mL) and stirred for 2 hours, after which RPHPLC showed complete reaction. The dioxane was concentrated by half, diethyl ether was added (100 mL) and the white solid (500 mg, 70% yield) filtered and dried under vacuum. $^{1}H$ NMR showed the desired compound. Mass spectroscopy showed:

$C_{25}H_{29}F_3N_4O_6S$—HCl; $M^{+H}_{found}$=607 ($M^{+H}_{calc}$=607).

EXAMPLE 45

Preparation of 1-(2-Furanylcarbonyl)-N-hydroxy-4-[[4-[4-(trifluoromethyl)-phenoxy]-1-piperidinyl]sulfonyl)-4-piperidinecarboxamide

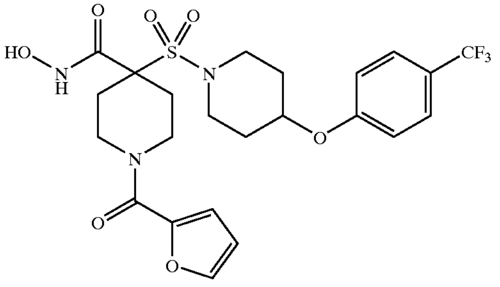

Part 1: Preparation of

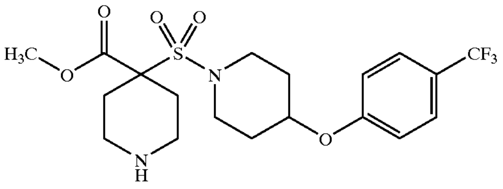

To a methanol (160 mL) solution of methyl 1-(phenylmethyl)-4-[[4-[4-(trifluoromethyl)phenoxy]-1-piperidinyl]sulfonyl)-4-piperidinecarboxylate of Example 12, Part F (40 g), and ammonium formate (15 g) was added 10%Pd on carbon (16 g, Degussa type catalyst). The black mixture was refluxed for 30–45 minuets. After complete reaction the mixture was cooled and filtered through a Celite® pad. The solvent was removed under reduced pressure to give 34 g of the amino ester as an oil that solidified on standing. $^1$H NMR and mass spectroscopy were consistent with the desired structure.

Part 2: Preparation of

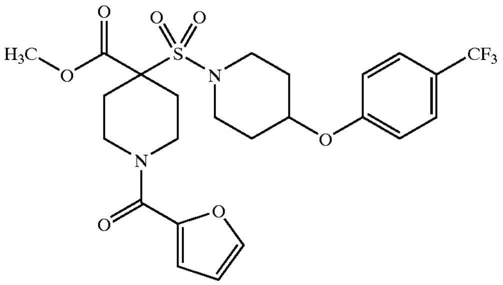

To a solution of the compound from Part 1 (4 g, 0.8 mmol) in methylene chloride (75 mL) was added furfuryl chloride (Aldrich, 1.2 g, 0.8 mmol), followed by N-methylmorpholine (4 mL, 2.3 mmol). The reaction mixture was stirred for 1 hour. The progress of the reaction was monitored by RPHPLC. Work up comprised removing the solvent under reduced pressure. Water (50 mL) was added to the resulting solid and the product as extracted with ethyl acetate (100 mL). The ethyl acetate was washed with brine and dried over sodium sulfate to give the amide ester as a solid (6 grams of product). $^1$H NMR and mass spectroscopy were consistent with the desired structure.

Part 3: Preparation of

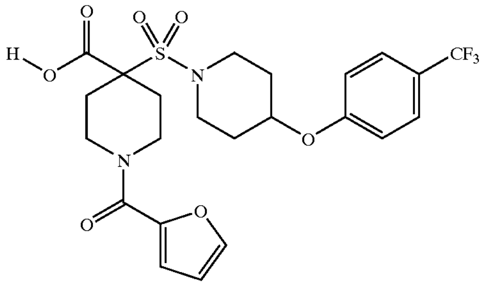

To a solution of the compound from Part 2 (6 g, 5 mmol) in tetrahydrofuran (20 mL) was added potassium trimethylsilonate (Aldrich, 5 g, 15 mmol). The reaction was complete overnight (about 18 hours) at room temperature. A nitrogen stream was blown over the surface of the solution to concentrate the mixture. Then water was added (20 mL), followed by aqueous 10% HCl until pH=7. The product was extracted with methylene chloride (100 mL). The methylene chloride layer was dried over sodium sulfate and the solvent removed under reduced pressure to result in the amide acid as a tan solid (39). $^1$H NMR and mass spectroscopy were consistent with the desired structure.

Part 4: Preparation of

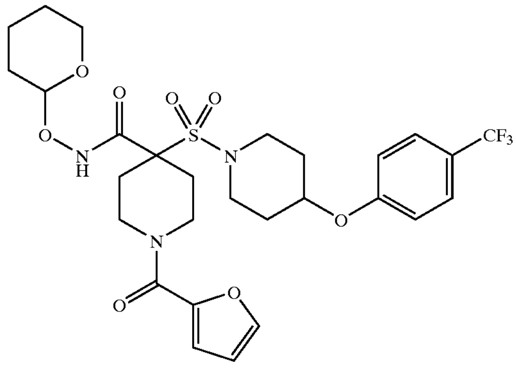

To a solution of the product in Part 3 (3 g, 5 mmol) in dimethylformamide (50 mL) were added 1-(3-dimethylaminopropyl)-3-ethylcarbodiimide hydrochloride (Sigma, 1.8 g, 9.4 mmol) and N-hydroxybenzotriazole hydrate (Aldrich, 1.0 g, 7.4 mmol), and the mixture was heated to 50° C. for 15 minutes. N-methylmorpholine (Aldrich, 2.0 mL, 18.6 mmol) was added, followed by O-(tetrahydro-2H-pyran-2-yl) hydroxylamine (1.1 g, 9.4 mmol). The mixture was stirred and heated or 1 hour then left to stir at room temperature overnight (about 18 hours). After complete reaction, the reaction mixture was concentrated under reduced pressure. The residue was taken up in ethyl acetate (250 mL) and washed with saturated potassium carbonate (1×–150 mL), and brine (1×–150 mL). The organic layer was then dried over $Na_2SO_4$ and concentrated to afford THP-protected hydroxamte as a viscous oil. The oil solidified (2.1 q) on standing. $^1$H NMR and mass spectroscopy were consistent with the desired structure.

Part 5: Preparation of

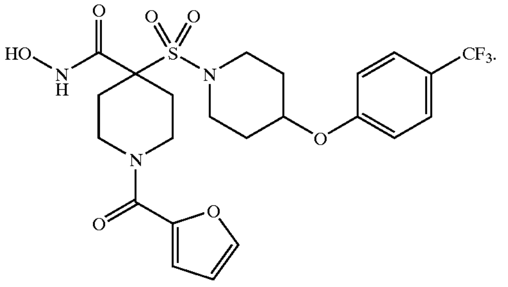

The solid from Part 4 (70 mg) was dissolved in acetonitrile (25 mL). To this was added 10% aq. HCl (25 mL), and stirring for 2 hours, after which RPHPLC showed complete reaction. A stream of nitrogen was blown of the surface on the reaction and concentrated by half to result in a precipitate. The white solid was filtered. The solid was crystallized in methanol to give (2.5 g) of a white solid and dried under vacum. $^1H$ NMR showed the desired compound. Mass spectroscopy showed: $C_{23}H_{26}E_3N_3O_7S$ ; $M^{+H}_{found}$=545 ($M^{+H}_{calc}$=545).

EXAMPLE 46

Preparation of N-Hydroxy-1-[2-(methylthio)-4-pyrimidinyl]-4-[[4-[4-(trifluoromethyl)phenoxy)-1-piperidinyl]sulfonyl]-4-piperidinecarboxamide, Monohydrochloride

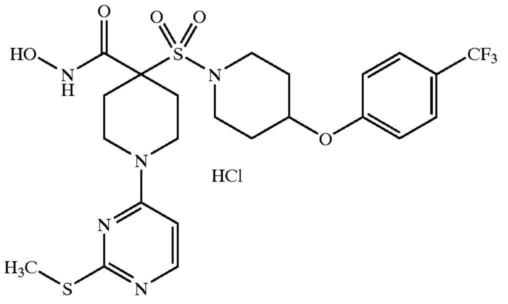

Part 1: Preparation of

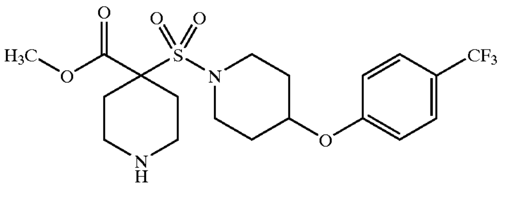

To a methanol (160 r) solution of methyl 1-(phenylmethyl)-4-[[4-[4-(trifluoromethyl)phenoxy]-1-piperidinyl]sulfonyl]-4-piperidinecarboxylate of Example 12, Part F (40 g), and ammonium formate (15 g) was added 10%Pd on carbon (16 g, Degussa type catalyst). The black mixture was refluxed for 30–45 minuets. After complete reaction the mixture is cooled and filtered through a Celite® pad. The solvent is removed under reduced pressure to give 34 g of the amino ester as an oil that solidified on standing. $^1H$ NMR and mass spectroscopy were consistent with the desired structure.

Part 2: Preparation of

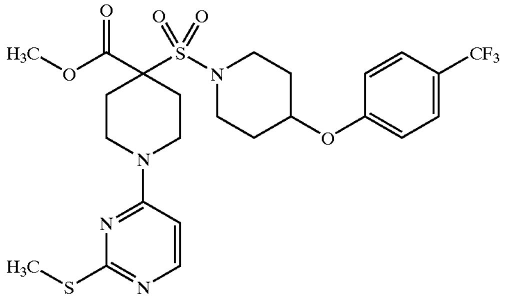

To a solution of the compound from Part 1 (5 g, 0.8 mmol) in dimethylformamide (50 mL) was added chloro-1-methylthiopiperizine (Aldrich, 1.2 g, 1.2 mmol) followed by potassium carbonate (4 g, 2.3 mmol). The reaction mixture was heated to 80 degrees Celsius and stirred for 1 hour, then stirred at room temperature for 12 hours. The progress of the reaction was monitored by RPHPLC. Work up comprised removing the solvent under reduced pressure. Water (50 mL) was added to the resulting solid and the product was filtered to give the N-heteroaryl ester as a solid (6.7 grams of product). $^1H$ NMR and mass spectroscopy were consistent with the desired structure.

Part 3: Preparation of

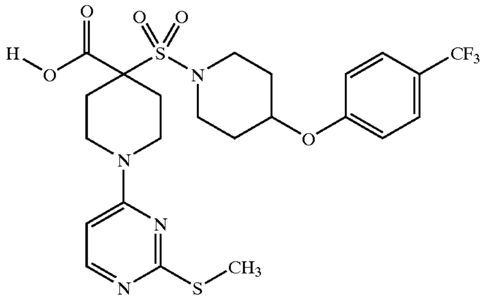

To a solution of the compound from Part 2 (6.5 g, 5 mmol) in tetrahydrofuran (50 mL) was added potassium trimethylsilonate (Aldrich, 5 g, 15 mmol). The reaction was complete overnight (about 18 hours) at room temperature. A nitrogen stream was blown over the surface of the solution to concentrate the mixture. Then water was added (20 mL) followed by aqueous 10% HCl until pH=7. The product was extracted with methylene chloride (100 mL). The methylene chloride layer was dried over sodium sulfate and the solvent removed under reduced pressure to result in N-heteroaryl acid as a tan solid (4.2 g). $^1H$ NMR and mass spectroscopy were consistent with the desired structure.

Part 4: Preparation of

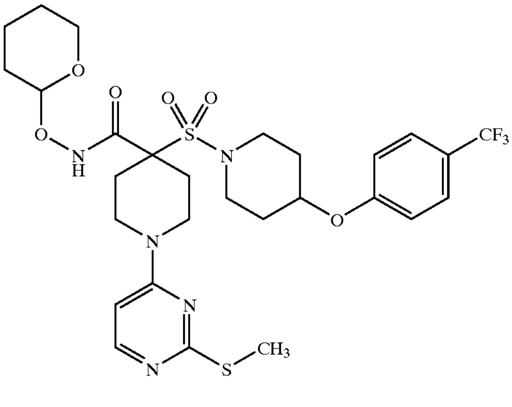

To a solution of the product in Part 3 (4.6 g, 5 mmol) in dimethylformamide (50 mL) were added 1-(3-dimethylaminopropyl)-3-ethylcarbodiimide hydrochloride (Sigma, 5 g, 9.4 mmol) and N-hydroxybenzotriazole hydrate (Aldrich, 1.0 g, 7.4 mmol), and the mixture was heated to 50° C. for 15 minutes. N-methylmorpholine (Aldrich, 4.0 mL, 18.6 mmol) was added, followed by O-(tetrahydro-2H-pyran-2-yl) hydroxylamine (6.1 g, 9.4 mmol). The mixture stirred and heated for 1 hour then left to stir at room temperature overnight (about 18 hours). After complete reaction, the reaction mixture was concentrated under reduced pressure. The residue was taken up in water (75 mL) and filtered to result in the N-heteroaryl THP-protected hydroxamate as a pink solid (4.1 g) $^1$H NMR and mass spectroscopy were consistent with the desired structure.

Part 5: Preparation of

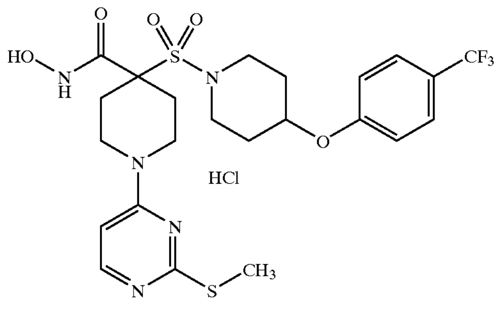

The solid from Part 4 (5.1 g) was dissolved in acetonitrile (25 mL). To this was added 10% aq. HCl (25 mL), and the mixture was stirred for 2 hours, after which RPHPLC showed complete reaction. A stream of nitrogen was blown of the surface of the reaction and the volume concentrated by half to result in a precipitate. The white solid was filtered. The solid was crystallized in methanol to give (2.5 g) of a white solid and dried under vacuum. $^1$H NMR showed the desired compound. Mass spectroscopy showed: $C_{23}H_{28}F_3N_5O_5S_2$—HCl; $M^{+H}_{found}$=612 ($M^{+H}_{calc}$=612).

EXAMPLE 47

Preparation of 1-Cyclopropyl-N-hydroxy-4-[[4-[4-(tri-fluoromethoxy)phenoxy]-1-piperidinyl]sulfonyl]-4-piperidinecarboxamide, Monohydrochloride

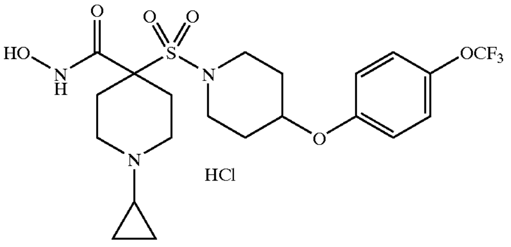

Part 1: Preparation of

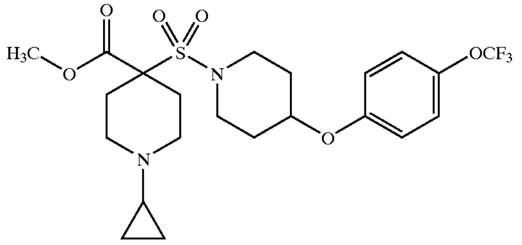

To a solution of 4-[[4-[4-(trifluoromethoxy)-phenoxy]-1-piperidinylsulfonyl]-4-piperidine-carboxylic acid, methyl ester from Part H of Example 15 (14 g, 30 mmol) in methanol (80 mL) were added [(1-ethoxycyclopropyl)oxy]trimethylsilane (Aldrich, 21 g, 120 mmol), acetic acid (18 g, 300 mmol), sodium cyanoborohydride (5.5 g, 90 mmol) and molecular sieves (7 g). The reaction mixture was stirred and heated for 8 hours. The progress of the reaction was monitored by RPHPLC. Work up comprised filtering the reaction mixture through a pad of Celite® then concentrating the methanol and partitioning the residue between in $H_2O$ (50 mL) and ethyl acetate (500 mL). The organics were washed with brine (1×–100 mL), dried over $Na_2SO_4$, and concentrated to afford the amino ester as a solid (8 g) after crystallization in methanol. $^1$H NMR and mass spectroscopy were consistent with the desired structure.

Part 2: Preparation of

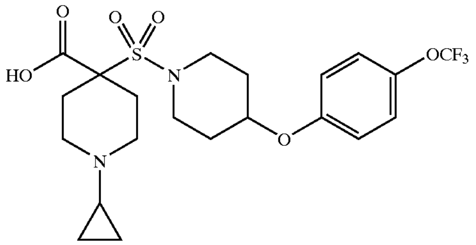

To a solution of the compound from Part 1 (8 g, 15 mmol) in tetrahydrofuran (20 mL) was added potassium trimethylsilonate (Aldrich, 4 g, 30 mmol) The reaction was complete overnight (about 18 hours) at room temperature. A nitrogen stream was blown over the surface of the solution to concentrate the mixture. Then water was added (20 mL) followed by aqueous 10% HCl until pH=7. The zwitterion was filtered washed with water (10 mL) and dried in vacuo with over phosphorous pentoxide yielding the amino acid as a solid (6.8 g). $^1$H NMR and mass spectroscopy were consistent with the desired structure.

Part 3: Preparation of

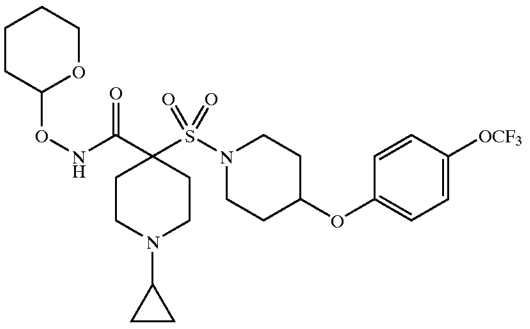

To a solution of the zwitterion product in Part 2 (6.8 g, 14 mmol) in dimethylformamide (50 mL) were added 1-(3-dimethylaminopropyl)-3-ethylcarbodiimide hydrochloride (Sigma, 5.2 g, 28 mmol) and N-hydroxybenzotriazole hydrate (Aldrich, 3.7 g, 28 mmol), and the mixture was heated to 50° C. for 15 minutes. N-methylmorpholine (Aldrich, 2.0 mL, 28 mmol) was added followed by O-(tetrahydro-2H-pyran-2-yl) hydroxylamine (3.2 g, 28 mmol). The mixture stirred and heated for 1 hour then left to stir at room temperature overnight (about 18 hours). After complete reaction, the reaction mixture was concentrated under reduced pressure. The residue was taken up in ethyl acetate (250 mL) and washed with saturated potassium carbonate (1×–150 mL), and brine (1×–150 mL). The organic layer was then dried over $Na_2SO_4$ and concentrated o afford a viscous oil. The oil was purified on $SiO_2$ using ethyl acetate in hexane to give 6.5 g of the THP-protected hydroxamate as a clear oil the solidified with addition of methanol. $^1H$ NMR and mass spectroscopy were consistent with the desired structure.

Part 4: Preparation of

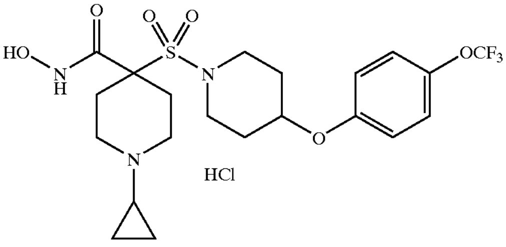

The solid from Part 3 (6.8 g) was slurried in methanol (4.5 mL). To this was added 4 N HCl in dioxane(60 mL), and the mixture stirred for 2 hours, after which RPHPLC showed complete reaction. The dioxane was concentrated by half, diethyl ether was added (100 mL) and the white solid (5.5 g, 90% yield) filtered and dried under vacuum. $^1H$ NMR showed the desired compound. Mass spectroscopy showed: $C_{21}H_{28}F_3N_3O_6S$—HCl; $M^{+H}_{found}$=543 ($M^{+H}_{calc}$=543)

EXAMPLE 48

Preparation of 4-(1,4-Dioxa-8-azaspiro-[4.5]dec-8-ylsulfonyl)tetrahydro-N-hydroxy-2H-pyran-4-carboxamide

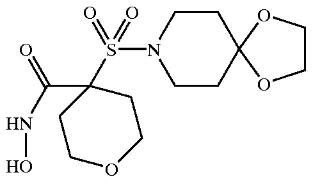

Part A: 1,4-Dioxa-8-azaspiro[4.5]-decane (Aldrich, 10.0 g, 69.8 mmol) and triethylamine (Aldrich, 14.6 mL, 105 mmol) were slurried in dichloromethane (150 mL) and cooled to zero° C. A solution of methane sulfonyl chloride (Aldrich, 8.1 mL, 105 mmol) in dichloromethane (60 mL) was slowly added, maintaining the temperature at less than 10° C. After the addition, the ice bath was removed and the reaction stirred 1 hour as it came to ambient temperature. After the disappearance of the starting material, the solvent was removed and the residue was taken up in ethyl acetate (200 mL) and $H_2O$ (50 mL). Once separated, the organic layer was washed with 5% $KHSO_{4aq}$ (3×–50 mL) and brine (1×–50 mL). The organic layer was then dried over $Na_2SO_4$, filtered, and concentrated to afford the sulfonamide as a yellow solid (15.3 g, 99% yield). $^1H$ NMR showed the desired compound.

Part B: Oven-dried glassware was charged with the sulfonamide of Part A (15.3 g, 69.1 mmol) and tetrahydrofuran (70 mL) and cooled to −75° C. Lithium bis(trimethylsilyl) amide (Aldrich, 1.0 M in tetrahydrofuran, 140 mL, 140 mmol) was slowly added, keeping temperature less than −60° C. The reaction was stirred for 30 minutes after the addition and was then charged with a solution of methyl chloroformate (Aldrich, 5.4 mL, 69.1 mmol) in tetrahydrofuran (30 mL), again keeping the temperature at less than −60° C. After stirring for 1 hour at −75° C., the reaction was quenched with saturate $NH_4Cl_{aq}$, keeping temperature below −20° C. The aqueous phase froze into a solid chunk of ice. After warming to 5° C., the mixture was extracted via ethyl acetate (3×–200 mL). Organics were washed with saturated $NH_4Cl_{aq}$ (2×–100 mL) and brine (1×–100 ml), then dried over $Na_2SO_4$ and concentrated to afford a yellow oil that slowly solidified The oily solid was recrystallized from ethyl acetate and hexanes to afford the methylene ester (8.2 g, 44% yield). $^1H$ showed the desired compound with some starting material present.

Part C: To a solution of the methylene ester of Part B (3.5 g, 12.5 mmol) and dibromo-diethylether (Lancaster, 1.7 mL, 13.8 mmol) in N,N-dimethylformamide (25 mL) was added 18-Crown-6 (Aldrich, 500 mg, 1.9 mmol ), followed by potassium carbonate (Aldrich, 6.0 g, 43.8 mmol). The mixture was heated at 60° C. for 4 hours after which more potassium carbonate (1.9 g, 13.7 mmol) was added, and the reaction continued at 60° C. for 14 hours. The reaction was worked up by pouring the mixture into stirring 10% $HCl_{aq}$ (200 mL). A gummy solid resulted that was extracted via ethyl acetate (3×–300 mL). Organics were washed with brine (2×–200 mL), dried over $Na_2SO_4$, and concentrated to afford the methyl ester, 9091–157, as a dark brown oil (2.2 g, 50% yield). $^1H$ NMR showed the desired compound.

Part D: To a solution of the methyl ester from Part C (2.2 g, 6.3 mmol) in tetrahydrofuran (15 mL) was added potassium trimethylsilonate (Aldrich, 1.9 g, 15.1 mmol). Work up comprised removing the tetrahydrofuran and taking the residue up in $H_2O$ (100 mL). The solution was washed with diethyl ether (50 mL). The aqueous was then cooled to zero° C. and 10% $HCl_{aq}$ was slowly added until pH=3. The acidic mixture was then extracted via ethyl acetate (3×–150 mL). The organics were washed with brine (1×–100 mL), dried over $Na_2SO_4$, and concentrated to afford the carboxylic acid as a dark oil (1.5 g, 70% yield). $^1H$ NMR showed the desired compound.

Part E: To a solution of the acid of Part D (1.5 g, 4.5 mmol) in dimethylacetamide (10 mL) was added N-methylmorpholine (Aldrich, 1.5 mL, 13.5 mmol), followed by N-hydroxybenzotriazole hydrate (Aldrich, 0.73 g, 5.4 mmol), O-(tetrahydro-2H-pyran-2-yl) hydroxylamine (0.77 g, 6.7 mmol), and 1-(3-dimethylaminopropyl)-3-ethylcarbodiimide hydrochloride (Sigma, 1.3 g, 6.7 mmol). The mixture stirred overnight (about 18 hours) and was then stripped of solvent The residue was taken up in ethyl acetate (300 m) and water (20 mL). After separation, the organic layer was washed with 5% $KHSO_{4aq}$ (1×–200 mL), saturated potassium carbonate (1×–100 mL), and brine (1×–150 mL). The organic layer was then dried over $Na_2SO_4$ and concentrated to afford the THP-protected hydroxamate, 9091–161, as a brown foam (1.6 g, 76% yield). $^1H$ NMR showed the desired compound.

Part F: The THP-protected hydroxamate of Part E (1.6 g, 3.7 mmol) was dissolved in acetonitrile (15 mL) and stirred with 10% $HCl_{aq}$ (20 mL) for 2 hours. The acetonitrile was removed via $N_2$ stream giving an oil that was crystallized from t-butylmethylether to afford the hydroxamate as a brown solid (0.82 g, 63% yield). $^1H$ NMR showed he desired compound. HRMS for $C_{13}H_{22}N_2O_7S$ showed $M^{+H}_{found}$=351 ($M^{+H}_{calc}$=351).

EXAMPLE 49

Preparation of 4-[[4-[[(3R,5R)-rel-3,5-Dimethyl-1-piperidinyl]carbonyl]-1-piperidinyl]sulfonyl] tetrahydro-N-hydroxy-2H-pyran-4-carboxamide and 4-[[4-[[(3R,5S)-rel-3,5-dimethyl-1-piperidinyl] carbonyl]-1-piperidinyl]sulfonyl]tetrahydro-N-hydroxy-2H-pyran-4-carboxamide

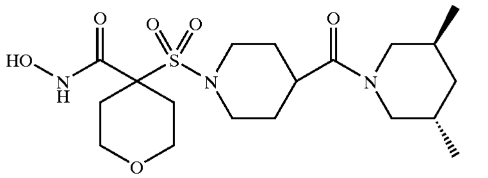

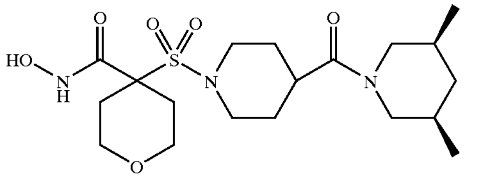

Part A: To a solution of N-BOC-isoponic acid (4.0 g, 17.4 mmol) in dimethylacetamide (30 mL) were added N-methylmorpholine (Aldrich, 5.7 mL, 52.2 mmol), 3,5-dimethylpiperadine (70% cis, Aldrich, 3.5 mL, 26.1 mmol), N-hydroxybenzotriazole hydrate (Aldrich, 2.8 g, 20.9 mmol), and 1-(3-dimethylaminopropyl)-3-ethylcarbodiimide hydrochloride (Sigma, 5.0 g, 26.1 mmol). The mixture was stirred overnight (about 18 hours) at ambient temperature. To work up, the solvent was removed and the residue was taken up in ethyl acetate (300 mL) then washed with 5% $KSO_{4aq}$ (1×ϕml), saturated $K_2CO_{3aq}$ (1×100 mL), and brine (1×100 mL). After drying over $Na_2SO_4$, the organic layer was filtered and concentrated to afford the BOC-piperidine as a tan oil that slowly crystallized (5.4 g, 96% yield). $^1H$ NMR showed the desired compound existing as both the cis- and trans-isomers.

Part B: To a solution of the BOC-piperidine of Part A, (5.4 g, 16.6 mmol) in 1,4-dioxane (20 mL) was added 4 N HCl in 1,4-dioxane (15 mL) and stirred. After 45 minutes, the solvent was removed and the solid was slurried in diethyl ether, filtered, and washed with diethyl ether (2×20 mL). Drying afforded the amine salt as a white solid (2.6 g, 60% yield). $^1H$ NMR showed desired product as both cis- and trans-isomers.

Part C: To a cooled solution (zero° C.) of the amine salt of Part B (2.2 g, 9.8 mmol) and triethylamine (Aldrich, 3.4 mL, 24.5 mmol) in dichloromethane (50 mL) was slowly added a solution of methane sulfonyl chloride (Aldrich, 1.1 mL, 14.7 mmol) in dichloromethane (25 mL), maintaining the temperature at less than 10° C. After the addition, the ice bath was removed and the reaction stirred 2 hours as it came to ambient temperature. After the disappearance of the starting material, the solvent was stripped and the residue was taken up in ethyl acetate (100 mL) and $H_2O$ (25 mL). Once separated, the organic layer was washed with 5% $KHSO_{4aq}$ (3×–50 mL) and brine (1×–50 mL). The organic layer was then dried over $Na_2SO_4$, filtered, and concentrated to afford the sulfonamide as a dried foamy oil (2.5 g, 83% yield). $^1H$ NMR showed the desired product as both the cis- and trans-isomers.

Part D: Oven-dried glassware was charged with the sulfonamide of Part C (2.5 g, 8.3 mmol) and tetrahydrofuran (17 mL) and cooled to −75° C. Lithium bis(trimethylsilyl) amide (Aldrich, 1.0 M in tetrahydrofuran, 16.5 mL, 16.5 mmol) was slowly added, keeping temperature less than −60° C. The reaction was stirred for 30 minutes after the addition and was then charged with a solution of methyl chloroformate (Aldrich, 0.64 mL, 8.3 mmol) in tetrahydrofuran (8 mL), again keeping the temperature at less than −60° C. After stirring for 1 hour at −75° C., the reaction was quenched with saturated $NH_4Cl_{aq}$ (50 mL), keeping temperature at less than −20° C. The aqueous portion froze into a solid chunk of ice. After warming to 50° C., the mixture was extracted with ethyl acetate (3×–100 mL). Organics were washed with saturated $NH_4Cl_{aq}$ (2×–50 mL) and brine (1×–50 mL), then dried over $Na_2SO_4$ and concentrated to afford the methylene ester as a brown oil (2.7 g, 90% crude yield). $^1H$ showed the desired compound (cis- and trans-).

Part E—To a solution of the methylene ester of Part D (2.7 g, 7.5 mmol) and dibromo-diethylether (Lancaster, 1.0 mL, 8.2 mmol) in N,N-dimethylformamide (15 mL) was added 18-Crown-6 (Aldrich, 200 mg, 1.0 mmol) followed by potassium carbonate (Aldrich, 3.6 g, 26.2 mmol). The mixture was heated at 60° C. for 4 hours, after which more potassium carbonate (1.0 g, 7.2 mmol) was added, and the reaction continued at 60° C. for 14 hours. The reaction was worked up by pouring the mixture into stirring 10% $HCl_{aq}$ (200 mL). The gummy solid that developed was extracted via ethyl acetate (3×100 mL). The organics were washed with brine (1×50 mL), dried over $Na_2SO_4$, and filtered to afford the methyl ester as a brown oil (3.4 g, quantitative yield). $^1H$ NMR showed the desired compound (cis- and trans-).

Part F: To a solution of the methyl ester from Part E (3.0 g, 7.0 mmol) in tetrahydrofuran (20 mL) was added potassium trimethylsilonate (Aldrich, 2.2 g, 17.4 mmol). The reaction was stirred overnight (about 18 hours) at ambient temperature. The work up consisted of stripping the tetrahydrofuran and taking the residue up in $H_2O$ (40 mL) The solution was washed with diethyl ether (30 mL). The aqueous composition was then cooled to 0° C. and 10% $HCl_{aq}$ was slowly added until pH=3. The acidic mixture was then extracted via ethyl acetate (3×–100 mL). The organics were washed with brine (1×–50 mL), dried over $Na_2SO_4$, and concentrated to give a brown oil (2.4 g). The oil was crystallized from acetone/diethylether to afford the carboxylic acid as a brown solid (2.2 g, 76% yield). $^1H$ showed the desired compound as cis- and trans-isomers.

Part G: To a solution of the acid from Part F (2.2 g, 5.3 mmol) in dimethylacetamide (12 mL) were added N-methylmorpholine (Aldrich, 1.7 mL, 15.9 mmol) followed by N-hydroxybenzotriazole hydrate (Aldrich, 0.86 g, 6.4 mmol), O-(tetrahydro-2H-pyran-2-yl) hydroxylamine (0.94 g, 8.0 mmol), and 1-(3-dimethylaminopropyl)-3-ethylcarbodiimide hydrochloride (Sigma, 1.5 g, 8.0 mmol). The mixture stirred overnight and was then stripped of solvent. The residue was taken up in ethyl acetate (250 mL) and washed with 5% $NaHSO_{4aq}$ (1×–150 mL), saturated potassium carbonate (1×–150 mL), and brine (1×–150 mL). The organic was then dried over $Na_2SO_4$ and concentrated to afford the THP-protected hydroxamate as a brown oil (2.2 g, 81% yield). $^1H$ NMR showed the desired compound as both isomers.

Part H—The THP-protected hydroxamate of Part G (2.2 g, 3.7 mmol) was dissolved in 1,4-dioxane (10 mL) and stirred with 4 N HCl in 1,4-dioxane (15 mL, 60 mmol) or 2 hours. The solvents were stripped and the residue was taken up in acetonitrile (10 mL) and $H_2O$ (10 mL). This solution was filtered and purified via prep RP LC to afford the cis isomer as a white solid (0.40 g, 22% yield) and the trans isomer as a white solid (0.20 g, 11%). $^1H$ NMR showed the desired compounds. HRMS for $C_{19}H_{33}N_3O_6S$ showed $M^{+H}_{found}$=432 ($M^{+H}_{calc}$=432) for both isomers.

EXAMPLE 50

Preparation of N-Hydroxy-1-(4-methylphenyl)-4-[[4-[4-(trifluoro-methyl)phenoxy]-1-piperidinyl]sulfonyl]-4-piperidinecarboxamide, Monohydrochloride

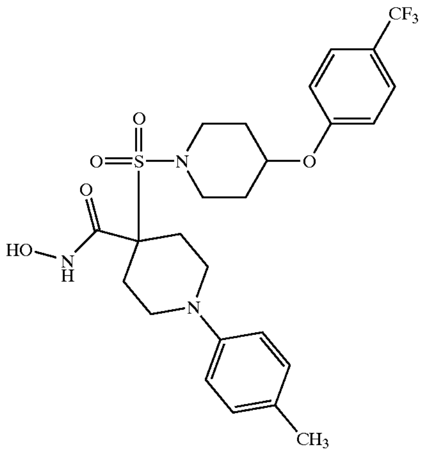

Part A: To a mixture of dibromotriphenyl-phosphorane (Aldrich, 50 g, 118 mmol) in dichloremethane (200 mL) at zero C was added N,N-bis-(2-hydroxyethyl)-P-toluidine (Fluka, 10.5 g, 54 mmol). A slight exotherm was detected. The ice bath was removed and the reaction stirred eighteen hours at ambient temperature. After completion, the solvent was evaporated affording an oily solid that was purified by silica gel (ethyl acetate) to yield the N,N-bis(2-bromoethyl)-p-toluidine as a white solid (12.6 g, 73% yield). $^1H$ NMR showed the desired compound.

Part B: To a solution of the sulfonamide ester of part D of Example 36 (12.0 g, 31.5 mmol) in N,N-dimethylformamide (63 mL) were added potassium carbonate (Aldrich, 13.0 g, 94.5 mmol), 18-crown-6 (Aldrich, 500 mg, 2.0 mmol), and N,N-bis(2-bromoethyl)-p-toluidine of Part A (10.0 g, 31.5 mmol). The mixture was heated at 80° C. for 18 hours after which more potassium carbonate (1.0 g, 7.2 mmol) was added, and the reaction continued at 80° C. for 3 hours. The reaction was worked up by removing the solvent by roto-evaporation. The residue was slurried in ethyl acetate and filtered through a Celite® pad. The filtrate was concentrated and the residue crystallized from hot methanol to afford the methyl ester as a yellow solid (9.0 g, 53% yield). $^1H$ and $^{19}F$ NMR showed the desired compound.

Part C: To a solution of the methyl ester of Part B (9.0 g, 16.6 mmol) in tetrahydrofuran (40 mL) was added potassium trimethylsilonate (Aldrich, 6.4 g, 50 mmol). The reaction stirred overnight (about 18 hours) at ambient temperature. Work up comprised stripping the tetrahydrofuran and taking the residue up in $H_2O$ (5 ML), cooling to zero° C., and titrating to pH 7 via 6 N HCl. Solids formed and were collected then washed with diethyl ether. The solid was dried in vacuo to afford the carboxylic acid as a white solid (8.7 g, 100% yield). $^1H$ and $^{19}F$ NMR showed the desired compound.

Part D: To a solution of the carboxylic acid of Part C (8.7 g, 16.5 mmol) in N,N-dimethylformamide (35 mL) was added N-methylmorpholine (Aldrich, 5.4 mL, 49.5 mmol) followed by N-hydroxybenzotriazole hydrate (Aldrich, 2.7 a, 19.8 mmol), O-(tetrahydro-2H-pyran-2-yl) hydroxylamine (3.9 g, 33 mmol), and 1-(3-dimethylaminopropyl)-3-ethylcarbodiimide hydrochloride (Sigma, 4.7 g, 24.8 mmol). The mixture stirred at 40° C. for 4 hours and was then stripped of solvent. The residue was taken up in ethyl acetate/water (350 mL/50 mL). After separation, the aqueous layer was extracted with ethyl acetate (2x50 mL). The combined organic layers were washed with 5% $KHSO_{4aq}$ (1x–30 mL) and brine (1x–30 mL). The organic layer was then dried over $Na_2SO_4$ and concentrated yielding an orange oily foam that was recrystallized from methanol to afford the THP-protected hydroxamate as a white solid (0.74 g, 64% yield). $^1H$ and $^{19}F$ NMR showed the desired compound.

Part E: The THP-protected hydroxamate of Part D (8.9 g, 14.2 mmol) was wetted with methanol (3.6 mL) and stirred with 4 N HCl in dioxane (36 mL) for one hour. The solvents were evaporated and the oil slurried in diethyl ether to yield a solid which was filtered and dried. This afforded hydroxamate as a white solid (8.0 g, 98% yield). $^1H$ and $^{19}F$ NMR showed the desired compound. HRMS for $C_{25}H_{30}F_3N_3O_5S$ showed $M^{+H}_{found}$=542 ($M^{+H}_{calc}$=542).

EXAMPLE 51

Preparation of N-Hydroxy-1-(4-methylphenyl)-4-[[4-[4-(trifluoro-methoxy)phenoxy]-1-piperidinyl]-sulfonyl]-4-piperidinecarboxamide, Monohydrochloride

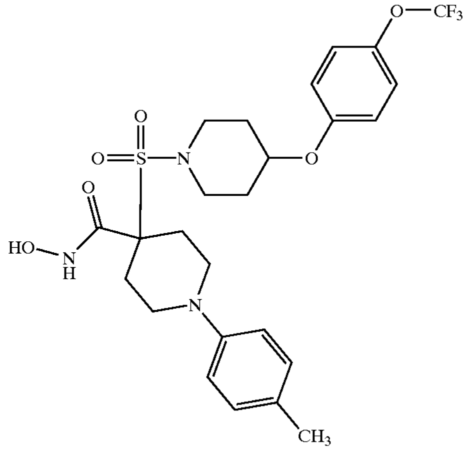

Part A: To a solution of N,N-bis(2-hydroxyethyl)-p-toluidine (Fluka, 30 g, 154 mmol) in dichloromethane (100 mL) was slowly added a solution of thionylchloride (Aldrich, 36 mL, 462 mmol) in dichloromethane (300 mL)). The reaction was stirred for 2 hours at ambient temperature then heated for 1 hour at reflux. After removing the solvent, the residue was slurried in ethyl acetate. The ethyl acetate was decanted, then the residue was slurried in hexanes giving a solid precipitate. The solid was filtered and washed with hexanes followed by diethyl ether. The solid was dried to afford the N,N-bis(2-dichloroethyl)-p-toluidine monochloride salt as a gray solid (24 g, 58% yield). $^1$H showed the desired compound.

Part B: The N,N-bis(2-dichloroethyl)-p-toluidine monochloride salt of Part A was suspended in water (200 mL) and neutralized (pH=7) with saturated sodium bicarbonate. This was then extracted with a mixture of diethyl ether (200 mL) and ethyl acetate (50 mL) which dissolved all solids. The organic layer was washed with brine (1×–100 mL) then dried over $Na_2SO_4$, filtered and concentrated to give the free base amine as a brown oil (6.59 g, 28.39 mmol). The oil was dissolved in 4-methyl-2-pentanone (50 mL) and lithium bromide (Aldrich, 24.66 g, 283.90 mmol) was added. The mixture was heated at reflux for 39 hours. After cooling, the dark mixture was filtered through a Celite pad. After washing the pad, the total filtrate was concentrated. The residue was partitioned between diethyl ether (100 mL) and water (50 mL). The organic layer was washed with water (50 ml), brine (50 mL), then dried over $Na_2SO_4$ and concentrated to afford the dibromo-amine as a brown oil (7.82 g, 86% yield). $^1$H showed the desired compound. LCMS showed mixture of dibromo- and monochloro/monobromo compounds.

Part C: To a slurry of 4-hydroxypiperadine (Aldrich, 273 g, 2.7 mol) in tetrahydrofuran (1.8 L) was added triethylamine (Aldrich, 402 mL, 2.9 mol), followed by slow addition of a solution of di-tert-butyl-dicarbonate (Aldrich, 600 g, 2.7 mol) in tetrahyrdofuran (1.2 L). The temperature was monitored and maintained below 32° C. The mixture was stirred for 4 hours before working up. Work up comprised removing the tetrahydrofuran by roto-evaporation and taking the residue up in ethyl acetate (300 mL). The organic was washed with 5% $KHSO_{4aq}$ (2×–1 L) and brine (1×–1 L) then dried over anhydrous $Na_2SO_4$, filtered, and concentrated to afford a crude brown oil. The oil was crystallized from hexanes providing the N-SOC-4-hydroxypiperidine as a tan solid (515 g, 95% yield). $^1$H NMR showed the desired compound.

Part D: To a slurry of the N-BOC-4-hydroxypiperidine of Part C (515 g, 2.6 mol) and triethylamine (390 mL, 2.8 mol) in dichloromethane (1.9 L) cooled to zero° C. under $N_2$ was slowly added a solution of methane sulfonyl chloride (Aldrich, 209 mL, 2.7 mol) in dichloromethane (100 mL). After the addition, the ice bath was removed and the reaction stirred 24 hours. Work up comprised removing the solvent by roto-evaporation and taking the residue up in ethyl acetate (2.0 L) then washing with $H_2O$ (2×–1 L), brine (1×–1 L), and drying over $Na_2SO_4$. The mixture was filtered and concentrated to afford the piperidine mesylate, SC 80998, as a cream colored solid (662 g, 91% crude yield). $^1$H NMR showed the desired compound.

Part E: Oven-dried glassware was charged with 4-trifluoromethoxyphenol (Apollo, 100.0 g, 561 mmol) and N,N-dimethylformamide (1.12 L). After cooling to –5° C., NaH (Aldrich, 60% oil dispersion, 11.2 g, 281 mmol) was slowly added. The ice bath was removed and the reaction stirred for 1.5 hours. The piperidine mesylate of Part D (78.4 g, 281 mmol) was then added and the reaction was heated to 80° C. for 2 hours. This process was repeated until a total of 2.5 equivalents (1.4 moles) of both the piperidine mesylate and NaH were added. Work up consisted of stripping the solvents by roto-evaporation and taking the residue up in diethyl ether (1 L) and $H_2O$ (400 mL). The layers were separated and the organic layer was washed with $H_2O$ (1×–500 mL) and brine (2×–500 mL) then dried over $Na_2SO_4$, filtered, and concentrated to afford the BOC-piperidine, SC 83075, as a crude oil (315 g, 100" crude yield). $^1$H NMR showed the desired compound along with the elimination byproduct, 1-tert-butoxycarbonyl-1,2,3,6-tetrahydropyridine.

Part F: To an overhead-stirring solution of 4 N HCl in dioxane (1.4 L, 5.6 mol) was poured the crude oil of the BOC-piperidine of Part E (203 g, 561 mmol). The solvents were then stripped and the residue was slurried in diethyl ether and filtered. The solid was dissolved in $H_2O$ (500 mL) and titrated to pH 10 with saturated potassium carbonate aqueous solution. The aqueous was extracted with dichloromethane (3×–800 ml). The organics were combined, dried over $Na_2SO_4$, filtered and concentrated to afford the piperidine, 10507–054, as a foamy solid (136 g, 93% yield). $^1$H NMR showed the desired compound.

Part G: The piperidine of Part F (136 g, 520 mmol) and triethylamine (Aldrich, 110 mL, 781 mmol) were slurried in dichloromethane (1.6 L) and cooled to zero° C. A solution of methane sulfonyl chloride (Aldrich, 60.2 mL, 781 mmol) in dichloromethane (200 mL) was slowly added, maintaining the temperature at less than 10° C. After the addition, the ice bath was removed and the reaction came to ambient temperature. After one hour, the starting material was gone. To work up, the solvent was stripped and the residue was taken up in ethyl acetate (1 L) and $H_2O$ (1 L). Once separated, the aqueous layer was extracted with ethyl acetate (2×–400 mL). The combined organic layers were washed with 5% $KHSO_{4aq}$ (2×–600 mL) and brine (1×–600 mL). The organic layers were then dried over $Na_2SO_4$, filtered, and concentrated to afford the piperidine mesylate, So 80766, as a brown solid (139 g, 79% yield. $^1$H NMR showed the desired compound.

Part H: Oven-dried glassware was charged with the piperidine mesylate of Part G (92 g, 271 mmol) and tetrahydrofuran (600 mL) and cooled to –75° C. Lithium bis (trimethylsilyl)amide (Aldrich, 1.0 M in tetrahydrofuran, 705 mL, 705 mmol) was slowly added, keeping temperature below –60° C. The reaction was stirred for 30 minutes after the addition and was then charged with a solution of methyl chloroformate (Aldrich, 27.4 mL, 325 mmol) in tetrahydrofuran (100 mL) again keeping the temperature below –60° C. After stirring for 1 hour at –75° C., the reaction was quenched with saturated $NH_4Cl_{aq}$ keeping temperature below –20° C. The aqueous phase froze into a solid chunk of ice. After warming to 5° C., the mixture was extracted via ethyl acetate (3×–200 mL). Organics were washed with saturated $NH_4Cl_{aq}$ (2×–100 mL) and brine (1×–100 ml), then dried over $Na_2SO_4$ and concentrated to afford a tan oil. The oil was crystallized from methanol. The solid was collected and washed with hexanes to afford the methylene ester as a tan solid (78 g, 72%). $^1$H NMR showed the desired compound with some starting material present.

Part I: To a mixture of the methylene ester of Part H (4.0 g, 10.0 mmol), potassium carbonate (Aldrich, 4.1 g, 30.0 mmol), and 18-crown-6 (Aldrich, 0.1 g, 0.04 mmol) in N,N-dimethylformamide (20 mL) was added the dibromo-amine of Part B (3.2 g, 10.0 mmol). The mixture was heated at 80° C. for 18 hours, after which more potassium carbonate (1.5 g, 12 mmol) was added, and the reaction continued at 80° C. for 14 hours. The reaction was worked up by removing the solvent by roto-evaporation. The residue was slurried in acetonitrile and filtered through a elite pad. The filtrate was concentrated and the residue was purified on silica gel (ethyl acetate/hexanes) to afford the methyl ester as an orange solid (2.6 g, 46% yield). $^1$H and $^{19}$F NMR showed the desired compound.

Part J: To a solution of the methyl ester of Part I (2.1 g, 3.8 mmol) in tetrahydrofuran (10 mL) was added potassium trimethylsilonate (Aldrich, 1.4 g, 11.3 mmol). The reaction was stirred overnight (about 18 hours) at ambient temperature. Work up comprised removing the tetrahydrofuran and taking the residue up in $H_2O$ (5 mL), cooling to zero° C., and titrating to pH 7 with 6 N HCl. Solids formed and were collected then washed with acetonitrile. The solid was dried in vacuo to afford the carboxylic acid, X14137, as a tan solid (1.0 g, 50% yield). $^1H$ and $^{19}F$ NMR showed the desired compound.

Part K: To a solution of the carboxylic acid of Part J (1.0 g, 1.8 mmol) in N,N-dimethylformamide (5 mL) was added N-methylmorpholine (Aldrich, 0.6 mL, 5.5 mmol) followed by N-hydroxybenzotriazole hydrate (Aldrich, 0.29 g, 2.2 mmol), O-(tetrahydro-2H-pyran-2-yl) hydroxylamine (0.42 g, 3.6 mmol), and 1-(3-dimethylaminopropyl)-3-ethylcarbodiimide hydrochloride (Sigma, 0.52 g, 2.7 mmol). The mixture was stirred at 40° C. for a hours and was then stripped of solvent. The residue was taken up in ethyl acetate/water (50 mL/10 mL). After separation, the aqueous layer was extracted with ethyl acetate (2×–20 mL). The combined organic layers were washed with 5% $NaHSO_{4aq}$ (1×–30 mL) and brine (1×–30 mL). The organic was then dried over $Na_2SO_4$ and concentrated yielding an orange oily foam that was recrystallized from methanol to afford the THP-protected hydroxamate as a white solid (0.74 g, 64% yield). $^1H$ and $^{19}F$ NMR showed the desired compound.

Part L: The protected hydroxamate of Part K (0.7 g, 1.1 mmol) was dissolved in methanol (0.5 mL) and stirred with 4 N HCl in dioxane (2.8 mL) for one hour. After which, LC showed no more starting material. The solvents were evaporated and the oil slurried in diethyl ether to yield a solid which was filtered and dried. This afforded the hydroxamate, as a white solid (0.6 g, 92% yield). $^1H$ and $^{19}F$ NMR showed the desired compound. HRMS for $C_{25}H_{30}F_3N_3O_6S$ showed $M^{+H}_{found}$=558 ($M^{+H}_{calc}$=558).

EXAMPLE 52

Preparation of Tetrahydro-N-hydroxy-4-[[4-(phenylmethyl)-1-piperazinyl]-sulfonyl]-2H-pyran-4-carboxamide, Monohydrochloride

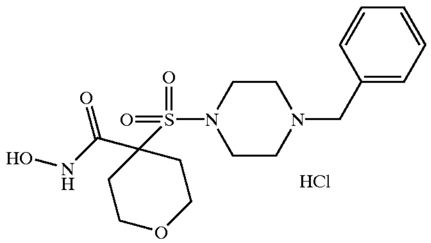

Part A: To a cooled solution, zero C, of N-benzylpiperazine (Aldrich, 10.0 g, 56.7 mmol) in dichloromethane (75 mL) was added triethylamine (Aldrich, 11.9 mL, 851mmol), followed by the slow addition of a solution of methane sulfonyl chloride (Aldrich, 6.6 mL, 85.1 mmol) in dichloromethane (25 mL) After the addition, the ice bath was removed and the reaction stirred at ambient temperature for 1.5 hours. Once completed, the solvent was evaporated and the residue was taken up in ethyl acetate (200 mL) and water (100 mL). The phases were separated and the aqueous phase was treated with 1 N $NaOH_{aq}$ (100 mL), then extracted with ethyl acetate (2×–200 mL). The combined organic layers were washed with 5% $KHSO_{4aq}$ (2×–100 mL) and brine (1×–100 mL) The ethyl acetate was then dried over $Na_2SO_4$ and concentrated to afford the piperazine mesylate, as an orange solid (13.0 g, 90% yield). $^1H$ NMR showed the desired compound.

Part B: Oven-dried glassware was charged with the piperazine mesylate of Part A (12.6 g, 50 mmol) and tetrahydrofuran (160 mL) and cooled to −75° C. Lithium bis (trimethylsilyl)amide (Aldrich, 1.0 M in tetrahydrofuran, 165 mL, 165 mmol) was slowly added, keeping temperature at less than −60° C. The reaction was stirred for 30 minutes after the addition and was then charged with a solution of methyl chloroformate (Aldrich, 3.9 mL, 94.5 mmol) in tetrahydrofuran (80 mL) again keeping the temperature at less than −60° C. After stirring for 1 hour at −75° C., the reaction was quenched with saturated $NH_4Cl_{aq}$, keeping temperature below −20° C. The aqueous portion froze into a solid chunk of ice. After warming to 50° C., the mixture was extracted with ethyl acetate (3×–200 mL). Organics were washed with saturated $NH_4Cl_{aq}$ (2×–100 mL) and brine (1×–100 ml), then dried over $Na_2SO_4$ and concentrated to afford the methylene ester as a brown oil (19.6 g, quantitative yield). $^1H$ NMR showed the desired compound.

Part C: To a solution of the methylene ester of art B (10.0 g, 32.0 mmol), potassium carbonate (Aldrich, 15.5 g, 112 mmol), and 18-crown-6 (Aldrich, 0.5 g, 2.0 mmol) in dimethylformamide (60 mL) was added dibromodiethylether (Lancaster, 4.4 mL, 35.3 mmol). The mixture was heated at 60° C. for 18 hours, after which more potassium carbonate (1.5 g, 12 mmol) was added, and the reaction continued at 60° C. for 4 hours. The reaction was worked up by removing the solvent by roto-evaporation. The residue was taken up in ethyl acetate (250 mL) and water (100 mL). The layers were separated and the organic was washed with water (1×–100 mL) and brine (2×–100 mL) then dried over $Na_2SO_4$ and concentrated to afford a black oil. The oil was purified via silica gel (ethyl acetate/hexanes) yielding the methyl ester as a yellow oil (7.3 g, 60% yield). $^1H$ NMR showed the desired compound.

Part D: To a solution of the methyl ester of Part C (3.5 g, 9.2 mmol) in tetrahydrofuran (20 mL) was added potassium trimethylsilonate (Aldrich, 3.5 g, 27.4 mmol). The reaction was stirred overnight (about 18 hours) at ambient temperature. Work up comprised removing the tetrahydrofuran and taking the residue up in $H_2O$ (8 mL), cooling to zero° C., and titrating to pH 7 with 6 N HCl. Solids formed and were collected and washed with water followed by diethyl ether. The solid was dried in vacuo to afford the carboxylic acid as an off white solid (0.75 a, 22% yield). $^1H$ NMR showed the desired compound.

Part E: To a solution of the carboxylic acid of Part D (0.75 g, 2.0 mmol) in dimethylacetamide (5 mL) was added N-methylmorpholine (Aldrich, 0.66 mL, 6.0 mmol) followed by N-hydroxybenzotriazole hydrate (Aldrich, 0.32 g, 2.4 mmol), O-(tetrahydro-2H-pyran-2-yl) hydroxylamine (0.35 g, 3.0 mmol), and 1-(3-dimethylaminopropyl)-3-ethylcarbodiimide hydrochloride (Sigma, 0.57 g, 3.0 mmol). The mixture was stirred at 40° C. for thirteen hours and was then stripped of solvent. The residue was purified by reverse phase chromatography (carbon-18, acetonitrile/water). The product was hydrolyzed on the column giving the hydroxamate as a white solid (0.54 g, 57% yield). $^1H$ and $^{19}F$ NMR showed the desired compound but as the trifluoracetic acid salt.

Part F: The hydroxamate of Part E (0.5 g, 1.0 mmol) was dissolved in 1,4-dioxane (3.0 mL) and stirred with 4 N HCl in dioxane (4 mL) for one hour. The solvent volume was reduced in half then diethyl ether was added, providing a solid that was filtered and washed with excess diethyl ether. The solid was dried to afford the hydrochloride salt as a white solid (0.4 g, 100% yield). $^1$H NMR showed the desired compound. HRMS for $C_{17}H_{25}F_3N_3O_5S$ showed $M^{+H}$found=384 ($M^{+H}_{calc}$=384).

EXAMPLE 53

Preparation of N-Hydroxy-1-(phenylmethyl)-4-[(4-phenyl-1-piperazinyl)sulfonyl]-4-piperidinecarboxamide, Bis(Trifluoroacetate)

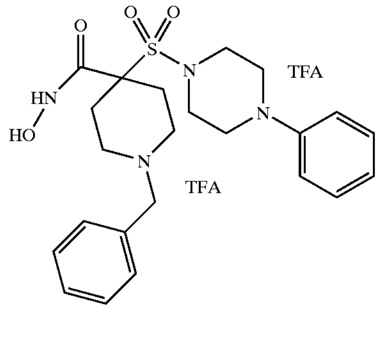

Part A: To a cooled solution, zero C, of N-phenylpiperazine (Aldrich, 10.0 g, 61.6 mmol) in dichloromethane (75 mL) was added triethylamine (Aldrich, 12.9 mL, 92.4 mmol) followed by the slow addition of a solution of methane sulfonyl chloride (Aldrich, 7.1 mL, 92.4 mmol) in dichloromethane (25 mL). After the addition, the ice bath was removed and the reaction stirred at ambient temperature for 1.5 hours. Once completed, the solvent was evaporated and the residue was taken up in ethyl acetate (200 mL) and water (100 mL). The phases were separated and the aqueous phase was treated with 1 N $NaOH_{aq}$ (100 mL) then extracted with ethyl acetate (2x–200 mL). The combined organic layers were washed with 5% $KHSO_{4aq}$ (2x–100 mL) and brine (1x–100 mL) The ethyl acetate was then dried over $Na_2SO_4$ and concentrated to afford the piperazine mesylate, SC 80658, as solid (13.0 g, 88% yield). $^1$H NMR showed the desired compound.

Part B: Oven-cried glassware was charged with the piperazine mesylate of Part A (12.6 g, 52.4 mmol) and tetrahydrofuran (160 mL) and cooled to −75° C. Lithium bis (trimethylsilyl)amide (Aldrich, 1.0 M in tetrahydrofuran, 184 mL, 184 mmol) was slowly added, keeping temperature below −60° C. The reaction was stirred for 30 minutes after the addition and was then charged with a solution of methyl chloroformate (Aldrich, 4.1 mL, 52.4 mmol) in tetrahydrofuran (80 mL) again keeping the temperature below −60° C. After stirring for 1 hour a. −75° C., the reaction was quenched with saturated $NH_4Cl_{aq}$, keeping temperature below −20° C. The aqueous does freeze into a solid chunk of ice. After warming to 5° C., the mixture was extracted via ethyl acetate (3x–200 mL). Organics were washed with saturated $NH_4Cl_{aq}$ (2x–100 mL) and brine (1x–100 ml), then dried over $Na_2SO_4$ and concentrated to afford the methylene ester, 9091–195, as a brown oil (14.1 g, 90%) $^1$H NMR showed the desired compound.

Part C: To a solution of the methylene ester of Part B (4.3 g, 14.4 mmol), potassium carbonate (Aldrich, 6.0 g, 43.2 mmol), and 18-crown-6 (Aldrich, 0.5 g, 2.0 mmol) in dimethylformamide (30 mL) was added N,N-bis(2-chloroethyl)-benzylamine, SC 9275A, (3.5 mL, 15.1 mmol). The mixture was heated at 60° C. for 18 hours. The reaction was worked up by removing the solvent by roto-evaporation. The residue was taken up in ethyl acetate (250 mL) and washed with water (1x–100 mL) and brine (2x–100 mL) then dried over $Na_2SO_4$ and concentrated to afford an orange solid. The solid was purified via silica gel (ethyl acetate/hexanes) yielding the methyl ester as a yellow solid (5.6 g, 35% yield). $^1$H NMR showed the desired compound.

Part D: To a solution of the methyl ester of Part C (2.0 g, 4.4 mmol) in tetrahydrofuran (10 mL) was added potassium trimethylsilonate (Aldrich, 1.7 g, 13.2 mmol). The reaction was stirred overnight (about 18 hours) at ambient temperature. Work up comprised removing the tetrahydrofuran and taking the residue up in $H_2O$ (8 mL), cooling to zero° C., and titrating to pH 6 with 6 N HCl. Solids formed and were collected, then washed with water followed by diethyl ether. The solid was dried in vacuo to afford the carboxylic acid as an off white solid (1.6 g, 84% yield). $^1$H NMR showed the desired compound.

Part E: To a solution of the carboxylic acid of Part D (1.6 g, 3.6 mmol) in dimethylacetamide (8 mL) was added N-methylmorpholine (Aldrich, 1.2 mL, 10.8 mmol) followed by by N-hydroxybenzotriazole hydrate (Aldrich, 0.58 g, 4.3 mmol), O-(tetrahydro-2H-pyran-2-yl) hydroxylamine (0.84 g, 7.2 mmol), and 1-(3-dimethylaminopropyl)-3-ethylcarbodiimide hydrochloride (Sigma, 1.0 g, 5.4 mmol). The mixture stirred overnight at ambient temperature and was then stripped of solvent. The residue was taken up in ethyl acetate (100 mL) then washed with aqueous saturated sodium bicarbonate (2x–50 mL) and brine (3x–50 mL). The organic was dried over $Na_2SO_4$ concentrated to afford the tetrahydropyran-protected hydroxamate as an oily foam (1.9 g, 95% yield). $^1$H NMR showed the desired compound.

Part F: The teurahydropyran-protected hydroxamate of Part E (1.6 g, 2.9 mmol) was dissolved in 1,4-dioxane (10.0 mL) and stirred with 4 N HCl in dioxane (12 mL) for 30 minutes. A solid formed that was filtered, washed with diethyl ether and dried. The solid was then purified by reverse phase chromatography (acetonitrile/water) affording the hydroxamate as a tan solid (1.4 g, 70% yield). $^1$H and $^{19}$F NMR showed the desired compound. HRMS for $C_{23}H_{30}N_4O_4S$ showed $M^{+H}_{found}$=439 ($M^{+H}_{calc}$=439)

EXAMPLE 54

Preparation of N-Hydroxy-1-(phenylmethyl)-4-[(4-phenyl-1-piperazinyl)sulfonyl]-4-piperidinecarboxamide, Dihydrochloride

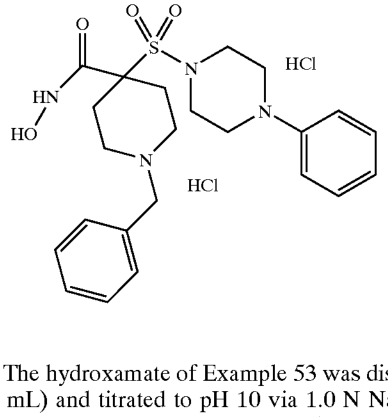

Part A: The hydroxamate of Example 53 was dissolved in water (10 mL) and titrated to pH 10 via 1.0 N NaOH. The mixture was extracted with ethyl acetate (4x–20 mL). The organics were combined, dried over $Na_2SO_4$, and concentrated to afford a foamy solid. This solid was dissolved in acetonitrile (5 mL) and then concentrated HCl (1 mL) was dripped in slowly. The mixture was stirred for ten minutes and then was concentrated to a tan oil. The oil was triturated with diethyl ether to form a solid that was dried in vacuo to afford the hydrochloride hydroxamate as a yellow solid (0.82 g, 53% yield). $^1$H and $^{19}$F NMR showed he desired compound. HRMS for $C_{23}H_{30}N_4O_4S$ showed $M^{+H}_{found}$=439 ($M^{+H}_{calc}$=439).

EXAMPLE 55

Preparation of 4-[[4-(4-Butoxy-3-methylphenyl)-1-piperazinyl]sulfonyl]-tetrahydro-N-hydroxy-2H-pyran-4-carboxamide

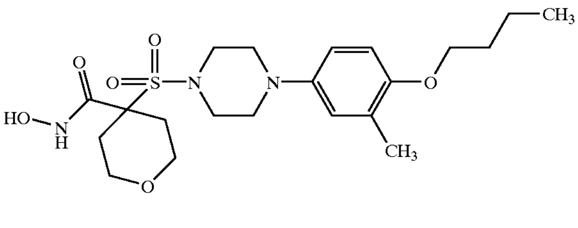

Part A: To a solution of 4-bromo-2-methylphenol (Transworld, 10.0 g, 53.5 mmol) in acetone (105 mL) was added potassium carbonate (Aldrich, 16.6 g, 120 mmol) followed by 1-iodobutane (7.3 mL, 64.2 mmol). The reaction stirred at reflux for 12 hours. After cooling to ambient temperature, the mixture was filtered through a Celite® pad. The filtrate was concentrated giving a yellow oil which was purified on silica gel (ethyl acetate/hexanes) to afford the bromophenyl ether, SC 83965, as a clear oil (10.8 g, 83% yield). $^1$H NMR showed the desired compound. HRMS for $C_{11}H1_{15}BrO$ showed $M^{+H}_{found}$=244 ($M^{+H}_{calc}$=244).

Part B: To a solution of the bromophenyl ether of Part A (10.0 g, 41.1 mmol) in toluene (80 mL) was added 1-tert-butylcarbonylpiperazine (Lancaster, 9.2 g, 49.4 mmol) and sodium tert-butoxide (Fluka, 5.5 g, 57.5 mmol). The reaction stirred at ambient temperature for twenty minutes. BINAP (Aldrich, 0.8 g, 1.2 mmol) and tris(dibenzylideacetone) dipalladium (0) (Aldrich, 0.4 g, 0.4 mmol) were then added and the reaction was stirred at 80° C. until the bromide was exhausted. Work up comprised cooling the mixture to ambient temperature, filtering through a Celite® pad, and concentrating the filtrate. The resulting residue was purified on silica gel (ethyl acetate/hexanes) to afford the BOC-piperazine as a black oil (6.4 g, 44% yield). $^1$H NMR showed the desired compound.

Part C: The oil of the BOC-piperazine of Part B (6.4 g, 18.4 mmol) was stirred with 4 N HCl in dioxane 23 mL, 92 mmol) for twenty minutes during which a solid formed. The solid was filtered and washed with diethyl ether and dried affording the phenylpiperazine as an off white solid, which was recrystallized from methanol to yield a white solid (3.6 g, 69% yield). $^1$H NMR showed the desired compound.

Part D: To a cooled solution, zero C, of the phenylpiperazine of Part C (3.5 g, 12.3 mmol) in dichloromethane (15 my) was added triethylamine (Aldrich, 4.3 mL, 30.8 mmol), followed by the slow addition of a solution of methane sulfonyl chloride (Aldrich, 1.4 mL, 18.4 mmol) in dichloromethane (10 mL). After the addition, the ice bath was removed and the reaction stirred at ambient temperature for 3 hours. Once completed, the solvent was evaporated and the residue was taken up in ethyl acetate (200 mL) and water (100 mL). The phases were separated and the aqueous was treated with 1 N $NaOH_{aq}$ (100 mL) then extracted with ethyl acetate (2x–200 mL). The combined organic layers were washed with water (1x–100 mL) and brine (1x–100 mL). The ethyl acetate layer was then dried over $Na_2SO_4$ and concentrated to afford a brown oil that was purified on silica gel (ethyl acetate/hexanes) to give the piperazine mesylate as a tan solid (3.1 g, 78% yield). $^1$H NMR showed the desired compound.

Part E: Oven-dried glassware was charged with the piperazine mesylate of Part D (3.1 g, 9.5 mmol) and tetrahydrofuran (20 mL) and cooled to −75° C. Lithium bis (trimethylsilyl)amide (Aldrich, 1.0 M in tetrahydrofuran, 28.5 mL, 28.5 mmol) was slowly added, keeping temperature below −60° C. The reaction was stirred for 30 minutes after the addition and was then charged with a solution of methyl chloroformate (Aldrich, 0.8 mL, 10 mmol) in tetrahydrofuran (10 mL) again keeping the temperature below −60° C. After stirring for 1 hour at −75° C., the reaction was quenched with saturated $NH_4Cl_{aq}$, keeping temperature less than −20° C. The aqueous phase froze into a solid chunk of ice. After warming to 5° C., the mixture was extracted via ethyl acetate (3x–100 mL). Organics were washed with saturated $NH_4Cl_{aq}$ (2x–100 mL) and brine (1x–100 ml), then dried over $Na_2SO_4$ and concentrated to give a brown solid that was recrystallized from methanol to afford methylene ester as a yellow solid (1.3 g, 36%) $^1$H NMR showed the desired compound.

Part F: To a solution of the methylene ester of Part E (1.3 g, 3.4 mmol), potassium carbonate (Aldrich, 1.4 g, 10.2 mmol), and 18-crown-6 (Aldrich, 0.08 g, 8 mmol) in N,N-dimethylformamide (10 mL) was added dibromodiethylether (Lancaster, 0.5 mL, 3.6 mmol). The mixture was heated at 60° C. for 18 hours and then worked up by removing the solvent by roto-evaporation. The residue was dissolved in ethyl acetate (250 mL) and water (100 mL). The layers were separated and the aqueous was extracted with ethyl acetate (2x–100 mL). The organics were combined and washed with 5% $HCl_{aq}$ (1x–50 mL), water (1x–100 mL), and brine (2x–100 mL) then dried over $Na_2SO_4$ and concentrated to afford a brown oil that was washed with hexanes to afford the methyl ester as an oil (1.5 g, quantitative yield). $^1$H NMR showed the desired compound.

Part G: To a solution of the methyl ester of Part F (1.5 g, 3.3 mmol) in tetrahydrofuran (10 mL) was added potassium trimethylsilonate (Aldrich, 1.3 g, 9.9 mmol). The was stirred overnight (about 18 hours) at ambient temperature. Work up comprised removing the tetrahydrofuran and taking the residue up in $H_2O$ (8 mL). The aqueous was washed with diethyl ether, which resulted in an emulsion. The emulsion was filtered affording a gummy solid that was slurried in acetone to give the carboxylic acid as a white powder (0.71 g, 51% yield). $^1$H NMR showed the desired compound.

Part H: To a solution of the carboxylic acid of Part G (0.7 g, 1.6 mmol) in N,N-dimethylformamide (5 mL) was added N-methylmorpholine (Aldrich, 0.5 mL, 4.8 mmol), followed by by N-hydroxybenzotriazole hydrate (Aldrich, 0.27 g, 2.0 mmol), O-(tetrahydro-2H-pyran-2-yl) hydroxylamine (0.37 g, 3.2 mmol), and 1-(3-dimethylaminopropyl)-3-ethylcarbodiimide hydrochloride (Sigma, 0.46 g, 2.4 mmol). The mixture was stirred at 40° C. for 8 hours, and was then stripped of solvent. The residue was purified by reverse phase chromatography (carbon-18, acetonitrile/water) After removing the acetonitrile from the desired fractions by roto-evaporation, the aqueous layer was extracted with ethyl acetate (2x–100 mL). The organics were dried over $Na_2SO_4$ and concentrated to afford the tetrahydropyran(THP)-protected hydroxamate as a white solid (0.57 g, 66% yield). $^1$H NMR showed the desired compound.

Part F: To the tetrahydropyran-protected hydroxamate of Part E (0.6 g, 1.0 mmol) was added methanol (0.2 mL) and 4 N HCl in dioxane (2.5 mL) and the mixture was stirred for one hour. The solvent was stripped and the residue was slurried in diethyl ether to provide a solid that was filtered and washed with excess diethyl ether. The solid was dried to afford the hydroxamate as a white solid (0.12 g, 26% yield). $^1$H NMR showed :he desired compound. HRMS for $C_{21}H_{33}N_3O_6S$ showed $M^{+H}_{found}$=456 ($M^{+H}_{calc}$=456).

EXAMPLE 56

In Vitro Metalloprotease Inhibition

The compounds prepared in the manner described in the Examples above were assayed for activity by an in vitro assay. Following the procedures of Knight et al., *FEDS Lett.* 296(3):263 (1992). Briefly, 4-aminophenylmercuric acetate (APMA) or trypsin-activated MMPs were incubated with various concentrations of the inhibitor compound at room temperature for 5 minutes.

More specifically, recombinant human MMP-13 and MMP-1 enzymes were prepared in laboratories of the assignee following usual laboratory procedures. MMP-13 from a full length cDNA clone was expressed as a proenzyme using a baculovirus as discussed in V.A. Luckow, insect Cell Expression Technology, pages 183–218, in *Protein Engineering: Principles and Practice*, J. L. Cleland et al eds., Wiley-Liss, Inc., (1996). See, also, Luckow et al., *J. Virol.*, 67:4566–4579 (1993); O'Reilly et al., *Baculovirus Expression Vectors: A Laboratory Manual*, W. H. Freeman and Company, New York, (1992); and King et al., *The Baculovirus Expression System: A Laboratory Guide*, Chapman & Hall, London (1992) for further details on use of baculovirus expression systems. The expressed enzyme was purified first over a heparin agarose column and then over a chelating zinc chloride column. The proenzyme was activated by APMA for use in the assay.

MMP-1 expressed in transfected HT-1080 cells was provided by Dr. Harold Welgus of Washington University, St. Louis, MO. The enzyme was also activated using APMA and was then purified over a hydroxamic acid column. Further specifics for preparation and use of these enzymes can be found in the scientific literature describing these enzymes. See, for example, *Enzyme Nomenclature*, Academic Press, San Diego, Calif. (1992) and the citations therein, and Frije et al., *J. Biol. Chem.*, 26(24): 16766–16773 (1994).

The enzyme substrate is a methoxycoumarin-containing polypeptide having the following sequence:

MCA-ProLeuGlyLeuDpaAlaArg$NH_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor T White Plates (Dynatech). The inhibitor or control solution was maintained in the plate for minutes and the substrate was added to provide a final concentration of 4 $\mu$M.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Table below, reported in terms of $IC_{50}$ to three significant figures, where appropriate.

Inhibition Table

| | $ED_{50}$ nM | | | | | | | |
|---|---|---|---|---|---|---|---|---|
| Example | MMP-1 | MMP-2 | MMP-3 | MMP-7 | MMP-8 | MMP-9 | MMP-13 | MMP-14 |
| 1 | <10,000 | 7.0 | — | — | — | — | 20.0 | — |
| 2 | 4,080 | <0.1 | 94.0 | 9,000 | 1.9 | 1.8 | 0.3 | 80.0 |
| 3 | 7,300 | <0.1 | 290 | — | 3.2 | 3.0 | 0.9 | 47.0 |
| 4 | <10,000 | 9.0 | 400 | — | 285 | 37.3 | 11.4 | 8,000 |
| 5 | <10,000 | 46.4 | — | — | — | — | 64 | — |
| 6 | 6,400 | 0.2 | 50.0 | — | 1.0 | 0.7 | 0.6 | 73.0 |
| 7 | 5,500 | 3,000 | — | — | — | — | 9,000 | — |
| 8 | 6,000 | 2.0 | 120 | — | 3.6 | 15.8 | 4.0 | 55.3 |
| 9 | <10,000 | 0.7 | 186 | — | 3.0 | 2.0 | 0.9 | 200 |
| 10 | 5,500 | 0.35 | 175 | — | 2.0 | 18.5 | 1.4 | 500 |
| 11 | <10,000 | 2.7 | 2,000 | — | 8.8 | 30.0 | 8.0 | 900 |
| 12 | 7,000 | 0.1 | 42.5 | <10,000 | 0.8 | 1.1 | 0.6 | 80.0 |
| | 4,500 | <0.1 | | | | | 0.25 | |
| | | | | | | | <0.1 | |
| 13 | 1,100 | 0.2 | — | — | — | — | 0.7 | — |
| 14 | <10,000 | <0.1 | 250 | <10,000 | 6.7 | 0.7 | <0.1 | 150 |
| | | 0.4 | | | | | 0.6 | |
| | | 0.1 | | | | | 0.5 | |
| 15 | 8,000 | 0.15 | 23.5 | <10,000 | 2.4 | 0.19 | 0.6 | 67.5 |
| | 3,000 | <0.1 | | | 2.0 | | <0.1 | |
| 16 | <10,000 | 1.4 | — | — | — | — | 8.0 | — |
| 17 | 2,200 | 0.1 | 23.5 | — | 1.9 | 0.7 | 0.1 | 45.4 |
| | 3,000 | <0.1 | | | 1.6 | | <0.1 | |
| 18 | <10,000 | 0.7 | 160 | — | 2.2 | 1.0 | 0.8 | 145 |
| 19 | 2,800 | — | 30.6 | <10,000 | 2.5 | 0.5 | 0.7 | 32.7 |
| 20 | — | — | — | — | — | — | — | — |

-continued

Inhibition Table
ED$_{50}$ nM

| Example | MMP-1 | MMP-2 | MMP-3 | MMP-7 | MMP-8 | MMP-9 | MMP-13 | MMP-14 |
|---|---|---|---|---|---|---|---|---|
| 21 | — | — | — | — | — | — | — | — |
| 22 | — | — | — | — | — | — | — | — |
| 23 | — | 0.1 | — | — | 12.0 | — | 0.4 | — |
| 24 | — | — | — | — | — | — | — | — |
| 25 | — | — | — | — | — | — | — | — |
| 26 | <10,000 | <10,000 | — | — | — | — | 2,000 | — |
| 27 | <10,000 | 5,300 | — | — | — | — | 670 | — |
| 28 | <10,000 | 0.3 | 270 | — | 4.3 | 1.8 | 1.0 | 360 |
| 29 | — | — | — | — | — | — | — | — |
| 30 | 4,000 | 0.3 | 28.6 | | 1.6 | 1.0 | 0.9 | 45.5 |
| 31 | <10,000 | 1.3 | 100 | — | 22.0 | 100 | 0.8 | 2,100 |
| 32 | <10,000 | <0.1 | — | — | — | — | <0.1 | — |
| 33 | 2,400 | 4.4 | — | — | — | — | 22.2 | — |
| 34 | <10,000 | 27.0 | — | — | — | — | 200 | — |
| 35 | <10,000 | <0.1 | 210 | — | 14.8 | 0.6 | <0.1 | 540 |
| 36 | <10,000 | 0.2 | — | — | — | — | 1.4 | — |
| 37 | <10,000 | 300 | — | — | — | — | 190 | — |
| 38 | <10,000 | 3.0 | 66.4 | — | 136 | 2.7 | 0.8 | <10,000 |
| 39 | <10,000 | 3,700 | — | — | — | — | 290 | — |
| 40 | 7,300 | 8.3 | — | — | — | — | 13.9 | — |
| 41 | <10,000 | 5.0 | — | — | — | — | 3.7 | — |
| 42 | 5,300 | 0.1 | 37.3 | <10,000 | 1.6 | 1.3 | 0.3 | 40.0 |
| 43 | 6,000 | 0.2 | 165 | — | 3.4 | 1.0 | 1.4 | 220 |
| 44 | 7,700 | 0.2 | — | — | — | — | 0.7 | — |
| 45 | — | — | — | — | — | — | — | — |
| 46 | <10,000 | 0.25 | — | — | — | — | 0.6 | — |
| 47 | <10,000 | <0.1 | 46.9 | <10,000 | 1.8<br>1.6 | 0.48 | <0.1 | 83.1 |
| 48 | 370 | 200 | — | — | — | — | 42.5 | — |
| 49 | <10,000 | <10,000 | — | — | — | — | <10,000 | — |
| 50 | <10,000 | 0.4 | — | — | — | — | 3.0 | — |
| 51 | <10,000 | <0.1 | 3,500 | — | 13.0 | 9.0 | 0.3<br><0.1 | 9,000 |
| 52 | <10,000 | 115 | — | — | — | — | 195 | — |
| 53 | 3,500 | 4.4 | — | — | — | — | 13.5 | — |
| 54 | 6,000 | 12.8 | — | — | — | — | 33.0 | — |
| 55 | <10,000 | 2.7 | — | — | — | — | 4.2 | — |

From the foregoing, it will be observed that numerous modifications and variations can be effected without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed:

1. A compound or a pharmaceutically acceptable salt thereof, wherein:

the compound corresponds in structure to the following formula:

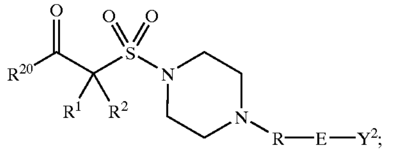

as to $R^1$ and $R^2$:

$R^1$ and $R^2$, taken together with the carbon to which they are bonded, form a heterocyclo or cycloalkyl, wherein: the heterocyclo or cycloalkyl optionally is substituted with up to 3 independently selected $R^x$ substituents, or $R^1$ and $R^2$ are independently selected from the group consisting of hydrogen, alkyl, alkoxyalkyl, alkylthioalkyl, alkenyl, alkynyl, aryl, arylalkyl, arylalkoxyalkyl, aryloxyalkyl, arylthioalkyl, arylalkylthioalkyl, cycloalkyl, bicycloalkyl, cycloalkenyl, cycloalkylalkyl, bicycloalkylalkyl, cycloalkyloxyalkyl, bicycloalkyloxyalkyl, cycloalkylalkoxyalkyl, bicycloalkyloxyalkyl, cycloalkylthioalkyl, bicycloalkylthioalkyl, cycloalkylalkylthioalkyl, bicycloalkylalkylthioalkyl, heterocyclo, heterocycloalkyl, heteroaryl, biarylalkyl, arylalkenyl, arylalkynyl, heterocycloalkylthio, heterocycloalkyloxyalkyl, heteroarylalkenyl, and heteroarylalkoxyalkyl, wherein:

any such substituent (other than hydrogen) optionally is substituted with up to 3 independently selected $R^x$ substituents;

each $R^x$ is independently selected from the group consisting of aryl, heteroaryl, heterocyclo, arylcarbonyl, alkylcarbonyl, heteroarylcarbonyl, halogen, cyano, aldehydo, hydroxy, $R^cR^d$-amino, $R^cR^d$-aminoalkyl, nitro, nitroso, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, alkoxyalkyl, $R^c$-oxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, alkoxycarbonyl-$R^c$-amino, arylalkoxycarbonyl-$R^c$-amino, aryloxycarbonyloxy, carboxy, $R^cR^d$-aminocarbonyloxy, $R^cR^d$-aminocarbonyl, $R^cR^d$-aminoalkylcarbonyl, hydroxy-$R^c$-aminocarbonyl, $R^cR^d$-aminosulfonyl, arylsulfonyl($R^c$)amino, $R^cR^d$-aminoalkoxy, $R^cR^d$-aminocarbonyl($R^c$)amino, trifluoromethylsulfonyl ($R^c$)amino, heteroarylsulfonyl-($R^c$)amino, alkylsulfonyl, arylsulfonyl($R^c$)amino, arylsulfonyl ($R^c$)aminocarbonyl, alkylsulfonyl-($R^c$)amino, arylcarbonyl($R^c$)-aminosulfonyl, and alkylsulfonyl ($R^c$)aminocarbonyl;

each $R^c$ and $R^d$ is independently selected from the group consisting of hydrogen, alkylcarbonyl, arylalkyl, arylcarbonyl, bisalkoxyalkyl, alkyl, haloalkyl, perfluoroalkyl, trifluoromethylalkyl, perfluoroalkoxyalkyl, alkoxyalkyl, cycloalkyl, heterocycloalkyl, heterocycloalkylcarbonyl, aryl, heterocyclo, heteroaryl, cycloalkylalkyl, aryloxyalkyl, heteroaryloxyalkyl, heteroarylalkoxyalkyl, heteroarylthioalkyl, arylsulfonyl, alkylsulfonyl, heteroarylsulfonyl, carboxyalkyl, alkoxycarbonylalkyl, aminocarbonyl, alkyliminocarbonyl, aryliminocarbonyl, heterocycloiminocarbonyl, arylthioalkyl, alkylthioalkyl, arylthioalkenyl, alkylthioalkenyl, heteroarylalkyl, haloalkylcarbonyl, hydroxyalkylcarbonyl, thiolalkylcarbonyl, alkenyl, alkynyl, alkoxycarbonyl, aryloxycarbonyl, aminoalkylcarbonyl, hydroxyalkyl, aminoalkyl, aminoalkylsulfonyl, and aminosulfonyl, wherein:

any amino nitrogen of $R^c$ or $R^d$ optionally is substituted with up to 2 independently selected $R^Y$ substituents, and any amino nitrogen of $R^c$ or $R^d$ optionally is substituted with 2 substituents such that the 2 substituents, taken together with the amino nitrogen, form:

a saturated or partially unsaturated heterocyclo group optionally substituted with up to 3 independently selected $R^w$ substituents, or a heteroaryl group optionally substituted with up to 3 independently selected $R^v$ substituents;

each $R^y$ is independently selected from the group consisting of arylalkyl, aryl, heteroaryl, heterocyclo, alkyl, alkynyl, alkenyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

any such substituent optionally is substituted by up to 2 independently selected Ru substituents, and the amino nitrogen of the substituted aminoalkyl or substituted aminoalkylcarbonyl is substituted with 1 or 2 independently selected $R^u$ substituents;

each $R^v$ is independently selected from the group consisting of aryl, heteroaryl, heterocyclo, arylcarbonyl, alkylcarbonyl, heteroarylcarbonyl, halogen, cyano, aldehydo, hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, arylalkoxycarbonylamino, aryloxycarbonyloxy, carboxy, $R^yR^z$-aminocarbonyloxy, $R^yR^z$-aminocarbonyl, $R^yR^z$-aminoalkylcarbonyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl-($R^y$)amino, arylsulfonyl($R^y$)amino, arylsulfonyl($R^y$)-aminocarbonyl, alkylsulfonyl($R^y$) amino, arylcarbonyl-($R^y$)aminosulfonyl, and alkylsulfonyl($R^y$)-aminocarbonyl;

each $R^w$ is independently selected from the group consisting of hydrogen, aryl, heteroaryl, heterocyclo, arylcarbonyl, alkylcarbonyl, heteroarylcarbonyl, halogen, cyano, aldehydo, hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, arylalkoxycarbonylamino, aryloxycarbonyloxy, carboxy, $R^yR^z$-aminocarbonyloxy, $R^yR^z$-aminocarbonyl, $R^yR^z$-aminoalkylcarbonyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl-($R^y$)amino, arylsulfonyl($R^y$)amino, arylsulfonyl($R^y$)-aminocarbonyl, alkylsulfonyl($R^y$)amino, arylcarbonyl-($R^y$)aminosulfonyl, and alkylsulfonyl ($R^y$)-aminocarbonyl;

each $R^z$ is independently selected from the group consisting of arylalkyl, aryl, heteroaryl, heterocyclo, alkyl, alkynyl, alkenyl, alkoxyalkyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

each such substituent optionally is substituted by up to 2 independently selected $R^u$ substituents, and the amino nitrogen of the substituted aminoalkyl or substituted aminoalkylcarbonyl is substituted with 1 or 2 independently selected $R^u$ substituents;

each $R^u$ is independently selected from the group consisting of arylalkyl, aryl, heteroaryl, heterocyclo, alkyl, alkynyl, alkenyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

the amino nitrogen of the substituted aminoalkyl or substituted aminoalkylcarbonyl is substituted with 1 or 2 substituents independently selected from the group consisting of alkyl, alkenyl, aryl, arylalkyl, heteroaryl, heteroarylalkyl, aryloxycarbonyl, and alkoxycarbonyl;

R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkyloxyalkyl, heterocycloalkyloxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to 2 substituents (in addition to $-EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl;

E is selected from the group consisting of:
(1) —CO($R^w$)—,
(2) —($R^w$)CO—,
(3) —CONH—,
(4) —HNCO—,
(5) —CO—,
(6) —$SO_2R^w$,
(7) —$R^wSO_2$,
(8) —$SO_2$—,
(9) —NH—$SO_2$—,
(10) —$SO_2$—NH—, and
(11) a bond;

$Y^2$ is selected from the group consisting of hydrogen, alkyl, alkoxy, haloalkyl, haloalkoxy, aryl, arylalkyl, cycloalkyl, heteroaryl, hydroxy, aryloxy, arylalkoxy, heteroaryloxy, heteroarylalkyl, haloalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl;

$R^{20}$ is selected from the group consisting of —O—$R^{21}$, —NH—O—$R^{22}$, and —NH—O—$R^{14}$;

$R^{21}$ is selected from the group consisting of hydrogen, $C_1$–$C_6$-alkyl, aryl, and aryl-$C_1$–$C_6$-alkyl;

$R^{22}$ is a selectively removable protecting group;

$R^{14}$ is selected from the group consisting of hydrogen and C(W)$R^{15}$;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkylcarbonyl, or the amino-$C_1$–$C_6$-alkyl nitrogen optionally is substituted with 2 substituents such that the 2 substituents, together with the nitrogen, form a 5- to 8-membered heterocyclo or heteroaryl ring;

W is selected from the group consisting of O and S; and in addition to any other possible substitutions, any heterocyclo or heteroaryl substituent optionally is substituted:

on any carbon ring atom with up to 2 substituents independently selected from the group consisting of halogen, alkyl, alkoxy, and oxo, on any sulfur ring atom with up to 2 oxo, and on any secondary nitrogen ring atom with a substituent independently selected from the group consisting of alkyl, arylalkoxycarbonyl, alkylcarbonyl, aryl, and arylalkyl.

2. A compound or salt according to claim 1, wherein R is aryl optionally substituted with up to 2 substituents (in addition to $-EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

3. A compound or salt according to claim 2, wherein R is aryl.

4. A compound or salt according to claim 2, wherein R is phenyl optionally substituted with up to 2 substituents (in addition to $-EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

5. A compound or salt according to claim 4, wherein $Y^2$ is selected from the group consisting of hydrogen, alkyl, alkoxy, haloalkyl, fluoroalkoxy, aryl, arylalkyl, cycloalkyl, heteroaryl, hydroxy, aryloxy, arylalkoxy, heteroaryloxy, heteroarylalkyl, fluoroalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl.

6. A compound or salt according to claim 5, wherein $Y^2$ is selected from the group consisting of hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl.

7. A compound or salt according to claim 6, wherein $Y^2$ is selected from the group consisting of trifluoromethylalkyl and trifluoromethyl.

8. A compound or salt according to claim 4, wherein the compound corresponds in structure to the following formula:

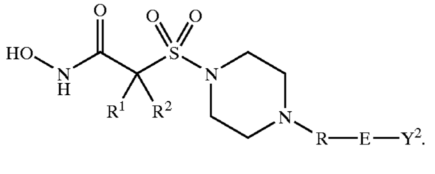

9. A compound or salt according to claim 8, wherein $R^1$ and $R^2$, taken together with the carbon to which they are bonded, form a heterocyclo or cycloalkyl, wherein:

the heterocyclo or cycloalkyl optionally is substituted with up to 3 independently selected $R^x$ substituents.

10. A compound or salt according to claim 9, wherein the compound corresponds in structure to the following formula:

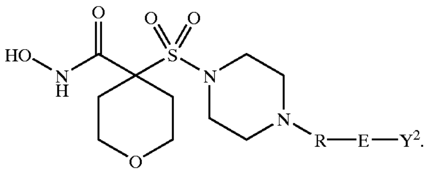

11. A compound or salt according to claim 9, wherein the compound corresponds in structure to the following formula:

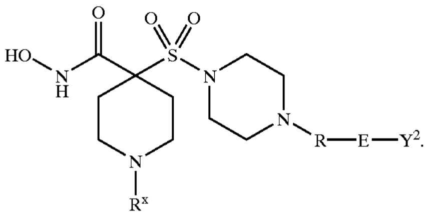

12. A compound or salt according to claim 9, wherein R is phenyl substituted with a substituent (in addition to $-EY^2$) selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

13. A compound or salt according to claim 12, wherein R is phenyl substituted with alkyl (in addition to $-EY^2$).

14. A compound or salt according to claim 13, wherein the compound corresponds in structure to the following formula:

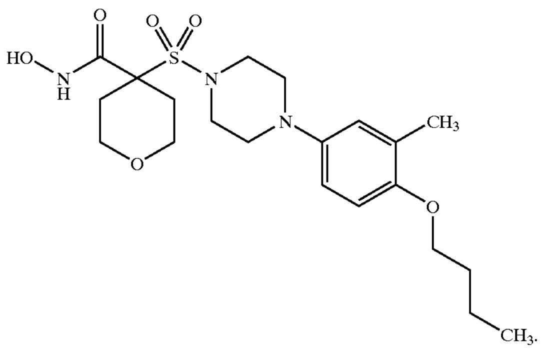

15. A salt according to claim 14, wherein the salt comprises HCl.

16. A compound or salt according to claim 9, wherein R is phenyl substituted with 2 substituents (in addition to $-EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

17. A compound or salt according to claim 9, wherein the compound corresponds in structure to the following formula:

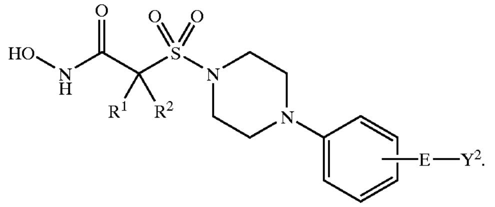

18. A compound or salt according to claim 17, wherein the compound corresponds in structure to the following formula:

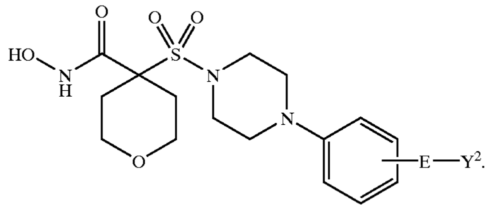

19. A compound or salt according to claim 17, wherein the compound corresponds in structure to the following formula:

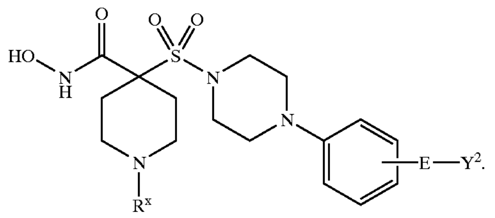

20. A compound or salt according to claim 17, wherein the compound corresponds in structure to the following formula:

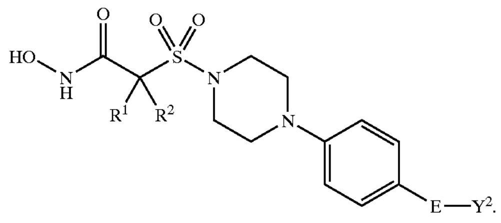

21. A compound or salt according to claim 20, wherein the compound corresponds in structure to the following formula:

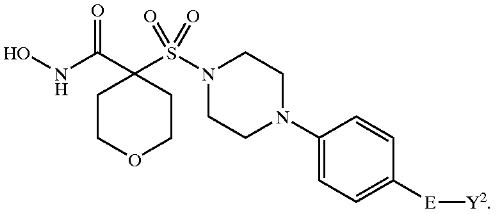

22. A compound or salt according to claim 21, wherein the compound corresponds in structure to the following formula:

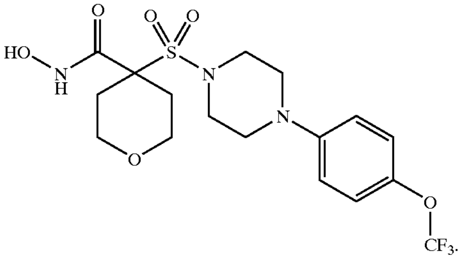

23. A salt according to claim 22, wherein the salt comprises HCl.

24. A compound or salt according to claim 21, wherein the compound corresponds in structure to the following formula:

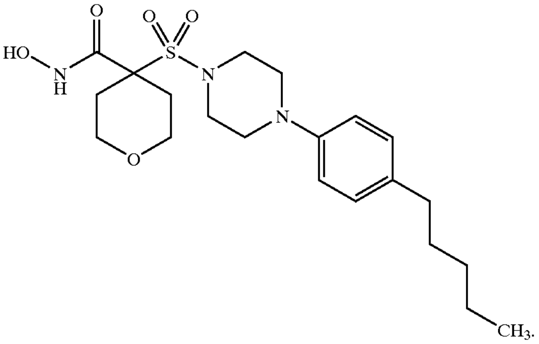

25. A salt according to claim 24, wherein the salt comprises HCl.

26. A compound or salt according to claim 21, wherein the compound corresponds in structure to the following formula:

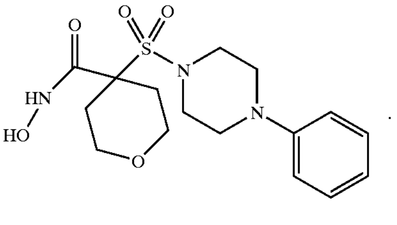

27. A salt according to claim 26, wherein the salt comprises HCl.

28. A compound or salt according to claim 20, wherein the compound corresponds in structure to the following formula:

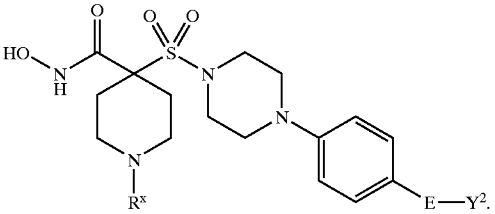

29. A compound or a salt pharmaceutically acceptable salt thereof, wherein:

the compound corresponds in structure to the following formula:

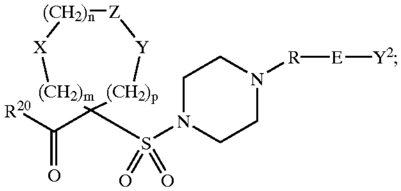

m is zero, 1, or 2;

n is zero, 1, or 2;

p is zero, 1, or 2;

the sum of m+n+p is 1, 2, 3, or 4;

as to X, Y, and Z:

one of X, Y, and Z is selected from the group consisting of C(O), $NR^6$, O, S, S(O), $S(O)_2$ and $NS(O)_2R^7$, and the remaining two of X, Y, and Z are $CR^8R^9$ and $CR^{10}R^{11}$, X and Z or Z and Y together constitute a substituent selected from the group consisting of $NR^6C(O)$, $NR^6S(O)$, $NR^6S(O)_2$, $NR^6S$, $NR^6O$, SS, $NR^6NR_6$ and OC(O), with the remaining one of X and Y being $CR^8R^9$, or n is zero and X, Y, and Z together constitute a substituent selected from the group consisting of the following substituents (wherein wavy lines are bonds to the atoms of the depicted ring):

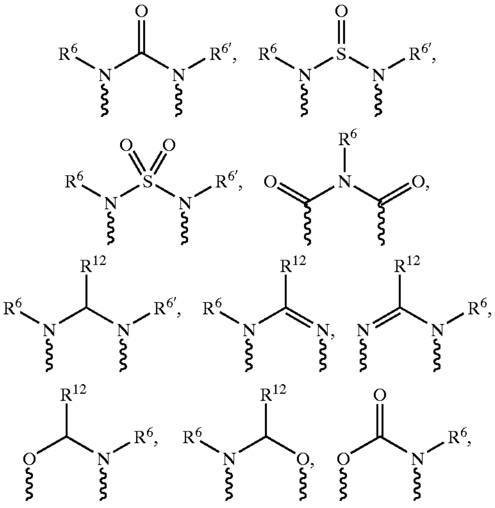

-continued

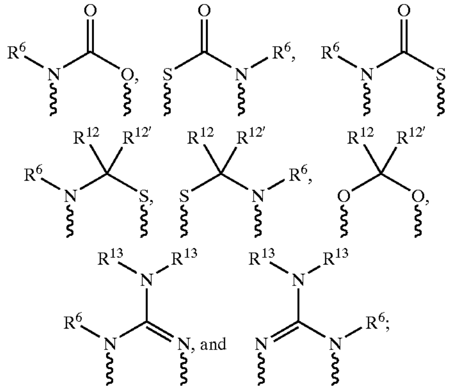

and $R^6$ and $R^{6'}$ are independently selected from the group consisting of hydrogen, $C_1$–$C_6$-alkylcarbonyl, $C_6$-aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heterocyclo-$C_1$–$C_6$-alkyl (wherein the heterocyclo has 3 to 8 ring members), heterocyclo-$C_1$–$C_6$-alkylcarbonyl (wherein the heterocyclo has 3 to 8 ring members), $C_6$-aryl, heterocyclo having 5 to 6 ring members, heteroaryl having 5 to 6 ring members, $C_1$–$C_6$-alkyl-$C_6$-aryl, $C_1$–$C_6$-alkylheteroaryl (wherein the heteroaryl has 5 to 6 ring members), $C_1$–$C_6$-haloalkylheteroaryl (wherein the heteroaryl has 5 to 6 ring members), $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl (wherein the heteroaryl has 5 to 6 ring members), heteroaryl-$C_1$–$C_6$-alkoxy-$C_1$–$C_6$-alkyl (wherein the heteroaryl has 5 to 6 ring members), heteroarylthio-$C_1$–$C_6$-alkyl (wherein the heteroaryl has 5 to 6 ring members), $C_6$-arylsulfonyl, $C_1$–$C_6$-alkylsulfonyl, heteroarylsulfonyl (wherein the heteroaryl has 5 to 6 ring members), carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, heterocycloiminocarbonyl (wherein the heterocyclo has 5 to 6 ring members), $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$heteroaryl-$C_1$–$C_6$-alkyl (wherein the heteroaryl has 5 to 6 ring members), halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, hydroxyaminocarbonyl, aminosulfonyl, amino-$C_1$–$C_6$-alkylsulfonyl, and amino-$C_1$–$C_6$-alkyl, wherein:

the aminocarbonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the aminosulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the amino-$C_1$–$C_6$-alkylsulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, and the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl;

$R^7$ is selected from the group consisting of arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and $C_1$–$C_6$-hydroxyalkyl; as to $R^8$:

$R^8$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, $R^8$ and $R^9$, together with the carbon to which they are bonded, form a carbonyl group, or $R^8$ and $R^9$ or $R^8$ and $R^{10}$, together with the atom(s) to which they are bonded, form a 5- to 8-membered carbocyclic ring or a 5- to 8-membered heterocyclic ring containing 1 or 2 heteroatoms that are independently selected from the group consisting of nitrogen, oxygen, and sulfur; as to $R^9$:

$R^9$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, or $R^9$ and $R^8$, together with the carbon to which they are bonded, form:

a carbonyl group, or a 5- to 8-membered carbocyclic ring or a 5- to 8-membered heterocyclic ring containing 1 or 2 heteroatoms that are independently selected from the group consisting of nitrogen, oxygen, and sulfur; as to $R^{10}$:

$R^{10}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, $R^{10}$ and $R^{11}$, together with the carbon to which they are bonded, form a carbonyl group, or $R^{10}$ and $R^{11}$ or $R^{10}$ and $R^8$, together with the atom(s) to which they are bonded, form a 5- to 8-membered carbocyclic ring or a 5- to 8-membered heterocyclic ring containing 1 or 2 heteroatoms that are independently selected from the group consisting of nitrogen, oxygen, and sulfur; as to $R^{11}$:

$R^{11}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, amninocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, or $R^{11}$ and $R^{10}$, together with the carbon to which they are bonded, form:

a carbonyl group, or a 5- to 8-membered carbocyclic ring or a 5- to 8-membered heterocyclic ring containing 1 or 2 heteroatoms that are independently selected from the group consisting of nitrogen, oxygen, and sulfur;

only one of $R^8$ and $R^9$ or $R^{10}$ and $R^{11}$ is hydroxy;

$R^{12}$ and $R^{12}$ are independently selected from the group consisting of a hydrogen, $C_1$–$C_6$-alkyl, aryl, aryl-$C_1$–$C_6$-alkyl, heteroaryl, heteroarylalkyl, $C_2$–$C_6$-alkynyl, $C_2$–$C_6$-alkenyl thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl; and $R^{13}$ is selected from the group consisting of hydrogen, benzyl, phenyl, $C_1$–$C_6$-alkyl, $C_2$–$C_6$-alkynyl, $C_2$–$C_6$-alkenyl, and $C_1$–$C_6$-hydroxyalkyl;

$R^{13}$ is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkyloxyalkyl, heterocycloalkyloxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to 2 substituents (in addition to -$EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylenedioxy, hydroxycarbonylalkyl, hydroxycarbonylalkylamino, nitro, hydroxy, hydroxyalkyl, alkylcarbonylamino, and alkoxycarbonyl;

E is selected from the group consisting of:

(1) —CO($R^w$)—,
(2) —($R^w$)CO—,
(3) —CONH—,
(4) —HNCO—,
(5) —CO—,
(6) —$SO_2$—$R^w$—,
(7) —$R^w$—$SO_2$—,
(8) —$SO_2$—,
(9) —NH—$SO_2$—,
(10) —$SO_2$—NH—, and
(11) a bond;

$Y^2$ is selected from the group consisting of hydrogen, alkyl alkoxy, haloalkyl, haloalkoxy, aryl, arylalkyl, cycloalkyl, heteroaryl, hydroxy, aryloxy, arylalkoxy, heteroaryloxy, heteroarylalkyl, haloalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl;

$R^{20}$ is selected from the group consisting of —O—$R^{21}$, —NH—O—$R^{22}$, and —NH—O—$R^{14}$;

$R^{21}$ is selected from the group consisting of hydrogen, $C_1$–$C_6$-alkyl, aryl, and aryl-$C_1$–$C_6$-alkyl;

$R^{22}$ is a selectively removable protecting group;

$R^{14}$ is selected from the group consisting of hydrogen and C(W)$R^{15}$;

W is selected from the group consisting of O and S;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkylcarbonyl, or the amino-$C_1$–$C_6$-alkyl nitrogen optionally is substituted with 2 substituents such that the 2 substituents, together with the nitrogen, form a 5- to 8-membered heterocyclo or heteroaryl ring; and in addition to any other possible substitutions, any heterocyclo or heteroaryl substituent optionally is substituted:

on any carbon ring atom with up to 2 substituents independently selected from the group consisting of halogen, alkyl, alkoxy, and oxo, on any sulfur ring atom with up to 2 oxo, and on any secondary nitrogen ring atom with a substituent independently selected from the group consisting of alkyl, arylalkoxycarbonyl, alkylcarbonyl, aryl, and arylalkyl.

30. A compound or salt according to claim 29, wherein R is aryl optionally substituted with up to 2 substituents (in addition to -E$Y^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

31. A compound or salt according to claim 30, wherein R is aryl.

32. A compound or salt according to claim 31, wherein R is phenyl optionally substituted with up to 2 substituents (in addition to -E$Y^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl.

33. A compound or salt according to claim 32, wherein $Y^2$ is selected from the group consisting of hydrogen, alkyl, alkoxy, haloalkyl, fluoroalkoxy, aryl, arylalkyl, cycloalkyl, heteroaryl, hydroxy, aryloxy, arylalkoxy, heteroaryloxy, heteroarylalkyl, fluoroalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl.

34. A compound or salt according to claim 33, wherein $Y^2$ is selected from the group consisting of hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl.

35. A compound or salt according to claim 32, wherein the compound corresponds in structure to the following formula:

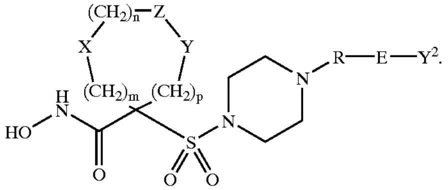

36. A compound or salt according to claim 35, wherein $R^6$ and $R^{6'}$ are independently selected from the group consisting of hydrogen, $C_1$–$C_6$-alkylcarbonyl, $C_6$-aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, $C_1$–$C_6$-fluoroalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heterocyclo-$C_1$–$C_6$-alkyl (wherein the heterocyclo has 3 to 8 ring members), heterocyclo-$C_1$–$C_6$-alkylcarbonyl (wherein the heterocyclo has 3 to 8 ring members), $C_6$-aryl, heterocyclo having 5 to 6 ring members, heteroaryl having 5 to 6 ring members, $C_1$–$C_6$-alkyl-$C_6$-aryl, $C_1$–$C_6$-alkylheteroaryl (wherein the heteroaryl has 5 to 6 ring members), $C_1$–$C_6$-haloalkylheteroaryl (wherein the heteroaryl has 5 to 6 ring members), $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl (wherein the heteroaryl has 5 to 6 ring members), heteroaryl-$C_1$–$C_6$-alkoxy-$C_1$–$C_6$-alkyl (wherein the heteroaryl has 5 to 6 ring members), heteroarylthio-$C_1$–$C_6$-alkyl (wherein the heteroaryl has 5 to 6 ring members), $C_6$-arylsulfonyl, $C_1$–$C_6$-alkylsulfonyl, heteroarylsulfonyl (wherein the heteroaryl has 5 to 6 ring members), carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, heterocycloiminocarbonyl (wherein the heterocyclo has 5 to 6 ring members), $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$-$C_6$-alkenyl, heteroaryl-$C_1$–$C_6$-alkyl (wherein the heteroaryl has 5 to 6 ring members), halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, $C_1$–$C_5$-alkoxycarbonyl, aryloxycarbonyl, $NR^8R^9$-$C_1$–$C_5$-alkylcarbonyl, hydroxy-$C_1$–$C_5$-alkyl, hydroxyaminocarbonyl, aminosulfonyl, amino-$C_1$–$C_6$-alkylsulfonyl, and amino-$C_1$–$C_6$-alkyl, wherein:

the aminocarbonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the aminosulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the amino-$C_1$–$C_6$-alkylsulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, and the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl.

37. A compound or salt according to claim 36, wherein $R^6$ and $R^6$ are independently selected from the group consisting of hydrogen, $C_1$–$C_6$-alkylcarbonyl, $C_6$-aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heterocyclo-$C_1$–$C_6$-alkyl (wherein the heterocyclo has 3 to 8 ring members), heterocyclo-$C_1$–$C_6$-alkylcarbonyl (wherein the heterocyclo has 3 to 8 ring members), $C_6$-aryl, heterocyclo having 5 to 6 ring members, heteroaryl having 5 to 6 ring members, $C_1$–$C_6$-haloalkylheteroaryl (wherein the heteroaryl has 5 to 6 ring members), $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl (wherein the heteroaryl has 5 to 6 ring members), heteroaryl-$C_1$–$C_6$-alkoxy-$C_1$–$C_6$-alkyl (wherein the heteroaryl has 5 to 6 ring members), heteroarylthio-$C_1$–$C_6$-alkyl (wherein the heteroaryl has 5 to 6 ring members), $C_6$-arylsulfonyl, $C_1$–$C_6$-alkylsulfonyl, heteroarylsulfonyl (wherein the heteroaryl has 5 to 6 ring members), carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, heterocycloiminocarbonyl (wherein the heterocyclo has 5 to 6 ring members), $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, heteroaryl-$C_1$–$C_6$-alkyl (wherein the heteroaryl has 5 to 6 ring members), halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, $C_1$–$C_5$-alkoxycarbonyl, aryloxycarbonyl, $NR^8R^9$–$C_1$–$C_5$-alkylcarbonyl, hydroxy-$C_1$–$C_5$-alkyl, hydroxyaminocarbonyl, aminosulfonyl, amino-$C_1$–$C_6$-alkylsulfonyl, and amino-$C_1$–$C_6$-alkyl, wherein:

the aminocarbonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the aminosulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the amino-$C_1$–$C_6$-alkylsulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, and the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl.

38. A method for treating a mammal having a condition associated with pathological matrix metalloprotease activity, wherein:

the method comprises administering a compound or a pharmaceutically acceptable salt thereof in an effective amount to the mammal;

the compound or salt inhibits the activity of one or more of MMP-2, MMP-9, and MMP-13, while exhibiting substantially less inhibitory activity against MMP-1;

the compound corresponds in structure to the following formula:

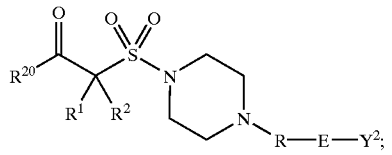

as to $R^1$ and $R^2$:

$R^1$ and $R^2$, taken together with the carbon to which they are bonded, form a heterocyclo or cycloalkyl, wherein:

the heterocyclo or cycloalkyl optionally is substituted with up to 3 independently selected $R^x$ substituents, or $R^1$ and $R^2$ are independently selected from the group consisting of hydrogen, alkyl, alkoxyalkyl, alkylthioalkyl, alkenyl, alkynyl, aryl, arylalkyl, arylalkoxyalkyl, aryloxyalkyl, arylthioalkyl, arylalkylthioalkyl, cycloalkyl, bicycloalkyl, cycloalkenyl, cycloalkylalkyl, bicycloalkylalkyl, cycloalkyloxyalkyl, bicycloalkyloxyalkyl, cycloalkylalkoxyalkyl, bicycloalkyloxyalkyl, cycloalkylthioalkyl, bicycloalkylthioalkyl, cycloalkylalkylthioalkyl, bicycloalkylalkylthioalkyl, heterocyclo, heterocycloalkyl, heteroaryl, biarylalkyl, arylalkenyl, arylalkynyl, heterocycloalkylthio, heterocycloalkyloxyalkyl, heteroarylalkenyl, and heteroarylalkoxyalkyl, wherein:

any such substituent (other than hydrogen) optionally is substituted with up to 3 independently selected $R^x$ substituents;

each $R^x$ is independently selected from the group consisting of aryl, heteroaryl, heterocyclo, arylcarbonyl, alkylcarbonyl, heteroarylcarbonyl, halogen, cyano, aldehydo, hydroxy, $R^cR^d$-amino, $R^cR^d$-aminoalkyl, nitro, nitroso, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, alkoxyalkyl, $R^c$-oxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, alkoxycarbonyl-$R^c$-amino, arylalkoxycarbonyl-$R^c$-amino, aryloxycarbonyloxy, carboxy, $R^cR^d$-aminocarbonyloxy, $R^cR^d$-aminocarbonyl, $R^cR^d$-aminoalkylcarbonyl, hydroxy-$R^c$-aminocarbonyl, $R^cR^d$-aminosulfonyl, arylsulfonyl ($R^c$)amino, $R^cR^d$-aminoalkoxy, $R^cR^d$-aminocarbonyl ($R^c$)amino, trifluoromethylsulfonyl($R^c$)amino, heteroarylsulfonyl-($R^c$)amino, alkylsulfonyl, arylsulfonyl($R^c$)amino, arylsulfonyl($R^c$)aminocarbonyl, alkylsulfonyl-($R^c$)amino, arylcarbonyl($R^c$)-aminosulfonyl, and alkylsulfonyl($R^c$)aminocarbonyl;

each $R^c$ and $R^d$ is independently selected from the group consisting of hydrogen, alkylcarbonyl, arylalkyl, arylcarbonyl, bisalkoxyalkyl, alkyl, haloalkyl, perfluoroalkyl, trifluoromethylalkyl, perfluoroalkoxyalkyl, alkoxyalkyl, cycloalkyl, heterocycloalkyl, heterocycloalkylcarbonyl, aryl, heterocyclo, heteroaryl, cycloalkylalkyl, aryloxyalkyl, heteroaryloxyalkyl, heteroarylalkoxyalkyl, heteroarylthioalkyl, arylsulfonyl, alkylsulfonyl, heteroarylsulfonyl, carboxyalkyl, alkoxycarbonylalkyl, aminocarbonyl, alkyliminocarbonyl, aryliminocarbonyl, heterocycloiminocarbonyl, arylthioalkyl, alkylthioalkyl, arylthioalkenyl, alkylthioalkenyl, heteroarylalkyl, haloalkylcarbonyl, hydroxyalkylcarbonyl, thiolalkylcarbonyl, alkenyl, alkynyl, alkoxycarbonyl, aryloxycarbonyl, aminoalkylcarbonyl, hydroxyalkyl, aminoalkyl, aminoalkylsulfonyl, and aminosulfonyl, wherein:

any amino nitrogen of $R^c$ or $R^d$ optionally is substituted with up to 2 independently selected $R^y$ substituents, and any amino nitrogen of $R^c$ or $R^d$ optionally is substituted with 2 substituents such that the 2 substituents, taken together with the amino nitrogen, form:

a saturated or partially unsaturated heterocyclo group optionally substituted with up to 3 independently selected $R^w$ substituents, or a heteroaryl group optionally substituted with up to 3 independently selected $R^v$ substituents;

each $R^y$ is independently selected from the group consisting of arylalkyl, aryl, heteroaryl, heterocyclo, alkyl, alkynyl, alkenyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

any such substituent optionally is substituted by up to 2 independently selected Ru substituents, and the amino nitrogen of the substituted aminoalkyl or substituted aminoalkylcarbonyl is substituted with 1 or 2 independently selected $R^u$ substituents;

each $R^v$ is independently selected from the group consisting of aryl, heteroaryl, heterocyclo, arylcarbonyl, alkylcarbonyl, heteroarylcarbonyl, halogen, cyano, aldehydo, hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, arylalkoxycarbonylamino, aryloxycarbonyloxy, carboxy, $R^yR^z$-aminocarbonyloxy, $R^yR^z$-aminocarbonyl, $R^yR^z$-aminoalkylcarbonyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl-($R^y$)amino, arylsulfonyl($R^y$)amino, arylsulfonyl($R^y$)-aminocarbonyl, alkylsulfonyl($R^y$)amino, arylcarbonyl-($R^y$)aminosulfonyl, and alkylsulfonyl($R^y$)-aminocarbonyl;

each $R^w$ is independently selected from the group consisting of hydrogen, aryl, heteroaryl, heterocyclo, arylcarbonyl, alkylcarbonyl, heteroarylcarbonyl, halogen, cyano, aldehydo, hydroxy, amino, alkyl, alkenyl, alkynyl, cycloalkyl, cycloalkenyl, alkoxy, aryloxy, heteroaryloxy, alkenyloxy, alkynyloxy, alkoxyaryl, alkoxyheteroaryl, $R^yR^z$-amino, alkoxyalkyl, alkylenedioxy, aryloxyalkyl, perfluoroalkyl, trifluoroalkyl, alkylthio, arylthio, alkoxycarbonyl, alkoxycarbonyloxy, aryloxycarbonyl, arylalkoxycarbonyl, arylalkoxycarbonylamino, aryloxycarbonyloxy, carboxy, $R^yR^z$-aminocarbonyloxy, $R^yR^z$-aminocarbonyl, $R^yR^z$-aminoalkylcarbonyl, hydroxyaminocarbonyl, $R^yR^z$-aminosulfonyl, $R^yR^z$-aminocarbonyl($R^y$)amino, trifluoromethylsulfonyl($R^y$)amino, heteroarylsulfonyl-($R^y$)amino, arylsulfonyl($R^y$)amino, arylsulfonyl($R^y$)-aminocarbonyl, alkylsulfonyl($R^y$)amino, arylcarbonyl-($R^y$)aminosulfonyl, and alkylsulfonyl($R^y$)-aminocarbonyl;

each $R^z$ is independently selected from the group consisting of arylalkyl, aryl, heteroaryl, heterocyclo, alkyl, alkynyl, alkenyl, alkoxyalkyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

each such substituent optionally is substituted by up to 2 independently selected $R^u$ substituents, and the amino nitrogen of the substituted aminoalkyl or substituted aminoalkylcarbonyl is substituted with 1 or 2 independently selected $R^u$ substituents;

each $R^u$ is independently selected from the group consisting of arylalkyl, aryl, heteroaryl, heterocyclo, alkyl, alkynyl, alkenyl, alkoxyalkyl, substituted aminoalkyl, unsubstituted aminoalkyl, alkoxycarbonyl, arylalkoxycarbonyl, carboxyalkyl, haloalkyl, alkylcarbonyl, arylcarbonyl, substituted aminoalkylcarbonyl, unsubstituted aminoalkylcarbonyl, haloalkylcarbonyl, and hydroxyalkyl, wherein:

the amino nitrogen of the substituted aminoalkyl or substituted aminoalkylcarbonyl is substituted with 1 or 2 substituents independently selected from the group consisting of alkyl, alkenyl, aryl, arylalkyl, heteroaryl, heteroarylalkyl, aryloxycarbonyl, and alkoxycarbonyl;

R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkyloxyalkyl, heterocycloalkyloxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to 2 substituents (in addition to -$EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkylcarbonylamino, and alkoxycarbonyl;

E is selected from the group consisting of:

(1) —CO($R^w$)—, (2) —($R^w$)CO—, (3) —CONH—,
(4) —HNCO—,
(5) —CO—,
(6) —$SO_2$—$R^w$—,
(7) —$R^w$—$SO_2$,
(8) —$SO_2$—,
(9) —NH—$SO_2$—,
(10) —$SO_2$—NH—, and
(11) a bond;

$Y^2$ is selected from the group consisting of hydrogen, alkyl, alkoxy, haloalkyl, haloalkoxy, aryl, arylalkyl, cycloalkyl, heteroaryl, hydroxy, aryloxy, arylalkoxy, heteroaryloxy, heteroarylalkyl, haloalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl;

$R^{20}$ is selected from the group consisting of —O—$R^{21}$, —NH—O—$R^{22}$, and —NH—O—$R^{14}$;

$R^{21}$ is selected from the group consisting of hydrogen, $C_1$–$C_6$-alkyl, aryl, and aryl-$C_1$–$C_6$-alkyl;

$R^{22}$ is a selectively removable protecting group;

$R^{14}$ is selected from the group consisting of hydrogen and C(W)$R^{15}$;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkylcarbonyl, or the amino-$C_1$–$C_6$-alkyl nitrogen optionally is substituted with 2 substituents such that the 2 substituents, together with the nitrogen, form a 5- to 8-membered heterocyclo or heteroaryl ring;

W is selected from the group consisting of O and S; and in addition to any other possible substitutions, any heterocyclo or heteroaryl substituent optionally is substituted:

on any carbon ring atom with up to 2 substituents independently selected from the group consisting of halogen, alkyl, alkoxy, and oxo, on any sulfur ring atom with up to 2 oxo, and on any secondary nitrogen ring atom with a substituent independently selected from the group consisting of alkyl, arylalkoxycarbonyl, alkylcarbonyl, aryl, and arylalkyl.

39. A method according to claim 38, wherein $R^1$ and $R^2$, taken together with the carbon to which they are bonded, form a heterocyclo or cycloalkyl, wherein:

the heterocyclo or cycloalkyl optionally is substituted with up to 3 independently selected $R^x$ substituents.

40. A method according to claim 38, wherein the compound corresponds in structure to the following formula:

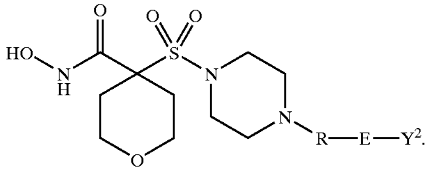

41. A method according to claim 38, wherein the compound corresponds in structure to the following formula:

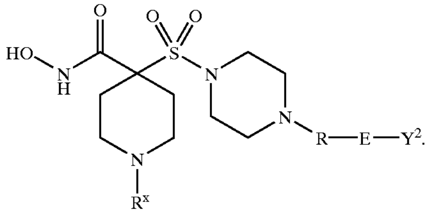

42. A method according to claim 38, wherein the compound corresponds in structure to a formula selected from the group consisting of:

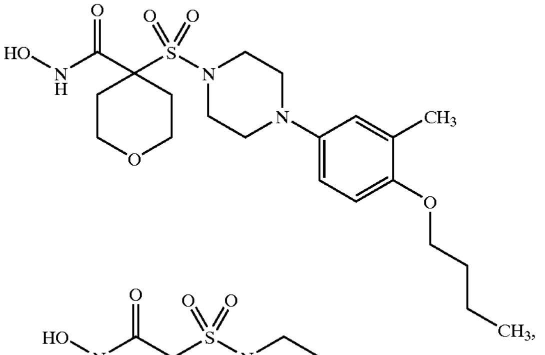

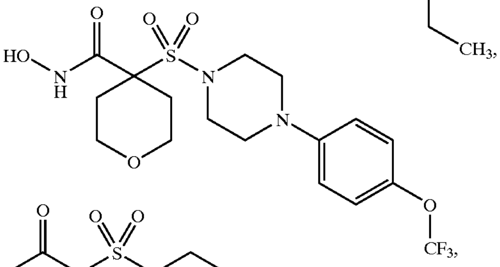

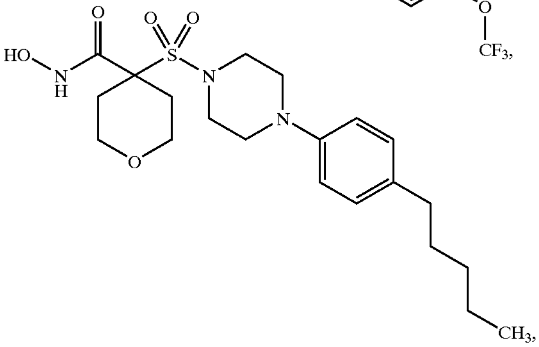

and

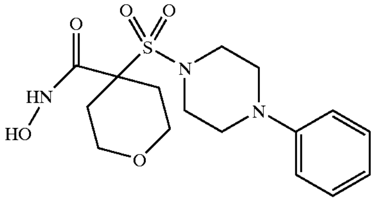

.

43. A method for treating a mammal having a condition associated with pathological matrix metalloprotease activity, wherein:

the method comprises administering a compound or a pharmaceutically acceptable salt thereof in an effective amount to the mammal;

the compound or salt inhibits the activity of one or more of MMP-2, MMP-9, and MMP-13, while exhibiting substantially less inhibitory activity against MMP-1;

the compound corresponds in structure to the following formula:

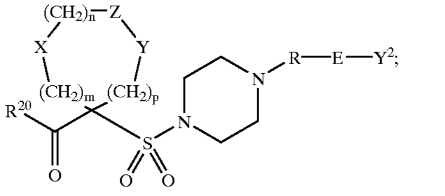

m is zero, 1, or 2;

n is zero, 1, or 2;

p is zero, 1, or 2;

the sum of m+n+p is 1, 2, 3, or 4;

as to X, Y, and Z:

one of X, Y, and Z is selected from the group consisting of C(O), $NR^6$, O, S, S(O), $S(O)_2$ and $NS(O)_2R^7$, and the remaining two of X, Y, and Z are $CR^8R^9$ and $CR^{10}R^{11}$, X and Z or Z and Y together constitute a substituent selected from the group consisting of $NR^6C(O)$, $NR^6S(O)$, $NR^6S(O)2$, $NR^6S$, $NR^6O$, SS, $NR^6NR_6$ and OC(O), with the remaining one of X and Y being $CR^8R^9$, or n is zero and X, Y, and Z together constitute a substituent selected from the group consisting of the following substituents (wherein wavy lines are bonds to the atoms of the depicted ring):

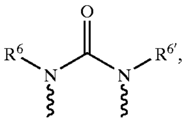 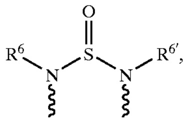

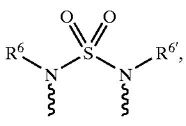 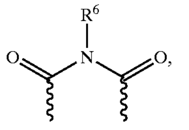

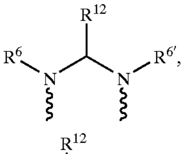 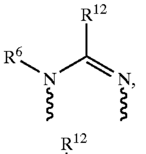 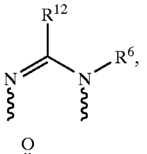

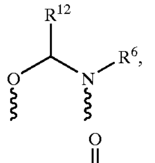 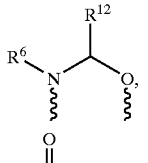 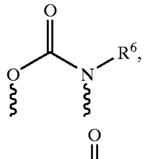

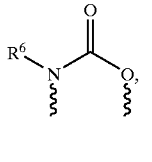 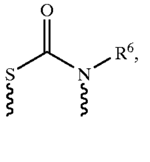 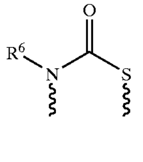

-continued

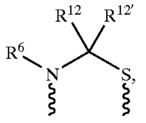 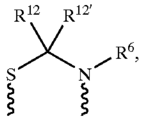 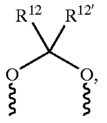

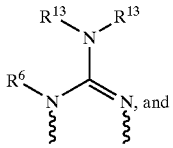 and 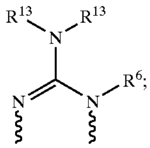

$R^6$ and $R^{6'}$ are independently selected from the group consisting of hydrogen, $C_1$–$C_6$-alkylcarbonyl, $C_6$-aryl-$C_1$–$C_6$-alkyl, arylcarbonyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalklyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, heterocyclo-$C_1$–$C_6$-alkyl (wherein the heterocyclo has 3 to 8 ring members), heterocyclo-$C_1$–$C_6$-alkylcarbonyl (wherein the heterocyclo has 3 to 8 ring members), $C_6$-aryl, heterocyclo having 5 to 6 ring members, heteroaryl having 5 to 6 ring members, $C_1$–$C_6$-alkyl-$C_6$-aryl, $C_1$–$C_6$-alkylheteroaryl (wherein the heteroaryl has 5 to 6 ring members), $C_1$–$C_6$-haloalkylheteroaryl (wherein the heteroaryl has 5 to 6 ring members), $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl (wherein the heteroaryl has 5 to 6 ring members), heteroaryl-$C_1$–$C_6$-alkoxy-$C_1$–$C_6$-alkyl (wherein the heteroaryl has 5 to 6 ring members), heteroarylthio-$C_1$–$C_6$-alkyl (wherein the heteroaryl has 5 to 6 ring members), $C_6$-arylsulfonyl, $C_1$–$C_6$-alkylsulfonyl, heteroarylsulfonyl (wherein the heteroaryl has 5 to 6 ring members), carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, heterocycloiminocarbonyl (wherein the heterocyclo has 5 to 6 ring members), $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$-$C_6$-allyl, heteroaryl-$C_1$–$C_6$-alkyl (wherein the heteroaryl has 5 to 6 ring members), halo-$C_1$–$C_6$-alkylcarbonyl, hydroxy-$C_1$–$C_6$-alkylcarbonyl, thiol-$C_1$–$C_6$-alkylcarbonyl, $C_3$–$C_6$-alkenyl, $C_3$–$C_6$-alkynyl, $C_1$–$C_5$-alkoxycarbonyl, aryloxycarbonyl, $NR^8R^9$-$C_1$–$C_5$-alkylcarbonyl, hydroxy-$C_1$–$C_5$-alkyl, hydroxyaminocarbonyl, aminosulfonyl, amino-$C_1$–$C_6$-alkylsulfonyl, and amino-$C_1$–$C_6$-alkyl, wherein:

the aminocarbonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the aminosulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, the amino-$C_1$–$C_6$-alkylsulfonyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl, and the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, $C_3$–$C_8$-cycloalkyl, and $C_1$–$C_6$-alkylcarbonyl;

$R^7$ is selected from the group consisting of arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and $C_1$–$C_6$-hydroxyalkyl; as to $R^8$:

$R^8$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, $R^8$ and $R^9$, together with the carbon to which they are bonded, form a carbonyl group, or $R^8$ and $R^9$ or $R^8$ and $R^{10}$, together with the atom(s) to which they are bonded, form a 5- to 8-membered carbocyclic ring or a 5- to 8-membered heterocyclic ring containing 1 or 2 heteroatoms that are independently selected from the group consisting of nitrogen, oxygen, and sulfur; as to $R^9$:

$R^9$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, or $R^9$ and $R^8$, together with the carbon to which they are bonded, form:

a carbonyl group, or a 5- to 8-membered carbocyclic ring or a 5- to 8-membered heterocyclic ring containing 1 or 2 heteroatoms that are independently selected from the group consisting of nitrogen, oxygen, and sulfur; as to $R^{10}$:

$R^{10}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, $R^{10}$ and $R^{11}$, together with the carbon to which they are bonded, form a carbonyl group, or $R^{10}$ and $R^{11}$ or $R^{10}$ and $R^8$, together with the atom(s) to which they are bonded, form a 5- to 8-membered carbocyclic ring or a 5- to 8-membered heterocyclic ring containing 1 or 2 heteroatoms that are independently selected from the group consisting of nitrogen, oxygen, and sulfur; as to $R^{11}$:

$R^{11}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, a sulfoxide of any said thio substituents, a sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl, or $R^{11}$ and $R^{10}$, together with the carbon to which they are bonded, form:

a carbonyl group, or a 5- to 8-membered carbocyclic ring or a 5- to 8-membered heterocyclic ring containing 1 or 2 heteroatoms that are independently selected from the group consisting of nitrogen, oxygen, and sulfur;

only one of $R^8$ and $R^9$ or $R^{10}$ and $R^{11}$ is hydroxy;

$R^{12}$ and $R^{12'}$ are independently selected from the group consisting of a hydrogen, $C_1$–$C_6$-alkyl, aryl, aryl-$C_1$–$C_6$-alkyl, heteroaryl, heteroarylalkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to 2 substituents independently selected from the group consisting of $C_1$–$C_6$-alkyl, aryl-$C_1$–$C_6$-alkyl, cycloalkyl, and $C_1$–$C_6$-alkylcarbonyl; and $R^{13}$ is selected from the group consisting of hydrogen, benzyl, phenyl, $C_1$–$C_6$-alkyl, $C_2$–$C_6$-alkynyl, $C_2$–$C_6$-alkenyl, and $C_1$–$C_6$-hydroxyalkyl;

R is selected from the group consisting of alkyl, alkoxyalkyl, aryl, heteroaryl, cycloalkyl, heterocycloalkyl, aralkyl, heteroaralkyl, heterocycloalkyl, cycloalkylalkyl, cycloalkyloxyalkyl, heterocycloalkyloxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to 2 substituents (in addition to -$EY^2$) independently selected from the group consisting of halogen, alkyl, perfluoroalkyl, perfluoroalkoxy, perfluoroalkylthio, trifluoromethylalkyl, amino, alkoxycarbonylalkyl, alkoxy, $C_1$–$C_2$-alkylenedioxy, hydroxycarbonylalkyl, hydroxycarbonylalkylamino, nitro, hydroxy, hydroxyalkyl, alkylcarbonylamino, and alkoxycarbonyl;

E is selected from the group consisting of:

(1) —CO($R^w$)—,
(2) —($R^w$)CO—,
(3) —CONH—,
(4) —HNCO—,
(5) —CO—,
(6) —$SO_2R^w$—,
(7) —$R^wSO_2$—,
(8) —$SO_2$—,
(9) —NH—$SO_2$—,
(10) —$SO_2$—NH—, and
(11) a bond;

$Y^2$ is selected from the group consisting of hydrogen, alkyl, alkoxy, haloalkyl, haloalkoxy, aryl, arylalkyl, cycloalkyl, heteroaryl, hydroxy, aryloxy, arylalkoxy, heteroaryloxy, heteroarylalkyl, haloalkylthio, alkenyl, heterocycloalkyl, alkoxycarbonyl, and aminoalkyl, wherein:

the aryl, heteroaryl, or heterocycloalkyl optionally is substituted with up to 2 substituents independently selected from the group consisting of alkylcarbonyl, halogen, nitro, nitrile, alkyl, haloalkyl, arylalkyl, aryl, alkoxy, and amino, wherein:

the amino nitrogen optionally is substituted with up to 2 substituents independently selected from the group consisting of alkyl and arylalkyl;

$R^{20}$ is selected from the group consisting of —O—$R^{21}$, —NH—O—$R^{22}$, and —NH—O—$R^{14}$;

$R^{21}$ is selected from the group consisting of hydrogen, $C_1$–$C_6$-alkyl, aryl, and aryl-$C_1$–$C_6$-alkyl;

$R^{22}$ is a selectively removable protecting group;

$R^{14}$ is selected from the group consisting of hydrogen and C(W)$R^{15}$;

W is selected from the group consisting of O and S;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, and amino-$C_1$–$C_6$-alkyl, wherein:

the amino-$C_1$–$C_6$-alkyl nitrogen optionally is substituted with up to 2 substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkylcarbonyl, or the amino-$C_1$–$C_6$-alkyl nitrogen optionally is substituted with 2 substituents such that the 2 substituents, together with the nitrogen, form a 5- to 8-membered heterocyclo or heteroaryl ring; and in addition to any other possible substitutions, any heterocyclo or heteroaryl substituent optionally is substituted:

on any carbon ring atom with up to 2 substituents independently selected from the group consisting of halogen, alkyl, alkoxy, and oxo, on any sulfur ring atom with up to 2 oxo, and on any secondary nitrogen ring atom with a substituent independently selected from the group consisting of alkyl, arylalkoxycarbonyl, alkylcarbonyl, aryl, and arylalkyl.

44. A pharmaceutical composition, wherein the pharmaceutical composition comprises a therapeutically effective amount of a compound or a pharmaceutically acceptable salt recited in claim 1.

45. A pharmaceutical composition comprising a therapeutically effective amount of a compound or a pharmaceutically acceptable salt recited in claim 9.

46. A pharmaceutical composition comprising a therapeutically effective amount of a compound or a pharmaceutically acceptable salt recited in claim 10.

47. A pharmaceutical composition comprising a therapeutically effective amount of a compound or a pharmaceutically acceptable salt recited in claim 11.

48. A pharmaceutical composition comprising a therapeutically effective amount of a compound or a pharmaceutically acceptable salt recited in claim 14, 21, 23, or 25.

49. A pharmaceutical composition comprising a therapeutically effective amount of a compound or a pharmaceutically acceptable salt recited in claim 29.

* * * * *

UNITED STATES PATENT AND TRADEMARK OFFICE

CERTIFICATE OF CORRECTION

PATENT NO. : 6,492,367 B1
DATED : December 10, 2002
INVENTOR(S) : Gary A. DeCrescenzo et al.

It is certified that error appears in the above-identified patent and that said Letters Patent is hereby corrected as shown below:

Column 803,
Line 52, replace "Ru" with -- $R^u$ --.

Column 810,
Line 39, replace "$NR_6$" with -- $NR^6$ --;

Column 811,
Line 49, replace "$C_3$-$C_6$heteroaryl-" with -- $C_3$-$C_6$-alkenyl, heteroaryl- --;

Column 813,
Line 52, replace "amninocarbonyl-$C_1$-$C_6$-alkyl" with -- aminocarbonyl-$C_1$-$C_6$-alkyl --;

Column 814,
Line 5, replace "$R^{12}$" with -- $R^{12'}$ --; and
Line 31, replace "$R^{13}$" with -- R --.

Column 817,
Line 26, replace "$R^6$" with -- $R^{6'}$ --.

Column 819,
Line 45, replace "Ru" with -- $R^u$ --.

Column 823,
Line 34, replace "$NR^6S(O)2$" with -- $NR^6S(O)_2$ --;
Line 34, replace "$NR^6NR_6$" with -- $NR^6NR^6$ --;

UNITED STATES PATENT AND TRADEMARK OFFICE
CERTIFICATE OF CORRECTION

PATENT NO. : 6,492,367 B1 
DATED : December 10, 2002
INVENTOR(S) : Gary A. De Crscenzo et al.

It is certified that error appears in the above-identified patent and that said Letters Patent is hereby corrected as shown below:

Column 824,
Line 17, replace "-haloalklyl" with -- -haloalkyl --; and
Line 44, replace "-allyl" with -- -alkenyl --.

Signed and Sealed this

Seventeenth Day of February, 2004

JON W. DUDAS
*Acting Director of the United States Patent and Trademark Office*